(12) United States Patent
Ba-maung et al.

(10) Patent No.: US 9,051,315 B2
(45) Date of Patent: Jun. 9, 2015

(54) IMIDAZOPYRIDINES AS A NOVEL SCAFFOLD FOR MULTI-TARGETED KINASE INHIBITION

(75) Inventors: Nwe Y. Ba-maung, Niles, IL (US);
Richard F. Clark, Gurnee, IL (US);
Scott A. Erickson, Zion, IL (US); Steve D. Fidanze, Grayslake, IL (US);
Megumi Kawai, Libertyville, IL (US);
Robert A. Mantei, Franklin, WI (US);
George S. Sheppard, Wilmette, IL (US);
Bryan K. Sorensen, Antioch, IL (US);
Gary T. Wang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 440 days.

(21) Appl. No.: 12/906,681

(22) Filed: Oct. 18, 2010

(65) Prior Publication Data
US 2011/0124632 A1 May 26, 2011

Related U.S. Application Data

(60) Provisional application No. 61/257,120, filed on Nov. 2, 2009.

(51) Int. Cl.
| | |
|---|---|
| *A61K 31/55* | (2006.01) |
| *A61K 31/535* | (2006.01) |
| *A61K 31/497* | (2006.01) |
| *C07D 223/14* | (2006.01) |
| *C07D 413/04* | (2006.01) |
| *C07D 239/02* | (2006.01) |
| *C07D 471/04* | (2006.01) |

(52) U.S. Cl.
CPC .................................. *C07D 471/04* (2013.01)

(58) Field of Classification Search
CPC ... A61K 31/55; A61K 31/535; A61K 31/497; C07D 223/14; C07D 413/04; C07D 239/02
USPC .......... 514/275, 219, 233.2, 252.18; 540/543; 544/122, 297
See application file for complete search history.

(56) References Cited

U.S. PATENT DOCUMENTS

2008/0300242 A1* 12/2008 Kuntz et al. ................. 514/228.2

OTHER PUBLICATIONS

Bareschino M.A., et al., "Erlotinib in Cancer Treatment," Annals of Oncology, 2007, vol. 18 (6), pp. vi35-vi41.
Catrina S.B., et al., "Insulin-Like Growth Factor-I Receptor Activity is Essential for Kaposi'S Sarcoma Growth and Survival," British Journal of Cancer, 2005, vol. 92 (8), pp. 1467-1474.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Davies D.E., et al., "Targeting the Epidermal Growth Factor Receptor for Therapy of Carcinomas," Biochemical Pharmacology, 1996, vol. 51 (9), pp. 1101-1110.
Druker B.J., et al., "Activity of a Specific Inhibitor of the BCR-ABL Tyrosine Kinase in the Blast Crisis of Chronic Myeloid Leukemia and Acute Lymphoblastic Leukemia with the Philadelphia Chromosome," The New England Journal of Medicine, 2001, vol. 344, pp. 1038-1042.
Emmitte K.A., et al., "Discovery and Optimization of Imidazo[1,2-a]pyridine Inhibitors of Insulin-like Growth Factor-1 Receptor (IGF-1R)," Bioorganic & Medicinal Chemistry Letters, 2009, vol. 19 (3), pp. 1004-1008.
Gudmundsson K.S., et al., "Synthesis of Novel Imidazo[1,2-a]pyridines with Potent Activity against Herpesviruses," Organic Letters, 2003, vol. 5 (8), pp. 1369-1372.
Hirota S., et al., "Gain-of-Function Mutations of C-Kit in Human Gastrointestinal Stromal Tumors," Science, 1998, vol. 279 (5350), pp. 577-580.
Hynes N.E., et al., "The Biology of ErbB-2/Neu/HER-2 and its Role in Cancer," Biochimica et Biophysica Acta, 1994, vol. 1198 (2-3), pp. 165-184.
Jones, C.D. et al., "Effects of Substituent Modification on Face Selection in Reduction," Journal of Organic Chemistry, 1998, vol. 63 (8), pp. 2758-2760.
Khandwala H.M., et al., "The Effects of Insulin-Like Growth Factors on Tumorigenesis and Neoplastic Growth," Endocrine Reviews, 2000, vol. 21 (3), pp. 215-244.
Lutz M.P., et al., "Overexpression and Activation of the Tyrosine Kinase Src in Human Pancreatic Carcinoma," Biochemical and Biophysical Research Communications, 1998, vol. 243 (2), pp. 503-508.
Mathis G., "HTRF(R) Technology," Journal of Biomolecular Screening, 1999, vol. 4 (6), pp. 309-314.
Pollak M.N., et al., "Insulin and Insulin-Like Growth Factor Signalling in Neoplasia," Nature Reviews Cancer, 2008, vol. 8 (12), pp. 915-928.
Rusch V., et al., "The Epidermal Growth Factor Receptor and its Ligands as Therapeutic Targets in Human Tumors," Cytokine and Growth Factor Reviews, 1996, vol. 7 (2), pp. 133-141.
Slamon D.J., et al., "Use of Chemotherapy Plus a Monoclonal Antibody Against HER2 for Metastatic Breast Cancer that Overexpresses HER2," The New England Journal of Medicine, 2001, vol. 344 (11), pp. 783-792.
Summy J.M., et al., "Src Family Kinases in Tumor Progression and Metastasis," Cancer and Metastasis Reviews, 2003, vol. 22 (4), pp. 337-358.
Talamonti M.S., et al., "Increase in Activity and Level of pp60C-Src in Progressive Stages of Human Colorectal Cancer," Journal of Clinical Investigation, 1993, vol. 91 (1), pp. 53-60.

* cited by examiner

*Primary Examiner* — James O Wilson
*Assistant Examiner* — Ebenezer O Sackey
(74) *Attorney, Agent, or Firm* — Glen J. Gesicki

(57) ABSTRACT

Compounds that inhibit protein kinases, compositions containing the compounds and methods of treating diseases using the compounds are disclosed.

4 Claims, No Drawings

IMIDAZOPYRIDINES AS A NOVEL SCAFFOLD FOR MULTI-TARGETED KINASE INHIBITION

This application claims priority to U.S. Provisional Application Ser. No. 61/257,120, filed Nov. 2, 2009, which is incorporated by reference in its entirety.

FIELD OF THE INVENTION

This invention pertains to compounds that inhibit protein kinases, compositions containing the compounds and methods of treating diseases using the compounds.

BACKGROUND OF THE INVENTION

Numerous human diseases are characterized by increased and uncontrolled cell growth. This biology is driven, in many cases, by increased growth factor signaling. In addition, these pathologies often require an expanding blood supply and new vessel growth. Protein kinases are key components of both cell proliferation and endothelial cell expansion. Kinases are thus important targets for therapeutic intervention in pathologies characterized by uncontrolled cell growth.

SUMMARY OF THE INVENTION

One embodiment of this invention, therefore, pertains to compounds that inhibit protein kinases and have Formula I

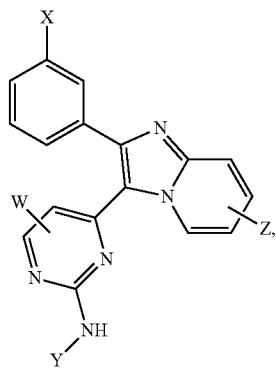

(I)

or a pharmaceutically acceptable salt thereof, wherein
W is alkyl, H, F, Cl, Br or I;
X is $C(O)R^1$, $C(O)NHR^1$, $C(O)N(R^1)_2$, $NHC(O)R^1$, $NR^1C(O)R^1$, $NHC(O)NHR^1$, $NHC(O)N(R^1)_2$, or $NR^1C(O)N(R^1)_2$;
wherein $R^1$ is $R^2$, $R^3$, $R^4$ or $R^5$;
$R^2$ is aryl;
$R^3$ is heteroaryl;
$R^4$ is cycloalkyl, cycloalkenyl, or heterocyclyl;
$R^5$ is C1-C6 alkyl; each of which is unsubstituted or substituted with one or two independently selected $R^6$, $NH_2$ or CN;
$R^6$ is $R^7$, $R^8$, or $R^9$;
$R^7$ is aryl;
$R^8$ is heteroaryl;
$R^9$ is cycloalkyl, cycloalkenyl, or heterocyclyl;
wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), $C(O)H$, $C(O)OH$, CN, $CF_3$, $OCF_3$, $CF_2CF_3$, F, Cl, Br or I;
$R^{10}$ is alkyl, alkenyl, alkynyl, aryl, heteroaryl, cycloalkyl, cycloalkenyl, or heterocyclyl;
Y is $R^{12}$ or $R^{13}$;
$R^{12}$ is aryl;
$R^{13}$ is heteroaryl;
Z is alkyl, H, $CF_3$, F, Cl, Br or I;
wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), $C(O)H$, $C(O)OH$, CN, $CF_3$, $OCF_3$, $CF_2CF_3$, F, Cl, Br or I;
wherein each $R^{14}$ is $R^{15}$, $R^{16}$, $R^{17}$ or $R^{18}$;
$R^{15}$ is aryl;
$R^{16}$ is heteroaryl;
$R^{17}$ is cycloalkyl, cycloalkenyl, or heterocyclyl;
$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, $C(O)OH$, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;
wherein each $R^{19}$ is $R^{20}$ or $R^{21}$;
$R^{20}$ is aryl, heteroaryl, cycloalkyl, cycloalkenyl, or heterocyclyl;
$R^{21}$ is alkyl, alkenyl or alkynyl; each of which is unsubstituted or substituted with one or two of independently selected $R^{22}$, $OR^{22}$, $C(O)OH$, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;
wherein each $R^{22}$ is alkyl, alkenyl, alkynyl, aryl, heteroaryl, cycloalkyl, cycloalkenyl, or heterocyclyl;
wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, $C(O)NHOH$, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, $C(O)H$, $C(O)OH$, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;
wherein each $R^{23}$ is $R^{24}$, $R^{25}$, $R^{26}$, $R^{27}$ or $R^{28}$;
$R^{24}$ is spirocycloalkyl or spiroheterocycloalkyl;
$R^{25}$ is aryl;
$R^{26}$ is heteroaryl;
$R^{27}$ is cycloalkyl, cycloalkenyl, or heterocyclyl;
$R^{28}$ is alkyl, alkenyl or alkynyl; each of which is unsubstituted or substituted with one or two of independently selected $R^{29}$, $OR^{29}$, $SR^{29}$, $S(O)_2R^{29}$, $C(O)OH$, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and $R^{30}$ is alkyl alkenyl, or alkynyl.

Another embodiment of this invention, therefore, pertains to compounds that inhibit protein kinases and have Formula I or a pharmaceutically acceptable salt thereof, wherein W is alkyl, H, F, Cl, Br or I;

X is $C(O)R^1$, $C(O)NHR^{1A}$, $C(O)N(R^1)_2$, $NHC(O)R^1$, $NR^1C(O)R^1$, $NHC(O)NHR^1$, $NHC(O)N(R^1)_2$, or $NR^1C(O)N(R^1)_2$;

wherein $R^1$ is $R^2$, $R^3$, $R^4$ or $R^5$;

$R^2$ is aryl;

$R^3$ is heteroaryl;

$R^4$ is cycloalkyl, cycloalkenyl, or heterocyclyl;

$R^5$ is C1-C6 alkyl; each of which is unsubstituted or substituted with one or two independently selected $R^6$, $NH_2$ or CN;

$R^6$ is $R^7$, $R^8$, or $R^9$;

$R^7$ is aryl;

$R^8$ is heteroaryl;

$R^9$ is cycloalkyl, cycloalkenyl, or heterocyclyl;

wherein $R^{1A}$ is $R^{2A}$, $R^{3A}$, $R^{4A}$ or $R^{5A}$;

$R^{2A}$ is aryl;

$R^{3A}$ is heteroaryl;

$R^{4A}$ is cycloalkyl, cycloalkenyl, or heterocyclyl;

$R^{5A}$ is C1-C6 alkyl; each of which is unsubstituted or substituted with one or two independently selected $R^{6A}$, $NH_2$ or CN;

$R^{6A}$ is $R^{7A}$, $R^{8A}$, or $R^{9A}$;

$R^{7A}$ is aryl;

$R^{8A}$ is heteroaryl;

$R^{9A}$ is cycloalkyl, cycloalkenyl, or heterocyclyl;

wherein the moieties represented by $R^2$, $R^3$, $R^4$, $R^7$, $R^8$, $R^{3A}$, $R^{4A}$, $R^{7A}$, $R^{8A}$, and $R^{9A}$ are independently unsubstituted or substituted with one or two or three or four of independently selected, $R^{10}$, $OR^{10}$, $SR^{10}$, $S(O)R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;

wherein the moiety represented by $R^{2A}$ is independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, or $CF_2CF_3$;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and $R^{30}$ is alkyl alkenyl, or alkynyl.

Another embodiment of this invention, therefore, pertains to compounds that inhibit protein kinases and have Formula I or a pharmaceutically acceptable salt thereof, wherein W is alkyl, H, F, Cl, Br or I;
X is $C(O)R^1$, $C(O)NHR^{1A}$, $C(O)N(R^1)_2$, $NHC(O)R^{1A}$, $NR^1C(O)R^1$, $NHC(O)NHR^1$, $NHC(O)N(R^1)_2$, or $NR^1C(O)N(R^1)_2$;
  wherein $R^1$ is $R^2$, $R^3$, $R^4$ or $R^5$;
  $R^2$ is aryl;
  $R^3$ is heteroaryl;
  $R^4$ is cycloalkyl, cycloalkenyl, or heterocyclyl;
  $R^5$ is C1-C6 alkyl; each of which is unsubstituted or substituted with one or two independently selected $R^6$, $NH_2$ or CN;
  $R^6$ is $R^7$, $R^8$, or $R^9$;
  $R^7$ is aryl;
  $R^8$ is heteroaryl;
  $R^9$ is cycloalkyl, cycloalkenyl, or heterocyclyl;
  wherein $R^{1A}$ is $R^{2A}$, $R^{3A}$, $R^{4A}$ or $R^{5A}$;
  $R^{2A}$ is aryl;
  $R^{3A}$ is heteroaryl;
  $R^{4A}$ is cycloalkyl, cycloalkenyl, or heterocyclyl;
  $R^{5A}$ is C1-C6 alkyl; each of which is unsubstituted or substituted with one or two independently selected $R^{6A}$, $NH_2$ or CN;
  $R^{6A}$ is $R^{7A}$, $R^{8A}$, or $R^{9A}$;
  $R^{7A}$ is aryl;
  $R^{8A}$ is heteroaryl;
  $R^{9A}$ is cycloalkyl, cycloalkenyl, or heterocyclyl;
  wherein the moieties represented by $R^2$, $R^3$, $R^4$, $R^7$, $R^8$, $R^9$, $R^{3A}$, $R^{4A}$, $R^{7A}$, $R^{8A}$, and $R^{9A}$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), $C(O)H$, $C(O)OH$, CN, $CF_3$, $OCF_3$, $CF_2CF_3$, F, Cl, Br or I;
    wherein the moiety represented by $R^{2A}$ is independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^1)_2$, $NHC(O)NH_2$, $NHC(O)NHR^{10}$, $NHC(O)N(R^{10})_2$, $NR^{10}C(O)N(R^{10})_2$, $NO_2$, OH, (O), $C(O)H$, $C(O)OH$, CN, $CF_3$, $OCF_3$, or $CF_2CF_3$;
  $R^{10}$ is alkyl, alkenyl, alkynyl, aryl, heteroaryl, cycloalkyl, cycloalkenyl, or heterocyclyl;
  Y is $R^{12}$ or $R^{13}$;
  $R^{12}$ is aryl;
  $R^{13}$ is heteroaryl;
  Z is alkyl, H, $CF_3$, F, Cl, Br or I;
    wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), $C(O)H$, $C(O)OH$, CN, $CF_3$, $OCF_3$, $CF_2CF_3$, F, Cl, Br or I;
      wherein each $R^{14}$ is $R^{15}$, $R^{16}$, $R^{17}$ or $R^{18}$;
  $R^{15}$ is aryl;
  $R^{16}$ is heteroaryl;
  $R^{17}$ is cycloalkyl, cycloalkenyl, or heterocyclyl;
  $R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, $C(O)OH$, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;
    wherein each $R^{19}$ is $R^{20}$ or $R^{21}$;
  $R^{20}$ is aryl, heteroaryl, cycloalkyl, cycloalkenyl, or heterocyclyl;
  $R^{21}$ is alkyl, alkenyl or alkynyl; each of which is unsubstituted or substituted with one or two of independently selected $R^{22}$, $OR^{22}$, $C(O)OH$, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;
    wherein each $R^{22}$ is alkyl, alkenyl, alkynyl, aryl, heteroaryl, cycloalkyl, cycloalkenyl, or heterocyclyl;
    wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, $C(O)NHOH$, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, $C(O)H$, $C(O)OH$, $C(N)NH_2$, $C(N)NHR^{23}$, $C(N)N(R^{23})_2$, $CNOH$, $CNOCH_3$, OH, (O), CN, $N_3$, $NO_2$, $CF_3$, $CF_2CF_3$, $OCF_3$, $OCF_2CF_3$, F, Cl, Br or I;
      wherein each $R^{23}$ is $R^{24}$, $R^{25}$, $R^{26}$, $R^{27}$ or $R^{28}$;
  $R^{24}$ is spirocycloalkyl or spiroheterocycloalkyl;
  $R^{25}$ is aryl;
  $R^{26}$ is heteroaryl;
  $R^{27}$ is cycloalkyl, cycloalkenyl, or heterocyclyl;
  $R^{28}$ is alkyl, alkenyl or alkynyl; each of which is unsubstituted or substituted with one or two of independently selected $R^{29}$, $OR^{29}$, $SR^{29}$, $S(O)_2R^{29}$, $C(O)OH$, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;
    wherein each $R^{29}$ is alkyl, alkenyl or alkynyl each of which is unsubstituted or substituted with one or two of independently selected F, Cl, Br or I;
    wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), $C(O)OH$, CN, $CF_3$, $OCF_3$, $CF_2CF_3$, F, Cl, Br or I; and
  $R^{30}$ is alkyl alkenyl, or alkynyl.

Another embodiment of this invention, therefore, pertains to compounds that inhibit protein kinases and have Formula I or a pharmaceutically acceptable salt thereof, wherein
W is alkyl, H, F, Cl, Br or I;
X is $C(O)R^1$, $NHC(O)NHR^1$, $NHC(O)N(R^1)_2$, or $NR^1C(O)N(R^1)_2$;
  wherein $R^1$ is $R^2$, $R^3$, $R^4$ or $R^5$;
  $R^2$ is aryl;
  $R^3$ is heteroaryl;
  $R^4$ is cycloalkyl, cycloalkenyl, or heterocyclyl;
  $R^5$ is C1-C6 alkyl; each of which is unsubstituted or substituted with one or two independently selected $R^6$, $NH_2$ or CN;
  $R^6$ is $R^7$, $R^8$, or $R^9$;
  $R^7$ is aryl;
  $R^8$ is heteroaryl;
  $R^9$ is cycloalkyl, cycloalkenyl, or heterocyclyl;

wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, $OH$, $(O)$, $C(O)H$, $C(O)OH$, $CN$, $CF_3$, $OCF_3$, $CF_2CF_3$, F, Cl, Br or I;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, $OH$, $(O)$, $C(O)H$, $C(O)OH$, $CN$, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, $C(O)OH$, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, $OH$, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, $C(O)OH$, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, $OH$, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, $C(O)NHOH$, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, $C(O)H$, $C(O)OH$, $C(N)NH_2$, $C(N)NHR^{23}$, $C(N)N(R^{23})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, $C(O)OH$, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, $OH$, $(O)$, F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^+$, $C(O)R^{30}$, $C(O)OR^{30}$, $OH$, $(O)$, $C(O)OH$, $CN$, $CF_3$, $OCF_3$, $CF_2CF_3$, F, Cl, Br or I; and $R^{30}$ is alkyl alkenyl, or alkynyl.

Another embodiment pertains to compositions comprising a therapeutically effective amount of a compound having Formula I.

Still another embodiment pertains to methods of treating cancer in a mammal having bladder cancer, breast cancer, cervical cancer, colorectal cancer, endometrial cancer, esophageal cancer, lung cancer, ovarian cancer, pancreatic cancer, prostate cancer, rectal cancer, skin cancer, stomach cancer, Ewing's sarcoma, head and neck cancer, or thyroid cancer comprising administering thereto a therapeutically effective amount of a compound of claim 1.

Still another embodiment pertains to the compounds 2,6-difluoro-N-[3-(3-{2-[(3-morpholin-4-ylphenyl)amino]pyrimidin-4-yl}imidazo[1,2-a]pyridin-2-yl)phenyl]benzamide;

N-[3-(3-{2-[(3-morpholin-4-ylphenyl)amino]pyrimidin-4-yl}imidazo[1,2-a]pyridin-2-yl)phenyl]-2-phenylacetamide;

N-[3-(3-{2-[(3-morpholin-4-ylphenyl)amino]pyrimidin-4-yl}imidazo[1,2-a]pyridin-2-yl)phenyl]-N'-phenylurea;

2,6-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-2-phenylacetamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-2-thien-2-ylacetamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-N'-phenylurea;

N-benzyl-N'-[3-(3-{2-[(3-morpholin-4-ylphenyl)amino]pyrimidin-4-yl}imidazo[1,2-a]pyridin-2-yl)phenyl]urea;

N-(2,6-difluorophenyl)-N'-[3-(3-{2-[(3-morpholin-4-ylphenyl)amino]pyrimidin-4-yl}imidazo[1,2-a]pyridin-2-yl)phenyl]urea;

N-(2-methylphenyl)-N'-[3-(3-{2-[(3-morpholin-4-ylphenyl)amino]pyrimidin-4-yl}imidazo[1,2-a]pyridin-2-yl)phenyl]urea;

N-(2-chlorophenyl)-N'-[3-(3-{2-[(3-morpholin-4-ylphenyl)amino]pyrimidin-4-yl}imidazo[1,2-a]pyridin-2-yl)phenyl]urea;

N-(4-fluorophenyl)-N'-[3-(3-{2-[(3-morpholin-4-ylphenyl)amino]pyrimidin-4-yl}imidazo[1,2-a]pyridin-2-yl)phenyl]urea;

N-(3-methoxyphenyl)-N'-[3-(3-{2-[(3-morpholin-4-ylphenyl)amino]pyrimidin-4-yl}imidazo[1,2-a]pyridin-2-yl)phenyl]urea;

N-[3-(3-{2-[(3-morpholin-4-ylphenyl)amino]pyrimidin-4-yl}imidazo[1,2-a]pyridin-2-yl)phenyl]cyclopropanecarboxamide;

N-isopropyl-N'-[3-(3-{2-[(3-morpholin-4-ylphenyl)amino]pyrimidin-4-yl}imidazo[1,2-a]pyridin-2-yl)phenyl]urea;

2,6-difluoro-N-{3-[3-(2-{[3-(2-oxopyrrolidin-1-yl)phenyl]amino}pyrimidin-4-yl)imidazo[1,2-a]pyridin-2-yl]phenyl}benzamide;

2-fluoro-N-{3-[3-(2-{[3-(2-oxopyrrolidin-1-yl)phenyl]amino}pyrimidin-4-yl)imidazo[1,2-a]pyridin-2-yl]phenyl}benzamide;

N-{3-[3-(2-{[3-(2-oxopyrrolidin-1-yl)phenyl]amino}pyrimidin-4-yl)imidazo[1,2-a]pyridin-2-yl]phenyl}-2-phenylacetamide;

N-{3-[3-(2-{[3-(2-oxopyrrolidin-1-yl)phenyl]amino}pyrimidin-4-yl)imidazo[1,2-a]pyridin-2-yl]phenyl}-2-thien-2-ylacetamide;

N-{3-[3-(2-{[3-(2-oxopyrrolidin-1-yl)phenyl]amino}pyrimidin-4-yl)imidazo[1,2-a]pyridin-2-yl]phenyl}-N-phenylurea;

N-(2-fluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea;

N-(2,6-difluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea;

2-(2-fluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide;

2-(2,6-difluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide;

N-benzyl-N'-{3-[3-(2-{[3-(2-oxopyrrolidin-1-yl)phenyl]amino}pyrimidin-4-yl)imidazo[1,2-a]pyridin-2-yl]phenyl}urea;

N-(3-{3-[2-({3-[(dimethylamino)methyl]phenyl}amino)pyrimidin-4-yl]imidazo[1,2-a]pyridin-2-yl}phenyl)benzamide;

N-(3-{3-[2-({3-[(dimethylamino)methyl]phenyl}amino)pyrimidin-4-yl]imidazo[1,2-a]pyridin-2-yl}phenyl)-2-fluorobenzamide;

N-(3-{3-[2-({3-[(dimethylamino)methyl]phenyl}amino)pyrimidin-4-yl]imidazo[1,2-a]pyridin-2-yl}phenyl-2,6-difluorobenzamide;

N-(3-{3-[2-({3-[(dimethylamino)methyl]phenyl}amino)pyrimidin-4-yl]imidazo[1,2-a]pyridin-2-yl}phenyl)-2-phenylacetamide;

N-(3-{3-[2-({3-[(dimethylamino)methyl]phenyl}amino)pyrimidin-4-yl]imidazo[1,2-a]pyridin-2-yl}phenyl)-2-thien-2-ylacetamide;

N-(3-{3-[2-({3-[dimethylamino)methyl]phenyl}amino)pyrimidin-4-yl]imidazo[1,2-a]pyridin-2-yl}phenyl)-N'-phenylurea;

N-(2,6-difluorophenyl)-N'-(3-{3-[2-({3-[(dimethylamino)methyl]phenyl}amino)pyrimidin-4-yl]imidazo[1,2-a]pyridin-2-yl}phenyl)urea;

N-[3-(8-chloro-3-{2-[(3-morpholin-4-ylphenyl)amino]pyrimidin-4-yl}imidazo[1,2-a]pyridin-2-yl)phenyl]-2,6-difluorobenzamide;

N-[3-(8-chloro-3-{2-[(3-morpholin-4-ylphenyl)amino]pyrimidin-4-yl}imidazo[1,2-a]pyridin-2-yl)phenyl]-2-phenylacetamide;

N-[3-(8-chloro-3-{2-[(3-morpholin-4-ylphenyl)amino]pyrimidin-4-yl}imidazo[1,2-a]pyridin-2-yl)phenyl]-2-thien-2-ylacetamide;

N-[3-(8-chloro-3-{2-[(3-morpholin-4-ylphenyl)amino)]pyrimidin-4-yl}imidazo[1,2-a]pyridin-2-yl)phenyl]-N'-phenylurea;

N-(3-{3-[2-({3-[2-(dimethylamino)ethyl]phenyl}amino)pyrimidin-4-yl]imidazo[1,2-a]pyridin-2-yl}phenyl)-2,6-difluorobenzamide;

N-(3-{3-[2-({3-[2-(dimethylamino)ethyl]phenyl}amino)pyrimidin-4-yl]imidazo[1,2-a]pyridin-2-yl}phenyl)-2-phenylacetamide;

N-(3-{3-[2-({3-[2-(dimethylamino)ethyl]phenyl}amino)pyrimidin-4-yl]imidazo[1,2-a]pyridin-2-yl}phenyl)-2-thien-2-ylacetamide;

N-(3-{3-[2-({3-[2-(dimethylamino)ethyl]phenyl}amino)pyrimidin-4-yl]imidazo[1,2-a]pyridin-2-yl}phenyl)-N'-phenylurea;

N-{3-[3-(2-{[4-(4-ethylpiperazin-1-yl)phenyl]amino}pyrimidin-4-yl)imidazo[1,2-a]pyridin-2-yl]phenyl}-2-phenylacetamide;

N-{3-[3-(2-{[4-(4-ethylpiperazin-1-yl)phenyl]amino}pyrimidin-4-yl)imidazo[1,2-a]pyridin-2-yl]phenyl}-2-thien-2-ylacetamide;

N-{3-[3-(2-{[4-(4-ethylpiperazin-1-yl)phenyl]amino}pyrimidin-4-yl)imidazo[1,2-a]pyridin-2-yl]phenyl}benzamide;

N-{3-[3-(2-{[4-(4-ethylpiperazin-1-yl)phenyl]amino}pyrimidin-4-yl)imidazo[1,2-a]pyridin-2-yl]phenyl}-2,6-difluorobenzamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2,6-difluorobenzamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2-phenylacetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2-thien-2-ylacetamide;

N-(3-{3-[2-({3-[2-(dimethylamino)ethoxy]phenyl}amino)pyrimidin-4-yl]imidazo[1,2-a]pyridin-2-yl}phenyl)-2,6-difluorobenzamide;

N-(3-{3-[2-({3-[2-(dimethylamino)ethoxy]phenyl}amino)pyrimidin-4-yl]imidazo[1,2-a]pyridin-2-yl}phenyl)-2-phenylacetamide;

N-(3-{3-[2-({3-[2-(dimethylamino)ethoxy]phenyl}amino)pyrimidin-4-yl]imidazo[1,2-a]pyridin-2-yl}phenyl)-2-thien-2-ylacetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-5-methylthiophene-2-carboxamide;

N-(3-{3-[2-({3-[2-(dimethylamino)ethoxy]phenyl}amino)pyrimidin-4-yl]imidazo[1,2-a]pyridin-2-yl}phenyl)-5-methylthiophene-2-carboxamide;

N-(3-{3-[2-({4-[2-(dimethylamino)ethyl]phenyl}amino)pyrimidin-4-yl]imidazo[1,2-a]pyridin-2-yl}phenyl)-2,6-difluorobenzamide;

N-(3-{3-[2-({4-[2-(dimethylamino)ethyl]phenyl}amino)pyrimidin-4-yl]imidazo[1,2-a]pyridin-2-yl}phenyl)-2-phenylacetamide;

N-(3-{3-[2-({4-[2-(dimethylamino)ethyl]phenyl}amino)pyrimidin-4-yl]imidazo[1,2-a]pyridin-2-yl}phenyl)-2-thien-2-ylacetamide;

2,6-difluoro-N-{3-[3-(2-{[3-(2-pyrrolidin-1-ylethyl)phenyl]amino}pyrimidin-4-yl)imidazo[1,2-a]pyridin-2-yl]phenyl}benzamide;

2-phenyl-N-{3-[3-(2-{[3-(2-pyrrolidin-1-ylethyl)phenyl]amino}pyrimidin-4-yl)imidazo[1,2-a]pyridin-2-yl]phenyl}acetamide;

N-{3-[3-(2-{[3-(2-pyrrolidin-1-ylethyl)phenyl]amino}pyrimidin-4-yl)imidazo[1,2-a]pyridin-2-yl]phenyl}-2-thien-2-ylacetamide;

2,6-difluoro-N-(3-{3-[2-({3-[(3-hydroxyazetidin-1-yl)methyl]phenyl}amino)pyrimidin-4-yl]imidazo[1,2-a]pyridin-2-yl}phenyl)benzamide;

N-(3-{3-[2-({3-[(3-hydroxyazetidin-1-yl)methyl]phenyl}amino)pyrimidin-4-yl]imidazo[1,2-a]pyridin-2-yl}phenyl)-2-phenylacetamide;

N-(3-{3-[2-({3-[(3-hydroxyazetidin-1-yl)methyl]phenyl}amino)pyrimidin-4-yl]imidazo[1,2-a]pyridin-2-yl}phenyl)-2-thien-2-ylacetamide;

2,6-difluoro-N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]benzamide;

N-[3-(3-{2-[(3-{2-[(2-hydroxyethyl)(methyl)amino]ethyl}phenyl)amino)]pyrimidin-4-yl}imidazo[1,2-a]pyridin-2-yl)phenyl]-2-phenylacetamide;

N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]-2-thien-2-ylacetamide;

N-{3-[3-{2-[(3-{[3-(dimethylamino)pyrrolidin-1-yl]methyl}phenyl)amino]pyrimidin-4-yl)imidazo[1,2-a]pyridin-2-yl)phenyl]-2,6-difluorobenzamide;

N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-phenylacetamide;

N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-thien-2-ylacetamide;

N-{3-[3-(2-{[4-(1-acetylpiperidin-4-yl)phenyl]amino}pyrimidin-4-yl)imidazo[1,2-a]pyridin-2-yl]phenyl}-2-thien-2-ylacetamide;

N-{3-[3-(2-{[4-1-acetylpiperidin-4-yl)phenyl]amino}pyrimidin-4-yl)imidazo[1,2-a]pyridin-2-yl]phenyl}-2,6-difluorobenzamide;

N-[3-(3-{2-[(3-cyanophenyl)amino]pyrimidin-4-yl}imidazo[1,2-a]pyridin-2-yl)phenyl]-2,6-difluorobenzamide;

N-[3-(3-{2-[(3-cyanophenyl)amino]pyrimidin-4-yl}imidazo[1,2-a]pyridin-2-yl)phenyl]-2-phenylacetamide;

N-[3-(3-{2-[(3-cyanophenyl)amino]pyrimidin-4-yl}imidazo[1,2-a]pyridin-2-yl)phenyl]-2-thien-2-ylacetamide;

2,6-difluoro-N-(3-{3-[2-({3-[2-(methylsulfonyl)ethoxy]phenyl}amino)pyrimidin-4-yl]imidazo[1,2-a]pyridin-2-yl}phenyl)benzamide;

N-(3-{3-[2-({3-[2-(methylsulfonyl)ethoxy]phenyl}amino)pyrimidin-4-yl]imidazo[1,2-a]pyridin-2-yl}phenyl)-2-phenylacetamide;

N-(3-{3-[2-({3-[2-(methylsulfonyl)ethoxy]phenyl}amino)pyrimidin-4-yl]imidazo[1,2-a]pyridin-2-yl}phenyl)-2-thien-2-ylacetamide;

2,6-difluoro-N-{3-[3-(2-{[4-(1-isopropylpiperidin-4-yl)phenyl]amino}pyrimidin-4-yl)imidazo[1,2-a]pyridin-2-yl]phenyl}benzamide;

N-{3-[3-(2-{[4-(1-isopropylpiperidin-4-yl)phenyl]amino}pyrimidin-4-yl)imidazo[1,2-a]pyridin-2-yl]phenyl}-2-thien-2-ylacetamide;

N-(3-{3-[2-({3-[(Z)-amino(hydroxyimino)methyl]phenyl}amino)pyrimidin-4-yl]imidazo[1,2-a]pyridin-2-yl}phenyl)-2,6-difluorobenzamide;

N-(3-{3-[2-({3-[(Z)-amino(hydroxyimino)methyl]phenyl}amino)pyrimidin-4-yl]imidazo[1,2-a]pyridin-2-yl}phenyl)-2-thien-2-ylacetamide;

N-{3-[3-(2-{[3-(2-amino-2-oxoethyl)phenyl]amino}pyrimidin-4-yl)imidazo[1,2-a]pyridin-2-yl]phenyl}-2,6-difluorobenzamide;

N-{3-[3-(2-{[3-(2-amino-2-oxoethyl)phenyl]amino}pyrimidin-4-yl)imidazo[1,2-a]pyridin-2-yl]phenyl}-2-thien-2-ylacetamide;

N-{3-[3-(2-{[3-(2-amino-2-oxoethyl)phenyl]amino}pyrimidin-4-yl)imidazo[1,2-a]pyridin-2-yl]phenyl}-2-phenylacetamide;

isopropyl (3-{[4-(2-{3-[(phenylacetyl)amino]phenyl}imidazo[1,2-a]pyridin-3-yl)pyrimidin-2-yl]amino}phenyl)acetate;

N-{3-[3-(2-{[4-(1-ethylpiperidin-4-yl)phenyl]amino}pyrimidin-4-yl)imidazo[1,2-a]pyridin-2-yl]phenyl}-2-thien-2-ylacetamide;

N-{3-[3-(2-{[4-(1-ethylpiperidin-4-yl)phenyl]amino}pyrimidin-4-yl)imidazo[1,2-a]pyridin-2-yl]phenyl}-2,6-difluorobenzamide;

N-{3-[3-(2-{[4-(4-ethylpiperazin-1-yl)phenyl]amino}pyrimidin-4-yl)imidazo[1,2-a]pyridin-2-yl]phenyl}-2-(1-methyl-1H-imidazol-4-yl)acetamide;

2,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

3,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

2,3-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

N-{3-[3-(2-{[4-(4-ethylpiperazin-1-yl)phenyl]amino}pyrimidin-4-yl)imidazo[1,2-a]pyridin-2-yl]phenyl}-2-thien-3-ylacetamide;

N-{3-[3-(2-{[4-(4-ethylpiperazin-1-yl)phenyl]amino}pyrimidin-4-yl)imidazo[1,2-a]pyridin-2-yl]phenyl}-2-(3-methylisoxazol-5-yl)acetamide;

N-[3-(3-{2-[(1-acetyl-2,3-dihydro-1H-indol-5-yl)amino]pyrimidin-4-yl}imidazo[1,2-a]pyridin-2-yl)phenyl]-2,6-difluorobenzamide;

N-[3-(3-{2-[(1-acetyl-2,3-dihydro-1H-indol-5-yl-amino]pyrimidin-4-yl}imidazo[1,2-a]pyridin-2-yl)phenyl]-2-phenylacetamide;

N-[3-(3-{2-[(1-acetyl-2,3-dihydro-1H-indol-5-yl)amino]pyrimidin-4-yl}imidazo[1,2-a]pyridin-2-yl)phenyl]-2-thien-2-ylacetamide;

2,4-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

2-chloro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

2-fluoro-N-[3-(3-{2-[(2-methyl-1,2,3,4-tetrahydro isoquinolin-7-yl)amino]pyrimidin-4-yl}imidazo[1,2-a]pyridin-2-yl)phenyl]benzamide;

N-{3-[3-(2-{[4-(1-ethylpyrrolidin-3-yl)phenyl]amino}pyrimidin-4-yl)imidazo[1,2-a]pyridin-2-yl]phenyl}-2-thien-2-ylacetamide;

N-{3-[3-(2-{[3-(1-ethylpyrrolidin-3-yl)phenyl]amino}pyrimidin-4-yl)imidazo[1,2-a]pyridin-2-yl]phenyl}-2-thien-2-ylacetamide;

N-{3-[3-(2-{[4-(1-acetylpyrrolidin-3-yl)phenyl]amino}pyrimidin-4-yl)imidazo[1,2-a]pyridin-2-yl]phenyl}-2-thien-2-ylacetamide;

N-{3-[3-(2-{[3-(1-acetylpyrrolidin-3-yl)phenyl]amino}pyrimidin-4-yl)imidazo[1,2— a]pyridin-2-yl]phenyl}-2-thien-2-ylacetamide;

N-{3-[3-(2-{[3-(1-acetylpyrrolidin-3-yl)phenyl]amino}pyrimidin-4-yl)imidazo[1,2-a]pyridin-2-yl]phenyl}-2,6-difluorobenzamide;

N-[3-(3-{2-[(2-ethyl-2,3-dihydro-1H-isoindol-5-yl)amino]
pyrimidin-4-yl}imidazo[1,2-a]pyridin-2-yl)phenyl]-2-
thien-2-ylacetamide;
N-[3-(3-{2-[(2-ethyl-2,3-dihydro-1H-isoindol-5-yl)amino]
pyrimidin-4-yl}imidazo[1,2-a]pyridin-2-yl)phenyl]-2,6-
difluorobenzamide;
N-[3-(3-{2-[(2-ethyl-2,3-dihydro-1H-isoindol-5-yl)amino]
pyrimidin-4-yl}imidazo[1,2-a]pyridin-2-yl)phenyl]-2-
phenylacetamide;
N-{3-[3-(2-{[2-(dimethylamino)-2,3-dihydro-1H-inden-5-
yl]amino}pyrimidin-4-yl)imidazo[1,2-a]pyridin-2-yl]
phenyl}-2-thien-2-ylacetamide;
N-{3-[3-(2-{[2-(dimethylamino)-2,3-dihydro-1H-inden-5-
yl]amino}pyrimidin-4-yl)imidazo[1,2-a]pyridin-2-yl]
phenyl}-2,6-difluorobenzamide;
N-{3-[3-(2-{[2-(dimethylamino)-2,3-dihydro-1H-inden-5-
yl]amino}pyrimidin-4-yl)imidazo[1,2-a]pyridin-2-yl]
phenyl}-2-phenylacetamide;
2,6-difluoro-N-methyl-N-[3-(3-{2-[(2-methyl-1,2,3,4-tet-
rahydroisoquinolin-7-yl)amino]pyrimidin-4-yl}imidazo
[1,2-a]pyridin-2-yl)phenyl]benzamide;
2,6-difluoro-N-{3-[3-(2-{[4-(2-pyrrolidin-1-ylethyl)phenyl]
amino}pyrimidin-4-yl)imidazo[1,2-a]pyridin-2-yl]
phenyl}benzamide;
4-methyl-N-{3-[3-(2-{[4-(2-pyrrolidin-1-ylethyl)phenyl]
amino}pyrimidin-4-yl)imidazo[1,2-a]pyridin-2-yl]
phenyl}thiophene-2-carboxamide;
2-phenyl-N-{3-[3-(2-{[4-(2-pyrrolidin-1-ylethyl)phenyl]
amino}pyrimidin-4-yl)imidazo[1,2-a]pyridin-2-yl]
phenyl}acetamide;
N-{3-[3-(2-{[4-(2-pyrrolidin-1-ylethyl)phenyl]
amino}pyrimidin-4-yl)imidazo[1,2-a]pyridin-2-yl]phe-
nyl}-2-thien-2-ylacetamide;
5-methyl-N-[3-(3-{2-[(2-methyl-1,2,3,4-tetrahydroiso-
quinolin-7-yl)amino]pyrimidin-4-yl}imidazo[1,2-a]pyri-
din-2-yl)phenyl]thiophene-2-carboxamide;
N-[3-(3-{2-[(2-methyl-1,2,3,4-tetrahydro isoquinolin-7-yl)
amino]pyrimidin-4-yl}imidazo[1,2-a]pyridin-2-yl)phe-
nyl]thiophene-2-carboxamide;
4-methyl-N-[3-(3-{2-[(2-methyl-1,2,3,4-tetrahydroiso-
quinolin-7-yl)amino]pyrimidin-4-yl}imidazo[1,2-a]pyri-
din-2-yl)phenyl]thiophene-2-carboxamide;
2,5-dichloro-N-[3-(3-{2-[(2-methyl-1,2,3,4-tetrahydroiso-
quinolin-7-yl)amino]pyrimidin-4-yl}imidazo[1,2-a]pyri-
din-2-yl)phenyl]thiophene-3-carboxamide;
5-chloro-N-[3-(3-{2-[(2-methyl-1,2,3,4-tetrahydroisoquino-
lin-7-yl)amino]pyrimidin-4-yl}imidazo[1,2-a]pyridin-2-
yl)phenyl]thiophene-2-carboxamide;
3-methyl-N-[3-(3-{2-[(2-methyl-1,2,3,4-tetrahydroiso-
quinolin-7-yl)amino]pyrimidin-4-yl}imidazo[1,2-a]pyri-
din-2-yl)phenyl]thiophene-2-carboxamide;
N-[3-(3-{2-[(2-methyl-1,2,3,4-tetrahydroisoquinolin-7-yl)
amino]pyrimidin-4-yl}imidazo[1,2-a]pyridin-2-yl)phe-
nyl]-1-benzothiophene-2-carboxamide;
N-{3-[3-(2-{[2-(methoxyacetyl)-1,2,3,4-tetrahydroiso-
quinolin-7-yl]amino}pyrimidin-4-yl)imidazo[1,2-a]pyri-
din-2-yl]phenyl}-2-thien-2-ylacetamide;
N-{3-[3-(2-{[4-(1-acetylpyrrolidin-3-yl)phenyl]
amino}pyrimidin-4-yl)imidazo[1,2-a]pyridin-2-yl]phe-
nyl}-2,6-difluorobenzamide;
N-{3-[3-(2-{[2-(3-methoxypropanoyl)-1,2,3,4-tetrahy-
droisoquinolin-7-yl]amino}pyrimidin-4-yl)imidazo[1,2-
a]pyridin-2-yl]phenyl}-2-thien-2-ylacetamide;
N-[3-(3-{2-[(2-methyl-1,2,3,4-tetrahydroisoquinolin-7-yl)
amino]pyrimidin-4-yl}imidazo[1,2-a]pyridin-2-yl)phe-
nyl]thiophene-3-carboxamide;
N-(2-fluorophenyl)-3-(3-{2-[(2-methyl-1,2,3,4-tetrahy-
droisoquinolin-7-yl)amino]pyrimidin-4-yl}imidazo[1,2-
a]pyridin-2-yl)benzamide;
3-(3-{2-[(2-methyl-1,2,3,4-tetrahydroisoquinolin-7-yl)
amino]pyrimidin-4-yl}imidazo[1,2-a]pyridin-2-yl)-N-
(thien-2-ylmethyl)benzamide;
2-chloro-N-{3-[3-(2-{[4-(4-ethylpiperazin-1-yl)phenyl]
amino}pyrimidin-4-yl)imidazo[1,2-a]pyridin-2-yl]
phenyl}benzamide;
2-chloro-N-{3-[3-(2-{[4-(4-ethylpiperazin-1-yl)phenyl]
amino}pyrimidin-4-yl)imidazo[1,2-a]pyridin-2-yl]phe-
nyl}-6-fluorobenzamide;
N-{3-[3-(2-{[4-(4-ethylpiperazin-1-yl)phenyl]
amino}pyrimidin-4-yl)imidazo[1,2-a]pyridin-2-yl]phe-
nyl}-2-(5-methylthien-2-yl)acetamide;
N-{3-[3-(2-{[4-(4-ethylpiperazin-1-yl)phenyl]
amino}pyrimidin-4-yl)imidazo[1,2-a]pyridin-2-yl]phe-
nyl}-2-(2-methyl-1,3-thiazol-5-yl)acetamide;
N-{3-[3-(2-{[4-(4-isopropylpiperazin-1-yl)phenyl]
amino}pyrimidin-4-yl)imidazo[1,2-a]pyridin-2-yl]phe-
nyl}-2-thien-2-ylacetamide;
N-{3-[3-(2-{[4-(4-isopropylpiperazin-1-yl)phenyl]
amino}pyrimidin-4-yl)imidazo[1,2-a]pyridin-2-yl]phe-
nyl}-2-phenylacetamide;
2,6-difluoro-N-{3-[3-(2-{[4-(4-isopropylpiperazin-1-yl)
phenyl]amino}pyrimidin-4-yl)imidazo[1,2-a]pyridin-2-
yl]phenyl}benzamide;
2-chloro-N-{3-[3-(2-{[4-(4-isopropylpiperazin-1-yl)phe-
nyl]amino}pyrimidin-4-yl)imidazo[1,2-a]pyridin-2-yl]
phenyl}benzamide;
N-[3-(3-{2-[(1-methyl-2,3-dihydro-1H-indol-5-yl)amino]
pyrimidin-4-yl}imidazo[1,2-a]pyridin-2-yl)phenyl]-2-
phenylacetamide;
2,6-difluoro-N-{3-[3-(2-{[3-(pyrrolidin-1-ylmethyl)phenyl]
amino}pyrimidin-4-yl)imidazo[1,2-a]pyridin-2-yl]phe-
nyl)benzamide;
2-phenyl-N-{3-[3-(2-{[3-(pyrrolidin-1-ylmethyl)phenyl]
amino}pyrimidin-4-yl)imidazo[1,2-a]pyridin-2-yl]
phenyl}acetamide;
N-{3-[3-(2-{[3-(pyrrolidin-1-ylmethyl)phenyl]
amino}pyrimidin-4-yl)imidazo[1,2-a]pyridin-2-yl]phe-
nyl}-2-thien-2-ylacetamide;
2,6-difluoro-N-{3-[3-(2-{[3-(1H-imidazol-1-ylmethyl)phe-
nyl]amino}pyrimidin-4-yl)imidazo[1,2-a]pyridin-2-yl]
phenyl}benzamide;
N-{3-[3-(2-{[3-(1H-imidazol-1-ylmethyl)phenyl]
amino}pyrimidin-4-yl)imidazo[1,2-a]pyridin-2-yl]phe-
nyl)-2-phenylacetamide;
N-{3-[3-(2-{[3-(1H-imidazol-1-ylmethyl)phenyl]
amino}pyrimidin-4-yl)imidazo[1,2-a]pyridin-2-yl]phe-
nyl}-2-thien-2-ylacetamide;
2,6-difluoro-N-{3-[3-(2-{[3-(1H-1,2,4-triazol-1-ylmethyl)
phenyl]amino}pyrimidin-4-yl)imidazo[1,2-a]pyridin-2-
yl]phenyl benzamide;
5-methyl-N-{3-[3-(2-{[3-(1H-1,2,4-triazol-1-ylmethyl)phe-
nyl]amino}pyrimidin-4-yl)imidazo[1,2-a]pyridin-2-yl]
phenyl}thiophene-2-carboxamide;
2-phenyl-N-{3-[3-(2-{[3-(1H-1,2,4-triazol-1-ylmethyl)phe-
nyl]amino}pyrimidin-4-yl)imidazo[1,2-a]pyridin-2-yl]
phenyl}acetamide;
2-thien-2-yl-N-{3-[3-(2-{[3-(1H-1,2,4-triazol-1-ylmethyl)
phenyl]amino}pyrimidin-4-yl)imidazo[1,2-a]pyridin-2-
yl]phenyl}acetamide;
2,6-difluoro-N-[3-(3-{2-[(1-methyl-2,3-dihydro-1H-indol-
5-yl)amino]pyrimidin-4-yl}imidazo[1,2-a]pyridin-2-yl)
phenyl]benzamide;

5-methyl-N-[3-(3-{2-[(1-methyl-2,3-dihydro-1H-indol-5-yl)amino]pyrimidin-4-yl}imidazo[1,2-a]pyridin-2-yl)phenyl]thiophene-2-carboxamide;

N-[3-(3-{2-[(1-methyl-2,3-dihydro-1H-indol-5-yl)amino]pyrimidin-4-yl}imidazo[1,2-a]pyridin-2-yl)phenyl]-2-thien-2-ylacetamide;

2,6-difluoro-N-(3-{3-[2-({3-[(3-hydroxypyrrolidin-1-yl)methyl]phenyl}amino)pyrimidin-4-yl]imidazo[1,2-a]pyridin-2-yl}phenyl)benzamide;

N-(3-{3-[2-({3-[(3-hydroxypyrrolidin-1-yl)methyl]phenyl}amino)pyrimidin-4— yl]imidazo[1,2-a]pyridin-2-yl}phenyl)-2-phenylacetamide;

N-(3-{3-[2-({3-[(3-hydroxypyrrolidin-1-yl)methyl]phenyl}amino)pyrimidin-4-yl]imidazo[1,2-a]pyridin-2-yl}phenyl)-2-thien-2-ylacetamide;

N-[3-(3-{2-[(2-ethyl-2,3-dihydro-1H-isoindol-5-yl)amino]pyrimidin-4-yl}imidazo[1,2-a]pyridin-2-yl)phenyl]-2-thien-3-ylacetamide;

2-chloro-N-[3-(3-{2-[(2-ethyl-2,3-dihydro-1H-isoindol-5-yl)amino]pyrimidin-4-yl}imidazo[1,2-a]pyridin-2-yl)phenyl]benzamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-3-ylacetamide;

2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}benzamide;

2,6-difluoro-N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}benzamide;

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-2-thien-2-ylacetamide;

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-2-phenylacetamide;

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl)-N'-phenylurea;

N-{3-[3-(2-{[4-(4-ethylpiperazin-1-yl)phenyl]amino}pyrimidin-4-yl)imidazo[1,2-a]pyridin-2-yl]phenyl}-2-(1,3-thiazol-5-yl)acetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-N'-phenylurea;

N-{3-[3-(2-{[4-(2,7-diazaspiro[4.4]non-2-yl)phenyl]amino}pyrimidin-4-yl)imidazo[1,2-a]pyridin-2-yl]phenyl}-2-thien-2-ylacetamide;

N-{3-[3-(2-{[4-(7-acetyl-2,7-diazaspiro[4.4]non-2-yl)phenyl]amino}pyrimidin-4-yl)imidazo[1,2-a]pyridin-2-yl]phenyl}-2,6-difluorobenzamide;

tert-butyl 7-(4-{[4-(2-{3-[(2,6-difluorobenzoyl)amino]phenyl}imidazo[1,2-a]pyridin-3-yl)pyrimidin-2-yl]amino}phenyl)-2,7-diazaspiro[4.4]nonane-2-carboxylate;

tert-butyl 7-(4-{[4-(2-{3-[(thien-2-ylacetyl)amino]phenyl}imidazo[1,2-a]pyridin-3-yl)pyrimidin-2-yl]amino}phenyl)-2,7-diazaspiro[4.4]nonane-2-carboxylate;

N-(3-{3-[2-({3-[2-(dimethylamino)ethyl]phenyl}amino)pyrimidin-4-yl]imidazo[1,2-a]pyridin-2-yl}phenyl)-5-methylthiophene-2-carboxamide;

N-(2,6-difluorophenyl)-N'-(3-{3-[2-({3-[2-(dimethylamino)ethyl]phenyl}amino)pyrimidin-4-yl]imidazo[1,2-a]pyridin-2-yl}phenyl)urea;

N-{3-[3-(2-{[4-(2,7-diazaspiro[4.4]non-2-yl)phenyl]amino}pyrimidin-4-yl)imidazo[1,2-a]pyridin-2-yl]phenyl}-2,6-difluorobenzamide;

3-[3-(2-{[4-(4-ethylpiperazin-1-yl)phenyl]amino}pyrimidin-4-yl)imidazo[1,2-a]pyridin-2-yl]-N-(2-fluorophenyl)benzamide;

3-[3-(2-{[4-(4-ethylpiperazin-1-yl)phenyl]amino}pyrimidin-4-yl)imidazo[1,2-a]pyridin-2-yl]-N-phenylbenzamide;

N-benzyl-3-[3-(2-{[4-(4-ethylpiperazin-1-yl)phenyl]amino}pyrimidin-4-yl)imidazo[1,2-a]pyridin-2-yl]benzamide;

2,6-difluoro-N-{3-[3-(2-{[3-(2-pyrrolidin-1-ylethoxy)phenyl]amino}pyrimidin-4-yl)imidazo[1,2-a]pyridin-2-yl]phenyl}benzamide;

2,6-difluoro-N-{3-[3-(2-{[3-(tetrahydrofuran-2-ylmethoxy)phenyl]amino}pyrimidin-4-yl)imidazo[1,2-a]pyridin-2-yl]phenyl}benzamide;

2-chloro-N-{3-[3-(2-{[3-(tetrahydrofuran-2-ylmethoxy)phenyl]amino}pyrimidin-4-yl)imidazo[1,2-a]pyridin-2-yl]phenyl}benzamide;

N-{3-[3-(2-{[3-(tetrahydrofuran-2-ylmethoxy)phenyl]amino}pyrimidin-4-yl)imidazo[1,2-a]pyridin-2-yl]phenyl}thiophene-2-carboxamide;

N-{3-[3-(2-{[3-(tetrahydrofuran-2-ylmethoxy)phenyl]amino}pyrimidin-4-yl)imidazo[1,2-a]pyridin-2-yl]phenyl}-2-thien-2-ylacetamide;

N-{3-[3-(2-{[3-(tetrahydrofuran-2-ylmethoxy)phenyl]amino}pyrimidin-4-yl)imidazo[1,2-a]pyridin-2-yl]phenyl}-N'-thien-2-ylurea;

2,6-difluoro-N-{3-[3-(2-{[3-(tetrahydrofuran-3-yloxy)phenyl]amino}pyrimidin-4-yl)imidazo[1,2-a]pyridin-2-yl]phenyl)benzamide;

2-chloro-N-{3-[3-(2-{[3-(tetrahydrofuran-3-yloxy)phenyl]amino}pyrimidin-4-yl)imidazo[1,2-a]pyridin-2-yl]phenyl}benzamide;

N-{3-[3-(2-{[3-(tetrahydrofuran-3-yloxy)phenyl]amino}pyrimidin-4-yl)imidazo[1,2-a]pyridin-2-yl]phenyl}-2-thien-2-ylacetamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-1,3-thiazole-2-carboxamide;

N-[3-(3-{2-[(2-methyl-1,2,3,4-tetrahydro isoquinolin-7-yl)amino]pyrimidin-4-yl}imidazo[1,2-a]pyridin-2-yl)phenyl]-1,3-thiazole-5-carboxamide;

4-bromo-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;

4-bromo-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-3-carboxamide;

N-{3-[3-(2-{[3-(tetrahydrofuran-3-yloxy)phenyl]amino}pyrimidin-4-yl)imidazo[1,2-a]pyridin-2-yl]phenyl}-N'-thien-2-ylurea;

N-(3-{3-[2-({3-[(dimethylamino)sulfonyl]-4-methoxyphenyl}amino)pyrimidin-4-yl]imidazo[1,2-a]pyridin-2-yl}phenyl)-2,6-difluorobenzamide;

N-(3-{3-[2-({3-[(dimethylamino)sulfonyl]-4-methoxyphenyl}amino)pyrimidin-4-yl]imidazo[1,2-a]pyridin-2-yl}phenyl)-2-thien-2-ylacetamide;

N-(3-{3-[2-{2-({4-(dimethylamino)piperidin-1-yl]phenyl}amino)pyrimidin-4-yl]imidazo[1,2-a]pyridin-2-yl}phenyl)-2-thien-2-ylacetamide;

N-(3-{3-[2-({4-[4-(dimethylamino)piperidin-1-yl]phenyl}amino)pyrimidin-4-yl]imidazo[1,2-a]pyridin-2-yl}phenyl)-2,6-difluorobenzamide;

N-(3-{3-[2-({4-[4-(dimethylamino)piperidin-1-yl]phenyl}amino)pyrimidin-4-yl]imidazo[1,2-a]pyridin-2-yl}phenyl)-2-phenylacetamide;

2-chloro-N-(3-{3-[2-({4-[4-(dimethylamino)piperidin-1-yl]phenyl}amino)pyrimidin-4-yl]imidazo[1,2-a]pyridin-2-yl}phenyl)benzamide;

N-(3-{3-[2-({4-[4-(dimethylamino)piperidin-1-yl]phenyl}amino)pyrimidin-4-yl]imidazo[1,2-a]pyridin-2-yl}phenyl)thiophene-2-carboxamide;

N-(3-{3-[2-({4-[4-(dimethylamino)piperidin-1-yl]phenyl}amino)pyrimidin-4-yl]imidazo[1,2-a]pyridin-2-yl}phenyl)-4-methylthiophene-2-carboxamide;

1-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]-1H-pyrazole-3-carboxamide;

2-chloro-N-(3-{3-[2-({4-[2-(dimethylamino)ethyl]phenyl}amino)pyrimidin-4-yl]imidazo[1,2-a]pyridin-2-yl}phenyl)-3-fluorobenzamide;

N-(3-{3-[2-({4-[2-(dimethylamino)ethyl]phenyl}amino)pyrimidin-4-yl]imidazo[1,2-a]pyridin-2-yl}phenyl)-2-fluorobenzamide;

2-chloro-N-(3-{3-[2-({4-[2-(dimethylamino)ethyl]phenyl}amino)pyrimidin-4-yl]imidazo[1,2-a]pyridin-2-yl}phenyl)benzamide;

N-(3-{3-[2-({4-[2-(dimethylamino)ethyl]phenyl}amino)pyrimidin-4-yl]imidazo[1,2-a]pyridin-2-yl}phenyl)-2,3-difluorobenzamide;

N-(3-{3-[2-({4-[2-(dimethylamino)ethyl]phenyl}amino)pyrimidin-4-yl]imidazo[1,2-a]pyridin-2-yl}phenyl)-2,5-difluorobenzamide;

N-(3-{3-[2-({4-[2-(dimethylamino)ethyl]phenyl}amino)pyrimidin-4-yl]imidazo[1,2-a]pyridin-2-yl}phenyl)-3,5-difluorobenzamide;

N-(3-{3-[2-({4-[2-(dimethylamino)ethyl]phenyl}amino)pyrimidin-4-yl]imidazo[1,2-a]pyridin-2-yl}phenyl)-N'-phenylurea;

N-(3-{3-[2-({4-[1-(methoxyacetyl)piperidin-4-yl]phenyl}amino)pyrimidin-4-yl]imidazo[1,2-a]pyridin-2-yl}phenyl)-2-thien-2-ylacetamide;

2,6-difluoro-N-(3-{3-[2-({4-[1-(methoxyacetyl)piperidin-4-yl]phenyl}amino)pyrimidin-4-yl]imidazo[1,2-a]pyridin-2-yl}phenyl)benzamide;

N-(3-{3-[2-({3-[1-(methoxyacetyl)piperidin-4-yl]phenyl}amino)pyrimidin-4-yl]imidazo[1,2-a]pyridin-2-yl}phenyl)-2-thien-2-ylacetamide;

2,6-difluoro-N-(3-{3-[2-({3-[1-(methoxyacetyl)piperidin-4-yl]phenyl}amino)pyrimidin-4-yl]imidazo[1,2-a]pyridin-2-yl}phenyl)benzamide;

N-{3-[3-(2-{[4-(4-ethylpiperazin-1-yl)-3-fluorophenyl]amino}pyrimidin-4-yl)imidazo[1,2-a]pyridin-2-yl]phenyl}-2-thien-2-ylacetamide;

2-chloro-N-{3-[3-(2-{([4-(4-ethylpiperazin-1-yl)-3-fluorophenyl]amino}pyrimidin-4-yl)imidazo[1,2-a]pyridin-2-yl]phenyl}benzamide;

N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)-2-thien-2-ylacetamide;

N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)-2-thien-3-ylacetamide;

2,6-difluoro-N-(3-{3-[2-({4-[1-(2-hydroxy-2-methylpropyl)piperidin-4-yl]phenyl}amino)pyrimidin-4-yl]imidazo[1,2-a]pyridin-2-yl)phenyl)benzamide;

2-chloro-N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)benzamide;

N-(3-{3-[2-({3-[(N,N-dimethylglycyl)amino]phenyl}amino)pyrimidin-4-yl]imidazo[1,2-a]pyridin-2-yl}phenyl)-2,6-difluorobenzamide;

2-chloro-N-(3-{3-[2-({3-[(N,N-dimethylglycyl)amino]phenyl}amino)pyrimidin-4-yl]imidazo[1,2-a]pyridin-2-yl}phenyl)benzamide;

N-(3-{3-[2-({3-[(N,N-dimethylglycyl)amino]phenyl}amino)pyrimidin-4-yl]imidazo[1,2-a]pyridin-2-yl}phenyl)thiophene-2-carboxamide;

$N^2,N^2$-dimethyl-$N^1$-(3-{[4-(2-{3-[(thien-2-ylacetyl)amino]phenyl}imidazo[1,2-a]pyridin-3-yl)pyrimidin-2-yl]amino}phenyl)glycinamide;

2,6-difluoro-N-(3-{3-[2-({3-[(methoxyacetyl)amino]phenyl}amino)pyrimidin-4-yl]imidazo[1,2-a]pyridin-2-yl}phenyl)benzamide;

2-chloro-N-(3-{3-[2-({3-[(methoxyacetyl)amino]phenyl}amino)pyrimidin-4-yl]imidazo[1,2-a]pyridin-2-yl}phenyl)benzamide;

N-(3-{3-[2-({3-[(2-methoxyacetyl)amino]phenyl}amino)pyrimidin-4-yl]imidazo[1,2-a]pyridin-2-yl}phenyl)thiophene-2-carboxamide;

2-methoxy-N-(3-{[4-(2-{3-[(thien-2-ylacetyl)amino]phenyl}imidazo[1,2-a]pyridin-3-yl)pyrimidin-2-yl]amino}phenyl)acetamide;

2-methoxy-N-[3-({[4-(2-{3-{[(thien-2-ylamino)carbonyl]amino}phenyl}imidazo[1,2-a]pyridin-3-yl]pyrimidin-2-yl]amino)phenyl]acetamide;

N-(3-{3-[2-({4-[3-(dimethylamino)pyrrolidin-1-yl]phenyl}amino)pyrimidin-4-yl]imidazo[1,2-a]pyridin-2-yl}phenyl)-2,6-difluorobenzamide;

2-chloro-N-(3-{3-[2-({4-[3-(dimethylamino)pyrrolidin-1-yl]phenyl}amino)pyrimidin-4-yl]imidazo[1,2-a]pyridin-2-yl}phenyl)benzamide;

N-(3-{3-[2-({4-[3-(dimethylamino)pyrrolidin-1-yl]phenyl}amino)pyrimidin-4-yl]imidazo[1,2-a]pyridin-2-yl}phenyl)thiophene-2-carboxamide;

N-(3-{3-[2-({4-[3-(dimethylamino)pyrrolidin-1-yl]phenyl}amino)pyrimidin-4-yl]imidazo[1,2-a]pyridin-2-yl}phenyl)-2-thien-2-ylacetamide;

N-(3-{3-[2-({4-[3-(dimethylamino)pyrrolidin-1-yl]phenyl}amino)pyrimidin-4-yl]imidazo[1,2-a]pyridin-2-yl}phenyl)-N'-thien-2-ylurea;

2,6-difluoro-N-(3-{3-[2-({3-[2-(methylamino)-2-oxoethyl]phenyl}amino)pyrimidin-4-yl]imidazo[1,2-a]pyridin-2-yl}phenyl)benzamide;

N-(3-{3-[2-({3-[2-(methylamino)-2-oxoethyl]phenyl}amino)pyrimidin-4-yl]imidazo[1,2-a]pyridin-2-yl}phenyl)-2-phenylacetamide;

N-(3-{3-[2-({3-[2-(methylamino)-2-oxoethyl]phenyl}amino)pyrimidin-4-yl]imidazo[1,2-a]pyridin-2-yl}phenyl)-2-thien-2-ylacetamide;

N-(3-{3-[2-({3-[2-(dimethylamino)-2-oxoethyl]phenyl}amino)pyrimidin-4-yl]imidazo[1,2-a]pyridin-2-yl}phenyl)-2,6-difluorobenzamide;

N-(3-{3-[2-({3-[2-(dimethylamino)-2-oxoethyl]phenyl}amino)pyrimidin-4-yl]imidazo[1,2-a]pyridin-2-yl}phenyl)-2-phenylacetamide;

N-(3-{3-[2-({3-[2-(dimethylamino)-2-oxoethyl]phenyl}amino)pyrimidin-4-yl]imidazo[1,2-a]pyridin-2-yl}phenyl-2-thien-2-ylacetamide;

N-{3-[3-(2-{[2-(dimethylamino)-2,3-dihydro-1H-inden-5-yl]amino}pyrimidin-4-yl)imidazo[1,2-a]pyridin-2-yl]phenyl}thiophene-2-carboxamide;

N-{3-[3-(2-{[2-(dimethylamino)-2,3-dihydro-1H-inden-5-yl]amino}pyrimidin-4-yl)imidazo[1,2-a]pyridin-2-yl]phenyl)-4-methylthiophene-2-carboxamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-5-methylthiophene-2-carboxamide;

2-chloro-N-(3-{3-[2-({4-[2-(dimethylamino)ethyl]phenyl}amino)pyrimidin-4-yl]imidazo[1,2-a]pyridin-2-yl}phenyl)-5-fluorobenzamide;

2,6-difluoro-N-(3-{3-[2-({4-[2-(methylamino)ethyl]phenyl}amino)pyrimidin-4-yl]imidazo[1,2-a]pyridin-2-yl}phenyl)benzamide;

2-chloro-N-(3-{3-[2-({4-[2-(methylamino)ethyl]phenyl}amino)pyrimidin-4-yl]imidazo[1,2-a]pyridin-2-yl}phenyl)benzamide;

N-(3-{3-[2-({4-[2-(methylamino)ethyl]phenyl}amino)pyrimidin-4-yl]imidazo[1,2-a]pyridin-2-yl}phenyl)-2-phenylacetamide;

N-(3-{3-[2-({4-[2-(methylamino)ethyl]phenyl}amino)pyrimidin-4-yl]imidazo[1,2-a]pyridin-2-yl}phenyl)-2-thien-2-ylacetamide;

N-(3-{3-[2-({4-[2-(methylamino)ethyl]phenyl}amino)pyrimidin-4-yl]imidazo[1,2-a]pyridin-2-yl)phenyl)-N'-phenylurea;

N-(3-{3-[2-({4-[4-(dimethylamino)piperidin-1-yl]phenyl}amino)pyrimidin-4-yl]imidazo[1,2-a]pyridin-2-yl}phenyl)-2-methylbenzamide;

N-(3-{3-[2-({4-[4-(dimethylamino)piperidin-1-yl]phenyl}amino)pyrimidin-4-yl]imidazo[1,2-a]pyridin-2-yl}phenyl)-2-thien-3-ylacetamide;

N-(3-{3-[2-({4-[2-(dimethylamino)ethyl]phenyl}amino)-5-fluoropyrimidin-4-yl]imidazo[1,2-a]pyridin-2-yl}phenyl)-2,6-difluorobenzamide;

N-[3-(3-{2-[(4-piperidin-4-ylphenyl)amino]pyrimidin-4-yl}imidazo[1,2-a]pyridin-2-yl)phenyl]-2-thien-3-ylacetamide;

2-chloro-N-[3-(3-{2-[(4-piperidin-4-ylphenyl)amino]pyrimidin-4-yl}imidazo[1,2-a]pyridin-2-yl)phenyl]benzamide;

N-[3-(3-{2-[(3-piperidin-4-ylphenyl)amino]pyrimidin-4-yl}imidazo[1,2-a]pyridin-2-yl)phenyl]-2-thien-3-ylacetamide;

N-[3-(3-{2-[(3-piperidin-4-ylphenyl)amino]pyrimidin-4-yl}imidazo[1,2-a]pyridin-2-yl)phenyl]-2-thien-2-ylacetamide;

2-chloro-N-[3-(3-{2-[(3-piperidin-4-ylphenyl)amino]pyrimidin-4-yl}imidazo[1,2-a]pyridin-2-yl)phenyl]benzamide;

N-[3-(3-{2-[(3-piperidin-4-ylphenyl)amino]pyrimidin-4-yl}imidazo[1,2-a]pyridin-2-yl)phenyl]thiophene-2-carboxamide;

2-methyl-N-[3-(3-{2-[(3-piperidin-4-ylphenyl)amino]pyrimidin-4-yl}imidazo[1,2-a]pyridin-2-yl)phenyl]benzamide;

N-[3-(3-{2-[(3-piperidin-4-ylphenyl)amino]pyrimidin-4-yl}imidazo[1,2-a]pyridin-2-yl)phenyl]indoline-1-carboxamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2,6-difluorobenzamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2-thien-2-ylacetamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}thiophene-2-carboxamide;

N-[3-(3-{2-[(4-pyrrolidin-3-ylphenyl)amino]pyrimidin-4-yl}imidazo[1,2-a]pyridin-2-yl)phenyl]-2-thien-3-ylacetamide;

N-[3-(3-{2-[(4-pyrrolidin-3-ylphenyl)amino]pyrimidin-4-yl}imidazo[1,2-a]pyridin-2-yl)phenyl]-2-thien-2-ylacetamide;

2-chloro-N-[3-(3-(2-[(4-pyrrolidin-3-ylphenyl)amino]pyrimidin-4-yl}imidazo[1,2-a]pyridin-2-yl)phenyl]benzamide;

2,3-difluoro-N-[3-(3-{2-[(4-pyrrolidin-3-ylphenyl)amino]pyrimidin-4-yl}imidazo[1,2-a]pyridin-2-yl)phenyl]benzamide;

2,5-difluoro-N-[3-(3-{2-[(4-pyrrolidin-3-ylphenyl)amino]pyrimidin-4-yl}imidazo[1,2-a]pyridin-2-yl)phenyl]benzamide;

2-methyl-N-[3-(3-{2-[(4-pyrrolidin-3-ylphenyl)amino]pyrimidin-4-yl}imidazo[1,2-a]pyridin-2-yl)phenyl]benzamide;

2,6-dimethyl-N-[3-(3-{2-[(4-pyrrolidin-3-ylphenyl)amino]pyrimidin-4-yl}imidazo[1,2-a]pyridin-2-yl)phenyl]benzamide;

N-[3-(3-{2-[(4-pyrrolidin-3-ylphenyl)amino]pyrimidin-4-yl}imidazo[1,2-a]pyridin-2-yl)phenyl]thiophene-2-carboxamide;

N-(3-{3-[2-({4-[4-(dimethylamino)piperidin-1-yl]phenyl}amino)pyrimidin-4-yl]imidazo[1,2-a]pyridin-2-yl}phenyl)-2,3-difluorobenzamide;

N-(3-{3-[2-({4-[4-(dimethylamino)piperidin-1-yl]phenyl}amino)pyrimidin-4-yl]imidazo[1,2-a]pyridin-2-yl}phenyl)-2,5-difluorobenzamide;

2-chloro-N-(3-{3-[2-({4-[4-(dimethylamino)piperidin-1-yl]phenyl}amino)pyrimidin-4-yl]imidazo[1,2-a]pyridin-2-yl}phenyl)-5-fluorobenzamide;

N-(3-{3-[2-({4-[4-(dimethylamino)piperidin-1-yl]phenyl}amino)pyrimidin-4-yl]imidazo[1,2-a]pyridin-2-yl}phenyl)indoline-1-carboxamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-2,3-difluorobenzamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-2,5-difluorobenzamide;

2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}-5-fluorobenzamide;

N-(3-[3-(2-{[2-(dimethylamino)-2,3-dihydro-1H-inden-5-yl]amino}pyrimidin-4-yl)imidazo[1,2-a]pyridin-2-yl]phenyl}indoline-1-carboxamide;

N-(3-{3-[2-({3-[(dimethylamino)methyl]-4-methoxyphenyl}amino)pyrimidin-4-yl]imidazo[1,2-a]pyridin-2-yl}phenyl)-2,6-difluorobenzamide;

N-(3-{3-[2-({3-[(dimethylamino)methyl]-4-methoxyphenyl}amino)pyrimidin-4-yl]imidazo[1,2-a]pyridin-2-yl}phenyl)-2,3-difluorobenzamide;

N-(3-{3-[2-({3-[(dimethylamino)methyl]-4-methoxyphenyl}amino)pyrimidin-4-yl]imidazo[1,2-a]pyridin-2-yl}phenyl)-2-thien-2-ylacetamide;

N-(3-{3-[2-({3-[(dimethylamino)methyl]-4-methoxyphenyl}amino)pyrimidin-4-yl]imidazo[1,2-a]pyridin-2-yl}phenyl)-N'-thien-2-ylurea;

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]thiophene-2-carboxamide;

2,6-difluoro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide;

2-chloro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide;

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]-N'-thien-2-ylurea;

N-[3-(3-{2-[(3-{2-[(3S)-3-fluoropyrrolidin-1-yl]
ethyl}phenyl)amino]pyrimidin-4-yl}imidazo[1,2-a]pyridin-2-yl)phenyl]-N'-thien-3-ylurea;

N-[3-(3-{2-[(4-pyrrolidin-3-ylphenyl)amino]pyrimidin-4-yl}imidazo[1,2-a]pyridin-2-yl)phenyl]indoline-1-carboxamide;

N-ethyl-N-phenyl-N'-[3-(3-{2-[(4-pyrrolidin-3-ylphenyl)amino]pyrimidin-4-yl}imidazo[1,2-a]pyridin-2-yl)phenyl]urea;

N-[3-(3-{2-[(4-pyrrolidin-3-ylphenyl)amino]pyrimidin-4-yl}imidazo[1,2-a]pyridin-2-yl)phenyl]-1-benzothiophene-7-carboxamide;

N-(3-{3-[2-({4-[2-(dimethylamino)ethyl]phenyl}amino)-5-fluoropyrimidin-4-yl]imidazo[1,2-a]pyridin-2-yl}phenyl)-2-thien-2-ylacetamide;

2,6-difluoro-N-{3-[3-(2-{[4-(4-hydroxypiperidin-1-yl)phenyl]amino}pyrimidin-4-yl)imidazo[1,2-a]pyridin-2-yl]phenyl}benzamide;

2-chloro-N-{3-[3-(2-{[4-(4-hydroxypiperidin-1-yl)phenyl]amino}pyrimidin-4-yl)imidazo[1,2-a]pyridin-2-yl]phenyl}benzamide;

N-{3-[3-(2-{[4-(4-hydroxypiperidin-1-yl)phenyl]amino}pyrimidin-4-yl)imidazo[1,2-a]pyridin-2-yl]phenyl}thiophene-2-carboxamide;

N-{3-[3-(2-{[4-(4-hydroxypiperidin-1-yl)phenyl]amino}pyrimidin-4-yl)imidazo[1,2-a]pyridin-2-yl]phenyl}-2-thien-2-ylacetamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,6-difluorobenzamide;

2-chloro-N-[3-(3-{2-[(4-{2-[(N,N-dimethylglycyl)amino]ethyl}phenyl)amino]pyrimidin-4-yl}imidazo[1,2-a]pyridin-2-yl)phenyl]benzamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]thiophene-2-carboxamide;

$N^2,N^2$-dimethyl-$N^1$-[2-(4-{[4-(2-{3-[(thien-2-ylacetyl)amino]phenyl}imidazo[1,2-a]pyridin-3-yl)pyrimidin-2-yl]amino}phenyl)ethyl]glycinamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,3-difluorobenzamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,5-difluorobenzamide;

$N^2,N^2$-dimethyl-$N^1$-[2-(4-{[4-(2-{3-[(phenylacetyl)amino]phenyl}imidazo[1,2-a]pyridin-3-yl)pyrimidin-2-yl]amino}phenyl)ethyl]glycinamide;

2,6-difluoro-N-[3-(3-{2-[(4-{2-[(methoxyacetyl)amino]ethyl}phenyl)amino]pyrimidin-4-yl}imidazo[1,2-a]pyridin-2-yl)phenyl]benzamide;

2-methoxy-N-[2-(4-{[4-(2-{3-[(thien-2-ylacetyl)amino]phenyl}imidazo[1,2-a]pyridin-3-yl)pyrimidin-2-yl]amino}phenyl)ethyl]acetamide;

N-(3-{3-[2-({4-[2-(4-aminopiperidin-1-yl)ethyl]phenyl}amino)pyrimidin-4-yl]imidazo[1,2-a]pyridin-2-yl}phenyl)thiophene-2-carboxamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2,6-difluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-chlorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-fluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2,3-difluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2,5-difluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-chloro-5-fluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-phenylacetamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-thien-2-ylacetamide;

N-(3-{3-[2-({4-[2-(4-aminopiperidin-1-yl)ethyl]phenyl}amino)pyrimidin-4-yl]imidazo[1,2-a]pyridin-2-yl}phenyl)-N'-phenylurea;

N-(3-{3-[2-({4-[2-(4-aminopiperidin-1-yl)ethyl]phenyl}amino)pyrimidin-4-yl]imidazo[1,2-a]pyridin-2-yl}phenyl)indoline-1-carboxamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-chloro-3-fluorobenzamide;

N-[2-(4-{[4-(2-{3-[(2-thien-2-ylacetyl)amino]phenyl}imidazo[1,2-a]pyridin-3-yl)pyrimidin-2-yl]amino}phenyl)ethyl]cyclopropanecarboxamide;

N-[3-(3-{2-[(4-{2-(cyclopropylcarbonyl)amino]ethyl}phenyl)amino]pyrimidin-4-yl}imidazo[1,2-a]pyridin-2-yl)phenyl]-2,6-difluorobenzamide;

2-chloro-N-[3-(3-{2-[(4-{2-[(cyclopropylcarbonyl)amino]ethyl}phenyl)amino)]pyrimidin-4-yl}imidazo[1,2-a]pyridin-2-yl)phenyl]benzamide;

N-[3-(3-{2-(4-{2-[(cyclopropylcarbonyl)amino]ethyl}phenyl)amino]pyrimidin-4-yl}imidazo[1,2-a]pyridin-2-yl)phenyl]thiophene-2-carboxamide;

2,6-difluoro-N-[3-(3-{2-[(4-{2-[(methylsulfonyl)amino]ethyl}phenyl)amino]pyrimidin-4-yl}imidazo[1,2-a]pyridin-2-yl)phenyl]benzamide;

2-chloro-N-[3-(3-{2-[(4-{2-[(methylsulfonyl)amino]ethyl}phenyl)amino]pyrimidin-4-yl}imidazo[1,2-a]pyridin-2-yl)phenyl]benzamide;

N-[3-(3-{2-[(4-{2-[(methylsulfonyl)amino]ethyl}phenyl)amino]pyrimidin-4-yl}imidazo[1,2-a]pyridin-2-yl)phenyl]thiophene-2-carboxamide;

N-[3-(3-{2-[(4-{2-[(methylsulfonyl)amino]ethyl}phenyl)amino]pyrimidin-4-yl}imidazo[1,2-a]pyridin-2-yl)phenyl]-2-thien-2-ylacetamide;

2-chloro-N-[3-(3-{2-[(4-{2-[(methoxyacetyl)amino]ethyl}phenyl)amino]pyrimidin-4-yl}imidazo[1,2-a]pyridin-2-yl)phenyl]benzamide;

N-[3-(3-{2-[(4-{2-[(2-methoxyacetyl)amino]ethyl}phenyl)amino]pyrimidin-4-yl}imidazo[1,2-a]pyridin-2-yl)phenyl]thiophene-2-carboxamide;

N-(2,6-difluorophenyl)-3-[3-(2-{[4-(4-ethylpiperazin-1-yl)phenyl]amino}pyrimidin-4-yl)imidazo[1,2-a]pyridin-2-yl]benzamide;

2,6-difluoro-N-[3-(3-{2-[(4-{2-[(2-hydroxyethyl)(methyl)amino]ethyl}phenyl)amino]pyrimidin-4-yl}imidazo[1,2-a]pyridin-2-yl)phenyl]benzamide;

2-chloro-N-[3-(3-{2-[(4-{2-[(2-hydroxyethyl)(methyl)amino]ethyl}phenyl)amino]pyrimidin-4-yl}imidazo[1,2-a]pyridin-2-yl)phenyl]benzamide;

3-{3-[2-({4-[2-(dimethylamino)ethyl]phenyl}amino)pyrimidin-4-yl]imidazo[1,2-a]pyridin-2-yl}-N-phenylbenzamide;

3-{3-[2-({4-[2-(dimethylamino)ethyl]phenyl}amino)pyrimidin-4-yl]imidazo[1,2-a]pyridin-2-yl}-N-(2-fluorophenyl)benzamide;

3-{3-[2-({4-[2-(dimethylamino)ethyl]phenyl}amino)pyrimidin-4-yl]imidazo[1,2-a]pyridin-2-yl}-N-(3-fluorophenyl)benzamide;

3-{3-[2-({4-[2-(dimethylamino)ethyl]phenyl}amino)pyrimidin-4-yl)imidazo[1,2-a]pyridin-2-yl}-N-(4-fluorophenyl)benzamide;

N-cyclopentyl-3-{3-[2-({4-[2-(dimethylamino)ethyl]phenyl}amino)pyrimidin-4-yl]imidazo[1,2-a]pyridin-2-yl}benzamide;

N-cyclohexyl-3-{3-[2-({4-[2-(dimethylamino)ethyl]phenyl}amino)pyrimidin-4-yl]imidazo[1,2-a]pyridin-2-yl}benzamide;

N-{4-[2-(dimethylamino)ethyl]phenyl}-4-{2-[3-(piperidin-1-ylcarbonyl)phenyl]imidazo[1,2-a]pyridin-3-yl}pyrimidin-2-amine;

3-{3-[2-({4-[2-(dimethylamino)ethyl]phenyl}amino)pyrimidin-4-yl]imidazo[1,2-a]pyridin-2-yl}-N-(2-methylphenyl)benzamide;

N-(2-chlorophenyl)-3-{3-[2-({4-[2-(dimethylamino)ethyl]phenyl}amino)pyrimidin-4-yl]imidazo[1,2-a]pyridin-2-yl}benzamide;

3-{3-[2-({4-[2-(dimethylamino)ethyl]phenyl}amino)pyrimidin-4-yl]imidazo[1,2-a]pyridin-2-yl}-N-(2-methoxyphenyl)benzamide;

N-{4-[2-(dimethylamino)ethyl]phenyl}-4-{2-[3-(morpholin-4-ylcarbonyl)phenyl]imidazo[1,2-a]pyridin-3-yl}pyrimidin-2-amine;

N-[3-(3-{2-[(3-pyrrolidin-3-ylphenyl)amino]pyrimidin-4-yl}imidazo[1,2-a]pyridin-2-yl)phenyl]indoline-1-carboxamide;

N-[3-(3-{2-[(3-pyrrolidin-3-ylphenyl)amino]pyrimidin-4-yl}imidazo[1,2-a]pyridin-2-yl)phenyl]-3,4-dihydroquinoline-1(2H)-carboxamide;

N-[3-(3-{2-[(3-pyrrolidin-3-ylphenyl)amino]pyrimidin-4-yl}imidazo[1,2-a]pyridin-2-yl)phenyl]-3,4-dihydroisoquinoline-2(1H)-carboxamide;

4-{2-[3-(2,3-dihydro-1H-indol-1-ylcarbonyl)phenyl]imidazo[1,2-a]pyridin-3-yl}-N-{4-[2-(dimethylamino)ethyl]phenyl}pyrimidin-2-amine;

4-{2-[3-(1,3-dihydro-2H-isoindol-2-ylcarbonyl)phenyl]imidazo[1,2-a]pyridin-3-yl}-N-{4-[2-(dimethylamino)ethyl]phenyl}pyrimidin-2-amine;

N-{4-[2-(dimethylamino)ethyl]phenyl}-4-{2-[3-(pyrrolidin-1-ylcarbonyl)phenyl]imidazo[1,2-a]pyridin-3-yl}pyrimidin-2-amine;

N-{3-[3-(2-{[4-(1-acetylazetidin-3-yl)phenyl]amino}pyrimidin-4-yl)imidazo[1,2-a]pyridin-2-yl]phenyl}-2-chlorobenzamide;

N-{3-[3-(2-{[4-(1-acetylazetidin-3-yl)phenyl]amino}pyrimidin-4-yl)imidazo[1,2-a]pyridin-2-yl]phenyl}-2-thien-3-ylacetamide;

N-cyclohexyl-N'-(3-{3-[2-({3-[2-(dimethylamino)ethyl]phenyl}amino)pyrimidin-4-yl]imidazo[1,2-a]pyridin-2-yl}phenyl)urea;

N-(sec-butyl)-N'-(3-{3-[2-({3-[2-(dimethylamino)ethyl]phenyl}amino)pyrimidin-4-yl]imidazo[1,2-a]pyridin-2-yl}phenyl)urea;

N-(tert-butyl)-N'-(3-{3-[2-({3-[2-(dimethylamino)ethyl]phenyl}amino)pyrimidin-4-yl]imidazo[1,2-a]pyridin-2-yl}phenyl)urea;

N-(3-{3-[2-({3-[2-(dimethylamino)ethyl]phenyl}amino)pyrimidin-4-yl]imidazo[1,2-a]pyridin-2-yl}phenyl)-N'-isopropylurea;

N-cyclopentyl-N'-(3-{3-[2-({3-[2-(dimethylamino)ethyl]phenyl}amino)pyrimidin-4-yl]imidazo[1,2-a]pyridin-2-yl}phenyl)urea;

N-(3-{3-[2-({3-[2-(dimethylamino)ethyl]phenyl}amino)pyrimidin-4-yl]imidazo[1,2-a]pyridin-2-yl}phenyl)-N'-[(1S)-1,2-dimethylpropyl]urea;

N-(3-{3-[2-({3-[2-(dimethylamino)ethyl]phenyl}amino)pyrimidin-4-yl]imidazo[1,2-a]pyridin-2-yl}phenyl)-N'-[(1S)-1-phenylethyl]urea;

N-(3-{3-[2-({3-[2-(dimethylamino)ethyl]phenyl}amino)pyrimidin-4-yl]imidazo[1,2-a]pyridin-2-yl}phenyl)-N'-(3,5-dimethylisoxazol-4-yl)urea;

N-(3-{3-[2-({3-[2-(dimethylamino)ethyl]phenyl}amino)pyrimidin-4-yl]imidazo[1,2-a]pyridin-2-yl}phenyl)-N'-thien-2-ylurea;

N-(3-{3-[2-({3-[2-(dimethylamino)ethyl]phenyl}amino)pyrimidin-4-yl]imidazo[1,2-a]pyridin-2-yl}phenyl)-N'-(2-methylphenyl)urea;

N-(3-{3-[2-({3-[2-(dimethylamino)ethyl]phenyl}amino)pyrimidin-4-yl]imidazo[1,2-a]pyridin-2-yl}phenyl)indoline-1-carboxamide;

N-(3-{3-[2-({3-[2-(dimethylamino)ethyl]phenyl}amino)pyrimidin-4-yl]imidazo[1,2-a]pyridin-2-yl}phenyl)piperidine-1-carboxamide;

N-(3-{3-[2-({3-[2-(dimethylamino)ethyl]phenyl}amino)pyrimidin-4-yl]imidazo[1,2-a]pyridin-2-yl}phenyl)-N'-thien-3-ylurea;

N-(3-{3-[2-({3-[2-(dimethylamino)ethyl]phenyl}amino)pyrimidin-4-yl]imidazo[1,2-a]pyridin-2-yl}phenyl)morpholine-4-carboxamide;

2,3-dimethyl-N-[3-(3-{2-[(4-pyrrolidin-3-ylphenyl)amino]pyrimidin-4-yl}imidazo[1,2-a]pyridin-2-yl)phenyl]benzamide;

N-[3-(3-{2-[(4-pyrrolidin-2-ylphenyl)amino]pyrimidin-4-yl}imidazo[1,2-a]pyridin-2-yl)phenyl]-2-thien-2-ylacetamide;

2-chloro-N-[3-(3-{2-[(4-pyrrolidin-2-ylphenyl)amino]pyrimidin-4-yl}imidazo[1,2-a]pyridin-2-yl)phenyl]benzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,6-difluorobenzamide;

2-chloro-N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]benzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]thiophene-2-carboxamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2-thien-2-ylacetamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,3-difluorobenzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,5-difluorobenzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2-phenylacetamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-N'-phenylurea;

N-{3-[3-(2-{[4-(1-acetylazetidin-3-yl)phenyl]amino}pyrimidin-4-yl)imidazo[1,2-a]pyridin-2-yl]phenyl}indoline-1-carboxamide;

N-{3-[3-(2-{[2-(dimethylamino)-2,3-dihydro-1H-inden-5-yl]amino}pyrimidin-4-yl)imidazo[1,2-a]pyridin-2-yl]phenyl)-2,3-dimethylbenzamide;

N-(3-{3-[2-({4-[4-(dimethylamino)piperidin-1-yl]phenyl}amino)pyrimidin-4-yl]imidazo[1,2-a]pyridin-2-yl}phenyl)-2,3-dimethylbenzamide;

2-amino-N-[3-(3-{2-[(4-pyrrolidin-3-ylphenyl)amino]pyrimidin-4-yl}imidazo[1,2-a]pyridin-2-yl)phenyl]-2-thien-2-ylacetamide;

2-amino-N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-2-ylacetamide;

2-amino-N-(3-{3-[2-({4-[4-(dimethylamino)piperidin-1-yl]phenyl}amino)pyrimidin-4-yl]imidazo[1,2-a]pyridin-2-yl}phenyl)-2-thien-2-ylacetamide;

N-(3-{3-[2-({3-[2-(dimethylamino)ethyl]phenyl}amino)pyrimidin-4-yl]imidazo[1,2-a]pyridin-2-yl}phenyl)-N'-[(1R)-1-phenylethyl]urea;

N-(3-{3-[2-({3-[2-(dimethylamino)ethyl]phenyl}amino)pyrimidin-4-yl]imidazo[1,2-a]pyridin-2-yl}phenyl)-N'-(2-phenylcyclopropyl)urea;

N'-(3-{3-[2-({3-[2-(dimethylamino)ethyl]phenyl}amino)pyrimidin-4-yl]imidazo[1,2-a]pyridin-2-yl}phenyl)-N,N-dimethylurea;

N'-(3-{3-[2-({3-[2-(dimethylamino)ethyl]phenyl}amino)pyrimidin-4-yl]imidazo[1,2-a]pyridin-2-yl}phenyl)-N-methyl-N-phenylurea;

N-(3-{3-[2-({3-[2-(dimethylamino)ethyl]phenyl}amino)pyrimidin-4-yl]imidazo[1,2-a]pyridin-2-yl}phenyl)pyrrolidine-1-carboxamide;

N-{3-[3-(2-({3-[2-(dimethylamino)ethyl]phenyl}amino)pyrimidin-4-yl]-7-(trifluoromethyl)imidazo[1,2-a]pyridin-2-yl]phenyl}-2,6-difluorobenzamide;

N-{3-[3-(2-({3-[2-(dimethylamino)ethyl]phenyl}amino)pyrimidin-4-yl]-7-(trifluoromethyl)imidazo[1,2-a]pyridin-2-yl]phenyl}-2-thien-2-ylacetamide;

N-{3-[3-(2-({3-[2-(dimethylamino)ethyl]phenyl}amino)pyrimidin-4-yl]-7-(trifluoromethyl)imidazo[1,2-a]pyridin-2-yl]phenyl}-N'-phenylurea;

N-{3-[3-(2-({3-[2-(dimethylamino)ethyl]phenyl}amino)pyrimidin-4-yl]-7-(trifluoromethyl)imidazo[1,2-a]pyridin-2-yl]phenyl}-N'-[(1S)-1-phenylethyl]urea;

N-{3-[3-(2-{[4-(1-ethylpyrrolidin-2-yl)phenyl]amino}pyrimidin-4-yl)imidazo[1,2-a]pyridin-2-yl]phenyl}-2-thien-2-ylacetamide;

2-chloro-N-{3-[3-(2-{[4-(1-ethylpyrrolidin-2-yl)phenyl]amino}pyrimidin-4-yl)imidazo[1,2-a]pyridin-2-yl]phenyl}benzamide;

N-{3-[3-(2-{[4-(1-isopropylpyrrolidin-3-yl)phenyl]amino}pyrimidin-4-yl)imidazo[1,2-a]pyridin-2-yl]phenyl}-2-thien-3-ylacetamide;

N-{3-[3-(2-{[4-(1-isopropylpyrrolidin-3-yl)phenyl]amino}pyrimidin-4-yl)imidazo[1,2-a]pyridin-2-yl]phenyl}-2-thien-2-ylacetamide;

2-chloro-N-{3-[3-(2-{[4-(1-isopropylpyrrolidin-3-yl)phenyl]amino}pyrimidin-4-yl)imidazo[1,2-a]pyridin-2-yl]phenyl}benzamide;

2,3-difluoro-N-{3-[3-(2-{[4-(1-isopropylpyrrolidin-3-yl)phenyl]amino}pyrimidin-4-yl)imidazo[1,2-a]pyridin-2-yl]phenyl}benzamide;

N-{3-[3-(2-{[4-(1-isopropylpyrrolidin-3-yl)phenyl]amino}pyrimidin-4-yl)imidazo[1,2-a]pyridin-2-yl]phenyl)-N'-[(1S)-1-phenylethyl]urea;

N-(2-fluorophenyl)-3-{3-[2-({3-[2-(4-hydroxypiperidin-1-yl)ethyl]phenyl}amino)pyrimidin-4-yl]imidazo[1,2-a]pyridin-2-yl}benzamide;

3-{3-[2-({3-[2-(4-hydroxypiperidin-1-yl)ethyl]phenyl}amino)pyrimidin-4-yl]imidazo[1,2-a]pyridin-2-yl}-N-phenylbenzamide;

N'-{3-[3-(2-{[4-(1-isopropylpyrrolidin-3-yl)phenyl]amino}pyrimidin-4-yl)imidazo[1,2-a]pyridin-2-yl]phenyl}-N,N-dimethylurea;

N'-{3-[3-(2-{[4-(1-isopropylpyrrolidin-3-yl)phenyl]amino}pyrimidin-4-yl)imidazo[1,2-a]pyridin-2-yl]phenyl}-N-methyl-N-phenylurea;

3-{3-[2-({3-[2-(4-hydroxypiperidin-1-yl)ethyl]phenyl}amino)pyrimidin-4-yl]imidazo[1,2-a]pyridin-2-yl}-N-thien-2-ylbenzamide;

N-(3-{3-[2-({3-[2-(dimethylamino)ethyl]phenyl}amino)pyrimidin-4-yl]-8-fluoroimidazo[1,2-a]pyridin-2-yl}phenyl)-2,6-difluorobenzamide;

N-(3-{3-[2-({3-[2-(dimethylamino)ethyl]phenyl}amino)pyrimidin-4-yl]-8-fluoroimidazo[1,2-a]pyridin-2-yl}phenyl)-2-phenylacetamide;

N-(3-{3-[2-({3-[2-(dimethylamino)ethyl]phenyl}amino)pyrimidin-4-yl]-8-fluoroimidazo[1,2-a]pyridin-2-yl}phenyl)-2-thien-2-ylacetamide;

N-(3-{3-[2-({3-[2-(dimethylamino)ethyl]phenyl}amino)pyrimidin-4-yl)-8-fluoroimidazo[1,2-a]pyridin-2-yl}phenyl)-N'-phenylurea;

N-{3-[3-(2-{[4-(1-isopropylpyrrolidin-3-yl)phenyl]amino}pyrimidin-4-yl)imidazo[1,2-a]pyridin-2-yl]phenyl}-3,4-dihydroquinoline-1(2H)-carboxamide;

N-benzyl-N'-{3-[3-(2-{[4-(1-isopropylpyrrolidin-3-yl)phenyl]amino}pyrimidin-4-yl)imidazo[1,2-a]pyridin-2-yl]phenyl}-N-methylurea;

N-benzyl-N-(2-cyanoethyl)-N'-{3-[3-(2-{[4-(1-isopropylpyrrolidin-3-yl)phenyl]amino}pyrimidin-4-yl)imidazo[1,2-a]pyridin-2-yl]phenyl}urea;

N'-{3-[3-(2-{[4-(1-isopropylpyrrolidin-3-yl)phenyl]amino}pyrimidin-4-yl)imidazo[1,2-a]pyridin-2-yl]phenyl)-N-methyl-N-[(1S)-1-phenylethyl]urea;

N-{3-[3-(2-{[4-(1-isopropylpyrrolidin-3-yl)phenyl]amino}pyrimidin-4-yl)imidazo[1,2-a]pyridin-2-yl]phenyl}-5-methylindoline-1-carboxamide;

N-(3-{3-[2-({3-[2-(dimethylamino)ethyl]phenyl}amino)pyrimidin-4-yl]-6-fluoroimidazo[1,2-a]pyridin-2-yl}phenyl)-N'-phenylurea;

N-(3-{3-[2-({3-[2-(dimethylamino)ethyl]phenyl}amino)pyrimidin-4-yl]-6-fluoroimidazo[1,2-a]pyridin-2-yl}phenyl)-2-thien-2-ylacetamide;

N-(3-{3-[2-({3-[2-(dimethylamino)ethyl]phenyl}amino)pyrimidin-4-yl]-6-fluoroimidazo[1,2-a]pyridin-2-yl}phenyl)-2,6-difluorobenzamide;

N-{3-[3-(2-({3-[2-(dimethylamino)ethyl]phenyl}amino)pyrimidin-4-yl]-6-(trifluoromethyl)imidazo[1,2-a]pyridin-2-yl]phenyl}-N'-phenylurea;

N-{3-[3-(2-({3-[2-(dimethylamino)ethyl]phenyl}amino)pyrimidin-4-yl]-6-(trifluoromethyl)imidazo[1,2-a]pyridin-2-yl]phenyl}-2-thien-2-ylacetamide;

N-{3-[3-(2-({3-[2-(dimethylamino)ethyl]phenyl}amino)pyrimidin-4-yl]-6-(trifluoromethyl)imidazo[1,2-a]pyridin-2-yl]phenyl}-2,6-difluorobenzamide; and salts, esters, amides, prodrugs and salts of esters, amides and prodrugs thereof.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "C1-C6 alkyl" as used herein, means a straight or branched chain hydrocarbon containing from 1 to 6 carbon atoms.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means phenyl, a bicyclic aryl or a tricyclic aryl. The bicyclic aryl is naphthyl, or a phenyl fused to a cycloalkyl, or a phenyl fused to a cycloalkenyl, or a phenyl fused to a monocyclic heteroaryl ring as defined herein, or a phenyl fused to a monocyclic heterocycle as defined herein. The bicyclic aryl of the present invention must be attached to the parent molecular moiety through any available carbon atom contained within the phenyl ring. Representative examples of the bicyclic aryl include, but are not limited to, 2,3-dihydro-1,4-benzodioxin-5-yl, 2,3-dihydro-1,4-benzodioxin-6-yl, 3,4-dihydro-2H-1,5-benzodioxepin-6-yl, dihydroindenyl, indenyl, indol-4-yl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, and tetrahydrophenanthrenyl.

The term "cycloalkenyl" as used herein, means a monocyclic, bicyclic, tricyclic, spirocyclic, or bridged ring system containing from 3 to 12 carbons and containing at least one carbon-carbon double bond formed by the removal of two hydrogens. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring system which is fused to another monocyclic cycloalkyl ring as defined herein, a monocyclic aryl ring as defined herein, a monocyclic heterocycle as defined herein or a monocyclic heteroaryl as defined herein. The bicyclic ring systems of the present invention must be appended to the parent molecular moiety through an available carbon atom within the cycloalkenyl ring. Representative examples of bicyclic ring systems include, but are not limited to, 4,5-dihydro-benzo[1,2,5]oxadiazole, 3a, 4, 5, 6, 7, 7a-hexahydro-1H-indenyl, 1, 2, 3, 4, 5, 6-hexahydro-pentalenyl, 1, 2, 3, 4, 4a, 5, 6, 8a-octahydro-pentalenyl.

The term "cycloalkyl" as used herein, means a monocyclic, bicyclic, tricyclic, spirocyclic, or bridged ring system containing a saturated cyclic hydrocarbon group containing from 3 to 12 carbon atoms. Examples of monocyclic ring systems include cyclopropyl, cyclobutyl, cyclopentyl, cyclohexyl, cycloheptyl, and cyclooctyl. Bicyclic cycloalkyl groups of the present invention are exemplified by a monocyclic cycloalkyl ring fused to another monocyclic cycloalkyl ring, or a monocyclic cycloalkyl ring fused cycloalkenyl, or a monocyclic cycloalkyl ring fused to a phenyl ring, or a monocyclic cycloalkyl ring fused to a monocyclic heteroaryl ring as defined herein, or a monocyclic cycloalkyl ring fused to a monocyclic heterocycle as defined herein. The bicyclic cycloalkyl ring systems of the present invention must be appended to the parent molecular moiety through an available carbon atom within the monocycloalkyl ring.

The term "heteroaryl," as used herein, means a monocyclic heteroaryl, a bicyclic heteroaryl, or a tricyclic heteroaryl. The monocyclic heteroaryl is a 5 or 6 membered ring containing at least one heteroatom independently selected from O, N, or S. The 5 membered ring contains two double bonds may contain one, two, three or four heteroatoms. The 6 membered ring contains three double bonds may contain one, two, three or four heteroatoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a monocyclic aryl ring as defined herein, a monocyclic cycloalkyl ring as defined herein, a monocyclic cycloalkenyl ring as defined herein, another monocyclic heteroaryl or a monocyclic heterocycle ring as defined herein. The bicyclic heteroaryl ring systems of the present invention must be appended to the parent molecular moiety through an available carbon atom within the heteroaryl ring. The bicyclic heteroaryl is connected to the parent molecular moiety through any carbon atom or any nitrogen atom contained within the bicyclic heteroaryl. Representative examples of bicyclic heteroaryl include, but are not limited to, benzofuranyl, benzoxadiazolyl, 1,3-benzothiazolyl, benzimidazolyl, benzodioxolyl, benzothiophenyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl.

The term "heterocycle" or "heterocyclic" or "heterocyclyl" as used herein, refers to a monocyclic, bicyclic, tricyclic, spirocyclic, or bridged ring system that contains at least one heteroatom. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, isoindoline-1,3-dione, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is defined as a monocyclic heterocycle fused to a phenyl group, a cycloalkylgroup as defined herein, a cycloalkenyl group as defined herein, another monocyclic heterocycle group as defined herein, or a spirocyclic ring wherein one carbon atom of the monocyclic heterocycle is bridged by two ends of an alkylene chain. The bicyclic heterocycle of the present invention is connected to the parent molecular moiety through any carbon atom or any nitrogen atom contained within the heterocyclic ring. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 3,4-dihydro-1H-isochromen-4-yl, 2,3-dihydro-1H-indolyl, succinmidyl, and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The term "phenyl," as used herein, means a monovalent radical formed by removal of a hydrogen atom from benzene.

The term "spiroalkyl," as used herein, means a spirocyclic cycloalkyl as defined herein.

The term, "spirocyclic," as used herein, means a ring system wherein one atom is common to two different rings.

The term "heterospiroalkyl," as used herein, means a spirocyclic heterocyclyl as defined herein.

The term, "bridged," as used herein, means a ring system wherein the rings share at least two common non-adjacent atoms.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydropyranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760.

Compounds of this invention may contain asymmetrically substituted carbon atoms in the R or S configuration, in which the terms "R" and "S" are as defined by the IUPAC 1974

Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Compounds of this invention can exist in an isotopic form containing one or more atoms having an atomic mass or mass number different from the atomic mass or mass number most abundantly found in nature. Isotopes of atoms such as hydrogen, carbon, phosphorous, sulfur fluorine, chlorine, and iodine include, but are not limited to, $^2$H, $^3$H, $^{14}$C, $^{32}$P, $^{35}$S, $^{18}$F, $^{36}$Cl, and $^{125}$I, respectively. Compounds that contain other isotopes of these and/or other atoms are within the scope of this invention. Compounds containing tritium ($^3$H) and $^{14}$C radioisotopes are preferred in general for their ease in preparation and detectability for radiolabeled compounds. Isotopically labeled compounds of this invention can be prepared by the general methods well known to persons having ordinary skill in the art. Such isotopically labeled compounds can be conveniently prepared by carrying out the procedures disclosed in the Examples and Schemes herein by substituting a readily available isotopically labeled reagent for a non-isotopically labeled reagent.

One embodiment of this invention, therefore, pertains to compounds that inhibit protein kinases and have Formula I

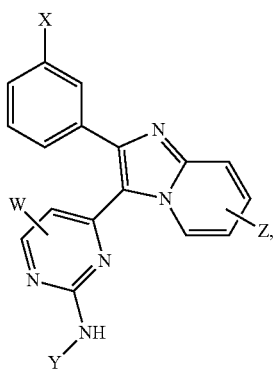

(I)

or a pharmaceutically acceptable salt thereof, wherein
W is alkyl, H, F, Cl, Br or I;
X is $C(O)R^1$, $C(O)NHR^1$, $C(O)N(R^1)_2$, $NHC(O)R^1$, $NR^1C(O)R^1$, $NHC(O)NHR^1$, $NHC(O)N(R^1)_2$, or $NR^1C(O)N(R^1)_2$;
wherein $R^1$ is $R^2$, $R^3$, $R^4$ or $R^5$;
$R^2$ is aryl;
$R^3$ is heteroaryl;
$R^4$ is cycloalkyl, cycloalkenyl, or heterocyclyl;

$R^5$ is C1-C6 alkyl; each of which is unsubstituted or substituted with one or two independently selected $R^6$, $NH_2$ or CN;
$R^6$ is $R^7$, $R^8$, or $R^9$;
$R^7$ is aryl;
$R^8$ is heteroaryl;
$R^9$ is cycloalkyl, cycloalkenyl, or heterocyclyl;
wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^1)_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;
$R^{10}$ is alkyl, alkenyl, alkynyl, aryl, heteroaryl, cycloalkyl, cycloalkenyl, or heterocyclyl;
Y is $R^{12}$ or $R^{13}$;
$R^{12}$ is aryl;
$R^{13}$ is heteroaryl;
Z is alkyl, H, $CF_3$, F, Cl, Br or I;
wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;
wherein each $R^{14}$ is $R^{15}$, $R^{16}$, $R^{17}$ or $R^{18}$;
$R^{15}$ is aryl;
$R^{16}$ is heteroaryl;
$R^{17}$ is cycloalkyl, cycloalkenyl, or heterocyclyl;
$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;
wherein each $R^{19}$ is $R^{20}$ or $R^{21}$;
$R^{20}$ is aryl, heteroaryl, cycloalkyl, cycloalkenyl, or heterocyclyl;
$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;
wherein each $R^{22}$ is alkyl, alkenyl, alkynyl, aryl, heteroaryl, cycloalkyl, cycloalkenyl, or heterocyclyl;
wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, C(N)N($R^{23}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, OR$^{29}$, SR$^{29}$, S(O)$_2$R$^{29}$, C(O)OH, NH$_2$, NHR$^{29}$N(R$^{29}$)$_2$, C(O)R$^{29}$, C(O)NH$_2$, C(O)NHR$^{29}$, C(O)N(R$^{29}$)$_2$, NHC(O)R$^{29}$, NR$^{29}$C(O)R$^{29}$, NHC(O)OR$^{29}$, NR$^{29}$C(O)OR$^{29}$, NHS(O)$_2$R$^{29}$, NR$^{29}$S(O)$_2$R$^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, OR$^{30}$, C(O)R$^{30}$, C(O)OR$^{30}$, OH, (O), C(O)OH, CN, CF$_3$, OCF$_3$, CF$_2$CF$_3$, F, Cl, Br or I; and $R^{30}$ is alkyl alkenyl, or alkynyl.

Another embodiment of this invention, therefore, pertains to compounds that inhibit protein kinases and have Formula I or a pharmaceutically acceptable salt thereof, wherein W is alkyl, H, F, Cl, Br or I;

X is C(O)R$^1$, NHC(O)R$^1$, NR$^1$C(O)R$^1$, NHC(O)NHR$^1$, NHC(O)N(R$^1$)$_2$, or NR$^1$C(O)N(R$^1$)$_2$;

wherein $R^1$ is $R^2$, $R^3$, $R^4$ or $R^5$;

$R^2$ is aryl;

$R^3$ is heteroaryl;

$R^4$ is cycloalkyl, cycloalkenyl, or heterocyclyl;

$R^5$ is C1-C6 alkyl; each of which is unsubstituted or substituted with one or two independently selected $R^6$, NH$_2$ or CN;

$R^6$ is $R^7$, $R^8$, or $R^9$;

$R^7$ is aryl;

$R^8$ is heteroaryl;

$R^9$ is cycloalkyl, cycloalkenyl, or heterocyclyl;

wherein the moieties represented by $R^2$, $R^3$, $R^4$, $R^7$, $R^8$, and $R^9$ are independently unsubstituted or substituted with one or two or three or four of independently selected, $R^{10}$, OR$^{10}$, SR$^{10}$, S(O)R$^{10}$, SO$_2$R$^{10}$, NH$_2$, NHR$^{10}$, N(R$^{10}$)$_2$, C(O)R$^{10}$, C(O)OR$^{10}$, C(O)NH$_2$, C(O)NHR$^{10}$, C(O)N(R$^{10}$)$_2$, C(NOH)NH$_2$, NHC(O)R$^{10}$, NR$^{10}$C(O)R$^{10}$, NHSO$_2$R$^{10}$, NR$^{10}$SO$_2$R$^{10}$, NHC(O)OR$^{10}$, NR$^{10}$C(O)OR$^{10}$, NHSO$_2$NH$_2$, NHSO$_2$NHR$^{10}$, NHSO$_2$N(R$^{10}$)$_2$, SO$_2$NH$_2$, SO$_2$NHR$^{10}$, SO$_2$N(R$^{10}$)$_2$, NHC(O)NH$_2$, NHC(O)NHR$^{10}$, NHC(O)N(R$^{10}$)$_2$, NR$^{10}$C(O)N(R$^{10}$)$_2$, NO$_2$, OH, (O), C(O)H, C(O)OH, CN, CF$_3$, OCF$_3$, CF$_2$CF$_3$, F, Cl, Br or I;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, CF$_3$, F, Cl, Br or I;

wherein the moieties represented by $R^{12}$ and $R^{13}$ are independently unsubstituted or substituted with one or two or three or four of independently selected, $R^{14}$, OR$^{14}$, SR$^{14}$, S(O)R$^{14}$, SO$_2$R$^{14}$, NH$_2$, NHR$^{14}$, N(R$^{14}$)$_2$, C(O)R$^{14}$, C(O)OR$^{14}$, C(O)NH$_2$, C(O)NHR$^{14}$, C(O)N(R$^{14}$)$_2$, C(NOH)NH$_2$, NHC(O)R$^{14}$, NR$^{14}$C(O)R$^{14}$, NHSO$_2$R$^{14}$, NR$^{14}$SO$_2$R$^{14}$, NHC(O)OR$^{14}$, NR$^{14}$C(O)OR$^{14}$, NHSO$_2$NH$_2$, NHSO$_2$NHR$^{14}$, NHSO$_2$N(R$^{14}$)$_2$, SO$_2$NH$_2$, SO$_2$NHR$^{14}$, SO$_2$N(R$^{14}$)$_2$, NHC(O)NH$_2$, NHC(O)NHR$^{14}$, NHC(O)N(R$^{14}$)$_2$, NR$^{14}$C(O)N(R$^{14}$)$_2$, NO$_2$, OH, (O), C(O)H, C(O)OH, CN, CF$_3$, OCF$_3$, CF$_2$CF$_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, OR$^{19}$, SR$^{19}$, S(O)$_2$R$^{19}$, NHS(O)$_2$R$^{19}$, C(O)OH, NH$_2$, NHR$^{19}$, N(R$^{19}$)$_2$, C(O)R$^{19}$, C(O)OR$^{19}$, C(O)NH$_2$, C(O)NHR$^{19}$, C(O)N(R$^{19}$)$_2$, NHC(O)R$^{19}$, NR$^{19}$C(O)R$^{19}$, NHC(O)OR$^{19}$, NR$^{19}$C(O)OR$^{19}$, OH, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, OR$^{22}$, C(O)OH, NH$_2$, NHR$^{22}$, N(R$^{22}$)$_2$, C(O)R$^{22}$, C(O)NH$_2$, C(O)NHR$^{22}$, C(O)N(R$^{22}$)$_2$, NHC(O)R$^{22}$, NR$^{22}$C(O)R$^{22}$, OH, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, OR$^{23}$, SR$^{23}$, S(O)R$^{23}$, SO$_2$R$^{23}$, C(O)R$^{23}$, CO(O)R$^{23}$, OC(O)R$^{23}$, OC(O)OR$^{23}$, NH$_2$, NHR$^{23}$, N(R$^{23}$)$_2$, NHC(O)R$^{23}$, NR$^{23}$C(O)R$^{23}$, NHS(O)$_2$R$^{23}$, NR$^{23}$S(O)$_2$R$^{23}$, NHC(O)OR$^{23}$, NR$^{23}$C(O)OR$^{23}$, NHC(O)NH$_2$, NHC(O)NHR$^{23}$, NHC(O)N(R$^{23}$)$_2$, NR$^{23}$C(O)NHR$^{23}$, NR$^{23}$C(O)N(R$^{23}$)$_2$, C(O)NH$_2$, C(O)NHR$^{23}$, C(O)N(R$^{23}$)$_2$, C(O)NHOH, C(O)NHOR$^{23}$, C(O)NHSO$_2$R$^{23}$, C(O)NR$^{23}$SO$_2$R$^{23}$, SO$_2$NH$_2$, SO$_2$NHR$^{23}$, SO$_2$N(R$^{23}$)$_2$, C(O)H, C(O)OH, C(N)NH$_2$, C(N)NHR$^{23}$, C(N)N(R$^{23}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, OR$^{29}$, SR$^{29}$, S(O)$_2$R$^{29}$, C(O)OH, NH$_2$, NHR$^{29}$N(R$^{29}$)$_2$, C(O)R$^{29}$, C(O)NH$_2$, C(O)NHR$^{29}$, C(O)N(R$^{29}$)$_2$, NHC(O)R$^{29}$, NR$^{29}$C(O)R$^{29}$, NHC(O)OR$^{29}$, NR$^{29}$C(O)OR$^{29}$, NHS(O)$_2$R$^{29}$, NR$^{29}$S(O)$_2$R$^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, OR$^{30}$, C(O)R$^{30}$, C(O)OR$^{30}$, OH, (O), C(O)OH, CN, CF$_3$, OCF$_3$, CF$_2$CF$_3$, F, Cl, Br or I; and $R^{30}$ is alkyl alkenyl, or alkynyl.

Another embodiment of this invention, therefore, pertains to compounds that inhibit protein kinases and have Formula I or a pharmaceutically acceptable salt thereof, wherein W is alkyl, H, F, Cl, Br or I;

X is C(O)R$^1$, C(O)NHR$^1$, C(O)N(R$^1$)$_2$, NHC(O)NHR$^1$, NHC(O)N(R$^1$)$_2$, or NR$^1$C(O)N(R$^1$)$_2$;

wherein $R^1$ is $R^2$, $R^3$, $R^4$ or $R^5$;

$R^2$ is aryl;

$R^3$ is heteroaryl;

$R^4$ is cycloalkyl, cycloalkenyl, or heterocyclyl;

$R^5$ is C1-C6 alkyl; each of which is unsubstituted or substituted with one or two independently selected $R^6$, NH$_2$ or CN;

$R^6$ is $R^7$, $R^8$, or $R^9$;

$R^7$ is aryl;
$R^8$ is heteroaryl;
$R^9$ is cycloalkyl, cycloalkenyl, or heterocyclyl;
  wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2O$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, $OH$, $(O)$, $C(O)H$, $C(O)OH$, $CN$, $CF_3$, $OCF_3$, $CF_2CF_3$, F, Cl, Br or I;
$R^{10}$ is alkyl, alkenyl, alkynyl, aryl, heteroaryl, cycloalkyl, cycloalkenyl, or heterocyclyl;
Y is $R^{12}$ or $R^{13}$;
$R^{12}$ is aryl;
$R^{13}$ is heteroaryl;
Z is alkyl, H, $CF_3$, F, Cl, Br or I;
  wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})^2$, $NO_2$, $OH$, $(O)$, $C(O)H$, $C(O)OH$, $CN$, $CF_3$, $OCF_3$, $CF_2CF_3$, F, Cl, Br or I;
  wherein each $R^{14}$ is $R^{15}$, $R^{16}$, $R^{17}$ or $R^{18}$;
$R^{15}$ is aryl;
$R^{16}$ is heteroaryl;
$R^{17}$ is cycloalkyl, cycloalkenyl, or heterocyclyl;
$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, $C(O)OH$, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, $OH$, F, Cl, Br or I;
  wherein each $R^{19}$ is $R^{20}$ or $R^{21}$;
$R^{20}$ is aryl, heteroaryl, cycloalkyl, cycloalkenyl, or heterocyclyl;
$R^{21}$ is alkyl, alkenyl or alkynyl; each of which is unsubstituted or substituted with one or two of independently selected $R^{22}$, $OR^{22}$, $C(O)OH$, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, $OH$, F, Cl, Br or I;
  wherein each $R^{22}$ is alkyl, alkenyl, alkynyl, aryl, heteroaryl, cycloalkyl, cycloalkenyl, or heterocyclyl;
  wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, $C(O)NHOH$, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, $C(O)H$, $C(O)OH$, $C(N)NH_2$, $C(N)NHR^{23}$, $C(N)N(R^{23})_2$, $CNOH$, $CNOCH_3$, $OH$, $(O)$, $CN$, $N_3$, $NO_2$, $CF_3$, $CF_2CF_3$, $OCF_3$, F, Cl, Br or I;
    wherein each $R^{23}$ is $R^{24}$, $R^{25}$, $R^{26}$, $R^{27}$ or $R^{28}$;
$R^{24}$ is spirocycloalkyl or spiroheterocycloalkyl;
$R^{25}$ is aryl;

$R^{26}$ is heteroaryl;
$R^{27}$ is cycloalkyl, cycloalkenyl, or heterocyclyl;
$R^{28}$ is alkyl, alkenyl or alkynyl; each of which is unsubstituted or substituted with one or two of independently selected $R^{29}$, $OR^{29}$, $SR^{29}$, $S(O)_2R^{29}$, $C(O)OH$, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, $OH$, $(O)$, F, Cl, Br or I;
  wherein each $R^{29}$ is alkyl, alkenyl or alkynyl each of which is unsubstituted or substituted with one or two of independently selected F, Cl, Br or I;
    wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, $OH$, $(O)$, $C(O)OH$, $CN$, $CF_3$, $OCF_3$, $CF_2CF_3$, F, Cl, Br or I; and
$R^{30}$ is alkyl alkenyl, or alkynyl.
Another embodiment of this invention, therefore, pertains to compounds that inhibit protein kinases and have Formula I or a pharmaceutically acceptable salt thereof, wherein
W is alkyl, H, F, Cl, Br or I;
X is $C(O)R^1$, $C(O)NHR^{1A}$, $C(O)N(R^1)_2$, $NHC(O)R^1$, $NR^1C(O)R^1$, $NHC(O)NHR^1$, $NHC(O)N(R^1)_2$, or $NR^1C(O)N(R^1)_2$;
  wherein $R^1$ is $R^2$, $R^3$, $R^4$ or $R^5$;
$R^2$ is aryl;
$R^3$ is heteroaryl;
$R^4$ is cycloalkyl, cycloalkenyl, or heterocyclyl;
$R^5$ is C1-C6 alkyl; each of which is unsubstituted or substituted with one or two independently selected $R^6$, $NH_2$ or $CN$;
$R^6$ is $R^7$, $R^8$, or $R^9$;
$R^7$ is aryl;
$R^8$ is heteroaryl;
$R^9$ is cycloalkyl, cycloalkenyl, or heterocyclyl;
  wherein $R^{1A}$ is $R^{2A}$, $R^{3A}$, $R^{4A}$ or $R^{5A}$;
$R^{2A}$ is aryl;
$R^{3A}$ is heteroaryl;
$R^{4A}$ is cycloalkyl, cycloalkenyl, or heterocyclyl;
$R^{5A}$ is C1-C6 alkyl; each of which is unsubstituted or substituted with one or two independently selected $R^{6A}$, $NH_2$ or $CN$;
$R^{6A}$ is $R^{7A}$, $R^{8A}$, or $R^{9A}$;
$R^{7A}$ is aryl;
$R^{8A}$ is heteroaryl;
$R^{9A}$ is cycloalkyl, cycloalkenyl, or heterocyclyl;
  wherein the moieties represented by $R^2$, $R^3$, $R^4$, $R^7$, $R^8$, $R^{3A}$, $R^{4A}$, $R^{7A}$, $R^{8A}$, and $R^{9A}$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, $OH$, $(O)$, $C(O)H$, $C(O)OH$, $CN$, $CF_3$, $OCF_3$, $CF_2CF_3$, F, Cl, Br or I;
    wherein the moiety represented by $R^{2A}$ is independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, $OH$, $(O)$, $C(O)H$, $C(O)OH$, $CN$, $CF_3$, $OCF_3$, or $CF_2CF_3$;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and $R^{30}$ is alkyl alkenyl, or alkynyl.

Another embodiment of this invention, therefore, pertains to compounds that inhibit protein kinases and have Formula I or a pharmaceutically acceptable salt thereof, wherein W is alkyl, H, F, Cl, Br or I;

X is $C(O)R^1$, $C(O)NHR^{1A}$, $C(O)N(R^1)_2$, $NHC(O)R^{1A}$, $NR^1C(O)R^1$, $NHC(O)NHR^1$, $NHC(O)N(R^1)_2$, or $NR^1C(O)N(R^1)_2$;

wherein $R^1$ is $R^2$, $R^3$, $R^4$ or $R^5$;

$R^2$ is aryl;

$R^3$ is heteroaryl;

$R^4$ is cycloalkyl, cycloalkenyl, or heterocyclyl;

$R^5$ is C1-C6 alkyl; each of which is unsubstituted or substituted with one or two independently selected $R^6$, $NH_2$ or CN;

$R^6$ is $R^7$, $R^8$, or $R^9$;

$R^7$ is aryl;

$R^8$ is heteroaryl;

$R^9$ is cycloalkyl, cycloalkenyl, or heterocyclyl;

wherein $R^{1A}$ is $R^{2A}$, $R^{3A}$, $R^{4A}$ or $R^{5A}$;

$R^{2A}$ is aryl;

$R^{3A}$ is heteroaryl;

$R^{4A}$ is cycloalkyl, cycloalkenyl, or heterocyclyl;

$R^{5A}$ is C1-C6 alkyl; each of which is unsubstituted or substituted with one or two independently selected $R^{6A}$, $NH_2$ or CN;

$R^{6A}$ is $R^{7A}$, $R^{8A}$, or $R^{9A}$;

$R^{7A}$ is aryl;

$R^{8A}$ is heteroaryl;

$R^{9A}$ is cycloalkyl, cycloalkenyl, or heterocyclyl;

wherein the moieties represented by $R^2$, $R^3$, $R^4$, $R^7$, $R^8$, $R^9$, $R^{3A}$, $R^{4A}$, $R^{7A}$, $R^{8A}$, and $R^{9A}$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{19}$, $N(R^{19})_2$, $C(O)R^{10}$, $C(O)N(R^{10})_2$, $C(O)OR^{10}$, $C(O)NH_2$, $C(O)NHR^{10})_2$, $C(NOH)NH_2$, $NHC(O)R^{10}$, $NR^{10}C(O)R^{10}$, $NHSO_2R^{10}$, $NR^{10}SO_2R^{10}$; $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;

wherein the moiety represented by $R^{2A}$ is independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, or $CF_2CF_3$;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, NHSO$_2$NHR$^{14}$, NHSO$_2$N(R$^{14}$)$_2$, SO$_2$NH$_2$, SO$_2$NHR$^{14}$, SO$_2$N(R$^{14}$)$_2$, NHC(O)NH$_2$, NHC(O)NHR$^{14}$, NHC(O)N(R$^{14}$)$_2$, NR$^{14}$C(O)N(R$^{14}$)$_2$, NO$_2$, OH, (O), C(O)H, C(O)OH, CN, CF$_3$, OCF$_3$, CF$_2$CF$_3$, F, Cl, Br or I;
  wherein each R$^{14}$ is R$^{15}$, R$^{16}$, R$^{17}$ or R$^{18}$;
  R$^{15}$ is aryl;
  R$^{16}$ is heteroaryl;
  R$^{17}$ is cycloalkyl, cycloalkenyl, or heterocyclyl;
  R$^{18}$ is alkyl, alkenyl or alkynyl; each of which is unsubstituted or substituted with one or two of independently selected R$^{19}$, OR$^{19}$, SR$^{19}$, S(O)$_2$R$^{19}$, NHS(O)$_2$R$^{19}$, C(O)OH, NH$_2$, NHR$^{19}$, N(R$^{19}$)$_2$, C(O)R$^{19}$, C(O)OR$^{19}$, C(O)NH$_2$, C(O)NHR$^{19}$, C(O)N(R$^{19}$)$_2$, NHC(O)R$^{19}$, NR$^{19}$C(O)R$^{19}$, NHC(O)OR$^{19}$, NR$^{19}$C(O)OR$^{19}$, OH, F, Cl, Br or I;
  wherein each R$^{19}$ is R$^{20}$ or R$^{21}$;
  R$^{20}$ is aryl, heteroaryl, cycloalkyl, cycloalkenyl, or heterocyclyl;
  R$^{21}$ is alkyl, alkenyl or alkynyl; each of which is unsubstituted or substituted with one or two of independently selected R$^{22}$, OR$^{22}$, C(O)OH, NH$_2$, NHR$^{22}$, N(R$^{22}$)$_2$, C(O)R$^{22}$, C(O)NH$_2$, C(O)NHR$^{22}$, C(O)N(R$^{22}$)$_2$, NHC(O)R$^{22}$, NR$^{22}$C(O)R$^{22}$, OH, F, Cl, Br or I;
  wherein each R$^{22}$ is alkyl, alkenyl, alkynyl, aryl, heteroaryl, cycloalkyl, cycloalkenyl, or heterocyclyl;
  wherein the moieties represented by R$^{15}$, R$^{16}$, R$^{17}$, and R$^{20}$ are independently unsubstituted or substituted with one or two or three or four of independently selected R$^{23}$, OR$^{23}$, SR$^{23}$, S(O)R$^{23}$, SO$_2$R$^{23}$, C(O)R$^{23}$, CO(O)R$^{23}$, OC(O)R$^{23}$, OC(O)OR$^{23}$, NH$_2$, NHR$^{23}$, N(R$^{23}$)$_2$, NHC(O)R$^{23}$, NR$^{23}$C(O)R$^{23}$, NHS(O)$_2$R$^{23}$, NR$^{23}$S(O)$_2$R$^{23}$, NHC(O)OR$^{23}$, NR$^{23}$C(O)OR$^{23}$, NHC(O)NH$_2$, NHC(O)NHR$^{23}$, NHC(O)N(R$^{23}$)$_2$, NR$^{23}$C(O)NHR$^{23}$, NR$^{23}$C(O)N(R$^{23}$)$_2$, C(O)NH$_2$, C(O)NHR$^{23}$, C(O)N(R$^{23}$)$_2$, C(O)NHOH, C(O)NHOR$^{23}$, C(O)NHSO$_2$R$^{23}$, C(O)NR$^{23}$SO$_2$R$^{23}$, SO$_2$NH$_2$, SO$_2$NHR$^{23}$, SO$_2$N(R$^{23}$)$_2$, C(O)H, C(O)OH, C(N)NH$_2$, C(N)NHR$^{23}$, C(N)N(R$^{23}$)$_2$, CNOH, CNOCH$_3$, OH, (O), CN, N$^3$, NO$_2$, CF$_3$, CF$_2$CF$_3$, OCF$_3$, OCF$_2$CF$_3$, F, Cl, Br or I;
  wherein each R$^{23}$ is R$^{24}$, R$^{25}$, R$^{26}$, R$^{27}$ or R$^{28}$;
  R$^{24}$ is spirocycloalkyl or spiroheterocycloalkyl;
  R$^{25}$ is aryl;
  R$^{26}$ is heteroaryl;
  R$^{27}$ is cycloalkyl, cycloalkenyl, or heterocyclyl;
  R$^{28}$ is alkyl, alkenyl or alkynyl; each of which is unsubstituted or substituted with one or two of independently selected R$^{29}$, OR$^{29}$, SR$^{29}$, S(O)$_2$R$^{29}$, C(O)OH, NH$_2$, NHR$^{29}$N(R$^{29}$)$_2$, C(O)R$^{29}$, C(O)NH$_2$, C(O)NHR$^{29}$, C(O)N(R$^{29}$)$_2$, NHC(O)R$^{29}$, NR$^{29}$C(O)R$^{29}$, NHC(O)OR$^{29}$, NR$^{29}$C(O)OR$^{29}$, NHS(O)$_2$R$^{29}$, NR$^{29}$S(O)$_2$R$^{29}$, OH, (O), F, Cl, Br or I;
  wherein each R$^{29}$ is alkyl, alkenyl or alkynyl each of which is unsubstituted or substituted with one or two of independently selected F, Cl, Br or I;
  wherein the moieties represented by R$^{24}$, R$^{25}$, R$^{26}$, and R$^{27}$ are independently unsubstituted or substituted with one or two of independently selected R$^{30}$, OR$^{30}$, C(O)R$^{30}$, C(O)OR$^{30}$, OH, (O), C(O)OH, CN, CF$_3$, OCF$_3$, CF$_2$CF$_3$, F, Cl, Br or I; and
  R$^{30}$ is alkyl alkenyl, or alkynyl.

Another embodiment of this invention, therefore, pertains to compounds that inhibit protein kinases and have Formula I or a pharmaceutically acceptable salt thereof, wherein
  W is alkyl, H, F, Cl, Br or I;
  X is C(O)R$^1$, NHC(O)NHR$^1$, NHC(O)N(R$^1$)$_2$, or NR$^1$C(O)N(R$^1$)$_2$;
  wherein R$^1$ is R$^2$, R$^3$, R$^4$ or R$^5$;
  R$^2$ is aryl;
  R$^3$ is heteroaryl;
  R$^4$ is cycloalkyl, cycloalkenyl, or heterocyclyl;
  R$^5$ is C1-C6 alkyl; each of which is unsubstituted or substituted with one or two independently selected R$^6$, NH$_2$ or CN;
  R$^6$ is R$^7$, R$^8$, or R$^9$;
  R$^7$ is aryl;
  R$^8$ is heteroaryl;
  R$^9$ is cycloalkyl, cycloalkenyl, or heterocyclyl;
  wherein the moieties represented by R$^2$, R$^3$, R$^4$, R$^7$, R$^8$, and R$^9$ are independently unsubstituted or substituted with one or two or three or four of independently selected, R$^{10}$, OR$^{10}$, SR$^{10}$, S(O)R$^{10}$, SO$_2$R$^{10}$, NH$_2$, NHR$^{10}$, N(R$^{10}$)$_2$, C(O)R$^{10}$, C(O)OR$^{10}$, C(O)NH$_2$, C(O)NHR$^{10}$, C(O)N(R$^{10}$)$_2$, C(NOH)NH$_2$, NHC(O)R$^{10}$, NR$^{10}$C(O)R$^{10}$, NHSO$_2$R$^{10}$, NR$^{10}$SO$_2$R$^{10}$, NHC(O)OR$^{10}$, NR$^{10}$C(O)OR$^{10}$, NHSO$_2$NH$_2$, NHSO$_2$NHR$^{10}$, NHSO$_2$N(R$^{10}$)$_2$, SO$_2$NH$_2$, SO$_2$NHR$^{10}$, SO$_2$N(R$^{10}$)$_2$, NHC(O)NH$_2$, NHC(O)NHR$^{10}$, NHC(O)N(R$^1$)$_2$, NR$^{10}$C(O)N(R$^{10}$)$_2$, NO$_2$, OH, (O), C(O)H, C(O)OH, CN, CF$_3$, OCF$_3$, CF$_2$CF$_3$, F, Cl, Br or I;
  R$^{10}$ is alkyl, alkenyl, alkynyl, aryl, heteroaryl, cycloalkyl, cycloalkenyl, or heterocyclyl;
  Y is R$^{12}$ or R$^{13}$;
  R$^{12}$ is aryl;
  R$^{13}$ is heteroaryl;
  Z is alkyl, H, CF$_3$, F, Cl, Br or I;
  wherein the moieties represented by R$^{12}$ and R$^{13}$ are independently unsubstituted or substituted with one or two or three or four of independently selected, R$^{14}$, OR$^{14}$, SR$^{14}$, S(O)R$^{14}$, SO$_2$R$^{14}$, NH$_2$, NHR$^{14}$, N(R$^{14}$)$_2$, C(O)R$^{14}$, C(O)OR$^{14}$, C(O)NH$_2$, C(O)NHR$^{14}$, C(O)N(R$^{14}$)$_2$, C(NOH)NH$_2$, NHC(O)R$^{14}$, NR$^{14}$C(O)R$^{14}$, NHSO$_2$R$^{14}$, NR$_{14}$SO$_2$R$^{14}$, NHC(O)OR$^{14}$, NR$^{14}$C(O)OR$^{14}$, NHSO$_2$NH$_2$, NHSO$_2$NHR$^{14}$, NHSO$_2$N(R$^{14}$)$_2$, SO$_2$NH$_2$, SO$_2$NHR$^{14}$, SO$_2$N(R$^{14}$)$_2$, NHC(O)NH$_2$, NHC(O)NHR$^{14}$, NHC(O)N(R$^{14}$)$_2$, NR$^{14}$C(O)N(R$^{14}$)$_2$, NO$_2$, OH, (O), C(O)H, C(O)OH, CN, CF$_3$, OCF$_3$, CF$_2$CF$_3$, F, Cl, Br or I;
  wherein each R$^{14}$ is R$^{15}$, R$^{16}$, R$^{17}$ or R$^{18}$;
  R$^{15}$ is aryl;
  R$^{16}$ is heteroaryl;
  R$^{17}$ is cycloalkyl, cycloalkenyl, or heterocyclyl;
  R$^{18}$ is alkyl, alkenyl or alkynyl; each of which is unsubstituted or substituted with one or two of independently selected R$^{19}$, OR$^{19}$, SR$^{19}$, S(O)$_2$R$^{19}$, NHS(O)$_2$R$^{19}$, C(O)OH, NH$_2$, NHR$^{19}$, N(R$^{19}$)$_2$, C(O)R$^{19}$, C(O)OR$^{19}$, C(O)NH$_2$, C(O)NHR$^{19}$, C(O)N(R$^{19}$)$_2$, NHC(O)R$^{19}$, NR$^{19}$C(O)R$^{19}$, NHC(O)OR$^{19}$, NR$^{19}$C(O)OR$^{19}$, OH, F, Cl, Br or I;
  wherein each R$^{19}$ is R$^{20}$ or R$^{21}$;
  R$^{20}$ is aryl, heteroaryl, cycloalkyl, cycloalkenyl, or heterocyclyl;
  R$^{21}$ is alkyl, alkenyl or alkynyl; each of which is unsubstituted or substituted with one or two of independently selected R$^{22}$, OR$^{22}$, C(O)OH, NH$_2$, NHR$^{22}$, N(R$^{22}$)$_2$, C(O)R$^{22}$, C(O)NH$_2$, C(O)NHR$^{22}$, C(O)N(R$^{22}$)$_2$, NHC(O)R$^{22}$, NR$^{22}$C(O)R$^{22}$, OH, F, Cl, Br or I;
  wherein each R$^{22}$ is alkyl, alkenyl, alkynyl, aryl, heteroaryl, cycloalkyl, cycloalkenyl, or heterocyclyl;
  wherein the moieties represented by R$^{15}$, R$^{16}$, R$^{17}$, and R$^{20}$ are independently unsubstituted or substituted with one or two or three or four of independently selected R$^{23}$, OR$^{23}$, SR$^{23}$, S(O)R$^{23}$, SO$_2$R$^{23}$, C(O)R$^{23}$, CO(O)R$^{23}$, OC(O)R$^{23}$, OC(O)OR$^{23}$, NH$_2$, NHR$^{23}$, N(R$^{23}$)$_2$, NHC(O)R$^{23}$, NR$^{23}$C(O)R$^{23}$, NHS(O)$_2$R$^{23}$, NR$^{23}$S(O)$_2$R$^{23}$, NHC(O)OR$^{23}$, NR$^{23}$C(O)OR$^{23}$, NHC(O)NH$_2$, NHC(O)NHR$^{23}$, NHC(O)N(R$^{23}$)$_2$, NR$^{23}$C(O)NHR$^{23}$, NR$^{23}$C(O)N(R$^{23}$)$_2$, C(O)NH$_2$, C(O)NHR$^{23}$, C(O)N(R$^{23}$)$_2$, C(O)NHOH, C(O)NHOR$^{23}$, C(O)NHSO$_2$R$^{23}$, C(O)NR$^{23}$SO$_2$R$^{23}$, SO$_2$NH$_2$, SO$_2$NHR$^{23}$, SO$_2$N(R$^{23}$)$_2$, C(O)H, C(O)OH, C(N)NH$_2$, C(N)NHR$^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, NHC(O)$R^{29}$, $NR^{29}C(O)R^{29}$, $NHC(O)OR^{29}$, $NR^{29}C(O)OR^{29}$, NHS$(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, C(O)$OR^{30}$, OH, (O), C(O)OH, CN, $CF_3$, $OCF_3$, $CF_2CF_3$, F, Cl, Br or I; and $R^{30}$ is alkyl alkenyl, or alkynyl.

Another embodiment of this invention, therefore, pertains to compounds that inhibit protein kinases and have Formula I or a pharmaceutically acceptable salt thereof, wherein X is $C(O)R^1$, $C(O)NHR^1$, $NHC(O)R^1$, $NR^1C(O)R^1$, NHC(O)$NHR^1$, or $NHC(O)N(R^1)_2$;

W is alkyl, H, F, Cl, Br or I;

wherein $R^1$ is $R^2$, $R^3$, $R^4$ or $R^5$;

$R^2$ is aryl;

$R^3$ is heteroaryl;

$R^4$ is cycloalkyl, or heterocyclyl;

$R^5$ is C1-C6 alkyl; each of which is unsubstituted or substituted with one or two independently selected $R^6$, $NH_2$ or CN;

$R^6$ is $R^7$, or $R^8$;

$R^7$ is aryl;

$R^8$ is heteroaryl;

wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;

$R^{10}$ is alkyl, or aryl;

Y is $R^{12}$;

$R^{12}$ is aryl;

Z is alkyl, H, $CF_3$, F, Cl, Br or I;

wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;

wherein each $R^{14}$ is $R^{17}$ or $R^{18}$;

$R^{17}$ is heterocyclyl;

$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;

wherein each $R^{19}$ is $R^{20}$ or $R^{21}$;

$R^{20}$ is heteroaryl, cycloalkyl, or heterocyclyl;

$R^{21}$ is alkyl, each of which is unsubstituted or substituted with one or two of independently selected $OR^{22}$, $N(R^{22})_2$, OH, F, Cl, Br or I;

wherein each $R^{22}$ is alkyl;

wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each $R^{23}$ is $R^{24}$, or $R^{28}$;

$R^{24}$ is spirocycloalkyl or spiroheterocycloalkyl;

$R^{28}$ is alkyl, alkenyl or alkynyl; each of which is unsubstituted or substituted with one or two of independently selected $OR^{29}$, OH, F, Cl, Br or I;

wherein each $R^{29}$ is alkyl;

wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (I), W is alkyl, H, F, Cl, Br, or I. In another embodiment of Formula (I), W is H, F, Cl, Br, or I. In another embodiment of Formula (I), W is H or F.

In one embodiment of Formula (I), Z is alkyl, H, $CF_3$, F, Cl, Br or I. In another embodiment of Formula (I), Z is H, $CF_3$, F, Cl, Br or I. In another embodiment of Formula (I), Z is H, $CF_3$, F, or Cl. In another embodiment of Formula (I), W is H or F; and Z is H, $CF_3$, F, or Cl.

In one embodiment of Formula (I), X is $C(O)R^1$, $C(O)NHR^1$, $C(O)N(R^1)_2$, $NHC(O)R^1$, $NR^1C(O)R^1$, NHC(O)$NHR^1$, $NHC(O)N(R^1)_2$, or $NR^1C(O)N(R^1)_2$. In another embodiment of Formula (I), X is $C(O)R^1$, $C(O)NHR^1$, NHC$(O)R^1$, $NR^1C(O)R^1$, $NHC(O)NHR^1$, or $NHC(O)N(R^1)_2$. In another embodiment of Formula (I), X is $C(O)R^1$, $NR^1C(O)$ $R^1$, $NHC(O)NHR^1$, or $NHC(O)N(R^1)_2$. In another embodiment of Formula (I), W is H or F; Z is H, $CF_3$, F, or Cl; and X is $C(O)R^1$, $C(O)NHR^1$, $NHC(O)R^1$, $NR^1C(O)R^1$, NHC(O)$NHR^1$, or $NHC(O)N(R^1)_2$.

In one embodiment of Formula (I), Y is $R^{12}$ or $R^{13}$, wherein $R^{12}$ is aryl; and $R^{13}$ is heteroaryl. In another embodiment of Formula (I), Y is $R^{12}$; wherein $R^{12}$ is aryl. In another embodiment of Formula (I), W is H or F; Z is H, $CF_3$, F, or Cl; X is $C(O)R^1$, $C(O)NHR^1$, $NHC(O)R^1$, $NR^1C(O)R^1$, NHC(O)$NHR^1$, or $NHC(O)N(R^1)_2$; and Y is $R^{12}$; wherein $R^{12}$ is aryl. In another embodiment of Formula (I), Y is aryl; which is substituted with one or two or three or four of independently selected, $R^{14}$, $OR^{14}$, $N(R^{14})_2$, $C(O)R^{14}$, $C(NOH)NH_2$, NHC$(O)R^{14}$, $SO_2N(R^{14})_2$, CN, F, Cl, Br or I; wherein each $R^{14}$ is $R^{17}$ or $R^{18}$; $R^{17}$ is heterocyclyl; $R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I; wherein each $R^{19}$ is $R^{20}$ or $R^{21}$; $R^{20}$ is heteroaryl, cycloalkyl, or heterocyclyl; $R^{21}$ is alkyl, each of which is unsubstituted or substituted with one or two of independently selected $OR^{22}$, $N(R^{22})_2$, OH, F, Cl, Br or I; wherein each $R^{22}$ is alkyl; wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I; wherein each $R^{23}$ is $R^{24}$, or $R^{28}$; $R^{24}$ is spirocycloalkyl or spiroheterocycloalkyl; $R^{28}$ is alkyl, alkenyl or alkynyl; each of which is unsubstituted or substituted with one or two of independently selected $OR^{29}$, OH, F, Cl, Br or I; wherein each $R^{29}$ is alkyl; wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (I), $R^1$ is aryl, heteroaryl, cycloalkyl, cycloalkenyl, or heterocyclyl. In another embodiment of Formula (I), $R^1$ is aryl, heteroaryl, cycloalkyl, or heterocyclyl, wherein the aryl, heteroaryl, cycloalkyl, or heterocyclyl are unsubstituted or substituted. In another embodiment of Formula (I), $R^1$ is aryl, heteroaryl, cycloalkyl, or heterocyclyl, wherein the aryl, heteroaryl, cycloalkyl, or heterocyclyl are unsubstituted. In another embodiment of Formula (I), $R^1$ is aryl, heteroaryl, cycloalkyl, or heterocyclyl, wherein the aryl, heteroaryl, cycloalkyl, or heterocyclyl are substituted. In another embodiment of Formula (I), $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are unsubstituted. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are unsubstituted.

In another embodiment of Formula (I), $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is heteroaryl, cycloalkyl, or heterocyclyl, wherein the heteroaryl, cycloalkyl, or heterocyclyl are unsubstituted. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$;

wherein $R^{12}$ is aryl; and $R^1$ is heteroaryl, cycloalkyl, or heterocyclyl, wherein the heteroaryl, cycloalkyl, or heterocyclyl are unsubstituted. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is heteroaryl, cycloalkyl, or heterocyclyl, wherein the heteroaryl, cycloalkyl, or heterocyclyl are unsubstituted.

In another embodiment of Formula (I), $R^1$ is aryl, wherein the aryl is substituted with one or two independently selected $R^{10}$, or $OR^{10}$. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, wherein the aryl is substituted with one or two independently selected $R^{10}$, or $OR^{10}$. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, wherein the aryl is substituted with one or two independently selected $R^{10}$, or $OR^{10}$. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, wherein the aryl is unsubstituted. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, wherein the aryl is unsubstituted.

In one embodiment of Formula (I), $R^{10}$ is alkyl or aryl. In another embodiment of Formula (I), $R^{10}$ is alkyl. In another embodiment of Formula (I), $R^{10}$ is aryl. In another embodiment of Formula (I), W is H or F; Z is H, $CF_3$, F, or Cl; X is $C(O)R^1$, $C(O)NHR^1$, $NHC(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (I), W is H or F; Z is H, $CF_3$, F, or Cl; X is $C(O)R^1$, $NR^1C(O)R^1$, $NHC(O)NHR^1$, or $NHC(O)N(R^1)_2$; Y is $R^{12}$; wherein $R^{12}$ is aryl; and $R^1$ is aryl, wherein the aryl is substituted with one or two independently selected $R^{10}$ or $OR^{10}$; and $R^{10}$ is alkyl or aryl.

One embodiment of this invention, therefore, pertains to compounds that inhibit protein kinases and have Formula II (II)

or a pharmaceutically acceptable salt thereof, wherein
W is alkyl, H, F, Cl, Br or I;
wherein $R^1$ is $R^2$, $R^3$, $R^4$ or $R^5$;
$R^2$ is aryl;
$R^3$ is heteroaryl;
$R^4$ is cycloalkyl, cycloalkenyl, or heterocyclyl;

$R^5$ is C1-C6 alkyl; each of which is unsubstituted or substituted with one or two independently selected $R^6$, $NH_2$ or CN;

$R^6$ is $R^7$, $R^8$, or $R^9$;

$R^7$ is aryl;

$R^8$ is heteroaryl;

$R^9$ is cycloalkyl, cycloalkenyl, or heterocyclyl;

wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, so $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and $R^{30}$ is alkyl alkenyl, or alkynyl.

Another embodiment of this invention, therefore, pertains to compounds that inhibit protein kinases and have Formula II or a pharmaceutically acceptable salt thereof, wherein W is alkyl, H, F, Cl, Br or I;

wherein $R^1$ is $R^2$, $R^3$, $R^4$ or $R^5$;

$R^2$ is aryl;

$R^3$ is heteroaryl;

$R^4$ is cycloalkyl, or heterocyclyl;

$R^5$ is C1-C6 alkyl; each of which is unsubstituted or substituted with one or two independently selected $R^6$, $NH_2$ or CN;

$R^6$ is $R^7$, or $R^8$;

$R^7$ is aryl;

$R^8$ is heteroaryl;

wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;

$R^{10}$ is alkyl, or aryl;

Y is $R^{12}$;

$R^{12}$ is aryl;

Z is alkyl, H, $CF_3$, F, Cl, Br or I;

wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;

wherein each $R^{14}$ is $R^{17}$ or $R^{18}$;

$R^{17}$ is heterocyclyl;

$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;

wherein each $R^{19}$ is $R^{20}$ or $R^{21}$;

$R^{20}$ is heteroaryl, cycloalkyl, or heterocyclyl;

$R^{21}$ is alkyl, each of which is unsubstituted or substituted with one or two of independently selected $OR^{22}$, $N(R^{22})_2$, OH, F, Cl, Br or I;

wherein each $R^{22}$ is alkyl;

wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each $R^{23}$ is $R^{24}$, or $R^{28}$;

$R^{24}$ is spirocycloalkyl or spiroheterocycloalkyl;

$R^{28}$ is alkyl, alkenyl or alkynyl; each of which is unsubstituted or substituted with one or two of independently selected $OR^{29}$, OH, F, Cl, Br or I;

wherein each $R^{29}$ is alkyl;

wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (II), W is alkyl, H, F, Cl, Br, or I. In another embodiment of Formula (II), W is H, F, Cl, Br, or I. In another embodiment of Formula (II), W is H or F.

In one embodiment of Formula (II), Z is alkyl, H, $CF_3$, F, Cl, Br or I. In another embodiment of Formula (II), Z is H, $CF_3$, F, Cl, Br or I. In another embodiment of Formula (II), Z is H, $CF_3$, F, or Cl. In another embodiment of Formula (II), W is H or F; and Z is H, $CF_3$, F, or Cl.

In one embodiment of Formula (II), Y is $R^{12}$ or $R^{13}$, wherein $R^{12}$ is aryl; and $R^{13}$ is heteroaryl. In another embodiment of Formula (II), Y is $R^{12}$; wherein $R^{12}$ is aryl. In another embodiment of Formula (II), W is H or F; Z is H, $CF_3$, F, or Cl; and Y is $R^{12}$; wherein $R^{12}$ is aryl. In another embodiment of Formula (II), Y is aryl; which is substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I; wherein each $R^{14}$ is $R^{17}$ or $R^{18}$; $R^{17}$ is heteroaryl; $R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I; wherein each $R^{19}$ is $R^{20}$ or $R^{21}$; $R^{20}$ is heteroaryl, cycloalkyl, or heterocyclyl; $R^{21}$ is alkyl, each of which is unsubstituted or substituted with one or two of independently selected $OR^{22}$, $N(R^{22})_2$, OH, F, Cl, Br or I; wherein each $R^{22}$ is alkyl; wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I; wherein each $R^{23}$ is $R^{24}$, or $R^{28}$; $R^{24}$ is spirocycloalkyl or spiroheterocycloalkyl; $R^{28}$ is alkyl, alkenyl or alkynyl; each of which is unsubstituted or substituted with one or two of independently selected $OR^{29}$, OH, F, Cl, Br or I; wherein each $R^{29}$ is alkyl; wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (II), $R^1$ is aryl, heteroaryl, cycloalkyl, cycloalkenyl, or heterocyclyl. In another embodiment of Formula (II), $R^1$ is aryl, heteroaryl, cycloalkyl, or heterocyclyl, wherein the aryl, heteroaryl, cycloalkyl, or heterocyclyl are unsubstituted or substituted. In another embodiment of Formula (II), $R^1$ is aryl, heteroaryl, cycloalkyl, or heterocyclyl, wherein the aryl, heteroaryl, cycloalkyl, or heterocyclyl are unsubstituted. In another embodiment of Formula (II), $R^1$ is aryl, heteroaryl, cycloalkyl, or heterocyclyl, wherein the aryl, heteroaryl, cycloalkyl, or heterocyclyl are substituted. In another embodiment of Formula (II), $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (II), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (II), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are unsubstituted.

In another embodiment of Formula (II), $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (II), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (II), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are unsubstituted.

In another embodiment of Formula (II), $R^1$ is aryl, wherein the aryl is substituted with one or two independently selected $R^{10}$, or $OR^{10}$. In another embodiment of Formula (II), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$, or $OR^{10}$. In another embodiment of Formula (II), W is H or F; Z is H, $CF_3$, F, or Cl; Y is $R^{12}$; wherein $R^{12}$ is aryl; and $R^1$ is aryl, wherein the aryl is unsubstituted.

In one embodiment of Formula (II), $R^{10}$ is alkyl or aryl. In another embodiment of Formula (II), $R^{10}$ is alkyl. In another embodiment of Formula (II), $R^{10}$ is aryl. In another embodiment of Formula (II), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (II), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (II), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$ or $OR^{10}$; and $R^{10}$ is alkyl or aryl.

One embodiment of this invention, therefore, pertains to compounds that inhibit protein kinases and have Formula III

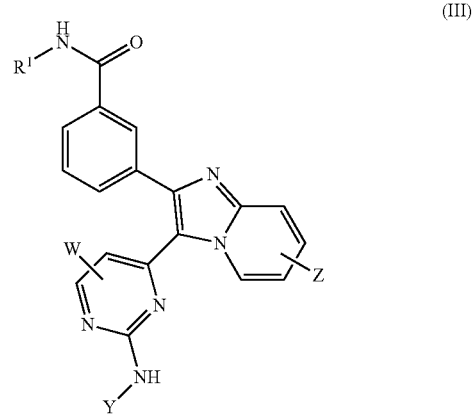

(III)

or a pharmaceutically acceptable salt thereof, wherein

W is alkyl, H, F, Cl, Br or I;

wherein $R^1$ is $R^2$, $R^3$, $R^4$ or $R^5$;

$R^2$ is aryl;

$R^3$ is heteroaryl;

$R^4$ is cycloalkyl, cycloalkenyl, or heterocyclyl;

$R^5$ is C1-C6 alkyl; each of which is unsubstituted or substituted with one or two independently selected $R^6$, $NH_2$ or CN;

$R^6$ is $R^7$, $R^8$, or $R^9$;

$R^7$ is aryl;

$R^8$ is heteroaryl;

$R^9$ is cycloalkyl, cycloalkenyl, or heterocyclyl;

wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and $R^{30}$ is alkyl alkenyl, or alkynyl.

Another embodiment of this invention, therefore, pertains to compounds that inhibit protein kinases and have Formula III or a pharmaceutically acceptable salt thereof, wherein W is alkyl, H, F, Cl, Br or I;

wherein $R^1$ is $R^2$, $R^3$, $R^4$ or $R^5$;

$R^2$ is aryl;

$R^3$ is heteroaryl;

$R^4$ is cycloalkyl, or heterocyclyl;

$R^5$ is C1-C6 alkyl; each of which is unsubstituted or substituted with one or two independently selected $R^6$, $NH_2$ or CN;

$R^6$ is $R^7$, or $R^8$;

$R^7$ is aryl;

$R^8$ is heteroaryl;

wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;

$R^{10}$ is alkyl, or aryl;

Y is $R^{12}$;

$R^{12}$ is aryl;

Z is alkyl, H, $CF_3$, F, Cl, Br or I;

wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;

wherein each $R^{14}$ is $R^{17}$ or $R^{18}$;

$R^{17}$ is heterocyclyl;

$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;

wherein each $R^{19}$ is $R^{20}$ or $R^{21}$;

$R^{20}$ is heteroaryl, cycloalkyl, or heterocyclyl;

$R^{21}$ is alkyl, each of which is unsubstituted or substituted with one or two of independently selected $OR^{22}$, $N(R^{22})_2$, OH, F, Cl, Br or I;

wherein each $R^{22}$ is alkyl;

wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each $R^{23}$ is $R^{24}$, or $R^{28}$;

$R^{24}$ is spirocycloalkyl or spiroheterocycloalkyl;

R²⁸ is alkyl, alkenyl or alkynyl; each of which is unsubstituted or substituted with one or two of independently selected OR²⁹, OH, F, Cl, Br or I;
wherein each R²⁹ is alkyl;
wherein the moieties represented by R²⁴ are independently unsubstituted or substituted with one or two of independently selected R³⁰, C(O)R³⁰, C(O)OR³⁰; and
R³⁰ is alkyl.

In one embodiment of Formula (III), W is alkyl, H, F, Cl, Br, or I. In another embodiment of Formula (III), W is H, F, Cl, Br, or I. In another embodiment of Formula (III), W is H or F.

In one embodiment of Formula (III), Z is alkyl, H, CF₃, F, Cl, Br or I. In another embodiment of Formula (III), Z is H, CF₃, F, Cl, Br or I. In another embodiment of Formula (III), Z is H, CF₃, F, or Cl. In another embodiment of Formula (III), W is H or F; and Z is H, CF₃, F, or Cl.

In one embodiment of Formula (III), Y is R¹² or R¹³, wherein R¹² is aryl; and R¹³ is heteroaryl. In another embodiment of Formula (III), Y is R¹²; wherein R¹² is aryl. In another embodiment of Formula (III), W is H or F; Z is H, CF₃, F, or Cl; and Y is R¹²; wherein R¹² is aryl. In another embodiment of Formula (III), Y is aryl; which is substituted with one or two or three or four of independently selected, R¹⁴, OR¹⁴, N(R¹⁴)₂, C(O)R¹⁴, C(NOH)NH₂, NHC(O)R¹⁴, SO₂N(R¹⁴)₂, CN, F, Cl, Br or I; wherein each R¹⁴ is R¹⁷ or R¹⁸; R¹⁷ is heterocyclyl; R¹⁸ is alkyl; each of which is unsubstituted or substituted with one or two of independently selected R¹⁹, OR¹⁹, S(O)₂R¹⁹, NHS(O)₂R¹⁹, NHR¹⁹, N(R¹⁹)₂, C(O)OR¹⁹, C(O)NH₂, C(O)NHR¹⁹, C(O)N(R¹⁹)₂, NHC(O)R¹⁹, OH, F, Cl, Br or I; wherein each R¹⁹ is R²⁰ or R²¹; R²⁰ is heteroaryl, cycloalkyl, or heterocyclyl; R²¹ is alkyl, each of which is unsubstituted or substituted with one or two of independently selected OR²², N(R²²)₂, OH, F, Cl, Br or I; wherein each R²² is alkyl; wherein the moieties represented by R¹⁷, and R²⁰ are independently unsubstituted or substituted with one or two or three or four of independently selected R²³, C(O)R²³, NH₂, N(R²³)₂, OH, (O), F, Cl, Br or I; wherein each R²³ is R²⁴, or R²⁸; R²⁴ is spirocycloalkyl or spiroheterocycloalkyl; R²⁸ is alkyl, alkenyl or alkynyl; each of which is unsubstituted or substituted with one or two of independently selected OR²⁹, OH, F, Cl, Br or I; wherein each R²⁹ is alkyl; wherein the moieties represented by R²⁴ are independently unsubstituted or substituted with one or two of independently selected R³⁰, C(O)R³⁰, C(O)OR³⁰; and R³⁰ is alkyl.

In one embodiment of Formula (III), R¹ is aryl, heteroaryl, cycloalkyl, cycloalkenyl, or heterocyclyl. In another embodiment of Formula (III), R¹ is aryl, heteroaryl, cycloalkyl, or heterocyclyl, wherein the aryl, heteroaryl, cycloalkyl, or heterocyclyl are unsubstituted or substituted. In another embodiment of Formula (III), R¹ is aryl, heteroaryl, cycloalkyl, or heterocyclyl, wherein the aryl, heteroaryl, cycloalkyl, or heterocyclyl are unsubstituted. In another embodiment of Formula (III), R¹ is aryl, heteroaryl, cycloalkyl, or heterocyclyl, wherein the aryl, heteroaryl, cycloalkyl, or heterocyclyl are substituted. In another embodiment of Formula (III), R¹ is aryl, heteroaryl, cycloalkyl, or heterocyclyl, wherein the aryl, heteroaryl, cycloalkyl, or heterocyclyl are substituted with one or two independently selected R¹⁰, OR¹⁰, F, Cl, Br or I. In another embodiment of Formula (III), W is H or F; Z is H, CF₃, F, or Cl; Y is R¹²; wherein R¹² is aryl; and R¹ is aryl, heteroaryl, cycloalkyl, or heterocyclyl, wherein the aryl, heteroaryl, cycloalkyl, or heterocyclyl are substituted with one or two independently selected R¹⁰, OR¹⁰, F, Cl, Br or I. In another embodiment of Formula (III), W is H or F; Z is H, CF₃, F, or Cl; Y is R¹²; wherein R¹² is aryl; and R¹ is aryl, heteroaryl, cycloalkyl, or heterocyclyl, wherein the aryl, heteroaryl, cycloalkyl, or heterocyclyl are unsubstituted.

In another embodiment of Formula (III), R¹ is heteroaryl, cycloalkyl, or heterocyclyl, wherein the heteroaryl, cycloalkyl, or heterocyclyl are substituted with one or two independently selected R¹⁰, OR¹⁰, F, Cl, Br or I. In another embodiment of Formula (III), W is H or F; Z is H, CF₃, F, or Cl; Y is R¹²; wherein R¹² is aryl; and R¹ is heteroaryl, cycloalkyl, or heterocyclyl, wherein the heteroaryl, cycloalkyl, or heterocyclyl are substituted with one or two independently selected R¹⁰, OR¹⁰, F, Cl, Br or I. In another embodiment of Formula (III), W is H or F; Z is H, CF₃, F, or Cl; Y is R¹²; wherein R¹² is aryl; and R¹ is heteroaryl, cycloalkyl, or heterocyclyl, wherein the heteroaryl, cycloalkyl, or heterocyclyl are unsubstituted.

In another embodiment of Formula (III), R¹ is aryl, wherein the aryl is substituted with one or two independently selected R¹⁰, or OR¹⁰. In another embodiment of Formula (III), W is H or F; Z is H, CF₃, F, or Cl; Y is R¹²; wherein R¹² is aryl; and R¹ is aryl, wherein the aryl is substituted with one or two independently selected R¹⁰, or OR¹⁰. In another embodiment of Formula (III), W is H or F; Z is H, CF₃, F, or Cl; Y is R¹²; wherein R¹² is aryl; and R¹ is aryl, wherein the aryl is unsubstituted.

In one embodiment of Formula (III), R¹⁰ is alkyl or aryl. In another embodiment of Formula (III), R¹⁰ is alkyl. In another embodiment of Formula (III), R¹⁰ is aryl. In another embodiment of Formula (III), W is H or F; Z is H, CF₃, F, or Cl; Y is R¹²; wherein R¹² is aryl; and R¹ is aryl, heteroaryl, cycloalkyl, or heterocyclyl, wherein the aryl, heteroaryl, cycloalkyl, or heterocyclyl are substituted with one or two independently selected R¹⁰, OR¹⁰, F, Cl, Br or I; and R¹⁰ is alkyl or aryl. In another embodiment of Formula (III), W is H or F; Z is H, CF₃, F, or Cl; Y is R¹²; wherein R¹² is aryl; and R¹ is heteroaryl, cycloalkyl, or heterocyclyl, wherein the heteroaryl, cycloalkyl, or heterocyclyl are substituted with one or two independently selected R¹⁰, OR¹⁰, F, Cl, Br or I; and R¹⁰ is alkyl or aryl. In another embodiment of Formula (III), W is H or F; Z is H, CF₃, F, or Cl; Y is R¹²; wherein R¹² is aryl; and R¹ is aryl, wherein the aryl is substituted with one or two independently selected R¹⁰ or OR¹⁰; and R¹⁰ is alkyl or aryl.

One embodiment of this invention, therefore, pertains to compounds that inhibit protein kinases and have Formula IV

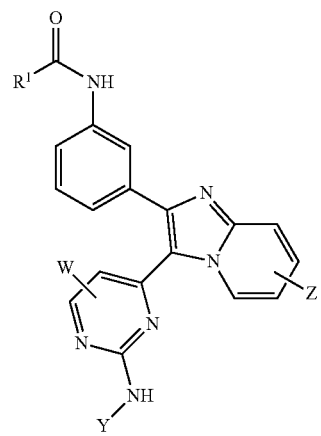

(IV)

or a pharmaceutically acceptable salt thereof, wherein
W is alkyl, H, F, Cl, Br or I;
wherein R¹ is R², R³, R⁴ or R⁵;
R² is aryl;
R³ is heteroaryl;

$R^4$ is cycloalkyl, cycloalkenyl, or heterocyclyl;

$R^5$ is C1-C6 alkyl; each of which is unsubstituted or substituted with one or two independently selected $R^6$, $NH_2$ or CN;

$R^6$ is $R^7$, $R^8$, or $R^9$;

$R^7$ is aryl;

$R^8$ is heteroaryl;

$R^9$ is cycloalkyl, cycloalkenyl, or heterocyclyl;

wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NH_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and $R^+$ is alkyl alkenyl, or alkynyl.

Another embodiment of this invention, therefore, pertains to compounds that inhibit protein kinases and have Formula IV or a pharmaceutically acceptable salt thereof, wherein W is alkyl, H, F, Cl, Br or I;

wherein $R^1$ is $R^2$, $R^3$, $R^4$ or $R^5$;

$R^2$ is aryl;

$R^3$ is heteroaryl;

$R^4$ is cycloalkyl, or heterocyclyl;

$R^5$ is C1-C6 alkyl; each of which is unsubstituted or substituted with one or two independently selected $R^6$, $NH_2$ or CN;

$R^6$ is $R^7$, or $R^8$;

$R^7$ is aryl;

$R^8$ is heteroaryl;

wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;

$R^{10}$ is alkyl, or aryl;

Y is $R^{12}$;

$R^{12}$ is aryl;

Z is alkyl, H, $CF_3$, F, Cl, Br or I;

wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;

wherein each $R^{14}$ is $R^{17}$ or $R^{18}$;

$R^{17}$ is heterocyclyl;

$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;

wherein each $R^{19}$ is $R^{20}$ or $R^{21}$;

$R^{20}$ is heteroaryl, cycloalkyl, or heterocyclyl;

$R^{21}$ is alkyl, each of which is unsubstituted or substituted with one or two of independently selected $OR^{22}$, $N(R^{22})_2$, OH, F, Cl, Br or I;

wherein each $R^{22}$ is alkyl;

wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each $R^{23}$ is $R^{24}$, or $R^{28}$;

$R^{24}$ is spirocycloalkyl or spiroheterocycloalkyl;

$R^{28}$ is alkyl, alkenyl or alkynyl; each of which is unsubstituted or substituted with one or two of independently selected $OR^{29}$, OH, F, Cl, Br or I;

wherein each $R^{29}$ is alkyl;

wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (IV), W is alkyl, H, F, Cl, Br, or I. In another embodiment of Formula (IV), W is H, F, Cl, Br, or I. In another embodiment of Formula (IV), W is H or F.

In one embodiment of Formula (IV), Z is alkyl, H, $CF_3$, F, Cl, Br or I. In another embodiment of Formula (IV), Z is H, $CF_3$, F, Cl, Br or I. In another embodiment of Formula (IV), Z is H, $CF_3$, F, or Cl. In another embodiment of Formula (IV), W is H or F; and Z is H, $CF_3$, F, or Cl.

In one embodiment of Formula (IV), Y is $R^{12}$ or $R^{13}$, wherein $R^{12}$ is aryl; and $R^{13}$ is heteroaryl. In another embodiment of Formula (IV), Y is $R^{12}$; wherein $R^{12}$ is aryl. In another embodiment of Formula (IV), W is H or F; Z is H, $CF_3$, F, or Cl; and Y is $R^{12}$; wherein $R^{12}$ is aryl. In another embodiment of Formula (IV), Y is aryl; which is substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I; wherein each $R^{14}$ is $R^{17}$ or $R^{18}$; $R^{17}$ is heterocyclyl; $R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I; wherein each $R^{19}$ is $R^{20}$ or $R^{21}$; $R^{20}$ is heteroaryl, cycloalkyl, or heterocyclyl; $R^{21}$ is alkyl, each of which is unsubstituted or substituted with one or two of independently selected $OR^{22}$, $N(R^{22})_2$, OH, F, Cl, Br or I; wherein each $R^{22}$ is alkyl; wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I; wherein each $R^{23}$ is $R^{24}$, or $R^{28}$; $R^{24}$ is spirocycloalkyl or spiroheterocycloalkyl; $R^{28}$ is alkyl, alkenyl or alkynyl; each of which is unsubstituted or substituted with one or two of independently selected $OR^{29}$, OH, F, Cl, Br or I; wherein each $R^{29}$ is alkyl; wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (IV), $R^1$ is aryl, heteroaryl, cycloalkyl, cycloalkenyl, or heterocyclyl. In another embodiment of Formula (IV), $R^1$ is aryl, heteroaryl, cycloalkyl, or heterocyclyl, wherein the aryl, heteroaryl, cycloalkyl, or heterocyclyl are unsubstituted or substituted. In another embodiment of Formula (IV), $R^1$ is aryl, heteroaryl, cycloalkyl, or heterocyclyl, wherein the aryl, heteroaryl, cycloalkyl, or heterocyclyl are unsubstituted. In another embodiment of Formula (IV), $R^1$ is aryl, heteroaryl, cycloalkyl, or heterocyclyl, wherein the aryl, heteroaryl, cycloalkyl, or heterocyclyl are substituted. In another embodiment of Formula (IV), $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (IV), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (IV), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are unsubstituted.

In another embodiment of Formula (IV), $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (IV), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (IV), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are unsubstituted.

In another embodiment of Formula (IV), $R^1$ is aryl, wherein the aryl is substituted with one or two independently selected $R^{10}$, or $OR^{10}$. In another embodiment of Formula (IV), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$, or $OR^{10}$. In another embodiment of Formula (IV), W is H or F; Z is H, $CF_3$, F, or Cl; Y is $R^{12}$; wherein $R^{12}$ is aryl; and $R^1$ is aryl, wherein the aryl is unsubstituted.

In one embodiment of Formula (IV), $R^{10}$ is alkyl or aryl. In another embodiment of Formula (IV), $R^{10}$ is alkyl. In another embodiment of Formula (IV), $R^{10}$ is aryl. In another embodiment of Formula (IV), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (IV), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (IV), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$ or $OR^{10}$; and $R^{10}$ is alkyl or aryl.

One embodiment of this invention, therefore, pertains to compounds that inhibit protein kinases and have Formula V

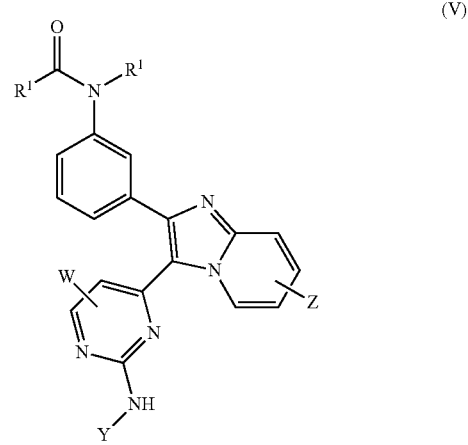

(V)

or a pharmaceutically acceptable salt thereof, wherein
W is alkyl, H, F, Cl, Br or I;

wherein $R^1$ is $R^2$, $R^3$, $R^4$ or $R^5$;
$R^2$ is aryl;
$R^3$ is heteroaryl;
$R^4$ is cycloalkyl, cycloalkenyl, or heterocyclyl;
$R^5$ is C1-C6 alkyl; each of which is unsubstituted or substituted with one or two independently selected $R^6$, $NH_2$ or CN;
$R^6$ is $R^7$, $R^8$, or $R^9$;
$R^7$ is aryl;
$R^8$ is heteroaryl;
$R^9$ is cycloalkyl, cycloalkenyl, or heterocyclyl;
wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;
$R^{10}$ is alkyl, alkenyl, alkynyl, aryl, heteroaryl, cycloalkyl, cycloalkenyl, or heterocyclyl;
Y is $R^{12}$ or $R^{13}$;
$R^{12}$ is aryl;
$R^{13}$ is heteroaryl;
Z is alkyl, H, $CF_3$, F, Cl, Br or I;
wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;
wherein each $R^{14}$ is $R^{15}$, $R^{16}$, $R^{17}$ or $R^{18}$;
$R^{15}$ is aryl;
$R^{16}$ is heteroaryl;
$R^{17}$ is cycloalkyl, cycloalkenyl, or heterocyclyl;
$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;
wherein each $R^{19}$ is $R^{20}$ or $R^{21}$;
$R^{20}$ is aryl, heteroaryl, cycloalkyl, cycloalkenyl, or heterocyclyl;
$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;
wherein each $R^{22}$ is alkyl, alkenyl, alkynyl, aryl, heteroaryl, cycloalkyl, cycloalkenyl, or heterocyclyl;
wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;
wherein each $R^{23}$ is $R^{24}$, $R^{25}$, $R^{26}$, $R^{27}$ or $R^{28}$;
$R^{24}$ is spirocycloalkyl or spiroheterocycloalkyl;
$R^{25}$ is aryl;
$R^{26}$ is heteroaryl;
$R^{27}$ is cycloalkyl, cycloalkenyl, or heterocyclyl;
$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, NHC(O)$R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;
wherein each $R^{29}$ is alkyl, alkenyl or alkynyl each of which is unsubstituted or substituted with one or two of independently selected F, Cl, Br or I;
wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and
$R^{30}$ is alkyl alkenyl, or alkynyl.

Another embodiment of this invention, therefore, pertains to compounds that inhibit protein kinases and have Formula V or a pharmaceutically acceptable salt thereof, wherein
W is alkyl, H, F, Cl, Br or I;
wherein $R^1$ is $R^2$, $R^3$, $R^4$ or $R^5$;
$R^2$ is aryl;
$R^3$ is heteroaryl;
$R^4$ is cycloalkyl, or heterocyclyl;
$R^5$ is C1-C6 alkyl; each of which is unsubstituted or substituted with one or two independently selected $R^6$, $NH_2$ or CN;
$R^6$ is $R^7$, or $R^8$;
$R^7$ is aryl;
$R^8$ is heteroaryl;
wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;
$R^{10}$ is alkyl, or aryl;
Y is $R^{12}$;
$R^{12}$ is aryl;
Z is alkyl, H, $CF_3$, F, Cl, Br or I;
wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;
wherein each $R^{14}$ is $R^{17}$ or $R^{18}$;
$R^{17}$ is heterocyclyl;
$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;
wherein each $R^{19}$ is $R^{20}$ or $R^{21}$;
$R^{20}$ is heteroaryl, cycloalkyl, or heterocyclyl;
$R^{21}$ is alkyl, each of which is unsubstituted or substituted with one or two of independently selected $OR^{22}$, $N(R^{22})_2$, OH, F, Cl, Br or I;
wherein each $R^{22}$ is alkyl;
wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each $R^{23}$ is $R^{24}$, or $R^{28}$;

$R^{24}$ is spirocycloalkyl or spiroheterocycloalkyl;

$R^{28}$ is alkyl, alkenyl or alkynyl; each of which is unsubstituted or substituted with one or two of independently selected $OR^{29}$, OH, F, Cl, Br or I;

wherein each $R^{29}$ is alkyl;

wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (V), W is alkyl, H, F, Cl, Br, or I. In another embodiment of Formula (V), W is H, F, Cl, Br, or I. In another embodiment of Formula (V), W is H or F.

In one embodiment of Formula (V), Z is alkyl, H, $CF_3$, F, Cl, Br or I. In another embodiment of Formula (V), Z is H, $CF_3$, F, Cl, Br or I. In another embodiment of Formula (V), Z is H, $CF_3$, F, or Cl. In another embodiment of Formula (V), W is H or F; and Z is H, $CF_3$, F, or Cl.

In one embodiment of Formula (V), Y is $R^{12}$ or $R^{13}$, wherein $R^{12}$ is aryl; and $R^{13}$ is heteroaryl. In another embodiment of Formula (V), Y is $R^{12}$; wherein $R^{12}$ is aryl. In another embodiment of Formula (V), W is H or F; Z is H, $CF_3$, F, or Cl; and Y is $R^{12}$; wherein $R^{12}$ is aryl. In another embodiment of Formula (V), Y is aryl; which is substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I; wherein each $R^{14}$ is $R^{17}$ or $R^{18}$; $R^{17}$ is heteroaryl; $R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, Cl, F, Cl, Br or I; wherein each $R^{19}$ is $R^{20}$ or $R^{21}$; $R^{20}$ is heteroaryl, cycloalkyl, or heterocyclyl; $R^{21}$ is alkyl, each of which is unsubstituted or substituted with one or two of independently selected $OR^{22}$, $N(R^{22})_2$, OH, F, Cl, Br or I; wherein each $R^{22}$ is alkyl; wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I; wherein each $R^{23}$ is $R^{24}$, or $R^{28}$; $R^{24}$ is spirocycloalkyl or spiroheterocycloalkyl; $R^{28}$ is alkyl, alkenyl or alkynyl; each of which is unsubstituted or substituted with one or two of independently selected $OR^{29}$, OH, F, Cl, Br or I; wherein each $R^{29}$ is alkyl; wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (V), $R^1$ is aryl, heteroaryl, cycloalkyl, cycloalkenyl, or heterocyclyl. In another embodiment of Formula (V), $R^1$ is aryl, heteroaryl, cycloalkyl, or heterocyclyl, wherein the aryl, heteroaryl, cycloalkyl, or heterocyclyl are unsubstituted or substituted. In another embodiment of Formula (V), $R^1$ is aryl, heteroaryl, cycloalkyl, or heterocyclyl, wherein the aryl, heteroaryl, cycloalkyl, or heterocyclyl are unsubstituted. In another embodiment of Formula (V), $R^1$ is aryl, heteroaryl, cycloalkyl, or heterocyclyl, wherein the aryl, heteroaryl, cycloalkyl, or heterocyclyl are substituted. In another embodiment of Formula (V), $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (V), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (V), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are unsubstituted.

In another embodiment of Formula (V), $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (V), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (V), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are unsubstituted.

In another embodiment of Formula (V), $R^1$ is aryl, wherein the aryl is substituted with one or two independently selected $R^{10}$, or $OR^{10}$. In another embodiment of Formula (V), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$, or $OR^{10}$. In another embodiment of Formula (V), W is H or F; Z is H, $CF_3$, F, or Cl; Y is $R^{12}$; wherein $R^{12}$ is aryl; and $R^1$ is aryl, wherein the aryl is unsubstituted.

In one embodiment of Formula (V), $R^{10}$ is alkyl or aryl. In another embodiment of Formula (V), $R^{10}$ is alkyl. In another embodiment of Formula (V), $R^{10}$ is aryl. In another embodiment of Formula (V), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (V), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (V), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$ or $OR^{10}$; and $R^{10}$ is alkyl or aryl.

One embodiment of this invention, therefore, pertains to compounds that inhibit protein kinases and have Formula VI (VI)

or a pharmaceutically acceptable salt thereof, wherein
W is alkyl, H, F, Cl, Br or I;
wherein $R^1$ is $R^2$, $R^3$, $R^4$ or $R^5$;

$R^2$ is aryl;
$R^3$ is heteroaryl;
$R^4$ is cycloalkyl, cycloalkenyl, or heterocyclyl;
$R^5$ is C1-C6 alkyl; each of which is unsubstituted or substituted with one or two independently selected $R^6$, $NH_2$ or CN;
$R^6$ is $R^7$, $R^8$, or $R^9$;
$R^7$ is aryl;
$R^8$ is heteroaryl;
$R^9$ is cycloalkyl, cycloalkenyl, or heterocyclyl;
wherein the moieties represented by $R^2$, $R^3$, $R^4$, $R^7$, $R^8$, $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;
$R^{10}$ is alkyl, alkenyl, alkynyl, aryl, heteroaryl, cycloalkyl, cycloalkenyl, or heterocyclyl;
Y is $R^{12}$ or $R^{13}$;
$R^{12}$ is aryl;
$R^{13}$ is heteroaryl;
Z is alkyl, H, $CF_3$, F, Cl, Br or I;
wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;
wherein each $R^{14}$ is $R^{15}$, $R^{16}$, $R^{17}$ or $R^{18}$;
$R^{15}$ is aryl;
$R^{16}$ is heteroaryl;
$R^{17}$ is cycloalkyl, cycloalkenyl, or heterocyclyl;
$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;
wherein each $R^{19}$ is $R^{20}$ or $R^{21}$;
$R^{20}$ is aryl, heteroaryl, cycloalkyl, cycloalkenyl, or heterocyclyl;
$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;
wherein each $R^{22}$ is alkyl, alkenyl, alkynyl, aryl, heteroaryl, cycloalkyl, cycloalkenyl, or heterocyclyl;
wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR_{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;
wherein each $R^{23}$ is $R^{24}$, $R^{25}$, $R^{26}$, $R^{27}$ or $R^{28}$;
$R^{24}$ is spirocycloalkyl or spiroheterocycloalkyl;
$R^{25}$ is aryl;
$R^{26}$ is heteroaryl;
$R^{27}$ is cycloalkyl, cycloalkenyl, or heterocyclyl;
$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, OH, (O), F, Cl, Br or I;
wherein each $R^{29}$ is alkyl, alkenyl or alkynyl each of which is unsubstituted or substituted with one or two of independently selected F, Cl, Br or I;
wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and
$R^{30}$ is alkyl alkenyl, or alkynyl.

Another embodiment of this invention, therefore, pertains to compounds that inhibit protein kinases and have Formula VI or a pharmaceutically acceptable salt thereof,
wherein
W is alkyl, H, F, Cl, Br or I;
wherein $R^1$ is $R^2$, $R^3$, $R^4$ or $R^5$;
$R^2$ is aryl;
$R^3$ is heteroaryl;
$R^4$ is cycloalkyl, or heterocyclyl;
$R^5$ is C1-C6 alkyl; each of which is unsubstituted or substituted with one or two independently selected $R^6$, $NH_2$ or CN;
$R^6$ is $R^7$, or $R^8$;
$R^7$ is aryl;
$R^8$ is heteroaryl;
wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;
$R^{10}$ is alkyl, or aryl;
Y is $R^{12}$;
$R^{12}$ is aryl;
Z is alkyl, H, $CF_3$, F, Cl, Br or I;
wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;
wherein each $R^{14}$ is $R^{17}$ or $R^{18}$;
$R^{17}$ is heterocyclyl;
$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;
wherein each $R^{19}$ is $R^{20}$ or $R^{21}$;
$R^{20}$ is heteroaryl, cycloalkyl, or heterocyclyl;
$R^{21}$ is alkyl, each of which is unsubstituted or substituted with one or two of independently selected $OR^{22}$, $N(R^{22})_2$, OH, F, Cl, Br or I;
wherein each $R^{22}$ is alkyl;
wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each R²³ is R²⁴, or R²⁸;
R²⁴ is spirocycloalkyl or spiroheterocycloalkyl;
R²⁸ is alkyl, alkenyl or alkynyl; each of which is unsubstituted or substituted with one or two of independently selected OR²⁹, OH, F, Cl, Br or I;
wherein each R²⁹ is alkyl;
wherein the moieties represented by R²⁴ are independently unsubstituted or substituted with one or two of independently selected R³⁰, C(O)R³⁰, C(O)OR³⁰; and
R³⁰ is alkyl.

In one embodiment of Formula (VI), W is alkyl, H, F, Cl, Br, or I. In another embodiment of Formula (VI), W is H, F, Cl, Br, or I. In another embodiment of Formula (VI), W is H or F.

In one embodiment of Formula (VI), Z is alkyl, H, CF₃, F, Cl, Br or I. In another embodiment of Formula (VI), Z is H, CF₃, F, Cl, Br or I. In another embodiment of Formula (VI), Z is H, CF₃, F, or Cl. In another embodiment of Formula (VI), W is H or F; and Z is H, CF₃, F, or Cl.

In one embodiment of Formula (VI), Y is R¹² or R¹³, wherein R¹² is aryl; and R¹³ is heteroaryl. In another embodiment of Formula (VI), Y is R¹²; wherein R¹² is aryl. In another embodiment of Formula (VI), W is H or F; Z is H, CF₃, F, or Cl; and Y is R¹²; wherein R¹² is aryl. In another embodiment of Formula (VI), Y is aryl; which is substituted with one or two or three or four of independently selected, R¹⁴, OR¹⁴, N(R¹⁴)₂, C(O)R¹⁴, C(NOH)NH₂, NHC(O)R¹⁴, SO₂N(R¹⁴)₂, CN, F, Cl, Br or I; wherein each R¹⁴ is R¹⁷ or R¹⁸; R¹⁷ is heterocyclyl; R¹⁸ is alkyl; each of which is unsubstituted or substituted with one or two of independently selected R¹⁹, OR¹⁹, S(O)₂R¹⁹, NHS(O)₂R¹⁹, NHR¹⁹, N(R¹⁹)₂, C(O)OR¹⁹, C(O)NH₂, C(O)NHR¹⁹, C(O)N(R¹⁹)₂, NHC(O)R¹⁹, OH, F, Cl, Br or I; wherein each R¹⁹ is R²⁰ or R²¹; R²⁰ is heteroaryl, cycloalkyl, or heterocyclyl; R²¹ is alkyl, each of which is unsubstituted or substituted with one or two of independently selected OR²², N(R²²)₂, OH, F, Cl, Br or I; wherein each R²² is alkyl; wherein the moieties represented by R¹⁷, and R²⁰ are independently unsubstituted or substituted with one or two or three or four of independently selected R²³, C(O)R²³, NH₂, N(R²³)₂, OH, (O), F, Cl, Br or I; wherein each R²³ is R²⁴, or R²⁸; R²⁴ is spirocycloalkyl or spiroheterocycloalkyl; R²⁸ is alkyl, alkenyl or alkynyl; each of which is unsubstituted or substituted with one or two of independently selected OR²⁹, OH, F, Cl, Br or I; wherein each R²⁹ is alkyl; wherein the moieties represented by R²⁴ are independently unsubstituted or substituted with one or two of independently selected R³⁰, C(O)R³⁰, C(O)OR³⁰; and R³⁰ is alkyl.

In one embodiment of Formula (VI), R¹ is aryl, heteroaryl, cycloalkyl, cycloalkenyl, or heterocyclyl. In another embodiment of Formula (VI), R¹ is aryl, heteroaryl, cycloalkyl, or heterocyclyl, wherein the aryl, heteroaryl, cycloalkyl, or heterocyclyl are unsubstituted or substituted. In another embodiment of Formula (VI), R¹ is aryl, heteroaryl, cycloalkyl, or heterocyclyl, wherein the aryl, heteroaryl, cycloalkyl, or heterocyclyl are unsubstituted. In another embodiment of Formula (VI), R¹ is aryl, heteroaryl, cycloalkyl, or heterocyclyl, wherein the aryl, heteroaryl, cycloalkyl, or heterocyclyl are substituted. In another embodiment of Formula (VI), R¹ is aryl, heteroaryl, cycloalkyl, or heterocyclyl, wherein the aryl, heteroaryl, cycloalkyl, or heterocyclyl are substituted with one or two independently selected R¹⁰, OR¹⁰, F, Cl, Br or I. In another embodiment of Formula (VI), W is H or F; Z is H, CF₃, F, or Cl; Y is R¹²; wherein R¹² is aryl; and R¹ is aryl, heteroaryl, cycloalkyl, or heterocyclyl, wherein the aryl, heteroaryl, cycloalkyl, or heterocyclyl are substituted with one or two independently selected R¹⁰, OR¹⁰, F, Cl, Br or I. In another embodiment of Formula (VI), W is H or F; Z is H, CF₃, F, or Cl; Y is R¹²; wherein R¹² is aryl; and R¹ is aryl, heteroaryl, cycloalkyl, or heterocyclyl, wherein the aryl, heteroaryl, cycloalkyl, or heterocyclyl are unsubstituted.

In another embodiment of Formula (VI), R¹ is heteroaryl, cycloalkyl, or heterocyclyl, wherein the heteroaryl, cycloalkyl, or heterocyclyl are substituted with one or two independently selected R¹⁰, OR¹⁰, F, Cl, Br or I. In another embodiment of Formula (VI), W is H or F; Z is H, CF₃, F, or Cl; Y is R¹²; wherein R¹² is aryl; and R¹ is heteroaryl, cycloalkyl, or heterocyclyl, wherein the heteroaryl, cycloalkyl, or heterocyclyl are substituted with one or two independently selected R¹⁰, OR¹⁰, F, Cl, Br or I. In another embodiment of Formula (VI), W is H or F; Z is H, CF₃, F, or Cl; Y is R¹²; wherein R¹² is aryl; and R¹ is heteroaryl, cycloalkyl, or heterocyclyl, wherein the heteroaryl, cycloalkyl, or heterocyclyl are unsubstituted.

In another embodiment of Formula (VI), R¹ is aryl, wherein the aryl is substituted with one or two independently selected R¹⁰, or OR¹⁰. In another embodiment of Formula (VI), W is H or F; Z is H, CF₃, F, or Cl; Y is R¹²; wherein R¹² is aryl; and R¹ is aryl, wherein the aryl is substituted with one or two independently selected R¹⁰, or OR¹⁰. In another embodiment of Formula (VI), W is H or F; Z is H, CF₃, F, or Cl; Y is R¹²; wherein R¹² is aryl; and R¹ is aryl, wherein the aryl is unsubstituted.

In one embodiment of Formula (VI), R¹⁰ is alkyl or aryl. In another embodiment of Formula (VI), R¹⁰ is alkyl. In another embodiment of Formula (VI), R¹⁰ is aryl. In another embodiment of Formula (VI), W is H or F; Z is H, CF₃, F, or Cl; Y is R¹²; wherein R¹² is aryl; and R¹ is aryl, heteroaryl, cycloalkyl, or heterocyclyl, wherein the aryl, heteroaryl, cycloalkyl, or heterocyclyl are substituted with one or two independently selected R¹⁰, OR¹⁰, F, Cl, Br or I; and R¹⁰ is alkyl or aryl. In another embodiment of Formula (VI), W is H or F; Z is H, CF₃, F, or Cl; Y is R¹²; wherein R¹² is aryl; and R¹ is heteroaryl, cycloalkyl, or heterocyclyl, wherein the heteroaryl, cycloalkyl, or heterocyclyl are substituted with one or two independently selected R¹⁰, OR¹⁰, F, Cl, Br or I; and R¹⁰ is alkyl or aryl. In another embodiment of Formula (VI), W is H or F; Z is H, CF₃, F, or Cl; Y is R¹²; wherein R¹² is aryl; and R¹ is aryl, wherein the aryl is substituted with one or two independently selected R¹⁰ or OR¹⁰; and R¹⁰ is alkyl or aryl.

One embodiment of this invention, therefore, pertains to compounds that inhibit protein kinases and have Formula VII

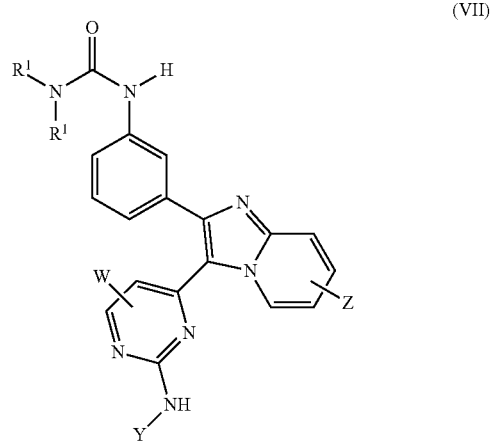

(VII)

or a pharmaceutically acceptable salt thereof, wherein
W is alkyl, H, F, Cl, Br or I;

wherein $R^1$ is $R^2$, $R^3$, $R^4$ or $R^5$;
$R^2$ is aryl;
$R^3$ is heteroaryl;
$R^4$ is cycloalkyl, cycloalkenyl, or heterocyclyl;
$R^5$ is C1-C6 alkyl; each of which is unsubstituted or substituted with one or two independently selected $R^6$, $NH_2$ or CN;
$R^6$ is $R^7$, $R^8$, or $R^9$;
$R^7$ is aryl;
$R^8$ is heteroaryl;
$R^9$ is cycloalkyl, cycloalkenyl, or heterocyclyl;
wherein the moieties represented by $R^2$, $R^3$, $R^4$, $R^7$, $R^8$, and $R^9$ are independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^1)_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, OH, (O), C(O)H, C(O)OH, CN, $CF_3$, $OCF_3$, $CF_2CF_3$, F, Cl, Br or I;
$R^{10}$ is alkyl, alkenyl, alkynyl, aryl, heteroaryl, cycloalkyl, cycloalkenyl, or heterocyclyl;
Y is $R^{12}$ or $R^{13}$;
$R^{12}$ is aryl;
$R^{13}$ is heteroaryl;
Z is alkyl, H, $CF_3$, F, Cl, Br or I;
wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, OH, (O), C(O)H, C(O)OH, CN, $CF_3$, $OCF_3$, $CF_2CF_3$, F, Cl, Br or I;
wherein each $R^{14}$ is $R^{15}$, $R^{16}$, $R^{17}$ or $R^{18}$;
$R^{15}$ is aryl;
$R^{16}$ is heteroaryl;
$R^{17}$ is cycloalkyl, cycloalkenyl, or heterocyclyl;
$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, C(O)OH, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, OH, F, Cl, Br or I;
wherein each $R^{19}$ is $R^{20}$ or $R^{21}$;
$R^{20}$ is aryl, heteroaryl, cycloalkyl, cycloalkenyl, or heterocyclyl;
$R^{21}$ is alkyl, alkenyl or alkynyl; each of which is unsubstituted or substituted with one or two of independently selected $R^{22}$, $OR^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, OH, F, Cl, Br or I;
wherein each $R^{22}$ is alkyl, alkenyl, alkynyl, aryl, heteroaryl, cycloalkyl, cycloalkenyl, or heterocyclyl;
wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, C(O)NHOH, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, C(O)H, C(O)OH, $C(N)NH_2$, $C(N)NHR^{23}$, $C(N)N(R^{23})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;
wherein each $R^{23}$ is $R^{24}$, $R^{25}$, $R^{26}$, $R^{27}$ or $R^{28}$;
$R^{24}$ is spirocycloalkyl or spiroheterocycloalkyl;
$R^{25}$ is aryl;
$R^{26}$ is heteroaryl;
$R^{27}$ is cycloalkyl, cycloalkenyl, or heterocyclyl;
$R^{28}$ is alkyl, alkenyl or alkynyl; each of which is unsubstituted or substituted with one or two of independently selected $R^{29}$, $OR^{29}$, $SR^{29}$, $S(O)_2R^{29}$, C(O)OH, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$; $NHS(O)_2R^{29}$; $NR^{29}S(O)_2R^{29}$, OH, (O), F, Cl, Br or I;
wherein each $R^{29}$ is alkyl, alkenyl or alkynyl each of which is unsubstituted or substituted with one or two of independently selected F, Cl, Br or I;
wherein the moieties represented by $R^{24}$, $R^{25}$, $R^{26}$, and $R^{27}$ are independently unsubstituted or substituted with one or two of independently selected $R^{30}$, $OR^{30}$, $C(O)R^{30}$, $C(O)OR^{30}$, OH, (O), C(O)OH, CN, $CF_3$, $OCF_3$, $CF_2CF_3$, F, Cl, Br or I; and
$R^{30}$ is alkyl alkenyl, or alkynyl.

Another embodiment of this invention, therefore, pertains to compounds that inhibit protein kinases and have Formula VII or a pharmaceutically acceptable salt thereof, wherein
W is alkyl, H, F, Cl, Br or I;
wherein $R^1$ is $R^2$, $R^3$, $R^4$ or $R^5$;
$R^2$ is aryl;
$R^3$ is heteroaryl;
$R^4$ is cycloalkyl, or heterocyclyl;
$R^5$ is C1-C6 alkyl; each of which is unsubstituted or substituted with one or two independently selected $R^6$, $NH_2$ or CN;
$R^6$ is $R^7$, or $R^8$;
$R^7$ is aryl;
$R^8$ is heteroaryl;
wherein the moieties represented by $R^2$, $R^3$, $R^4$, $R^7$, and $R^8$ are independently unsubstituted or substituted with one or two or three or four of independently selected, $R^{10}$, $OR^{10}$, F, Cl, Br or I;
$R^{10}$ is alkyl, or aryl;
Y is $R^{12}$;
R is aryl;
Z is alkyl, H, $CF_3$, F, Cl, Br or I;
wherein the moieties represented by $R^{12}$ are independently unsubstituted or substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I;
wherein each $R^{14}$ is $R^{17}$ or $R^{18}$;
$R^{17}$ is heterocyclyl;
$R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I;
wherein each $R^{19}$ is $R^{20}$ or $R^{21}$;
$R^{20}$ is heteroaryl, cycloalkyl, or heterocyclyl;
$R^{21}$ is alkyl, each of which is unsubstituted or substituted with one or two of independently selected $OR^{22}$, $N(R^{22})_2$, OH, F, Cl, Br or I;
wherein each $R^{22}$ is alkyl;
wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I;

wherein each $R^{23}$ is $R^{24}$, or $R^{28}$;

$R^{24}$ is spirocycloalkyl or spiroheterocycloalkyl;

$R^{28}$ is alkyl, alkenyl or alkynyl; each of which is unsubstituted or substituted with one or two of independently selected $OR^{29}$, OH, F, Cl, Br or I;

wherein each $R^{29}$ is alkyl;

wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (VII), W is alkyl, H, F, Cl, Br, or I. In another embodiment of Formula (VII), W is H, F, Cl, Br, or I. In another embodiment of Formula (VII), W is H or F.

In one embodiment of Formula (VII), Z is alkyl, H, $CF_3$, F, Cl, Br or I. In another embodiment of Formula (VII), Z is H, $CF_3$, F, Cl, Br or I. In another embodiment of Formula (VII), Z is H, $CF_3$, F, or Cl. In another embodiment of Formula (VII), W is H or F; and Z is H, $CF_3$, F, or Cl.

In one embodiment of Formula (VII), Y is $R^{12}$ or $R^{13}$, wherein $R^{12}$ is aryl; and $R^{13}$ is heteroaryl. In another embodiment of Formula (VII), Y is $R^{12}$; wherein $R^{12}$ is aryl. In another embodiment of Formula (VII), W is H or F; Z is H, $CF_3$, F, or Cl; and Y is $R^{12}$; wherein $R^{12}$ is aryl. In another embodiment of Formula (VII), Y is aryl; which is substituted with one or two or three or four of independently selected, $R^{14}$, $OR^{14}$, $N(R^{14})_2$, $C(O)R^{14}$, $C(NOH)NH_2$, $NHC(O)R^{14}$, $SO_2N(R^{14})_2$, CN, F, Cl, Br or I; wherein each $R^{14}$ is $R^{17}$ or $R^{18}$; $R^{17}$ is heterocyclyl; $R^{18}$ is alkyl; each of which is unsubstituted or substituted with one or two of independently selected $R^{19}$, $OR^{19}$, $S(O)_2R^{19}$, $NHS(O)_2R^{19}$, $NHR^{19}$, $N(R^{19})_2$, $C(O)OR^{19}$, $C(O)NH_2$, $C(O)NHR^{19}$, $C(O)N(R^{19})_2$, $NHC(O)R^{19}$, OH, F, Cl, Br or I; wherein each $R^{19}$ is $R^{20}$ or $R^{21}$; $R^{20}$ is heteroaryl, cycloalkyl, or heterocyclyl; $R^{21}$ is alkyl, each of which is unsubstituted or substituted with one or two of independently selected $OR^{22}$, $N(R^{22})_2$, OH, F, Cl, Br or I; wherein each $R^{22}$ is alkyl; wherein the moieties represented by $R^{17}$, and $R^{20}$ are independently unsubstituted or substituted with one or two or three or four of independently selected $R^{23}$, $C(O)R^{23}$, $NH_2$, $N(R^{23})_2$, OH, (O), F, Cl, Br or I; wherein each $R^{23}$ is $R^{24}$, or $R^{28}$; $R^{24}$ is spirocycloalkyl or spiroheterocycloalkyl; $R^{28}$ is alkyl, alkenyl or alkynyl; each of which is unsubstituted or substituted with one or two of independently selected $OR^{29}$, OH, F, Cl, Br or I; wherein each $R^{29}$ is alkyl; wherein the moieties represented by $R^{24}$ are independently unsubstituted or substituted with one or two of independently selected $R^{30}$, $C(O)R^{30}$, $C(O)OR^{30}$; and $R^{30}$ is alkyl.

In one embodiment of Formula (VII), $R^1$ is aryl, heteroaryl, cycloalkyl, cycloalkenyl, or heterocyclyl. In another embodiment of Formula (VII), $R^1$ is aryl, heteroaryl, cycloalkyl, or heterocyclyl, wherein the aryl, heteroaryl, cycloalkyl, or heterocyclyl are unsubstituted or substituted. In another embodiment of Formula (VII), $R^1$ is aryl, heteroaryl, cycloalkyl, or heterocyclyl, wherein the aryl, heteroaryl, cycloalkyl, or heterocyclyl are unsubstituted. In another embodiment of Formula (VII), $R^1$ is aryl, heteroaryl, cycloalkyl, or heterocyclyl, wherein the aryl, heteroaryl, cycloalkyl, or heterocyclyl are substituted. In another embodiment of Formula (VII), $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (VII), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I. In another embodiment of Formula (VII), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are unsubstituted.

In another embodiment of Formula (VII), $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (VII), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I. In another embodiment of Formula (VII), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are unsubstituted.

In another embodiment of Formula (VII), $R^1$ is aryl, wherein the aryl is substituted with one or two independently selected $R^{10}$, or $OR^{10}$. In another embodiment of Formula (VII), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$, or $OR^{10}$. In another embodiment of Formula (VII), W is H or F; Z is H, $CF_3$, F, or Cl; Y is $R^{12}$; wherein $R^{12}$ is aryl; and $R^1$ is aryl, wherein the aryl is unsubstituted.

In one embodiment of Formula (VII), $R^{10}$ is alkyl or aryl. In another embodiment of Formula (VII), $R^{10}$ is alkyl. In another embodiment of Formula (VII), $R^{10}$ is aryl. In another embodiment of Formula (VII), W is H or F; Z is H, $CF_3$, F, or Cl; Y is $R^{12}$; wherein $R^{12}$ is aryl; and $R^1$ is aryl, heteroaryl, cycloalkyl, or heterocyclyl, wherein the aryl, heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (VII), W is H or F; Z is H, $CF_3$, F, or Cl; Y is $R^{12}$; wherein $R^{12}$ is aryl; and $R^1$ is heteroaryl, cycloalkyl, or heterocyclyl, wherein the heteroaryl, cycloalkyl, or heterocyclyl are substituted with one or two independently selected $R^{10}$, $OR^{10}$, F, Cl, Br or I; and $R^{10}$ is alkyl or aryl. In another embodiment of Formula (VII), W is H or F; Z is H, $CF_3$, F, or Cl; Y is $R^{12}$; wherein $R^{12}$ is aryl; and $R^1$ is aryl, wherein the aryl is substituted with one or two independently selected $R^{10}$ or $OR^{10}$; and $R^{10}$ is alkyl or aryl.

Another embodiment pertains to compositions comprising a therapeutically effective amount of a compound having Formula I.

Another embodiment pertains to compositions comprising an excipient and a therapeutically effective amount of a compound having Formula I. Still another embodiment pertains to compositions comprising an excipient and therapeutically effective amounts of a compound having Formula I and one or more than one additional therapeutic agents.

Still another embodiment pertains to compositions for treating cancer, said compositions comprising a therapeutically effective amount of the compound having Formula I.

Still another embodiment pertains to compositions for treating cancer, said compositions comprising an excipient and a therapeutically effective amount of the compound having Formula I.

Still another embodiment pertains to compositions for treating cancer, said compositions comprising an excipient and a therapeutically effective amount of the compound having Formula I and one or more than one additional therapeutic agents.

Still another embodiment pertains to methods of treating a mammal having a disease involving overexpression or unregulation of a protein kinase comprising administering thereto a therapeutically effective amount of a compound having Formula I.

Still another embodiment pertains to methods of treating a mammal having a disease involving overexpression or unregulation of a protein kinase comprising administering thereto radiotherapy and a therapeutically effective amount of a compound having Formula I.

Still another embodiment pertains to methods of treating diseases involving overexpression or unregulation of a protein kinase in a mammal comprising administering thereto therapeutically effective amounts of a compound having Formula I and one or more than one additional therapeutic agents.

Still another embodiment pertains to methods of treating diseases involving overexpression or unregulation of a protein kinase in a mammal comprising administering thereto radiotherapy and therapeutically effective amounts of a compound having Formula I and one or more than one additional therapeutic agents.

Still another embodiment pertains to methods of treating a mammal having cancer comprising administering thereto a therapeutically effective amount of a compound having Formula I.

Still another embodiment pertains to methods of treating a mammal having cancer comprising administering thereto radiotherapy and a therapeutically effective amount of a compound having Formula I.

Still another embodiment pertains to methods of treating cancer in a mammal comprising administering thereto a therapeutically effective amount of a compound having Formula I and one or more than one additional therapeutic agents.

Still another embodiment pertains to methods of treating cancer in a mammal comprising administering thereto radiotherapy and a therapeutically effective amount of a compound having Formula I and one or more than one additional therapeutic agents.

Still another embodiment pertains to the compounds
2,6-difluoro-N-[3-(3-{2-[(3-morpholin-4-ylphenyl)amino]pyrimidin-4-yl}imidazo[1,2-a]pyridin-2-yl)phenyl]benzamide;
N-[3-(3-{2-[(3-morpholin-4-ylphenyl)amino]pyrimidin-4-yl}imidazo[1,2-a]pyridin-2-yl)phenyl]-2-phenylacetamide;
N-[3-(3-{2-[(3-morpholin-4-ylphenyl)amino]pyrimidin-4-yl}imidazo[1,2-a]pyridin-2-yl)phenyl]-N'-phenylurea;
2,6-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
N-[3-(3-{2-[(2-methyl-1,2,3,4-tetrahydroisoquinolin-7-yl)amino]pyrimidin-4-yl}imidazo[1,2-a]pyridin-2-yl)phenyl]-2-phenylacetamide;
N-[3-(3-{2-[(2-methyl-1,2,3,4-tetrahydroisoquinolin-7-yl)amino]pyrimidin-4-yl}imidazo[1,2-a]pyridin-2-yl)phenyl]-2-thien-2-ylacetamide;
N-[3-(3-{2-[(2-methyl-1,2,3,4-tetrahydroisoquinolin-7-yl)amino]pyrimidin-4-yl}imidazo[1,2-a]pyridin-2-yl)phenyl]-N'-phenylurea;
N-benzyl-N'-[3-(3-{2-[(3-morpholin-4-ylphenyl)amino]pyrimidin-4-yl}imidazo[1,2-a]pyridin-2-yl)phenyl]urea;
N-(2,6-difluorophenyl)-N'-[3-(3-{2-[(3-morpholin-4-ylphenyl)amino]pyrimidin-4-yl}imidazo[1,2-a]pyridin-2-yl)phenyl]urea;
N-(2-methylphenyl)-N'-[3-(3-{2-[(3-morpholin-4-ylphenyl)amino]pyrimidin-4-yl}imidazo[1,2-a]pyridin-2-yl)phenyl]urea;
N-(2-chlorophenyl)-N'-[3-(3-{2-[(3-morpholin-4-ylphenyl)amino]pyrimidin-4-yl}imidazo[1,2-a]pyridin-2-yl)phenyl]urea;
N-(4-fluorophenyl)-N'-[3-(3-{2-[(3-morpholin-4-ylphenyl)amino]pyrimidin-4-yl}imidazo[1,2-a]pyridin-2-yl)phenyl]urea;
N-(3-methoxyphenyl)-N'-[3-(3-{2-[(3-morpholin-4-ylphenyl)amino]pyrimidin-4-yl}imidazo[1,2-a]pyridin-2-yl)phenyl]urea;
N-[3-(3-{2-[(3-morpholin-4-ylphenyl)amino]pyrimidin-4-yl}imidazo[1,2-a]pyridin-2-yl)phenyl]cyclopropanecarboxamide;
N-isopropyl-N'-[3-(3-{2-[(3-morpholin-4-ylphenyl)amino]pyrimidin-4-yl}imidazo[1,2-a]pyridin-2-yl)phenyl]urea;
2,6-difluoro-N-{3-[3-(2-{[3-(2-oxopyrrolidin-1-yl)phenyl]amino}pyrimidin-4-yl)imidazo[1,2-a]pyridin-2-yl]phenyl}benzamide;
2-fluoro-N-{3-[3-(2-{[3-(2-oxopyrrolidin-1-yl)phenyl]amino}pyrimidin-4-yl)imidazo[1,2-a]pyridin-2-yl]phenyl}benzamide;
N-{3-[3-(2-{[3-(2-oxopyrrolidin-1-yl)phenyl]amino}pyrimidin-4-yl)imidazo[1,2-a]pyridin-2-yl]phenyl}-2-phenylacetamide;
N-{3-[3-(2-{[3-(2-oxopyrrolidin-1-yl)phenyl]amino}pyrimidin-4-yl)imidazo[1,2-a]pyridin-2-yl]phenyl}-2-thien-2-ylacetamide;
N-{3-[3-(2-{[3-(2-oxopyrrolidin-1-yl)phenyl]amino}pyrimidin-4-yl)imidazo[1,2-a]pyridin-2-yl]phenyl)-N-phenylurea;
N-(2-fluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea;
N-(2,6-difluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea;
2-(2-fluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide;
2-(2,6-difluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide;
N-benzyl-N'-{3-[3-(2-{[3-(2-oxopyrrolidin-1-yl)phenyl]amino}pyrimidin-4-yl)imidazo[1,2-a]pyridin-2-yl]phenyl}urea;
N-(3-{3-[2-({3-[(dimethylamino)methyl]phenyl}amino)pyrimidin-4-yl]imidazo[1,2-a]pyridin-2-yl}phenyl)benzamide;
N-(3-{3-[2-({3-[(dimethylamino)methyl]phenyl}amino)pyrimidin-4-yl]imidazo[1,2-a]pyridin-2-yl}phenyl)-2-fluorobenzamide;
N-(3-{3-[2-({3-[(dimethylamino)methyl]phenyl}amino)pyrimidin-4-yl]imidazo[1,2-a]pyridin-2-yl}phenyl)-2,6-difluorobenzamide;
N-(3-{3-[2-({3-[(dimethylamino)methyl]phenyl}amino)pyrimidin-4-yl]imidazo[1,2-a]pyridin-2-yl}phenyl)-2-phenylacetamide;
N-(3-{3-[2-({3-[(dimethylamino)methyl]phenyl}amino)pyrimidin-4-yl]imidazo[1,2-a]pyridin-2-yl}phenyl)-2-thien-2-ylacetamide;
N-(3-{3-[2-({3-[(dimethylamino)methyl]phenyl}amino)pyrimidin-4-yl]imidazo[1,2-a]pyridin-2-yl}phenyl)-N'-phenylurea;

N-(2,6-difluorophenyl)-N'-(3-{3-[2-({3-[(dimethylamino) methyl]phenyl}amino)pyrimidin-4-yl]imidazo[1,2-a]pyridin-2-yl}phenyl)urea;

N-[3-(8-chloro-3-{2-[(3-morpholin-4-ylphenyl)amino]pyrimidin-4-yl}imidazo[1,2-a]pyridin-2-yl)phenyl]-2,6-difluorobenzamide;

N-[3-(8-chloro-3-{2-[(3-morpholin-4-ylphenyl)amino]pyrimidin-4-yl}imidazo[1,2-a]pyridin-2-yl)phenyl]-2-phenylacetamide;

N-[3-(8-chloro-3-{2-[(3-morpholin-4-ylphenyl)amino]pyrimidin-4-yl}imidazo[1,2-a]pyridin-2-yl)phenyl]-2-thien-2-ylacetamide;

N-[3-(8-chloro-3-{2-[(3-morpholin-4-ylphenyl)amino]pyrimidin-4-yl}imidazo[1,2-a]pyridin-2-yl)phenyl]-N'-phenylurea;

N-(3-{3-[2-({3-[2-(dimethylamino)ethyl]phenyl}amino)pyrimidin-4-yl]imidazo[1,2-a]pyridin-2-yl}phenyl)-2,6-difluorobenzamide;

N-(3-{3-[2-({3-[2-(dimethylamino)ethyl]phenyl}amino)pyrimidin-4-yl]imidazo[1,2-a]pyridin-2-yl}phenyl)-2-phenylacetamide;

N-(3-{3-[2-({3-[2-(dimethylamino)ethyl]phenyl}amino)pyrimidin-4-yl]imidazo[1,2-a]pyridin-2-yl}phenyl)-2-thien-2-ylacetamide;

N-(3-{3-[2-({3-[2-(dimethylamino)ethyl]phenyl}amino)pyrimidin-4-yl]imidazo[1,2-a]pyridin-2-yl)phenyl)-N'-phenylurea;

N-{3-[3-(2-{[4-(4-ethylpiperazin-1-yl)phenyl]amino}pyrimidin-4-yl)imidazo[1,2-a]pyridin-2-yl]phenyl}-2-phenylacetamide;

N-{3-[3-(2-{[4-(4-ethylpiperazin-1-yl)phenyl]amino}pyrimidin-4-yl)imidazo[1,2-a]pyridin-2-yl]phenyl}-2-thien-2-ylacetamide;

N-{3-[3-(2-{[4-(4-ethylpiperazin-1-yl)phenyl]amino}pyrimidin-4-yl)imidazo[1,2-a]pyridin-2-yl]phenyl}benzamide;

N-{3-[3-(2-{[4-(4-ethylpiperazin-1-yl)phenyl]amino}pyrimidin-4-yl)imidazo[1,2-a]pyridin-2-yl]phenyl}-2,6-difluorobenzamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2,6-difluorobenzamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2-phenylacetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2-thien-2-ylacetamide;

N-(3-{3-[2-{(3-[2-(dimethylamino)ethoxy]phenyl}amino)pyrimidin-4-yl]imidazo[1,2-a]pyridin-2-yl}phenyl)-2,6-difluorobenzamide;

N-(3-{3-[2-{(3-[2-(dimethylamino)ethoxy]phenyl}amino)pyrimidin-4-yl]imidazo[1,2-a]pyridin-2-yl}phenyl)-2-phenylacetamide;

N-(3-{3-[2-({3-[2-(dimethylamino)ethoxy]phenyl}amino)pyrimidin-4-yl]imidazo[1,2-a]pyridin-2-yl}phenyl)-2-thien-2-ylacetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-5-methylthiophene-2-carboxamide;

N-(3-{3-[2-({3-[2-(dimethylamino)ethoxy]phenyl}amino)pyrimidin-4-yl]imidazo[1,2-a]pyridin-2-yl}phenyl)-5-methylthiophene-2-carboxamide;

N-(3-{3-[2-({4-[2-(dimethylamino)ethyl]phenyl}amino)pyrimidin-4-yl]imidazo[1,2-a]pyridin-2-yl}phenyl)-2,6-difluorobenzamide;

N-(3-{3-[2-({4-[2-(dimethylamino)ethyl]phenyl}amino)pyrimidin-4-yl]imidazo[1,2-a]pyridin-2-yl}phenyl)-2-phenylacetamide;

N-(3-{3-[2-({4-[2-(dimethylamino)ethyl]phenyl}amino)pyrimidin-4-yl]imidazo[1,2-a]pyridin-2-yl}phenyl)-2-thien-2-ylacetamide;

2,6-difluoro-N-{3-[3-(2-{[3-(2-pyrrolidin-1-ylethyl)phenyl]amino}pyrimidin-4-yl)imidazo[1,2-a]pyridin-2-yl]phenyl}benzamide;

2-phenyl-N-{3-[3-(2-{[3-(2-pyrrolidin-1-ylethyl)phenyl]amino}pyrimidin-4-yl)imidazo[1,2-a]pyridin-2-yl]phenyl}acetamide;

N-{3-[3-(2-{[3-(2-pyrrolidin-1-ylethyl)phenyl]amino}pyrimidin-4-yl)imidazo[1,2-a]pyridin-2-yl]phenyl}-2-thien-2-ylacetamide;

2,6-difluoro-N-(3-{3-[2-({3-[(3-hydroxyazetidin-1-yl)methyl]phenyl}amino)pyrimidin-4-yl]imidazo[1,2-a]pyridin-2-yl}phenyl)benzamide;

N-(3-{3-[2-({3-[(3-hydroxyazetidin-1-yl)methyl]phenyl}amino)pyrimidin-4-yl]imidazo[1,2-a]pyridin-2-yl}phenyl)-2-phenylacetamide;

N-(3-{3-[2-({3-[(3-hydroxyazetidin-1-yl)methyl]phenyl}amino)pyrimidin-4-yl]imidazo[1,2-a]pyridin-2-yl}phenyl)-2-thien-2-ylacetamide;

2,6-difluoro-N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]benzamide;

N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]-2-phenylacetamide;

N-(3-{3-{2-[(3-{2-[(2-hydroxyethyl)(methyl)amino]ethyl}phenyl)amino)pyrimidin-4-yl}imidazo[1,2-a]pyridin-2-yl)phenyl]-2-thien-2-ylacetamide;

N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2,6-difluorobenzamide;

N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-phenylacetamide;

N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-thien-2-ylacetamide;

N-{3-[3-(2-{[4-(1-acetylpiperidin-4-yl)phenyl]amino}pyrimidin-4-yl)imidazo[1,2-a]pyridin-2-yl]phenyl}-2-thien-2-ylacetamide;

N-{3-[3-(2-{[4-(1-acetylpiperidin-4-yl)phenyl]amino}pyrimidin-4-yl)imidazo[1,2-a]pyridin-2-yl]phenyl}-2,6-difluorobenzamide;

N-[3-(3-{2-[(3-cyanophenyl)amino]pyrimidin-4-yl}imidazo[1,2-a]pyridin-2-yl)phenyl]-2,6-difluorobenzamide;

N-[3-(3-{2-[(3-cyanophenyl)amino]pyrimidin-4-yl}imidazo[1,2-a]pyridin-2-yl)phenyl]-2-phenylacetamide;

N-[3-(3-{2-[(3-cyanophenyl)amino]pyrimidin-4-yl}imidazo[1,2-a]pyridin-2-yl)phenyl]-2-thien-2-ylacetamide;

2,6-difluoro-N-(3-{3-[2-({3-[2-(methylsulfonyl)ethoxy]phenyl}amino)pyrimidin-4-yl]imidazo[1,2-a]pyridin-2-yl}phenyl)benzamide;

N-(3-{3-[2-({3-[2-(methylsulfonyl)ethoxy]phenyl}amino)pyrimidin-4-yl]imidazo[1,2-a]pyridin-2-yl}phenyl)-2-phenylacetamide;

N-(3-{3-[2-({3-[2-(methylsulfonyl)ethoxy]phenyl}amino)pyrimidin-4-yl]imidazo[1,2-a]pyridin-2-yl}phenyl)-2-thien-2-ylacetamide;

2,6-difluoro-N-{3-[3-(2-{[4-(1-isopropylpiperidin-4-yl)phenyl]amino}pyrimidin-4-yl)imidazo[1,2-a]pyridin-2-yl]phenyl}benzamide;
N-{3-[3-(2-{[4-(1-isopropylpiperidin-4-yl)phenyl]amino}pyrimidin-4-yl)imidazo[1,2-a]pyridin-2-yl]phenyl}-2-thien-2-ylacetamide;
N-(3-{3-[2-({3-[(Z)-amino(hydroxyimino)methyl]phenyl}amino)pyrimidin-4-yl]imidazo[1,2-a]pyridin-2-yl}phenyl)-2,6-difluorobenzamide;
N-(3-{3-[2-({3-[(Z)-amino(hydroxyimino)methyl]phenyl}amino)pyrimidin-4-yl]imidazo[1,2-a]pyridin-2-yl}phenyl)-2-thien-2-ylacetamide;
N-{3-[3-(2-{[3-(2-amino-2-oxoethyl)phenyl]amino}pyrimidin-4-yl)imidazo[1,2-a]pyridin-2-yl]phenyl}-2,6-difluorobenzamide;
N-{3-[3-(2-{[3-(2-amino-2-oxoethyl)phenyl]amino}pyrimidin-4-yl)imidazo[1,2-a]pyridin-2-yl]phenyl}-2-thien-2-ylacetamide;
N-{3-[3-(2-{[3-(2-amino-2-oxoethyl)phenyl]amino}pyrimidin-4-yl)imidazo[1,2-a]pyridin-2-yl]phenyl}-2-phenylacetamide;
isopropyl (3-{[4-(2-{3-[(phenylacetyl)amino]phenyl}imidazo[1,2-a]pyridin-3-yl)pyrimidin-2-yl]amino}phenyl)acetate;
N-{3-[3-(2-{[4-(1-ethylpiperidin-4-yl)phenyl]amino}pyrimidin-4-yl)imidazo[1,2-a]pyridin-2-yl]phenyl}-2-thien-2-ylacetamide;
N-{3-[3-(2-{[4-(1-ethylpiperidin-4-yl)phenyl]amino}pyrimidin-4-yl)imidazo[1,2-a]pyridin-2-yl]phenyl}-2,6-difluorobenzamide;
N-{3-[3-(2-{[4-(4-ethylpiperazin-1-yl)phenyl]amino}pyrimidin-4-yl)imidazo[1,2-a]pyridin-2-yl]phenyl}-2-(1-methyl-1H-imidazol-4-yl)acetamide;
2,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
3,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2,3-difluoro-N-[3-(3-{2-[(2-methyl-1,2,3,4-tetrahydro isoquinolin-7-yl)amino]pyrimidin-4-yl}imidazo[1,2-a]pyridin-2-yl)phenyl]benzamide;
N-{3-[3-(2-{[4-(4-ethylpiperazin-1-yl)phenyl]amino}pyrimidin-4-yl)imidazo[1,2-a]pyridin-2-yl]phenyl}-2-thien-3-ylacetamide;
N-{3-[3-(2-{[4-(4-ethylpiperazin-1-yl)phenyl]amino}pyrimidin-4-yl)imidazo[1,2-a]pyridin-2-yl]phenyl}-2-(3-methylisoxazol-5-yl)acetamide;
N-[3-(3-{2-[(1-acetyl-2,3-dihydro-1H-indol-5-yl)amino]pyrimidin-4-yl}imidazo[1,2-a]pyridin-2-yl)phenyl]-2,6-difluorobenzamide;
N-[3-(3-{2-[(1-acetyl-2,3-dihydro-1H-indol-5-yl)amino]pyrimidin-4-yl}imidazo[1,2-a]pyridin-2-yl)phenyl]-2-phenylacetamide;
N-[3-(3-{2-[(1-acetyl-2,3-dihydro-1H-indol-5-yl)amino]pyrimidin-4-yl}imidazo[1,2-a]pyridin-2-yl)phenyl]-2-thien-2-ylacetamide;
2,4-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2-chloro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2-fluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
N-{3-[3-(2-{[4-(1-ethylpyrrolidin-3-yl)phenyl]amino}pyrimidin-4-yl)imidazo[1,2-a]pyridin-2-yl]phenyl}-2-thien-2-ylacetamide;
N-{3-[3-(2-{[3-(1-ethylpyrrolidin-3-yl)phenyl]amino}pyrimidin-4-yl)imidazo[1,2-a]pyridin-2-yl]phenyl}-2-thien-2-ylacetamide;
N-{3-[3-(2-{[4-(1-acetylpyrrolidin-3-yl)phenyl]amino}pyrimidin-4-yl)imidazo[1,2-a]pyridin-2-yl]phenyl}-2-thien-2-ylacetamide;
N-{3-[3-(2-{[3-(1-acetylpyrrolidin-3-yl)phenyl]amino}pyrimidin-4-yl)imidazo[1,2-a]pyridin-2-yl]phenyl}-2-thien-2-ylacetamide;
N-{3-[3-(2-{[3-(1-acetylpyrrolidin-3-yl)phenyl]amino}pyrimidin-4-yl)imidazo[1,2-a]pyridin-2-yl]phenyl}-2,6-difluorobenzamide;
N-[3-(3-{2-[(2-ethyl-2,3-dihydro-1H-isoindol-5-yl)amino]pyrimidin-4-yl}imidazo[1,2-a]pyridin-2-yl)phenyl]-2-thien-2-ylacetamide;
N-[3-(3-{2-[(2-ethyl-2,3-dihydro-1H-isoindol-5-yl)amino]pyrimidin-4-yl}imidazo[1,2-a]pyridin-2-yl)phenyl]-2,6-difluorobenzamide;
N-[3-(3-{2-[(2-ethyl-2,3-dihydro-1H-isoindol-5-yl)amino]pyrimidin-4-yl}imidazo[1,2-a]pyridin-2-yl)phenyl]-2-phenylacetamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-2-ylacetamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-2,6-difluorobenzamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-2-phenylacetamide;
2,6-difluoro-N-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2,6-difluoro-N-{3-[3-(2-{[4-(2-pyrrolidin-1-ylethyl)phenyl]amino}pyrimidin-4-yl)imidazo[1,2-a]pyridin-2-yl]phenyl}benzamide;
4-methyl-N-{3-[3-(2-{[4-(2-pyrrolidin-1-ylethyl)phenyl]amino}pyrimidin-4-yl)imidazo[1,2-a]pyridin-2-yl]phenyl}thiophene-2-carboxamide;
2-phenyl-N-{3-[3-(2-{[4-(2-pyrrolidin-1-ylethyl)phenyl]amino}pyrimidin-4-yl)imidazo[1,2-a]pyridin-2-yl]phenyl}acetamide;
N-{3-[3-(2-{[4-(2-pyrrolidin-1-ylethyl)phenyl]amino}pyrimidin-4-yl)imidazo[1,2-a]pyridin-2-yl]phenyl}-2-thien-2-ylacetamide;
5-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;
N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;
4-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;
2,5-dichloro-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-3-carboxamide;
5-chloro-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;
3-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;

N-[3-(3-{2-[(2-methyl-1,2,3,4-tetrahydroisoquinolin-7-yl) amino]pyrimidin-4-yl}imidazo[1,2-a]pyridin-2-yl)phenyl]-1-benzothiophene-2-carboxamide;

N-{3-[3-(2-{[2-(methoxyacetyl)-1,2,3,4-tetrahydroisoquinolin-7-yl]amino}pyrimidin-4-yl)imidazo[1,2-a]pyridin-2-yl]phenyl}-2-thien-2-ylacetamide;

N-{3-[3-(2-{[4-(1-acetylpyrrolidin-3-yl)phenyl] amino}pyrimidin-4-yl)imidazo[1,2-a]pyridin-2-yl]phenyl}-2,6-difluorobenzamide;

N-{3-[3-(2-{[2-(3-methoxypropanoyl)-1,2,3,4-tetrahydroisoquinolin-7-yl]amino}pyrimidin-4-yl)imidazo[1,2-a]pyridin-2-yl]phenyl}-2-thien-2-ylacetamide;

N-{3-(3-{2-[(2-methyl-1,2,3,4-tetrahydroisoquinolin-7-yl) amino]pyrimidin-4-yl}imidazo[1,2-a]pyridin-2-yl)phenyl]thiophene-3-carboxamide;

N-(2-fluorophenyl)-3-(3-{2-[(2-methyl-1,2,3,4-tetrahydroisoquinolin-7-yl)amino]pyrimidin-4-yl}imidazo[1,2-a]pyridin-2-yl)benzamide;

3-(3-{2-[(2-methyl-1,2,3,4-tetrahydroisoquinolin-7-yl) amino]pyrimidin-4-yl}imidazo[1,2-a]pyridin-2-yl)-N-(thien-2-ylmethyl)benzamide;

2-chloro-N-{3-[3-(2-{[4-(4-ethylpiperazin-1-yl)phenyl] amino}pyrimidin-4-yl)imidazo[1,2-a]pyridin-2-yl] phenyl}benzamide;

2-chloro-N-{3-[3-(2-{[4-(4-ethylpiperazin-1-yl)phenyl] amino}pyrimidin-4-yl)imidazo[1,2-a]pyridin-2-yl]phenyl}-6-fluorobenzamide;

N-{3-[3-(2-{[4-(4-ethylpiperazin-1-yl)phenyl] amino}pyrimidin-4-yl)imidazo[1,2-a]pyridin-2-yl]phenyl}-2-(5-methylthien-2-yl)acetamide;

N-{3-[3-(2-{[4-(4-ethylpiperazin-1-yl)phenyl] amino}pyrimidin-4-yl)imidazo[1,2-a]pyridin-2-yl]phenyl}-2-(2-methyl-1,3-thiazol-5-yl)acetamide;

N-{3-[3-(2-{[4-(4-isopropylpiperazin-1-yl)phenyl] amino}pyrimidin-4-yl)imidazo[1,2-a]pyridin-2-yl]phenyl}-2-thien-2-ylacetamide;

N-{3-[3-(2-{[4-(4-isopropylpiperazin-1-yl)phenyl] amino}pyrimidin-4-yl)imidazo[1,2-a]pyridin-2-yl]phenyl}-2-phenylacetamide;

2,6-difluoro-N-{3-[3-(2-{[4-(4-isopropylpiperazin-1-yl)phenyl]amino}pyrimidin-4-yl)imidazo[1,2-a]pyridin-2-yl]phenyl}benzamide;

2-chloro-N-{3-[3-(2-{[4-(4-isopropylpiperazin-1-yl)phenyl]amino}pyrimidin-4-yl)imidazo[1,2-a]pyridin-2-yl]phenyl}benzamide;

N-[3-(3-{2-[(1-methyl-2,3-dihydro-1H-indol-5-yl)amino]pyrimidin-4-yl}imidazo[1,2-a]pyridin-2-yl)phenyl]-2-phenylacetamide;

2,6-difluoro-N-{3-[3-(2-{[3-(pyrrolidin-1-ylmethyl)phenyl] amino}pyrimidin-4-yl)imidazo[1,2-a]pyridin-2-yl] phenyl}benzamide;

2-phenyl-N-{3-[3-(2-{[3-(pyrrolidin-1-ylmethyl)phenyl] amino}pyrimidin-4-yl)imidazo[1,2-a]pyridin-2-yl] phenyl}acetamide;

N-{3-[3-(2-{[3-(pyrrolidin-1-ylmethyl)phenyl] amino}pyrimidin-4-yl)imidazo[1,2-a]pyridin-2-yl]phenyl}-2-thien-2-ylacetamide;

2,6-difluoro-N-{3-[3-(2-{[3-(1H-imidazol-1-ylmethyl)phenyl]amino}pyrimidin-4-yl)imidazo[1,2-a]pyridin-2-yl] phenyl}benzamide;

N-{3-[3-(2-{[3-(1H-imidazol-1-ylmethyl)phenyl] amino}pyrimidin-4-yl)imidazo[1,2-a]pyridin-2-yl]phenyl}-2-phenylacetamide;

N-{3-[3-(2-{[3-(1H-imidazol-1-ylmethyl)phenyl] amino}pyrimidin-4-yl)imidazo[1,2-a]pyridin-2-yl]phenyl}-2-thien-2-ylacetamide;

2,6-difluoro-N-{3-[3-(2-{[3-(1H-1,2,4-triazol-1-ylmethyl) phenyl]amino}pyrimidin-4-yl)imidazo[1,2-a]pyridin-2-yl]phenyl}benzamide;

5-methyl-N-{3-[3-(2-{[3-(1H-1,2,4-triazol-1-ylmethyl)phenyl]amino}pyrimidin-4-yl)imidazo[1,2-a]pyridin-2-yl] phenyl}thiophene-2-carboxamide;

2-phenyl-N-{3-[3-(2-{[3-(1H-1,2,4-triazol-1-ylmethyl)phenyl]amino}pyrimidin-4-yl)imidazo[1,2-a]pyridin-2-yl] phenyl}acetamide;

2-thien-2-yl-N-{3-[3-(2-{[3-(1H-1,2,4-triazol-1-ylmethyl) phenyl]amino}pyrimidin-4-yl)imidazo[1,2-a]pyridin-2-yl]phenyl}acetamide;

2,6-difluoro-N-[3-(3-{2-[(1-methyl-2,3-dihydro-1H-indol-5-yl)amino]pyrimidin-4-yl}imidazo[1,2-a]pyridin-2-yl) phenyl]benzamide;

5-methyl-N-[3-(3-{2-[(1-methyl-2,3-dihydro-1H-indol-5-yl)amino]pyrimidin-4-yl}imidazo[1,2-a]pyridin-2-yl) phenyl]thiophene-2-carboxamide;

N-[3-(3-{2-[(1-methyl-2,3-dihydro-1H-indol-5-yl)amino] pyrimidin-4-yl}imidazo[1,2-a]pyridin-2-yl)phenyl]-2-thien-2-ylacetamide;

2,6-difluoro-N-(3-{3-[2-({3-[(3-hydroxypyrrolidin-1-yl) methyl]phenyl}amino)pyrimidin-4-yl]imidazo[1,2-a]pyridin-2-yl}phenyl)benzamide;

N-(3-{3-[2-({3-[(3-hydroxypyrrolidin-1-yl)methyl] phenyl}amino)pyrimidin-4-yl]imidazo[1,2-a]pyridin-2-yl}phenyl)-2-phenylacetamide;

N-(3-{3-[2-({3-[(3-hydroxypyrrolidin-1-yl)methyl] phenyl}amino)pyrimidin-4-yl]imidazo[1,2-a]pyridin-2-yl}phenyl)-2-thien-2-ylacetamide;

N-[3-(3-{2-[(2-ethyl-2,3-dihydro-1H-isoindol-5-yl)amino] pyrimidin-4-yl}imidazo[1,2-a]pyridin-2-yl)phenyl]-2-thien-3-ylacetamide;

2-chloro-N-[3-(3-{2-[(2-ethyl-2,3-dihydro-1H-isoindol-5-yl)amino]pyrimidin-4-yl}imidazo[1,2-a]pyridin-2-yl)phenyl]benzamide;

N-{3-[3-(2-{[2-(dimethylamino)-2,3-dihydro-1H-inden-5-yl]amino}pyrimidin-4-yl)imidazo[1,2-a]pyridin-2-yl] phenyl}-2-thien-3-ylacetamide;

2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}benzamide;

2,6-difluoro-N-{3-[3-(2-{[2-(methoxyacetyl)-1,2,3,4-tetrahydroisoquinolin-6-yl]amino}pyrimidin-4-yl)imidazo [1,2-a]pyridin-2-yl]phenyl)benzamide;

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-2-thien-2-ylacetamide;

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-2-phenylacetamide;

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-N'-phenylurea;

N-{3-[3-(2-{[4-(4-ethylpiperazin-1-yl)phenyl] amino}pyrimidin-4-yl)imidazo[1,2-a]pyridin-2-yl]phenyl}-2-(1,3-thiazol-5-yl)acetamide;

N-[3-(3-{2-[(3-{[4-(dimethylamino)piperidin-1-yl] methyl}phenyl)amino]pyrimidin-4-yl}imidazo[1,2-a]pyridin-2-yl)phenyl]-N'-phenylurea;

N-{3-[3-(2-{[4-(2,7-diazaspiro[4.4]non-2-yl)phenyl] amino}pyrimidin-4-yl)imidazo[1,2-a]pyridin-2-yl]phenyl}-2-thien-2-ylacetamide;

N-{3-[3-(2-{[4-(7-acetyl-2,7-diazaspiro[4.4]non-2-yl)phenyl]amino}pyrimidin-4-yl)imidazo[1,2-a]pyridin-2-yl] phenyl}-2,6-difluorobenzamide;

tert-butyl 7-(4-{[4-(2-{3-[(2,6-difluorobenzoyl)amino]phenyl}imidazo[1,2-a]pyridin-3-yl)pyrimidin-2-yl]amino}phenyl)-2,7-diazaspiro[4.4]nonane-2-carboxylate;
tert-butyl 7-(4-{[4-(2-{3-[(thien-2-ylacetyl)amino]phenyl}imidazo[1,2-a]pyridin-3-yl)pyrimidin-2-yl]amino}phenyl)-2,7-diazaspiro[4.4]nonane-2-carboxylate;
N-(3-{3-[2-({3-[2-(dimethylamino)ethyl]phenyl}amino)pyrimidin-4-yl]imidazo[1,2-a]pyridin-2-yl}phenyl)-5-methylthiophene-2-carboxamide;
N-(2,6-difluorophenyl)-N'-(3-{3-[2-({3-[2-(dimethylamino)ethyl]phenyl}amino)pyrimidin-4-yl]imidazo[1,2-a]pyridin-2-yl}phenyl)urea;
N-{3-[3-(2-{[4-(2,7-diazaspiro[4.4]non-2-yl)phenyl]amino}pyrimidin-4-yl)imidazo[1,2-a]pyridin-2-yl]phenyl}-2,6-difluorobenzamide;
3-[3-(2-{[4-(4-ethylpiperazin-1-yl)phenyl]amino}pyrimidin-4-yl)imidazo[1,2-a]pyridin-2-yl]-N-(2-fluorophenyl)benzamide;
3-[3-(2-{[4-(4-ethylpiperazin-1-yl)phenyl]amino}pyrimidin-4-yl)imidazo[1,2-a]pyridin-2-yl]-N-phenylbenzamide;
N-benzyl-3-[3-(2-{[4-(4-ethylpiperazin-1-yl)phenyl]amino}pyrimidin-4-yl)imidazo[1,2-a]pyridin-2-yl]benzamide;
2,6-difluoro-N-{3-[3-(2-{[3-(2-pyrrolidin-1-ylethoxy)phenyl]amino}pyrimidin-4-yl)imidazo[1,2-a]pyridin-2-yl]phenyl}benzamide;
2,6-difluoro-N-{3-[3-(2-{[3-(tetrahydrofuran-2-ylmethoxy)phenyl]amino}pyrimidin-4-yl)imidazo[1,2-a]pyridin-2-yl]phenyl}benzamide;
2-chloro-N-{3-[3-(2-{[3-(tetrahydrofuran-2-ylmethoxy)phenyl]amino}pyrimidin-4-yl)imidazo[1,2-a]pyridin-2-yl]phenyl}benzamide;
N-{3-[3-(2-{[3-(tetrahydrofuran-2-ylmethoxy)phenyl]amino}pyrimidin-4-yl)imidazo[1,2-a]pyridin-2-yl]phenyl}thiophene-2-carboxamide;
N-{3-[3-(2-{[3-(tetrahydrofuran-2-ylmethoxy)phenyl]amino}pyrimidin-4-yl)imidazo[1,2-a]pyridin-2-yl]phenyl}-2-thien-2-ylacetamide;
N-{3-[3-(2-{[3-(tetrahydrofuran-2-ylmethoxy)phenyl]amino}pyrimidin-4-yl)imidazo[1,2-a]pyridin-2-yl]phenyl}-N'-thien-2-ylurea;
2,6-difluoro-N-{3-[3-(2-{[3-(tetrahydrofuran-3-yloxy)phenyl]amino}pyrimidin-4-yl)imidazo[1,2-a]pyridin-2-yl]phenyl}benzamide;
2-chloro-N-{3-[3-(2-{[3-(tetrahydrofuran-3-yloxy)phenyl]amino}pyrimidin-4-yl)imidazo[1,2-a]pyridin-2-yl]phenyl}benzamide;
N-{3-[3-(2-{[3-(tetrahydrofuran-3-yloxy)phenyl]amino}pyrimidin-4-yl)imidazo[1,2-a]pyridin-2-yl]phenyl}-2-thien-2-ylacetamide;
N-[3-(3-{2-[(2-methyl-1,2,3,4-tetrahydroisoquinolin-7-yl)amino]pyrimidin-4-yl}imidazo[1,2-a]pyridin-2-yl)phenyl]-1,3-thiazole-2-carboxamide;
N-[3-(3-{2-[(2-methyl-1,2,3,4-tetrahydroisoquinolin-7-yl)amino]pyrimidin-4-yl}imidazo[1,2-a]pyridin-2-yl)phenyl]-1,3-thiazole-5-carboxamide;
4-bromo-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide;
4-bromo-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-3-carboxamide;
N-{3-[3-(2-{[3-(tetrahydrofuran-3-yloxy)phenyl]amino}pyrimidin-4-yl)imidazo[1,2-a]pyridin-2-yl]phenyl}-N'-thien-2-ylurea;
N-(3-{3-[2-({3-[(dimethylamino)sulfonyl]-4-methoxyphenyl}amino)pyrimidin-4-yl]imidazo[1,2-a]pyridin-2-yl}phenyl)-2,6-difluorobenzamide;
N-(3-{3-[2-({3-[(dimethylamino)sulfonyl]-4-methoxyphenyl}amino)pyrimidin-4-yl]imidazo[1,2-a]pyridin-2-yl}phenyl)-2-thien-2-ylacetamide;
N-(3-{3-[2-({4-[4-(dimethylamino)piperidin-1-yl]phenyl}amino)pyrimidin-4-yl]imidazo[1,2-a]pyridin-2-yl}phenyl)-2-thien-2-ylacetamide;
N-(3-{3-[2-({4-[4-(dimethylamino)piperidin-1-yl]phenyl}amino)pyrimidin-4-yl]imidazo[1,2-a]pyridin-2-yl}phenyl)-2,6-difluorobenzamide;
N-(3-{3-[2-({4-[4-(dimethylamino)piperidin-1-yl]phenyl}amino)pyrimidin-4-yl]imidazo[1,2-a]pyridin-2-yl}phenyl)-2-phenylacetamide;
2-chloro-N-(3-{3-[2-({4-[4-(dimethylamino)piperidin-1-yl]phenyl}amino)pyrimidin-4-yl]imidazo[1,2-a]pyridin-2-yl}phenyl)benzamide;
N-(3-{3-[2-({4-[4-(dimethylamino)piperidin-1-yl]phenyl}amino)pyrimidin-4-yl]imidazo[1,2-a]pyridin-2-yl}phenyl)thiophene-2-carboxamide;
N-(3-{3-[2-({4-[4-(dimethylamino)piperidin-1-yl]phenyl}amino)pyrimidin-4-yl]imidazo[1,2-a]pyridin-2-yl}phenyl)-4-methylthiophene-2-carboxamide;
1-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]-1H-pyrazole-3-carboxamide;
2-chloro-N-(3-{3-[2-({4-[2-(dimethylamino)ethyl]phenyl}amino)pyrimidin-4-yl]imidazo[1,2-a]pyridin-2-yl}phenyl)-3-fluorobenzamide;
N-(3-{3-[2-({4-[2-(dimethylamino)ethyl]phenyl}amino)pyrimidin-4-yl]imidazo[1,2-a]pyridin-2-yl}phenyl)-2-fluorobenzamide;
2-chloro-N-(3-{3-[2-({4-[2-(dimethylamino)ethyl]phenyl}amino)pyrimidin-4-yl]imidazo[1,2-a]pyridin-2-yl}phenyl)benzamide;
N-(3-{3-[2-({4-[2-(dimethylamino)ethyl]phenyl}amino)pyrimidin-4-yl]imidazo[1,2-a]pyridin-2-yl}phenyl)-2,3-difluorobenzamide;
N-(3-{3-[2-({4-[2-(dimethylamino)ethyl]phenyl}amino)pyrimidin-4-yl]imidazo[1,2-a]pyridin-2-yl}phenyl)-2,5-difluorobenzamide;
N-(3-{3-[2-({4-[2-(dimethylamino)ethyl]phenyl}amino)pyrimidin-4-yl]imidazo[1,2-a]pyridin-2-yl}phenyl)-3,5-difluorobenzamide;
N-(3-{3-[2-({4-[2-(dimethylamino)ethyl]phenyl}amino)pyrimidin-4-yl]imidazo[1,2-a]pyridin-2-yl}phenyl)-N'-phenylurea;
N-(3-{3-[2-({4-[1-(methoxyacetyl)piperidin-4-yl]phenyl}amino)pyrimidin-4-yl]imidazo[1,2-a]pyridin-2-yl}phenyl)-2-thien-2-ylacetamide;
2,6-difluoro-N-(3-{3-[2-({4-[1-(methoxyacetyl)piperidin-4-yl]phenyl}amino)pyrimidin-4-yl]imidazo[1,2-a]pyridin-2-yl}phenyl)benzamide;
N-(3-{3-[2-({3-[1-(methoxyacetyl)piperidin-4-yl]phenyl}amino)pyrimidin-4-yl]imidazo[1,2-a]pyridin-2-yl}phenyl)-2-thien-2-ylacetamide;
2,6-difluoro-N-(3-{3-[2-({3-[1-(methoxyacetyl)piperidin-4-yl]phenyl}amino)pyrimidin-4-yl]imidazo[1,2-a]pyridin-2-yl}phenyl)benzamide;
N-{3-[3-(2-{[4-(4-ethylpiperazin-1-yl)-3-fluorophenyl]amino}pyrimidin-4-yl)imidazo[1,2-a]pyridin-2-yl]phenyl}-2-thien-2-ylacetamide;
2-chloro-N-{3-[3-(2-{[4-(4-ethylpiperazin-1-yl)-3-fluorophenyl]amino}pyrimidin-4-yl)imidazo[1,2-a]pyridin-2-yl]phenyl}benzamide;

N-(3-{3-[2-({4-(1-(2-hydroxy-2-methylpropyl)piperidin-4-yl]phenyl}amino)pyrimidin-4-yl]imidazo[1,2-a]pyridin-2-yl}phenyl)-2-thien-2-ylacetamide;
N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)-2-thien-3-ylacetamide;
2,6-difluoro-N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)benzamide;
2-chloro-N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)benzamide;
N-(3-{3-[2-({3-[(N,N-dimethylglycyl)amino]phenyl}amino)pyrimidin-4-yl]imidazo[1,2-a]pyridin-2-yl}phenyl)-2,6-difluorobenzamide;
2-chloro-N-(3-{3-[2-({3-[(N,N-dimethylglycyl)amino]phenyl}amino)pyrimidin-4-yl]imidazo[1,2-a]pyridin-2-yl}phenyl)benzamide;
N-(3-{3-[2-({3-[(N,N-dimethylglycyl)amino]phenyl}amino)pyrimidin-4-yl]imidazo[1,2-a]pyridin-2-yl}phenyl)thiophene-2-carboxamide;
$N^2,N^2$-dimethyl-$N^1$-(3-{[4-(2-{3-[(thien-2-ylacetyl)amino]phenyl}imidazo[1,2-a]pyridin-3-yl)pyrimidin-2-yl]amino}phenyl)glycinamide;
2,6-difluoro-N-(3-{3-[2-({3-[(methoxyacetyl)amino]phenyl}amino)pyrimidin-4-yl]imidazo[1,2-a]pyridin-2-yl}phenyl)benzamide;
2-chloro-N-(3-{3-[2-({3-[(methoxyacetyl)amino]phenyl}amino)pyrimidin-4-yl]imidazo[1,2-a]pyridin-2-yl}phenyl)benzamide;
N-(3-{3-[2-({3-[(2-methoxyacetyl)amino]phenyl}amino)pyrimidin-4-yl]imidazo[1,2-a]pyridin-2-yl}phenyl)thiophene-2-carboxamide;
2-methoxy-N-(3-{[4-(2-{3-[(thien-2-ylacetyl)amino]phenyl}imidazo[1,2-a]pyridin-3-yl)pyrimidin-2-yl]amino}phenyl)acetamide;
2-methoxy-N-[3-{[4-[2-(3-{[(thien-2-ylamino)carbonyl]amino}phenyl)imidazo[1,2-a]pyridin-3-yl]pyrimidin-2-yl]amino)phenyl]acetamide;
N-(3-{3-[2-({4-[3-(dimethylamino)pyrrolidin-1-yl]phenyl}amino)pyrimidin-4-yl]imidazo[1,2-a]pyridin-2-yl}phenyl)-2,6-difluorobenzamide;
2-chloro-N-(3-{3-[2-({4-[3-(dimethylamino)pyrrolidin-1-yl]phenyl}amino)pyrimidin-4-yl]imidazo[1,2-a]pyridin-2-yl}phenyl)benzamide;
N-(3-{3-[2-({4-[3-(dimethylamino)pyrrolidin-1-yl]phenyl}amino)pyrimidin-4-yl]imidazo[1,2-a]pyridin-2-yl}phenyl)thiophene-2-carboxamide;
N-(3-{3-[2-({4-[3-(dimethylamino)pyrrolidin-1-yl]phenyl}amino)pyrimidin-4-yl]imidazo[1,2-a]pyridin-2-yl}phenyl)-2-thien-2-ylacetamide;
N-(3-{3-[2-({4-[3-(dimethylamino)pyrrolidin-1-yl]phenyl}amino)pyrimidin-4-yl]imidazo[1,2-a]pyridin-2-yl}phenyl)-N'-thien-2-ylurea;
2,6-difluoro-N-(3-{3-[2-({3-[2-(methylamino)-2-oxoethyl]phenyl}amino)pyrimidin-4-yl]imidazo[1,2-a]pyridin-2-yl}phenyl)benzamide;
N-(3-{3-[2-({3-[2-(methylamino)-2-oxoethyl]phenyl}amino)pyrimidin-4-yl]imidazo[1,2-a]pyridin-2-yl}phenyl)-2-phenylacetamide;
N-(3-{3-[2-({3-[2-(methylamino)-2-oxoethyl]phenyl}amino)pyrimidin-4-yl]imidazo[1,2-a]pyridin-2-yl}phenyl)-2-thien-2-ylacetamide;
N-(3-{3-[2-({3-[2-(dimethylamino)-2-oxoethyl]phenyl}amino)pyrimidin-4-yl]imidazo[1,2-a]pyridin-2-yl}phenyl)-2,6-difluorobenzamide;
N-(3-{3-[2-({3-[2-(dimethylamino)-2-oxoethyl]phenyl}amino)pyrimidin-4-yl]imidazo[1,2-a]pyridin-2-yl}phenyl)-2-phenylacetamide;
N-(3-{3-[2-({3-[2-(dimethylamino)-2-oxoethyl]phenyl}amino)pyrimidin-4-yl]imidazo[1,2-a]pyridin-2-yl}phenyl)-2-thien-2-ylacetamide;
N-{3-[3-(2-{[2-(dimethylamino)-2,3-dihydro-1H-inden-5-yl]amino}pyrimidin-4-yl)imidazo[1,2-a]pyridin-2-yl]phenyl}thiophene-2-carboxamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-4-methylthiophene-2-carboxamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-5-methylthiophene-2-carboxamide;
2-chloro-N-(3-{3-[2-({4-[2-(dimethylamino)ethyl]phenyl}amino)pyrimidin-4-yl]imidazo[1,2-a]pyridin-2-yl}phenyl)-5-fluorobenzamide;
2,6-difluoro-N-(3-{3-[2-({4-[2-(methylamino)ethyl]phenyl}amino)pyrimidin-4-yl]imidazo[1,2-a]pyridin-2-yl}phenyl)benzamide;
2-chloro-N-(3-{3-[2-({4-[2-(methylamino)ethyl]phenyl}amino)pyrimidin-4-yl]imidazo[1,2-a]pyridin-2-yl}phenyl)benzamide;
N-(3-{3-[2-({4-[2-(methylamino)ethyl]phenyl}amino)pyrimidin-4-yl]imidazo[1,2-a]pyridin-2-yl}phenyl)-2-phenylacetamide;
N-(3-{3-[2-({4-[2-(methylamino)ethyl]phenyl}amino)pyrimidin-4-yl]imidazo[1,2-a]pyridin-2-yl}phenyl)-2-thien-2-ylacetamide;
N-(3-{3-[2-({4-[2-(methylamino)ethyl]phenyl}amino)pyrimidin-4-yl]imidazo[1,2-a]pyridin-2-yl}phenyl)-N'-phenylurea;
N-(3-{3-[2-({4-[4-(dimethylamino)piperidin-1-yl]phenyl}amino)pyrimidin-4-yl]imidazo[1,2-a]pyridin-2-yl}phenyl)-2-methylbenzamide;
N-(3-{3-[2-({4-[4-(dimethylamino)piperidin-1-yl]phenyl}amino)pyrimidin-4-yl]imidazo[1,2-a]pyridin-2-yl}phenyl)-2-thien-3-ylacetamide;
N-(3-{3-[2-({4-[2-(dimethylamino)ethyl]phenyl}amino)-5-fluoropyrimidin-4-yl]imidazo[1,2-a]pyridin-2-yl}phenyl)-2,6-difluorobenzamide;
N-[3-(3-{2-[(4-piperidin-4-ylphenyl)amino]pyrimidin-4-yl}imidazo[1,2-a]pyridin-2-yl)phenyl]-2-thien-3-ylacetamide;
2-chloro-N-[3-(3-{2-[(4-piperidin-4-ylphenyl)amino]pyrimidin-4-yl}imidazo[1,2-a]pyridin-2-yl)phenyl]benzamide;
N-[3-(3-{2-[(3-piperidin-4-ylphenyl)amino]pyrimidin-4-yl}imidazo[1,2-a]pyridin-2-yl)phenyl]-2-thien-3-ylacetamide;
N-[3-(3-{2-[(3-piperidin-4-ylphenyl)amino]pyrimidin-4-yl}imidazo[1,2-a]pyridin-2-yl)phenyl]-2-thien-2-ylacetamide;
2-chloro-N-[3-(3-{2-[(3-piperidin-4-ylphenyl)amino]pyrimidin-4-yl}imidazo[1,2-a]pyridin-2-yl)phenyl]benzamide;
N-[3-(3-{2-[(3-piperidin-4-ylphenyl)amino]pyrimidin-4-yl}imidazo[1,2-a]pyridin-2-yl)phenyl]thiophene-2-carboxamide;
2-methyl-N-[3-(3-{2-[(3-piperidin-4-ylphenyl)amino]pyrimidin-4-yl}imidazo[1,2-a]pyridin-2-yl)phenyl]benzamide;
N-[3-(3-{2-[(3-piperidin-4-ylphenyl)amino]pyrimidin-4-yl}imidazo[1,2-a]pyridin-2-yl)phenyl]indoline-1-carboxamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2,6-difluorobenzamide;
N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2-thien-2-ylacetamide;
N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}thiophene-2-carboxamide;
N-[3-(3-{2-[(4-pyrrolidin-3-ylphenyl)amino]pyrimidin-4-yl}imidazo[1,2-a]pyridin-2-yl)phenyl]-2-thien-3-ylacetamide;
N-[3-(3-{2-[(4-pyrrolidin-3-ylphenyl)amino]pyrimidin-4-yl}imidazo[1,2-a]pyridin-2-yl)phenyl]-2-thien-2-ylacetamide;
2-chloro-N-[3-(3-{2-[(4-pyrrolidin-3-ylphenyl)amino]pyrimidin-4-yl}imidazo[1,2-a]pyridin-2-yl)phenyl]benzamide;
2,3-difluoro-N-[3-(3-{2-[(4-pyrrolidin-3-ylphenyl)amino]pyrimidin-4-yl}imidazo[1,2-a]pyridin-2-yl)phenyl]benzamide;
2,5-difluoro-N-[3-(3-{2-[(4-pyrrolidin-3-ylphenyl)amino]pyrimidin-4-yl}imidazo[1,2-a]pyridin-2-yl)phenyl]benzamide;
2-methyl-N-[3-(3-{2-[(4-pyrrolidin-3-ylphenyl)amino]pyrimidin-4-yl}imidazo[1,2-a]pyridin-2-yl)phenyl]benzamide;
2,6-dimethyl-N-[3-(3-{2-[(4-pyrrolidin-3-ylphenyl)amino]pyrimidin-4-yl}imidazo[1,2-a]pyridin-2-yl)phenyl]benzamide;
N-[3-(3-{2-[(4-pyrrolidin-3-ylphenyl)amino]pyrimidin-4-yl}imidazo[1,2-a]pyridin-2-yl)phenyl]thiophene-2-carboxamide;
N-(3-{3-[2-({4-[4-(dimethylamino)piperidin-1-yl]phenyl}amino)pyrimidin-4-yl]imidazo[1,2-a]pyridin-2-yl}phenyl)-2,3-difluorobenzamide;
N-(3-{3-[2-({4-[4-(dimethylamino)piperidin-1-yl]phenyl}amino)pyrimidin-4-yl]imidazo[1,2-a]pyridin-2-yl}phenyl)-2,5-difluorobenzamide;
2-chloro-N-(3-{3-[2-({4-[4-(dimethylamino)piperidin-1-yl]phenyl}amino)pyrimidin-4-yl]imidazo[1,2-a]pyridin-2-yl}phenyl)-5-fluorobenzamide;
N-(3-{3-[2-({4-[4-(dimethylamino)piperidin-1-yl]phenyl}amino)pyrimidin-4-yl]imidazo[1,2-a]pyridin-2-yl}phenyl)indoline-1-carboxamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-2,3-difluorobenzamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-2,5-difluorobenzamide;
2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}-5-fluorobenzamide;
N-{3-[3-{2-{[2-(dimethylamino)-2,3-dihydro-1H-inden-5-yl]amino]pyrimidin-4-yl)imidazo[1,2-a]pyridin-2-yl]phenyl}indoline-1-carboxamide;
N-(3-{3-[2-({3-[(dimethylamino)methyl]-4-methoxyphenyl}amino)pyrimidin-4-yl]imidazo[1,2-a]pyridin-2-yl}phenyl)-2,6-difluorobenzamide;
N-(3-{3-[2-({3-[(dimethylamino)methyl]-4-methoxyphenyl}amino)pyrimidin-4-yl]imidazo[1,2-a]pyridin-2-yl}phenyl)-2,3-difluorobenzamide;
N-(3-{3-[2-({3-[(dimethylamino)methyl]-4-methoxyphenyl}amino)pyrimidin-4-yl]imidazo[1,2-a]pyridin-2-yl}phenyl)-2-thien-2-ylacetamide;
N-(3-{3-[2-{(3-[(dimethylamino)methyl]-4-methoxyphenyl}amino)pyrimidin-4-yl]imidazo[1,2-a]pyridin-2-yl}phenyl)-N'-thien-2-ylurea;
N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]thiophene-2-carboxamide;
2,6-difluoro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide;
2-chloro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide;
N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]-N'-thien-2-ylurea;
N-[3-(3-{2-[(3-{2-[(3S)-3-fluoropyrrolidin-1-yl]ethyl}phenyl)amino]pyrimidin-4-yl}imidazo[1,2-a]pyridin-2-yl]phenyl}-N'-thien-3-ylurea;
N-[3-(3-{2-[(4-pyrrolidin-3-ylphenyl)amino]pyrimidin-4-yl}imidazo[1,2-a]pyridin-2-yl)phenyl]indoline-1-carboxamide;
N-ethyl-N-phenyl-N'-[3-(3-{2-[(4-pyrrolidin-3-ylphenyl)amino]pyrimidin-4-yl}imidazo[1,2-a]pyridin-2-yl)phenyl]urea;
N-[3-(3-{2-[(4-pyrrolidin-3-ylphenyl)amino]pyrimidin-4-yl}imidazo[1,2-a]pyridin-2-yl)phenyl]-1-benzothiophene-7-carboxamide;
N-(3-{3-[2-({4-[2-(dimethylamino)ethyl]phenyl}amino)-5-fluoropyrimidin-4-yl]imidazo[1,2-a]pyridin-2-yl}phenyl)-2-thien-2-ylacetamide;
2,6-difluoro-N-{3-[3-(2-{[4-(4-hydroxypiperidin-1-yl)phenyl]amino}pyrimidin-4-yl)imidazo[1,2-a]pyridin-2-yl]phenyl}benzamide;
2-chloro-N-{3-[3-(2-{[4-(4-hydroxypiperidin-1-yl)phenyl]amino}pyrimidin-4-yl)imidazo[1,2-a]pyridin-2-yl]phenyl}benzamide;
N-{3-[3-(2-{[4-(4-hydroxypiperidin-1-yl)phenyl]amino}pyrimidin-4-yl)imidazo[1,2-a]pyridin-2-yl]phenyl}thiophene-2-carboxamide;
N-{3-[3-(2-{[4-(4-hydroxypiperidin-1-yl)phenyl]amino}pyrimidin-4-yl)imidazo[1,2-a]pyridin-2-yl]phenyl}-2-thien-2-ylacetamide;
N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,6-difluorobenzamide;
2-chloro-N-[3-(3-{2-[(4-{2-[(N,N-dimethylglycyl)amino]ethyl}phenyl)amino]pyrimidin-4-yl}imidazo[1,2-a]pyridin-2-yl)phenyl]benzamide;
N-[3-(3-{2-[(4-{2-[(N,N-dimethylglycyl)amino]ethyl}phenyl)amino]pyrimidin-4-yl}imidazo[1,2-a]pyridin-2-yl)phenyl]thiophene-2-carboxamide;
$N^2,N^2$-dimethyl-$N^1$-[2-(4-{[4-[2-{3-[(thien-2-ylacetyl)amino]phenyl}imidazo[1,2-a]pyridin-3-yl)pyrimidin-2-yl]amino}phenyl)ethyl]glycinamide;
N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,3-difluorobenzamide;
N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,5-difluorobenzamide;
$N^2,N^2$-dimethyl-$N^1$-[2-(4-{[4-(2-{3-[(phenylacetyl)amino]phenyl}imidazo[1,2-a]pyridin-3-yl)pyrimidin-2-yl]amino}phenyl)ethyl]glycinamide;
2,6-difluoro-N-[3-(3-{2-[(4-{2-[(methoxyacetyl)amino]ethyl}phenyl)amino]pyrimidin-4-yl}imidazo[1,2-a]pyridin-2-yl)phenyl]benzamide;

2-methoxy-N-[2-(4-{[4-(2-{3-[(thien-2-ylacetyl)amino]
  phenyl}imidazo[1,2-a]pyridin-3-yl)pyrimidin-2-yl]
  amino}phenyl)ethyl]acetamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)thiophene-2-carboxamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2,6-difluorobenzamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2-chlorobenzamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2-fluorobenzamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2,3-difluorobenzamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2,5-difluorobenzamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2-chloro-5-fluorobenzamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2-phenylacetamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2-thien-2-ylacetamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-N'-phenylurea;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)indoline-1-carboxamide;
N-(3-{3-[2-({4-[2-(4-aminopiperidin-1-yl)ethyl]
  phenyl}amino)pyrimidin-4-yl]imidazo[1,2-a]pyridin-2-
  yl}phenyl)-2-chloro-3-fluorobenzamide;
N-[2-(4-{[4-(2-{3-[(2-thien-2-ylacetyl)amino]phenyl)imi-
  dazo[1,2-a]pyridin-3-yl)pyrimidin-2-yl]amino}phenyl)
  ethyl]cyclopropanecarboxamide;
N-[3-(3-{2-[(4-{2-[(cyclopropylcarbonyl)amino]
  ethyl}phenyl)amino]pyrimidin-4-yl}imidazo[1,2-a]pyri-
  din-2-yl)phenyl]-2,6-difluorobenzamide;
2-chloro-N-[3-(3-{2-[(4-{2-[(cyclopropylcarbonyl)amino]
  ethyl}phenyl)amino]pyrimidin-4-yl}imidazo[1,2-a]pyri-
  din-2-yl)phenyl]benzamide;
N-[3-(3-{2-[(4-{2-(cyclopropylcarbonyl)amino]
  ethyl}phenyl)amino]pyrimidin-4-yl}imidazo[1,2-a]pyri-
  din-2-yl)phenyl]thiophene-2-carboxamide;
2,6-difluoro-N-[3-(3-{2-[(4-{2-[(methylsulfonyl)amino]
  ethyl}phenyl)amino]pyrimidin-4-yl}imidazo[1,2-a]pyri-
  din-2-yl)phenyl]benzamide;
2-chloro-N-[3-(3-{2-[(4-{2-[(methylsulfonyl)amino]
  ethyl}phenyl)amino]pyrimidin-4-yl}imidazo[1,2-a]pyri-
  din-2-yl)phenyl]benzamide;
N-[3-(3-{2-[(4-{2-[(methylsulfonyl)amino]ethyl}phenyl)
  amino]pyrimidin-4-yl}imidazo[1,2-a]pyridin-2-yl)phe-
  nyl]thiophene-2-carboxamide;
N-[3-(3-{2-[(4-{2-[(methylsulfonyl)amino]ethyl}phenyl)
  amino]pyrimidin-4-yl}imidazo[1,2-a]pyridin-2-yl)phe-
  nyl]-2-thien-2-ylacetamide;
2-chloro-N-[3-(3-{2-[(4-{2-[(methoxyacetyl)amino]
  ethyl}phenyl)amino]pyrimidin-4-yl}imidazo[1,2-a]pyri-
  din-2-yl)phenyl]benzamide;
N-[3-(3-{2-[(4-{2-[(2-methoxyacetyl)amino]ethyl}phenyl)
  amino]pyrimidin-4-yl}imidazo[1,2-a]pyridin-2-yl)phe-
  nyl]thiophene-2-carboxamide;
N-(2,6-difluorophenyl)-3-[3-(2-{[4-(4-ethylpiperazin-1-yl)
  phenyl]amino}pyrimidin-4-yl)imidazo[1,2-a]pyridin-2-
  yl]benzamide;
2,6-difluoro-N-[3-(3-{2-[(4-{2-[(2-hydroxyethyl)(methyl)
  amino)ethyl}phenyl)amino]pyrimidin-4-yl}imidazo[1,2-
  a]pyridin-2-yl)phenylbenzamide;
2-chloro-N-[3-(3-{2-[(4-{2-[(2-hydroxyethyl)(methyl)
  amino)ethyl}phenyl)amino]pyrimidin-4-yl}imidazo[1,2-
  a]pyridin-2-yl)phenyl]benzamide;
3-{3-[2-({4-[2-(dimethylamino)ethyl]phenyl}amino)pyri-
  midin-4-yl]imidazo[1,2-a]pyridin-2-yl}-N-phenylbenza-
  mide;
3-{3-[2-({4-[2-(dimethylamino)ethyl]phenyl}amino)pyri-
  midin-4-yl]imidazo[1,2-a]pyridin-2-yl}-N-(2-fluorophe-
  nyl)benzamide;
3-{3-[2-({4-[2-(dimethylamino)ethyl]phenyl}amino)pyri-
  midin-4-yl]imidazo[1,2-a]pyridin-2-yl}-N-(3-fluorophe-
  nyl)benzamide;
3-{3-[2-({4-[2-(dimethylamino)ethyl]phenyl}amino)pyri-
  midin-4-yl]imidazo[1,2-a]pyridin-2-yl}-N-(4-fluorophe-
  nyl)benzamide;
N-cyclopentyl-3-(3-[2-({4-[2-(dimethylamino)ethyl]
  phenyl}amino)pyrimidin-4-yl]imidazo[1,2-a]pyridin-2-
  yl}benzamide;
N-cyclohexyl-3-{3-[2-({4-[2-(dimethylamino)ethyl]
  phenyl}amino)pyrimidin-4-yl]imidazo[1,2-a]pyridin-2-
  yl}benzamide;
N-{4-[2-(dimethylamino)ethyl]phenyl}-4-{2-[3-(piperidin-
  1-ylcarbonyl)phenyl]imidazo[1,2-a]pyridin-3-
  yl}pyrimidin-2-amine;
3-{3-[2-({4-[2-(dimethylamino)ethyl]phenyl}amino)pyri-
  midin-4-yl]imidazo[1,2-a]pyridin-2-yl}-N-(2-methylphe-
  nyl)benzamide;
N-(2-chlorophenyl)-3-{3-[2-({4-[2-(dimethylamino)ethyl]
  phenyl}amino)pyrimidin-4-yl]imidazo[1,2-a]pyridin-2-
  yl}benzamide;
3-{3-[2-({4-[2-(dimethylamino)ethyl]phenyl}amino)pyri-
  midin-4-yl]imidazo[1,2-a]pyridin-2-yl}-N-(2-methox-
  yphenyl)benzamide;
N-{4-[2-(dimethylamino)ethyl]phenyl}-4-{2-[3-(morpho-
  lin-4-ylcarbonyl)phenyl]imidazo[1,2-a]pyridin-3-
  yl}pyrimidin-2-amine;
N-[3-(3-{2-[(3-pyrrolidin-3-ylphenyl)amino]pyrimidin-4-
  yl}imidazo[1,2-a]pyridin-2-yl)phenyl]indoline-1-car-
  boxamide;
N-[3-(3-{2-[(3-pyrrolidin-3-ylphenyl)amino]pyrimidin-4-
  yl}imidazo[1,2-a]pyridin-2-yl)phenyl]-3,4-dihydroquino-
  line-1(2H)-carboxamide;
N-[3-(3-{2-[(3-pyrrolidin-3-ylphenyl)amino]pyrimidin-4-
  yl}imidazo[1,2-a]pyridin-2-yl)phenyl]-3,4-dihydroiso-
  quinoline-2(1H)-carboxamide;
4-{2-[3-(2,3-dihydro-1H-indol-1-ylcarbonyl)phenyl]imi-
  dazo[1,2-a]pyridin-3-yl}-N-{4-[2-(dimethylamino)ethyl]
  phenyl}pyrimidin-2-amine;
4-{2-[3-(1,3-dihydro-2H-isoindol-2-ylcarbonyl)phenyl]imi-
  dazo[1,2-a]pyridin-3-yl}-N-{4-[2-(dimethylamino)ethyl]
  phenyl}pyrimidin-2-amine;
N-{4-[2-(dimethylamino)ethyl]phenyl}-4-{2-[3-(pyrroli-
  din-1-ylcarbonyl)phenyl]imidazo[1,2-a]pyridin-3-
  yl}pyrimidin-2-amine;
N-{3-[3-(2-{[4-(1-acetylazetidin-3-yl)phenyl]
  amino}pyrimidin-4-yl)imidazo[1,2-a]pyridin-2-yl]phe-
  nyl}-2-chlorobenzamide;

N-{3-[3-(2-{[4-(1-acetylazetidin-3-yl)phenyl] amino}pyrimidin-4-yl)imidazo[1,2-a]pyridin-2-yl]phenyl}-2-thien-3-ylacetamide;
N-cyclohexyl-N'-(3-{3-[2-({3-[2-(dimethylamino)ethyl] phenyl}amino)pyrimidin-4-yl]imidazo[1,2-a]pyridin-2-yl}phenyl)urea;
N-(sec-butyl)-N'-(3-{3-[2-({3-[2-(dimethylamino)ethyl] phenyl}amino)pyrimidin-4-yl]imidazo[1,2-a]pyridin-2-yl}phenyl)urea;
N-(tert-butyl)-N'-(3-{3-[2-({3-[2-(dimethylamino)ethyl] phenyl}amino)pyrimidin-4-yl]imidazo[1,2-a]pyridin-2-yl}phenyl)urea;
N-(3-{3-[2-({3-[2-(dimethylamino)ethyl]phenyl}amino)pyrimidin-4-yl]imidazo[1,2-a]pyridin-2-yl}phenyl)-N'-isopropylurea;
N-cyclopentyl-N'-(3-{3-[2-({3-[2-(dimethylamino)ethyl] phenyl}amino)pyrimidin-4-yl]imidazo[1,2-a]pyridin-2-yl}phenyl)urea;
N-(3-{3-[2-({3-[2-(dimethylamino)ethyl]phenyl}amino)pyrimidin-4-yl]imidazo[1,2-a]pyridin-2-yl}phenyl)-N'-[(1S)-1,2-dimethylpropyl]urea;
N-(3-{3-[2-({3-[2-(dimethylamino)ethyl]phenyl}amino)pyrimidin-4-yl]imidazo[1,2-a]pyridin-2-yl}phenyl)-N'-[(1S)-1-phenylethyl]urea;
N-(3-{3-[2-({3-[2-(dimethylamino)ethyl]phenyl}amino)pyrimidin-4-yl]imidazo[1,2-a]pyridin-2-yl}phenyl)-N'-(3,5-dimethylisoxazol-4-yl)urea;
N-(3-{3-[2-({3-[2-(dimethylamino)ethyl]phenyl}amino)pyrimidin-4-yl]imidazo[1,2-a]pyridin-2-yl}phenyl)-N'-thien-2-ylurea;
N-(3-{3-[2-({3-[2-(dimethylamino)ethyl]phenyl}amino)pyrimidin-4-yl]imidazo[1,2-a]pyridin-2-yl}phenyl)-N'-(2-methylphenyl)urea;
N-(3-{3-[2-({3-[2-(dimethylamino)ethyl]phenyl}amino)pyrimidin-4-yl]imidazo[1,2-a]pyridin-2-yl}phenyl)indoline-1-carboxamide;
N-(3-{3-[2-({3-[2-(dimethylamino)ethyl]phenyl}amino)pyrimidin-4-yl]imidazo[1,2-a]pyridin-2-yl}phenyl)piperidine-1-carboxamide;
N-(3-{3-[2-({3-[2-(dimethylamino)ethyl]phenyl}amino)pyrimidin-4-yl]imidazo[1,2-a]pyridin-2-yl}phenyl)-N'-thien-3-ylurea;
N-(3-{3-[2-({3-[2-(dimethylamino)ethyl]phenyl}amino)pyrimidin-4-yl]imidazo[1,2-a]pyridin-2-yl}phenyl)morpholine-4-carboxamide;
2,3-dimethyl-N-[3-(3-{2-[(4-pyrrolidin-3-ylphenyl)amino]pyrimidin-4-yl}imidazo[1,2-a]pyridin-2-yl)phenyl]benzamide;
N-[3-(3-{2-[(4-pyrrolidin-2-ylphenyl)amino]pyrimidin-4-yl}imidazo[1,2-a]pyridin-2-yl)phenyl]-2-thien-2-ylacetamide;
2-chloro-N-[3-(3-{2-[(4-pyrrolidin-2-ylphenyl)amino]pyrimidin-4-yl}imidazo[1,2-a]pyridin-2-yl)phenyl]benzamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]-2,6-difluorobenzamide;
2-chloro-N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]benzamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]thiophene-2-carboxamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]-2-thien-2-ylacetamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]-2,3-difluorobenzamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]-2,5-difluorobenzamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]-2-phenylacetamide;
N-[3-(3-{2-[(3-{2-[3-(dimethylamino)pyrrolidin-1-yl] ethyl}phenyl)amino]pyrimidin-4-yl}imidazo[1,2-a]pyridin-2-yl)phenyl]-N'-phenylurea;
N-{3-[3-(2-{[4-(1-acetylazetidin-3-yl)phenyl] amino}pyrimidin-4-yl)imidazo[1,2-a]pyridin-2-yl] phenyl}indoline-1-carboxamide;
N-{3-[3-(2-{[2-(dimethylamino)-2,3-dihydro-1H-inden-5-yl]amino}pyrimidin-4-yl)imidazo[1,2-a]pyridin-2-yl] phenyl}-2,3-dimethylbenzamide;
N-(3-{3-[2-({4-[4-(dimethylamino)piperidin-1-yl] phenyl}amino)pyrimidin-4-yl]imidazo[1,2-a]pyridin-2-yl}phenyl)-2,3-dimethylbenzamide;
2-amino-N-[3-(3-{2-[(4-pyrrolidin-3-ylphenyl)amino]pyrimidin-4-yl}imidazo[1,2-a]pyridin-2-yl)phenyl]-2-thien-2-ylacetamide;
2-amino-N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-2-ylacetamide;
2-amino-N-(3-{3-[2-({4-[4-(dimethylamino)piperidin-1-yl] phenyl}amino)pyrimidin-4-yl]imidazo[1,2-a]pyridin-2-yl}phenyl)-2-thien-2-ylacetamide;
N-(3-{3-[2-({3-[2-(dimethylamino)ethyl]phenyl}amino)pyrimidin-4-yl]imidazo[1,2-a]pyridin-2-yl}phenyl)-N'-[(1R)-1-phenylethyl]urea;
N-(3-{3-[2-({3-[2-(dimethylamino)ethyl]phenyl}amino)pyrimidin-4-yl]imidazo[1,2-a]pyridin-2-yl}phenyl)-N'-(2-phenylcyclopropyl)urea;
N'-(3-{3-[2-({3-[2-(dimethylamino)ethyl]phenyl}amino)pyrimidin-4-yl]imidazo[1,2-a]pyridin-2-yl}phenyl)-N,N-dimethylurea;
N'-(3-{3-[2-({3-[2-(dimethylamino)ethyl]phenyl}amino)pyrimidin-4-yl]imidazo[1,2-a]pyridin-2-yl}phenyl)-N-methyl-N-phenylurea;
N-(3-{3-[2-({3-[2-(dimethylamino)ethyl]phenyl}amino)pyrimidin-4-yl]imidazo[1,2-a]pyridin-2-yl}phenyl)pyrrolidine-1-carboxamide;
N-{3-[3-(2-({3-[2-(dimethylamino)ethyl]phenyl}amino)pyrimidin-4-yl)-7-(trifluoromethyl)imidazo[1,2-a]pyridin-2-yl]phenyl}-2,6-difluorobenzamide;
N-{3-[3-(2-({3-[2-(dimethylamino)ethyl]phenyl}amino)pyrimidin-4-yl)-7-(trifluoromethyl)imidazo[1,2-a]pyridin-2-yl]phenyl}-2-thien-2-ylacetamide;
N-{3-[3-(2-({3-[2-(dimethylamino)ethyl]phenyl}amino)pyrimidin-4-yl)-7-(trifluoromethyl)imidazo[1,2-a]pyridin-2-yl]phenyl}-N'-phenylurea;
N-{3-[3-(2-({3-[2-(dimethylamino)ethyl]phenyl}amino)pyrimidin-4-yl)-7-(trifluoromethyl)imidazo[1,2-a]pyridin-2-yl]phenyl}-N'-[(1S)-1-phenylethyl]urea;
N-{3-[3-(2-{[4-(1-ethylpyrrolidin-2-yl)phenyl] amino}pyrimidin-4-yl)imidazo[1,2-a]pyridin-2-yl]phenyl}-2-thien-2-ylacetamide;
2-chloro-N-{3-[3-(2-{[4-(1-ethylpyrrolidin-2-yl)phenyl] amino}pyrimidin-4-yl)imidazo[1,2-a]pyridin-2-yl] phenyl}benzamide;
N-{3-[3-(2-{[4-(1-isopropylpyrrolidin-3-yl)phenyl] amino}pyrimidin-4-yl)imidazo[1,2-a]pyridin-2-yl]phenyl}-2-thien-3-ylacetamide;

N-{3-[3-(2-{[4-(1-isopropylpyrrolidin-3-yl)phenyl]
amino}pyrimidin-4-yl)imidazo[1,2-a]pyridin-2-yl]phe-
nyl}-2-thien-2-ylacetamide;
2-chloro-N-{3-[3-(2-{[4-(1-isopropylpyrrolidin-3-yl)phe-
nyl]amino}pyrimidin-4-yl)imidazo[1,2-a]pyridin-2-yl]
phenyl}benzamide;
2,3-difluoro-N-{3-[3-(2-{[4-(1-isopropylpyrrolidin-3-yl)
phenyl]amino}pyrimidin-4-yl)imidazo[1,2-a]pyridin-2-
yl]phenyl}benzamide;
N-{3-[3-(2-{[4-(1-isopropylpyrrolidin-3-yl)phenyl]
amino}pyrimidin-4-yl)imidazo[1,2-a]pyridin-2-yl]phe-
nyl}-N'-[(1S)-1-phenylethyl]urea;
N-(2-fluorophenyl)-3-{3-[2-({3-[2-(4-hydroxypiperidin-1-
yl)ethyl]phenyl}amino)pyrimidin-4-yl]imidazo[1,2-a]py-
ridin-2-yl}benzamide;
3-{3-[2-({3-[2-(4-hydroxypiperidin-1-yl)ethyl]
phenyl}amino)pyrimidin-4-yl]imidazo[1,2-a]pyridin-2-
yl}-N-phenylbenzamide;
N'-{3-[3-(2-{[4-(1-isopropylpyrrolidin-3-yl)phenyl]
amino}pyrimidin-4-yl)imidazo[1,2-a]pyridin-2-yl]phe-
nyl}-N,N-dimethylurea;
N'-{3-[3-(2-{[4-(1-isopropylpyrrolidin-3-yl)phenyl]
amino}pyrimidin-4-yl)imidazo[1,2-a]pyridin-2-yl]phe-
nyl}-N-methyl-N-phenylurea;
3-{3-[2-({3-[2-(4-hydroxypiperidin-1-yl)ethyl]
phenyl}amino)pyrimidin-4-yl]imidazo[1,2-a]pyridin-2-
yl}-N-thien-2-ylbenzamide;
N-(3-{3-[2-({3-[2-(dimethylamino)ethyl]phenyl}amino)py-
rimidin-4-yl]-8-fluoroimidazo[1,2-a]pyridin-2-
yl}phenyl)-2,6-difluorobenzamide;
N-(3-{3-[2-({3-[2-(dimethylamino)ethyl]phenyl}amino)py-
rimidin-4-yl]-8-fluoroimidazo[1,2-a]pyridin-2-
yl}phenyl)-2-phenylacetamide;
N-(3-{3-[2-({3-[2-(dimethylamino)ethyl]phenyl}amino)py-
rimidin-4-yl]-8-fluoroimidazo[1,2-a]pyridin-2-
yl}phenyl)-2-thien-2-ylacetamide;
N-(3-{3-[2-({3-[2-(dimethylamino)ethyl]phenyl}amino)py-
rimidin-4-yl]-8-fluoroimidazo[1,2-a]pyridin-2-
yl}phenyl)-N'-phenylurea;
N-{3-[3-(2-{[4-(1-isopropylpyrrolidin-3-yl)phenyl]
amino}pyrimidin-4-yl)imidazo[1,2-a]pyridin-2-yl]phe-
nyl}-3,4-dihydroquinoline-1(2H)-carboxamide;
N-benzyl-N'-{3-[3-(2-{[4-(1-isopropylpyrrolidin-3-yl)phe-
nyl]amino}pyrimidin-4-yl)imidazo[1,2-a]pyridin-2-yl]
phenyl)-N-methylurea;
N-benzyl-N-(2-cyanoethyl)-N'-{3-[3-(2-{[4-(1-isopropy-
lpyrrolidin-3-yl)phenyl]amino}pyrimidin-4-yl)imidazo
[1,2-a]pyridin-2-yl]phenyl}urea;
N'-{3-[3-(2-{[4-(1-isopropylpyrrolidin-3-yl)phenyl]
amino}pyrimidin-4-yl)imidazo[1,2-a]pyridin-2-yl]phe-
nyl}-N-methyl-N-[(1S)-1-phenylethyl]urea;
N-{3-[3-(2-{[4-(1-isopropylpyrrolidin-3-yl)phenyl]
amino}pyrimidin-4-yl)imidazo[1,2-a]pyridin-2-yl]phe-
nyl}-5-methylindoline-1-carboxamide;
N-(3-{3-[2-({3-[2-(dimethylamino)ethyl]phenyl}amino)py-
rimidin-4-yl]-6-fluoroimidazo[1,2-a]pyridin-2-
yl}phenyl)-N'-phenylurea;
N-(3-{3-[2-({3-[2-(dimethylamino)ethyl]phenyl}amino)py-
rimidin-4-yl]-6-fluoroimidazo[1,2-a]pyridin-2-
yl}phenyl)-2-thien-2-ylacetamide;
N-(3-{3-[2-({3-[2-(dimethylamino)ethyl]phenyl}amino)py-
rimidin-4-yl]-6-fluoroimidazo[1,2-a]pyridin-2-
yl}phenyl)-2,6-difluorobenzamide;
N-{3-[3-[2-({3-[2-(dimethylamino)ethyl]phenyl}amino)py-
rimidin-4-yl]-6-(trifluoromethyl)imidazo[1,2-a]pyridin-
2-yl]phenyl)-N'-phenylurea;
N-{3-[3-[2-({3-[2-(dimethylamino)ethyl]phenyl}amino)py-
rimidin-4-yl]-6-(trifluoromethyl)imidazo[1,2-a]pyridin-
2-yl]phenyl}-2-thien-2-ylacetamide;
N-{3-[3-[2-({3-[2-(dimethylamino)ethyl]phenyl}amino)py-
rimidin-4-yl]-6-(trifluoromethyl)imidazo[1,2-a]pyridin-
2-yl]phenyl)-2,6-difluorobenzamide; and salts, esters, amides, prodrugs and salts of esters, amides and prodrugs thereof.

Metabolites of compounds having Formula I produced by in vitro or in vivo metabolic processes may also have utility for treating diseases associated with overexpression or unregulation of a kinase.

Certain precursor compounds which may be metabolized in vitro or in vivo to form compounds having Formula I may also have utility for treating diseases associated with overexpression or unregulation of a kinase.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a mammal in a single dose or in divided doses is from about 0.001 to about 200 mg/kg body weight. Single dose compositions contain these amounts or a combination of submultiples thereof.

Compounds having Formula I may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having Formula I to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having Formula I to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having Formula I to be administered osmotically include, but are not limited to, chlorofluorohydrocarbons, ethanol, water, mixtures thereof and the like. Excipients for preparation of compositions comprising a compound having Formula I to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having Formula I to be administered rectally or vaginally include, but are not limited to, cocoa butter, polyethylene glycol, wax, mixtures thereof and the like.

Compounds of Formula I are expected to be useful to treat diseases involving overexpression or unregulation of a protein kinase family member such as but not limited to cancer. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula I would be useful in treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Compounds having Formula I are expected to be useful when used with alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, biologic response modifiers, cyclindependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPs) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Aurora kinase inhibitors include ABT-348, AZD-1152, MLN-8054, VX-680 and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMAThi (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARD10×ANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF I R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula I may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

To determine the binding of compounds having Formula I to representative protein tyrosine kinase receptors, the following assays were used:

EGFR Assay

EGFR (L858R) kinase activity was assayed by a homogenous time-resolved fluorescence (HTRF) in vitro kinase assay (Mathis, G., *HTRF(R) Technology*. J Biomol Screen, 1999. 4(6): p. 309-314). Specifically, 10 µL C-terminal GST-tagged, recombinant, human EGFR, amino acids 696-end containing the mutation L858R expressed by baculovirus in Sf21 cells (Millipore) was mixed with 10 ul inhibitor (various concentrations, 2% final DMSO) and 10 ul of ATP (50 µM final concentration) in reaction buffer (50 mM HEPES, pH 7.5, 10 mM MgCl$_2$, 2 mM MnCl$_2$, 0.1% BSA and 1 mM DTT, 40 µL final volume). The reaction was initiated by addition of 10 ul of biotinylated peptide substrate (Biotin-Ahx-AEEEY-FFLFA, 0.5 µM final concentration) in a black 384-well plate (Packard). After 60 minutes incubation at room temperature, the reaction was quenched by addition 60 µL stop/revelation buffer to give 30 mM EDTA, 1 µg/ml streptavidin-APC (Prozyme), 50 ng/ml anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the IC$_{50}$. Results (in nM) are shown in TABLE 1, wherein A=<0.010, B=0.010-0.049, C=0.050-0.100, D=0.101-2.00, E=>2.00.

TABLE 1

| Example | EGFR IC50 (nm) |
|---|---|
| 1 | A |
| 2 | A |
| 3 | C |
| 4 | A |
| 5 | B |
| 6 | B |
| 7 | C |
| 8 | A |
| 9 | A |
| 10 | B |
| 11 | B |
| 12 | B |
| 13 | B |
| 14 | A |
| 15 | B |
| 16 | A |
| 17 | A |
| 18 | A |
| 19 | A |
| 20 | A |
| 21 | D |
| 22 | B |
| 23 | B |
| 24 | B |
| 25 | B |
| 26 | A |
| 27 | A |
| 28 | A |
| 29 | A |
| 30 | B |
| 31 | C |
| 32 | C |
| 33 | A |
| 34 | B |
| 35 | B |
| 36 | C |
| 37 | A |
| 38 | B |
| 39 | B |
| 40 | C |
| 41 | B |
| 42 | B |
| 43 | A |
| 44 | A |
| 45 | A |
| 46 | B |
| 47 | B |
| 48 | A |
| 49 | A |
| 50 | B |
| 51 | B |
| 52 | A |
| 53 | A |
| 54 | B |
| 55 | B |
| 56 | A |
| 57 | B |
| 58 | C |
| 59 | A |
| 60 | B |
| 61 | C |
| 62 | A |
| 63 | B |
| 64 | B |
| 65 | A |

TABLE 1-continued

| Example | EGFR IC50 (nm) |
|---|---|
| 66 | B |
| 67 | C |
| 68 | D |
| 69 | D |
| 70 | A |
| 71 | B |
| 72 | B |
| 73 | A |
| 74 | C |
| 75 | C |
| 76 | B |
| 77 | B |
| 78 | A |
| 79 | B |
| 80 | A |
| 81 | B |
| 82 | B |
| 83 | C |
| 84 | B |
| 85 | B |
| 86 | D |
| 87 | A |
| 88 | B |
| 89 | A |
| 90 | B |
| 91 | C |
| 92 | A |
| 93 | B |
| 94 | B |
| 95 | B |
| 96 | A |
| 97 | A |
| 98 | A |
| 99 | A |
| 100 | B |
| 101 | B |
| 102 | A |
| 103 | B |
| 104 | A |
| 105 | B |
| 106 | A |
| 107 | A |
| 108 | A |
| 109 | B |
| 110 | A |
| 111 | A |
| 112 | A |
| 113 | A |
| 114 | A |
| 115 | A |
| 116 | A |
| 117 | A |
| 118 | B |
| 119 | A |
| 120 | B |
| 121 | B |
| 122 | A |
| 123 | B |
| 124 | A |
| 125 | B |
| 126 | B |
| 127 | A |
| 128 | A |
| 129 | A |
| 130 | D |
| 131 | B |
| 132 | B |
| 133 | A |
| 134 | A |
| 135 | B |
| 136 | A |
| 137 | C |
| 138 | C |
| 139 | A |
| 140 | B |
| 141 | C |
| 142 | A |
| 143 | B |
| 144 | B |
| 145 | B |
| 146 | A |
| 147 | A |
| 148 | B |
| 149 | A |
| 150 | B |
| 151 | D |
| 152 | B |
| 153 | A |
| 154 | A |
| 155 | A |
| 156 | A |
| 157 | B |
| 158 | B |
| 159 | B |
| 160 | C |
| 161 | E |
| 162 | B |
| 163 | A |
| 164 | C |
| 165 | E |
| 166 | A |
| 167 | D |
| 168 | A |
| 169 | B |
| 170 | C |
| 171 | B |
| 172 | A |
| 173 | A |
| 174 | B |
| 175 | B |
| 176 | C |
| 177 | D |
| 178 | A |
| 179 | A |
| 180 | B |
| 181 | A |
| 182 | B |
| 183 | A |
| 184 | A |
| 185 | D |
| 186 | B |
| 187 | D |
| 188 | A |
| 189 | A |
| 190 | A |
| 191 | A |
| 192 | A |
| 193 | A |
| 194 | D |
| 195 | A |
| 196 | A |
| 197 | A |
| 198 | A |
| 199 | A |
| 200 | B |
| 201 | D |
| 202 | C |
| 203 | A |
| 204 | C |
| 205 | A |
| 206 | B |
| 207 | A |
| 208 | B |
| 209 | A |
| 210 | A |
| 211 | A |
| 212 | A |
| 213 | A |
| 214 | A |
| 215 | B |
| 216 | A |
| 217 | A |

TABLE 1-continued

| Example | EGFR IC50 (nm) |
|---|---|
| 218 | A |
| 219 | D |
| 220 | C |
| 221 | A |
| 222 | A |
| 223 | A |
| 224 | B |
| 225 | B |
| 226 | A |
| 227 | B |
| 228 | B |
| 229 | B |
| 230 | C |
| 231 | B |
| 232 | A |
| 233 | B |
| 234 | A |
| 235 | A |
| 236 | A |
| 237 | A |
| 238 | A |
| 239 | B |
| 240 | B |
| 241 | A |
| 242 | A |
| 243 | A |
| 244 | D |
| 245 | A |
| 246 | B |
| 247 | B |
| 248 | A |
| 249 | A |
| 250 | A |
| 251 | B |
| 252 | A |
| 253 | B |
| 254 | A |
| 255 | B |
| 256 | B |
| 257 | A |
| 258 | A |
| 259 | A |
| 260 | A |
| 261 | B |
| 262 | A |
| 263 | A |
| 264 | A |
| 265 | A |
| 266 | B |
| 267 | A |
| 268 | A |
| 269 | A |
| 270 | B |
| 271 | A |
| 272 | A |
| 273 | D |
| 274 | D |
| 275 | B |
| 276 | B |
| 277 | A |
| 278 | D |
| 279 | D |
| 280 | B |
| 281 | D |
| 282 | A |
| 283 | B |
| 284 | B |
| 285 | B |
| 286 | B |
| 287 | B |
| 288 | A |
| 289 | B |
| 290 | B |
| 291 | C |
| 292 | A |
| 293 | B |

TABLE 1-continued

| Example | EGFR IC50 (nm) |
|---|---|
| 294 | B |
| 295 | A |
| 296 | B |
| 297 | A |
| 298 | A |
| 299 | A |
| 300 | A |
| 301 | A |
| 302 | A |
| 303 | B |
| 304 | A |
| 305 | A |
| 306 | B |
| 307 | A |
| 308 | A |
| 309 | C |
| 310 | B |
| 311 | B |
| 312 | B |
| 313 | A |
| 314 | A |
| 315 | B |
| 316 | B |
| 317 | B |
| 318 | C |
| 319 | A |
| 320 | A |
| 321 | A |
| 322 | B |
| 323 | A |
| 324 | B |
| 325 | D |
| 326 | D |
| 327 | D |
| 328 | D |
| 329 | A |
| 330 | A |
| 331 | B |
| 332 | D |
| 333 | B |
| 334 | B |
| 335 | C |
| 336 | B |
| 337 | B |
| 338 | D |
| 339 | B |
| 340 | C |
| 341 | D |
| 342 | D |
| 343 | D |
| 344 | D |
| 345 | D |
| 346 | D |
| 347 | B |
| 348 | D |
| 349 | B |
| 350 | D |
| 351 | B |
| 352 | D |
| 353 | C |
| 354 | D |
| 355 | A |
| 356 | B |
| 357 | A |
| 358 | A |
| 359 | A |
| 360 | A |
| 361 | A |
| 362 | A |
| 363 | A |
| 364 | A |
| 365 | B |
| 366 | B |
| 367 | A |
| 368 | A |
| 369 | C |

TABLE 1-continued

| Example | EGFR IC50 (nm) |
|---|---|
| 370 | D |
| 371 | C |
| 372 | D |
| 373 | B |
| 374 | D |
| 375 | C |
| 376 | D |
| 377 | A |
| 378 | D |
| 379 | D |
| 380 | D |
| 381 | C |
| 382 | A |
| 383 | B |
| 384 | B |
| 385 | A |
| 386 | A |
| 387 | C |
| 388 | B |
| 389 | B |
| 390 | D |
| 391 | D |
| 392 | B |
| 393 | A |
| 394 | D |
| 395 | D |
| 396 | D |
| 397 | C |
| 398 | D |
| 399 | D |
| 400 | D |
| 401 | D |
| 402 | D |
| 403 | D |
| 404 | A |
| 405 | C |
| 406 | B |
| 407 | A |

IGFR Assay

IGF1r kinase activity was assayed by a homogenous time-resolved fluorescence (HTRF) in vitro kinase assay (Mathis, G., *HTRF(R) Technology*. J Biomol Screen, 1999. 4(6): p. 309-314). Specifically, 10 µL C-terminal GST-tagged, recombinant, human IGF1r, amino acids 954-1367 expressed by baculovirus in Sf21 cells (Cell Signaling Technology) was mixed with 10 ul inhibitor (various concentrations, 2% final DMSO) and 10 ul of ATP (50 µM final concentration) in reaction buffer (50 mM HEPES, pH 7.5, 10 mM $MgCl_2$, 2 mM $MnCl_2$, 0.1% BSA and 1 mM DTT, 40 µL final volume). The reaction was initiated by addition of 10 ul of biotinylated peptide substrate (Biotin-Ahx-AEEEYFFLFA, 0.5 µM final concentration) in a black 384-well plate (Packard). After 60 minutes incubation at room temperature, the reaction was quenched by addition 60 µL stop/revelation buffer to give 30 mM EDTA, 1 µg/ml streptavidin-APC (Prozyme), 50 ng/ml anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the $IC_{50}$. Results (in nM) are shown in Table 2, wherein A=<0.010, B=0.010-0.049, C=0.050-0.100, D=0.101-2.00, E=>2.00.

TABLE 2

| Example | IGFIR IC 50 (nm) |
|---|---|
| 1 | D |
| 2 | C |
| 3 | D |
| 4 | D |
| 5 | C |
| 6 | B |
| 7 | C |
| 8 | D |
| 9 | D |
| 10 | D |
| 11 | D |
| 12 | E |
| 13 | E |
| 14 | D |
| 15 | D |
| 16 | D |
| 17 | D |
| 18 | C |
| 19 | B |
| 20 | D |
| 21 | D |
| 22 | D |
| 23 | B |
| 24 | C |
| 25 | D |
| 26 | D |
| 27 | D |
| 28 | D |
| 29 | B |
| 30 | B |
| 31 | D |
| 32 | D |
| 33 | E |
| 34 | E |
| 35 | D |
| 36 | E |
| 37 | D |
| 38 | B |
| 39 | A |
| 40 | C |
| 41 | B |
| 42 | A |
| 43 | D |
| 44 | D |
| 45 | D |
| 46 | C |
| 47 | B |
| 48 | C |
| 49 | B |
| 50 | A |
| 51 | D |
| 52 | C |
| 53 | D |
| 54 | A |
| 55 | A |
| 56 | D |
| 57 | B |
| 58 | A |
| 59 | D |
| 60 | B |
| 61 | B |
| 62 | D |
| 63 | B |
| 64 | A |
| 65 | D |
| 66 | B |
| 67 | B |
| 68 | B |
| 69 | D |
| 70 | E |
| 71 | D |
| 72 | D |
| 73 | D |
| 74 | C |
| 75 | B |
| 76 | D |

TABLE 2-continued

| Example | IGFIR IC 50 (nm) |
|---|---|
| 77 | A |
| 78 | D |
| 79 | B |
| 80 | D |
| 81 | B |
| 82 | C |
| 83 | D |
| 84 | A |
| 85 | C |
| 86 | D |
| 87 | D |
| 88 | D |
| 89 | D |
| 90 | B |
| 91 | D |
| 92 | E |
| 93 | D |
| 94 | B |
| 95 | D |
| 96 | D |
| 97 | D |
| 98 | A |
| 99 | A |
| 100 | B |
| 101 | B |
| 102 | D |
| 103 | A |
| 104 | D |
| 105 | B |
| 106 | A |
| 107 | C |
| 108 | B |
| 109 | E |
| 110 | D |
| 111 | C |
| 112 | B |
| 113 | A |
| 114 | D |
| 115 | D |
| 116 | D |
| 117 | D |
| 118 | D |
| 119 | D |
| 120 | D |
| 121 | A |
| 122 | D |
| 123 | B |
| 124 | D |
| 125 | B |
| 126 | D |
| 127 | C |
| 128 | D |
| 129 | B |
| 130 | D |
| 131 | A |
| 132 | B |
| 133 | D |
| 134 | D |
| 135 | D |
| 136 | D |
| 137 | C |
| 138 | B |
| 139 | E |
| 140 | D |
| 141 | B |
| 142 | D |
| 143 | E |
| 144 | B |
| 145 | B |
| 146 | D |
| 147 | D |
| 148 | B |
| 149 | D |
| 150 | C |
| 151 | B |
| 152 | B |

TABLE 2-continued

| Example | IGFIR IC 50 (nm) |
|---|---|
| 153 | D |
| 154 | A |
| 155 | B |
| 156 | D |
| 157 | A |
| 158 | B |
| 159 | C |
| 160 | B |
| 161 | E |
| 162 | A |
| 163 | E |
| 164 | E |
| 165 | D |
| 166 | C |
| 167 | B |
| 168 | C |
| 169 | B |
| 170 | B |
| 171 | D |
| 172 | D |
| 173 | E |
| 174 | D |
| 175 | E |
| 176 | C |
| 177 | D |
| 178 | E |
| 179 | D |
| 180 | B |
| 181 | D |
| 182 | D |
| 183 | D |
| 184 | C |
| 185 | D |
| 186 | D |
| 187 | B |
| 188 | A |
| 189 | D |
| 190 | B |
| 191 | B |
| 192 | B |
| 193 | C |
| 194 | E |
| 195 | C |
| 196 | C |
| 197 | D |
| 198 | B |
| 199 | B |
| 200 | B |
| 201 | D |
| 202 | A |
| 203 | D |
| 204 | B |
| 205 | D |
| 206 | B |
| 207 | D |
| 208 | A |
| 209 | A |
| 210 | B |
| 211 | C |
| 212 | C |
| 213 | D |
| 214 | B |
| 215 | A |
| 216 | D |
| 217 | D |
| 218 | D |
| 219 | C |
| 220 | C |
| 221 | C |
| 222 | C |
| 223 | C |
| 224 | A |
| 225 | B |
| 226 | D |
| 227 | D |
| 228 | A |

TABLE 2-continued

| Example | IGFIR IC 50 (nm) |
|---|---|
| 229 | E |
| 230 | D |
| 231 | B |
| 232 | C |
| 233 | D |
| 234 | C |
| 235 | B |
| 236 | D |
| 237 | D |
| 238 | B |
| 239 | A |
| 240 | C |
| 241 | D |
| 242 | A |
| 243 | D |
| 244 | D |
| 245 | B |
| 246 | B |
| 247 | B |
| 248 | C |
| 249 | B |
| 250 | D |
| 251 | D |
| 252 | D |
| 253 | B |
| 254 | D |
| 255 | B |
| 256 | B |
| 257 | D |
| 258 | D |
| 259 | C |
| 260 | D |
| 261 | E |
| 262 | D |
| 263 | B |
| 264 | C |
| 265 | D |
| 266 | D |
| 267 | C |
| 268 | C |
| 269 | D |
| 270 | D |
| 271 | D |
| 272 | C |
| 273 | B |
| 274 | C |
| 275 | D |
| 276 | D |
| 277 | D |
| 278 | D |
| 279 | D |
| 280 | C |
| 281 | D |
| 282 | D |
| 283 | B |
| 284 | D |
| 285 | D |
| 286 | D |
| 287 | B |
| 288 | D |
| 289 | D |
| 290 | D |
| 291 | B |
| 292 | D |
| 293 | D |
| 294 | D |
| 295 | D |
| 296 | C |
| 297 | D |
| 298 | D |
| 299 | D |
| 300 | D |
| 301 | C |
| 302 | C |
| 303 | D |
| 304 | B |

TABLE 2-continued

| Example | IGFIR IC 50 (nm) |
|---|---|
| 305 | A |
| 306 | C |
| 307 | D |
| 308 | C |
| 309 | C |
| 310 | E |
| 311 | E |
| 312 | E |
| 313 | E |
| 314 | E |
| 315 | E |
| 316 | B |
| 317 | E |
| 318 | D |
| 319 | B |
| 320 | D |
| 321 | D |
| 322 | B |
| 323 | B |
| 324 | B |
| 325 | D |
| 326 | D |
| 327 | C |
| 328 | E |
| 329 | D |
| 330 | C |
| 331 | D |
| 332 | E |
| 333 | D |
| 334 | C |
| 335 | D |
| 336 | E |
| 337 | D |
| 338 | E |
| 339 | D |
| 340 | C |
| 341 | D |
| 342 | D |
| 343 | D |
| 344 | D |
| 345 | D |
| 346 | D |
| 347 | B |
| 348 | E |
| 349 | B |
| 350 | C |
| 351 | D |
| 352 | D |
| 353 | D |
| 354 | E |
| 355 | D |
| 356 | A |
| 357 | D |
| 358 | D |
| 359 | D |
| 360 | B |
| 361 | B |
| 362 | B |
| 363 | C |
| 364 | B |
| 365 | C |
| 366 | E |
| 367 | D |
| 368 | D |
| 369 | D |
| 370 | D |
| 371 | D |
| 372 | D |
| 373 | D |
| 374 | E |
| 375 | D |
| 376 | D |
| 377 | E |
| 378 | D |
| 379 | D |
| 380 | D |

TABLE 2-continued

| Example | IGFIR IC 50 (nm) |
|---|---|
| 381 | A |
| 382 | D |
| 383 | A |
| 384 | A |
| 385 | D |
| 386 | B |
| 387 | B |
| 388 | B |
| 389 | C |
| 390 | E |
| 391 | B |
| 392 | D |
| 393 | D |
| 394 | D |
| 395 | C |
| 396 | D |
| 397 | B |
| 398 | D |
| 399 | E |
| 400 | D |
| 401 | D |
| 402 | C |
| 403 | A |
| 404 | D |
| 405 | E |
| 406 | D |
| 407 | E |

This data demonstrates the utility of compounds having Formula I as protein kinase inhibitors and are therefore expected to have utility in treatment of diseases involving overexpression or unregulation of a protein kinase family member.

Involvement of protein kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer are reported in Endocrine Rev. 21, 215 (2000), Br. J. Cancer 92, 1467 (2005), Cytokine Growth Factor Rev. 7, 133 (1996) and Biochem. Pharm. 51, 1101 (1996) (IGF1R-1); Biochem. Biophys. Acta 1198, 165 (1994), New Eng. J. Med. 344,783 (2001) (ErbB2); Cancer Metastasis Rev. 22, 337 (2003), J. Clin. Invest. 91, 53 (1993) and BBRC 243,503 (1998) (SRC-1); Science 279, 577 (1998) and NELM 344, 1038 (2001).

Involvement of IGF and IGFR in cancer is reported in Nature Reviews Cancer 8, 915 (2008).

Involvement of EGFR in cancer is reported in Annals of Oncology 18 (Supplement 6): vi35-vi41, 2007.

Schemes and Experimentals

Compounds having Formula I may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo(3.3.1)nonane; Cp means cyclopentadiene; $(DHQD)_2PHAL$ means hydroquinidine 1,4-phthalazinediyl diethyl ether; DBU means 1,8-diazabicyclo (5.4.0)undec-7-ene; DCC means dicyclohexylcarbodiimide; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppa means diphenylphosphoryl azide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); MP-BH$_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TDA-1 means tris(2-(2-methoxyethoxy)ethyl)amine; TEA means triethylamine; TFA means trifluoroacetic acid; THF means tetrahydrofuran; NCS means N-chlorosuccin imide; NMM means N-methylmorpholine; NMP means N-methylpyrrolidine; PPh$_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

SCHEME 1

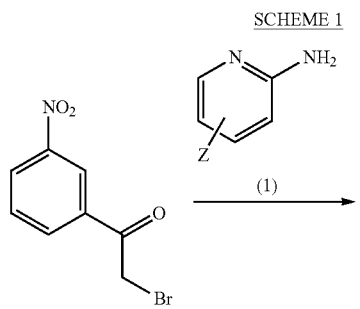

(1)

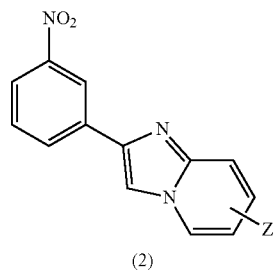

(2)

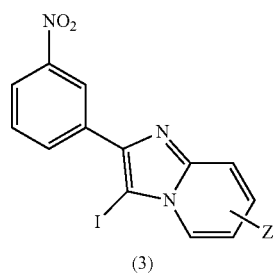

(3)

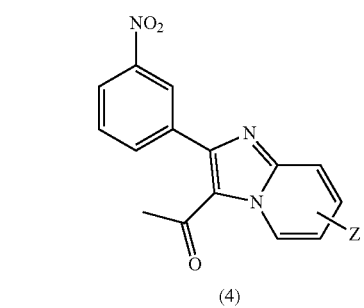

(4)

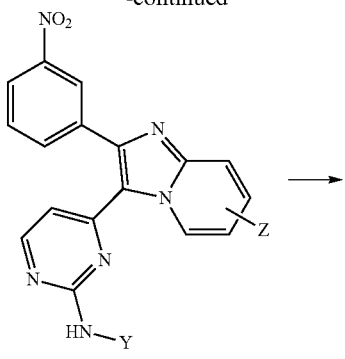

(5)

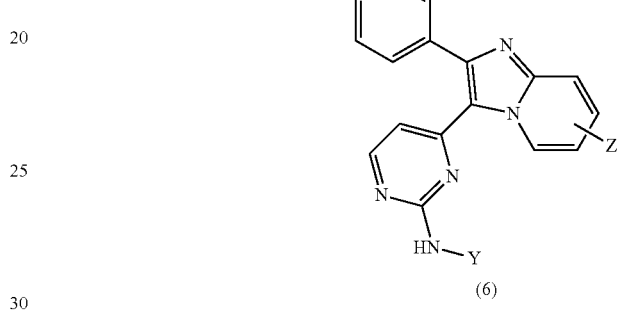

(6)

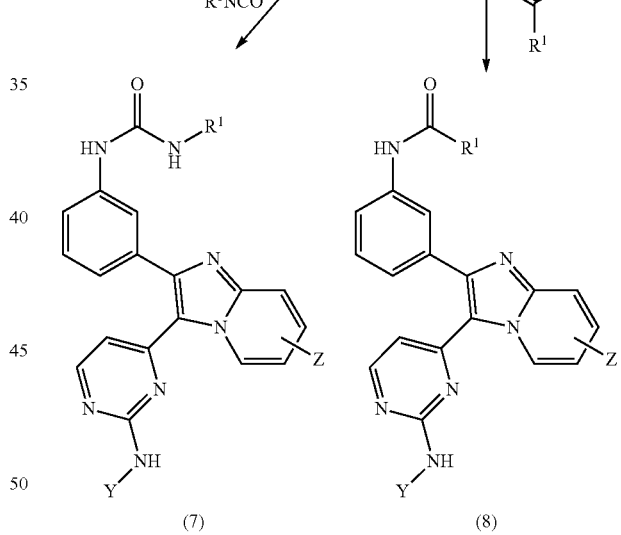

(7)                    (8)

As shown in SCHEME 1, amines of formula (1) when reacted with 2-bromo-1-(3-nitrophenyl)ethanone and a base such as but not limited to sodium bicarbonate, will provide compounds of formula (2) wherein Z is as described herein. The reaction is typically performed in a solvent such as but not limited to ethanol. Compounds of formula (3) can be prepared from compounds of formula (2) using N-iodosuccinimide in a solvent such as but not limited to N,N-dimethylformamide. Compounds of formula (3) in a solvent such as DMF can be reacted with tributyl(1-ethoxyvinyl)stannane, and catalyst such as but not limited to bis(triphenylphosphine)palladium(II) chloride, followed by treatment with an acid such as HCl to provide compounds of formula (4). Heat is typically employed in the first step. Compounds of formula (4A) can be prepared form compounds of formula (4) using N,N-dimethylformamide di-tert-butyl acetal and heat. The reaction is typically performed in a solvent such as but not limited to N-methyl-2-pyrrolidinone. Compounds of formula (5) can be prepared by reacting compounds of formula (4A) with compounds of formula (4B) wherein Y is as described herein, using a base such as but not limited to potassium carbonate. Compounds of formula (5) can be reduced to compounds of formula (6) using iron under acidic conditions, in a solvent such as ethanol, water, and the like or mixtures thereof. Alternatively, compounds of formula (5) can be reduced to amines of formula (6) using a method chosen from those widely available in the literature and known to those skilled in the art.

Ureas of formula (7), which are representative of the compounds of this invention, can be prepared from an amine of formula (6) and an icocyanate, $R^1NCO$, using methods widely available in the literature, known to those skilled in the art, as well as those methods described herein. Also, amides of formula (8), which are representative of the compounds of this invention, can be prepared from an amine of formula (6) and an acid chloride, $R^1COCl$, using methods widely available in the literature, known to those skilled in the art, as well as those methods described herein.

SCHEME 2

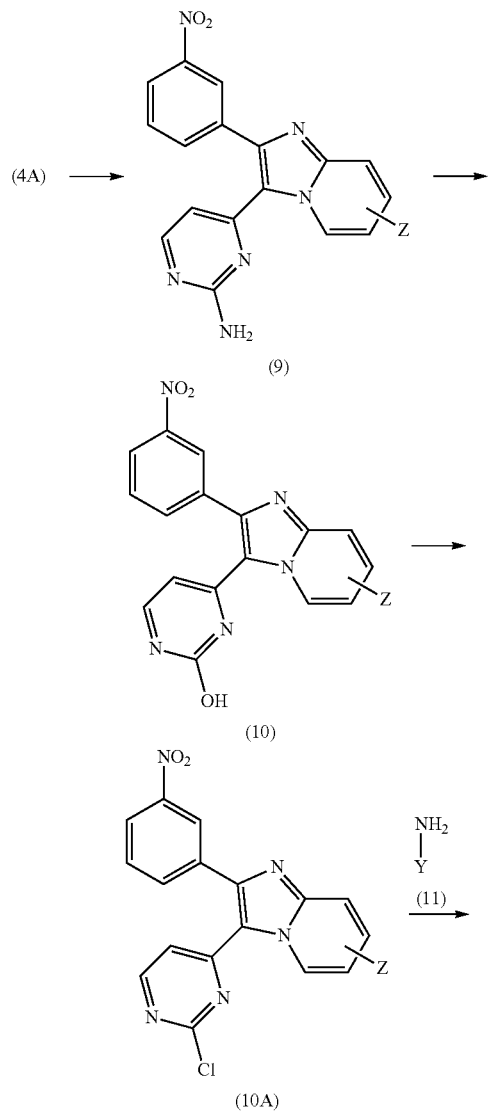

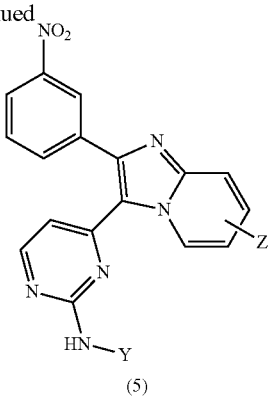

As shown in SCHEME 2, compounds of formula (9) can be prepared from compounds of formula (4A) using guanidine hydrochloride and a base such as but not limited to potassium carbonate. The reaction is typically performed with heat in a solvent such as but not limited to N-methyl-2-pyrrolidinone. Amines of formula (9) can be reacted with sodium nitrite in acetic acid and water to provide compounds of formula (10). The reaction typically employs the use of heat. Compounds of formula (10A) can be prepared form compounds of formula (10) using $POCl_3$ and heat. An amine of formula (11) can be reacted with a compound of formula (10A) to provide a compound of formula (5), which can be used as described in SCHEME 1 to prepare compounds of this invention. The reaction can be performed at elevated temperatures in a microwave using an acid such as HCl in a solvent such as but not limited to 2-propanol.

SCHEME 3

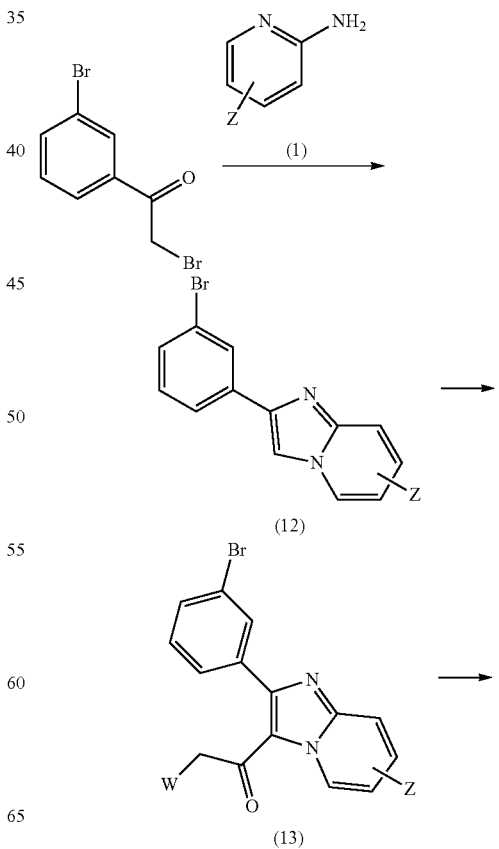

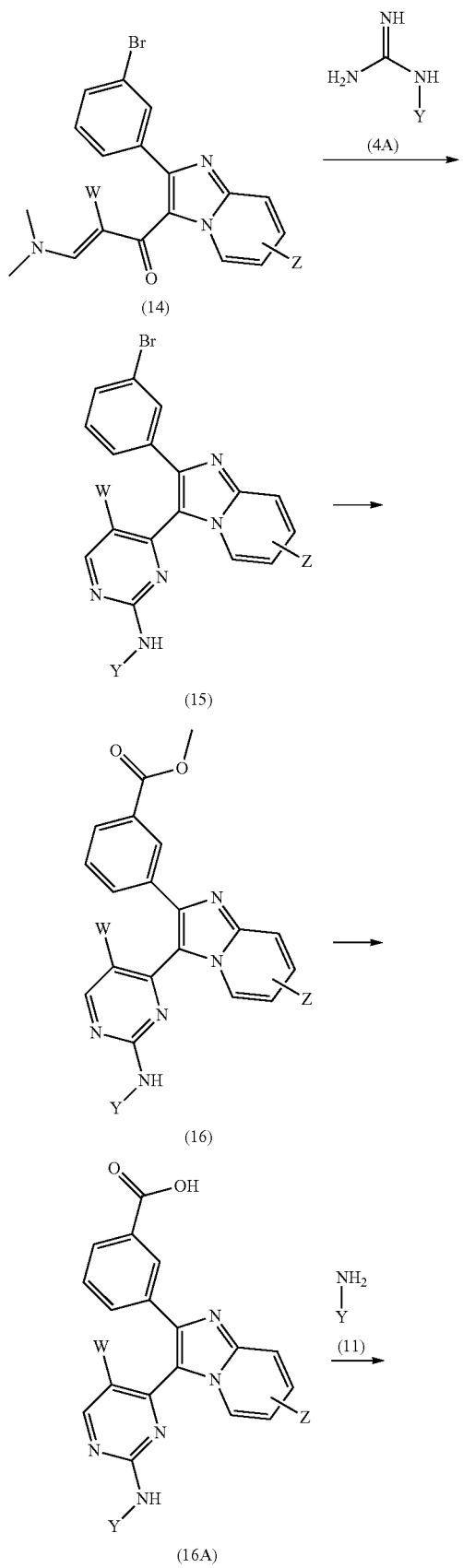
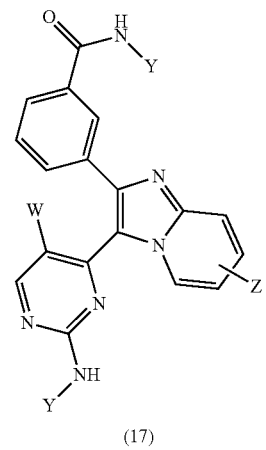

As shown in SCHEME 3, 2-bromo-1-(3-bromophenyl)ethanone can be reacted with an amine of formula (1) wherein Z is as described herein, to provide a compound of formula (12). The reaction typically requires the use of heat and is typically performed in a solvent such as but not limited to N,N-dimethylformamide. Compounds of formula (13), wherein W is H, can be prepared from compounds of formula (12) using sulfuric acid and acetic anhydride. The reaction is typically performed at elevated temperatures. Compounds of formula (13) wherein W is a halide can be prepared from compounds of formula (13), wherein W is H, as described herein. Compounds of formula (13), wherein W is H or a halide, can be reacted with 1,1-di-tert-butoxy-N,N-dimethylmethanamine with heat in a solvent such as N-methyl-2-pyrrolidinone to provide compounds of formula (14). Compounds of formula (4A), wherein Y is as described herein, can be reacted with compounds of formula (14) to provide compounds of formula (15). The reaction is typically performed in a solvent such as but not limited to N-methyl-2-pyrrolidinone, with heat. Bromides of formula (15) can be reacted with carbon monoxide, methanol, a base such as but not limited to triethylamine, and a catalyst such as but not limited to 1,1'-bis(diphenylphosphino)ferrocene palladium dichloride with heat to provide esters of formula (16). Carboxylic acids of formula (16A) can be prepared from esters of formula (16) using lithium hydroxide hydrate with heat in a solvent such as but not limited to ethanol. Amides of formula (17), which are representative of the compounds of this invention, can be prepared from acids of formula (16A) and amines of formula (11), using coupling conditions known to those skilled in the art and widely available in the literature.

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), or ChemDraw® Ver. 9.0.5 (CambridgeSoft, Cambridge, Mass.). Intermediates were named using ChemDraw®Ver. 9.0.5 (CambridgeSoft, Cambridge, Mass.).

Example 1

2,6-difluoro-N-[3-(3-{2-[(3-morpholin-4-ylphenyl)amino]pyrimidin-4-yl}imidazo[1,2-a]pyridin-2-yl)phenyl]benzamide

Example 1A

A 250 mL round bottom flask was charged 2-bromo-1-(3-nitrophenyl)ethanone (10 g, 41.0 mmol) and ethanol (60 mL). The suspension was heated at 90° C. until a homogeneous solution formed. The flask was removed from the heating bath and was immediately treated with pyridin-2-amine (3.95 g, 42.0 mmol) and sodium bicarbonate (5.37 g, 63.9 mmol) with vigorous stirring. The mixture was stirred at room temperature for 4 hours. The reaction was diluted with 250 mL water and the suspension was stirred for 30 minutes and filtered. The solid collected was washed with water (2×40 mL) and ether (2×75 mL). The solid was dissolved in 10% methanol/dichloromethane (350 mL), and the resulting solution was dried over $MgSO_4$, filtered, and concentrated to provide the title compound. MS (ESI(+)) m/e 239.8 $(M+H)^+$.

Example 1B

A 500 mL round bottom flask was charged with EXAMPLE 1A (6.55 g, 27.4 mmol) and N,N-dimethylformamide (165 mL). The mixture was heated at 90° C. until a homogeneous solution formed, which was then was allowed to cool to room temperature. N-iodosuccinimide (6.71 g, 29.8 mmol) was added and the reaction was allowed to stir at room temperature for 4 hours. 500 mL water was added to the reaction and the mixture was stirred at room temperature for 16 hours. The suspension was filtered and the collected solid was washed with water (2×130 mL) and ether (2×60 mL). The solid was air dried briefly on the filter and dissolved in 12% methanol/dichloromethane (600 mL). The organic layer was dried over $MgSO_4$, filtered, and concentrated to provide the title compound. MS (ESI(+)) m/e 365.8 $(M+H)^+$.

Example 1C

A 250 mL round bottom flask was charged with EXAMPLE 1B (9.84 g, 26.9 mmol), tributyl(1-ethoxyvinyl)stannane (10.71 g, 29.6 mmol), bis(triphenylphosphine)palladium(II) chloride (0.946 g, 1.347 mmol) and toluene (165 mL) and the resulting mixture was heated with stirring at 110° C. for 27 hours. The reaction mixture was filtered and concentrated to give the crude enol ether. The concentrate was diluted with methanol (48 mL) and 3M HCl (44.9 mL, 135 mmol) was added. The reaction mixture was stirred at ambient temperature for 16 hours. Water (50 mL) was added and the mixture was stirred for 10 minutes. The mixture was filtered and the solid was washed with 2×50 mL ether. The solid was suspended in 700 mL 10% methanol/dichloromethane and 5% aq. $Na_2CO_3$ (200 mL) was added. The biphasic mixture was stirred for 1 hour. The organic layer was separated, dried over $MgSO_4$, filtered and concentrated to provide the title compound. MS (ESI(+)) m/e 281.8 $(M+H)^+$.

Example 1D

A mixture of 1-(2-(3-nitrophenyl)imidazo[1,2-a]pyridin-3-yl)ethanone (7.2 g, 25.6 mmol) in N-methyl-2-pyrrolidinone (27.7 mL) was treated with N,N-dimethylformamide di-tert-butyl acetal (30.7 mL, 128 mmol) and the resulting solution was stirred at 90° C. for 1.5 hours. The reaction was concentrated under high vacuum on a rotary evaporator at 50° C. to remove residual N,N-dimethylformamide di-tert-butyl acetal. The concentrate was treated with 200 mL ether and the resulting suspension was stirred for 24 hours at ambient temperature. The mixture was filtered and the collected solid was washed with ether (2×60 mL) and dried to provide the title compound. MS (ESI(+)) m/e 336.98 $(M+H)^+$.

Example 1E

A 250 mL round-bottomed flask was charged with 3-morpholinoaniline (5.029 g, 28.2 mmol), 2,2,10,10-tetramethyl-6-thioxo-3,9-dioxa-5,7-diazaundecane-4,8-dione (8.58 g, 31.0 mmol), 1-ethyl-3-[3-(dimethylamino)propyl]-carbodiimide hydrochloride (5.95 g, 31.0 mmol) and triethylamine (5.90 ml, 42.3 mmol) in dichloromethane (100 ml) to give a brown solution. The reaction was stirred at room temperature for 18 hours. The reaction was diluted with water, the layers were separated, and the organic phase was adsorbed onto silica gel. The residue was purified by flash chromatography on a 40 g silica gel column using an AnaLogix IntelliFlash 280 system eluting with a gradient of 0% to 2% methanol in dichloromethane to provide the title compound. MS (ESI(+)) m/e 421.1 $(M+H)^+$.

Example 1F

Into a 500 mL round-bottomed flask was charged EXAMPLE 1E (10.58 g, 25.2 mmol) and $CH_2Cl_2$ (35 mL). The resulting solution was treated with 4M hydrochloric acid in dioxane (75.0 mL, 302 mmol). The reaction was stirred at room temperature for 72 hours. The suspension was treated with ether (200 mL) and the mixture stirred for 2 hours. The ether supernatant was decanted from the solids. The solids were triturated with ether (100 mL). The suspension was filtered and the solid was washed with ether and ethyl acetate. The solid was dried to constant weight to provide the title compound. MS DCI(+)) m/e 221.1 $(M+^{14})^+$.

Example 1G

Into a 50 mL round bottom flask was charged EXAMPLE 1D (1 g, 2.97 mmol), EXAMPLE 1F (0.84 g, 3.27 mmol) and potassium carbonate (0.863 g, 6.24 mmol). N-Methyl-2-pyrrolidinone (11 mL) was added and the resulting suspension was heated at 90° C. for 10 hours. Additional EXAMPLE 1F (0.916 g, 3.6 mmol) and potassium carbonate (0.658 g, 4.77 mmol) were added and the suspension was heated for 72 hours. The reaction was cooled to room temperature and was treated with 125 mL water. The suspension was stirred 20 minutes and filtered. The collected solid was washed with water and then ether. The solid was allowed to dry on the filter under vacuum for 24 hours. The solid was dissolved in 40 mL hot 10% methanol/$CHCl_3$ and adsorbed onto silica gel. The residue was purified by flash chromatography on a 10 silica gel column eluting with a gradient of 0% to 5% methanol in $CH_2Cl_2$ to provide the title compound. MS ESI(+)) m/e 494.1 $(M+H)^+$.

Example 1H

Into a 100 mL round bottom flask was charged EXAMPLE 1G (0.85 g, 1.72 mmol), iron (0.962 g, 17.22 mmol), ammonium chloride (0.092 g, 1.722 mmol), ethanol (13 ml) and water (3.2 ml). The reaction was heated to 90° C. for 2.5 hours. The reaction mixture was filtered while hot and the collected solid was washed with 2×40 mL ethyl acetate and 15 mL methanol. The combined filtrate was washed with water and brine. The organic layer was dried over $Na_2SO_4$, filtered, and concentrated to provide the title compound. MS ESI(+)) m/e 464.1 (M+H)$^+$.

Example 1I

Into a 4 mL vial was charged EXAMPLE 1H (50 mg, 0.108 mmol) and tetrahydrofuran (1 mL). The solution was treated with 2,6-difluorobenzoyl chloride (0.019 g, 0.108 mmol) and a suspension formed. The mixture was allowed to stir at room temperature for 18 hours. The reaction was partitioned between ethyl acetate and 5% aq. $Na_2CO_3$. The organic layer was washed with brine, dried over $Na_2SO_4$, filtered, and concentrated. The concentrate was purified by reverse phase HPLC on a Shimadzu LC10 HPLC system with a Phenominex Luna 10 micron C18(2) 100 150×30 mm column, eluting with a gradient of 25-65% $CH_3CN$/water/0.1% trifluoroacetic acid to provide the title compound. MS ESI(+)) m/e 604.2 (M+H)$^+$; $^1$H NMR (300 MHz, dimethylsulfoxide-$d_6$) δ ppm 10.94 (s, 1 H) 9.70 (s, 1 H) 9.54 (d, J=6.44 Hz, 1 H) 8.40 (d, J=5.09 Hz, 1 H) 8.07-8.10 (m, 1 H) 7.77-7.85 (m, 2 H) 7.55-7.68 (m, 2 H) 7.39-7.52 (m, 3 H) 7.12-7.28 (m, 5 H) 6.68 (d, J=5.09 Hz, 1 H) 6.61 (dd, J=7.63, 1.86 Hz, 1 H) 3.68-3.72 (m, 4 H) 3.02-3.06 (m, 4 H).

Example 2

N-[3-(3-{2-[(3-morpholin-4-ylphenyl)amino]pyrimidin-4-yl}imidazo[1,2-a]pyridin-2-yl)phenyl]-2-phenylacetamide The title compound was prepared as described in EXAMPLE 1I, substituting phenylacetyl chloride for 2,6-difluorobenzoyl chloride. MS (ESI(+)) m/e 582.3 (M+H)$^+$; $^1$H NMR (300 MHz, METHANOL-$d_4$) δ ppm 9.79 (d, J=6.78 Hz, 1 H) 8.32 (d, J=5.43 Hz, 1 H) 8.09-8.12 (m, 1 H) 7.89-8.00 (m, 2 H) 7.65-7.69 (m, 1 H) 7.54 (t, J=7.63 Hz, 1 H) 7.39-7.44 (m, 3 H) 7.14-7.34 (m, 7 H) 6.77 (dd, J=7.63, 1.86 Hz, 1 H) 6.68 (d, J=5.09 Hz, 1 H) 3.79-3.82 (m, 4 H) 3.69 (s, 2 H) 3.14-3.17 (m, 4 H).

Example 3

N-[3-(3-{2-[(3-morpholin-4-ylphenyl)amino]pyrimidin-4-yl}imidazo[1,2-a]pyridin-2-yl)phenyl]-N'-phenylurea Into a 4 mL vial was charged EXAMPLE 1H (50 mg, 0.108 mmol) and tetrahydrofuran (1 mL). The solution was treated with phenylisocyanate (0.013 g, 0.108 mmol) and the reaction was allowed to stir at ambient temperature for 16 hours. The reaction was concentrated and the residue was purified by reverse-phase HPLC on a Shimadzu LC10 HPLC system with a Phenominex Luna 10 micron C18(2) 100 150×30 mm column, eluting with a gradient of 25-65% $CH_3CN$/water/ 0.1% trifluoroacetic acid to provide the title compound. MS (ESI(+)) m/e 583.3 (M+H)$^+$; $^1$H NMR (300 MHz, dimethylsulfoxide-$d_6$) δ ppm 9.71 (s, 1 H) 9.58 (d, J=6.78 Hz, 1 H) 8.87 (s, 1 H) 8.68 (s, 1 H) 8.41 (d, J=5.09 Hz, 1 H) 7.81-7.88 (m, 2 H) 7.65-7.71 (m, 1 H) 7.53-7.58 (m, 1 H) 7.38-7.47 (m, 4 H) 7.13-7.29 (m, 6 H) 6.97 (t, J=7.29 Hz, 1 H) 6.66 (d, J=5.09 Hz, 1 H) 6.62 (dd, J=7.63, 1.86 Hz, 1 H) 3.68-3.72 (m, 4 H) 3.02-3.06 (m, 4 H).

Example 4

2,6-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide

Example 4A

Into a 250 mL round bottom flask was charged EXAMPLE 1D (6.3 g, 18.73 mmol), guanidine hydrochloride (2.68 g, 28.1 mmol) and potassium carbonate (6.47 g, 46.8 mmol). N-methyl-2-pyrrolidinone (59 mL) was added and resulting suspension was heated at 97° C. for 20 hours. Additional guanidine hydrochloride (2.76 g, 28.5 mmol) and potassium carbonate (7.21 g, 52.22 mmol) was added and the reaction was heated for 45 hours. The reaction was cooled to ambient temperature and 375 mL water was added. The resulting suspension was stirred 45 minutes and filtered. The collected solid was dissolved in 300 mL 15% methanol/$CH_2Cl_2$, dried over $Na_2SO_4$, filtered, and concentrated. The concentrate was dried to constant weight under vacuum to provide the title compound. MS (ESI(+)) m/e 332.9 (M+H)$^+$.

Example 4B

Into a 500 mL round bottom flask was charged EXAMPLE 4A (8.8 g, 26.5 mmol) and acetic acid (75 mL). The reaction was heated at 60° C. and a solution of sodium nitrite (5.48 g, 79 mmol) in water (14 mL) was added dropwise over 15 minutes. Upon complete addition, the suspension was stirred at 60° C. for 30 minutes. The reaction was cooled to ambient temperature and then further cooled in an ice bath at 0° C. The reaction was quenched to pH 7 with 10% NaOH (~600 mL). The resulting cold suspension was filtered and the collected solid was washed with 3×400 mL water and 2×150 mL ether. The solid was dried in a vacuum oven at 75° C. for 20 hours to provide the title compound. MS (ESI(+)) m/e 333.9 (M+H)$^+$.

Example 4C

Into a 250 mL round bottom flask was charged EXAMPLE 4B (8.19 g, 24.57 mmol) and $POCl_3$ (57.3 mL, 614 mmol). The resulting suspension was heated to 80° C. for 5 hours and allowed to cool to ambient temperature. The mixture was added slowly with stirring to 290 mL of water cooled in an ice bath at such a rate that the internal temperature did not exceed 20° C. Upon complete addition, the suspension was stirred 30 minutes and then was basified to pH 11 with 15% aqueous sodium hydroxide added in a rapid dropwise manner at such a rate to keep internal temp below 20° C. Upon basification, the suspension was stirred 30 minutes and filtered. The solid collected was washed with 4×500 mL water and dried to a constant weight in a vacuum oven at 75° C. for 20 hours to provide the title compound. MS (ESI(+)) m/e 351.8 (M+H)$^+$.

Example 4D

Into a 500 mL erlenmeyer flask was charged 7-nitro-1,2,3,4-tetrahydroisoquinoline hydrochloride (5 g, 23.30 mmol) and 1,2-dichloroethane (250 mL). The solution was treated with 1 N NaOH (~50 mL) and stirred 10 minutes. The layers were separated and the organic layer was treated with paraformaldehyde (3.50 g, 116 mmol), acetic acid (6.67 mL, 24.48 mmol) and sodium cyanoborohydride (5.42 g, 86 mmol). The reaction was heated at 90° C. for 16 hours. The reaction was cooled to ambient temperature and saturated sodium bicarbonate (60 mL) was added. The bilayer was stirred for 1 hour and charged to a separatory funnel. The organic layer was dried ($Na_2SO_4$) and concentrated. The concentrate was purified by flash chromatography on a 130 g silica gel column with a gradient of from 0% to 1% methanol in $CH_2Cl_2$ to provide the title compound. MS (DCI(+)) m/e 193.0 $(M+H)^+$.

Example 4E

A solution of EXAMPLE 4D (3.3 g, 17.17 mmol) in ethyl acetate (60 ml) was added to 10% palladium on carbon (0.330 g, 3.10 mmol) in a 250 mL pressure bottle. The suspension was stirred under a hydrogen atmosphere, 30 psi, and ambient temperature for 16 hours. The mixture was filtered through a bed of Celite and concentrated to provide the title compound. MS (DCI(+)) m/e 163.0 $(M+H)^+$.

Example 4F

A suspension of EXAMPLE 4C (0.25 g, 0.711 mmol) and EXAMPLE 4E (0.138 g, 0.853 mmol) in 2-propanol (4.5 ml) was treated with 4 M HCl in dioxane (0.143 mL, 0.57 mmol) and the mixture was heated in a Biotage Initiator microwave reactor at 140° C. for 55 minutes. The reaction was cooled to ambient temperature, the suspension was filtered, and the collected solid was washed with 2-propanol. The solid was dissolved in 15% methanol/$CH_2Cl_2$ and washed with 5% $NaHCO_3$ (aqueous) and brine. The organic layer was dried ($Na_2SO_4$) filtered, and concentrated to provide the title compound. MS (ESI(+)) m/e 478.1 $(M+H)^+$.

Example 4G

Into a 50 mL round bottom flask was charged EXAMPLE 4F (0.25 g, 0.524 mmol), iron (0.292 g, 5.24 mmol), and ammonium chloride (0.056 g, 1.047 mmol) in ethanol (10 ml) and water (1.5 ml) to give a suspension. The mixture was heated at 90° C. for 1.5 hours. The reaction was filtered while hot and the filter pad was washed with 100 mL ethyl acetate and 20 mL methanol. The combined filtrate was washed with saturated aqueous. $NaHCO_3$ (40 mL) and brine, dried over $Na_2SO_4$, filtered, and concentrated to provide the title compound. MS (ESI(+)) m/e 448.1 $(M+H)^+$.

Example 4H 2,6-difluoro-N-(3-{3-(2-(2-methyl-1,2,3,4-tetrahydroisoquinolin-7-ylamino)pyrimidin-4-yl)imidazo[1,2-a]pyridin-2-yl)phenyl)benzamide Into a 4 mL vial was charged EXAMPLE 4G (46 mg, 0.103 mmol), tetrahydrofuran (1 mL) and N-methyl-2-pyrrolidinone (0.5 mL). 2,6-Difluorobenzoyl chloride (0.013 mL, 0.108 mmol) was added and the reaction mixture was stirred at ambient temperature for 18 hours. The reaction was concentrated and the residue purified by reverse-phase HPLC on a Shimadzu LC10 HPLC system with a Phenominex Luna 10 micron C18(2) 100 150×30 mm column, eluting with a gradient of 25-65% $CH_3CN$/water/0.1% trifluoroacetic acid to provide the title compound. MS (ESI(+)) m/e 588.3 $(M+H)^+$; $^1H$ NMR (300 MHz, dimethylsulfoxide-$d_6$) δ ppm 10.88 (s, 1 H) 9.61 (s, 1 H) 9.51 (d, J=6.78 Hz, 1 H) 8.35 (d, J=5.43 Hz, 1 H) 8.03-8.04 (m, 1 H) 7.74-7.83 (m, 2 H) 7.38-7.64 (m, 6 H) 7.21-7.30 (m, 2 H) 7.04-7.10 (m, 1 H) 7.02 (d, J=8.14 Hz, 1 H) 6.65 (d, J=5.43 Hz, 1 H) 3.41 (s, 2 H) 2.74-2.79 (m, 2 H) 2.55-2.60 (m, 2 H) 2.33 (s, 3 H).

Example 5

N-[3-(3-{2-[(2-methyl-1,2,3,4-tetrahydroisoquinolin-7-yl)amino]pyrimidin-4-yl}imidazo[1,2-a]pyridin-2-yl)phenyl]-2-phenylacetamide The title compound was prepared as described in EXAMPLE 4H, substituting phenylacetyl chloride for 2,6-difluorobenzoyl chloride. MS (ESI(+)) m/e 566.3 $(M+H)^+$; $^1H$ NMR (300 MHz, dimethylsulfoxide-$d_6$) δ ppm 10.27 (s, 1 H) 9.61 (s, 1 H) 9.51 (d, J=7.12 Hz, 1 H) 8.32 (d, J=5.09 Hz, 1 H) 7.90-7.93 (m, 1 H) 7.74 (d, J=8.82 Hz, 2 H) 7.23-7.54 (m, 10 H) 6.99-7.10 (m, 2 H) 6.60 (d, J=5.43 Hz, 1 H) 3.64 (s, 2 H) 3.41 (s, 2 H) 2.74-2.79 (m, 2 H) 2.55-2.60 (m, 2 H) 2.32 (s, 3 H).

Example 6

N-[3-(3-{2-[(2-methyl-1,2,3,4-tetrahydroisoquinolin-7-yl)amino]pyrimidin-4-yl}imidazo[1,2-a]pyridin-2-yl)phenyl]-2-thien-2-ylacetamide The title compound was prepared as described in EXAMPLE 4H, substituting 2-thiopheneacetyl chloride for 2,6-difluorobenzoyl chloride. MS (ESI(+)) m/e 572.2 $(M+H)^+$; $^1H$ NMR (300 MHz, dimethylsulfoxide-$d_6$) δ ppm 10.31 (s, 1 H) 9.62 (s, 1 H) 9.51 (d, J=6.74 Hz, 1 H) 8.33 (d, J=5.16 Hz, 1 H) 7.90-7.93 (m, 1 H) 7.69-7.78 (m, 2 H) 7.28-7.54 (m, 6 H) 6.93-7.11 (m, 4 H) 6.60 (d, J=5.16 Hz, 1 H) 3.87 (s, 2 H) 3.40 (s, 2 H) 2.73-2.80 (m, 2 H) 2.54-2.61 (m, 2 H) 2.32 (s, 3 H).

Example 7

N-[3-(3-{2-[(2-methyl-1,2,3,4-tetrahydroisoquinolin-7-yl)amino]pyrimidin-4-yl}imidazo[1,2-a]pyridin-2-yl)phenyl]-N'-phenylurea Into a 4 mL vial was charged EXAMPLE 4G (47 mg, 0.105 mmol), tetrahydrofuran (1 mL), and N-methyl-2-pyrrolidinone (0.2 mL). The solution was treated with isocyanatobenzene (12 uL, 0.110 mmol) and the reaction was stirred at ambient temperature for 18 hours. The reaction was concentrated and the residue was purified by reverse-phase HPLC on a Shimadzu LC10 HPLC system with a Phenominex Luna 10 micron C18(2) 100 150×30 mm column, eluting with a gradient of 25-65% $CH_3CN$/water/0.1% trifluoroacetic acid to provide the title compound. MS (ESI(+)) m/e 567.3 $(M+H)^+$; $^1H$ NMR (300 MHz, dimethylsulfoxide-$d_6$) δ ppm 9.62 (s, 1 H) 9.55 (d, J=6.74 Hz, 1 H) 8.83 (s, 1 H) 8.66 (s, 1 H) 8.34 (d, J=5.55 Hz, 1 H) 7.72-7.80 (m, 2 H) 7.42-7.57 (m, 6 H) 7.37 (t, J=7.93 Hz, 1 H) 7.19-7.30 (m, 3 H) 6.90-7.10 (m, 3 H) 6.63 (d, J=5.16 Hz, 1 H) 3.41 (s, 2 H) 2.74-2.79 (m, 2 H) 2.55-2.60 (m, 2 H) 2.32 (s, 3 H).

Example 8

N-benzyl-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting (isocyanatomethyl)benzene for phenyl isocyanate. MS (ESI(+)) m/e 597.3 $(M+H)^+$; $^1H$ NMR MHz, dimethylsulfoxide-d$_6$) δ ppm 9.69 (s, 1 H) 9.60 (d, 1 H) 8.75 (s, 1 H) 8.39 (d, 1 H) 7.76-7.87 (m, 2 H) 7.60-7.74 (m, 1 H) 7.48-7.55 (m, 1 H) 7.42 (m, 1 H) 7.11-7.38 (m, 10 H) 6.55-6.70 (m, 3 H) 4.29 (d, 2 H) 3.70 (m, 4 H) 3.05 (m, 4 H).

Example 9

N-(2,6-difluorophenyl)-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting 1,3-difluoro-2-isocyanatobenzene for phenyl isocyanate. MS (ESI(+)) m/e 619.2 (M+H)$^+$; $^1$H NMR (300 MHz, dimethylsulfoxide-d$_6$) δ ppm 9.68 (s, 1 H) 9.59 (d, 1 H) 9.13 (s, 1 H) 8.39 (d, 1 H) 8.13 (s, 1 H) 7.77-7.84 (m, 2 H) 7.55-7.69 (m, 2 H) 7.10-7.45 (m, 9 H) 6.58-6.67 (m, 2 H) 3.70 (m, 4 H) 3.05 (m, 4 H).

Example 10

N-(2-methylphenyl)-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting 1-isocyanato-2-methylbenzene for phenyl isocyanate. MS (ESI(+)) m/e 597.3 (M+H)$^+$; $^1$H NMR (300 MHz, dimethylsulfoxide-d$_6$) δ ppm 9.68 (s, 1 H) 9.57 (d, 1 H) 9.17 (s, 1 H) 8.40 (d, 1 H) 7.91 (s, 1 H) 7.78-7.84 (m, 3 H) 7.54-7.66 (m, 2 H) 7.37-7.44 (m, 2 H) 7.10-7.25 (m, 6 H) 6.92-6.98 (m, 1 H) 6.66 (d, 1 H) 6.60 (m, 1 H) 3.70 (m, 4 H) 3.05 (m, 4 H) 2.24 (s, 3 H).

Example 11

N-(2-chlorophenyl)-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting 1-chloro-2-isocyanatobenzene for phenyl isocyanate. MS (ESI(+)) m/e 617.3 (M+H)$^+$; $^1$H NMR (300 MHz, dimethylsulfoxide-d$_6$) δ ppm 9.68 (s, 1 H) 9.56 (m, 2 H) 8.41 (d, 1 H) 8.29 (s, 1 H) 8.14 (dd, 1 H) 7.80-7.85 (m, 2 H) 7.55-7.65 (m, 2 H) 7.40-7.48 (m, 3 H) 7.12-7.31 (m, 6 H) 7.00-7.07 (m, 1 H) 6.66 (d, 1 H) 6.61 (m, 1 H) 3.70 (m, 4 H) 3.05 (m, 4 H).

Example 12

N-(4-fluorophenyl)-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting 1-fluoro-4-isocyanatobenzene for phenyl isocyanate. MS (ESI(+)) m/e 601.3 (M+H)$^+$; $^1$H NMR (300 MHz, dimethylsulfoxide-d$_6$) δ ppm 9.69 (s, 1 H) 9.57 (d, 1 H) 8.86 (s, 1 H) 8.71 (s, 1 H) 8.40 (d, 1 H) 7.81 (m, 2 H) 7.61-7.71 (m, 1 H) 7.56 (m, 1 H) 7.38-7.48 (m, 4 H) 7.07-7.27 (m, 6 H) 6.66 (d, 1 H) 6.61 (m, 1 H) 3.70 (m, 4 H) 3.05 (m, 4 H).

Example 13

N-(3-methoxyphenyl)-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting 1-isocyanato-3-methoxybenzene for phenyl isocyanate. MS (ESI(+)) m/e 613.3 (M+H)$^+$; $^1$H NMR (300 MHz, dimethylsulfoxide-d$_6$) δ ppm 9.71 (s, 1 H) 9.59 (d, 1 H) 8.86 (s, 1 H) 8.70 (s, 1 H) 8.41 (d, 1 H) 7.81-7.88 (m, 2 H) 7.64-7.72 (m, 1 H) 7.55 (m, 1 H) 7.38-7.44 (m, 2 H) 7.12-7.28 (m, 6 H) 6.92 (m, 1 H) 6.66 (d, 1 H) 6.62 (m, 1 H) 6.55 (dd, 1 H) 3.70 (m, 7 H) 3.05 (m, 4 H).

Example 14

N-[3-(3-{2-[(3-morpholin-4-ylphenyl)amino]pyrimidin-4-yl}imidazo[1,2-a]pyridin-2-yl)phenyl]cyclopropanecarboxamide The title compound was prepared as described in EXAMPLE 1I, substituting cyclopropanecarbonyl chloride for 2,6-difluorobenzoyl chloride. MS (ESI(+)) m/e 532.2 (M+H)$^+$; $^1$H NMR (300 MHz, dimethylsulfoxide-d$_6$) δ ppm 10.35 (s, 1 H) 9.71 (s, 1 H) 9.57 (d, 1 H) 8.40 (d, 1 H) 7.95 (m, 1 H) 7.83 (d, 1 H) 7.63-7.77 (m, 2 H) 7.38-7.44 (m, 2 H) 7.13-7.31 (m, 4 H) 6.62 (m, 2 H) 3.70 (m, 4 H) 3.05 (m, 4 H) 1.73-1.85 (m, 1 H) 0.79 (m, 4 H).

Example 15

N-isopropyl-N'-[3-(3-{2-[(3-morpholin-4-ylphenyl)amino]pyrimidin-4-yl}imidazo[1,2-a]pyridin-2-yl)phenyl]urea The title compound was prepared as described in EXAMPLE 3, substituting 2-isocyanatopropane for phenyl isocyanate. MS (ESI(+)) m/e 549.3 (M+H)$^+$; $^1$H NMR (300 MHz, dimethylsulfoxide-d$_6$) δ ppm 9.71 (s, 1 H) 9.61 (d, 1 H) 8.48 (s, 1 H) 8.39 (d, 1 H) 7.84 (m, 1 H) 7.66-7.74 (m, 2 H) 7.49 (m, 1 H) 7.42 (m, 1 H) 7.35 (t, 1 H) 7.12-7.28 (m, 4 H) 6.62 (m, 2 H) 6.01 (d, 1 H) 3.68-3.77 (m, 5 H) 3.05 (m, 4 H) 1.09 (d, 6 H).

Example 16

2,6-difluoro-N-{3-[3-(2-{[3-(2-oxopyrrolidin-1-yl)phenyl]amino}pyrimidin-4-yl)imidazo[1,2-a]pyridin-2-yl]phenyl}benzamide

Example 16A

The title compound was prepared as described in EXAMPLES 1E and 1F, substituting 1-(3-aminophenyl)pyrrolidin-2-one for 3-morpholinoaniline in EXAMPLE 1E. MS (APCI(+)) m/e 218.6 (M+H)$^+$.

Example 16B

The title compound was prepared as described in EXAMPLE 1G, substituting EXAMPLE 16A for EXAMPLE 1F. MS ESI(+)) m/e 492.1 (M+H)$^+$.

Example 16C

The title compound was prepared as described in EXAMPLE 1H, substituting EXAMPLE 16B for EXAMPLE 1G. MS ESI(+)) m/e 462.1 (M+H)+.

Example 16D

The title compound was prepared as described in EXAMPLE 1I, substituting EXAMPLE 16C for EXAMPLE 1H. MS ESI(+)) m/e 462.1 (M+H)+. MS ESI(+)) m/e 602.2 (M+H)+; $^1$H NMR (300 MHz, dimethylsulfoxide-$d_6$) δ ppm 10.93 (s, 1 H) 9.85 (s, 1 H) 9.59 (d, 1 H) 8.40 (d, 1 H) 8.05 (m, 2 H) 7.79-7.84 (m, 2 H) 7.40-7.66 (m, 5 H) 7.16-7.30 (m, 5 H) 6.69 (d, 1 H) 3.77 (t, 2 H) 2.47 (t, 2 H) 1.97-2.08 (m, 2 H).

Example 17

2-fluoro-N-{3-[3-(2-{[3-(2-oxopyrrolidin-1-yl)phenyl]amino}pyrimidin-4-yl)imidazo[1,2-a]pyridin-2-yl]phenyl}benzamide The title compound was prepared as described in EXAMPLE 1I, substituting EXAMPLE 16C for EXAMPLE 1H and 2-fluorobenzoyl chloride for 2,6-difluorobenzoyl chloride. MS (ESI(+)) m/e 584.2 (M+H)+; $^1$H NMR (300 MHz, dimethylsulfoxide-$d_6$) δ ppm 10.56 (s, 1 H) 9.82-9.83 (m, 1 H) 9.61 (d, 1 H) 8.40 (d, 1 H) 8.08 (m, 2 H) 7.80-7.88 (m, 2 H) 7.55-7.70 (m, 4 H) 7.48 (m, 1 H) 7.27-7.42 (m, 5 H) 7.17 (t, 1 H) 6.68 (d, 1 H) 3.77 (t, 2 H) 2.47 (t, 2 H) 1.98-2.10 (m, 2 H).

Example 18

N-{3-[3-(2-{[3-(2-oxopyrrolidin-1-yl)phenyl]amino}pyrimidin-4-yl)imidazo[1,2-a]pyridin-2-yl]phenyl}-2-phenylacetamide The title compound was prepared as described in EXAMPLE 1I, substituting EXAMPLE 16C for EXAMPLE 1H and phenylacetyl chloride for 2,6-difluorobenzoyl chloride. MS (ESI(+)) m/e 580.2 (M+H)+; $^1$H NMR (300 MHz, dimethylsulfoxide-$d_6$) δ ppm 10.30 (s, 1 H) 9.85 (s, 1 H) 9.59 (d, 1 H) 8.38 (d, 1 H) 8.06 (m, 1 H) 7.95 (m, 1 H) 7.72-7.82 (m, 2 H) 7.53-7.66 (m, 2 H) 7.41 (m, 1 H) 7.24-7.35 (m, 8 H) 7.17 (t, 1 H) 6.64 (d, 1 H) 3.77 (t, 2 H) 3.64 (s, 2 H) 2.47 (t, 2 H) 1.99-2.10 (m, 2 H).

Example 19

N-{3-[3-(2-{[3-(2-oxopyrrolidin-1-yl)phenyl]amino}pyrimidin-4-yl)imidazo[1,2-a]pyridin-2-yl]phenyl}-2-thien-2-ylacetamide The title compound was prepared as described in EXAMPLE 1I, substituting EXAMPLE 16C for EXAMPLE 1H and 2-(thiophen-2-yl)acetyl chloride for 2,6-difluorobenzoyl chloride. MS (ESI(+)) m/e 586.2 (M+H)+; $^1$H NMR (300 MHz, dimethylsulfoxide-$d_6$) δ ppm 10.35 (s, 1 H) 9.86 (s, 1 H) 9.60 (d, 1 H) 8.38 (d, 1 H) 8.06 (m, 1 H) 7.95 (m, 1 H) 7.73-7.83 (m, 2 H) 7.54-7.65 (m, 2 H) 7.27-7.46 (m, 5 H) 7.17 (m, 1 H) 6.97 (m, 2 H) 6.64 (d, 1 H) 3.88 (s, 2 H) 3.77 (t, 2 H) 2.47 (t, 2 H) 1.99-2.10 (m, 2 H).

Example 20

N-{3-[3-(2-{[3-(2-oxopyrrolidin-1-yl)phenyl]amino}pyrimidin-4-yl)imidazo[1,2-a]pyridin-2-yl]phenyl}-N'-phenylurea The title compound was prepared as described in EXAMPLE 7, substituting EXAMPLE 16C for EXAMPLE 4G. MS (ESI(+)) m/e 581.3 (M+H)+; $^1$H NMR (300 MHz, dimethylsulfoxide-$d_6$) δ ppm 9.86 (s, 1 H) 9.63 (d, 1 H) 8.85 (s, 1 H) 8.66 (s, 1 H) 8.40 (d, 1 H) 8.06 (m, 1 H) 7.79-7.84 (m, 2 H) 7.55-7.66 (m, 3 H) 7.38-7.46 (m, 3 H) 7.16-7.31 (m, 6 H) 6.97 (t, 1 H) 6.67 (d, 1 H) 3.78 (t, 2 H) 2.47 (t, 2 H) 1.99-2.10 (m, 2 H).

Example 21

N-(2-fluorophenyl)-N'-{3-[3-(2-{[3-(2-oxopyrrolidin-1-yl)phenyl]amino}pyrimidin-4-yl)imidazo[1,2-a]pyridin-2-yl}phenyl)urea The title compound was prepared as described in EXAMPLE 7, substituting EXAMPLE 16C for EXAMPLE 4G and 1-fluoro-2-isocyanatobenzene for isocyanatobenzene. MS (ESI(+)) m/e 599.2 (M+H)+; $^1$H NMR (300 MHz, dimethylsulfoxide-$d_6$) δ ppm 9.86 (s, 1 H) 9.62 (d, 1 H) 9.22 (s, 1 H) 8.53 (d, 1 H) 8.41 (d, 1 H) 8.06-8.16 (m, 2 H) 7.82 (m, 2 H) 7.54-7.66 (m, 3 H) 7.42 (t, 1 H) 7.09-7.31 (m, 6 H) 7.01 (m, 1 H) 6.67 (d, 1 H) 3.78 (t, 2 H) 2.47 (t, 2 H) 1.99-2.10 (m, 2 H).

Example 22

N-(2,6-difluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea The title compound was prepared as described in EXAMPLE 7, substituting EXAMPLE 16C for EXAMPLE 4G and 1,3-difluoro-2-isocyanatobenzene for isocyanatobenzene. MS (ESI(+)) m/e 617.2 (M+H)+; $^1$H NMR (300 MHz, dimethylsulfoxide-($d_6$) δ ppm 9.84 (s, 1 H) 9.64 (d, 1 H) 9.12 (s, 1 H) 8.39 (d, 1 H) 8.12 (s, 1 H) 8.05 (m, 1 H) 7.80 (m, 2 H) 7.55-7.64 (m, 3 H) 7.39 (t, 1 H) 7.12-7.32 (m, 7 H) 6.66 (d, 1 H) 3.78 (t, 2 H) 2.47 (t, 2 H) 1.99-2.09 (m, 2 H).

Example 23

2-(2-fluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide A solution of EXAMPLE 16C (45 mg, 0.098 mmol) in tetrahydrofuran (0.9 mL) and N-methyl-2-pyrrolidinone (0.3 mL) was treated with 2-(2-fluorophenyl)acetic acid (17.28 mg, 0.112 mmol), 1-hydroxybenzotriazole hydrate (14.93 mg, 0.098 mmol), and polystyren-carbodiimide (Argonaut P/N 800371, 1.42 mmole/g, 0.206 g, 0.293 mmol), and the resulting suspension was stirred at ambient temperature overnight. The reaction was filtered and the solids washed with ethyl acetate (5 mL). The filtrate was diluted with ethyl acetate (80 mL) and washed with 5% aqueous $Na_2CO_3$ (25 mL), water (3×25 mL) and brine (25 mL). The organic layer was dried over $Na_2SO_4$, filtered, and concentrated. The concentrate was purified by reverse-phase HPLC on a Waters Nova-Pakâ HR C18 6 um 60 Å Prep-Pakâ cartridge column (25 mm×100 mm) eluting with an acetonitrile gradient in water containing 0.15% trifluoroacetic acid to provide the title compound. MS (ESI(+)) m/e 598.2 (M+H)+; ¹H NMR (300 MHz, dimethylsulfoxide-$d_6$) δ ppm 10.36 (s, 1 H) 9.85 (s, 1 H) 9.60 (d, 1 H) 8.39 (d, 1 H) 8.05 (m, 1 H) 7.94 (m, 1 H) 7.74-7.82 (m, 2 H) 7.54-7.64 (m, 2 H) 7.28-7.45 (m, 6 H) 7.14-7.22 (m, 3 H) 6.65 (d, 1 H) 3.75 (m, 4 H) 2.47 (t, 2 H) 1.98-2.08 (m, 2 H).

Example 24

2-(2,6-difluorophenyl)-N-{3-[3-(2-[3-(2-oxopyrrolidin-1-yl)phenyl]amino}pyrimidin-4-yl)imidazo[1,2-a]pyridin-2-yl]phenyl}acetamide The title compound was prepared as described in EXAMPLE 23, substituting 2-(2,6-difluorophenyl)acetic acid for 2-(2-fluorophenyl)acetic acid. MS (ESI(+)) m/e 616.2 (M+H)+; ¹H NMR (300 MHz, dimethylsulfoxide-$d_6$) δ ppm 10.43 (s, 1 H) 9.85 (s, 1 H) 9.60 (d, 1 H) 8.38 (d, 1 H) 8.05 (m, 1 H) 7.92 (m, 1 H) 7.72-7.81 (m, 2 H) 7.54-7.64 (m, 2 H) 7.27-7.44 (m, 5 H) 7.07-7.18 (m, 3 H) 6.65 (d, 1 H) 3.76 (m, 4 H) 2.47 (t, 2 H) 1.99-2.10 (m, 2 H).

Example 25

N-benzyl-N'-{3-[3-(2-{[3-(2-oxopyrrolidin-1-yl)phenyl]amino}pyrimidin-4-yl)imidazo[1,2-a]pyridin-2-yl]phenyl}urea The title compound was prepared as described in EXAMPLE 7, substituting EXAMPLE 16C for EXAMPLE 4G and (isocyanatomethyl)benzene for isocyanatobenzene. MS (ESI(+)) m/e 595.3 (M+H)+; ¹H NMR (300 MHz, dimethylsulfoxide-$d_6$) δ ppm 9.84 (s, 1 H) 9.64 (d, 1 H) 8.74 (s, 1 H) 8.38 (d, 1 H) 8.05 (m, 1 H) 7.75-7.83 (m, 2 H) 7.51-7.65 (m, 3 H) 7.15-7.38 (m, 10 H) 6.64 (m, 2 H) 4.29 (d, 2 H) 3.78 (t, 2 H) 2.47 (m, 2 H) 1.98-2.10 (m, 2 H).

Example 26

N-(3-{3-[2-({3-[(dimethylamino)methyl]phenyl}amino)pyrimidin-4-yl]imidazo[1,2-a]pyridin-2-yl}phenyl)benzamide Example 26A In a 10 mL sealed tube were mixed 1-(bromomethyl)-3-nitrobenzene (10 g, 46.3 mmol), 2M dimethylamine (69.4 ml, 139 mmol) in methanol, and triethylamine (19.36 ml, 139 mmol) in acetonitrile (46 ml). The yellow solution was stirred overnight at ambient temperature. The reaction mixture was concentrated and the residue was taken up in ethyl acetate and washed with saturated NaHCO$_3$ and brine. The aqueous layer was with ethyl acetate. The combined organic layers were dried with Na$_2$SO$_4$, filtered, and concentrated to provide the title compound. MS (DCI(+)) m/e 181 (M+H)+.

Example 26B

A solution of N,N-dimethyl-1-(3-nitrophenyl)methanamine from EXAMPLE 26A (10.2 g, 56.6 mmol) in ethyl acetate (100 ml) was added to 5% palladium on carbon (1.0 g) in a 250 mL pressure bottle. The suspension was stirred under a 20 psi hydrogen atmosphere at ambient temperature for 2 hours. The mixture was filtered through a bed of Celite and concentrated. The residue was purified by flash chromatography on a 150 g silica gel column using an AnaLogix IntelliFlash 280 system eluting with a gradient of 10% to 40% methanol in dichloromethane to provide the title compound. MS (DCI(+)) m/e 151 (M+H)+.

Example 26C

The title compound was prepared as described in EXAMPLE 1E, substituting EXAMPLE 26B for 3-morpholinoaniline. MS (ESI(+)) m/e 393 (M+H)+.

Example 26D

The title compound was prepared as described in EXAMPLE 1F, substituting EXAMPLE 26C for EXAMPLE 1E. MS (DCI(+)) m/e 193 (M+H)+.

Example 26E

The title compound was prepared as described in EXAMPLE 1G, substituting EXAMPLE 26D for EXAMPLE 1D. MS (ESI(+)) m/e 466 (M+H)+.

Example 26F

The title compound was prepared as described in EXAMPLE 1H, substituting EXAMPLE 26E for EXAMPLE 1G. MS (ESI(+)) m/e 436 (M+H)+.

Example 26G

The title compound was prepared as described in EXAMPLE 1I, substituting EXAMPLE 26F for EXAMPLE 1H and benzoyl chloride for 2,6-difluorobenzoyl chloride. MS (ESI(+)) m/e 540 (M+H)+, ¹H NMR (400 MHz, dimethylsulfoxide-$d_6$) δ ppm 10.35 (s, 1 H) 9.72 (s, 1 H) 9.60 (d, 1 H) 8.36 (d, 1 H) 8.16 (s, 1 H) 7.96 (m, 3 H) 7.76 (d, 1 H) 7.70 (m, 2 H) 7.59 (m, 1 H) 7.53 (m, 3 H) 7.44 (m, 1 H) 7.37 (m, 1 H) 7.24 (t, 1 H) 7.08 (t, 1 H) 6.91 (d, 1 H) 6.67 (d, 1 H) 3.35 (s, 2 H) 2.14 (s, 6 H).

Example 27

N-(3-{3-[2-({3-[(dimethylamino)methyl]phenyl}amino)pyrimidin-4-yl]imidazo[1,2-a]pyridin-2-yl}phenyl)-2-fluorobenzamide The title compound was prepared as described in EXAMPLE 1I, substituting EXAMPLE 26F for EXAMPLE 1H and 2-fluorobenzoyl chloride for 2,6-difluorobenzoyl chloride. MS (ESI(+)) m/e 558 (M+H)+, ¹H NMR (400 MHz, dimethylsulfoxide-$d_6$) δ ppm 10.51 (s, 1 H) 9.71 (s, 1 H) 9.58 (d, 1 H) 8.37 (d, 1 H) 8.08 (s, 1 H) 7.85 (d, 1 H) 7.76 (d, 1 H) 7.68 (m, 3 H) 7.54-7.61 (m, 1 H) 7.51 (m, 1 H) 7.44 (t, 1 H) 7.36 (m, 3 H) 7.23 (t, 1 H) 7.08 (m, 1 H) 6.91 (d, 1 H) 6.66 (d, 1 H) 3.35 (s, 2 H) 2.14 (s, 6 H).

Example 28

N-(3-{3-[2-({3-[(dimethylamino)methyl]phenyl}amino)pyrimidin-4-yl]imidazo[1,2-a]pyridin-2-yl}phenyl)-2,6-difluorobenzamide The title compound was prepared as described in EXAMPLE 1I, substituting EXAMPLE 26F for EXAMPLE 1H. MS (ESI(+)) m/e 576 (M+H)+, ¹H NMR (400 MHz, dimethylsulfoxide-$d_6$) δ ppm 10.88 (s, 1 H) 9.72 (s, 1 H) 9.55 (d, 1 H) 8.37 (d, 1 H) 8.05 (s, 1 H) 7.80 (d, 1 H) 7.76 (d, 1 H)

7.69 (m, 2 H) 7.59 (m, 1 H) 7.50 (m, 1 H) 7.45 (d, 1 H) 7.41 (m, 1 H) 7.25 (m, 3 H) 7.07 (t, 1 H) 6.91 (d, 1 H) 6.67 (d, 1 H) 3.35 (s, 2 H) 2.14 (s, 6 H).

Example 29

N-(3-{3-[2-({3-[(dimethylamino)methyl]phenyl}amino)pyrimidin-4-yl]imidazo[1,2-a]pyridin-2-yl}phenyl)-2-phenylacetamide The title compound was prepared as described in EXAMPLE 1I, substituting EXAMPLE 26F for EXAMPLE 1H and phenylacetyl chloride for 2,6-difluorobenzoyl chloride. MS (ESI(+)) m/e 554 (M+H)$^+$, $^1$H NMR (400 MHz, dimethylsulfoxide-d$_6$) δ ppm 10.26 (s, 1 H) 9.72 (s, 1 H) 9.56 (d, 1 H) 8.34 (d, 1 H) 7.93 (s, 1 H) 7.66-7.76 (m, 4 H) 7.50 (m, 1 H) 7.37 (t, 1 H) 7.28-7.34 (m, 5 H) 7.24 (m, 2 H) 7.06 (t, 1 H) 6.91 (d, 1 H) 6.62 (d, 1 H) 3.64 (s, 2 H) 3.38 (s, 2 H) 2.15 (s, 6 H).

Example 30

N-(3-{3-[2-({3-[(dimethylamino)methyl]phenyl}amino)pyrimidin-4-yl]imidazo[1,2-a]pyridin-2-yl}phenyl)-2-thien-2-ylacetamide The title compound was prepared as described in EXAMPLE 1I, substituting EXAMPLE 26F for EXAMPLE 1H and 2-thiopheneacetyl chloride for 2,6-difluorobenzoyl chloride. MS (ESI(+)) m/e 560 (M+H)$^+$, $^1$H NMR (400 MHz, dimethylsulfoxide-d$_6$) δ ppm 10.30 (s, 1 H) 9.72 (s, 1 H) 9.56 (d, 1 H) 8.35 (d, 1 H) 7.93 (s, 1 H) 7.66-7.77 (m, 4 H) 7.50 (m, 1 H) 7.38 (m, 2 H) 7.32 (m, 1 H) 7.24 (t, 1 H) 7.06 (t, 1 H) 6.98 (m, 2 H) 6.91 (d, 1 H) 6.62 (d, 1 H) 3.88 (s, 2 H) 3.36 (s, 2 H) 2.14 (s, 6 H).

Example 31

N-(3-{3-[2-({3-[(dimethylamino)methyl]phenyl}amino)pyrimidin-4-yl]imidazo[1,2-a]pyridin-2-yl}phenyl)-N'-phenylurea The title compound was prepared as described in EXAMPLE 3, substituting EXAMPLE 26F for EXAMPLE 1H. MS (ESI(+)) m/e 555 (M+H)$^+$, $^1$H NMR (400 MHz, dimethylsulfoxide-d$_6$) δ ppm 9.72 (s, 1 H) 9.59 (d, 1 H) 8.80 (s, 1 H) 8.64 (s, 1 H) 8.36 (d, 1 H) 7.76 (m, 2 H) 7.69 (m, 2 H) 7.56 (m, 1 H) 7.50 (m, 1 H) 7.45 (d, 2 H) 7.37 (t, 1 H) 7.26 (m, 4 H) 7.07 (m, 1 H) 6.96 (t, 1 H) 6.91 (d, 1 H) 6.65 (d, 1 H) 3.37 (s, 2 H) 2.15 (s, 6 H).

Example 32

N-(2,6-difluorophenyl)-N'-(3-{3-[2-({3-[(dimethylamino)methyl]phenyl}amino)pyrimidin-4-yl]imidazo[1,2-a]pyridin-2-yl}phenyl)urea The title compound was prepared as described in EXAMPLE 3, substituting EXAMPLE 26F for EXAMPLE 1H and 2,6-difluorophenyl isocyanate for phenyl isocyanate. MS (ESI(+)) m/e 591 (M+H)$^+$, $^1$H NMR (400 MHz, dimethylsulfoxide-d$_6$) δ ppm 9.72 (s, 1 H) 9.60 (d, 1 H) 9.10 (s, 1 H) 8.36 (d, 1 H) 8.12 (s, 1 H) 7.76 (m, 2 H) 7.70 (m, 2 H) 7.59 (m, 1 H) 7.50 (m, 1 H) 7.36 (t, 1 H) 7.30 (m, 1 H) 7.23 (m, 2 H) 7.14 (m, 2 H) 7.07 (t, 1 H) 6.92 (d, 1 H) 6.64 (d, 1 H) 3.39 (s, 2 H) 2.17 (s, 6 H).

Example 33

N-[3-(8-chloro-3-{2-[(3-morpholin-4-ylphenyl)amino]pyrimidin-4-yl}imidazo[1,2-a]pyridin-2-yl)phenyl]-2,6-difluorobenzamide

Example 33A

The title compound was prepared as described in EXAMPLE 1A, substituting 3-chloropyridin-2-amine (Org. Lett., 2003, vol 5, No 8, 1369-1372) for pyridin-2-amine. MS (ESI(+)) m/e 273.8 (M+H)$^+$.

Example 33B

To a 50 mL round bottom flask was charged EXAMPLE 33A (0.925 g, 3.38 mmol), acetic anhydride (14 mL), and sulfuric acid (0.18 mL, 3.38 mmol). The mixture was heated at 130° C. for 15 hours. The reaction was cooled to ambient temperature, treated with cold water (40 mL) and extracted with 2×80 mL 10% methanol/CH$_2$Cl$_2$. The combined organic extracts were washed with 1N NaOH (50 mL) and brine (50 mL), dried over Na$_2$SO$_4$, filtered, and concentrated to a volume of ~5 mL. The concentrate was triturated with 25 mL ether at 0° C. and the suspension filtered. The solid was washed with ether and dried to constant weight to give the title compound. MS (ESI(+)) m/e 273.8 (M+H)$^+$.

Example 33C

The title compound was prepared as described in EXAMPLE 1D, substituting EXAMPLE 33B for EXAMPLE 1C. MS (ESI(+)) m/e 371.0 (M+H)$^+$.

Example 33D

The title compound was prepared as described in EXAMPLE 1G, substituting EXAMPLE 33C for EXAMPLE 1D. MS (ESI(+)) m/e 528.1 (M+H)$^+$.

Example 33E

The title compound was prepared as described in EXAMPLE 1H, substituting EXAMPLE 33D for EXAMPLE 1G. MS (ESI(+)) m/e 498.1 (M+H)$^+$.

Example 33F

The title compound was prepared as described in EXAMPLE 1I, substituting EXAMPLE 33E for EXAMPLE 1H. MS (ESI(+)) m/e 638.2 (M+H)$^+$; $^1$H NMR (300 MHz, dimethylsulfoxide-d$_6$) δ ppm 10.95 (s, 1 H) 9.72 (s, 1 H) 9.42 (d, 1 H) 8.42 (d, 1 H) 8.05 (m, 1 H) 7.83 (m, 1 H) 7.71 (d, 1 H) 7.55-7.65 (m, 1 H) 7.38-7.49 (m, 3 H) 7.05-7.30 (m, 5 H) 6.70 (d, 1 H) 6.61 (m, 1 H) 3.70 (m, 4 H) 3.04 (m, 4 H).

Example 34

N-[3-(8-chloro-3-{2-[(3-morpholin-4-yl)phenyl)amino]pyrimidin-4-yl)imidazo[1,2-a]pyridin-2-yl)phenyl]-2-phenylacetamide The title compound was prepared as described in EXAMPLE 1I, substituting EXAMPLE 33E for EXAMPLE 1H and phenylacetyl chloride for 2,6-difluorobenzoyl chloride. MS (ESI(+)) m/e 616.2 (M+H)$^+$; $^1$H NMR (300 MHz, dimethylsulfoxide-d$_6$) δ ppm 10.34 (s, 1 H) 9.72 (s, 1 H) 9.42

(d, 1 H) 8.39 (d, 1 H) 7.93 (m, 1 H) 7.79 (m, 1 H) 7.70 (d, 1 H) 7.44 (s, 1 H) 7.04-7.40 (m, 10 H) 6.65 (d, 1 H) 6.61 (dd, 1 H) 3.70 (m, 4 H) 3.64 (s, 2 H) 3.05 (m, 4 H).

Example 35

N-[3-(8-chloro-3-{2-[(3-morpholin-4-ylphenyl) amino]pyrimidin-4-yl}imidazo[1,2-a]pyridin-2-yl) phenyl]-2-thien-2-ylacetamide The title compound was prepared as described in EXAMPLE 1I, substituting EXAMPLE 33E for EXAMPLE 1H and 2-thiopheneacetyl chloride for 2,6-difluorobenzoyl chloride. MS (ESI(+)) m/e 622.2 (M+H)$^+$; $^1$H NMR (300 MHz, dimethylsulfoxide-d$_6$) δ ppm 10.39 (s, 1 H) 9.75 (s, 1 H) 9.42 (d, 1 H) 8.40 (d, 1 H) 7.93 (m, 1 H) 7.79 (m, 1 H) 7.71 (d, 1 H) 7.37-7.45 (m, 3 H) 7.13-7.33 (m, 3 H) 7.07 (t, 1 H) 6.98 (m, 2 H) 6.66 (d, 1 H) 6.62 (dd, 1 H) 3.88 (s, 2 H) 3.70 (m, 4 H) 3.05 (m, 4 H).

Example 36

N-[3-(8-chloro-3-{2-[(3-morpholin-4-ylphenyl) amino]pyrimidin-4-yl}imidazo[1,2-a]pyridin-2-yl) phenyl]-N'-phenylurea The title compound was prepared as described in EXAMPLE 7, substituting EXAMPLE 33E for EXAMPLE 4G. MS (ESI(+)) m/e 617.3 (M+H)$^+$; $^1$H NMR (300 MHz, dimethylsulfoxide-d$_6$) δ ppm 9.70 (s, 1 H) 9.45 (d, 1 H) 8.94 (s, 1 H) 8.71 (s, 1 H) 8.42 (d, 1 H) 7.79 (m, 1 H) 7.70 (d, 1 H) 7.58 (m, 1 H) 7.23-7.47 (m, 8 H) 7.14 (t, 1 H) 7.06 (t, 1 H) 6.96 (m, 1 H) 6.68 (d, 1 H) 6.60 (dd, 1 H) 3.70 (m, 4 H) 3.04 (m, 4 H).

Example 37

N-(3-{3-[2-({3-[2-(dimethylamino)ethyl] phenyl}amino)pyrimidin-4-yl]imidazo[1,2-a]pyridin-2-yl}phenyl)-2,6-difluorobenzamide Example 37A The title compound was prepared as described in EXAMPLE 1E, substituting EXAMPLE 40I for 3-morpholinoaniline. MS (ESI(+)) m/e 407 (M+H)$^+$.

Example 37B

The title compound was prepared as described in EXAMPLE 1F, substituting EXAMPLE 37A for EXAMPLE 1E. MS (DCI(+)) m/e 2073(M+H)$^+$.

Example 37C

The title compound was prepared as described in EXAMPLE 1G, substituting EXAMPLE 37B for EXAMPLE 1D. MS (ESI(+)) m/e 480 (M+H)$^+$.

Example 37D

The title compound was prepared as described in EXAMPLE 1H, substituting EXAMPLE 37C for EXAMPLE 1G. MS (ESI(+)) m/e 450 (M+H)$^+$.

Example 37E

The title compound was prepared as described in EXAMPLE 1I, substituting EXAMPLE 37D for EXAMPLE 1H. MS (ESI(+)) m/e 590 (M+H)$^+$, $^1$H NMR (400 MHz, dimethylsulfoxide-d$_6$) δ ppm 10.88 (s, 1 H) 9.67 (s, 1 H) 9.52 (d, 1 H) 8.37 (d, 1 H) 8.05 (s, 1 H) 7.80 (d, 1 H) 7.76 (d, 1 H) 7.64 (s, 1 H) 7.58 (m, 2 H) 7.48 (m, 2 H) 7.42 (t, 1 H) 7.25 (m, 2 H) 7.18 (t, 1 H) 7.07 (t, 1 H) 6.84 (d, 1 H) 6.67 (d, 1 H) 2.66 (m, 2 H) 2.44 (m, 2 H) 2.15 (s, 6 H).

Example 38

N-(3-{3-[2-({3-[2-(dimethylamino)ethyl] phenyl}amino)pyrimidin-4-yl]imidazo[1,2-a]pyridin-2-yl}phenyl)-2-phenylacetamide The title compound was prepared as described in EXAMPLE 1I, substituting EXAMPLE 37D for EXAMPLE 1H and phenylacetyl chloride for 2,6-difluorobenzoyl chloride. MS (ESI(+)) m/e 568 (M+H)$^+$, $^1$H NMR (400 MHz, dimethylsulfoxide-d$_6$) δ ppm 10.26 (s, 1 H) 9.67 (s, 1 H) 9.53 (d, 1 H) 8.34 (d, 1 H) 7.93 (s, 1 H) 7.74 (d, 2 H) 7.64 (s, 1 H) 7.58 (d, 1 H) 7.48 (m, 1 H) 7.37 (t, 1 H) 7.28-7.34 (m, 5 H) 7.25 (m, 1 H) 7.20 (t, 1 H) 7.06 (t, 1 H) 6.85 (d, 1 H) 6.62 (d, 1 H) 3.64 (s, 2 H) 2.67 (m, 2 H) 2.45 (m, 2 H) 2.16 (s, 6 H).

Example 39

N-(3-{3-[2-({3-[2-(dimethylamino)ethyl] phenyl}amino)pyrimidin-4-yl]imidazo[1,2-a]pyridin-2-yl}phenyl)-2-thien-2-ylacetamide The title compound was prepared as described in EXAMPLE 1I, substituting EXAMPLE 37D for EXAMPLE 1H and 2-thiopheneacetyl chloride for 2,6-difluorobenzoyl chloride. MS (ESI(+)) m/e 574 (M+H)$^+$, $^1$H NMR (400 MHz, dimethylsulfoxide-d$_6$) δ ppm 10.30 (s, 1 H) 9.67 (s, 1 H) 9.53 (d, 1 H) 8.35 (d, 1 H) 7.92 (s, 1 H) 7.73 (m, 2 H) 7.64 (s, 1 H) 7.58 (d, 1 H) 7.49 (m, 1 H) 7.38 (m, 2 H) 7.32 (m, 1 H) 7.19 (t, 1 H) 7.06 (t, 1 H) 6.97 (m, 2 H) 6.85 (d, 1 H) 6.62 (d, 1 H) 3.87 (s, 2 H) 2.67 (m, 2 H) 2.45 (m, 2 H) 2.16 (s, 6 H).

Example 40

N-(3-{3-[2-({3-[2-(dimethylamino)ethyl] phenyl}amino)pyrimidin-4-yl]imidazo[1,2-a]pyridin-2-yl}phenyl)-N'-phenylurea The title compound was prepared as described in EXAMPLE 3, substituting EXAMPLE 37D for EXAMPLE 1H. MS (ESI(+)) m/e 569 (M+H)$^+$, $^1$H NMR (400 MHz, dimethylsulfoxide-d$_6$) δ ppm 9.67 (s, 1 H) 9.56 (d, 1 H) 8.82 (s, 1 H) 8.66 (s, 1 H) 8.36 (d, 1 H) 7.76 (m, 2 H) 7.64 (s, 1 H) 7.57 (m, 2 H) 7.49 (m, 1 H) 7.45 (d, 2 H) 7.37 (t, 1 H) 7.26 (m, 3 H) 7.20 (m, 1 H) 7.07 (t, 1 H) 6.96 (t, 1 H) 6.85 (d, 1 H) 6.65 (d, 1 H) 2.67 (m, 2 H) 2.45 (m, 2 H) 2.16 (m, 6 H).

Example 41

N-{3-[3-(2-[4-(4-ethylpiperazin-1-yl)phenyl]amino] pyrimidin-4-yl)imidazo[1,2-a]pyridin-2-yl]phenyl}-2-phenylacetamide Example 41A The title compound was prepared as described in EXAMPLE 4F, substituting 4-(4'-ethylpiperidinyl)aniline for EXAMPLE 4E. MS ESI(+): m/e 521.2 (M+H)$^+$.

Example 41B

A solution of EXAMPLE 41A (0.29 g, 0.56 mmole) and tin(II) chloride in 20 mL of 1-methyl-2-pyrrolidinone and concentrated HCl (9:1, v/v) was stirred at 85° C. for 2 hours. The solvents were evaporated and the residue was taken up in 10% aqueous NaOH (15 mL) and CH$_2$Cl$_2$ (80 mL) and stirred for half hour. The two phases were separated and the aqueous phase was extracted with CH$_2$Cl$_2$. The combined organic solution was dried (MgSO$_4$), filtered and concentrated. The residue was triturated with water. The solid was filtered and dried under vacuum, providing the title compound. MS ESI (+): m/e 491.2 (M+H)$^+$.

Example 41C

N-{3-[3-(2-{[4-(4-ethylpiperazin-1-yl)phenyl]amino}pyrimidin-4-yl)imidazo[1,2-a]pyridin-2-yl]phenyl}-2-phenylacetamide, bis-trifluoroacetic acid salt A solution of EXAMPLE 41B (75 mg, 0.15 mmole), 2-phenylacetyl chloride (33 mg, 0.21 mmole) and pyridine (24 mmole) in dichloromethane (4 mL) was stirred at ambient temperature overnight. The mixture was concentrated and the residue was purified on a reverse phase HPLC using a gradient of trifluoroacetic acid-buffered water and acetonitrile as the mobile phase. MS ESI(+): m/e 609.3 (M+H)$^+$. $^1$H NMR (400 MHz, dimethylsulfoxide-d$_6$) δ ppm 10.31 (s, 1 H), 9.61 (s, 1 H), 9.52 (bs, 2 H), 8.31 (d, 1 H), 7.96 (s, 1 H) 7.79 (d, 1 H), 7.72 (s, 1 H) 7.57-7.62 (m, 3 H), 7.40 (t, 1 H), 7.23-7.33 (m, 6 H), 7.14 (t, 1 H), 6.99 (d, 2 H), 6.58 (d, 1 H), 3.65 (s, 2H), 3.57-3.60 (m, 4 H), 3.12-3.23 (m, 4 H), 2.93 (q, 2 H), 1.27 (t, 3H).

Example 42

N-{3-[3-(2-{[4-(4-ethylpiperazin-1-yl)phenyl]amino}pyrimidin-4-yl)imidazo[1,2-a]pyridin-2-yl]phenyl}-2-thien-2-ylacetamide The title compound as prepared as described in EXAMPLE 41, substituting 2-(thiophen-2-yl)acetyl chloride for 2-phenylacetyl chloride. MS ESI(+): m/e 615.3 (M+H)$^+$. $^1$H NMR (400 MHz, dimethylsulfoxide-d$_6$) δ ppm 10.34 (s, 1 H), 9.61 (s, 1 H), 9.52 (bs, 2 H), 8.32 (d, 1 H), 7.96 (s, 1 H) 7.79 (d, 1 H), 7.71 (d, 1 H) 7.56-7.62 (m, 3 H), 7.38-7.43 (m, 2 H), 7.31 (d, 1 H), 7.14 (t, 1 H), 6.95-7.00 (m, 4 H), 6.58 (d, 1 H), 3.88 (s, 2 H), 3.78 (d, 2 H), 3.57 (d, 2 H), 3.15-3.32 (m, 4 H), 2.93 (q, 2 H), 1.27 (t, 3H).

Example 43

N-{3-[3-(2-{[4-(4-ethylpiperazin-1-yl)phenyl]amino}pyrimidin-4-yl)imidazo[1,2-a]pyridin-2-yl]phenyl}benzamide The title compound as prepared as described in EXAMPLE 41, substituting benzoyl chloride for 2-phenylacetyl chloride. MS ESI(+): m/e 595.3 (M+H)$^+$. $^1$H NMR (400 MHz, dimethylsulfoxide-d$_6$) δ ppm 10.39 (s, 1 H), 9.61 (s, 1 H), 9.54 (bs, 2 H), 8.34 (d, 1 H), 8.19 (s, 1 H) 7.96 (d, 2 H), 7.92 (d, 1 H) 7.81 (d, 1 H), 7.52-7.62 (m, 6 H), 7.46 (t, 1 H), 7.35 (d, 1 H), 7.15 (t, 1 H), 6.98 (d, 2 H), 6.64 (d, 1 H), 3.75 (d, 2 H), 3.57 (d, 2 H), 3.10-3.22 (m, 4 H), 2.92 (q, 2 H), 1.26 (t, 3H).

Example 44

N-{3-[3-(2-{[4-(4-ethylpiperazin-1-yl)phenyl]amino}pyrimidin-4-yl)imidazo[1,2-a]pyridin-2-yl]phenyl}-2,6-difluorobenzamide The title compound as prepared as described in EXAMPLE 41, substituting 2,6-difluorobenzoyl chloride for 2-phenylacetyl chloride. MS ESI(+): m/e 631.3 (M+H)$^+$. $^1$H NMR (400 MHz, dimethylsulfoxide-d$_6$) δ ppm 10.92 (s, 1 H), 9.61 (s, 1 H), 9.51 (bs, 2 H), 8.34 (d, 1 H), 8.08 (s, 1 H) 7.81 (d, 1 H), 7.78 (d, 1 H), 7.57-7.63 (m, 3 H), 7.48 (t, 1 H), 7.40 (d, 1 H), 7.11-7.28 (m, 4 H), 6.98 (d, 2 H), 6.64 (d, 1 H), 3.76 (d, 2 H), 3.58 (d, 2 H), 3.10-3.23 (m, 4 H), 2.93 (q, 2 H), 1.26 (t, 3H).

Example 45

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2,6-difluorobenzamide Example 45A To a 25 ml round-bottom flask was added 1-(bromomethyl)-3-nitrobenzene (0.700 g, 3.24 mmol), N,N-dimethylpiperidin-4-amine (0.478 g, 3.73 mmol), and potassium carbonate (0.896 g, 6.48 mmol) in acetonitrile (11 ml). The reaction was stirred at ambient temperature 10 minutes. The reaction was filtered and the filtrate concentrated. The concentrate was purified by flash chromatography on a 10 g silica gel column with a gradient of 0% to 5% methanol in CH$_2$Cl$_2$ to provide the title compound. MS (DCI(+)) m/e 264.1 (M+H)$^+$.

Example 45B

To a 25 mL round-bottom flask was charged EXAMPLE 45A (0.34 g, 1.291 mmol), iron (0.721 g, 12.91 mmol), and ammonium chloride (0.242 g, 4.52 mmol) in ethanol (5 ml) and water (2 ml). The reaction was heated at 90° C. for 3 hours. The hot reaction was filtered and the pad washed with methanol. The combined filtrate was diluted with ethyl acetate (100 mL) and washed with 5% aqueous NaHCO$_3$. The aqueous layer was backwashed with 3×100 mL CH$_2$Cl$_2$. The combined organic layers were dried over MgSO$_4$ and concentrated to provide the title compound. MS (DCI(+)) m/e 234.1 (M+H)$^+$.

Example 45C

The title compound was prepared as described in EXAMPLE 4F, substituting EXAMPLE 45B for EXAMPLE 4E. MS (ESI(+)) m/e 549.2 (M+H)$^+$.

Example 45D

To a 50 mL round bottom flask was charged EXAMPLE 45C (0.20 g, 0.365 mmol), iron (0.204 g, 3.65 mmol), and ammonium chloride (0.068 g, 1.276 mmol) in ethanol (9 mL) and water (1.5 mL) to give a suspension. The reaction was heated to 90° C. for 2 hours. The reaction was filtered while hot and the filter pad was washed with 100 mL ethyl acetate and 20 mL methanol. The combined filtrate was washed with saturated aq. NaHCO$_3$ (40 mL). The aqueous layer was washed with 3×75 mL 10% methanol/ethyl acetate. The combined organic layers were dried over MgSO$_4$, filtered, and concentrated to provide the title compound. MS (ESI(+)) m/e 519.2 (M+H)$^+$.

Example 45E

The title compound was prepared as described in EXAMPLE 4H, substituting EXAMPLE 45D for EXAMPLE 4G. MS (ESI(+)) m/e 549.2 (M+H)$^+$; $^1$H NMR (300 MHz, deuterium oxide) δ ppm 9.02 (d, 1 H) 8.36 (d, 1 H) 7.91 (m, 1 H) 7.80 (m, 2 H) 7.45-7.61 (m, 5 H) 7.22-7.38 (m, 3 H) 7.06-7.18 (m, 3 H) 6.90 (d, 1 H) 4.20 (s, 2 H) 3.48-3.67 (m, 3 H) 3.04-3.15 (m, 2 H) 2.86 (s, 6 H) 2.32 (m, 2 H) 1.84-1.97 (m, 2 H).

Example 46

N-[3-(3-{2-[(3-{[4-(dimethylamino)piperidin-1-yl] methyl}phenyl)amino]pyrimidin-4-yl}imidazo[1,2-a]pyridin-2-yl)phenyl]-2-phenylacetamide The title compound was prepared as described in EXAMPLE 4H, substituting EXAMPLE 45D for EXAMPLE 4G and phenylacetyl chloride for 2,6-difluorobenzoyl chloride. MS (ESI(+)) m/e 637.3 (M+H)$^+$; $^1$H NMR (300 MHz, deuterium oxide) δ ppm 9.00 (d, 1 H) 8.28 (d, 1 H) 7.76 (m, 3 H) 7.22-7.56 (m, 12 H) 7.12 (m, 1 H) 6.83 (d, 1 H) 4.14 (s, 2 H) 3.69 (s, 2 H) 3.45-3.59 (m, 3 H) 2.96-3.06 (m, 2 H) 2.85 (s, 6 H) 2.26 (m, 2 H) 1.81-1.94 (m, 2 H).

Example 47

N-[3-(3-{2-[(3-{[4-(dimethylamino)piperidin-1-yl] methyl}phenyl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 45D for EXAMPLE 4G and 2-thiopheneacetyl chloride for 2,6-difluorobenzoyl chloride. MS (ESI(+)) m/e 643.3 (M+H)$^+$; $^1$H NMR (300 MHz, deuterium oxide) δ ppm 8.98 (d, 1 H) 8.30 (d, 1 H) 7.73 (m, 3 H) 7.43-7.56 (m, 4 H) 7.21-7.33 (m, 4 H) 7.14 (m, 1 H) 6.99 (m, 2 H) 6.84 (d, 1 H) 4.15 (s, 2 H) 3.90 (s, 2 H) 3.44-3.60 (m, 3 H) 2.96-3.07 (m, 2 H) 2.86 (s, 6 H) 2.28 (m, 2 H) 1.82-1.95 (m, 2 H).

Example 48

N-(3-{3-[2-({3-[2-(dimethylamino)ethoxy] phenyl}amino)pyrimidin-4-yl]imidazo[1,2-a]pyridin-2-yl}phenyl)-2,6-difluorobenzamide

Example 48A

To a 250 mL round bottom flask was charged 3-nitrophenol (3.5 g, 25.2 mmol), 2-bromoethanol (4.09 g, 32.7 mmol), and polymer bound triphenylphosphine (Fluka, 3 mmol/g, 12.58 g, 37.7 mmol) and tetrahydrofuran (90 mL). The resulting mixture was cooled to 0° C. with stirring and diisopropyl azodicarboxylate (6.849 mL, 35.22 mmol) was added dropwise over 10 minutes. The reaction was allowed to stir at ambient temperature for 35 hours. The reaction was filtered and the filtrate was concentrated in vacuo. The concentrate was purified by flash chromatography on an AnaLogix SF40-150 g silica gel column using an AnaLogix IntelliFlash 280 system eluting with a gradient of 0% to 3% ethyl acetate in hexanes to provide the title compound. MS (DCI(+)) m/e 262.9 (M+NH$_4$)$^+$.

Example 48B

In a 20 mL scintillation vial, a solution of EXAMPLE 48A (0.7 g, 2.84 mmol) in acetonitrile (3 mL) was treated with dimethylamine (2M in tetrahydrofuran, 4.27 mL, 8.53 mmol) and triethylamine (1.190 mL, 8.53 mmol). The resulting solution was stirred at ambient temperature for 18 hours. The reaction was concentrated. The concentrate was taken up in ethyl acetate and washed with 5% NaHCO$_3$ (aqueous) and brine. The organic layer was dried with Na$_2$SO$_4$, filtered, and concentrated. The concentrate was purified by flash chromatography on a 5 g silica gel column eluting with a step gradient of CH$_2$Cl$_2$ then CH$_2$Cl$_2$/methanol/NH$_4$OH (93:5:2) to provide the title compound. MS (DCI(+)) m/e 211.0 (M+H)$^+$.

Example 48C

In a 50 mL round bottom flask was charged EXAMPLE 48B (0.54 g, 2.57 mmol) and ethanol (11 mL). The suspension was treated with iron (1.148 g, 20.55 mmol) followed by a solution of ammonium chloride (0.137 g, 2.57 mmol) in water (2 mL). The mixture was heated at 90° C. for 2 hours. The reaction was filtered. The filtrate was diluted with CH$_2$Cl$_2$ (100 mL) and washed with 5% NaHCO$_3$ (aq.) and brine (40 mL). The organic layer was dried over MgSO$_4$, filtered, and concentrated to provide the title compound. MS (DCI(+)) m/e 181.0 (M+H)$^+$.

Example 48D

The title compound was prepared as described in EXAMPLE 4F, substituting EXAMPLE 48C for EXAMPLE 4E. MS (ESI(+)) m/e 549.2 (M+H)$^+$.

Example 48E

The title compound was prepared as described in EXAMPLE 4G, substituting EXAMPLE 48D for EXAMPLE 4F. MS (ESI(+)) m/e 466.2 (M+H)$^+$.

Example 48F

The title compound was prepared as described in EXAMPLE 4H, substituting EXAMPLE 48E for EXAMPLE 4G. MS (ESI(+)) m/e 606.3 (M+H)$^+$; $^1$H NMR (300 MHz, dimethylsulfoxide-d$_6$) δ ppm 10.91 (s, 1 H) 9.85 (s, 1 H) 9.54 (m, 2 H) 8.40 (d, 1 H) 8.10 (m, 1 H) 7.73-7.81 (m, 2 H) 7.38-7.64 (m, 5 H) 7.11-7.34 (m, 5 H) 6.71 (d, 1 H) 6.65 (m, 1 H) 4.26 (m, 2 H) 3.50 (m, 2 H) 2.85 (d, 6 H).

Example 49

N-(3-{3-[2-({3-[2-(dimethylamino)ethoxy] phenyl}amino)pyrimidin-4-yl]imidazo[1,2-a]pyridin-2-yl}phenyl)-2-phenylacetamide The title compound was prepared as described in EXAMPLE 4H, substituting EXAMPLE 48E for EXAMPLE 4G and phenylacetyl chloride for 2,6-difluorobenzoyl chloride. MS (ESI(+)) m/e 584.3 (M+H)$^+$; $^1$H NMR (300 MHz, methanol-d$_4$) δ ppm 9.78 (d,1 H) 8.33 (d, 1 H) 8.09 (m, 1 H) 7.87 (m, 2 H) 7.59-7.67 (m, 2 H) 7.51 (t, 1 H) 7.23-7.44 (m, 9 H) 6.68-6.75 (m, 2 H) 4.33 (m, 2 H) 3.69 (s, 2 H) 3.57 (m, 2 H) 2.96 (s, 6 H).

Example 50

N-(3-{3-[2-({3-[2-(dimethylamino)ethoxy] phenyl}amino)pyrimidin-4-yl]imidazo[1,2-a]pyridin-2-yl}phenyl)-2-thien-2-ylacetamide The title compound was prepared as described in EXAMPLE 4H, substituting EXAMPLE 48E for EXAMPLE 4G and 2-thiopheneacetyl chloride for 2,6-difluorobenzoyl chloride. MS (APCI(+)) m/e 590.5 (M+H)⁺; ¹H NMR (300 MHz, methanol-$d_4$) δ ppm 9.75 (d, 1 H) 8.32 (d, 1 H) 8.05 (m, 1 H) 7.77-7.85 (m, 2 H) 7.62-7.68 (m, 2 H) 7.50 (t, 1 H) 7.40 (m, 1 H) 7.24-7.32 (m, 4 H) 6.93-7.00 (m, 2 H) 6.68-6.75 (m, 2 H) 4.32 (m, 2 H) 3.89 (s, 2 H) 3.57 (m, 2 H) 2.96 (s, 6 H).

Example 51

N-[3-(3-{2-[(3-{[4-(dimethylamino)piperidin-1-yl]methyl}phenyl)amino]pyrimidin-4-yl}imidazo[1,2-a]pyridin-2-yl)phenyl]-5-methylthiophene-2-carboxamide The title compound was prepared as described in EXAMPLE 52, substituting EXAMPLE 45D for EXAMPLE 48E. MS (ESI(+)) m/e 643.4 (M+H)⁺; ¹H NMR (300 MHz, deuterium oxide) δ ppm 9.15 (d, 1 H) 8.34 (d, 1 H) 7.80-7.91 (m, 3 H) 7.32-7.59 (m, 8 H) 7.18 (m, 1 H) 6.88 (m, 2 H) 4.24 (s, 2 H) 3.48-3.68 (m, 3 H) 3.11 (m, 2 H) 2.87 (s, 6 H) 2.49 (s, 3 H) 2.33 (m, 2 H) 1.85-2.00 (m, 2 H).

Example 52

N-(3-{3-[2-({3-[2-(dimethylamino)ethoxy]phenyl}amino)pyrimidin-4-yl]imidazo[1,2-a]pyridin-2-yl}phenyl)-5-methylthiophene-2-carboxamide To a 4 mL vial was charged EXAMPLE 48E (0.045 g, 0.097 mmol), 5-methylthiophene-2-carboxylic acid (0.014 g, 0.101 mmol), 1-hydroxybenzotriazole hydrate (0.016 g, 0.101 mmol) and N-methylpyrrolidinone (1.5 ml). The reaction was treated with polystyrene-carbodiimide (Argonaut, 1.25 mmol/g, 0.232 g, 0.290 mmol) and stirred at ambient temperature for 20 hours. The reaction was filtered and purified by reverse-phase HPLC on a Phenomenex C18 column (3×15 cm) using a gradient of 10% to 50% acetonitrile:0.15% aqueous $CF_3COOH$ to provide 26 mg of a white solid. MS (ESI(+)) m/e 590.2 (M+H)⁺; ¹H NMR (300 MHz, methanol-$d_4$) δ ppm 9.84 (d, 1 H); 8.35 (d, 1 H); 8.17 (m, 1 H); 7.88 (m, 2 H); 7.77 (m, 1 H); 7.70 (d, 1 H); 7.63 (m, 1 H); 7.55 (t, 1 H); 7.25-7.45 (m, 4 H); 6.87 (m, 1 H); 6.73 (m, 2 H); 4.33 (m, 2 H); 3.58 (m, 2 H); 2.97 (s, 6 H); 2.53 (s, 3 H).

Example 53

N-(3-{3-[2-({4-[2-(dimethylamino)ethyl]phenyl}amino)pyrimidin-4-yl]imidazo[1,2-a]pyridin-2-yl}phenyl)-2,6-difluorobenzamide Example 53A The title compound was prepared as described in EXAMPLE 4F, substituting EXAMPLE 195B for EXAMPLE 4E. MS (ESI(+)) m/e 480 (M+H)⁺.

Example 53B

The title compound was prepared as described in EXAMPLE 4G, substituting EXAMPLE 53A for EXAMPLE 4F. MS (ESI(+)) m/e 450 (M+H)⁺.

Example 53C

The title compound was prepared as described in EXAMPLE 4H, substituting EXAMPLE 53B for EXAMPLE 4G. MS (ESI(+)) m/e 590 (M+H)⁺; ¹H NMR (400 MHz, dimethylsulfoxide-$d_6$) δ ppm 10.88 (s, 1 H) 9.63 (s, 1 H) 9.50 (d, 1 H) 8.35 (d, 1 H) 8.04 (s, 1 H) 7.78 (m, 2 H) 7.60 (m, 3 H) 7.49 (m, 1 H) 7.44 (d, 1 H) 7.39 (m, 1 H) 7.25 (t, 2 H) 7.14 (d, 2 H) 7.07 (t, 1 H) 6.65 (d, 1 H) 2.66 (m, 2 H) 2.45 (m, 2 H) 2.19 (s, 6 H).

Example 54

N-(3-{3-[2-({4-[2-(dimethylamino)ethyl]phenyl}amino)pyrimidin-4-yl]imidazo[1,2-a]pyridin-2-yl}phenyl)-2-phenylacetamide The title compound was prepared as described in EXAMPLE 4H, substituting EXAMPLE 53B for EXAMPLE 4G, and phenylacetyl chloride for 2,6-difluorobenzoyl chloride. MS (ESI(+)) m/e 568 (M+H)⁺, ¹H NMR (400 MHz, dimethylsulfoxide-$d_6$) δ ppm 10.26 (s, 1 H) 9.63 (s, 1 H) 9.53 (d, 1 H) 8.32 (d, 1 H) 7.92 (s, 1 H) 7.74 (d, 2 H) 7.62 (d, 2 H) 7.49 (m, 1 H) 7.37 (m, 1 H) 7.27-7.35 (m, 5 H) 7.26 (m, 1 H) 7.14 (d, 2 H) 7.06 (t, 1 H) 6.60 (d, 1 H) 3.64 (s, 2 H) 2.66 (m, 2 H) 2.45 (m, 2 H) 2.19 (s, 6 H).

Example 55

N-(3-{3-[2-({4-[2-(dimethylamino)ethyl]phenyl}amino)pyrimidin-4-yl]imidazo[1,2-a]pyridin-2-yl}phenyl)-2-thien-2-ylacetamide The title compound was prepared as described in EXAMPLE 4H, substituting EXAMPLE 53B for EXAMPLE 4G, and 2-thiopheneacetyl chloride for 2,6-difluorobenzoyl chloride. MS (ESI(+)) m/e 574 (M+H)⁺, ¹H NMR (400 MHz, dimethylsulfoxide-$d_6$) δ ppm 10.30 (s, 1 H) 9.64 (s, 1 H) 9.52 (d, 1 H) 8.32 (d, 1 H) 7.91 (s, 1 H) 7.73 (m, 2 H) 7.62 (d, 2 H) 7.49 (m, 1 H) 7.38 (m, 2 H) 7.31 (m, 1 H) 7.14 (d, 2 H) 7.06 (t, 1 H) 6.97 (m, 2 H) 6.60 (d, 1 H) 3.87 (s, 2 H) 2.66 (m, 2 H) 2.45 (m, 2 H) 2.19 (m, 6 H).

Example 56

2,6-difluoro-N-{3-[3-(2-{[3-(2-pyrrolidin-1-ylethyl)phenyl]amino}pyrimidin-4-yl)imidazo[1,2-a]pyridin-2-yl]phenyl}benzamide Example 56A The title compound was prepared as described in EXAMPLE 195A, substituting EXAMPLE 402G for 4-nitrophenethyl bromide, and pyrrolidine for dimethylamine. MS (DCI(+)) m/e 221 (M+H)⁺.

Example 56B

The title compound was prepared as described in EXAMPLE 26B, substituting EXAMPLE 56A for N,N-dimethyl-1-(3-nitrophenyl)methanamine. MS (DCI(+)) m/e 191 (M+H)⁺.

Example 56C

The title compound was prepared as described in EXAMPLE 4F, substituting EXAMPLE 56B for EXAMPLE 4E. MS (ESI(+)) m/e 506 (M+H)⁺.

Example 56D

The title compound was prepared as described in EXAMPLE 4G, substituting EXAMPLE 56C for EXAMPLE 4F. MS (ESI(+)) m/e 476 (M+H)+.

Example 56E

The title compound was prepared as described in EXAMPLE 4H, substituting EXAMPLE 56D for EXAMPLE 4G. MS (ESI(+)) m/e 616 (M+H)+, $^1$H NMR (400 MHz, dimethylsulfoxide-$d_6$) δ ppm 10.88 (s, 1 H) 9.68 (s, 1 H) 9.51 (d, 1 H) 8.37 (d, 1 H) 8.05 (s, 1 H) 7.78 (m, 2 H) 7.66 (s, 1 H) 7.55-7.61 (m, 2 H) 7.39-7.51 (m, 3 H) 7.25 (m, 2 H) 7.19 (t, 1 H) 7.07 (t, 1 H) 6.85 (d, 1 H) 6.67 (d, 1 H) 2.69 (m, 2 H) 2.60 (m, 2 H) 2.43 (m, 4 H) 1.65 (m, 4 H).

Example 57

2-phenyl-N-{3-[3-(2-{[3-(2-pyrrolidin-1-ylethyl)phenyl]amino}pyrimidin-4-yl)imidazo[1,2-a]pyridin-2-yl]phenyl}acetamide The title compound was prepared as described in EXAMPLE 4H, substituting EXAMPLE 56D for EXAMPLE 4G, and phenylacetyl chloride for 2,6-difluorobenzoyl chloride. MS (ESI(+)) m/e 594 (M+H)+, $^1$H NMR (400 MHz, dimethylsulfoxide-$d_6$) δ ppm 10.26 (s, 1 H) 9.67 (s, 1 H) 9.52 (d, 1 H) 8.34 (d, 1 H) 7.93 (s, 1 H) 7.74 (d, 2 H) 7.66 (s, 1 H) 7.57 (d, 1 H) 7.49 (m, 1 H) 7.28-7.40 (m, 6 H) 7.25 (m, 1 H) 7.19 (t, 1 H) 7.06 (t, 1 H) 6.85 (d, 1 H) 6.62 (d, 1 H) 3.64 (s, 2 H) 2.69 (m, 2 H) 2.60 (m, 2 H) 2.43 (m, 4 H) 1.65 (m, 4 H).

Example 58

N-{3-[3-(2-{[3-(2-pyrrolidin-1-ylethyl)phenyl]amino 1 pyrimidin-4-yl)imidazo[1,2-a]pyridin-2-yl]phenyl}-2-thien-2-ylacetamide The title compound was prepared as described in EXAMPLE 4H, substituting EXAMPLE 56D for EXAMPLE 4G, and 2-thiopheneacetyl chloride for 2,6-difluorobenzoyl chloride. MS (ESI(+)) m/e 600 (M+H)+, $^1$H NMR (400 MHz, dimethylsulfoxide-$d_6$) δ ppm 10.30 (s, 1 H) 9.68 (s, 1 H) 9.52 (d, 1 H) 8.35 (d, 1 H) 7.92 (s, 1 H) 7.73 (m, 2 H) 7.66 (s, 1 H) 7.57 (d, 1 H) 7.49 (m, 1 H) 7.38 (m, 2 H) 7.32 (m, 1 H) 7.20 (t, 1 H) 7.06 (t, 1 H) 6.98 (m, 2 H) 6.85 (d, 1 H) 6.62 (d,1 H) 3.87 (s, 2 H) 2.69 (m, 2 H) 2.61 (m, 2 H) 2.43 (m, 4 H) 1.65 (m, 4 H).

Example 59

2,6-difluoro-N-(3-{3-[2-({3-[(3-hydroxyazetidin-1-yl)methyl]phenyl}amino)pyrimidin-4-yl]imidazo[1,2-a]pyridin-2-yl}phenyl)benzamide

Example 59A

To a solution of 3-hydroxyazetidinium chloride (0.68 g, 6.2 mmol) and Hunig's base (2.5 mL, 14.1 mmol) in acetonitrile (10 ml) was added 1-(bromomethyl)-3-nitrobenzene. After the reaction mixture was stirred at room temperature for 18 hours, it was partitioned between ethyl acetate and NaHCO$_3$. The organic layer was washed with brine, dried and concentrated. The crude material was purified by silica gel column chromatography, eluting with 20% ethyl acetate/hexanes to give 0.54 g 1-(3-nitrobenzyl)azetidin-3-ol. MS (DCI(+)) m/e 209 (M+H)+.

Example 59B

The title compound was prepared as described in EXAMPLE 4E, substituting EXAMPLE 59A for EXAMPLE 4D.

Example 59C

The title compound was prepared as described in EXAMPLE 1E, substituting EXAMPLE 59B for 3-morpholinoaniline.

Example 59D

The title compound was prepared as described in EXAMPLE 1F, substituting EXAMPLE 59C for EXAMPLE 1E.

Example 59E

The title compound was prepared as described in EXAMPLE 1G, substituting EXAMPLE 59D for EXAMPLE 1F.

Example 59F

The title compound was prepared as described in EXAMPLE 1H, substituting EXAMPLE 59E for EXAMPLE 1G.

Example 59G

The title compound was prepared as described in EXAMPLE 1I, substituting EXAMPLE 59F for EXAMPLE 1H. MS (ESI(+)) m/e 604 (M+H)+; $^1$H NMR (300 MHz, dimethylsulfoxide-$d_6$) δ 10.91 (s, 1H); 10.17 & 9.67 (bs, 1H); 9.93 (s, 1H); 9.52 (d, 1H); 8.41 (d, 1H); 8.11 (s, 1H); 7.89 (s, 1H); 7.81-7.73 (m, 3H); 7.60-7.38 (m, 4H); 7.28-7.23 (m, 2H); 7.12-7.06 (m, 2H); 6.74 (d, 1H); 6.14 (bs, 1H); 4.60 & 4.43 (t, 1H); 4.32 (t, 2H); 4.21 (m, 2H); 3.85 (m, 2H).

Example 60

N-(3-{3-[2-({3-[(3-hydroxyazetidin-1-yl)methyl]phenyl}amino)pyrimidin-4-yl]imidazo[1,2-a]pyridin-2-yl}phenyl)-2-phenylacetamide The title compound was prepared as described in EXAMPLE 1I, substituting EXAMPLE 59F for EXAMPLE 1H and phenylacetyl chloride for 2,6-difluorobenzoyl chloride. MS (ESI(+)) m/e 582 (M+H)+; $^1$H-NMR (300 MHz, dimethylsulfoxide-$d_6$) δ 10.29 (s, 1H); 10.18 & 9.68 (bs, 1H); 9.93 (s, 1H); 9.53 (d, 1H); 8.38 (d, 1H); 7.99 (s, 1H); 7.89 (s, 1H); 7.77 (m, 2H); 7.68 (d, 1H); 7.53 (t, 1H); 7.41-7.24 (m, 7H); 7.11-7.06 (m, 2H); 6.68 (d, 1H); 6.14 (bs, 1H); 4.60 & 4.43 (t, 1H); 4.32 (t, 2H); 4.19 (m, 2H); 3.85 (m, 2H); 3.64 (s, 2H).

Example 61

N-(3-{3-[2-({3-[(3-hydroxyazetidin-1-yl)methyl]phenyl}amino)pyrimidin-4-yl]imidazo[1,2-a]pyridin-2-yl}phenyl)-2-thien-2-ylacetamide The title compound was prepared as described in EXAMPLE 1I, substituting EXAMPLE 59F for EXAMPLE 1H and 2-thienylacetyl chloride for 2,6-difluorobenzoyl chloride. MS (ESI(+)) m/e 588 (M+H)+; 1H-NMR (300 MHz, dimethylsulfoxide-d6) δ 10.34 (s, 1H); 10.19 & 9.71 (bs, 1H); 9.94 (s, 1H); 9.54 (d, 1H); 8.39 (d, 1H); 7.99 (s, 1H); 7.89 (s, 1H); 7.80-7.71 (m, 2H); 7.67 (d, 1H); 7.55 (t, 1H); 7.43-7.25 (m, 2H); 7.15-7.06 (m, 2H); 6.98 (d, 2H); 6.69 (d, 1H); 6.14 (bs, 1H); 4.59 & 4.43 (t, 1H); 4.32 (t, 2H); 4.19 (m, 2H); 3.87 (s, 2H); 3.84 (m, 2H).

Example 62

2,6-difluoro-N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]benzamide

Example 62A

The title compound was prepared as described in EXAMPLE 195A, substituting EXAMPLE 402G for 4-nitrophenethyl bromide, and 2-(methylamino)ethanol for dimethylamine. MS (DCI(+)) m/e 225 (M+H)+.

Example 62B

The title compound was prepared as described in EXAMPLE 26B, substituting EXAMPLE 62A for N,N-dimethyl-1-(3-nitrophenyl)methanamine. MS (DCI(+)) m/e 195 (M+H)+.

Example 62C

The title compound was prepared as described in EXAMPLE 4F, substituting EXAMPLE 62B for EXAMPLE 4E. MS (ESI(+)) m/e 510 (M+H)+.

Example 62D

The title compound was prepared as described in EXAMPLE 4G, substituting EXAMPLE 62C for EXAMPLE 4F. MS (ESI(+)) m/e 480 (M+H)+.

Example 62E

The title compound was prepared as described in EXAMPLE 4H, substituting EXAMPLE 62D for EXAMPLE 4G. MS (ESI(+)) m/e 620 (M+H)+, 1H NMR (400 MHz, dimethylsulfoxide-d6) δ ppm 10.88 (s, 1 H) 9.67 (s, 1 H) 9.53 (d, 1 H) 8.37 (d, 1 H) 8.05 (s, 1 H) 7.78 (m, 2 H) 7.63 (s, 1 H) 7.58 (m, 2 H) 7.50 (m, 1 H) 7.46 (m, 1 H) 7.42 (m, 1 H) 7.25 (m, 2 H) 7.19 (t, 1 H) 7.08 (t, 1 H) 6.85 (d, 1 H) 6.66 (d, 1 H) 4.28 (bs, 1 H) 3.46 (t, 2 H) 2.66 (m, 2 H) 2.58 (m, 2 H) 2.44 (t, 2 H) 2.22 (s, 3 H).

Example 63

N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]-2-phenylacetamide The title compound was prepared as described in EXAMPLE 4H, substituting EXAMPLE 62D for EXAMPLE 4G, and phenylacetyl chloride for 2,6-difluorobenzoyl chloride. MS (ESI(+)) m/e 598 (M+H)+, 1H NMR (400 MHz, dimethylsulfoxide-d6) δ ppm 10.26 (s, 1 H) 9.67 (s, 1 H) 9.53 (d, 1 H) 8.34 (d, 1 H) 7.92 (s, 1 H) 7.74 (d, 2 H) 7.63 (s, 1 H) 7.58 (d, 1 H) 7.49 (m, 1 H) 7.37 (m, 1 H) 7.28-7.35 (m, 5 H) 7.24 (m, 1 H) 7.19 (t, 1 H) 7.07 (t, 1 H) 6.85 (d, 1 H) 6.61 (d, 1 H) 4.28 (bs, 1 H) 3.64 (s, 2 H) 3.46 (t, 2 H) 2.66 (m, 2 H) 2.58 (m, 2 H) 2.44 (t, 2 H) 2.22 (s, 3 H).

Example 64

N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 62D for EXAMPLE 4G, and 2-thiopheneacetyl chloride for 2,6-difluorobenzoyl chloride. MS (ESI(+)) m/e 604 (M+H)+, 1H NMR (400 MHz, dimethylsulfoxide-d6) δ ppm 10.30 (s, 1 H) 9.67 (s, 1 H) 9.53 (d, 1 H) 8.35 (d, 1 H) 7.92 (s, 1 H) 7.73 (m, 2 H) 7.63 (s, 1 H) 7.58 (d, 1 H) 7.49 (m, 1 H) 7.38 (m, 2 H) 7.32 (m, 1 H) 7.20 (t, 1 H) 7.07 (m, 1 H) 6.97 (m, 2 H) 6.85 (d, 1 H) 6.62 (d, 1 H) 4.28 (bs, 1 H) 3.87 (s, 2 H) 3.46 (t, 2 H) 2.66 (m, 2 H) 2.58 (m, 2 H) 2.44 (t, 2 H) 2.22 (s, 3 H).

Example 65

N-[3-(3-{2-[(3-([3-(dimethylamino)pyrrolidin-1-yl]methyl}phenyl)amino]pyrimidin-4-yl}imidazo[1,2-a]pyridin-2-yl)phenyl]-2,6-difluorobenzamide

Example 65A

The title compound was prepared as described in EXAMPLES 26A and B, substituting N,N-dimethyl-1-(pyrrolidin-3-yl)methanamine for dimethylamine. MS (DCI(+)) m/e 220 (M+H).

Example 65B

The title compound was prepared as described in EXAMPLE 4F, substituting EXAMPLE 65A for EXAMPLE 4E. MS (ESI(+)) m/e 535 (M+H)+.

Example 65C

The title compound was prepared as described in EXAMPLE 4G, substituting EXAMPLE 65B for EXAMPLE 4F. MS (ESI(+)) m/e 505 (M+H)+.

Example 65D

The title compound was prepared as described in EXAMPLE 4H, substituting EXAMPLE 65C for EXAMPLE 4G. MS (ESI(+)) m/e 645 (M+H)+, 1H NMR (400 MHz, dimethylsulfoxide-d6) δ ppm 10.88 (s, 1 H) 9.72 (s, 1 H) 9.54 (d, 1 H) 8.36 (d, 1 H) 8.05 (s, 1 H) 7.76 (m, 3 H) 7.64 (d, 1 H) 7.59 (m, 1 H) 7.50 (m, 1 H) 7.45 (d, 1 H) 7.40 (m, 1 H) 7.24 (q, 3 H) 7.07 (t, 1 H) 6.91 (d, 1 H) 6.67 (d, 1 H) 3.50 (m, 2 H) 2.72 (m, 1 H) 2.61 (m, 1 H) 2.53 (m, 1 H) 2.44 (m, 1 H) 2.28 (m, 1 H) 2.07 (s, 6 H) 1.79 (m, 1 H) 1.57 (m, 1 H).

Example 66

N-[3-(3-{2-[(3-{[3-(dimethylamino)pyrrolidin-1-yl]methyl}phenyl)amino]pyrimidin-4-yl)imidazo[1,2-a]pyridin-2-yl)phenyl]-2-phenylacetamide The title compound was prepared as described in EXAMPLE 4H, substituting EXAMPLE 65C for EXAMPLE 4G, and phenylacetyl chloride for 2,6-difluorobenzoyl chloride. MS (ESI(+)) m/e 623 (M+H)+, 1H NMR (400 MHz, dimethylsulfoxide-d$_6$) δ ppm 10.26 (s, 1 H) 9.71 (s, 1 H) 9.54 (d, 1 H) 8.33 (d, 1 H) 7.92 (s, 1 H) 7.74 (m, 3 H) 7.64 (d, 1 H) 7.50 (t, 1 H), 7.37 (t, 1 H) 7.27-7.34 (m, 5 H) 7.23 (m, 2 H) 7.06 (t, 1 H) 6.90 (d, 1 H) 6.62 (d, 1 H) 3.64 (s, 2 H) 3.50 (m, 2 H) 2.63 (m, 2 H) 2.53 (m, 1 H) 2.41 (m, 1 H) 2.25 (m, 1 H) 2.04 (s, 6 H) 1.78 (m, 1 H) 1.56 (m, 1 H).

Example 67

N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 65C for EXAMPLE 4G, and 2-thiopheneacetyl chloride for 2,6-difluorobenzoyl chloride. MS (ESI(+)) m/e 629 (M+H)$^+$, $^1$H NMR (400 MHz, dimethylsulfoxide-d$_6$) δ ppm 10.30 (s, 1 H) 9.71 (s, 1 H) 9.54 (d, 1 H) 8.34 (d, 1 H) 7.92 (s, 1 H) 7.73 (m, 3 H) 7.64 (d, 1 H) 7.49 (m, 1 H) 7.38 (m, 2 H) 7.31 (m, 1 H) 7.23 (t, 1 H) 7.06 (t, 1 H) 6.98 (m, 2 H) 6.91 (d, 1 H) 6.62 (d, 1 H) 3.87 (s, 2 H) 3.50 (m, 2 H) 2.64 (m, 2 H) 2.52 (m, 1 H) 2.42 (m, 1 H) 2.26 (m, 1 H) 2.05 (s, 6 H) 1.79 (m, 1 H) 1.56 (m, 1 H).

Example 68

N-{3-[3-(2-{[4-(1-acetylpiperidin-4-yl)phenyl]amino}pyrimidin-4-yl)imidazo[1,2-a]pyridin-2-yl]phenyl}-2-thien-2-ylacetamide Example 68A In a 25 ml round bottom flask was added EXAMPLE 4C (352 mg, 1.0 mmol), 8 ml of 2-propanol and 4 M HCl in dioxane (0.238 ml, 0.95 mmol). To the mixture was added tert-butyl 4-(4-aminophenyl)piperidine-1-carboxylate (387 mg, 1.400 mmol). The mixture was stirred at 80° C. for 48 hours. The mixture was evaporated to dryness. The residue was treated with a mixture of CH$_2$Cl$_2$ (5 mL) and trifluoroacetic acid (5 mL) for 1 hour. The solvents were evaporated and the residue mixed with water (10 mL) and adjusted to pH ~12 with concentrated aqueous NaOH. The solid was collected by filtration and washed with water, then dried in vacuum. MS ESI(+): m/e 492.1 (M+H)$^+$.

Example 68B

To a solution of EXAMPLE 68A (149 mg, 0.303 mmol) in CH$_2$Cl$_2$ (8 mL) was added N-ethyl-N-isopropylpropan-2-amine (109 μl, 606 mmol) and acetic anhydride (34.4 μl, 0.364 mmol). The mixture was stirred at room temperature for 1 hour, and concentrated. The solid was triturated with water (2×5 ml) and vacuum dried.

Example 68C

Example 68B was reduced as described in EXAMPLE 1H, giving the title compound.

Example 68D

N-{3-[3-(2-{[4-(1-acetylpiperidin-4-yl)phenyl]amino}pyrimidin-4-yl)imidazo[1,2-a]pyridin-2-yl]phenyl}-2-thien-2-ylacetamide, trifluoroacetic acid salt The title compound was prepared as described in EXAMPLE 41 from EXAMPLE 68C and 2-phenylacetyl chloride. MS ESI(+): m/e 628.3 (M+H)$^+$. $^1$H NMR (400 MHz, dimethylsulfoxide-d$_6$) δ ppm 10.36 (s, 1 H), 9.73 (s, 1 H), 9.57 (bd, 1 H), 8.37 (d, 1 H), 7.96 (s, 1 H), 7.83 (d, 1 H), 7.43 (d, 1 H) 7.67 (d, 1 H), 7.63 (d, 2 H), 7.44 (t, 1 H), 7.39 (dd, 1 H), 7.33 (d, 1 H), 7.20 (t, 1 H), 7.17 (d, 2 H), 6.96-6.98 (m, 2 H), 6.63 (d, 1 H), 3.88 (s, 2 H), 3.10-3.13 (m, 1 H), 2.68-2.72 (m, 2 H), 2.54-2.58 (m, 2 H), 2.03 (s, 3 H), 1.70-1.80 (m, 2 H), 1.38-1.62 (m, 2H).

Example 69

N-{3-[3-(2-{[4-(1-acetylpiperidin-4-yl)phenyl]amino}pyrimidin-4-yl)imidazo[1,2-a]pyridin-2-yl]phenyl}-2,6-difluorobenzamide The title compound was prepared as described in EXAMPLE 41 from EXAMPLE 68C and 2,6-difluorobenzoyl chloride. MS ESI(+): m/e 644.3 (M+H)$^+$. $^1$H NMR (400 MHz, dimethylsulfoxide-d$_6$) δ ppm 10.56 (s, 1 H), 9.73 (s, 1 H), 9.58 (bd, 1 H), 8.39 (d, 1 H), 8.09 (s, 1 H), 7.85 (d, 2 H), 7.74-7.78 (m, 1 H) 7.68 (t, 1 H), 7.62 (d, 2 H), 7.49 (t, 1 H), 7.43 (dd, 1 H), 7.38 (d, 1 H), 7.20-7.25 (m, 2 H), 7.17 (d, 2 H), 6.67 (d, 1 H), 3.10-3.13 (m, 1 H), 2.68-2.72 (m, 2 H), 2.54-2.58 (m, 2 H), 2.02 (s, 3 H), 1.70-1.80 (m, 2 H), 1.38-1.62 (m, 2H).

Example 70

N-[3-(3-{2-[(3-cyanophenyl)amino]pyrimidin-4-yl)imidazo[1,2-a]pyridin-2-yl)phenyl]-2,6-difluorobenzamide Example 70A The title compound was prepared as described in EXAMPLE 4F, substituting 3-aminobenzonitrile for EXAMPLE 4E. MS (ESI(+)) m/e 434.1 (M+H)$^+$.

Example 70B

The title compound was prepared as described in EXAMPLE 40, substituting EXAMPLE 70A for EXAMPLE 4F. MS (ESI(+)) m/e 404.2 (M+H)$^+$.

Example 70C

The title compound was prepared as described in EXAMPLE 4H, substituting EXAMPLE 70B for EXAMPLE 4G. MS (ESI(+)) m/e 544.1 (M+H)$^+$; $^1$H NMR (300 MHz, dimethylsulfoxide-d$_6$) δ ppm 10.92 (s, 1 H) 10.17 (s, 1 H) 9.52 (d, 1 H) 8.48 (d,1 H) 8.32 (m, 1 H) 8.07 (s, 1 H) 7.97 (m, 1 H) 7.81 (m, 2 H) 7.40-7.65 (m, 6 H) 7.17-7.28 (m, 3 H) 6.79 (d, 1 H).

Example 71

N-[3-(3-{2-[(3-cyanophenyl)amino]pyrimidin-4-yl}imidazo[1,2-a]pyridin-2-yl)phenyl]-2-phenylacetamide The title compound was prepared as described in EXAMPLE 4H, substituting EXAMPLE 70B for EXAMPLE 4G and phenylacetyl chloride for 2,6-difluorobenzoyl chloride. MS (ESI(+)) m/e 522.1 (M+H)$^+$; $^1$H NMR (300 MHz, dimethylsulfoxide-d$_6$) δ ppm 10.30 (s, 1 H) 10.17 (s, 1 H) 9.52 (d, 1 H) 8.46 (d, 1 H) 8.33 (m, 1 H) 7.96 (m, 2 H) 7.81 (d, 1 H) 7.72 (m, 1 H) 7.61 (m, 1 H) 7.51 (t, 1 H) 7.40 (m, 2 H) 7.15-7.34 (m, 7 H) 6.74 (d, 1 H) 3.64 (s, 2 H).

Example 72

N-[3-(3-{2-[(3-cyanophenyl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 70B for EXAMPLE 4G and 2-thiopheneacetyl chloride for 2,6-difluorobenzoyl chloride. MS (ESI(+)) m/e 528.0 (M+H)$^+$; $^1$H NMR (300 MHz, dimethylsulfoxide-d$_6$) δ ppm 10.33 (s, 1 H) 10.17 (s, 1 H) 9.52 (d, 1 H) 8.46 (d, 1 H) 8.32 (m, 1 H) 7.97 (m, 2 H) 7.81 (m, 1 H) 7.72 (m, 1 H) 7.61 (m, 1 H) 7.51 (t, 1 H) 7.30-7.44 (m, 4 H) 7.19 (m, 1 H) 6.98 (m, 2 H) 6.74 (d, 1 H) 3.87 (s, 2 H).

Example 73

2,6-difluoro-N-(3-{3-[2-({3-[2-(methylsulfonypethoxy)phenyl}amino)pyrimidin-4-yl]imidazo[1,2-a]pyridin-2-yl}phenyl)benzamide

Example 73A

In a 20 mL scintillation vial, a solution of EXAMPLE 48A (0.7 g, 2.84 mmol) in ethanol (12 mL) and water (2 mL) was treated with sodium thiomethoxide (0.598 g, 8.53 mmol). The resulting solution was stirred at ambient temperature for 17 hours. The reaction was diluted with ethyl acetate (75 mL) and washed with water (15 mL) and brine (15 mL). The organic layer was dried with Na$_2$SO$_4$, filtered, and concentrated. The concentrate was purified by flash chromatography on a 10 g silica gel column eluting with a gradient of 25% to 50% CH$_2$Cl$_2$/hexanes to provide the title compound. MS (DCI(+)) m/e 231.0 (M+NH$_4$)$^+$.

Example 73B

A 0° C. solution of EXAMPLE 73A (0.35 g, 1.641 mmol) in CH$_2$Cl$_2$ (10 mL) was treated with 3-chloroperbenzoic acid (75%, 0.755 g, 3.28 mmol). The resulting mixture was allowed to stir at ambient temperature for 20 hours. The reaction was diluted with CH$_2$Cl$_2$ (60 mL) and washed with saturated aqueous NaHCO$_3$ (15 mL) and brine (15 mL). The organic layer was dried (Na$_2$SO$_4$), filtered, and concentrated. The concentrate was purified by flash chromatography on a 5 g silica gel column eluting with CH$_2$Cl$_2$ to provide the title compound. MS (DCI(+)) m/e 246.0 (M+H)$^+$.

Example 73C

The title compound was prepared as described in EXAMPLE 48C, substituting EXAMPLE 73B for EXAMPLE 48B. MS (DCI(+)) m/e 215.9 (M+H)$^+$.

Example 73D

The title compound was prepared as described in EXAMPLE 4F, substituting EXAMPLE 73C for EXAMPLE 4E. MS (ESI(+)) m/e 531.1 (M+H)$^+$.

Example 73E

The title compound was prepared as described in EXAMPLE 4G, substituting EXAMPLE 73D for EXAMPLE 4F. MS (ESI(+)) m/e 501.1 (M+H)$^+$.

Example 73F

The title compound was prepared as described in EXAMPLE 4H, substituting EXAMPLE 73E for EXAMPLE 4G. MS (ESI(+)) m/e 641.2 (M+H)$^+$; $^1$H NMR (300 MHz, methanol-d$_4$) δ ppm 9.78 (d,1 H) 8.41 (d, 1 H) 8.25 (m, 1 H) 7.93-8.04 (m, 2 H) 7.76 (m, 1 H) 7.43-7.63 (m, 5 H) 7.24 (m, 2 H) 7.11 (m, 2 H) 6.76 (d, 1 H) 6.71 (m, 1 H) 4.39 (t, 2 H) 3.53 (t, 2 H) 3.03 (s, 3 H).

Example 74

N-(3-{3-[2-({3-[2-(methylsulfonyl)ethoxy]phenyl}amino)pyrimidin-4-yl]imidazo[1,2-a]pyridin-2-yl}phenyl)-2-phenylacetamide The title compound was prepared as described in EXAMPLE 4H, substituting EXAMPLE 73E for EXAMPLE 4G and phenylacetyl chloride for 2,6-difluorobenzoyl chloride. MS (ESI(+)) m/e 619.2 (M+H)$^+$; $^1$H NMR (300 MHz, methanol-d$_4$) δ ppm 9.77 (d, 1 H) 8.37 (d, 1 H) 8.12 (m, 1 H) 7.91-8.04 (m, 2 H) 7.66 (m, 1 H) 7.21-7.56 (m, 11 H) 6.71 (m, 2 H) 4.38 (t, 2 H) 3.69 (s, 2 H) 3.53 (t, 2 H) 3.03 (s, 3 H).

Example 75

N-(3-{3-[2-({3-[2-(methylsulfonyl)ethoxy]phenyl}amino)pyrimidin-4-yl]imidazo[1,2-a]pyridin-2-yl}phenyl)-2-thien-2-ylacetamide The title compound was prepared as described in EXAMPLE 4H, substituting EXAMPLE 73E for EXAMPLE 4G and 2-thiopheneacetyl chloride for 2,6-difluorobenzoyl chloride. MS (ESI(+)) m/e 625.1 (M+H)$^+$; $^1$H NMR (300 MHz, methanol-d$_4$) δ ppm 9.76 (d, 1 H) 8.38 (d, 1 H) 8.13 (m, 1 H) 7.92-8.04 (m, 2 H) 7.66 (m, 1 H) 7.40-7.58 (m, 4 H) 7.20-7.29 (m, 3 H) 6.97 (m, 2 H) 6.71 (m, 2 H) 4.381 (t, 2 H) 3.90 (s, 2 H) 3.53 (t, 2 H) 3.03 (s, 3 H).

Example 76

2,6-difluoro-N-{3-[3-(2-{[4-(1-isopropylpiperidin-4-yl)phenylamino]pyrimidin-4-yl)imidazo[1,2-a]pyridin-2-yl]phenyl}benzamide

Example 76A

To a solution of EXAMPLE 68A (136 mg, 0.277 mmol) in N,N-dimethylformamide (8 mL) was added potassium carbonate (76 mg, 0.553 mmol) and 2-iodopropane (35.9 µl, 0.360 mmol). The mixture was stirred at room temperature for 48 hours and was concentrated. The residue was taken up in water (10 mL) and extracted with CH$_2$Cl$_2$ (4×15 mL). The combined organic solution was dried (MgSO$_4$), filtered and concentrated to provide the title compound. MS ESI(+): m/e 534.6 (M+H)$^+$.

Example 76B

EXAMPLE 76A was reduced as described in EXAMPLE 1H, giving the title compound.

Example 76C 2,6-difluoro-N-{3-[3-(2-{[4-(1-isopropylpiperidin-4-yl)phenyl]amino}pyrimidin-4-yl)imidazo[1,2-a]pyridin-2-yl]phenyl}benzamide, trifluoroacetic acid salt The title compound was prepared as described in EXAMPLE 41 from EXAMPLE 76B and 2,6-difluorobenzoyl chloride. MS ESI(+): m/e 644.2 (M+H)$^+$. $^1$H NMR (400 MHz, dimethylsulfoxide-d$_6$) δ ppm 10.53 (s, 1 H), 9.75 (s, 1 H), 9.54 (bd, 1 H), 9.03 (bs, 1 H), 8.37 (d, 1 H), 8.08 (s, 1 H) 7.74-7.83 (m, 3 H), 7.70 (d, 2 H), 7.57 (t, 1 H), 7.37-7.48 (m, 3 H), 7.22-7.24 (m, 1 H), 7.17 (d, 2 H), 7.12 (t, 1 H), 6.67 (d, 1 H), 3.29-3.31 (m, 3 H), 3.06-3.13 (m, 2 H), 2.80-2.84 (m, 1 H), 2.02-2.05 (m, 2 H), 1.82-1.90 (m, 2 H), 1.28 (d, 6H).

Example 77

N-{3-[3-(2-{[4-(1-isopropylpiperidin-4-yl)phenyl]amino}pyrimidin-4-yl)imidazo[1,2-a]pyridin-2-yl]phenyl}-2-thien-2-ylacetamide The title compound was prepared as described in EXAMPLE 41 from EXAMPLE 76B and 2-(thiophen-2-yl)acetyl chloride. MS ESI(+): m/e 628.2 (M+H)$^+$. $^1$H NMR (400 MHz, dimethylsulfoxide-d$_6$) δ ppm 10.32 (s, 1 H), 9.75 (s, 1 H), 9.52 (bd, 1 H), 9.00 (bs, 1 H), 8.35 (d, 1 H), 7.95 (s, 1 H) 7.78 (d, 1 H), 7.69-7.71 (m, 3 H), 7.55 (t, 1 H), 7.37-7.42 (m, 2 H), 7.31 (d, 1 H), 7.17 (d, 2 H), 7.11 (t, 1 H), 6.94-6.98 (m, 2 H), 6.63 (d, 1 H), 3.87 (s, 3 H), 3.29-3.31 (m, 3 H), 3.06-3.13 (m, 2 H), 2.80-2.84 (m, 1 H), 2.02-2.05 (m, 2 H), 1.84-1.92 (m, 2 H), 1.28 (d, 6H).

Example 78

N-(3-{3-[2-({3-[(Z)-amino(hydroxyimino)methyl]phenyl}amino)pyrimidin-4-yl]imidazo[1,2-a]pyridin-2-yl}phenyl)-2,6-difluorobenzamide To a solution of EXAMPLE 70C (50 mg, 0.092 mmol), in N-methylpyrrolidinone (1 mL), and ethanol (0.6 mL) was added hydroxylamine hydrochloride (22 mg, 0.322 mmol) and triethylamine (58 uL, 0.414 mmol). The reaction mixture was heated at 80° C. for 1 hour and was concentrated. The concentrate was treated with water (4 mL) and the resulting suspension was allowed to stir at ambient temperature for 10 minutes. The suspension was filtered and the solid collected was purified by reverse phase HPLC on a Shimadzu LC10 HPLC system with a Phenomenex C18 column (3×15 cm) eluting with a gradient of 10% to 50% acetonitrile in 0.15% aqueous CF$_3$COOH to provide the title compound. MS ESI (+)) m/e 577.2 (M+H)$^+$; $^1$H NMR (300 MHz, dimethylsulfoxide-d$_6$) δ ppm 11.03 (s, 1 H) 10.90 (s, 1 H) 10.12 (s, 1 H) 9.53 (d, 1 H) 8.43 (d, 1 H) 8.18 (s, 1 H) 8.09 (m, 1 H) 7.98 (m, 1 H) 7.71-7.81 (m, 2 H) 7.37-7.64 (m, 5 H) 7.24 (m, 3 H) 7.12 (m, 1 H) 6.76 (d, 1 H).

Example 79

N-(3-{3-[2-({3-[(Z)-amino(hydroxyimino)methyl]phenyl}amino)pyrimidin-4-yl]imidazo[1,2-a]pyridin-2-yl}phenyl)-2-thien-2-ylacetamide The title compound was prepared as described in EXAMPLE 78, substituting EXAMPLE 72 for EXAMPLE 70C. MS (ESI(+)) m/e 561.1 (M+H)$^+$; $^1$H NMR (300 MHz, dimethylsulfoxide-d$_6$) δ ppm 11.01 (s, 1 H) 10.32 (s, 1 H) 10.12 (s, 1 H) 9.54 (d, 1 H) 8.40 (d, 1 H) 8.18 (m, 1 H) 7.98 (m, 2 H) 7.77 (m, 1 H) 7.66 (m, 1 H) 7.48-7.56 (m, 2 H) 7.38 (m, 2 H) 7.28 (m, 2 H) 7.10 (m, 1 H) 6.96 (m, 2 H) 6.70 (d, 1 H) 3.86 (s, 2 H).

Example 80

N-{-3-[3-(2-{[3-(2-amino-2-oxoethyl)phenyl]amino}pyrimidin-4-yl)imidazo[1,2-a]pyridin-2-yl]phenyl}-2,6-difluorobenzamide

Example 80A

The title compound was prepared as described in EXAMPLE 226A, substituting ammonium hydroxide for methylamine.

Example 80B

The title compound was prepared as described in EXAMPLE 4E, substituting EXAMPLE 80A for EXAMPLE 4D.

Example 80C

The title compound was prepared as described in EXAMPLE 4F, substituting EXAMPLE 80B for EXAMPLE 4E.

Example 80D

The title compound was prepared as described in EXAMPLE 4G, substituting EXAMPLE 80C for EXAMPLE 4F

Example 80E

The title compound was prepared as described in EXAMPLE 1I, substituting EXAMPLE 80D for EXAMPLE 1H. MS (ESI(+)) m/e 576 (M+H)$^+$; $^1$H-NMR (300 MHz, dimethylsulfoxide-d$_6$) δ 10.93 (s, 1H); 9.77 (s, 1H); 9.61 (d, 1H); 8.38 (d, 1H); 8.04 (s, 1H); 7.80 (d, 2H); 7.65-7.57 (m, 4H); 7.49 (t, 1H); 7.42 (m, 2H); 7.28-7.15 (m, 4H); 6.92-6.86 (m, 2H); 6.66 (d, 1H); 3.34 (s, 2H).

Example 81

N-{3-[3-(2-{[3-(2-amino-2-oxoethyl)phenyl]amino}pyrimidin-4-yl)imidazo[1,2-a]pyridin-2-yl]phenyl}-2-thien-2-ylacetamide The title compound was prepared as described in EXAMPLE 1I, substituting EXAMPLE 80E for EXAMPLE 1H and 2-thienylacetyl chloride for 2,6-difluorobenzoyl chloride. MS (ESI(+)) m/e 560 (M+H)$^+$; $^1$H-NMR (300 MHz, dimethylsulfoxide-d$_6$) δ 10.34 (s, 1H); 9.77 (s, 1H); 9.62 (d, 1H); 8.36 (d, 1H); 7.92 (s, 1H); 7.80 (d, 1H); 7.73 (d, 1H); 7.65-7.58 (m, 3H); 7.45-7.37 (m, 2H); 7.31 (d, 1H); 7.24-7.15 (m, 3H); 6.97 (m, 2H); 6.91-6.85 (m, 2H); 6.60 (d, 1H); 3.86 (s, 2H); 3.34 (s, 2H).

Example 82

N-{3-[3-(2-{[3-(2-amino-2-oxoethyl)phenyl]amino}pyrimidin-4-yl)imidazo[1,2-a]pyridin-2-yl]phenyl}-2-phenylacetamide The title compound was prepared as described in EXAMPLE 1I, substituting EXAMPLE 80E for EXAMPLE 1H and phenylacetyl chloride for 2,6-difluorobenzoyl chloride. MS (ESI(+)) m/e 554 (M+H)+; $^1$H-NMR (300 MHz, dimethylsulfoxide-d$_6$) δ 10.30 (s, 1H); 9.77 (s, 1H); 9.62 (d, 1H); 8.36 (d, 1H); 7.93 (s, 1H); 7.80 (d, 1H); 7.75 (d, 1H); 7.65-7.58 (m, 3H); 7.41 (t, 2H); 7.34-7.18 (m, 8H); 6.92-6.98 (m, 2H); 6.61 (d, 1H); 3.64 (s, 2H); 3.35 (s, 2H).

Example 83 isopropyl (3-{[4-(2-{3-[(phenylacetyl)amino] phenyl}imidazo[1,2-a]pyridin-3-yl)pyrimidin-2-yl] amino}phenyl)acetate

Example 83A

The title compound was prepared as described in EXAMPLE 226A, substituting 2-propanol for methylamine.

Example 83B

The title compound was prepared as described in EXAMPLE 4E, substituting EXAMPLE 83A for EXAMPLE 4D.

Example 83C

The title compound was prepared as described in EXAMPLE 4F, substituting EXAMPLE 83B for EXAMPLE 4E.

Example 83D

The title compound was prepared as described in EXAMPLE 4G, substituting EXAMPLE 83C for EXAMPLE 4F

Example 83E

The title compound was prepared as described in EXAMPLE 1I, substituting EXAMPLE 83D for EXAMPLE 1H and phenylacetyl chloride for 2,6-difluorobenzoyl chloride. MS (ESI(+)) m/e 597 (M+H)+; $^1$H-NMR (300 MHz, dimethylsulfoxide-d$_6$) δ 10.28 (s, 1H); 9.79 (s, 1H); 9.57 (d, 1H); 8.36 (d, 1H); 7.93 (s, 1H); 7.80-7.71 (m, 3H); 7.64 (d, 1H); 7.56 (t, 1H); 7.40 (t, 1H); 7.33-7.22 (m, 7H); 7.14 (t, 1H); 6.88 (d, 1H); 6.63 (d, 1H); 4.87 (m, 1H) 3.64 (s, 2H); 3.57 (s, 2H); 1.15 (d, 6H).

Example 84

N-{3-[3-(2-{[4-(1-ethylpiperidin-4-yl)phenyl] amino}pyrimidin-4-yl)imidazo[1,2-a]pyridin-2-yl] phenyl}-2-thien-2-ylacetamide

Example 84A

The title compound was prepared according to the procedure of EXAMPLE 76A, substituting 1-iodoethane for 2-iodopropane. MS ESI(+): m/e 520.6 (M+H)+.

Example 84B

Example 84A was reduced as described in EXAMPLE 1H, giving the title compound.

Example 84C

N-{3-[3-(2-{[4-(1-ethylpiperidin-4-yl)phenyl] amino}pyrimidin-4-yl)imidazo[1,2-a]pyridin-2-yl] phenyl}-2-thien-2-ylacetamide The title compound was prepared as described in EXAMPLE 41 from EXAMPLE 84B and 2-(thiophen-2-yl) acetyl chloride. MS ESI(+): m/e 614.2 (M+H)+. $^1$H NMR (400 MHz, dimethylsulfoxide-d$_6$) δ ppm 10.32 (s, 1 H), 9.67 (s, 1 H), 9.52 (bs, 1 H), 8.32 (d, 1 H), 7.92 (s, 1 H) 7.72-7.75 (m, 2 H), 7.63 (d, 2 H), 7.49 (t, 1 H), 7.37-7.42 (m, 2 H), 7.31 (d, 1 H), 7.16 (d, 2 H), 7.06 (t, 1 H), 6.94-7.00 (m, 2 H), 6.60 (d, 1 H), 3.88 (s, 2 H), 2.94-3.00 (m, 2 H), 2.41-2.44 (m, 1 H), 2.34 (q, 2 H), 1.92-1.97 (m, 2 H), 1.72-1.75 (m, 2 H), 1.61-1.66 (m, 2 H), 1.02 (t, 3H).

Example 85

N-{3-[3-(2-{[4-(1-ethylpiperidin-4-yl)phenyl] amino}pyrimidin-4-yl)imidazo[1,2-a]pyridin-2-yl] phenyl}-2,6-difluorobenzamide The title compound was prepared as described in EXAMPLE 41 from EXAMPLE 84B and 2,6-difluorobenzoyl chloride. MS ESI(+): m/e 630.2 (M+H)+. $^1$H NMR (400 MHz, dimethylsulfoxide-d$_6$) δ ppm 10.53 (s, 1 H), 9.66 (s, 1 H), 9.52 (bs, 1 H), 8.34 (d, 1 H), 8.05 (s, 1 H) 7.83 (d, 1 H), 7.74-7.78 (m, 2 H), 7.62 (d, 2 H), 7.51 (t, 1 H), 7.37-7.46 (m, 2 H), 7.36 (d, 1 H), 7.20-7.24 (m, 1 H), 7.16 (d, 2 H), 7.06 (t, 1 H), 6.64 (d, 1 H), 2.94-2.98 (m, 2 H), 2.41-2.44 (m, 1 H), 2.34 (q, 2 H), 1.89-1.97 (m, 2 H), 1.70-1.76 (m, 2 H), 1.58-1.66 (m, 2 H), 1.02 (t, 3H).

Example 86

N-{3-[3-(2-{[4-(4-ethylpiperazin-1-yl)phenyl] amino}pyrimidin-4-yl)imidazo[1,2-a]pyridin-2-yl] phenyl}-2-(1-methyl-1H-imidazol-4-yl)acetamide A mixture of EXAMPLE 41B (75 mg, 0.15 mmol), 2-(1-methyl-1H-imidazol-4-yl)acetic acid hydrochloric acid (40 mg, 0.22 mmol) and N$_1$-((ethylimino)methylene)-N$_3$,N$_3$-dimethylpropane-1,3-diamine hydrochloric acid (44 mg, 0.22 mmol) in CH$_2$Cl$_2$ (3 mL) and 1-methyl-2-pyrrolidinone (1 mL) was stirred at room temperature overnight. The mixture was concentrated and the residue was dissolved in methanol/CH$_2$Cl$_2$ and purified on a silica gel column eluting with 5% methanol in CH$_2$Cl$_2$ saturated with ammonia to give the title compound. MS ESI(+): m/e 613.3 (M+H)+. $^1$H NMR (400 MHz, dimethylsulfoxide-d$_6$) δ ppm 10.18 (s, 1 H), 9.52 (bs, 1 H), 9.47 (s, 1 H), 8.27 (d, 1 H), 7.91 (s, 1 H), 7.70-7.75 (m, 2 H), 7.54 (d, 2 H), 7.46-7.49 (m, 2 H), 7.37 (t, 1 H), 7.27 (d, 1 H), 7.05 (t, 1 H), 6.97 (s, 1 H), 6.90 (d, 2 H), 6.53 (d, 1 H), 3.60 (s, 3 H), 3.51 (s, 2 H), 3.33-3.35 (m, 4 H), 3.06-3.10 (m, 4 H), 2.35 (q, 2 H), 1.04 (t, 3H).

Example 87

2,5-difluoro-N-[3-(3-{2-[(2-methyl-1,2,3,4-tetrahydroisoquinolin-7-yl)amino]pyrimidin-4-yl}imidazo [1,2-a]pyridin-2-yl)phenyl]benzamide The title compound was prepared as described in EXAMPLE 4H, substituting 2,5-difluorobenzoyl chloride for 2,6-difluorobenzoyl chloride. MS (ESI(+)) m/e 588 (M+H)+; $^1$H NMR (300 MHz, dimethylsulfoxide-d$_6$) δ ppm 10.50 (s, 1H), 9.88 (s, 1H), 9.56 (d, 1H), 8.40 (d, 1H), 8.17 (s, 1H), 7.90 (m, 1H), 7.81 (m, 1H), 7.46-7.71 (m, 8H), 7.40 (m, 1H), 6.71 (d, 1H), 4.32 (m, 2H), 3.65 (m, 2H), 3.07 (m, 2H), 2.92 (s, 3H).

Example 88

3,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide The title compound was prepared as described in EXAMPLE 4H, substituting 3,5-difluorobenzoyl chloride for 2,6-difluorobenzoyl chloride. MS (ESI(+)) m/e 588 (M+H)$^+$; $^1$H NMR (300 MHz, dimethylsulfoxide-d$_6$) δ ppm 10.61 (s, 1H), 9.86 (s, 1H), 9.53 (d, 1H), 8.36 (d, 1H), 8.10 (s, 1H), 7.78 (m, 2H), 7.68 (m, 1H), 7.37-7.60 (m, 7H), 7.15 (m, 2H), 6.70 (d, 1H), 4.35 (m, 2H), 3.65 (m, 2H), 3.07 (m, 2H), 2.92 (s, 3H).

Example 89

2,3-difluoro-N-[3-(3-{2-[(2-methyl-1,2,3,4-tetrahydroisoquinolin-7-yl]amino]pyrimidin-4-yl}imidazo[1,2-a]pyridin-2-yl)phenyl]benzamide The title compound was prepared as described in EXAMPLE 4H, substituting 2,3-difluorobenzoyl chloride for 2,6-difluorobenzoyl chloride. MS (ESI(+)) m/e 588 (M+H)$^+$; $^1$H NMR (300 MHz, dimethylsulfoxide-d$_6$) δ ppm 10.67 (s, 1H), 9.86 (s, 1H), 9.53 (d, 1H), 8.39 (d, 1H), 8.09 (s, 1H), 7.79 (m, 1H), 7.31-7.67 (m, 8H), 7.16 (m, 2H), 6.70 (d, 1H), 4.32 (m, 2H), 3.65 (m, 2H), 3.07 (m, 2H), 2.92 (s, 3H).

Example 90

N-{3-[3-(2-{[4-(4-ethylpiperazin-1-yl)phenyl]amino}pyrimidin-4-yl)imidazo[1,2-a]pyridin-2-yl]phenyl}-2-thien-3-ylacetamide The title compound was prepared as described in EXAMPLE 41 from EXAMPLE 41B and 2-(thiophen-3-1)acetyl chloride. MS ESI(+): m/e 615.2 (M+H)$^+$. $^1$H NMR (400 MHz, dimethylsulfoxide-d$_6$) δ ppm 10.27 (s, 1 H), 9.61 (s, 1 H), 9.45-9.58 (bs, 2 H), 8.32 (d, 1 H), 7.96 (s, 1 H), 7.80 (d, 1 H), 7.72 (d, 1 H), 7.58-7.61 (m, 3 H), 7.47-7.50 (m, 1 H), 7.41 (t, 1 H), 7.29-7.33 (m, 2 H), 7.15 (t, 1 H), 7.08 (dd, 1 H), 6.90 (d, 2 H), 6.59 (d, 1 H), 3.88 (s, 2 H), 3.78-3.81 (m, 2 H), 3.56-3.60 (m, 2 H), 3.17-3.32 (m, 4 H), 2.93 (q, 2 H), 1.04 (t, 3H).

Example 91

N-{3-[3-(2-{[4-(4-ethylpiperazin-1-yl)phenyl]amino}pyrimidin-4-yl)imidazo[1,2-a]pyridin-2-yl]phenyl}-2-(3-methylisoxazol-5-yl)acetamide The title compound was prepared as described in EXAMPLE 86, substituting 2-(3-methylisoxazol-5-yl)acetic acid for 2-(1-methyl-1H-imidazol-4-yl)acetic acid hydrochloric acid. MS ESI(+): m/e 614.2 (M+H)$^+$. $^1$H NMR (400 MHz, dimethylsulfoxide-d$_6$) δ ppm 10.42 (s, 1 H), 9.60 (s, 1 H), 9.40-9.58 (bs, 2 H), 8.32 (d, 1 H), 7.93 (s, 1 H), 7.79 (d, 1 H), 7.70 (d, 1 H), 7.60 (d, 2 H), 7.55 (d, 1 H), 7.42 (t, 1 H), 7.33 (d, 1 H), 7.13 (t, 1 H), 6.98 (d, 2 H), 6.59 (d, 1 H), 6.26 (s, 1 H), 3.89 (s, 2 H), 3.74-3.79 (m, 2 H), 3.56-3.60 (m, 2 H), 3.12-3.32 (m, 4 H), 2.93 (q, 2 H), 2.21 (s, 3 H), 1.26 (t, 3H).

Example 92

N-[3-(3-{2-[(1-acetyl-2,3-dihydro-1H-indol-5-yl)amino)pyrimidin-4-yl}imidazo[1,2-a]pyridin-2-yl)phenyl]-2,6-difluorobenzamide

Example 92A

The title compound was prepared as described in EXAMPLE 1H, substituting 1-(5-nitroindolin-1-yl)ethanone for EXAMPLE 1G. MS (DCI(+)) m/e 177 (M+H)$^+$.

Example 92B

The title compound was prepared as described in EXAMPLE 4F, substituting EXAMPLE 92A for EXAMPLE 4E. MS (ESI(+)) m/e 492 (M+H)$^+$.

Example 92C

The title compound was prepared as described in EXAMPLE 4G, substituting EXAMPLE 92B for EXAMPLE 4F. MS (ESI(+)) m/e 462 (M+H)$^+$.

Example 92D

The title compound was prepared as described in EXAMPLE 4H, substituting EXAMPLE 92C for EXAMPLE 4G. MS (ESI(+)) m/e 602 (M+H)$^+$, $^1$H NMR (400 MHz, dimethylsulfoxide-d$_6$) δ ppm 10.88 (s, 1 H) 9.65 (s, 1 H) 9.51 (d, 1 H) 8.34 (d, 1 H) 8.04 (s, 1 H) 7.95 (d, 1 H) 7.79 (m, 2 H) 7.71 (s, 1 H) 7.59 (m, 1 H) 7.47 (m, 2 H) 7.40 (d, 2 H) 7.25 (m, 2 H) 7.07 (t, 1 H) 6.64 (d, 1 H) 4.08 (t, 2 H) 3.11 (t, 2 H) 2.14 (s, 3 H).

Example 93

N-[3-(3-{2-[(1-acetyl-2,3-dihydro-1H-indol-5-yl)amino]pyrimidin-4-yl}imidazo[1,2-a]pyridin-2-yl)phenyl]-2-phenylacetamide The title compound was prepared as described in EXAMPLE 4H, substituting EXAMPLE 92C for EXAMPLE 4G, and phenylacetyl chloride for 2,6-difluorobenzoyl chloride. MS (ESI(+)) m/e 580 (M+H)$^+$, $^1$H NMR (400 MHz, dimethylsulfoxide-d$_6$) δ ppm 10.26 (s, 1 H) 9.64 (s, 1 H) 9.51 (d, 1 H) 8.32 (d, 1 H) 7.96 (d, 1 H) 7.92 (s, 1 H) 7.72 (m, 3 H) 7.49 (m, 1 H) 7.37 (m, 2 H) 7.21-7.34 (m, 6 H) 7.06 (t, 1 H) 6.59 (d, 1 H) 4.07 (t, 2 H) 3.64 (s, 2 H) 3.10 (t, 2 H) 2.14 (s, 3 H).

Example 94

N-[3-(3-{2-[(1-acetyl-2,3-dihydro-1H-indol-5-yl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 92C for EXAMPLE 4G, and 2-thiopheneacetyl chloride for 2,6-difluorobenzoyl chloride. MS (ESI(+)) m/e 586 (M+H)$^+$, $^1$H NMR (400 MHz, dimethylsulfoxide-d$_6$) δ ppm 10.30 (s, 1 H) 9.64 (s, 1 H) 9.52 (d, 1 H) 8.32 (d, 1 H) 7.96 (d, 1 H) 7.91 (s, 1 H) 7.73 (t, 3 H) 7.49 (m, 1 H) 7.39 (m, 3 H) 7.30 (m, 1 H)

7.06 (t, 1 H) 6.98 (m, 2 H) 6.60 (d, 1 H) 4.07 (t, 2 H) 3.87 (s, 2 H) 3.11 (t, 2 H) 2.14 (s, 3 H).

Example 95

2,4-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide The title compound was prepared as described in EXAMPLE 4H, substituting 2,4-difluorobenzoyl chloride for 2,6-difluorobenzoyl chloride. MS (ESI(+)) m/e 588 (M+H)$^+$; $^1$H NMR (300 MHz, dimethylsulfoxide-d$_6$) δ ppm 10.53 (s, 1H), 9.85 (s, 1H), 9.53 (d, 1H), 8.39 (d, 1H), 8.09 (s, 1H), 7.71-7.81 (m, 3H), 7.67 (m, 1H), 7.51-7.61 (m, 2H), 7.36-7.48 (m, 3H), 7.12-7.26 (m, 3H), 6.70 (d, 1H), 4.32 (m, 2H), 3.65 (m, 2H), 3.07 (m, 2H), 2.92 (s, 3H).

Example 96

2-chloro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide The title compound was prepared as described in EXAMPLE 4H, substituting 2-chlorobenzoyl chloride for 2,6-difluorobenzoyl chloride. MS (ESI(+)) m/e 586 (M+H)$^+$; $^1$H NMR (300 MHz, dimethylsulfoxide-d$_6$) δ ppm 10.60 (s, 1H), 9.84 (s, 1H), 9.53 (d, 1H), 8.39 (d, 1H), 8.11 (s, 1H), 7.79 (d, 2H), 7.68 (m, 1H), 7.55-7.63 (m, 3H), 7.52 (m, 2H), 7.48 (m, 1H), 7.45 (m, 1H), 7.39 (m, 2H), 7.16 (m, 2H), 6.71 (d, 1H), 4.32 (m, 2H), 3.65 (m, 2H), 3.07 (m, 2H), 2.92 (s, 3H).

Example 97

2-fluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide The title compound was prepared as described in EXAMPLE 4H, substituting 2-fluorobenzoyl chloride for 2,6-difluorobenzoyl chloride. MS (ESI(+)) m/e 570 (M+H)$^+$; $^1$H NMR (300 MHz, dimethylsulfoxide-d$_6$) δ ppm 10.53 (s, 1H), 9.85 (s, 1H), 9.55 (d, 1H), 8.39 (d, 1H), 8.11 (s, 1H), 7.73-7.83 (m, 3H), 7.68 (m, 2H), 7.51-7.61 (m, 2H), 7.36-7.48 (m, 3H), 7.11-7.20 (m, 3H), 6.70 (d, 1H), 4.32 (m, 2H), 3.65 (m, 2H), 3.07 (m, 2H), 2.92 (s, 3H).

Example 98

N-{3-[3-(2-{[4-(1-ethylpyrrolidin-3-yl)phenyl]amino}pyrimidin-4-yl)imidazo[1,2-a]pyridin-2-yl]phenyl}-2-thien-2-ylacetamide

Example 98A

A 20 ml vial was charged with EXAMPLE 4C (703 mg, 2.0 mmol) and 2-propanol (5 ml). To the stirred suspension was added hydrogen chloride, 4M in dioxane (0.475 ml, 1.90 mmol). After stirring 15 minutes, tert-butyl 3-(4-aminophenyl)pyrrolidine-1-carboxylate (735 mg, 2.80 mmol) in 2-propanol (10 ml) was added. The vial was sealed and heated at 80° C. for 40 hours. The reaction mixture was concentrated and the residue was dissolved in a mixture of anhydrous methylene chloride (20 ml) and trifluoroacetic acid (20 ml). After stirring 1 hour, the reaction was concentrated and the residue was diluted with water (25 ml) and basified with 50% caustic to ca. pH 14. After stirring 30 minutes, the resulting brown solid was collected by filtration, washed with water and dried on high vacuum to afford the title compound. MS (ESI(+)) m/e 478 (M+H)$^+$, (ESI(−)) m/e 476 (M−H)$^-$.

Example 98B

A 20 ml vial was charged with EXAMPLE 98A (200 mg, 0.419 mmol), potassium carbonate (145 mg, 1.047 mmol) and N,N-dimethylformamide (10 ml) under nitrogen. To the suspension was added iodoethane (0.037 ml, 0.461 mmol) dropwise, the vial was sealed and the reaction was stirred 18 hours at ambient temperature. The reaction mixture was added dropwise to stirring water (30 ml). The resulting solid was collected by filtration, washed with water and dried. The crude material was purified on an ISCO chromatography system on a silica gel cartridge (80 g) eluted with a 2.5, 5, and 10% 7N methanolic ammonia in methylene chloride step gradient to afford the title compound. MS (ESI(+)) m/e 506 (M+H)$^+$, (ESI(−)) m/e 504 (M−H)$^-$.

Example 98C

The title compound was prepared as described in EXAMPLE 4G substituting EXAMPLE 98B for EXAMPLE 4F. MS (ESI(+)) m/e 476 (M+H)$^+$, (ESI(−)) m/e 474 (M−H)$^-$

Example 98D

N-{3-[3-(2-{[4-(1-ethylpyrrolidin-3-yl)phenyl]amino}pyrimidin-4-yl)imidazo[1,2-a]pyridin-2-yl]phenyl}-2-thien-2-ylacetamide A 20 ml vial charged with EXAMPLE 98C (42 mg, 0.088 mmol), dichloromethane (6 ml), N-methyl-2-pyrrolidinone (0.5 ml) and pyridine (0.014 ml, 0.177 mmol). 2-(Thiophen-2-yl)acetyl chloride (0.013 ml, 0.106 mmol) was added dropwise and the reaction was stirred 18 hours at ambient temperature. The reaction was concentrated and the residue was purified by preparative HPLC on a Phenomenex Luna C8(2) 5 um 100 Å AXIA column (30 mm×75 mm) using a gradient of acetonitrile (A) and 0.1% trifluoroacetic acid in water (B) to afford the title compound. MS (ESI(+)) m/e 600 (M+H)$^+$, (ESI(−)) m/e 598 (M−H)$^-$; $^1$H-NMR MHz, dimethylsulfoxide-d$_6$) δ 10.34 (s, 1H), 9.81 (s, 1H), 9.54 (d, 1H), 8.37 (d, 1H), 7.96 (s, 1H), 7.79 (d, 1H), 7.72 (m, 3H), 7.56 (t, 1H), 7.41 (m, 2H), 7.28 (m, 3H), 7.13 (t, 1H), 6.97 (m, 2H), 6.65 (d, 1H), 3.87 (s, 2H), 3.74 (m, 1H), 3.62 (m, 2H), 3.46-3.00 (m, 4H), 2.39 (m, 1H), 2.13-1.91 (m, 1H), 1.25 (t, 3H).

Example 99

N-{3-[3-(2-{[3-(1-ethylpyrrolidin-3-yl)phenyl]amino}pyrimidin-4-yl)imidazo[1,2-a]pyridin-2-yl]phenyl}-2-thien-2-ylacetamide

Example 99A

The title compound was prepared as described in EXAMPLE 98A substituting tert-butyl 3-(3-aminophenyl)pyrrolidine-1-carboxylate for tert-butyl 3-(4-aminophenyl)pyrrolidine-1-carboxylate. MS (ESI(+)) m/e 478 (M+H)$^+$, (ESI(−)) m/e 476 (M−H)$^-$.

Example 99B

The title compound was prepared as described in EXAMPLE 98B substituting EXAMPLE 99A for EXAMPLE 98A. MS (ESI(+)) m/e 506 (M+H)⁺, (ESI(−)) m/e 504 (M−H)⁻.

Example 99C

The title compound was prepared as described in EXAMPLE 4G substituting EXAMPLE 99B for EXAMPLE 4F. MS (ESI(+)) m/e 476 (M+H)⁺, (ESI(−)) m/e 474 (M−H)⁻

Example 99D

N-{3-[3-(2-{[3-(1-ethylpyrrolidin-3-yl)phenyl]amino}pyrimidin-4-yl)imidazo[1,2-a]pyridin-2-yl]phenyl}-2-thien-2-ylacetamide The title compound was prepared as described in EXAMPLE 98D substituting EXAMPLE 99C for EXAMPLE 98C. MS (ESI(+)) m/e 600 (M+H)⁺, (ESI(−)) m/e 598 (M−H)⁻; ¹H-NMR (300 MHz, dimethylsulfoxide-$d_6$) δ 10.34 (s, 1H), 9.81 (s, 1H), 9.53 (d, 1H), 8.38 (d, 1H), 7.98 (s, 1H), 7.80-7.63 (m, 4H), 7.55 (t, 1H), 7.43-7.29 (m, 4H), 7.13 (t, 1H), 6.98 (m, 3H), 6.66 (dd, 1H), 3.87 (s, 2H), 3.74 (m, 1H), 3.63 (m, 2H), 3.40 (m, 1H), 3.24 (m, 2H), 3.04 (m, 1H), 2.39 (m, 1H), 2.13-1.91 (m, 1H), 1.22 (t, 3H).

Example 100

N-{3-[3-(2-{[4-(1-acetylpyrrolidin-3-yl)phenyl]amino}pyrimidin-4-yl)imidazo[1,2-a]pyridin-2-yl]phenyl}-2-thien-2-ylacetamide

Example 100A

A 20 ml vial was charged with EXAMPLE 98A (200 mg, 0.419 mmol), dichloromethane (12 ml) and N-ethyl-N-isopropylpropan-2-amine (0.146 ml, 0.838 mmol). To the suspension was added acetic anhydride (0.048 ml, 0.503 mmol) dropwise, the vial was sealed and the reaction was stirred 18 hours at ambient temperature. The reaction concentrated and the residue was purified on an ISCO chromatography system on a silica gel cartridge (60 g) eluted with a 1, 2.5, 5, and 10% methanol/methylene chloride step gradient to afford the title compound. MS (ESI(+)) m/e 520 (M+H)⁺, (ESI(−)) m/e 518 (M−H)⁻.

Example 100B

The title compound was prepared as described in EXAMPLE 4G substituting EXAMPLE 100A for EXAMPLE 4F. MS (ESI(+)) m/e 490 (M+H)⁻, (ESI(−)) m/e 488 (M−H)⁻.

Example 100C

N-{3-[3-(2-{[4-(1-acetylpyrrolidin-3-yl)phenyl]amino}pyrimidin-4-yl)imidazo[1,2-a]pyridin-2-yl]phenyl}-2-thien-2-ylacetamide The title compound was prepared as described in EXAMPLE 98D substituting EXAMPLE 100B for EXAMPLE 98C. MS (ESI(+)) m/e 614 (M+H)⁺, (ESI(−)) m/e 612 (M−H)⁻; ¹H-NMR (300 MHz, dimethylsulfoxide-$d_6$) δ 10.36 (s, 1H), 9.78 (s, 1H), 9.56 (d, 1H), 8.38 (d, 1H), 7.96 (m, 1H), 7.82 (d, 1H), 7.75-7.62 (m, 4H), 7.46-7.37 (m, 2H), 7.31 (m, 1H), 7.22 (m, 3H), 6.98 (m, 2H), 6.64 (d, 1H), 3.88 (s, 2H), 3.67-3.48 (m, 2H), 3.39-3.12 (m, 3H), 2.28-2.17 (m, 1H), 2.05-1.85 (m, 1H), 1.97 (s, 3H).

Example 101

N-{3-[3-(2-{[3-(1-acetylpyrrolidin-3-yl)phenyl]amino}pyrimidin-4-yl)imidazo[1,2-a]pyridin-2-yl]phenyl}-2-thien-2-ylacetamide

Example 101A

The title compound was prepared as described in EXAMPLE 100A substituting EXAMPLE 99A for EXAMPLE 98A. MS (ESI(+)) m/e 520 (M+H)⁺, (ESI(−)) m/e 518 (M−H)⁻.

Example 101B

The title compound was prepared as described in EXAMPLE 4G substituting EXAMPLE 101A for EXAMPLE 4F. MS (ESI(+)) m/e 490 (M+H)⁺, (ESI(−)) m/e 488 (M−H)⁻.

Example 101C

N-{3-[3-(2-{[3-(1-acetylpyrrolidin-3-yl)phenyl]amino}pyrimidin-4-yl)imidazo[1,2-a]pyridin-2-yl]phenyl}-2-thien-2-ylacetamide The title compound was prepared as described in EXAMPLE 98D substituting EXAMPLE 101B for EXAMPLE 98C. MS (ESI(+)) m/e 614 (M+H)⁺, (ESI(−)) m/e 612 (M−H)⁻; ¹H-NMR (300 MHz, dimethylsulfoxide-$d_6$) δ 10.34 (s, 1H), 9.79 (s, 1H), 9.53 (d, 1H), 8.39 (d, 1H), 7.96 (m, 1H), 7.80 (d, 1H), 7.73-7.58 (m, 4H), 7.45-7.15 (m, 5H), 6.98-6.90 (m, 3H), 6.65 (dd, 1H), 3.88 (s, 2H), 3.81 (m, 1H), 3.64-3.46 (m, 2H), 3.37-3.14 (m, 2H), 2.30-2.15 (m, 1H), 2.01-1.81 (m, 1H), 1.93 (d, 3H).

Example 102

N-{3-[3-(2-{[3-(1-acetylpyrrolidin-3-yl)phenyl]amino}pyrimidin-4-yl)imidazo[1,2-a]pyridin-2-yl]phenyl}-2,6-difluorobenzamide The title compound was prepared as described in EXAMPLE 98D substituting EXAMPLE 101B for EXAMPLE 98C and 2,6-difluorobenzoyl chloride for 2-(thiophen-2-yl)acetyl chloride. MS (ESI(+)) m/e 630 (M+H)⁺, (ESI(−)) m/e 628 (M−H)⁻; ¹H-NMR (300 MHz, dimethylsulfoxide-$d_6$) δ 10.94 (s, 1H), 9.80 (d, 1H), 9.54 (d, 1H), 8.42 (d, 1H), 8.08 (m, 1H), 7.85-7.79 (m, 2H), 7.73-7.55 (m, 4H), 7.52-7.41 (m, 2H), 7.29-7.18 (m, 4H), 6.93 (t, 1H), 6.71 (dd, 1H), 3.88-3.74 (m, 1H), 3.64-3.13 (m, 4H), 2.29-2.13 (m, 1H), 1.98-1.82 (m, 1H), 1.93 (d, 3H).

Example 103

N-[3-(3-{2-[(2-ethyl-2,3-dihydro-1H-isoindol-5-yl)amino]pyrimidin-4-yl}imidazo[1,2-a]pyridin-2-yl)phenyl]-2-thien-2-ylacetamide

Example 103A

A 100 ml flask was charged with the 5-nitroisoindoline hydrochloride (1.092 g, 5.44 mmol), potassium carbonate (2.63 g, 19.05 mmol) and N,N-dimethylformamide (50 ml) under nitrogen. Iodoethane (0.483 ml, 5.99 mmol) was added dropwise and the mixture was stirred 18 hours. The reaction was concentrated and the residue was partitioned between ethyl acetate (100 ml) and brine (100 ml). The aqueous layer was extracted with ethyl acetate (2×50 ml). The combined organics were dried over sodium sulfate, filtered and concentrated and purified on an ISCO chromatography system on a silica gel cartridge (110 g) eluted with a 0, 1, 2.5, 5, 10% methanol in methylene chloride step gradient to provide the title compound. MS (DCI) m/e 163 (M+H)$^+$.

Example 103B

The title compound was prepared as described in EXAMPLE 4G substituting EXAMPLE 103A for EXAMPLE 4F. MS (DCI) m/e 193 (M+H)$^+$, 210 (M+NH$_4$)$^+$.

Example 103C

A 20 ml vial was charged with EXAMPLE 4C (486 mg, 1.38 mmol) and 2-propanol (5 ml). To the stirred suspension was added hydrogen chloride, 4M in dioxane (0.345 ml, 1.38 mmol). After stirring 5 minutes, EXAMPLE 103B (269 mg, 1.66 mmol) in 2-propanol (10 ml) was added. The vial was sealed and heated at 80° C. for 18 hours. The reaction mixture was concentrated and the residue was diluted with water (25 ml) and basified with 50% caustic to ca. pH 14. After stirring 30 minutes, the resulting solid was collected by filtration, washed with water and dried on high vacuum. This was purified on a plug of silica gel (ca. 200 g) eluted with 5-10% methanol in methylene chloride to afford the title compound. MS (ESI(+)) m/e 478 (M+H)$^+$, (ESI(−)) m/e 476 (M−H)$^-$.

Example 103D

The title compound was prepared as described in EXAMPLE 4G substituting EXAMPLE 103C for EXAMPLE 4F. MS (ESI(+)) m/e 490 (M+H)$^+$, (ESI(−)) m/e 488 (M−H)$^-$.

Example 103E

N-[3-(3-{2-[(2-ethyl-2,3-dihydro-1H-isoindol-5-yl) amino]pyrimidin-4-yl}imidazo[1,2-a]pyridin-2-yl) phenyl]-2-thien-2-ylacetamide The title compound was prepared as described in EXAMPLE 98D substituting EXAMPLE 103D for EXAMPLE 98C. MS (ESI(+)) m/e 572 (M+H)$^+$, (ESI(−)) m/e 570 (M−H)$^-$; $^1$H-NMR (300 MHz, dimethylsulfoxide-d$_6$) δ 10.34 (s, 1H), 9.98 (s, 1H), 9.52 (d, 1H), 8.40 (d, 1H), 7.97 (s, 1H), 7.90 (s, 1H), 7.79 (d, 1H), 7.68 (m, 2H), 7.56 (t, 1H), 7.43-7.29 (m, 4H), 7.14 (t, 1H), 6.97 (m, 2H), 6.71 (d, 1H), 4.74 (m, 2H), 4.44 (m, 2H), 3.88 (s, 2H), 3.41 (m, 2H), 1.28 (t, 3H).

Example 104

N-[3-(3-{2-[(2-ethyl-2,3-dihydro-1H-isoindol-5-yl) amino]pyrimidin-4-yl}imidazo[1,2-a]pyridin-2-yl) phenyl]-2,6-difluorobenzamide The title compound was prepared as described in EXAMPLE 98D substituting EXAMPLE 103D for EXAMPLE 98C and 2,6-difluorobenzoyl chloride for 2-(thiophen-2-yl)acetyl chloride. MS (ESI(+)) m/e 588 (M+H)$^+$; $^1$H-NMR (300 MHz, dimethylsulfoxide-d$_6$) δ 10.91 (s, 1H), 9.98 (s, 1H), 9.52 (d, 1H), 8.43 (d, 1H), 8.09 (s, 1H), 7.91 (s, 1H), 7.82-7.74 (m, 2H), 7.68-7.53 (m, 3H), 7.50-7.39 (m, 2H), 7.34-7.22 (m, 3H), 7.14 (dt, 1H), 6.74 (d, 1H), 4.75 (m, 2H), 4.45 (m, 2H), 3.41 (m, 2H), 1.28 (t, 3H).

Example 105

N-[3-(3-{2-[(2-ethyl-2,3-dihydro-1H-isoindol-5-yl) amino]pyrimidin-4-yl}imidazo[1,2-a]pyridin-2-yl)phenyl]-2-phenylacetamide The title compound was prepared as described in EXAMPLE 98D substituting EXAMPLE 103D for EXAMPLE 98C and 2-phenylacetyl chloride for 2-(thiophen-2-yl)acetyl chloride. MS (ESI(+)) m/e 566 (M+H)$^+$, (ESI(−)) m/e 564 (M−H)$^-$; $^1$H-NMR (300 MHz, dimethylsulfoxide-d$_6$) δ 10.30 (s, 1H), 9.97 (s, 1H), 9.52 (d, 1H), 8.39 (d, 1H), 7.97 (m, 1H), 7.90 (s, 1H), 7.78 (d, 1H), 7.72-7.65 (m, 2H), 7.58-7.53 (dt, 1H), 7.42-7.23 (m, 8H), 7.14 (dt, 1H), 6.70 (d, 1H), 4.75 (m, 2H), 4.44 (m, 2H), 3.64 (s, 2H), 3.41 (m, 2H), 1.28 (t, 3H).

Example 106

N-{3-[3-(2-([2-(dimethylamino)-2,3-dihydro-1H-inden-5-yl]amino}pyrimidin-4-yl)imidazo[1,2-a] pyridin-2-yl]phenyl}-2-thien-2-ylacetamide Example 106A A 100 ml flask charged with 5-nitro-1H-inden-2(3H)-one (1 g, 5.64 mmol), dichloromethane (28 ml) and acetic acid (1.616 ml, 28.2 mmol). The resulting solution was cooled in an ice bath and dimethylamine, 2M in tetrahydrofuran (5.64 ml, 11.29 mmol) was added dropwise. After warming to ambient temperature, the reaction was stirred 15 minutes. Sodium triacetoxyborohydride (4.8 g, 22.6 mmol) was added and the reaction was stirred 72 hours. The reaction was concentrated and the residue was partitioned between methylene chloride (100 ml) and water (100 ml). The pH was adjusted to ca. 11 with 1 M sodium hydroxide, the layers were separated and the aqueous layer extracted with methylene chloride. The combined organics were washed with brine (200 ml), dried over sodium sulfate, filtered and concentrated and the residue was purified on a funnel plug of silica gel (150 g) eluted with 1, 2.5, and 5% methanol in methylene chloride to provide the title compound. MS (DCI) m/e 207 (M+H)$^+$.

Example 106B

The title compound was prepared as described in EXAMPLE 4G substituting EXAMPLE 106A for EXAMPLE 4F. MS (DCI) m/e 177 (M+H)$^+$.

Example 106C

The title compound was prepared as described in EXAMPLE 103C substituting EXAMPLE 106B for EXAMPLE 103B. MS (ESI(+)) m/e 492 (M+H)$^+$, (ESI(−)) m/e 490 (M−H)$^-$.

Example 106D

The title compound was prepared as described in EXAMPLE 4G substituting EXAMPLE 106C for EXAMPLE 4F. MS (ESI(+)) m/e 462 (M+H)$^+$, (ESI(−)) m/e 460 (M−H)$^-$.

Example 106E

N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-2-ylacetamide The title compound was prepared as described in EXAMPLE 98D substituting EXAMPLE 106D for EXAMPLE 98C. MS (ESI(+)) m/e 586 (M+H)$^+$, (ESI(−)) m/e 584 (M−H)$^−$; $^1$H-NMR (300 MHz, dimethylsulfoxide-d$_6$) δ 10.34 (s, 1H), 9.78 (s, 1H), 9.53 (d, 1H), 8.37 (d, 1H), 7.96 (m, 1H), 7.80-7.69 (m, 3H), 7.59-7.50 (m, 2H), 7.43-7.38 (m, 2H), 7.31 (m 1H), 7.20-7.12 (m, 2H), 6.98 (m, 2H), 6.64 (d, 1H), 4.09 (m, 1H), 3.87 (s, 2H), 3.33-3.22 (m, 2H), 3.14-3.03 (m, 2H), 2.83 (m, 6H).

Example 107

N-{3-[3-(2-{[2-(dimethylamino)-2,3-dihydro-1H-inden-5-yl]amino}pyrimidin-4-yl)imidazo[1,2-a]pyridin-2-yl]phenyl}-2,6-difluorobenzamide The title compound was prepared as described in EXAMPLE 98D substituting EXAMPLE 106D for EXAMPLE 98C and 2,6-difluorobenzoyl chloride for 2-(thiophen-2-yl)acetyl chloride. MS (ESI(+)) m/e 602 (M+H)$^+$; $^1$H-NMR (300 MHz, dimethylsulfoxide-d$_6$) δ 10.91 (s, 1H), 9.78 (s, 1H), 9.53 (d, 1H), 8.39 (d, 1H), 8.09 (m, 1H), 7.82-7.75 (m, 3H), 7.65-7.39 (m, 5H), 7.29-7.12 (m, 4H), 6.69 (d, 1H), 4.09 (m, 1H), 3.30-3.22 (m, 2H), 3.17-3.03 (m, 2H), 2.83 (m, 6H).

Example 108

N-{3-[3-(2-{[2-(dimethylamino)-2,3-dihydro-1H-inden-5-yl]amino}pyrimidin-4-yl)imidazo[1,2-a]pyridin-2-yl]phenyl}-2-phenylacetamide The title compound was prepared as described in EXAMPLE 98D substituting EXAMPLE 106D for EXAMPLE 98C and 2-phenylacetyl chloride for 2-(thiophen-2-yl)acetyl chloride. MS (ESI(+)) m/e 580 (M+H)$^+$, (ESI(−)) m/e 578 (M−H)$^−$; $^1$H-NMR (300 MHz, dimethylsulfoxide-d$_6$) δ 10.30 (s, 1 H), 9.78 (s, 1 H), 9.53 (d, 1 H), 8.37 (d, 1 H), 7.97 (m, 1 H), 7.80-7.70 (m, 3 H), 7.58-7.49 (m, 2 H), 7.42-7.38 (m, 9 H), 6.64 (d, 1 H), 4.09 (m, 1 H), 3.64 (s, 2 H), 3.33-3.22 (m, 2 H), 3.14-3.03 (m, 2 H), 2.83 (m, 6 H).

Example 109

2,6-difluoro-N-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide

Example 109A

The title compound was prepared as described in EXAMPLE 4G, substituting EXAMPLE 4C for EXAMPLE 4F. MS (ESI(+)) m/e 321.9 (M+H)$^+$.

Example 109B

To a 4 mL vial was charged EXAMPLE 109A (100 mg, 0.311 mmol) and tetrahydrofuran (2.5 mL). The resulting solution was treated with 2,6-difluorobenzoyl chloride (0.041 mL, 0.326 mmol) and the reaction was stirred at ambient temperature for 24 hours. The reaction was treated with 3 mL ether and filtered. The collected solid was washed with 1 mL ether and dried. The solid was dissolved in 70 mL 5% methanol/CH$_2$Cl$_2$ and washed with saturated aqueous NaHCO$_3$ and brine. The organic layer was dried over Na$_2$SO$_4$, filtered, and concentrated to give the title compound. MS (ESI(+)) m/e 461.9 (M+H)$^+$.

Example 109C

To a 4 mL vial was charged EXAMPLE 109B (0.078 g, 0.169 mmol), and sodium hydride (95%, 0.019 g, 0.76 mmol) followed by N,N-dimethylformamide (2.5 mL). The resulting suspension was stirred at ambient temperature for 1 hour and was cooled to 0° C. Methyl iodide (0.048 mL, 0.76 mmol) was added and the reaction was allowed to stir at ambient temperature for 1 hour. The reaction was cooled to 0° C., treated with 0.5 mL saturated aqueous NH$_4$Cl and poured into 10 mL water. The suspension was stirred 5 minutes and filtered. The collected solid was purified by flash chromatography on a 2 g silica gel column eluting with 40% ethyl acetate/hexane to provide the title compound. MS (ESI(+)) m/e 476.0 (M+H)$^+$.

Example 109D

To a 4 mL vial was charged EXAMPLE 109C (0.058 g, 0.122 mmol), EXAMPLE 4E (0.023 g, 0.140 mmol), 2-propanol (4.5 ml) and 4M HCl-dioxane (0.035 mL, 0.140 mmol). The vial was sealed and the reaction heated at 70° C. for 12 hours. The reaction was allowed to cool to ambient temperature, 2-propanol (2 mL) was added, and the suspension was filtered. The collected solid was purified by reverse-phase HPLC on a Phenomenex C18 column (3×15 cm) eluting with a gradient of from 45% to 80% acetonitrile:0.1% aqueous ammonium hydroxide to provide the title compound. MS (ESI(+)) m/e 602.2 (M+H)$^+$; $^1$H NMR (300 MHz, dimethylsulfoxide-d$_6$) δ ppm 9.63 (s, 1 H) 9.53 (d, 1 H) 8.27 (d, 1 H) 7.74 (m, 1 H) 7.32-7.53 (m, 7 H) 7.22 (m, 1 H) 6.97-7.10 (m, 4 H) 6.13 (d, 1 H) 3.43 (m, 5 H) 2.77 (m, 2 H) 2.58 (m, 2 H) 2.33 (s, 3 H).

Example 110

2,6-difluoro-N-{3-[3-(2-{[4-(2-pyrrolidin-1-ylethyl)phenyl]amino}pyrimidin-4-yl)imidazo[1,2-a]pyridin-2-yl]phenyl}benzamide

Example 110A

The title compound was prepared as described in EXAMPLE 195A, substituting pyrrolidine for dimethylamine. MS (DCI(+)) m/e 221 (M+H)$^+$.

Example 110B

The title compound was prepared as described in EXAMPLE 1H, substituting EXAMPLE 110A for EXAMPLE 1G. MS (DCI(+)) m/e 191 (M+H)$^+$.

Example 110C

The title compound was prepared as described in EXAMPLE 4F, substituting EXAMPLE 110B for EXAMPLE 4E. MS (ESI(+)) m/e 506 (M+H)$^+$.

Example 110D

The title compound was prepared as described in EXAMPLE 4G, substituting EXAMPLE 110C for EXAMPLE 4F. MS (ESI(+)) m/e 476 (M+H)+.

Example 110E

The title compound was prepared as described in EXAMPLE 4H, substituting EXAMPLE 110D for EXAMPLE 4G. MS (ESI(+)) m/e 616 (M+H)+, $^1$H NMR (400 MHz, dimethylsulfoxide-$d_6$) δ ppm 10.89 (s, 1 H) 9.66 (s, 1 H) 9.51 (d, 1 H) 8.35 (d, 1 H) 8.05 (s, 1 H) 7.78 (m, 2 H) 7.64 (d, 2 H) 7.59 (m, 1 H) 7.47 (m, 2 H) 7.39 (m, 1 H) 7.25 (m, 2 H) 7.16 (d, 2 H) 7.07 (m, 1 H) 6.66 (d, 1 H) 2.75 (s, 4 H) 2.65 (m, 4 H) 1.73 (m, 4 H).

Example 111

4-methyl-N-{3-[3-(2-{[4-(2-pyrrolidin-1-ylethyl) phenyl]amino}pyrimidin-4-yl)imidazo[1,2-a]pyridin-2-yl]phenyl}thiophene-2-carboxamide The title compound was prepared as described in EXAMPLE 4H, substituting EXAMPLE 110D for EXAMPLE 4G, and 4-methylthiophene-2-carbonyl chloride for 2,6-difluorobenzoyl chloride. MS (ESI(+)) m/e 600 (M+H)+, $^1$H NMR (400 MHz, dimethylsulfoxide-$d_6$) δ ppm 10.26 (s, 1 H) 9.65 (s, 1 H) 9.55 (d, 1 H) 8.34 (d, 1 H) 8.08 (s, 1 H) 7.88 (m, 2 H) 7.75 (d, 1 H) 7.62 (d, 2 H) 7.50 (m, 1 H) 7.43 (m, 2 H) 7.33 (d, 1 H) 7.15 (d, 2 H) 7.07 (t, 1 H) 6.65 (d, 1 H) 2.68 (m, 4 H) 2.50 (m, 4 H) 2.27 (s, 3 H) 1.69 (m, 4 H).

Example 112

2-phenyl-N-{3-[3-(2-{[4-(2-pyrrolidin-1-ylethyl) phenyl]amino}pyrimidin-4-yl)imidazo[1,2-a]pyridin-2-yl]phenyl}acetamide The title compound was prepared as described in EXAMPLE 4H, substituting EXAMPLE 110D for EXAMPLE 4G, and phenylacetyl chloride for 2,6-difluorobenzoyl chloride. MS (ESI(+)) m/e 594 (M+H)+, $^1$H NMR (400 MHz, dimethylsulfoxide-$d_6$) δ ppm 10.26 (s, 1 H) 9.64 (s, 1 H) 9.52 (d, 1 H) 8.32 (d, 1 H) 7.92 (s, 1 H) 7.73 (d, 2 H) 7.63 (d, 2 H) 7.48 (m, 1 H) 7.37 (t, 1 H) 7.27-7.33 (m, 5 H) 7.23 (m, 1 H) 7.15 (d, 2 H) 7.06 (t, 1 H) 6.60 (d, 1 H) 3.64 (s, 2 H) 2.67 (m, 4 H) 2.50 (m, 4 H) 1.68 (m, 4 H).

Example 113

N-{3-[3-(2-{[4-(2-pyrrolidin-1-ylethyl)phenyl] amino}pyrimidin-4-yl)imidazo[1,2-a]pyridin-2-yl] phenyl}-2-thien-2-ylacetamide The title compound was prepared as described in EXAMPLE 4H, substituting EXAMPLE 110D for EXAMPLE 4G, and 2-thiopheneacetyl chloride for 2,6-difluorobenzoyl chloride. MS (ESI(+)) m/e 600 (M+H)+, $^1$H NMR (400 MHz, dimethylsulfoxide-$d_6$) δ ppm 10.31 (s, 1 H) 9.65 (s, 1 H) 9.52 (d, 1 H) 8.31 (d, 1 H) 7.92 (s, 1 H) 7.73 (m, 2 H) 7.63 (d, 2 H) 7.49 (m, 1 H) 7.39 (m, 2 H) 7.31 (m, 1 H) 7.15 (d, 2 H) 7.06 (t, 1 H) 6.98 (m, 2 H) 6.60 (d, 1 H) 3.87 (s, 2 H) 2.68 (m, 4 H) 2.52 (m, 4 H) 1.69 (m, 4 H).

Example 114

5-methyl-N-[3-(3-{2-[(2-methyl-1,2,3,4-tetrahydroisoquinolin-7-yl)amino]pyrimidin-4-yl}imidazo [1,2-a]pyridin-2-yl)phenyl]thiophene-2-carboxamide The title compound was prepared as described in EXAMPLE 4H, substituting 5-methylthiophene-2-carbonyl chloride for 2,6-difluorobenzoyl chloride. MS (ESI(+)) m/e 572.2 (M+H)+; $^1$H NMR (300 MHz, dimethylsulfoxide-$d_6$) (300 MHz, dimethylsulfoxide-$d_6$) δ ppm 10.21 (s, 1 H) 9.62 (s, 1 H) 9.54 (d, 1 H) 8.34 (d, 1 H) 8.08 (m, 1 H) 7.84-7.90 (m, 2 H) 7.75 (d, 1 H) 7.39-7.53 (m, 4 H) 7.32 (m, 1 H) 7.01-7.10 (m, 2 H) 6.92 (m, 1 H) 6.64 (d, 1 H) 3.41 (s, 2 H) 2.76 (m, 2 H) 2.57 (m, 2 H) 2.51 (s, 3 H) 2.32 (s, 3 H).

Example 115

N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide The title compound was prepared as described in EXAMPLE 4H, substituting 5-thiophene-2-carbonyl chloride for 2,6-difluorobenzoyl chloride. MS (ESI(+)) m/e 558.1 (M+H)+; $^1$H NMR (300 MHz, dimethylsulfoxide-$d_6$) δ ppm 10.33 (s, 1 H) 9.63 (s, 1 H) 9.54 (d, 1 H) 8.35 (d, 1 H) 8.09 (m, 1 H) 8.04 (m, 1 H) 7.85-7.92 (m, 2 H) 7.75 (d, 1 H) 7.40-7.54 (m, 4 H) 7.34 (m, 1 H) 7.23 (dd, 1 H) 7.01-7.10 (m, 2 H) 6.65 (d, 1 H) 3.41 (s, 2 H) 2.76 (m, 2 H) 2.57 (m, 2 H) 2.32 (s, 3 H).

Example 116

4-methyl-N-[3-(3-{2-[(2-methyl-1,2,3,4-tetrahydroisoquinolin-7-yl)amino]pyrimidin-4-yl}imidazo [1,2-a]pyridin-2-yl)phenyl]thiophene-2-carboxamide The title compound was prepared as described in EXAMPLE 4H, substituting 4-methylthiophene-2-carbonyl chloride for 2,6-difluorobenzoyl chloride. MS (ESI(+)) m/e 572.2 (M+H)+; $^1$H NMR (300 MHz, dimethylsulfoxide-$d_6$) δ ppm 10.26 (s, 1 H) 9.63 (s, 1 H) 9.54 (d, 1 H) 8.33 (d, 1 H) 8.08 (m, 1 H) 7.88 (m, 2 H) 7.76 (d, 1 H) 7.40-7.54 (m, 5 H) 7.34 (m, 1 H) 7.01-7.10 (m, 2 H) 6.64 (d, 1 H) 3.41 (s, 2 H) 2.76 (m, 2 H) 2.57 (m, 2 H) 2.32 (s, 3 H) 2.27 (s, 3 H).

Example 117

2,5-dichloro-N-[3-(3-{2-[(2-methyl-1,2,3,4-tetrahydroisoquinolin-7-yl)amino]pyrimidin-4-yl}imidazo [1,2-a]pyridin-2-yl)phenyl]thiophene-3-carboxamide The title compound was prepared as described in EXAMPLE 4H, substituting 2,5-dichlorothiophene-3-carbonyl chloride for 2,6-difluorobenzoyl chloride. MS (ESI(+)) m/e 626.1 (M+H)+; $^1$H NMR (300 MHz, dimethylsulfoxide-$d_6$) δ ppm 10.42 (s, 1 H) 9.87 (s, 1 H) 9.53 (d, 1 H) 8.39 (d, 1 H) 8.08 (s, 1 H) 7.79 (m, 2 H) 7.68 (m, 1 H) 7.37-7.62 (m, 5 H) 7.12-7.20 (m, 2 H) 6.70 (m, 1 H) 4.42 (m, 1 H) 4.21-4.29 (m, 1 H) 3.33 (m, 2 H) 3.04 (m, 2 H) 2.93 (d, 3 H).

161

Example 118

5-chloro-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide The title compound was prepared as described in EXAMPLE 52, substituting EXAMPLE 4G for EXAMPLE 48E and 5-chlorothiophene-2-carboxylic acid for 5-methylthiophene-2-carboxylic acid. MS (ESI(+)) m/e 592.2 (M+H)$^+$; $^1$H NMR (300 MHz, dimethylsulfoxide-d$_6$) δ ppm 10.40 (s, 1 H) 9.63 (s, 1 H) 9.52 (d, 1 H) 8.35 (d, 1 H) 8.07 (m, 1 H) 7.93 (d, 1 H) 7.86 (m, 1 H) 7.76 (m, 1 H) 7.34-7.54 (m, 5 H) 7.27 (d, 1 H) 7.01-7.10 (m, 2 H) 6.64 (d, 1 H) 3.40 (s, 2 H) 2.76 (m, 2 H) 2.57 (m, 2 H) 2.31 (s, 3 H).

Example 119

3-methyl-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide The title compound was prepared as described in EXAMPLE 4H, substituting 3-methylthiophene-2-carbonyl chloride for 2,6-difluorobenzoyl chloride. MS (ESI(+)) m/e 572.2 (M+H)$^+$; $^1$H NMR (300 MHz, dimethylsulfoxide-d$_6$) δ ppm 10.08 (s, 1 H) 9.62 (s, 1 H) 9.53 (d, 1 H) 8.35 (d, 1 H) 8.04 (m, 1 H) 7.74-7.84 (m, 2 H) 7.67 (d, 1 H) 7.32-7.55 (m, 5 H) 7.00-7.10 (m, 3 H) 6.64 (d, 1 H) 3.41 (s, 2 H) 2.76 (m, 2 H) 2.57 (m, 2 H) 2.32 (s, 3 H) 1.90 (s, 3 H).

Example 120

N-[3-(3-{2-[(2-methyl-1,2,3,4-tetrahydroisoquinolin-7-yl)amino]pyrimidin-4-yl}imidazo[1,2-a]pyridin-2-yl)phenyl]-1-benzothiophene-2-carboxamide The title compound was prepared as described in EXAMPLE 4H, substituting benzo[b]thiophene-2-carbonyl chloride for 2,6-difluorobenzoyl chloride. MS (ESI(+)) m/e 608.2 (M+H)$^+$; $^1$H NMR (300 MHz, dimethylsulfoxide-d$_6$) δ ppm 10.63 (s, 1 H) 9.64 (s, 1 H) 9.54 (d, 1 H) 8.37 (m, 2 H) 8.14 (m, 1 H) 7.93-8.08 (m, 3 H) 7.77 (d, 1 H) 7.36-7.55 (m, 7 H) 7.01-7.11 (m, 2 H) 6.66 (d, 1 H) 3.40 (s, 2 H) 2.76 (m, 2 H) 2.57 (m, 2 H) 2.31 (s, 3 H).

Example 121

N-{3-[3-(2-{[2-(methoxyacetyl)-1,2,3,4-tetrahydroisoquinolin-7-yl]amino}pyrimidin-4-yl)imidazo[1,2-a]pyridin-2-yl]phenyl}-2-thien-2-ylacetamide Example 121A Into a 20 mL vial was charged 7-nitro-1,2,3,4-tetrahydroisoquinoline, hydrochloric acid salt (0.300 g, 1.398 mmol), methoxyacetyl chloride (0.141 ml, 1.537 mmol), triethylamine (0.429 ml, 3.07 mmol), and dichloromethane (6.99 ml). The reaction was stirred at room temperature for 2 hours. The reaction was diluted with dichloromethane, washed with 1N HCl, saturated aqueous sodium bicarbonate, and brine. The organic layer was dried over MgSO$_4$, filtered and concentrated to provide the title compound. MS (DCI(+)) m/e 251 (M+H)$^+$.

Example 121B

Into a 250 mL round bottom flask was charged EXAMPLE 121A (0.277 g, 1.107 mmol), iron (0.680 g, 12.18 mmol),

162 ammonium chloride (0.065 g, 1.218 mmol), ethanol (8.8 ml) and water (2.2 ml). The reaction was heated to 90° C. for 1 hour. The suspension was then filtered hot and rinsed with ethyl acetate. The filtrate was washed with water and brine, dried over MgSO$_4$, filtered and concentrated to provide the title compound. MS (DCI(+)) m/e 221 (M+H)$^+$.

Example 121C

Into a 5 mL microwave tube was charged EXAMPLE 4C (0.095 g, 0.271 mmol), EXAMPLE 121C (0.0777 g, 0.353 mmol), and 2-propanol (1.357 ml). Hydrochloric acid (0.102 ml, 0.407 mmol) was added, and the tube was sealed, and heated in an oil bath at 120° C. for 3 hours. The reaction was cooled to room temperature, and concentrated. The residue was taken up into 15% methanol:CH$_2$Cl$_2$, washed with saturated aqueous sodium bicarbonate, dried over MgSO$_4$, filtered and concentrated. The residue was taken up into tetrahydrofuran (2.5 mL), and methoxyacetyl chloride (22 uL, 0.250 mmol) was added. The reaction was stirred at room temperature overnight. The resulting suspension was diluted with ether and filtered to provide the title compound. MS (ESI(+)) m/e 536 (M+H)$^+$.

Example 121D

The title compound was prepared as described in EXAMPLE 4G, substituting EXAMPLE 121C for EXAMPLE 4F. MS (ESI(+)) m/e 506 (M+H)$^+$.

Example 121E

The title compound was prepared as described in EXAMPLE 4H, substituting EXAMPLE 121D for EXAMPLE 4G, and 2-thiopheneacetyl chloride for 2,6-difluorobenzoyl chloride. MS (ESI(+)) m/e 630 (M+H)$^+$; $^1$H NMR (300 MHz, dimethylsulfoxide-d$_6$) δ ppm 10.38 (s, 1H), 9.79 (s, 1H), 9.57 (d, 1H), 8.39 (d, 1H), 7.95 (s, 1H), 7.84 (m, 1H), 7.74 (m, 1H), 7.65 (m, 2H), 7.38-7.50 (m, 3H), 7.22-7.34 (m, 3H), 6.97 (m, 2H), 6.63 (d, 1H), 4.55 (m, 2H), 4.16 (m, 2H), 3.88 (s, 2H), 3.30 (m, 4H).

Example 122

N-{3-[3-(2-{[4-(1-acetylpyrrolidin-3-yl)phenyl]amino) pyrimidin-4-yl)imidazo[1,2-a]pyridin-2-yl]phenyl}-2,6-difluorobenzamide The title compound was prepared as described in EXAMPLE 98D substituting EXAMPLE 100B for EXAMPLE 98C and 2,6-difluorobenzoyl chloride for 2-(thiophen-2-yl)acetyl chloride. MS (ESI(+)) m/e 630 (M+H)$^+$, (ESI(−)) m/e 628 (M−H); $^1$H-NMR (300 MHz, dimethylsulfoxide-d$_6$) δ 10.90 (s, 1H), 9.73 (d, 1H), 9.51 (d, 1H), 8.36 (dd, 1H), 8.04 (m, 1H), 7.78 (m, 2H), 7.69 (d, 2H), 7.62-7.38 (m, 4H), 7.29-7.20 (m, 4H), 7.08 (t, 1H), 6.66 (dd, 1H), 3.88-3.77 (m, 1H), 3.67-3.42 (m, 2H), 3.37 (m, 1H), 3.22-3.11 (m, 1H), 2.31-2.15 (m, 1H), 2.02-1.87 (m, 1H), 1.96 (s, 3H).

Example 123

N-{3-[3-(2-{[2-(3-methoxypropanoyl)-1,2,3,4-tetrahydroisoquinolin-7-yl]amino}pyrimidin-4-yl)imidazo[1,2-a]pyridin-2-yl]phenyl}-2-thien-2-ylacetamide Example 123A Into a 20 mL vial was charged 7-nitro-1,2,3,4-tetrahydroisoquinoline, hydrochloric acid (0.300 g, 1.398 mmol), 1-hydroxybenzotriazole hydrate (0.214 g, 1.398 mmol), N-(3-dimethylaminopropyl)-N-ethylcarbodiimide hydrochloride (0.348 g, 1.817 mmol), triethylamine (0.195 ml, 1.398 mmol), 3-methoxypropionic acid (0.158 ml, 1.677 mmol), and tetrahydrofuran (7.0 ml). The reaction was stirred at room temperature for 2 hours. The reaction was diluted with ethyl acetate, and washed with 1N HCl, saturated aqueous sodium bicarbonate, and brine. The organic layer was dried over MgSO$_4$, filtered and concentrated to provide the title compound. MS (DCI(+)) m/e 265 (M+H)$^+$.

Example 123B

The title compound was prepared as described in EXAMPLE 121B, substituting EXAMPLE 123A for EXAMPLE 121A. MS (DCI(+)) m/e 235 (M+H)$^+$.

Example 123C

The title compound was prepared as described in EXAMPLE 4F, substituting EXAMPLE 123B for EXAMPLE 4E. MS (ESI(+)) m/e 550 (M+H)$^+$.

Example 123D

The title compound was prepared as described in EXAMPLE 4G, substituting EXAMPLE 123C for EXAMPLE 4F. MS (ESI(+)) m/e 520 (M+H)$^+$.

Example 123E

The title compound was prepared as described in EXAMPLE 4H, substituting EXAMPLE 123D for EXAMPLE 4G, and 2-thiopheneacetyl chloride for 2,6-difluorobenzoyl chloride. MS (ESI(+)) m/e 644 (M+H)$^+$; $^1$H NMR (300 MHz, dimethylsulfoxide-d$_6$) δ ppm 10.30 (s, 1H), 9.71 (s, 1H), 9.52 (d, 1H), 8.34 (d, 1H), 7.90 (d, 1H), 7.64-7.76 (m, 3H), 7.68 (m, 2H), 7.49 (m, 2H), 7.38 (m, 2H), 7.30 (m, 1H), 7.09 (m, 2H), 6.97 (m, 2H), 6.61 (m, 1H), 4.58 (m, 2H), 3.87 (s, 2H), 3.68 (m, 2H), 3.58 (m, 2H), 3.23 (s, 3H), 2.66 (m, 2H).

Example 124

N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-3-carboxamide The title compound was prepared as described in EXAMPLE 4H, substituting thiophene-3-carbonyl chloride for 2,6-difluorobenzoyl chloride. MS (ESI(+)) m/e 558.2 (M+H)$^+$; $^1$H NMR (300 MHz, dimethylsulfoxide-d$_6$) δ ppm 10.15 (s, 1 H) 9.62 (s, 1 H) 9.55 (d, 1 H) 8.35 (m, 2 H) 8.11 (m, 1 H) 7.92 (m, 1 H) 7.75 (m, 1 H) 7.64 (m, 2 H) 7.40-7.54 (m, 4 H) 7.33 (m, 1 H) 7.01-7.10 (m, 2 H) 6.64 (d, 1 H) 3.41 (s, 2 H) 2.76 (m, 2 H) 2.58 (m, 2 H) 2.32 (s, 3 H).

Example 125

N-(2-fluorophenyl)-3-(3-{2-[(2-methyl-1,2,3,4-tetrahydroisoquinolin-7-yl)amino]pyrimidin-4-yl}imidazo[1,2-a]pyridin-2-yl)benzamide Example 125A In a 200 mL pear flask was charged 2-bromo-1-(3-bromophenyl)ethanone (15.3 g, 55.0 mmol) and pyridin-2-amine (5.18 g, 55.0 mmol) in dimethylformamide (110 ml). The reaction was heated at 85° C. overnight. The solution was cooled and solvent was concentrated in vacuo. The residue was washed with water and the solid was collected by filtration. The solid was washed with water and then diethyl ether. MS (DCI(+)) m/e 273.9, 275.9 (M+H)$^+$.

Example 125B

In a 250 mL round-bottomed flask was placed EXAMPLE 125A (12.16 g, 44.5 mmol) and sulfuric acid (0.237 ml, 4.45 mmol) in acetic anhydride (178 ml). The reaction was heated at 146° C. for 24 hours. The solution was cooled and concentrated in vacuo, and was diluted with dichloromethane and washed with sodium bicarbonate. The organic layer was dried over magnesium sulfate and concentrated in vacuo to approximately 20 ml. The solution was placed on a 50 g silica gel column and purified by flash chromatography on an Argonaut Flash Master SOLO, eluting with a gradient of 100% dichloromethane to 50:50 dichloromethane/methanol to afford the title compound. MS (DCI(+)) m/e 315.0, 317.0 (M+H)$^+$.

Example 125C

In a 50 mL round-bottomed flask was placed EXAMPLE 125B (6.11 g, 19.39 mmol) in 1-methyl-2-pyrrolidinone (9.69 ml). 1,1-di-tert-butoxy-N,N-dimethylmethanamine (18.59 ml, 78 mmol) was added. The reaction was heated at 90° C. and complete after 72 hours by LC-MS. The mixture was diluted with dichloromethane, washed with water and dried over magnesium sulfate. The reaction mixture was concentrated in vacuo onto silica gel and purified by flash chromatography on an Argonaut Flash Master SOLO, using a 10 g silica gel column eluting with a gradient 100% dichloromethane to 50:50 dichloromethane/methanol to afford the title compound. MS (DCI(+)) m/e 370.1, 372.1 (M+H)$^+$.

Example 125D

The title compound was prepared as described in EXAMPLE 1F, substituting 1-(4-2-methyl-1,2,3,4-tetrahydroisoquinolin-7-amine for 3-morpholinoaniline. The solid was dried to a constant weight to provide the title compound. MS DCI(+)) m/e 205.0 (M+H)$^+$ Example 125E In a 20 mL vial was placed EXAMPLE 313C (0.295 g, 0.798 mmol), EXAMPLE 125D (0.192 g, 0.798 mmol), and potassium carbonate (0.441 g, 3.19 mmol) in 1-methyl-2-pyrrolidinone (3.99 ml). The reaction was heated at 85° C. and was complete after 64 hours by LC-MS. The mixture was diluted with dichloromethane, washed with water then brine and dried over magnesium sulfate. The reaction mixture was concentrated in vacuo onto silica gel and purified by flash chromatography on an Argonaut Flash Master SOLO, using a 10 g silica gel column eluting with a gradient 100% dichloromethane to 50:50 dichloromethane/methanol to afford the title compound. MS (ESI(+)) m/e 511.1, 513.1 (M+H)$^+$, (ESI(−)) m/e 509.0, 511.0 (M−H)$^−$.

Example 125F

Example 125E (0.173 g, 0.334 mmol) in methanol (10 ml) was added to 1,1'-bis(diphenylphosphino)ferrocene palladium dichloride (7.34 mg, 10.03 μmol and triethylamine (0.093 ml, 0.669 mmol) in a 50 ml pressure bottle. The mixture was pressurized with carbon monoxide (60 psi), and stirred 4 hours at 100° C. The reaction mixture was concentrated in vacuo onto silica gel and the residue was purified by flash chromatography on an Argonaut Flash Master SOLO, using a 10 g silica gel column eluting with a gradient 100% dichloromethane to 50:50 dichloromethane/methanol to afford the title compound. MS (ESI(+)) m/e 491.1 (M+H)$^+$, (ESI(–)) m/e 489.2 (M–H)$^-$.

Example 125G

In a 20 mL vial was placed EXAMPLE 125F (0.138 g, 0.281 mmol) and lithium hydroxide hydrate (0.059 g, 1.407 mmol) in ethanol (2.53 ml) and water (0.281 ml). The reaction mixture was heated at 85° C. for two hours and was cooled. The solvent was evaporated and the residue was purified by flash chromatography on an Argonaut Flash Master SOLO, using a 5 g silica gel column eluting with a gradient 100% dichloromethane to 50:50 dichloromethane/methanol to afford the title compound. MS (ESI(+)) m/e 477.1 (M+H)$^+$, (ESI(–)) m/e 475.1 (M–H)$^-$.

Example 125H

N-(2-fluorophenyl)-3-(3-{2-[(2-methyl-1,2,3,4-tetrahydroisoquinolin-7-yl)amino]pyrimidin-4-yl}imidazo[1,2-a]pyridin-2-yl)benzamide In a 4 ml vial was charged EXAMPLE 125G (50.0 mg, 0.105 mmol), O-(7-azabenzotriazol-1-yl)-N,N,N',N'-tetramethyluronium hexafluorophosphate (80 mg, 0.210 mmol), N-methylmorpholine (40.4 µl, 0.367 mmol), in N,N-dimethylformamide (1.049 ml). The reaction mixture was stirred at 0° C. for one hour. To the reaction mixture was added 2-fluoroaniline (30.3 µl, 0.315 mmol) and the solution was allowed to warm to room temperature and stirred overnight. The reaction was diluted with methanol (0.5 ml) and the residue was purified by reverse-phase HPLC on a Shimadzu LC10 HPLC system, with a Phenominex Luna 10 micron C18(2) 100 150×30 mm column, eluting with a gradient of 20-60% CH$_3$CN/water/0.15% trifluoroacetic acid to afford the title compound. MS (DCI(+)) m/e 570.3 (M+H)$^+$; $^1$H-NMR (300 MHz, dimethylsulfoxide-d$_6$) δ 10.23 (s, 1H) 9.77 (s, 1H) 9.53 (d, 1H) 8.32-8.42 (m, 2H) 8.06 (ddd, 1H) 7.85 (ddd, 1H) 7.79 (dt, 1H) 7.45-7.67 (m, 5H) 7.18-7.34 (m, 3H) 7.05-7.17 (m, 2H) 6.64 (d, 1H) 2.96-3.18 (m, 2H) 2.90 (d, 2H) 2.55-2.68 (m, 2H) 2.49 (s, 3H).

Example 126

3-(3-{2-[(2-methyl-1,2,3,4-tetrahydroisoquinolin-7-yl)amino]pyrimidin-4-yl}imidazo[1,2-a]pyridin-2-yl)-N-(thien-2-ylmethyl)benzamide The title compound was prepared as described in EXAMPLE 125, substituting thiophen-2-ylmethanamine for 2-fluoroaniline. MS (DCI(+)) m/e 572.3 (M+H)$^+$; $^1$H-NMR (300 MHz, dimethylsulfoxide-d$_6$) δ 9.65 (s, 1H) 9.53 (d, 1H) 9.24 (t, 1H) 8.32 (d, 1H) 8.24 (t, 1H) 7.94 (ddd, 1H) 7.73-7.81 (m, 2H) 7.46-7.62 (m, 3H) 7.43 (dd, 1H) 7.37 (dd, 1H) 7.08 (td, 1H) 6.98-7.04 (m, 2H) 6.92-6.98 (m, 1H) 6.56 (d, 1H) 4.63 (d, 2H) 3.37-3.44 (m, 2H) 2.71-2.79 (m, 2H) 2.54-2.61 (m, 2H) 2.31 (s, 3H).

Example 127

2-chloro-N-{3-[3-(2-{[4-(4-ethylpiperazin-1-yl)phenyl]amino}pyrimidin-4-yl)imidazo[1,2-a]pyridin-2-yl]phenyl}benzamide The title compound as prepared as described in EXAMPLE 41, substituting 2-chlorobenzoyl chloride for 2-phenylacetyl chloride. MS ESI(+): m/e 629.2 (M+H)$^+$. $^1$H NMR (400 MHz, dimethylsulfoxide-d$_6$) δ ppm 10.58 (s, 1H), 9.54 (bs, 1 H), 9.45 (s, 1 H), 8.30 (d, 1 H), 8.05 (s, 1 H), 7.83 (d, 1 H), 7.74 (d, 1 H) 7.43-7.59 (m, 8 H), 7.37 (m, 1 H), 7.05 (t, 1 H), 6.89 (d, 2 H), 6.58 (d, 1 H), 3.06-3.09 (m, 4 H), 2.49-2.51 (m, 4 H), 2.36 (q, 2 H), 1.03 (t, 3H).

Example 128

2-chloro-N-{3-[3-(2-{[4-(4-ethylpiperazin-1-yl)phenyl]amino}pyrimidin-4-yl)imidazo[1,2-a]pyridin-2-yl]phenyl}-6-fluorobenzamide The title compound as prepared as described in EXAMPLE 41, substituting 2-chloro-6-fluorobenzoyl chloride for 2-phenylacetyl chloride. MS ESI(+): m/e 647.2 (M+H)$^+$. $^1$H NMR (400 MHz, dimethylsulfoxide-d$_6$) δ ppm 10.85 (s, 1 H), 9.48 (bs, 1 H), 9.43 (s, 1 H), 8.28 (d, 1 H), 8.02 (s, 1 H), 7.72-7.77 (m, 2 H), 7.34-7.56 (m, 8 H), 7.04 (t, 1 H), 6.88 (d, 2 H), 6.58 (d, 1 H), 3.06-3.09 (m, 4 H), 2.49-2.51 (m, 4 H), 2.36 (q, 2 H), 1.02 (t, 3H).

Example 129

N-{3-[3-(2-{[4-(4-ethylpiperazin-1-yl)phenyl]amino}pyrimidin-4-yl)imidazo[1,2-a]pyridin-2-yl]phenyl}-2-(5-methylthien-2-yl)acetamide The title compound was prepared as described in EXAMPLE 86, substituting 2-(5-methylthiophen-2-yl)acetic acid for 2-(1-methyl-1H-imidazol-4-yl)acetic acid hydrochloric acid. MS ESI(+): m/e 629.3 (M+H)$^+$. $^1$H NMR (400 MHz, dimethylsulfoxide-d$_6$) δ ppm 10.25 (s, 1 H), 9.50 (bs, 1 H), 9.45 (s, 1 H), 8.27 (d, 1 H), 7.89 (s, 1 H), 7.71-7.74 (m, 2 H), 7.53 (d, 2 H), 7.48 (t, 1 H), 7.38 (t, 1 H), 7.29 (d, 1 H), 7.04 (t, 1 H), 6.90 (d, 2 H), 6.74 (d, 1 H), 6.62 (d, 1 H), 6.54 (d, 1 H), 3.76 (s, 2 H), 3.06-3.10 (m, 4 H), 2.49-2.51 (m, 4 H), 2.36-2.40 (m, 5 H), 1.03 (t, 3H).

Example 130

N-{3-[3-(2-{[4-(4-ethylpiperazin-1-yl)phenyl]amino}pyrimidin-4-yl)imidazo[1,2-a]pyridin-2-yl]phenyl}-2-(2-methyl-1,3-thiazol-5-yl)acetamide The title compound was prepared as described in EXAMPLE 86, substituting 2-(2-methylthiazol-5-yl)acetic acid for 2-(1-methyl-1H-imidazol-4-yl)acetic acid hydrochloric acid. MS ESI(+): m/e 630.2 (M+H)$^+$. $^1$H NMR (400 MHz, dimethylsulfoxide-d$_6$) δ ppm 10.32 (s, 1 H), 9.50 (bs, 1 H), 9.45 (s, 1 H), 8.27 (d, 1 H), 7.89 (s, 1 H), 7.70-7.74 (m, 2 H), 7.53 (d, 2 H), 7.45-7.48 (m, 2 H), 7.39 (t, 1 H), 7.31 (d, 1 H), 7.04 (t, 1 H), 6.89 (d, 2 H), 6.54 (d, 1 H), 3.88 (s, 2 H), 3.06-3.10 (m, 4 H), 2.59 (s, 3 H), 2.49-2.51 (m, 4 H), 2.38 (q, 2 H), 1.03 (t, 3H).

Example 131

N-{3-[3-(2-[4-(4-isopropylpiperazin-1-yl)phenyl]
amino}pyrimidin-4-yl)imidazo[1,2-a]pyridin-2-yl]
phenyl}-2-thien-2-ylacetamide

Example 131A

The title compound was prepared as described in EXAMPLE 4F, substituting 4-(4'-isopropylpiperidiny-1'-1) aniline for EXAMPLE 4E. MS ESI(+): m/e 535.2 (M+H)$^+$.

Example 131B

Example 131A was reduced as described in EXAMPLE 41B to give the title compound. MS ESI(+): m/e 505.2 (M+H)$^+$.

Example 131C

N-{3-[3-(2-{[4-(4-isopropylpiperazin-1-yl)phenyl]
amino}pyrimidin-4-yl)imidazo[1,2-a]pyridin-2-yl]
phenyl}-2-thien-2-ylacetamide The title compound was prepared as described in EXAMPLE 41 from EXAMPLE 131B and 2-(thiophen-2-yl)acetyl chloride. MS ESI(+): m/e 629.3 (M+H)$^+$. $^1$H NMR (400 MHz, dimethylsulfoxide-d$_6$) δ ppm 10.30 (s, 1 H), 9.50 (bs, 1 H), 9.45 (s, 1 H), 8.27 (d, 1 H), 7.91 (s, 1 H), 7.43 (d, 2 H), 7.42-7.54 (m, 3 H), 7.31-7.40 (m, 2 H), 7.30 (d, 1 H), 7.04 (t, 1 H), 6.94-6.98 (m, 2 H), 6.89 (d, 2 H), 6.54 (d, 1 H), 3.87 (s, 2 H), 3.03-3.07 (m, 4 H), 2.67 (m, 1 H), 2.54-2.60 (m, 2 H), 2.48-2.52 (m, 2 H), 1.01 (d, 6H).

Example 132

N-{3-[3-(2-{[4-(4-isopropylpiperazin-1-yl)phenyl]
amino}pyrimidin-4-yl)imidazo[1,2-a]pyridin-2-yl]
phenyl}-2-phenylacetamide The title compound was prepared as described in EXAMPLE 41 from EXAMPLE 131B and 2-phenylacetyl chloride. MS ESI(+): m/e 623.2 (M+H)$^+$. $^1$H NMR (400 MHz, dimethylsulfoxide-d$_6$) δ ppm 10.28 (s, 1 H), 9.58 (s, 1 H), 9.52 (bs, 1 H), 9.23 (bs, 1 H), 8.30 (d, 1 H), 7.95 (s, 1 H), 7.77 (d, 1 H), 7.71 (d, 1 H), 7.61 (d, 2 H), 7.55 (t, 1 H), 7.39 (t, 1 H), 7.24-7.33 (m, 5 H), 7.10 (t, 1 H), 6.98 (d, 2 H), 6.58 (d, 1 H), 3.64 (s, 2 H), 3.40-3.45 (m, 4 H), 3.37 (m, 1 H), 3.08-3.25 (m, 2 H), 2.90-2.95 (m, 2 H), 1.30 (d, 6H).

Example 133

2,6-difluoro-N-{3-[3-(2-{[4-(4-isopropylpiperazin-1-
yl)phenyl]amino}pyrimidin-4-yl)imidazo[1,2-a]pyri-
din-2-yl]phenyl}benzamide The title compound was prepared as described in EXAMPLE 41 from EXAMPLE 131B and 2,6-difluorobenzoyl chloride. MS ESI(+): m/e 645.2 (M+H)$^+$. $^1$H NMR (400 MHz, dimethylsulfoxide-d$_6$) δ ppm 10.89 (s, 1 H), 9.58 (s, 1 H), 9.49 (bs, 1 H), 9.21 (bs, 1 H), 8.33 (d, 1 H), 8.08 (s, 1 H), 7.75-7.79 (m, 2 H), 7.61 (d, 2 H), 7.50-7.58 (m, 2 H), 7.46 (t, 1 H), 7.39 (d, 1 H), 7.23-7.27 (m, 2 H), 7.10 (t, 1 H), 6.98 (d, 2 H), 6.63 (d, 1 H), 3.40-3.45 (m, 4 H), 3.37 (m, 1 H), 3.08-3.25 (m, 2 H), 2.90-2.95 (m, 2 H), 1.30 (d, 6H).

Example 134

2-chloro-N-{3-[3-(2-{[4-(4-isopropylpiperazin-1-yl)
phenyl]amino}pyrimidin-4-yl)imidazo[1,2-a]pyri-
din-2-yl]phenyl}benzamide The title compound was prepared as described in EXAMPLE 41 from EXAMPLE 131B and 2-chlorobenzoyl chloride. MS ESI(+): m/e 643.1 (M+H)$^+$. $^1$H NMR (400 MHz, dimethylsulfoxide-d$_6$) δ ppm 10.60 (s, 1 H), 9.59 (s, 1 H), 9.51 (bs, 1 H), 9.25 (bs, 1 H), 8.33 (d, 1 H), 8.10 (s, 1 H), 7.75-7.82 (m, 3 H), 7.37-7.62 (m, 8 H), 7.11 (t, 1 H), 6.99 (d, 2 H), 6.63 (d, 1 H), 3.40-3.45 (m, 4 H), 3.37 (m, 1 H), 3.08-3.25 (m, 2 H), 2.90-2.96 (m, 2 H), 1.30 (d, 6H).

Example 135

N-[3-(3-{2-[(1-methyl-2,3-dihydro-1H-indol-5-yl)
amino]pyrimidin-4-yl}imidazo[1,2-a]pyridin-2-yl)
phenyl]-2-phenylacetamide

Example 135A

In a 20 ml pressure tube were mixed 5-nitroindoline (500 mg, 3.05 mmol) and sodium carbonate (968 mg, 9.14 mmol) at ambient temperature in anhydrous tetrahydrofuran (5 ml). Methyl iodide (0.190 ml, 3.05 mmol) was added. The reaction mixture was stirred and heated for 24 hours at 60° C. the mixture was diluted with ethyl acetate and water, and the layers were separated. The organic layer was washed with brine, dried with Na$_2$SO$_4$, filtered, and concentrated. The residue was purified by flash chromatography on a 40 g silica gel column using an AnaLogix IntelliFlash 280 system eluting with a gradient of 10 to 20% ethyl acetate/hexane to provide the title compound. MS (DCI(+)) m/e 179 (M+H)$^+$.

Example 135B

The title compound was prepared as described in EXAMPLE 1H, substituting EXAMPLE 135A for EXAMPLE 1G. MS (DCI(+)) m/e 149 (M+H)$^+$.

Example 135C

The title compound was prepared as described in EXAMPLE 4F, substituting EXAMPLE 135B for EXAMPLE 4E. MS (ESI(+)) m/e 464 (M+H)$^+$.

Example 135D

The title compound was prepared as described in EXAMPLE 4G, substituting EXAMPLE 135C for EXAMPLE 4F. MS (ESI(+)) m/e 434 (M+H)$^+$.

Example 135E

The title compound was prepared as described in EXAMPLE 4H, substituting EXAMPLE 135D for EXAMPLE 4G, and phenylacetyl chloride for 2,6-difluorobenzoyl chloride. MS (ESI(+)) m/e 558 (M+H)$^+$, $^1$H NMR (400 MHz, dimethylsulfoxide-d$_6$) δ ppm 10.26 (s, 1 H) 9.49 (m, 1 H) 9.30 (s, 1 H) 8.24 (d, 1 H) 7.90 (s, 1 H) 7.73 (t, 2 H) 7.47 (m, 1 H) 7.31-7.42 (m, 6 H) 7.22-7.30 (m, 3 H) 7.01 (t, 1 H) 6.49 (m, 2 H) 3.64 (s, 2 H) 3.21 (m, 2 H) 2.84 (m, 2 H) 2.68 (s, 3 H).

Example 136

2,6-difluoro-N-{3-[3-(2-[3-(pyrrolidin-1-ylmethyl)phenyl]amino}pyrimidin-4-yl)imidazo[1,2-a]pyridin-2-yl]phenyl)benzamide

Example 136A

The title compound was prepared as described in EXAMPLE 4F, substituting 3-(pyrrolidin-1-ylmethyl)aniline for EXAMPLE 4E. MS (ESI(+)) m/e 492 (M+H)$^+$.

Example 136B

The title compound was prepared as described in EXAMPLE 4G, substituting EXAMPLE 136A for EXAMPLE 4F. MS (ESI(+)) m/e 462 (M+H)$^+$.

Example 136C

The title compound was prepared as described in EXAMPLE 4H, substituting EXAMPLE 136B for EXAMPLE 4G. MS (ESI(+)) m/e 602 (M+H)$^+$, $^1$H NMR (400 MHz, dimethylsulfoxide-d$_6$) δ ppm 10.89 (s, 1 H) 9.73 (s, 1 H) 9.54 (d, 1 H) 8.37 (d, 1 H) 8.05 (s, 1 H) 7.71-7.82 (m, 3 H) 7.67 (d, 1 H) 7.59 (m, 1 H) 7.38-7.52 (m, 3 H) 7.25 (m, 3 H) 7.06 (t, 1 H) 6.95 (d, 1 H) 6.67 (d, 1 H) 3.60 (s, 2 H) 2.50 (bs, 4 H) 1.68 (bs, 4 H).

Example 137

2-phenyl-N-{3-[3-(2-{[3-(pyrrolidin-1-ylmethyl)phenyl]amino}pyrimidin-4-yl)imidazo[1,2-a]pyridin-2-yl]phenyl}acetamide The title compound was prepared as described in EXAMPLE 4H, substituting EXAMPLE 136B for EXAMPLE 4G, and phenylacetyl chloride for 2,6-difluorobenzoyl chloride. MS (ESI(+)) m/e 580 (M+H)$^+$, $^1$H NMR (400 MHz, dimethylsulfoxide-d$_6$) δ ppm 10.26 (s, 1 H) 9.71 (s, 1 H) 9.55 (d, 1 H) 8.34 (d, 1 H) 7.93 (s, 1 H) 7.73 (m, 3 H) 7.67 (d, 1 H) 7.49 (m, 1 H) 7.28-7.39 (m, 6 H) 7.23 (m, 2 H) 7.05 (t, 1 H) 6.93 (d, 1 H) 6.62 (d, 1 H) 3.64 (s, 2 H) 3.57 (s, 2 H) 2.46 (bs, 4 H) 1.67 (bs, 4 H).

Example 138

N-{3-[3-(2-{[3-(pyrrolidin-1-ylmethyl)phenyl]amino}pyrimidin-4-yl)imidazo[1,2-a]pyridin-2-yl]phenyl}-2-thien-2-ylacetamide The title compound was prepared as described in EXAMPLE 4H, substituting EXAMPLE 136B for EXAMPLE 4G, and 2-thiopheneacetyl chloride for 2,6-difluorobenzoyl chloride. MS (ESI(+)) m/e 586 (M+H)$^+$, $^1$H NMR (400 MHz, dimethylsulfoxide-d$_6$) δ ppm 10.31 (s, 1 H) 9.72 (s, 1 H) 9.54 (d, 1 H) 8.35 (d, 1 H) 7.93 (s, 1 H) 7.73 (m, 3 H) 7.67 (d, 1 H) 7.50 (m, 1 H) 7.39 (m, 1 H) 7.32 (m, 1 H) 7.23 (t, 1 H) 7.06 (t, 1 H) 6.98 (m, 2 H) 6.93 (d, 1 H) 6.62 (d, 1 H) 3.87 (s, 2 H) 3.57 (s, 2 H) 2.46 (bs, 4 H) 1.67 (bs, 4 H).

Example 139

2,6-difluoro-N-{3-[3-(2-{[3-(1H-imidazol-1-ylmethyl)phenyl]amino}pyrimidin-4-yl)imidazo[1,2-a]pyridin-2-yl]phenyl}benzamide

Example 139A

The title compound was prepared as described in EXAMPLE 4F, substituting 3-((1H-imidazol-1-yl)methyl)aniline for EXAMPLE 4E. MS (ESI(+)) m/e 489 (M+H)$^+$.

Example 139B

The title compound was prepared as described in EXAMPLE 4G, substituting EXAMPLE 139A for EXAMPLE 4F. MS (ESI(+)) m/e 459 (M+H)$^+$.

Example 139C

The title compound was prepared as described in EXAMPLE 4H, substituting EXAMPLE 139B for EXAMPLE 4G. MS (ESI(+)) m/e 599 (M+H)$^+$, $^1$H NMR (400 MHz, dimethylsulfoxide-d$_6$) δ ppm 10.88 (s, 1 H) 9.79 (s, 1 H) 9.53 (d, 1 H) 8.36 (d, 1 H) 8.04 (s, 1 H) 7.77 (m, 2 H) 7.71 (s, 1 H) 7.66 (s, 1 H) 7.59 (m, 2 H) 7.50 (m, 2 H) 7.44 (d, 1 H) 7.40 (m, 1 H) 7.20-7.29 (m, 2 H) 7.12 (s, 1 H) 7.08 (m, 1 H) 6.89 (s, 1 H) 6.82 (d, 1 H) 6.68 (d, 1 H) 5.16 (s, 2 H).

Example 140

N-{3-[3-(2-{[3-(1H-imidazol-1-ylmethyl)phenyl]amino}pyrimidin-4-yl)imidazo[1,2-a]pyridin-2-yl]phenyl}-2-phenylacetamide The title compound was prepared as described in EXAMPLE 4H, substituting EXAMPLE 139B for EXAMPLE 4G, and phenylacetyl chloride for 2,6-difluorobenzoyl chloride. MS (ESI(+)) m/e 577 (M+H)$^+$, $^1$H NMR (400 MHz, dimethylsulfoxide-d$_6$) δ ppm 10.26 (s, 1 H) 9.79 (s, 1 H) 9.53 (d, 1 H) 8.34 (d, 1 H) 7.92 (s, 1 H) 7.72 (m, 4 H) 7.66 (s, 1 H) 7.50 (m, 1 H) 7.37 (t, 1 H) 7.22-7.33 (m, 6 H) 7.13 (d, 1 H) 7.06 (t, 1 H) 6.90 (m, 2 H) 6.82 (d, 1 H) 6.64 (d, 1 H) 5.16 (s, 2 H) 3.64 (s, 2 H).

Example 141

N-{3-[3-(2-{[3-(1H-imidazol-1-ylmethyl)phenyl]amino}pyrimidin-4-yl)imidazo[1,2-a]pyridin-2-yl]phenyl}-2-thien-2-ylacetamide The title compound was prepared as described in EXAMPLE 4H, substituting EXAMPLE 139B for EXAMPLE 4G, and 2-thiopheneacetyl chloride for 2,6-difluorobenzoyl chloride. MS (ESI(+)) m/e 583 (M+H)$^+$, $^1$H NMR (400 MHz, dimethylsulfoxide-d$_6$) δ ppm 10.30 (s, 1 H) 9.80 (s, 1 H) 9.53 (d, 1 H) 8.34 (d, 1 H) 7.92 (s, 1 H) 7.73 (m, 3 H) 7.66 (s, 1 H) 7.50 (m, 1 H) 7.40 (m, 2 H) 7.29 (m, 2 H) 7.14 (d, 1 H) 7.08 (m, 1 H) 6.97 (m, 2 H) 6.91 (d, 2 H) 6.82 (d, 1 H) 6.64 (d, 1 H) 5.16 (s, 2 H) 3.87 (s, 2 H).

Example 142

2,6-difluoro-N-{3-[3-(2-{[3-(1H-1,2,4-triazol-1-ylmethyl)phenyl]amino}pyrimidin-4-yl)imidazo[1,2-a]pyridin-2-yl]phenyl}benzamide

Example 142A

The title compound was prepared as described in EXAMPLE 4F, substituting 3-((1H-1,2,4-triazol-1-yl)methyl)aniline for EXAMPLE 4E. MS (ESI(+)) m/e 490 (M+H)$^+$.

Example 142B

The title compound was prepared as described in EXAMPLE 4G, substituting EXAMPLE 142A for EXAMPLE 4F. MS (ESI(+)) m/e 460 (M+H)$^+$.

Example 142C

The title compound was prepared as described in EXAMPLE 4H, substituting EXAMPLE 142B for EXAMPLE 4G. MS (ESI(+)) m/e 600 (M+H)$^+$, $^1$H NMR (400 MHz, dimethylsulfoxide-d$_6$) δ ppm 10.88 (s, 1 H) 9.80 (s, 1 H) 9.54 (d, 1 H) 8.61 (s, 1 H) 8.36 (d, 1 H) 8.03 (s, 1 H) 7.97 (s, 1 H) 7.76 (m, 3 H) 7.68 (s, 1 H) 7.59 (t, 1 H) 7.50 (m, 1 H) 7.42 (m, 2 H) 7.26 (m, 3 H) 7.09 (m, 1 H) 6.86 (d, 1 H) 6.68 (d, 1 H) 5.38 (s, 2 H).

Example 143

5-methyl-N-{3-[3-(2-{[3-(1H-1,2,4-triazol-1-ylmethyl)phenyl]amino}pyrimidin-4-yl)imidazo[1,2-a]pyridin-2-yl]phenyl}thiophene-2-carboxamide The title compound was prepared as described in EXAMPLE 4H, substituting EXAMPLE 142B for EXAMPLE 4G, and 5-methylthiophene-2-carbonyl chloride for 2,6-difluorobenzoyl chloride. MS (ESI(+)) m/e 584 (M+H)$^+$, $^1$H NMR (400 MHz, dimethylsulfoxide-d$_6$) δ ppm 10.20 (s, 1 H) 9.81 (s, 1 H) 9.59 (d, 1 H) 8.62 (s, 1 H) 8.35 (d, 1 H) 8.07 (s, 1 H) 7.97 (s, 1 H) 7.88 (d, 1 H) 7.84 (d, 1 H) 7.75 (m, 2 H) 7.68 (s, 1 H) 7.51 (m, 1 H) 7.42 (t, 1 H) 7.31 (m, 2 H) 7.10 (t, 1 H) 6.92 (d, 1 H) 6.87 (d, 1 H) 6.67 (d, 1 H) 5.39 (s, 2 H) 2.50 (s, 3 H).

Example 144

2-phenyl-N-{3-[3-(2-([3-(1H-1,2,4-triazol-1-ylmethyl)phenyl]amino}pyrimidin-4-yl)imidazo[1,2-a]pyridin-2-yl]phenyl}acetamide The title compound was prepared as described in EXAMPLE 4H, substituting EXAMPLE 142B for EXAMPLE 4G, and phenylacetyl chloride for 2,6-difluorobenzoyl chloride. MS (ESI(+)) m/e 578 (M+H)$^+$, $^1$H NMR (400 MHz, dimethylsulfoxide-d$_6$) δ ppm 10.26 (s, 1 H) 9.80 (s, 1 H) 9.55 (d, 1 H) 8.62 (s, 1 H) 8.34 (d, 1 H) 7.97 (s, 1 H) 7.92 (s, 1 H) 7.74 (m, 3 H) 7.68 (s, 1 H) 7.50 (m, 1 H) 7.38 (t, 1 H) 7.21-7.34 (m, 7 H) 7.08 (t, 1 H) 6.86 (d, 1 H) 6.64 (d, 1 H) 5.38 (s, 2 H) 3.64 (s, 2 H).

Example 145

2-thien-2-yl-N-{3-[3-(2-{[3-(1H-1,2,4-triazol-1-ylmethyl)phenyl]amino}pyrimidin-4-yl)imidazo[1,2-a]pyridin-2-yl]phenyl}acetamide The title compound was prepared as described in EXAMPLE 4H, substituting EXAMPLE 142B for EXAMPLE 4G, and 2-thiopheneacetyl chloride for 2,6-difluorobenzoyl chloride. MS (ESI(+)) m/e 584 (M+H)$^+$, $^1$H NMR (400 MHz, dimethylsulfoxide-d$_6$) δ ppm 10.30 (s, 1 H) 9.81 (s, 1 H) 9.55 (d, 1 H) 8.62 (s, 1 H) 8.34 (d, 1 H) 7.97 (s, 1 H) 7.92 (s, 1 H) 7.74 (m, 3 H) 7.68 (s, 1 H) 7.50 (m, 1 H) 7.39 (m, 2 H) 7.29 (m, 2 H) 7.08 (t, 1 H) 6.97 (m, 2 H) 6.86 (d, 1 H) 6.64 (d, 1 H) 5.38 (s, 2 H) 3.87 (s, 2 H).

Example 146

2,6-difluoro-N-[3-(3-{2-[(1-methyl-2,3-dihydro-1H-indol-5-yl)amino]pyrimidin-4-yl}imidazo[1,2-a]pyridin-2-yl)phenyl]benzamide The title compound was prepared as described in EXAMPLE 4H, substituting EXAMPLE 135C for EXAMPLE 4G. MS (ESI(+)) m/e 574 (M+H)$^+$, $^1$H NMR (400 MHz, dimethylsulfoxide-d$_6$) δ ppm 10.88 (s, 1 H) 9.49 (m, 1 H) 9.31 (m, 1 H) 8.25 (m, 1 H) 8.03 (m, 1 H) 7.79 (m, 1 H) 7.74 (d, 1 H) 7.59 (m, 1 H) 7.42-7.50 (m, 3 H) 7.39 (t, 2 H) 7.25 (m, 3 H) 7.02 (m, 1 H) 6.52 (m, 1 H) 2.90 (m, 2 H) 2.70 (m, 2 H) 2.50 (s, 3 H).

Example 147

5-methyl-N-[3-(3-{2-[(1-methyl-2,3-dihydro-1H-indol-5-yl)amino]pyrimidin-4-yl}imidazo[1,2-a]pyridin-2-yl)phenyl]thiophene-2-carboxamide The title compound was prepared as described in EXAMPLE 4H, substituting EXAMPLE 135C for EXAMPLE 4G, and 5-methylthiophene-2-carbonyl chloride for 2,6-difluorobenzoyl chloride. MS (ESI(+)) m/e 558 (M+H)$^+$, $^1$H NMR (400 MHz, dimethylsulfoxide-d$_6$) δ ppm 10.20 (s, 1 H) 9.52 (m, 1 H) 9.30 (m, 1 H) 8.26 (m, 1 H) 8.05 (s, 1 H) 7.86 (m, 2 H) 7.73 (d, 1 H) 7.48 (m, 1 H) 7.42 (m, 3 H) 7.32 (m, 2 H) 7.02 (m, 1 H) 6.92 (d, 1 H) 6.55 (m, 1 H) 2.85 (m, 2 H) 2.67 (m, 2 H) 2.50 (s, 6 H).

Example 148

N-[3-(3-{2-[(1-methyl-2,3-dihydro-1H-indol-5-yl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 135C for EXAMPLE 4G, and 2-thiopheneacetyl chloride for 2,6-difluorobenzoyl chloride. MS (ESI(+)) m/e 558 (M+H)$^+$, $^1$H NMR (400 MHz, dimethylsulfoxide-d$_6$) δ ppm 10.30 (s, 1 H) 9.49 (m, 1 H) 9.30 (s, 1 H) 8.24 (d, 1 H) 7.90 (s, 1 H) 7.72 (d, 2 H) 7.47 (m, 1 H) 7.41 (m, 1 H) 7.38 (m, 2 H) 7.27 (m, 2 H) 6.98 (m, 3 H) 6.49 (m, 2 H) 3.87 (s, 2 H) 3.21 (t, 2 H) 2.84 (t, 2 H) 2.68 (s, 3 H).

Example 149

2,6-difluoro-N-(3-{3-[2-({3-[(3-hydroxypyrrolidin-1-yl)methyl]phenyl}amino)pyrimidin-4-yl]imidazo[1,2-a]pyridin-2-yl}phenyl)benzamide

Example 149A

The title compound was prepared as described in EXAMPLE 26A, substituting pyrrolidin-3-ol for dimethylamine. MS (DCI(+)) m/e 223 (M+H).

Example 149B

The title compound was prepared as described in EXAMPLE 1H, substituting EXAMPLE 149A for EXAMPLE 1G. MS (DCI(+)) m/e 193 (M+H)$^+$.

Example 149C

The title compound was prepared as described in EXAMPLE 4F, substituting EXAMPLE 149B for EXAMPLE 4E. MS (ESI(+)) m/e 508 (M+H)$^+$.

Example 149D

The title compound was prepared as described in EXAMPLE 4G, substituting EXAMPLE 149C for EXAMPLE 4F. MS (ESI(+)) m/e 478 (M+H)$^+$.

Example 149E

The title compound was prepared as described in EXAMPLE 4H, substituting EXAMPLE 149D for EXAMPLE 4G. MS (ESI(+)) m/e 618 (M+H)$^+$, $^1$H NMR (400 MHz, dimethylsulfoxide-d$_6$) δ ppm 10.88 (s, 1 H) 9.71 (s, 1 H) 9.55 (d, 1 H) 8.37 (d, 1 H) 8.04 (s, 1 H) 7.78 (m, 2 H) 7.68 (m, 2 H) 7.59 (m, 1 H) 7.39-7.53 (m, 3 H) 7.25 (m, 3 H) 7.08 (t, 1 H) 6.93 (d, 1 H) 6.66 (d, 1 H) 4.66 (bs, 1 H) 4.18 (m, 1 H) 3.55 (m, 2 H) 2.70 (m, 1 H) 2.58 (m, 1 H) 2.44 (m, 1 H) 2.33 (m, 1 H) 1.96 (m, 1 H) 1.53 (m, 1 H).

Example 150

N-(3-{3-[2-({3-[(3-hydroxypyrrolidin-1-yl)methyl]phenyl}amino)pyrimidin-4-yl]imidazo[1,2-a]pyridin-2-yl}phenyl)-2-phenylacetamide The title compound was prepared as described in EXAMPLE 4H, substituting EXAMPLE 149D for EXAMPLE 4G, and phenylacetyl chloride for 2,6-difluorobenzoyl chloride. MS (ESI(+)) m/e 596 (M+H)$^+$, $^1$H NMR (400 MHz, dimethylsulfoxide-d$_6$) δ ppm 10.26 (s, 1 H) 9.72 (s, 1 H) 9.56 (d, 1 H) 8.34 (d, 1 H) 7.92 (s, 1 H) 7.74 (d, 2 H) 7.68 (m, 2 H) 7.49 (m, 1 H) 7.37 (m, 1 H) 7.28-7.34 (m, 5 H) 7.24 (m, 2 H) 7.07 (m, 1 H) 6.93 (d, 1 H) 6.62 (d, 1 H) 4.67 (bs, 1 H) 4.19 (m, 1 H) 3.64 (s, 2 H) 3.54 (m, 2 H) 2.70 (m, 1 H) 2.59 (m, 1 H) 2.44 (m, 1 H) 2.33 (m, 1 H) 1.96 (m, 1 H) 1.53 (m, 1 H).

Example 151

N-(3-{3-[2-({3-[(3-hydroxypyrrolidin-1-yl)methyl]phenyl}amino)pyrimidin-4-yl]imidazo[1,2-a]pyridin-2-yl}phenyl)-2-thien-2-ylacetamide The title compound was prepared as described in EXAMPLE 4H, substituting EXAMPLE 149D for EXAMPLE 4G, and 2-thiopheneacetyl chloride for 2,6-difluorobenzoyl chloride. MS (ESI(+)) m/e 602 (M+H)$^+$, $^1$H NMR (400 MHz, dimethylsulfoxide-d$_6$) δ ppm 10.30 (s, 1 H) 9.72 (s, 1 H) 9.56 (d, 1 H) 8.34 (d, 1 H) 7.92 (s, 1 H) 7.66-7.77 (m, 4 H) 7.50 (m, 1 H) 7.38 (m, 2 H) 7.31 (m, 1 H) 7.24 (t, 1 H) 7.07 (m, 1 H) 6.98 (m, 2 H) 6.94 (d, 1 H) 6.62 (d, 1 H) 4.68 (bs, 1 H) 4.19 (m, 1 H) 3.87 (s, 2 H) 3.57 (m, 2 H) 2.71 (m, 1 H) 2.60 (m, 1 H) 2.45 (m, 1 H) 2.33 (m, 1 H) 1.97 (m, 1 H) 1.53 (m, 1 H).

Example 152

N-[3-(3-{2-[(2-ethyl-2,3-dihydro-1H-isoindol-5-yl)amino]pyrimidin-4-yl}imidazo[1,2-a]pyridin-2-yl)phenyl]-2-thien-3-ylacetamide The title compound was prepared as described in EXAMPLE 98D substituting EXAMPLE 103D for EXAMPLE 98C and 2-(thiophen-3-yl)acetyl chloride for 2-(thiophen-2-yl)acetyl chloride. MS (ESI(+)) m/e 572 (M+H)$^+$, (ESI(−)) m/e 570 (M−H)$^-$; $^1$H-NMR (300 MHz, dimethylsulfoxide-d$_6$) δ 10.26 (s, 1H), 9.97 (s, 1H), 9.52 (d, 1H), 8.40 (d, 1H), 7.97 (m, 1H), 7.90 (s, 1H), 7.78 (d, 1H), 7.72-7.65 (m, 2H), 7.58-7.53 (dt, 1H), 7.48 (m, 1H), 7.42-7.28 (m, 4H), 7.14 (dt, 1H), 7.08 (dd, 1H), 6.70 (d, 1H), 4.75 (m, 2H), 4.44 (m, 2H), 3.64 (s, 2H), 3.41 (m, 2H), 1.29 (t, 3H).

Example 153

2-chloro-N-[3-(3-{2-[(2-ethyl-2,3-dihydro-1H-isoindol-5-yl)amino]pyrimidin-4-yl}imidazo[1,2-a]pyridin-2-yl)phenyl]benzamide The title compound was prepared as described in EXAMPLE 98D substituting EXAMPLE 103D for EXAMPLE 98C and 2-chlorobenzoyl chloride for 2-(thiophen-2-yl)acetyl chloride. MS (ESI(+)) m/e 586 (M+H)$^+$; $^1$H-NMR (300 MHz, dimethylsulfoxide-d$_6$) δ 10.62 (s, 1H), 9.98 (s, 1H), 9.52 (d, 1H), 8.42 (d, 1H), 8.12 (m, 1H), 7.91 (s, 1H), 7.80 (m, 2H), 7.67 (dd, 1H), 7.62-7.43 (m, 6H), 7.40-7.31 (m, 2H), 7.15 (dt, 1H), 6.74 (d, 1H), 4.75 (m, 2H), 4.45 (m, 2H), 3.41 (m, 2H), 1.29 (t, 3H).

Example 154

N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-3-ylacetamide The title compound was prepared as described in EXAMPLE 98D substituting EXAMPLE 106D for EXAMPLE 98C and 2-(thiophen-3-yl)acetyl chloride for 2-(thiophen-2-yl)acetyl chloride. MS (ESI(+)) m/e 586 (M+H)$^+$, (ESI(−)) m/e 584 (M−H)$^-$; $^1$H-NMR (300 MHz, dimethylsulfoxide-d$_6$) δ 10.27 (s, 1H), 9.78 (s, 1H), 9.53 (d, 1H), 8.37 (d, 1H), 7.97 (m, 1H), 7.80-7.69 (m, 3H), 7.59-7.47 (m, 3H), 7.40 (t, 1H), 7.31 (m 2H), 7.20-7.07 (m, 3H), 6.64 (d, 1H), 4.09 (m, 1H), 3.66 (s, 2H), 3.33-3.22 (m, 2H), 3.17-3.03 (m, 2H), 2.83 (m, 6H).

Example 155

2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}benzamide The title compound was prepared as described in EXAMPLE 98D substituting EXAMPLE 106D for EXAMPLE 98C and 2-chlorobenzoyl chloride for 2-(thiophen-2-yl)acetyl chloride. MS (ESI(+)) m/e 600 (M+H)⁺, (ESI(−)) m/e 598 (M−H)⁻; ¹H-NMR (300 MHz, dimethylsulfoxide-$d_6$) δ 10.62 (s, 1H), 9.78 (s, 1H), 9.53 (d, 1H), 8.38 (d, 1H), 8.11 (m, 1H), 7.82-7.75 (m, 3H), 7.59-7.38 (m, 8H), 7.20-7.12 (m, 2H), 6.68 (d, 1H), 4.09 (m, 1H), 3.33-3.22 (m, 2H), 3.17-3.03 (m, 2H), 2.83 (m, 6H).

Example 156

2,6-difluoro-N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}benzamide Example 156A Into a 4 mL vial was charged EXAMPLE 4E (0.200 g, 0.569 mmol) and tert-butyl 7-amino-3,4-dihydroisoquinoline-2(1H)-carboxylate (0.164 g, 0.660 mmol) in 2-propanol (5.69 ml). The reaction was heated to 70° C. overnight. 4N HCl in dioxane (0.17 mL) was added, and the reaction stirred at 70° C. for 48 hours. The reaction was cooled to room temperature and filtered to provide the title compound. MS (ESI(+)) m/e 464 (M+H)⁺.

Example 156B

Into a 20 mL vial was charged EXAMPLE 156A (0.3186 g, 0.637 mmol), methoxyacetyl chloride (0.064 ml, 0.701 mmol), triethylamine (0.195 ml, 1.402 mmol), and dichloromethane (3.19 ml). The reaction was stirred at room temperature overnight. The reaction was diluted with dichloromethane, washed with saturated aqueous sodium bicarbonate and brine, dried over MgSO₄, filtered and concentrated. The reaction was purified by HPLC using a Shimadzu SIL-10 HPLC system (2 mL injections, run on a 150×30 mm Phenominex Gemini 10 micron C18 column with 110 Angstrom pore size, flow rate of 20 mL/min, mobile phase gradient from 40% to 80% acetonitrile/water with 0.1% NH₄OH over 25 minutes) to provide the title compound. MS (ESI(+)) m/e 536 (M+H)⁺.

Example 156C

Into a pressure bottle were charged Ra—Ni, water-wet (47.7 mg, 0.366 mmol) (washed once with methanol), EXAMPLE 156B (101.0 mg, 0.189 mmol) and tetrahydrofuran (5.0 ml). The suspension was diluted with methanol (5.0 ml) and stirred for 1 hour under 50 psi H₂ at 50° C. The mixture was filtered through a membrane syringe filter and concentrated to provide the title compound. MS (ESI(+)) m/e 506 (M+H)⁺.

Example 156D

The title compound was prepared as described in EXAMPLE 4H, substituting EXAMPLE 156D for EXAMPLE 4G. MS (ESI(+)) m/e 646 (M+H)⁺; ¹H NMR (300 MHz, dimethylsulfoxide-$d_6$) δ ppm 10.92 (s, 1H), 9.75 (s, 1H), 9.54 (d, 1H), 8.39 (d, 1H), 8.07 (m, 1H), 7.80 (m, 2H), 7.60 (m, 3H), 7.49 (m, 2H), 7.40 (m, 1H), 7.25 (m, 2H), 7.13 (m, 2H), 6.68 (d, 1H), 4.55 (s, 2H), 4.16 (s, 2H), 3.61 (m, 2H), 3.30 (s, 3H), 2.80 (m, 2H).

Example 157

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-2-thien-2-ylacetamide The title compound was prepared as described in EXAMPLE 4H, substituting EXAMPLE 156D for EXAMPLE 4G, and 2-thiopheneacetyl chloride for 2,6-difluorobenzoyl chloride. MS (ESI(+)) m/e 630 (M+H)⁺; ¹H NMR (300 MHz, dimethylsulfoxide-$d_6$) δ ppm 10.35 (s, 1H) 9.76 (s, 1H) 9.56 (d, 1H) 8.37 (d, 1H), 7.94 (m, 1H), 7.80 (m, 1H), 7.72 (m, 1H), 7.62 (m, 2H), 7.51 (m, 2H), 7.40 (m, 2H), 7.31 (m, 1H), 7.14 (m, 2H), 6.61 (d, 1H) 4.55 (s, 2H) 4.17 (s, 2H), 3.88 (s, 2H), 3.63 (m, 2H), 3.31 (s, 3H), 2.80 (m, 2H).

Example 158

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-2-phenylacetamide The title compound was prepared as described in EXAMPLE 4H, substituting EXAMPLE 156D for EXAMPLE 4G, and phenylacetyl chloride for 2,6-difluorobenzoyl chloride. MS (ESI(+)) m/e 624 (M+H)⁺; ¹H NMR (300 MHz, dimethylsulfoxide-$d_6$) δ ppm 10.35 (s, 1H) 9.79 (s, 1H) 9.58 (d, 1H) 8.39 (d, 1H), 7.97 (m, 1H), 7.83 (m, 1H), 7.74 (m, 1H), 7.65 (m, 2H), 7.49 (m, 1H), 7.43 (m, 1H), 7.32 (m, 5H), 7.24 (m, 2H), 7.11 (m, 1H), 6.63 (d, 1H) 4.55 (s, 2H) 4.17 (s, 2H), 3.65 (s, 2H), 3.31 (s, 3H), 2.76 (m, 2H).

Example 159

N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}-N'-phenylurea The title compound was prepared as described in EXAMPLE 3, substituting EXAMPLE 156D for EXAMPLE 1H. MS (ESI(+)) m/e 625 (M+H)⁺; ¹H NMR (300 MHz, dimethylsulfoxide-$d_6$) δ ppm 9.71 (s, 1H) 9.56 (d, 1H), 8.82 (s, 1H), 8.66 (s, 1H), 8.36 (d, 1H), 7.76 (m, 2H), 7.66 (m, 1H), 7.53 (m, 3H), 7.44 (m, 2H), 7.37 (m, 1H), 7.26 (m, 3H), 7.10 (m, 2H), 6.96 (m, 1H), 6.65 (d, 1H) 4.55 (s, 2H) 4.16 (s, 2H), 3.61 (m, 2H), 3.29 (s, 3H), 2.76 (m, 2H).

Example 160

N-{3-[3-(2-{[4-(4-ethylpiperazin-1-yl)phenyl]amino}pyrimidin-4-yl)imidazo[1,2-a]pyridin-2-yl]phenyl}-2-(1,3-thiazol-5-yl)acetamide The title compound was prepared as described in EXAMPLE 86, substituting 2-(thiazol-5-yl)acetic acid for 2-(1-methyl-1H-imidazol-4-yl)acetic acid hydrochloric acid. MS ESI(+): m/e 614.2 (M+H)⁺. ¹H NMR (400 MHz, dimethylsulfoxide-$d_6$) δ ppm 10.41 (s, 1 H), 9.61 (s, 1 H), 9.55 (bs, 1 H), 9.45 (bs, 1 H), 8.99 (s, 1 H), 8.32 (d, 1 H), 7.95 (s, 1 H), 7.79 (d, 1 H), 7.77 (s, 1 H), 7.70 (d, 1 H), 7.57 (d, 2 H), 7.42 (t, 1 H), 7.32 (d, 1 H), 7.14 (t, 1 H), 6.98 (d, 1 H), 6.59 (d, 1 H), 6.26 (s, 1 H), 3.99 (s, 2 H), 3.74-3.79 (m, 2 H), 3.56-3.60 (m, 2 H), 3.10-3.25 (m, 4 H), 2.92 (q, 2 H), 1.26 (t, 3 H).

Example 161

N-[3-(3-{2-[(3-{[4-(dimethylamino)piperidin-1-yl] methyl}phenyl)amino]pyrimidin-4-yl}imidazo[1,2-a]pyridin-2-yl)phenyl]-N'-phenylurea The title compound was prepared as described in EXAMPLE 7, substituting EXAMPLE 45D for EXAMPLE 4G. MS (ESI(+)) m/e 638.3 (M+H)$^+$; $^1$H NMR (300 MHz, dimethylsulfoxide-d$_6$) δ ppm 9.73 (s, 1 H) 9.58 (d, 1 H) 8.81 (s, 1 H) 8.64 (s, 1 H) 8.36 (d, 1 H) 7.76 (m, 2 H) 7.67 (m, 2 H) 7.43-7.58 (m, 4 H) 7.37 (t, 1 H) 7.20-7.29 (m, 4 H) 7.07 (m, 1 H) 6.89-6.99 (m, 2 H) 6.65 (d, 1 H) 3.39 (s, 2 H) 2.81 (m, 2 H) 2.12 (s, 6 H) 1.84-2.05 (m, 3 H) 1.64 (m, 2 H) 1.24-1.38 (m, 2 H).

Example 162

N-{3-[3-(2-[4-(2,7-diazaspiro[4.4]non-2-yl)phenyl] amino}pyrimidin-4-yl)imidazo[1,2-a]pyridin-2-yl] phenyl}-2-thien-2-ylacetamide To a 4 mL vial was charged EXAMPLE 165 (0.065 g, 0.089 mmol), CH$_2$Cl$_2$ (1 mL) and CF$_3$COOH (0.344 mL, 4.47 mmol). The resulting solution was stirred at ambient temperature for 2 hours and was concentrated on a rotary evaporator. The concentrate was triturated with ether (2 mL) and filtered. The crude solid was purified by reverse-phase HPLC on a Phenomenex C18 column (3×15 cm) using a gradient of from 45% to 80% acetonitrile in 0.1% aqueous ammonium hydroxide to provide 20 mg of a yellow solid. MS (ESI(+)) m/e 627.2 (M+H)$^+$; $^1$H NMR (300 MHz, dimethylsulfoxide-d$_6$) δ ppm 10.30 (s, 1 H) 9.50 (brs, 1 H) 9.29 (s, 1 H) 8.23 (d, 1 H) 7.90 (m, 1 H) 7.72 (m, 2 H) 7.29-7.50 (m, 6 H) 6.96-7.04 (m, 3 H) 6.49 (m, 3 H) 3.87 (s, 2 H) 3.11-3.21 (m, 4 H) 2.86 (t, 2 H) 2.67 (m, 2 H) 1.84-1.98 (m, 2 H) 1.64-1.77 (m, 2 H).

Example 163

N-{3-[3-(2-{[4-(7-acetyl-2,7-diazaspiro[4.4]non-2-yl)phenyl]amino}pyrimidin-4-yl)imidazo[1,2-a]pyridin-2-yl]phenyl}-2,6-difluorobenzamide

Example 163A

A 4 mL vial equipped with a stir bar was charged with EXAMPLE 164D (0.043 g, 0.081 mmol), tetrahydrofuran (1 mL) and N-methyl-2-pyrrolidinone (0.5 mL). The solution was treated with acetyl chloride (9.54 mg, 0.122 mmol) and the reaction was stirred at ambient temperature for 30 minutes. The reaction was treated with 0.1 mL methanol and concentrated. The concentrate was dissolved in 30 mL 5% methanol/CH$_2$Cl$_2$ and washed with saturated aqueous sodium bicarbonate and brine. The organic layer was dried over Na$_2$SO$_4$ and concentrated to give the title compound. MS (APCI(+)) m/e 575.4 (M+H)$^+$.

Example 163B

The title compound was prepared as described in EXAMPLE 1H, substituting EXAMPLE 163A for EXAMPLE 1G. MS (ESI(+)) m/e 545.3 (M+H)$^+$.

Example 163C

The title compound was prepared as described in EXAMPLE 164F, substituting EXAMPLE 163B for EXAMPLE 164E. MS (ESI(+)) m/e 685.2 (M+H)$^+$; $^1$H NMR (300 MHz, dimethylsulfoxide-d$_6$) δ ppm 10.88 (s, 1 H) 9.49 (brs, 1 H) 9.31 (d, 1 H) 8.26 (dd, 1 H) 8.02 (m, 1 H) 7.72-7.81 (m, 2 H) 7.37-7.64 (m, 6 H) 7.25 (m, 2 H) 7.04 (m, 1 H) 6.53 (m, 3 H) 3.56 (t, 1 H) 3.33-3.44 (m, 3 H) 3.17-3.28 (m, 3 H) 1.83-2.00 (m, 8 H).

Example 164 tert-butyl 7-(4-{[4-(2-{3-[(2,6-difluorobenzoyl) amino]phenyl}imidazo[1,2-a]pyridin-3-yl)pyrimidin-2-yl]amino}phenyl)-2,7-diazaspiro[4.4]nonane-2-carboxylate

Example 164A

In a 25 mL round bottom flask, a solution of 1-fluoro-4-nitrobenzene (0.473 g, 3.354 mmol), tert-butyl 2,7-diazaspiro[4.4]nonane-2-carboxylate (0.8 g, 3.53 mmol), and triethylamine (0.94 mL, 6.71 mmol) in dimethylsulfoxide (9.5 mL) was heated at 90° C. for 3 hours. The reaction was poured into 150 mL water and the yellow suspension was stirred overnight and filtered. The solid collected was washed with water and dried to give the crude product which was used directly in EXAMPLE 164B. MS (ESI(+)) m/e 370.0 (M+Na)$^+$.

Example 164B

The title compound was prepared as described in EXAMPLE 45B, substituting EXAMPLE 164A for EXAMPLE 45A. MS (ESI(+)) m/e 318.0 (M+H)$^+$.

Example 164C

A 25 mL round bottom flask equipped with a stir bar was charged with EXAMPLE 4C (0.3 g, 0.853 mmol), EXAMPLE 164B (0.311 g, 0.981 mmol) and 2-propanol (8 ml). The mixture was heated at 80° C. for 9 hours. The reaction was cooled to ambient temperature and the suspension was filtered. The solid collected was washed with 5 mL isopropyl alcohol then 10 mL ether and was dried. The crude material was purified by flash chromatography on a 10 g silica gel column with a gradient of from 0% to 10% methanol in CH$_2$Cl$_2$ to provide EXAMPLE 164C. EXAMPLE 164C: MS (ESI(+)) m/e 633.2 (M+H)$^+$.

Example 164D

A 25 mL round bottom flask equipped with a stir bar was charged with EXAMPLE 4C (0.3 g, 0.853 mmol), EXAMPLE 164B (0.311 g, 0.981 mmol) and 2-propanol (8 ml). The mixture was heated at 80° C. for 9 hours. The reaction was cooled to ambient temperature and the suspension was filtered. The solid collected was washed with 5 mL isopropyl alcohol then 10 mL ether and was dried. The crude material was purified by flash chromatography on a 10 g silica gel column with a gradient of from 0% to 10% methanol in CH$_2$Cl$_2$ to provide EXAMPLE 164D. EXAMPLE 164D: MS (ESI(+)) m/e 533.1 (M+H)$^+$.

Example 164E

The title compound was prepared as described in EXAMPLE 1H, substituting EXAMPLE 164C for EXAMPLE 1G. MS (ESI(+)) m/e 603.3 (M+H)$^+$.

Example 164F

Into a 4 mL vial was charged EXAMPLE 164E (66 mg, 0.110 mmol), tetrahydrofuran (1 mL) and N-methyl-2-pyrrolidinone (0.5 mL). 2,6-Difluorobenzoyl chloride (0.014 mL, 0.113 mmol) was added and the reaction mixture was stirred at ambient temperature for 18 hours. The reaction was concentrated and the residue purified by reverse-phase HPLC on a Shimadzu LC10 HPLC system with a Phenomenex C18 column (3×15 cm) eluting with a gradient of 55% to 95% acetonitrile in 0.1% aqueous ammonium hydroxide to provide the title compound. MS (ESI(+)) m/e 743.2 (M+H)$^+$; $^1$H NMR (300 MHz, dimethylsulfoxide-d$_6$) δ ppm 10.89 (s, 1 H) 9.49 (brs, 1 H) 9.32 (s, 1 H) 8.26 (d, 1 H) 8.02 (s, 1 H) 7.73-7.82 (m, 2 H) 7.37-7.66 (m, 6 H) 7.22-7.30 (m, 2 H) 7.03 (m, 1 H) 6.52 (m, 3 H) 3.17-3.39 (m, 8 H) 1.83-1.99 (m, 4 H) 1.40 (s, 9 H).

Example 165 tert-butyl 7-(4-{[4-(2-{3-[(thien-2-ylacetyl)amino] phenyl}imidazo[1,2-a]pyridin-3-yl)pyrimidin-2-yl] amino}phenyl)-2,7-diazaspiro[4.4]nonane-2-carboxylate The title compound was prepared as described in EXAMPLE 4H, substituting EXAMPLE 164E for EXAMPLE 4G and 2-(thiophen-2-yl)acetyl chloride for 2,6-difluorobenzoyl chloride. MS (ESI(+)) m/e 727.2 (M+H)$^+$; $^1$H NMR (300 MHz, dimethylsulfoxide-d$_6$) δ ppm 10.31 (s, 1 H) 9.50 (brs, 1 H) 9.32 (s, 1 H) 8.24 (d, 1 H) 7.90 (s, 1 H) 7.72 (m, 2 H) 7.27-7.50 (m, 6 H) 6.96-7.05 (m, 3 H) 6.50 (m, 3 H) 3.87 (s, 2 H) 3.18-3.39 (m, 8 H) 1.85-1.98 (m, 4 H) 1.40 (s, 9 H).

Example 166

N-(3-{3-[2-({3-[2-(dimethylamino)ethyl] phenyl}amino)pyrimidin-4-yl]imidazo[1,2-a]pyridin-2-yl}phenyl)-5-methylthiophene-2-carboxamide The title compound was prepared as described in EXAMPLE 1I, substituting EXAMPLE 37D for EXAMPLE 1H and 5-methylthiophene-2-carbonyl chloride for 2,6-difluorobenzoyl chloride. MS (ESI(+)) m/e 574 (M+H)$^+$, $^1$H NMR (400 MHz, dimethylsulfoxide-d$_6$) δ ppm 10.20 (s, 1 H) 9.68 (s, 1 H) 9.56 (d, 1 H) 8.36 (d, 1 H) 8.07 (t, 1 H) 7.86 (m, 2 H) 7.75 (d, 1 H) 7.64 (s, 1 H) 7.58 (d, 1 H) 7.50 (m, 1 H) 7.42 (t, 1 H) 7.33 (m, 1 H) 7.20 (t, 1 H) 7.08 (t, 1 H) 6.91 (d, 1 H) 6.85 (d, 1 H) 6.65 (d, 1 H) 2.67 (m, 2 H) 2.50 (s, 3 H) 2.46 (m, 2 H) 2.16 (s, 6 H).

Example 167

N-(2,6-difluorophenyl)-N'-(3-{3-[2-({3-[2-(dimethylamino)ethyl]phenyl}amino)pyrimidin-4-yl]imidazo [1,2-a]pyridin-2-yl}phenyl)urea The title compound was prepared as described in EXAMPLE 3, substituting EXAMPLE 37D for EXAMPLE 1H and 2,6-difluorophenyl isocyanate for phenyl isocyanate. MS (ESI(+)) m/e 605 (M+H)$^+$, $^1$H NMR (400 MHz, dimethylsulfoxide-d$_6$) δ ppm 9.69 (s, 1 H) 9.58 (d, 1 H) 9.18 (s, 1 H) 8.35 (d, 1 H) 8.18 (s, 1 H) 7.76 (m, 2 H) 7.66 (s, 1 H) 7.58 (m, 2 H) 7.49 (m, 1 H) 7.32 (m, 2 H) 7.22 (m, 2 H) 7.14 (t, 2 H) 7.07 (t, 1 H) 6.87 (d, 1 H) 6.64 (d, 1 H) 2.72 (m, 2 H) 2.64 (m, 2 H) 2.30 (s, 6 H).

Example 168

N-{3-[3-(2-[4-(2,7-diazaspiro[4.4]non-2-yl)phenyl] amino}pyrimidin-4-yl)imidazo[1,2-a]pyridin-2-yl] phenyl}-2,6-difluorobenzamide To a 4 mL vial was charged EXAMPLE 165 (0.065 g, 0.088 mmol), CH$_2$Cl$_2$ (1 mL) and CF$_3$COOH (0.337 mL, 4.38 mmol). The resulting solution was stirred at ambient temperature for 2 hours and was concentrated on a rotary evaporator. The concentrate was triturated with ether (2 mL) and filtered. The crude solid was purified by reverse-phase HPLC on a Phenomenex C18 column (3×15 cm) using a gradient of from 20% to 60% acetonitrile in 0.15% CF$_3$COOH to provide the title compound. MS (ESI(+)) m/e 643.3 (M+14)$^+$; $^1$H NMR (300 MHz, dimethylsulfoxide-d$_6$) δ ppm 10.90 (s, 1 H) 9.50 (brs, 1 H) 9.38 (s, 1 H) 8.80 (m, 2 H) 8.27 (d, 1 H) 8.06 (s, 1 H) 7.76 (m, 2 H) 7.39-7.63 (m, 6 H) 7.25 (m, 2 H) 7.08 (m, 1 H) 6.50-6.56 (m, 3 H) 3.15-3.45 (m, 8 H) 1.91-2.08 (m, 4 H).

Example 169

3-[3-(2-{[4-(4-ethylpiperazin-1-yl)phenyl] amino}pyrimidin-4-yl)imidazo[1,2-a]pyridin-2-yl]-N-(2-fluorophenyl)benzamide The title compound was prepared as described in EXAMPLE 125, substituting 1-(4-(4-ethylpiperazin-1-yl) phenyl)guanidine hydrochloride for 1-(2-methyl-1,2,3,4-tetrahydroisoquinolin-7-yl)guanidine hydrochloride. MS (ESI (+)) m/e 613.2 (M+H)$^+$, (ESI(−)) m/e 611.1 (M–H)$^−$; $^1$H-NMR (300 MHz, dimethylsulfoxide-d$_6$) δ 10.22 (s, 1H) 9.50 (s, 2H) 8.35 (t, 1H) 8.30 (d, 1H) 8.06 (ddd, 1H) 7.83 (ddd, 1H) 7.77 (dt, 1H) 7.61 (t, 2H) 7.46-7.55 (m, 3H) 7.18-7.37 (m, 3H) 7.04-7.11 (m, 1H) 6.89 (d, 2H) 6.56 (d, 1H) 3.02-3.11 (m, 4H) 2.46-2.49 (m, 4H) 2.36 (q, 2H) 1.03 (t, 3H).

Example 170

3-[3-(2-{[4-(4-ethylpiperazin-1-yl)phenyl] amino}pyrimidin-4-yl)imidazo[1,2-a]pyridin-2-yl]-N-phenylbenzamide The title compound was prepared as described in EXAMPLE 125, substituting 1-(4-(4-ethylpiperazin-1-yl) phenyl)guanidine hydrochloride for 1-(2-methyl-1,2,3,4-tetrahydroisoquinolin-7-yl)guanidine hydrochloride and substituting aniline for 2-fluoroaniline. MS (ESI(+)) m/e 595.3 (M+H)$^+$, (ESI(−)) m/e 593.2 (M–H)$^−$; $^1$H-NMR (300 MHz, dimethylsulfoxide-d$_6$) δ 10.34 (s, 1H) 9.49 (s, 2H) 8.26-8.34 (m, 2H) 8.04 (ddd, 1H) 7.72-7.83 (m, 4H) 7.60 (t, 1H) 7.46-7.54 (m, 3H) 7.31-7.39 (m, 2H) 7.09 (q, 2H) 6.87 (d, 2H) 6.57 (d, 1H) 3.02-3.10 (m, 4H) 2.46 (m, 4H) 2.35 (q, 2H) 1.02 (t, 3H).

Example 171

N-benzyl-3-[3-(2-{[4-(4-ethylpiperazin-1-yl)phenyl] amino}pyrimidin-4-yl)imidazo[1,2-a]pyridin-2-yl] benzamide The title compound was prepared as described in EXAMPLE 125, substituting 1-(4-(4-ethylpiperazin-1-yl) phenyl)guanidine hydrochloride for 1-(2-methyl-1,2,3,4-tetrahydroisoquinolin-7-yl)guanidine hydrochloride and substituting benzylamine for 2-fluoroaniline. MS (ESI(+)) m/e 609.3 (M+H)⁺, (ESI(−)) m/e 607.1 (M−H)⁻; ¹H-NMR (300 MHz, dimethylsulfoxide-d₆) δ 9.47-9.55 (m, 2H) 9.14 (t, 1H) 8.28 (d, 1H) 8.25 (t, 1H) 7.94-7.99 (m, 1H) 7.72-7.81 (m, 2H) 7.46-7.59 (m, 4H) 7.20-7.37 (m, 5H) 7.07 (t, 1H) 6.89 (d, 2H) 6.51 (d, 1H) 4.48 (d, 2H) 3.04-3.11 (m, 4H) 2.48 (s, 4H) 2.37 (q, 2H) 1.03 (t, 3H).

Example 172

2,6-difluoro-N-{3-[3-(2-([3-(2-pyrrolidin-1-ylethoxy)phenyl]amino}pyrimidin-4-yl)imidazo[1,2-a]pyridin-2-yl]phenyl}benzamide

Example 172A

To a 250 mL round bottom flask was charged 3-nitrophenol (3.5 g, 25.2 mmol), 2-bromoethanol (4.09 g, 32.7 mmol), and polymer bound triphenylphosphine (Fluka, 3 mmol/g, 1.5 eq, 12.58 g, 37.7 mmol) and tetrahydrofuran (90 mL). The resulting mixture was cooled to 0° C. with stirring and was treated with diisopropyl azodicarboxylate (6.36 mL, 32.7 mmol) dropwise over 10 minutes. The reaction was allowed to stir at ambient temperature for 16 hours. The reaction was filtered. The filtrate was concentrated in vacuo. 8.5 g of the concentrate was adsorbed onto silica gel and purified by flash chromatography on an AnaLogix SF40-150 g silica gel column using an AnaLogix IntelliFlash 280 system eluting with a gradient of from 0% to 3% ethyl acetate in hexanes to provide the title compound. MS (DCI(+)) m/e 246.8 (M+H)⁺.

Example 172B

In a 20 mL round bottom flask, a solution of EXAMPLE 172A (1.3 g, 5.28 mmol) in acetonitrile (18 mL) was treated with pyrrolidine (0.752 g, 10.57 mmol) and potassium carbonate (1.825 g, 13.21 mmol). The resulting mixture was stirred at ambient temperature for 18 hours. The reaction was partitioned between saturated aqueous NaCl (75 mL) and ethyl acetate (100 mL). The aqueous layer was back-extracted with ethyl acetate (100 mL). The combined organic layers were dried over Na₂SO₄, filtered and concentrated. The concentrate was passed through a 10 g silica gel column eluting with CH₂Cl₂ followed by CHCl₃/methanol/NH₄OH (93:5:2) to provide the title compound. MS (DCI(+)) m/e 237.0 (M+¹⁴)⁺.

Example 172C

The title compound was prepared as described in EXAMPLE 4E, substituting EXAMPLE 172B for EXAMPLE 4D. MS (DCI(+)) m/e 207.1 (M+H)⁺.

Example 172D

The title compound was prepared as described in EXAMPLE 252D, substituting EXAMPLE 172C for EXAMPLE 252C. MS (ESI(+)) m/e 522.2 (M+H)⁺.

Example 172E

The title compound was prepared as described in EXAMPLE 4G, substituting EXAMPLE 172D for EXAMPLE 4F. MS (ESI(+)) m/e 492.1 (M+H)⁺.

Example 172F

The title compound was prepared as described in EXAMPLE 4H, substituting EXAMPLE 172E for EXAMPLE 4G. MS (ESI(+)) m/e 632.2 (M+H)⁺; ¹H NMR (300 MHz, dimethylsulfoxide-d₆) δ ppm 10.91 (s, 1 H) 9.84 (s, 1 H) 9.63 (m, brs, 1 H) 9.54 (d, 1 H) 8.40 (d, 1 H) 8.10 (m, 1 H) 7.76 (m, 2 H) 7.38-7.67 (m, 5 H) 7.20-7.36 (m, 4 H) 7.12 (m, 1 H) 6.71 (d, 1 H) 6.64 (dd, 1 H) 4.24 (m, 2 H) 3.29-3.70 (m, 4 H) 3.11 (m, 2 H) 1.83-2.08 (m, 4 H).

Example 173

2,6-difluoro-N-{3-[3-(2-{[3-(tetrahydrofuran-2-yl-methoxy)phenyl]amino}pyrimidin-4-yl)imidazo[1,2-a]pyridin-2-yl]phenyl}benzamide

Example 173A

The title compound was prepared as described in EXAMPLE 172A, substituting (tetrahydrofuran-2-yl)methanol for 2-bromoethanol.

Example 173B

The title compound was prepared as described in EXAMPLE 4E, substituting EXAMPLE 173A for EXAMPLE 4D. MS (DCI(+)) m/e 194.0 (M+H)⁺.

Example 173C

The title compound was prepared as described in EXAMPLE 252D, substituting EXAMPLE 173B for EXAMPLE 252C. MS (ESI(+)) m/e 509.1 (M+H)⁺.

Example 173D

The title compound was prepared as described in EXAMPLE 4G, substituting EXAMPLE 173C for EXAMPLE 4F. MS (ESI(+)) m/e 479.1 (M+H)⁺.

Example 173E

To a 4 mL vial was charged EXAMPLE 173D (35 mg, 0.073 mmol) and tetrahydrofuran (2 mL). The resulting solution was treated with 2,6-difluorobenzoyl chloride (0.014 g, 0.077 mmol) and the reaction mixture was stirred at ambient temperature for 18 hours. The reaction was treated with 5 mL ether. The suspension was allowed to stir for 10 minutes and was filtered. The collected solid was washed with ether (1 mL) and dried to provide the title compound. MS (ESI(+)) m/e 619.4 (M+H)⁺; ¹H NMR (300 MHz, dimethylsulfoxide-d₆) δ ppm 10.95 (s, 1 H) 9.81 (s, 1 H) 9.57 (d, 1 H) 8.43 (d, 1 H) 8.08 (m, 1 H) 7.83 (m, 2 H) 7.40-7.70 (m, 5 H) 7.15-7.30 (m, 5 H) 6.69 (d, 1 H) 6.57 (m, 1 H) 4.11 (m, 1 H) 3.60-3.92 (m, 4 H) 1.72-2.06 (m, 3 H) 1.51-1.66 (m, 1 H).

Example 174

2-chloro-N-{3-[3-(2-{[3-(tetrahydrofuran-2-yl-methoxy)phenyl]amino}pyrimidin-4-yl)imidazo[1,2-a]pyridin-2-yl]phenyl}benzamide The title compound was prepared as described in EXAMPLE 173E, substituting 2-chlorobenzoyl chloride for 2,6-difluorobenzoyl chloride. MS (ESI(+)) m/e 617.3 (M+H)⁺; ¹H NMR (300 MHz, dimethylsulfoxide-d₆) δ ppm 10.65 (s, 1 H) 9.81 (s, 1 H) 9.57 (d, 1 H) 8.43 (d, 1 H) 8.10 (m, 1 H) 7.84 (m, 2 H) 7.39-7.68 (m, 8 H) 7.15-7.30 (m, 3 H) 6.69

Example 175

N-{3-[3-(2-{[3-(tetrahydrofuran-2-ylmethoxy)phenyl]amino}pyrimidin-4-yl)imidazo[1,2-a]pyridin-2-yl]phenyl}thiophene-2-carboxamide The title compound was prepared as described in EXAMPLE 173E, substituting thiophene-2-carbonyl chloride for 2,6-difluorobenzoyl chloride. MS (ESI(+)) m/e 589.3 (M+H)$^+$; $^1$H NMR (300 MHz, dimethylsulfoxide-d$_6$) δ ppm 10.37 (s, 1 H) 9.81 (s, 1 H) 9.60 (d, 1 H) 8.42 (d, 1 H) 8.12 (m, 1 H) 8.04 (dd, 1 H) 7.82-7.93 (m, 3 H) 7.65 (m, 1 H) 7.48 (m, 2 H) 7.37 (m, 1 H) 7.29 (m, 1 H) 7.20 (m, 3 H) 6.69 (d, 1 H) 6.58 (m, 1.70 Hz, 1 H) 4.126 (m, 1 H) 3.60-3.92 (m, 4 H) 1.74-2.02 (m, 3 H) 1.54-1.66 (m, 1 H).

Example 176

N-{3-[3-(2-{[3-(tetrahydrofuran-2-ylmethoxy)phenyl]amino}pyrimidin-4-yl)imidazo[1,2-a]pyridin-2-yl]phenyl}-2-thien-2-ylacetamide The title compound was prepared as described in EXAMPLE 173E, substituting 2-(thiophen-2-yl)acetyl chloride for 2,6-difluorobenzoyl chloride. MS (ESI(+)) m/e 603.2 (M+H)$^+$; $^1$H NMR (300 MHz, dimethylsulfoxide-d$_6$) δ ppm 10.35 (s, 1 H) 9.79 (s, 1 H) 9.57 (d, 1 H) 8.40 (d, 1 H) 7.96 (m, 1 H) 7.82 (m, 1 H) 7.73 (m, 1 H) 7.64 (m, 1 H) 7.51 (m, 1 H) 7.26-7.47 (m, 4 H) 7.19 (m, 2 H) 6.97 (m, 2 H) 6.65 (d, 1 H) 6.58 (m, 1 H) 4.11 (m, 1 H) 3.88 (m, 4 H) 3.75 (m, 1 H) 3.67 (m, 1 H) 1.75-2.00 (m, 3 H) 1.54-1.66 (m, 1 H).

Example 177

N-{3-[3-(2-{[3-(tetrahydrofuran-2-ylmethoxy)phenyl]amino) pyrimidin-4-yl)imidazo[1,2-a]pyridin-2-yl]phenyl}-N'-thien-2-ylurea To a 4 mL vial was charged EXAMPLE 173D (25 mg, 0.052 mmol) and tetrahydrofuran (2 mL). The resulting solution was treated with 2-isocyanatothiophene (6.86 mg, 0.055 mmol) and stirred at ambient temperature for 18 hours. The reaction was treated with ether (3 mL), stirred 5 min. and filtered. The solid collected was dried in vacuo to give the title compound. MS (ESI(+)) m/e 604.2 (M+H)$^+$; $^1$H NMR (300 MHz, dimethylsulfoxide-d$_6$) δ ppm 9.75 (s, 1 H) 9.63 (s, 1 H) 9.55 (d, 1 H) 8.89 (s, 1 H) 8.38 (d, 1 H) 7.77 (m, 2 H) 7.52 (m, 3 H) 7.37 (t, 1 H) 7.15-7.31 (m, 3 H) 7.09 (m, 1 H) 6.87 (m, 1 H) 6.81 (m, 1 H) 6.66 (d, 1 H) 6.57 (m, 2 H) 4.12 (m, 1 H) 3.61-3.90 (m, 4 H) 1.75-2.02 (m, 3 H) 1.53-1.66 (m, 1 H).

Example 178

2,6-difluoro-N-{3-[3-(2-{[3-(tetrahydrofuran-3-yloxy)phenyl]amino}pyrimidin-4-yl)imidazo[1,2-a]pyridin-2-yl]phenyl}benzamide

Example 178A

The title compound was prepared as described in EXAMPLE 172A, substituting tetrahydrofuran-3-ol for 2-bromoethanol. MS (DCI(+)) m/e 227.0 (M+NH$_4$)$^+$.

Example 178B

The title compound was prepared as described in EXAMPLE 4E, substituting EXAMPLE 178A for EXAMPLE 4D. MS (DCI(+)) m/e 180.0 (M+H)$^+$.

Example 178C

The title compound was prepared as described in EXAMPLE 252D, substituting EXAMPLE 178B for EXAMPLE 252C. MS (ESI(+)) m/e 495.1 (M+H)$^+$.

Example 178D

The title compound was prepared as described in EXAMPLE 4G, substituting EXAMPLE 178C for EXAMPLE 4F. MS (ESI(+)) m/e 465.0 (M+H)$^+$.

Example 178E

The title compound was prepared as described in EXAMPLE 173E, substituting EXAMPLE 178D for EXAMPLE 173D. MS (ESI(+)) m/e 605.2 (M+H)$^+$; $^1$H NMR (300 MHz, dimethylsulfoxide-d$_6$) δ ppm 10.96 (s, 1 H) 9.84 (s, 1 H) 9.55 (d, 1 H) 8.44 (d, 1 H) 8.09 (m, 1 H) 7.82 (m, 2 H) 7.41-7.70 (m, 5 H) 7.17-7.32 (m, 5 H) 6.71 (d, 1 H) 6.54 (dd, 1 H) 4.93 (m, 1 H) 3.67-3.88 (m, 4 H) 2.16 (m, 1 H) 1.92 (m, 1 H).

Example 179

2-chloro-N-{3-[3-(2-{[3-(tetrahydrofuran-3-yloxy)phenyl]amino}pyrimidin-4-yl)imidazo[1,2-a]pyridin-2-yl]phenyl}benzamide The title compound was prepared as described in EXAMPLE 173E, substituting EXAMPLE 178D for EXAMPLE 173D and 2-chlorobenzoyl chloride for 2,6-difluorobenzoyl chloride. MS (ESI(+)) m/e 603.2 (M+H)$^+$; $^1$H NMR (300 MHz, dimethylsulfoxide-d$_6$) δ ppm 10.63 (s, 1 H) 9.81 (s, 1 H) 9.54 (d, 1 H) 8.43 (d, 1 H) 8.11 (m, 1 H) 7.83 (m, 2 H) 7.38-7.66 (m, 8 H) 7.29 (m, 1 H) 7.19 (m, 2 H) 6.70 (d, 1 H) 6.54 (dd, 1 H) 4.93 (m, 1 H) 3.66-3.86 (m, 4 H) 2.16 (m, 1 H) 1.93 (m, 1 H).

Example 180

N-{3-[3-(2-{[3-(tetrahydrofuran-3-yloxy)phenyl]amino}pyrimidin-4-yl)imidazo[1,2-a]pyridin-2-yl]phenyl}-2-thien-2-ylacetamide The title compound was prepared as described in EXAMPLE 173E, substituting EXAMPLE 178D for EXAMPLE 173D and 2-(thiophen-2-yl)acetyl chloride for 2,6-difluorobenzoyl chloride. MS (ESI(+)) m/e 589.2 (M+H)$^+$; $^1$H NMR (300 MHz, dimethylsulfoxide-d$_6$) δ ppm 10.38 (s, 1 H) 9.83 (s, 1 H) 9.55 (d, 1 H) 8.42 (d, 1 H) 7.96 (m, 1 H) 7.83 (m, 1 H) 7.73 (m, 1 H) 7.65 (m, 1 H) 7.27-7.50 (m, 5 H) 7.19 (m, 2 H) 6.97 (m, 2 H) 6.66 (d, 1 H) 6.55 (dd, 1 H) 4.93 (m, 1 H) 3.67-3.90 (m, 6 H) 2.15 (m, 1 H) 1.93 (m, 1 H).

Example 181

N-[3-(3-{2-[(2-methyl-1,2,3,4-tetrahydroisoquinolin-7-yl)amino]pyrimidin-4-yl}imidazo[1,2-a]pyridin-2-yl)phenyl]-1,3-thiazole-2-carboxamide To a 4 mL vial was charged EXAMPLE 4G (40 mg, 0.089 mmol), thiazole-2-carboxylic acid (12 mg, 0.096 mmol), 1-hydroxybenzotriazole hydrate (0.014 g, 0.094 mmol) and N,N-dimethylformamide (1.1 mL). The resulting solution was treated with polystyrene-carbodiimide (Argonaut, 1.25 mmol/g, 215 mg, 0.268 mmol) and the reaction was stirred at ambient temperature for 16 hours. The reaction was filtered and the filtrate was concentrated and purified by reverse-phase HPLC on a Phenomenex C18 column (3×15 cm) using a gradient of from 30% to 70% acetonitrile in 0.1% aqueous ammonium hydroxide to provide the title compound. MS (ESI(+)) m/e 559.1 (M+H)$^+$; $^1$H NMR (300 MHz, dimethylsulfoxide-d$_6$) δ ppm 10.90 (s, 1 H) 9.63 (s, 1 H) 9.55 (d, 1 H) 8.34 (d, 1 H) 8.24 (m, 1 H) 8.08-8.14 (m, 2 H) 7.96 (m, 1 H) 7.77 (d, 1 H) 7.38-7.53 (m, 5 H) 7.01-7.10 (m, 2 H) 6.62 (d, 1 H) 3.41 (s, 2 H) 2.77 (m, 2 H) 2.58 (m, 2 H) 2.32 (s, 3 H).

Example 182

N-[3-(3-{2-[(2-methyl-1,2,3,4-tetrahydroisoquinolin-7-yl)amino]pyrimidin-4-yl)imidazo[1,2-a]pyridin-2-yl)phenyl]-1,3-thiazole-5-carboxamide The title compound was prepared as described in EXAMPLE 181, substituting thiazole-5-carboxylic acid for thiazole-2-carboxylic acid. MS (ESI(+)) m/e 559.1 (M+H)$^+$; $^1$H NMR (300 MHz, dimethylsulfoxide-d$_6$) δ ppm $^1$H NMR (300 MHz, dimethylsulfoxide-d$_6$) δ ppm 10.55 (s, 1 H) 9.63 (s, 1 H) 9.52 (d, 1 H) 9.31 (s, 1 H) 8.71 (s, 1 H) 8.35 (d, 1 H) 8.08 (m, 1 H) 7.87 (m, 1 H) 7.76 (d, 1 H) 7.35-7.54 (m, 5 H) 7.01-7.10 (m, 2 H) 6.65 (d, 1 H) 3.40 (s, 2 H) 2.76 (m, 2 H) 2.57 (m, 2 H) 2.31 (s, 3 H).

Example 183

4-bromo-N-[3-(3-{2-[(2-methyl-1,2,3,4-tetrahydroisoquinolin-7-yl)amino]pyrimidin-4-yl}imidazo[1,2-a]pyridin-2-yl)phenyl]thiophene-2-carboxamide The title compound was prepared as described in EXAMPLE 181, substituting 4-bromothiophene-2-carboxylic acid for thiazole-2-carboxylic acid. MS (ESI(+)) m/e 638.1 (M+H)$^+$; $^1$H NMR (300 MHz, dimethylsulfoxide-d$_6$) δ ppm 10.40 (s, 1 H) 9.64 (s, 1 H) 9.52 (d, 1 H) 8.35 (d, 1 H) 8.10 (m, 2 H) 8.01 (d, 1 H) 7.89 (m, 1 H) 7.76 (m, 1 H) 7.36-7.54 (m, 5 H) 7.01-7.10 (m, 2 H) 6.65 (d, 1 H) 3.40 (s, 2 H) 2.76 (m, 2 H) 2.57 (m, 2 H) 2.31 (s, 3 H).

Example 184

4-bromo-N-[3-(3-(2-[(2-methyl-1,2,3,4-tetrahydroisoquinolin-7-yl)amino]pyrimidin-4-yl}imidazo[1,2-a]pyridin-2-yl)phenyl]thiophene-3-carboxamide The title compound was prepared as described in EXAMPLE 164F, substituting EXAMPLE 4G for EXAMPLE 164E and 4-bromothiophene-3-carbonyl chloride for 2,6-difluorobenzoyl chloride. MS (ESI(+)) m/e 636.1 (M+H)$^+$; $^1$H NMR (300 MHz, dimethylsulfoxide-d$_6$) δ ppm 10.45 (s, 1 H) 9.63 (s, 1 H) 9.53 (d, 1 H) 8.34 (d, 1 H) 8.14 (d, 1 H) 8.07 (m, 1 H) 7.75-7.85 (m, 3 H) 7.34-7.52 (m, 5 H) 7.00-7.10 (m, 2 H) 6.63 (d, 1 H) 3.41 (s, 2 H) 2.76 (m, 2 H) 2.58 (m, 2 H) 2.32 (s, 3 H).

Example 185

N-{3-[3-(2-{[3-(tetrahydrofuran-3-yloxy)phenyl]amino}pyrimidin-4-yl)imidazo[1,2-a]pyridin-2-yl]phenyl}-N'-thien-2-ylurea The title compound was prepared as described in EXAMPLE 177, substituting EXAMPLE 178D for EXAMPLE 173D. MS (ESI(+)) m/e 590.2 (M+H)$^+$; $^1$H NMR (300 MHz, dimethylsulfoxide-d$_6$) δ ppm 9.77 (s, 1 H) 9.63 (s, 1 H) 9.53 (d, 1 H) 8.88 (s, 1 H) 8.39 (d, 1 H) 7.77 (m, 2 H) 7.51 (m, 3 H) 7.16-7.40 (m, 4 H) 7.08 (m, 1 H) 6.85 (m, 1 H) 6.80 (m, 1 H) 6.67 (d, 1 H) 6.54 (m, 2 H) 4.93 (m, 1 H) 3.67-3.88 (m, 4 H) 2.15 (m, 1 H) 1.93 (m, 1 H).

Example 186

N-(3-{3-[2-({3-[(dimethylamino)sulfonyl]-4-methoxyphenyl}amino)pyrimidin-4-yl]imidazo[1,2-a]pyridin-2-yl}phenyl)-2,6-difluorobenzamide Example 186A The title compound was prepared as described in EXAMPLE 252D, substituting 5-amino-2-methoxy-N,N-dimethylbenzenesulfonamide for EXAMPLE 252C. MS (ESI(+)) m/e 546.2 (M+H)$^+$.

Example 186B

The title compound was prepared as described in EXAMPLE 4G, substituting EXAMPLE 186A for EXAMPLE 4F. MS (ESI(+)) m/e 516.1 (M+H)$^+$.

Example 186C

The title compound was prepared as described in EXAMPLE 164F, substituting EXAMPLE 186B for EXAMPLE 164E. MS (ESI(+)) m/e 656.2 (M+H)$^+$; $^1$H NMR (300 MHz, dimethylsulfoxide-d$_6$) δ ppm 10.88 (s, 1 H) 9.82 (s, 1 H) 9.50 (m, 1 H) 8.35 (d, 1 H) 8.11 (d, 1 H) 7.80 (m, 2 H) 7.77 (m, 2 H) 7.36-7.65 (m, 4 H) 7.23 (m, 3 H) 7.09 (m, 1 H) 6.67 (d, 1 H) 3.86 (s, 3 H) 2.73 (s, 6 H).

Example 187

N-(3-{3-[2-({3-[(dimethylamino)sulfonyl]-4-methoxyphenyl]amino}pyrimidin-4-yl]imidazo[1,2-a]pyridin-2-yl}phenyl)-2-thien-2-ylacetamide The title compound was prepared as described in EXAMPLE 164F, substituting EXAMPLE 186B for EXAMPLE 164E and 2-(thiophen-2-yl)acetyl chloride for 2,6-difluorobenzoyl chloride. MS (APCI(+)) m/e 640.2 (M+H)$^+$; $^1$H NMR (300 MHz, dimethylsulfoxide-d$_6$) δ ppm 10.31 (s, 1 H) 9.83 (s, 1 H) 9.51 (m, 1 H) 8.33 (d, 1 H) 8.12 (d, 1 H) 8.00 (dd, 1 H) 7.92 (m, 1 H) 7.73 (m, 2 H) 7.50 (m, 1 H) 7.39 (m, 2 H) 7.30 (m, 1 H) 7.22 (d, 1 H) 7.09 (m, 1 H) 6.97 (m, 2 H) 6.62 (d, 1 H) 3.86 (m, 5 H) 2.73 (s, 6 H).

Example 188

N-(3-{3-[2-({4-[4-(dimethylamino)piperidin-1-yl]phenyl}amino)pyrimidin-4-yl]imidazo[1,2-a]pyridin-2-yl}phenyl)-2-thien-2-ylacetamide Example 188A A 100 ml flask charged with 1-fluoro-4-nitrobenzene (2.122 ml, 20 mmol), dimethylsulfoxide (30 ml), N,N-dimethylpiperidin-4-amine (2.82 g, 22.00 mmol) and triethylamine (5.58 ml, 40.0 mmol). The resulting solution was heated at 100° C. for 24 hours. After cooling to ca. 40° C. the reaction mixture was poured in stirring cold water (1000 ml)

and the resulting solid was collected by filtration, washed well with water and dried. MS (ESI(+)) m/e 250 (M+H)⁺, (ESI(−)) m/e 248 (M−H)⁻.

Example 188B

The title compound was prepared as described in EXAMPLE 4G substituting EXAMPLE 188A for EXAMPLE 4F. MS (DCI) m/e 220 (M+H)⁺.

Example 188C

The title compound was prepared as described in EXAMPLE 103C substituting EXAMPLE 188B for EXAMPLE 103B. MS (ESI(+)) m/e 535 (M+H)⁺, (ESI(−)) m/e 533 (M−H)⁻.

Example 188D

The title compound was prepared as described in EXAMPLE 4G substituting EXAMPLE 188C for EXAMPLE 4F. MS (ESI(+)) m/e 505 (M+H)⁺, (ESI(−)) m/e 503 (M−H)⁻.

Example 188E

N-(3-{3-[2-({4-[4-(dimethylamino)piperidin-1-yl]phenyl}amino)pyrimidin-4-yl]imidazo[1,2-a]pyridin-2-yl}phenyl)-2-thien-2-ylacetamide The title compound was prepared as described in EXAMPLE 98D substituting EXAMPLE 188D for EXAMPLE 98C. MS (ESI(+)) m/e 629 (M+H)⁺; ¹H-NMR (300 MHz, dimethylsulfoxide-d₆) δ 10.35 (s, 1H), 9.58 (s, 1H), 9.53 (m, 1H), 8.31 (d, 1H), 7.95 (m, 1H), 7.78 (d, 1H), 7.71 (d, 1H), 7.59-7.55 (m, 3H), 7.44-7.38 (m, 2H), 7.32 (m, 1H), 7.13 (t, 1H), 6.99-6.92 (m, 4H), 6.59 (d, 1H), 3.88 (s, 2H), 3.78 (m, 2H), 3.30 (m, 1H), 2.79 (d, 6H), 2.70 (m, 2H), 2.07 (m, 2H), 1.77-1.67 (m, 2H).

Example 189

N-(3-{3-[2-({4-[4-(dimethylamino)piperidin-1-yl]phenyl}amino)pyrimidin-4-yl]imidazo[1,2-a]pyridin-2-yl}phenyl)-2,6-difluorobenzamide The title compound was prepared as described in EXAMPLE 98D substituting EXAMPLE 188D for EXAMPLE 98C and 2,6-difluorobenzoyl chloride for 2-(thiophen-2-yl)acetyl chloride. MS (ESI(+)) m/e 645 (M+H)⁺, (ESI(−)) m/e 643 (M−H)⁻; ¹H-NMR (300 MHz, dimethylsulfoxide-d₆) δ 10.92 (s, 1H), 9.58 (s, 1H), 9.53 (m, 1H), 8.33 (d, 1H), 8.08 (s, 1H), 7.79 (m, 2H), 7.65-7.55 (m, 4H), 7.47 (t, 1H), 7.39 (d, 1H), 7.29-7.21 (m, 2H), 7.13 (m, 1H), 6.96 (d, 2H), 6.62 (d, 1H), 3.76 (m, 2H), 3.28 (m, 1H), 2.79 (d, 6H), 2.68 (m, 2H), 2.07 (m, 2H), 1.72 (m, 2H).

Example 190

N-(3-{3-[2-({4-[4-(dimethylamino)piperidin-1-yl]phenyl}amino)pyrimidin-4-yl]imidazo[1,2-a]pyridin-2-yl}phenyl)-2-phenylacetamide The title compound was prepared as described in EXAMPLE 98D substituting EXAMPLE 188D for EXAMPLE 98C and 2-phenylacetyl chloride for 2-(thiophen-2-yl)acetyl chloride. MS (ESI(+)) m/e 623 (M+H)⁺, (ESI(−)) m/e 621 (M−H)⁻; ¹H-NMR (300 MHz, dimethylsulfoxide-d₆) δ 10.31 (s, 1H), 9.59 (s, 1H), 9.52 (m, 1H), 8.31 (d, 1H), 7.96 (s, 1H), 7.80 (m, 2H), 7.61-7.55 (m, 3H), 7.40 (t, 1H), 7.34-7.23 (m, 6H), 7.14 (t, 1H), 6.97 (d, 2H), 6.57 (d, 1H), 3.76 (m, 2H), 3.64 (s, 2H), 3.28 (m, 1H), 2.79 (d, 6H), 2.69 (m, 2H), 2.07 (m, 2H), 1.72 (m, 2H).

Example 191

2-chloro-N-(3-{3-[2-({4-[4-(dimethylamino)piperidin-1-yl]phenyl}amino)pyrimidin-4-yl]imidazo[1,2-a]pyridin-2-yl}phenyl)benzamide The title compound was prepared as described in EXAMPLE 98D substituting EXAMPLE 188D for EXAMPLE 98C and 2-chlorobenzoyl chloride for 2-(thiophen-2-yl)acetyl chloride. MS (ESI(+)) m/e 643 (M+H)⁺, (ESI(−)) m/e 641 (M−H)⁻; ¹H-NMR (300 MHz, dimethylsulfoxide-d₆) δ 10.93 (s, 1H), 9.58 (s, 1H), 9.53 (m, 1H), 8.33 (d, 1H), 8.11 (m, 1H), 7.81 (m, 2H), 7.61-7.43 (m, 8H), 7.37 (m, 1H), 7.15 (t, 1H), 6.96 (d, 2H), 6.62 (d, 1H), 3.76 (m, 2H), 3.28 (m, 1H), 2.79 (d, 6H), 2.70 (m, 2H), 2.07 (m, 2H), 1.72 (m, 2H).

Example 192

N-(3-{3-[2-({4-[4-(dimethylamino)piperidin-1-yl]phenyl}amino)pyrimidin-4-yl]imidazo[1,2-a]pyridin-2-yl}phenyl)thiophene-2-carboxamide The title compound was prepared as described in EXAMPLE 98D substituting EXAMPLE 188D for EXAMPLE 98C and thiophene-2-carbonyl chloride for 2-(thiophen-2-yl)acetyl chloride. MS (ESI(+)) m/e 615 (M+H)⁺; ¹H-NMR (300 MHz, dimethylsulfoxide-d₆) δ 10.37 (s, 1H), 9.59 (s, 1H), 9.52 (m, 1H), 8.34 (d, 1H), 8.12 (m, 1H), 8.05 (dd, 1H), 7.91-7.86 (m, 2H), 7.80 (d, 1H), 7.62-7.53 (m, 3H), 7.46 (t, 1H), 7.33 (dd, 1H), 7.22 (m, 1H), 7.15 (m, 1H), 6.95 (d, 2H), 6.64 (d, 1H), 3.76 (m, 2H), 3.28 (m, 1H), 2.79 (d, 6H), 2.68 (m, 2H), 2.05 (m, 2H), 1.71 (m, 2H).

Example 193

N-(3-{3-[2-({4-[4-(dimethylamino)piperidin-1-yl]phenyl}amino)pyrimidin-4-yl]imidazo[1,2-a]pyridin-2-yl}phenyl)-4-methylthiophene-2-carboxamide The title compound was prepared as described in EXAMPLE 98D substituting EXAMPLE 188D for EXAMPLE 98C and 4-methylthiophene-2-carbonyl chloride for 2-(thiophen-2-yl)acetyl chloride. MS (ESI(+)) m/e 629 (M+H)⁺, (ESI(−)) m/e 627 (M−H)⁻; ¹H-NMR (300 MHz, dimethylsulfoxide-d₆) δ 10.29 (s, 1H), 9.58 (s, 1H), 9.53 (m, 1H), 8.34 (d, 1H), 8.12 (m, 1H), 7.88 (m, 2H), 7.80 (d, 1H), 7.62-7.53 (m, 3H), 7.48-7.42 (m, 2H), 7.32 (m, 1H), 7.15 (t, 1H), 6.96 (d, 2H), 6.64 (d, 1H), 3.76 (m, 2H), 3.28 (m, 1H), 2.79 (d, 6H), 2.68 (m, 2H), 2.27 (s, 3H), 2.05 (m, 2H), 1.69 (m, 2H).

Example 194

1-methyl-N-[3-(3-{2-[(2-methyl-1,2,3,4-tetrahydroisoquinolin-7-yl-amino]pyrimidin-4-yl}imidazo[1,2-a]pyridin-2-yl)phenyl]-1H-pyrazole-3-carboxamide To a 4 mL vial was charged EXAMPLE 4G (40 mg, 0.089 mmol) and tetrahydrofuran (2.2 mL). The resulting solution was treated with 1-methyl-1H-pyrazole-3-carbonyl chloride (14.2 mg, 0.098 mmol) and the reactions was stirred at ambient temperature for 16 hours. The reaction was treated with 0.1 mL methanol and concentrated. The concentrate was triturated with 2 mL ether and filtered to give the desired product as a hydrochloride salt. MS (ESI(+)) m/e 556.2 (M+H)+; $^1$H NMR (300 MHz, METHANOL-$d_4$) δ ppm 9.67 (d, 1 H) 8.29 (d, 1 H) 8.11 (m, 1 H) 7.38-7.83 (m, 8 H) 7.22 (d, 1 H) 7.14 (m, 1 H) 6.80 (d, 1 H) 6.72 (d, 1 H) 4.21-4.54 (m, 2 H) 3.99 (s, 3 H) 3.40-3.83 (m, 2 H) 3.12-3.25 (m, 2 H) 3.04 (s, 3 H).

Example 195

2-chloro-N-(3-{3-[2-({4-[2-(dimethylamino)ethyl]phenyl}amino)pyrimidin-4-yl]imidazo[1,2-a]pyridin-2-yl}phenyl)-3-fluorobenzamide Example 195A Into a 250 mL round-bottomed flask was charged dimethylamine (19.56 ml, 39.1 mmol), 4-nitrophenethyl bromide (3.000 g, 13.04 mmol), and acetonitrile (13.04 ml). Triethylamine (5.45 ml, 39.1 mmol) was added. The reaction was stirred at room temperature 48 hours. The reaction was poured onto saturated aqueous sodium bicarbonate and extracted with ethyl acetate. The organic layer was washed with brine, dried over MgSO$_4$, filtered and concentrated. The reaction was purified by flash chromatography using an Argonaut Flashmaster Solo, 25 g column (100% CH$_2$Cl$_2$ for 5 minutes, then to 10% methanol:CH$_2$Cl$_2$ over 20 minutes, then hold 5 minutes.) to provide the title compound. MS (DCI(+)) m/e 195 (M+H)+.

Example 195B

Into a 100 mL stainless steel pressure bottle was charged 5% Pd—C, wet (0.412 g, 3.87 mmol). N,N-dimethyl-2-(4-nitrophenyl)ethanamine (2.0600 g, 10.61 mmol) in ethanol (40 ml) was added, and the reaction shaken under 30 psi of H$_2$ at room temperature for 2 hours. The mixture was filtered through a nylon membrane and concentrated to provide the title compound. MS (DCI(+)) m/e 165 (M+H)+.

Example 195C

The title compound was prepared as described in EXAMPLE 4F, substituting EXAMPLE 123B for EXAMPLE 4E. MS (ESI(+)) m/e 480 (M+H)+.

Example 195D

The title compound was prepared as described in EXAMPLE 4G, substituting EXAMPLE 195C for EXAMPLE 4F. MS (ESI(+)) m/e 450 (M+H)+.

Example 195E

Into a 4 mL vial was charged EXAMPLE 195D (0.050 g, 0.111 mmol) in tetrahydrofuran (1.0 ml) to give an orange solution. 2-chloro-3-fluorobenzoic acid (0.023 g, 0.133 mmol), 1-hydroxybenzotriazole hydrate (0.017 g, 0.111 mmol) and PS-carbodiimide (0.235 g, 0.334 mmol) were added. The reaction was stirred at room temperature. overnight. The reaction was filtered and rinsed with ethyl acetate. The filtrated was washed with brine, dried over MgSO$_4$, and concentrated onto silica gel. The crude material was purified by flash chromatography using an Argonaut Flashmaster Solo, 10 g column (CH$_2$Cl$_2$ for 5 minutes, then 100% CH$_2$Cl$_2$ to 90% CH$_2$Cl$_2$: 9% methanol:1% NH$_4$OH over 25 minutes, then hold 5 minutes) to provide the title compound. MS (ESI(+)) m/e 606 (M+H)+; $^1$H NMR (300 MHz, dimethylsulfoxide-$d_6$) δ ppm 10.68 (s, 1H), 9.65 (s, 1H), 9.52 (d, 1H), 8.35 (d, 1H), 8.05 (m, 1H), 7.81 (d, 1H), 7.76 (m, 2H), 7.62 (m, 2H), 7.52 (m, 2H), 7.42 (m, 3H), 7.19 (m, 1H), 7.13 (m, 2H), 7.07 (m, 1H), 6.64 (d, 1H), 2.66 (m, 2H), 2.43 (m, 2H), 2.18 (s, 6H).

Example 196

N-(3-{3-[2-({4-[2-(dimethylamino)ethyl]phenyl}amino)pyrimidin-4-yl]imidazo[1,2-a]pyridin-2-yl}phenyl)-2-fluorobenzamide The title compound was prepared as described in EXAMPLE 4H, substituting EXAMPLE 195D for EXAMPLE 4G, and 2-fluorobenzoyl chloride for 2,6-difluorobenzoyl chloride. MS (ESI(+)) m/e 572 (M+H)+; $^1$H NMR (300 MHz, dimethylsulfoxide-$d_6$) δ ppm 10.52 (s, 1H), 9.76 (s, 1H), 9.53 (d, 1H), 8.37 (d, 1H), 8.10 (m, 1H), 7.82 (m, 1H), 7.77 (m, 1H), 7.72 (m, 2H), 7.61-7.69 (m, 2H), 7.59 (m, 1H), 7.51 (m, 1H), 7.44 (t, 1H), 7.36 (m, 2H), 7.33 (m, 1H), 7.28 (m, 1H), 7.20 (m, 2H), 7.09 (td, 1H), 6.67 (d, 1H), 2.94 (m, 2H), 2.82 (s, 6H).

Example 197

2-chloro-N-(3-{3-[2-({4-[2-(dimethylamino)ethyl]phenyl}amino)pyrimidin-4-yl]imidazo[1,2-a]pyridin-2-yl}phenyl)benzamide The title compound was prepared as described in EXAMPLE 4H, substituting EXAMPLE 195D for EXAMPLE 4G, and 2-chlorobenzoyl chloride for 2,6-difluorobenzoyl chloride. MS (ESI(+)) m/e 588 (M+H)+; $^1$H NMR (300 MHz, dimethylsulfoxide-$d_6$) δ ppm 10.60 (s, 1H), 9.76 (s, 1H), 9.52 (d, 1H), 8.37 (d, 1H), 8.10 (m, 1H), 7.77 (m, 2H), 7.72 (m, 2H), 7.68 (m, 1H), 7.58 (m, 1H), 7.54 (m, 1H), 7.49 (m, 2H), 7.44 (m, 1H), 7.39 (m, 1H), 7.20 (m, 2H), 7.08 (td, 1H), 6.68 (d, 1H), 2.93 (m, 2H), 2.81 (s, 6H).

Example 198

N-(3-{3-[2-({4-[2-(dimethylamino)ethyl]phenyl}amino)pyrimidin-4-yl]imidazo[1,2-a]pyridin-2-yl}phenyl)-2,3-difluorobenzamide The title compound was prepared as described in EXAMPLE 4H, substituting EXAMPLE 195D for EXAMPLE 4G, and 2,3-difluorobenzoyl chloride for 2,6-difluorobenzoyl chloride. MS (ESI(+)) m/e 590 (M+H)+; $^1$H NMR (300 MHz, dimethylsulfoxide-$d_6$) δ ppm 10.65 (s, 1H), 9.77 (s, 1H), 9.52 (d, 1H), 8.37 (d, 1H), 8.08 (m, 1H), 7.79 (m, 2H), 7.72 (m, 2H), 7.68 (m, 1H), 7.62 (m, 1H), 7.50 (m, 2H), 7.45 (m, 1H), 7.36 (m, 1H), 7.28 (m, 1H), 7.20 (m, 2H), 7.09 (td, 1H), 6.68 (d, 1H), 2.94 (m, 2H), 2.83 (s, 6H).

Example 199

N-(3-{3-[2-({4-[2-(dimethylamino)ethyl]phenyl}amino)pyrimidin-4-yl]imidazo[1,2-a]pyridin-2-yl}phenyl)-2,5-difluorobenzamide The title compound was prepared as described in EXAMPLE 4H, substituting EXAMPLE 195D for EXAMPLE 4G, and 2,5-difluorobenzoyl chloride for 2,6-difluorobenzoyl chloride. MS (ESI(+)) m/e 590 (M+H)+; $^1$H NMR (300 MHz, dimethylsulfoxide-$d_6$) δ ppm 10.61 (s, 1H), 9.77 (s, 1H), 9.53 (d, 1H), 8.37 (d, 1H), 8.09 (m, 1H), 7.79 (m, 2H), 7.73 (m, 2H), 7.68 (m, 1H), 7.52 (m, 2H), 7.44 (m, 3H), 7.39 (m, 1H), 7.36 (m, 1H), 7.28 (m, 1H), 7.21 (m, 2H), 7.09 (td, 1H), 6.67 (d, 1H), 2.94 (m, 2H), 2.83 (s, 6H).

Example 200

N-(3-{3-[2-({4-[2-(dimethylamino)ethyl]phenyl}amino)pyrimidin-4-yl]imidazo[1,2-a]pyridin-2-yl}phenyl)-3,5-difluorobenzamide The title compound was prepared as described in EXAMPLE 4H, substituting EXAMPLE 195D for EXAMPLE 4G, and 3,5-difluorobenzoyl chloride for 2,6-difluorobenzoyl chloride. MS (ESI(+)) m/e 590 (M+H)+; $^1$H NMR (300 MHz, dimethylsulfoxide-$d_6$) δ ppm 10.61 (s, 1H), 9.77 (s, 1H), 9.53 (d, 1H), 8.37 (d, 1H), 8.09 (m, 1H), 7.79 (m, 2H), 7.73 (m, 2H), 7.68 (m, 1H), 7.52 (m, 2H), 7.44 (m, 3H), 7.39 (m, 1H), 7.36 (m, 1H), 7.28 (m, 1H), 7.21 (m, 2H), 7.09 (td, 1H), 6.67 (d, 1H), 2.94 (m, 2H), 2.83 (s, 6H).

Example 201

N-(3-{3-[2-({4-[2-(dimethylamino)ethyl]phenyl}amino)pyrimidin-4-yl]imidazo[1,2-a]pyridin-2-yl}phenyl)-N'-phenylurea The title compound was prepared as described in EXAMPLE 3, substituting EXAMPLE 195D for EXAMPLE 1H. MS (ESI(+)) m/e 569 (M+H)+; $^1$H NMR (300 MHz, dimethylsulfoxide-$d_6$) δ ppm 9.64 (s, 1H), 8.92 (s, 1H), 8.76 (s, 1H), 8.34 (d, 1H), 7.76 (m, 2H), 7.62 (d, 2H), 7.52 (m, 1H), 7.44 (m, 3H), 7.36 (m, 1H), 7.26 (m, 2H), 7.21 (m, 1H), 7.14 (m, 2H), 7.07 (m, 1H), 6.96 (m, 1H), 6.63 (m, 1H), 2.66 (m, 2H), 2.43 (m, 2H), 2.18 (s, 6H).

Example 202

N-(3-{3-[2-({4-[1-(methoxyacetyl)piperidin-4-yl]phenyl}amino)pyrimidin-4-yl]imidazo[1,2-a]pyridin-2-yl}phenyl)-2-thien-2-ylacetamide Example 202A The title compound was prepared as described in EXAMPLE 68B, substituting 2-methoxyacetyl chloride for acetic anhydride. MS ESI(+): m/e 564.2 (M+H)+.

Example 202B

Example 202A was reduced as described in EXAMPLE 1H to give the title compound. MS ESI(+): m/e 534.2 (M+H)+.

Example 202C

N-(3-{3-[2-({4-[1-(methoxyacetyl)piperidin-4-yl]phenyl}amino)pyrimidin-4-yl]imidazo[1,2-a]pyridin-2-yl}phenyl)-2-thien-2-ylacetamide, trifluoroacetic acid salt The title compound was prepared as described in EXAMPLE 41 from EXAMPLE 202B and 2-(thiophen-2-1)acetyl chloride. MS ESI(+): m/e 658.2 (M+H)+. $^1$H NMR (400 MHz, dimethylsulfoxide-$d_6$) δ ppm 10.37 (s, 1 H), 9.75 (s, 1 H), 9.56 (bs, 1 H), 8.36 (d, 1 H), 7.95 (s, 1 H), 7.82 (d, 1 H), 7.43 (d, 1 H) 7.60-7.68 (m, 3 H), 7.43 (t, 1 H), 7.39 (dd, 1 H), 7.31 (d, 1 H), 7.21 (t, 1 H), 7.17 (d, 2 H), 6.96-6.98 (m, 2 H), 6.63 (d, 1 H), 4.11 (dd, 2 H), 3.88 (s, 2 H), 3.44-3.48 (m, 2 H), 3.30 (s, 3 H), 3.05-3.07 (m, 1 H), 2.63-2.73 (m, 2 H), 1.76-1.82 (m, 2 H), 1.40-1.60 (m, 2H).

Example 203

2,6-difluoro-N-(3-{3-[2-({4-[1-(methoxyacetyl)piperidin-4-yl]phenyl}amino)pyrimidin-4-yl]imidazo[1,2-a]pyridin-2-yl}phenyl)benzamide The title compound was prepared as described in EXAMPLE 41 from EXAMPLE 202B and 2,6-difluorobenzoyl chloride. MS ESI(+): m/e 674.2 (M+H)+. $^1$H NMR (400 MHz, dimethylsulfoxide-$d_6$) δ ppm 10.96 (s, 1 H), 9.76 (s, 1 H), 9.56 (bs, 1 H), 8.39 (d, 1 H), 8.09 (s, 1 H), 7.85 (d, 1 H), 7.80 (d, 1 H), 7.67 (t, 1 H), 7.57-7.63 (m, 3 H), 7.50 (t, 1 H), 7.40 (d, 1 H), 7.21-7.28 (m, 3 H), 7.15 (d, 2 H), 6.68 (d, 1 H), 4.12 (dd, 2 H), 3.44-3.48 (m, 2 H), 3.30 (s, 3 H), 3.05-3.07 (m, 1 H), 2.63-2.75 (m, 2 H), 1.76-1.82 (m, 2 H), 1.40-1.60 (m, 2H).

Example 204

N-(3-{3-[2-({3-[1-(methoxyacetyl)piperidin-4-yl]phenyl}amino)pyrimidin-4-yl]imidazo[1,2-a]pyridin-2-yl}phenyl)-2-thien-2-ylacetamide Example 204A The title compound was prepared according to EXAMPLE 68A, substituting tert-butyl 4-(3-aminophenyl)piperidine-1-carboxylate for tert-butyl 4-(4-aminophenyl)piperidine-1-carboxylate. MS ESI(+): m/e 492.0 (M+H)+.

Example 204B

The title compound was prepared as described in EXAMPLE 68B from EXAMPLE 204A and 2-methoxyacetyl chloride. MS ESI(+): m/e 584.2 (M+H)+.

Example 204C

EXAMPLE 204B was reduced as described in EXAMPLE 1H to give the title compound. MS ESI(+): m/e 534.2 (M+H)+.

Example 204D

N-(3-{3-[2-({3-[1-(methoxyacetyl)piperidin-4-yl]phenyl}amino)pyrimidin-4-yl]imidazo[1,2-a]pyridin-2-yl}phenyl)-2-thien-2-ylacetamide, trifluoroacetic acid salt The title compound was prepared as described in EXAMPLE 41 from EXAMPLE 204C and 2-(thiophen-2-1)acetyl chloride. MS ESI(+): m/e 658.2 (M+H)+. $^1$H NMR (400 MHz, dimethylsulfoxide-$d_6$) δ ppm 10.37 (s, 1 H), 9.79 (s, 1 H), 9.56 (bs, 1 H), 8.40 (d, 1 H), 7.97 (s, 1 H), 7.84 (d, 1 H), 7.43 (d, 1 H), 7.64-7.68 (m, 2 H), 7.58 (d, 1 H), 7.74 (t, 1 H), 7.38 (dd, 1 H), 7.33 (d, 1 H), 7.20-7.25 (m, 2 H), 6.96-6.98 (m, 2 H), 6.88 (d, 1 H), 6.64 (d, 1 H), 4.12 (dd, 2 H), 3.88 (s, 2 H), 3.44-3.48 (m, 2 H), 3.29 (s, 3 H), 3.05-3.07 (m, 1 H), 2.63-2.75 (m, 2 H), 1.76-1.82 (m, 2 H), 1.40-1.60 (m, 2H).

Example 205

2,6-difluoro-N-(3-{3-[2-({3-[1-(methoxyacetyl)piperidin-4-yl]phenyl}amino)pyrimidin-4-yl]imidazo[1,2-a]pyridin-2-yl}phenyl)benzamide The title compound was prepared as described in EXAMPLE 41 from EXAMPLE 204C and 2,6-difluorobenzoyl chloride. MS ESI(+): m/e 674.2 (M+H)$^+$. $^1$H NMR (400 MHz, dimethylsulfoxide-d$_6$) δ ppm 10.97 (s, 1 H), 9.80 (s, 1 H), 9.56 (bs, 1 H), 8.42 (d, 1 H), 8.10 (s, 1 H), 7.87 (d, 1 H), 7.81 (d, 1 H), 7.70 (t, 1 H), 7.65 (s, 1 H), 7.57-7.60 (m, 2 H), 7.51 (t, 1 H), 7.42 (d, 1 H), 7.20-7.28 (m, 4 H), 6.88 (d, 1 H), 6.69 (d, 1 H), 4.12 (dd, 2 H), 3.44-3.48 (m, 2 H), 3.29 (s, 3 H), 3.05-3.07 (m, 1 H), 2.63-2.75 (m, 2 H), 1.76-1.80 (m, 2 H), 1.40-1.58 (m, 2H).

Example 206

N-{3-[3-(2-{[4-(4-ethylpiperazin-1-yl)-3-fluorophenyl]amino}pyrimidin-4-yl)imidazo[1,2-a]pyridin-2-yl]phenyl}-2-thien-2-ylacetamide Example 206A A solution of 2,3-difluoro-nitro-benzene (1.59 g, 10 mmol), N-ethyl-piperazine (1.26 g, 11 mmol) and triethylamine (4.18 ml, 30 mmol) in dry N,N-dimethylformamide (30 ml) was stirred at room temperature for two days. The mixture was poured into ice-water and was extracted with CH$_2$Cl$_2$. The organic solution was dried (MgSO$_4$), filtered and concentrated. MS DCI/NH$_3$: m/e 254.1 (M+H)$^+$.

Example 206B

Example 206A was reduced as described in EXAMPLE 1H to give the title compound. MS DCI/NH$_3$: m/e 224.0 (M+H)$^+$.

Example 206C

The title compound was prepared as described in EXAMPLE 4F, substituting EXAMPLE 206B for EXAMPLE 4E. MS ESI(+): m/e 539.2 (M+H)$^+$.

Example 206D

Example 206C was reduced as described in EXAMPLE 41B to give the title compound. MS ESI(+): m/e 509.2 (M+H)$^+$.

Example 206E

N-{3-[3-(2-{[4-(4-ethylpiperazin-1-yl)-3-fluorophenyl]amino}pyrimidin-4-yl)imidazo[1,2-a]pyridin-2-yl]phenyl}-2-thien-2-ylacetamide, trifluoroacetic acid salt The title compound was prepared as described in EXAMPLE 41 from EXAMPLE 206D and 2-(thiophen-2-yl) acetyl chloride. MS ESI(+): m/e 633.2 (M+H)$^+$. $^1$H NMR (400 MHz, dimethylsulfoxide-d$_6$) δ ppm 10.33 (s, 1 H), 9.87 (s, 1 H), 9.51 (bd, 1 H), 9.45 (bs, 1 H), 8.38 (d, 1 H), 7.96 (s, 1 H), 7.75-7.81 (m, 2 H), 7.69 (d, 1 H), 7.58 (t, 1 H), 7.65 (s, 1 H), 7.37-7.45 (m, 3 H), 7.30 (d, 1 H), 7.15 (t, 1 H), 7.08 (t, 1 H), 6.95-6.98 (m, 2 H), 6.66 (d, 1 H), 3.84 (s, 2 H), 3.43-3.48 (m, 4 H), 3.17-3.23 (m, 4 H), 3.00 (q, 2 H), 1.26 (t, 3H).

Example 207

2-chloro-N-{3-[3-(2-{[4-(4-ethylpiperazin-1-yl)-3-fluorophenyl]amino}pyrimidin-4-yl)imidazo[1,2-a]pyridin-2-yl]phenyl}benzamide The title compound was prepared as described in EXAMPLE 41 from EXAMPLE 206D and 2-chlorobenzoyl chloride. MS ESI(+): m/e 647.2 (M+H)$^+$. NMR (400 MHz, dimethylsulfoxide-d$_6$) δ ppm 10.60 (s, 1 H), 9.87 (s, 1 H), 9.51 (bd, 1 H), 9.43 (bs, 1 H), 8.40 (d, 1 H), 8.11 (s, 1 H), 7.75-7.82 (m, 3 H), 7.37-7.60 (m, 8 H), 7.15 (t, 1 H), 7.08 (t, 1 H), 6.70 (d, 1 H), 3.43-3.48 (m, 4 H), 3.14-3.26 (m, 4 H), 3.00 (q, 2 H), 1.26 (t, 3H).

Example 208

N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)-2-thien-2-ylacetamide Example 208A To a solution of EXAMPLE 68A (200 mg, 0.407 mmol) in methanol (5 mL) was added 2,2-dimethyloxirane (46.7 µl, 0.53 mmol). The mixture was stirred at 150° C. for 30 minutes in a Personal Chemistry microwave instrument. The solution was concentrated to give the title compound.

Example 208B

Example 208 A was reduced as described in EXAMPLE 1H to give the title compound. MS ESI(+): m/e 534.3 (M+H)$^+$.

Example 208C

N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)-2-thien-2-ylacetamide The title compound was prepared as described in EXAMPLE 41 from EXAMPLE 208B and 2-(thiophen-2-yl) acetyl chloride. MS ESI(+): m/e 658.2 (M+H)$^+$. $^1$H NMR (400 MHz, dimethylsulfoxide-d$_6$) δ ppm 10.32 (s, 1 H), 9.66 (s, 1 H), 9.52 (bs, 1 H), 8.32 (d, 1 H), 7.91 (s, 1 H), 7.72-7.75 (m, 2 H), 7.63 (d, 2 H), 7.50 (t, 1 H), 7.37-7.40 (m, 2 H), 7.27-7.32 (m, 1 H), 7.16 (d, 2 H), 7.07 (t, 1 H), 6.97-6.99 (m, 2 H), 6.60 (d, 1 H), 4.05 (bs, 1 H), 3.87 (s, 2 H), 3.05 (d, 2 H), 2.40 (m, 1 H), 2.20-2.26 (m, 4 H), 1.65-1.68 (m, 4 H), 1.10 (s, 6H).

Example 209

N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)-2-thien-3-ylacetamide The title compound was prepared as described in EXAMPLE 41 from EXAMPLE 208B and 2-(thiophen-3-yl) acetyl chloride. MS ESI(+): m/e 658.2 (M+H)$^+$. $^1$H NMR (400 MHz, dimethylsulfoxide-d$_6$) δ ppm 10.23 (s, 1 H), 9.64 (s, 1 H), 9.52 (bd, 1 H), 8.32 (d, 1 H), 7.92 (s, 1 H), 7.72-7.75

(m, 2 H), 7.64 (d, 2 H), 7.46-7.51 (m, 2 H), 7.38 (t, 1 H), 7.28-7.34 (m, 2 H), 7.16 (d, 2 H), 7.04-7.10 (m, 2 H), 6.60 (d, 1 H), 4.07 (bs, 1 H), 3.66 (s, 2 H), 3.05 (d, 2 H), 2.40 (m, 1 H), 2.20-2.26 (m, 4 H), 1.65-1.70 (m, 4 H), 1.11 (s, 6H).

Example 210

2,6-difluoro-N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)benzamide The title compound was prepared as described in EXAMPLE 41 from EXAMPLE 208B and 2,6-difluorobenzoyl chloride. MS ESI(+): m/e 674.2 (M+H)$^+$. $^1$H NMR (400 MHz, dimethylsulfoxide-d$_6$) δ ppm 10.88 (s, 1 H), 9.64 (s, 1 H), 9.52 (bd, 1 H), 8.34 (d, 1 H), 8.04 (s, 1 H), 7.80 (d, 1 H), 7.75 (d, 1 H), 7.63 (d, 2 H), 7.59 (m, 1 H), 7.50 (t, 1 H), 7.45 (d, 1 H), 7.39 (d, 1 H), 7.23-7.27 (m, 2 H), 7.16 (d, 2 H), 7.07 (t, 1 H), 6.64 (d, 1 H), 4.02 (bs, 1H), 3.05 (d, 2 H), 2.40 (m, 1 H), 2.16-2.22 (m, 4 H), 1.65-1.70 (m, 4 H), 1.10 (s, 6H).

Example 211

2-chloro-N-(3-{3-[2-({4-[1-(2-hydroxy-2-methylpropyl)piperidin-4-yl]phenyl}amino)pyrimidin-4-yl]imidazo[1,2-a]pyridin-2-yl}phenyl)benzamide The title compound was prepared as described in EXAMPLE 41 from EXAMPLE 208B and 2-chlorobenzoyl chloride. MS ESI(+): m/e 672.2 (M+H)$^+$. $^1$H NMR (400 MHz, dimethylsulfoxide-d$_6$) δ ppm 10.58(s, 1 H), 9.63(s, 1 H), 9.52 (bd, 1 H), 8.34 (d, 1 H), 8.06(s, 1 H), 7.82 (d, 1 H), 7.75 (d, 1 H), 7.63 (d, 2 H), 7.55-7.58 (m, 2 H), 7.47-7.52 (m, 4 H), 7.38 (d, 1 H), 7.16 (d, 2 H), 7.07 (t, 1 H), 6.64 (d, 1 H), 4.01(s, 1 H), 3.03(d, 2 H), 2.40 (m, 1 H), 2.20-2.24(m, 4 H), 1.65-1.70 (m, 4 H), 1.11 (s, 6H).

Example 212

N-(3-{3-[2-({3-[(N,N-dimethylglycyl)amino]phenyl}amino)pyrimidin-4-yl]imidazo[1,2-a]pyridin-2-yl}phenyl)-2,6-difluorobenzamide

Example 212A

The title compound was prepared as described in EXAMPLE 4F, substituting tert-butyl 3-aminophenylcarbamate for EXAMPLE 4E. MS (ESI(+)) m/e 424 (M+H)$^+$.

Example 212B

In a 25 ml round-bottom flask, EXAMPLE 212A (250 mg, 0.590 mmol), N,N-dimethylglycine (67.0 mg, 0.649 mmol), N-(3-dimethylaminopropyl)-N'-ethylcarbodiimide hydrochloride (226 mg, 1.181 mmol), and 1-hydroxybenzotriazole (181 mg, 1.181 mmol) were combined in anhydrous N,N-dimethylformamide (2 ml). Once a solution formed, N-methylmorpholine (0.649 ml, 5.90 mmol) was added. The mixture stirred for 12 hours at ambient temperature. To the mixture was added 4-dimethylaminopyridine (50 mg, 0.409 mmol), and reaction stirred 12 hours at 60° C. The mixture was diluted with water, and extracted with CHCl$_3$. The organic extracts were washed with saturated NaHCO$_3$ and brine, dried with Na$_2$SO$_4$, filtered, and concentrated. The residue was purified by flash chromatography on a 24 g silica gel column using an AnaLogix IntelliFlash 280 system eluting with a gradient of 2% to 5% methanol in dichloromethane to provide the title compound. MS (ESI(+)) m/e 509 (M+H)$^+$.

Example 212C

The title compound was prepared as described in EXAMPLE 4G, substituting EXAMPLE 212B for EXAMPLE 4F. MS (ESI(+)) m/e 479 (M+H)$^+$.

Example 212D

The title compound was prepared as described in EXAMPLE 4H, substituting EXAMPLE 212C for EXAMPLE 4G. MS (ESI(+)) m/e 619 (M+H)$^+$, $^1$H NMR (400 MHz, dimethylsulfoxide-d$_6$) δ ppm 11.09 (s, 1 H) 9.96 (s, 1 H) 9.80 (m, 2 H) 8.57 (d, 1 H) 8.25 (d, 2 H) 8.02 (d, 1 H) 7.96 (d, 1 H) 7.80 (m, 1 H) 7.60-7.73 (m, 4 H) 7.41-7.53 (m, 4 H) 7.27 (t, 1 H) 6.87 (d, 1 H) 3.28 (s, 2 H) 2.49 (s, 6 H).

Example 213

2-chloro-N-(3-{3-[2-({3-[(N,N-dimethylglycyl)amino]phenyl}amino)pyrimidin-4-yl]imidazo[1,2-a]pyridin-2-yl}phenyl)benzamide The title compound was prepared as described in EXAMPLE 4H, substituting EXAMPLE 212C for EXAMPLE 4G, and 2-chlorobenzoyl chloride for 2,6-difluorobenzoyl chloride. MS (ESI(+)) m/e 618 (M+H)$^+$, $^1$H NMR (400 MHz, dimethylsulfoxide-d$_6$) δ ppm 10.80 (s, 1 H) 9.95 (s, 1 H) 9.82 (m, 2 H) 8.56 (d, 1 H) 8.27 (s, 2 H) 8.05 (d, 1 H) 7.97 (d, 1 H) 7.79 (m, 2 H) 7.64-7.74 (m, 5 H) 7.60 (m, 1 H) 7.43 (t, 1 H) 7.27 (t, 1 H) 6.87 (d, 1 H) 3.28 (s, 2 H) 2.49 (s, 6 H).

Example 214

N-(3-{3-[2-({3-[(N,N-dimethylglycyl)amino]phenyl}amino)pyrimidin-4-yl]imidazo[1,2-a]pyridin-2-yl}phenyl)thiophene-2-carboxamide The title compound was prepared as described in EXAMPLE 4H, substituting EXAMPLE 212C for EXAMPLE 4G, and thiophene-2-carbonyl chloride for 2,6-difluorobenzoyl chloride. MS (ESI(+)) m/e 589 (M+H)$^+$, $^1$H NMR (400 MHz, dimethylsulfoxide-d$_6$) δ ppm 10.54 (s, 1 H) 9.96 (s, 1 H) 9.86 (d, 1 H) 9.82 (s, 1 H) 8.56 (d, 1 H) 8.28 (m, 2 H) 8.25 (d, 1 H) 8.12 (m, 1 H) 8.07 (d, 1 H) 7.97 (d, 1 H) 7.63-7.75 (m, 3 H) 7.57 (d, 1 H) 7.51 (m, 1 H) 7.44 (m, 2 H) 7.28 (t, 1 H) 6.86 (d, 1 H) 3.28 (s, 2 H) 2.49 (s, 6 H).

Example 215

N$^2$,N$^2$-dimethyl-N$^1$-(3-{[4-(2-{3-[(thien-2-ylacetyl)amino]phenyl}imidazo[1,2-a]pyridin-3-yl)pyrimidin-2-yl]amino}phenyl)glycinamide The title compound was prepared as described in EXAMPLE 4H, substituting EXAMPLE 212C for EXAMPLE 4G, and 2-thiopheneacetyl chloride for 2,6-difluorobenzoyl chloride. MS (ESI(+)) m/e 603 (M+H)$^+$, $^1$H NMR (400 MHz, dimethylsulfoxide-d$_6$) δ ppm 10.52 (s, 1 H) 9.96 (s, 1 H) 9.82 (m, 2 H) 8.54 (d, 1 H) 8.27 (s, 1 H) 8.12 (s, 1 H) 7.95 (d, 2 H) 7.69 (m, 2 H) 7.60 (m, 2 H) 7.52 (m, 2 H) 7.43 (t, 1 H) 7.27 (t, 1 H) 7.19 (m, 2 H) 6.82 (d, 1 H) 4.09 (s, 2 H) 3.28 (s, 2 H) 2.49 (s, 6 H).

Example 216

2,6-difluoro-N-(3-{3-[2-({3-[(methoxyacetyl)amino]phenyl}amino)pyrimidin-4-yl]imidazo[1,2-a]pyridin-2-yl}phenyl)benzamide

Example 216A

The title compound was prepared as described in EXAMPLE 4H, substituting EXAMPLE 212A for EXAMPLE 4G, and methoxyacetyl chloride for 2,6-difluorobenzoyl chloride. MS (ESI(+)) m/e 496 (M+H)$^+$.

Example 216B

The title compound was prepared as described in EXAMPLE 4G, substituting EXAMPLE 216A for EXAMPLE 4F. MS (ESI(+)) m/e 466 (M+H)$^+$.

Example 216C

The title compound was prepared as described in EXAMPLE 4H, substituting EXAMPLE 216B for EXAMPLE 4G. MS (ESI(+)) m/e 606 (M+H)$^+$, $^1$H NMR (400 MHz, dimethylsulfoxide-d$_6$) δ ppm 10.87 (s, 1 H) 9.74 (s, 1 H) 9.64 (s, 1 H) 9.59 (d, 1 H) 8.34 (d, 1 H) 8.07 (s, 1 H) 8.01 (s, 1 H) 7.80 (d, 1 H) 7.75 (d, 1 H) 7.58 (m, 1 H) 7.43-7.51 (m, 3 H) 7.39 (m, 1 H) 7.20-7.29 (m, 4 H) 7.05 (t, 1 H) 6.64 (d, 1 H) 3.97 (s, 2 H) 3.35 (s, 3 H).

Example 217

2-chloro-N-(3-{3-[2({3-[(methoxyacetyl)amino]phenyl}amino)pyrimidin-4-yl]imidazo[1,2-a]pyridin-2-yl}phenyl)benzamide The title compound was prepared as described in EXAMPLE 4H, substituting EXAMPLE 216B for EXAMPLE 4G, and 2-chlorobenzoyl chloride for 2,6-difluorobenzoyl chloride. MS (ESI(+)) m/e 605 (M+H)$^+$, $^1$H NMR (400 MHz, dimethylsulfoxide-d$_6$) δ ppm 10.58 (s, 1 H) 9.74 (s, 1 H) 9.64 (s, 1 H) 9.61 (d, 1 H) 8.34 (d, 1 H) 8.07 (s, 1 H) 8.04 (s, 1 H) 7.83 (d, 1 H) 7.75 (d, 1 H) 7.57 (m, 2 H) 7.42-7.52 (m, 5 H) 7.37 (m, 1 H) 7.28 (m, 1 H) 7.21 (t, 1 H) 7.05 (m, 1 H) 6.64 (d, 1 H) 3.97 (s, 2 H) 3.35 (s, 3 H).

Example 218

N-(3-{3-[2-({3-[(2-methoxyacetyl)amino]phenyl}amino)pyrimidin-4-yl]imidazo[1,2-a]pyridin-2-yl}phenyl)thiophene-2-carboxamide The title compound was prepared as described in EXAMPLE 4H, substituting EXAMPLE 216B for EXAMPLE 4G, and thiophene-2-carbonyl chloride for 2,6-difluorobenzoyl chloride. MS (ESI(+)) m/e 576 (M+H)$^+$, $^1$H NMR (400 MHz, dimethylsulfoxide-d$_6$) δ ppm 10.31 (s, 1 H) 9.75 (s, 1 H) 9.64 (m, 2 H) 8.33 (d, 1 H) 8.07 (d, H) 8.03 (d, 1 H) 7.90 (m, 1 H) 7.84 (d, 1 H) 7.74 (d, 1 H) 7.41-7.51 (m, 3 H) 7.34 (d, 1 H) 7.28 (m, 1 H) 7.22 (m, 2 H) 7.05 (m, 1 H) 6.64 (d, 1 H) 3.97 (s, 2 H) 3.35 (s, 3 H).

Example 219

2-methoxy-N-(3-{[4-(2-{3-[(thien-2-ylacetyl)amino]phenyl}imidazo[1,2-a]pyridin-3-yl)pyrimidin-2-yl]amino}phenyl)acetamide The title compound was prepared as described in EXAMPLE 4H, substituting EXAMPLE 216B for EXAMPLE 4G, and 2-thiopheneacetyl chloride for 2,6-difluorobenzoyl chloride. MS (ESI(+)) m/e 590 (M+H)$^+$, $^1$H NMR (400 MHz, dimethylsulfoxide-d$_6$) δ ppm 10.29 (s, 1 H) 9.74 (s, 1 H) 9.65 (s, 1 H) 9.60 (d, 1 H) 8.32 (d, 1 H) 8.08 (s, 1 H) 7.89 (s, 1 H) 7.73 (d, 2 H) 7.47 (m, 2 H) 7.38 (m, 2 H) 7.29 (m, 2 H) 7.21 (t, 1 H) 7.04 (m, 1 H) 6.96 (m, 2 H) 6.60 (d, 1 H) 3.97 (s, 2 H) 3.86 (s, 2 H) 3.35 (s, 3 H).

Example 220

2-methoxy-N-[3-({4-[2-(3-{[(thien-2-ylamino)carbonyl]amino}phenyl)imidazo[1,2-a]pyridin-3-yl]pyrimidin-2-yl}amino)phenyl]acetamide The title compound was prepared as described in EXAMPLE 3, substituting EXAMPLE 216B for EXAMPLE 1H and 2-thienyl isocyanate for phenyl isocyanate. MS (ESI(+)) m/e 591 (M+H)$^+$, $^1$H NMR (400 MHz, dimethylsulfoxide-d$_6$) δ ppm 9.74 (s, 1 H) 9.64 (m, 2 H) 8.89 (bs, 1 H) 8.33 (d, 1 H) 8.07 (s, 1 H) 7.75 (m, 2 H) 7.56 (m, 1 H) 7.47 (m, 2 H) 7.37 (t, 1 H) 7.28 (m, 1 H) 7.22 (m, 2 H) 7.04 (t, 1 H) 6.85 (m, 1 H) 6.79 (m, 1 H) 6.62 (d, 1 H) 6.55 (dd, 1 H) 3.97 (s, 2 H) 3.35 (s, 3 H).

Example 221

N-(3-{3-[2-({4-[3-(dimethylamino)pyrrolidin-1-yl]phenyl}amino)pyrimidin-4-yl]imidazo[1,2-a]pyridin-2-yl}phenyl)-2,6-difluorobenzamide

Example 221A

A 20 ml pressure tube was charged with 1-fluoro-4-nitrobenzene (1.00 g, 7.09 mmol), N,N-dimethylpyrrolidin-3-amine (0.890 g, 7.80 mmol), triethylamine (1.98 ml, 14.2 mmol), and anhydrous dimethylsulfoxide (10 ml). The mixture was stirred for 12 hours at 100° C. The reaction mixture was diluted with water, and extracted with dichloromethane. The extracts were washed with water and brine, dried with Na$_2$SO$_4$, filtered, and concentrated. The residue was purified by flash chromatography on a 60 g silica gel column using an AnaLogix IntelliFlash 280 system eluting with a gradient of 2% to 5% methanol in dichloromethane to provide the title compound. MS (DCI(+)) m/e 236 (M+H)$^+$.

Example 221B

The title compound was prepared as described in EXAMPLE 1H, substituting EXAMPLE 221A for EXAMPLE 1G. MS (DCI(+)) m/e 206 (M+H)$^+$.

Example 221C

The title compound was prepared as described in EXAMPLE 4F, substituting EXAMPLE 221B for EXAMPLE 4E. MS (ESI(+)) m/e 521 (M+H)$^+$.

Example 221D

The title compound was prepared as described in EXAMPLE 4G, substituting EXAMPLE 221C for EXAMPLE 4F. MS (ESI(+)) m/e 491 (M+H)$^+$.

Example 221E

The title compound was prepared as described in EXAMPLE 4H, substituting EXAMPLE 221D for EXAMPLE 4G. MS (ESI(+)) m/e 631 (M+H)+, 1H NMR (400 MHz, dimethylsulfoxide-$d_6$) δ ppm 10.87 (s, 1 H) 9.49 (bs, 1 H) 9.28 (s, 1 H) 8.24 (d, 1 H) 8.01 (s, 1 H) 7.78 (d, 1 H) 7.72 (d, 1 H) 7.58 (m, 1 H) 7.41-7.49 (m, 4 H) 7.38 (m, 1 H) 7.24 (m, 2 H) 7.02 (t, 1 H) 6.52 (m, 3 H) 3.39 (m, 2 H) 3.21 (m, 1 H) 3.02 (m, 1 H) 2.81 (m, 1 H) 2.20 (s, 6 H) 2.13 (m, 1 H) 1.81 (m, 1 H).

Example 222

2-chloro-N-(3-{3-[2-({4-[3-(dimethylamino)pyrrolidin-1-yl]phenyl}amino)pyrimidin-4-yl]imidazo[1,2-a]pyridin-2-yl}phenyl)benzamide The title compound was prepared as described in EXAMPLE 4H, substituting EXAMPLE 221D for EXAMPLE 4G, and 2-chlorobenzoyl chloride for 2,6-difluorobenzoyl chloride. MS (ESI(+)) m/e 630 (M+H)+, 1H NMR (400 MHz, dimethylsulfoxide-$d_6$) δ ppm 10.57 (s, 1 H) 9.50 (bs, 1 H) 9.28 (s, 1 H) 8.23 (d, 1 H) 8.04 (s, 1 H) 7.81 (d, 1 H) 7.72 (d, 1 H) 7.57 (m, 2 H) 7.40-7.51 (m, 6 H) 7.36 (m, 1 H) 7.01 (t, 1 H) 6.51 (m, 3 H) 3.40 (m, 2 H) 3.21 (m, 1 H) 3.03 (m, 1 H) 2.83 (m, 1 H) 2.21 (s, 6 H) 2.14 (m, 1 H) 1.81 (m, 1 H).

Example 223

N-(3-{3-[2-({4-[3-(dimethylamino)pyrrolidin-1-yl]phenyl}amino)pyrimidin-4-yl]imidazo[1,2-a]pyridin-2-yl}phenyl)thiophene-2-carboxamide The title compound was prepared as described in EXAMPLE 4H, substituting EXAMPLE 221D for EXAMPLE 4G, and thiophene-2-carbonyl chloride for 2,6-difluorobenzoyl chloride. MS (ESI(+)) m/e 601 (M+H)+, 1H NMR (400 MHz, dimethylsulfoxide-$d_6$) δ ppm 10.31 (s, 1 H) 9.51 (bs, 1 H) 9.28 (s, 1 H) 8.25 (d, 1 H) 8.06 (s, 1 H) 8.03 (d, 1 H) 7.89 (d, 1 H) 7.84 (m, 1 H) 7.72 (d, 1 H) 7.39-7.49 (m, 4 H) 7.32 (d, 1 H) 7.21 (m, 1 H) 7.02 (t, 1 H) 6.52 (m, 3 H) 3.39 (m, 2 H) 3.21 (m, 1 H) 3.02 (m, 1 H) 2.81 (m, 1 H) 2.20 (s, 6 H) 2.13 (m, 1 H) 1.80 (m, 1 H).

Example 224

N-(3-{3-[2-({4-[3-(dimethylamino)pyrrolidin-1-yl]phenyl}amino)pyrimidin-4-yl]imidazo[1,2-a]pyridin-2-yl}phenyl)-2-thien-2-ylacetamide The title compound was prepared as described in EXAMPLE 4H, substituting EXAMPLE 221D for EXAMPLE 4G, and 2-thiopheneacetyl chloride for 2,6-difluorobenzoyl chloride. MS (ESI(+)) m/e 615 (M+H)+, 1H NMR (400 MHz, dimethylsulfoxide-$d_6$) δ ppm 10.29 (s, 1 H) 9.49 (bs, 1 H) 9.28 (s, 1 H) 8.22 (d, 1 H) 7.89 (s, 1 H) 7.71 (m, 2 H) 7.45 (m, 3 H) 7.37 (m, 2 H) 7.29 (d, 1 H) 6.98 (m, 3 H) 6.50 (m, 3 H) 3.86 (s, 2 H) 3.39 (m, 2 H) 3.21 (m, 1 H) 3.02 (m, 1 H) 2.81 (m, 1 H) 2.21 (s, 6 H) 2.14 (m, 1 H) 1.81 (m, 1 H).

Example 225

N-(3-{3-[2-({4-[3-(dimethylamino)pyrrolidin-1-yl]phenyl}amino)pyrimidin-4-yl]imidazo[1,2-a]pyridin-2-yl}phenyl)-N'-thien-2-ylurea The title compound was prepared as described in EXAMPLE 3, substituting EXAMPLE 221D for EXAMPLE 1H, and 2-thienyl isocyanate for phenyl isocyanate. MS (ESI (+)) m/e 616 (M+H)+, 1H NMR (400 MHz, dimethylsulfoxide-$d_6$) δ ppm 9.63 (s, 1 H) 9.51 (bs, 1 H) 9.28 (s, 1 H) 8.89 (s, 1 H) 8.24 (d, 1 H) 7.73 (m, 2 H) 7.54 (d, 1 H) 7.46 (m, 3 H) 7.35 (t, 1 H) 7.21 (d, 1 H) 7.01 (t, 1 H) 6.85 (m, 1 H) 6.79 (dd, 1 H) 6.49-6.56 (m, 4 H) 3.39 (m, 2 H) 3.21 (m, 1 H) 3.03 (m, 1 H) 2.84 (m, 1 H) 2.22 (s, 6 H) 2.14 (m, 1 H) 1.81 (m, 1 H).

Example 226

2,6-difluoro-N-(3-{3-[2-({3-[2-(methylamino)-2-oxoethyl]phenyl}amino)pyrimidin-4-yl]imidazo[1,2-a]pyridin-2-yl}phenyl)benzamide Example 226A To a solution of 2-(3-nitrophenyl)acetic acid (0.18 g, 1.0 mmol) in $CH_2Cl_2$ (10 ml) was added oxalyl chloride (88 uL, 1 mmol) followed by 3 drops of N,N-dimethylformamide. The reaction mixture was stirred at room temperature for 2 hours. To the resulting acid chloride was added methylamine (2.5 mL of a 2M solution in tetrahydrofuran, 5 mmol) and stirred for one additional hour. The reaction mixture was partitioned between ethyl acetate and 1N HCl. The organic layer was washed with $NaHCO_3$, and then brine, dried and concentrated. The crude material was used without further purification. MS (DCI(+)) m/e 195 (M+H)+.

Example 226B

The title compound was prepared as described in EXAMPLE 4E, substituting EXAMPLE 226A for EXAMPLE 4D.

Example 226C

The title compound was prepared as described in EXAMPLE 4F, substituting EXAMPLE 226B for EXAMPLE 4E.

Example 226D

The title compound was prepared as described in EXAMPLE 4G, substituting EXAMPLE 226C for EXAMPLE 4F.

Example 226E

The title compound was prepared as described in EXAMPLE 1I, substituting EXAMPLE 226D for EXAMPLE 1H. MS (ESI(+)) m/e 590 (M+H)+; 1H-NMR (300 MHz, dimethylsulfoxide-$d_6$) δ 10.89 (s, 1H); 9.73 (s, 1H); 9.58 (d, 1H); 8.35 (d, 1H); 8.02 (s, 1H); 7.90 (m, 1H); 7.82-7.75 (m, 2H); 7.66-7.56 (m, 3H); 7.53-7.41 (m, 31-1); 7.29-7.19 (m, 3H); 7.08 (t, 1H); 6.89 (d, 1H); 6.65 (d, 1H); 3.36 (s, 2H); 2.57 (d, 3H).

Example 227

N-(3-{3-[2-({3-[2-(methylamino)-2-oxoethyl]phenyl}amino)pyrimidin-4-yl]imidazo[1,2-a]pyridin-2-yl}phenyl)-2-phenylacetamide The title compound was prepared as described in EXAMPLE 1I, substituting EXAMPLE 226D for EXAMPLE 1H and phenylacetyl chloride for 2,6-difluorobenzoyl chloride. MS (ESI(+)) m/e 568 (M+H)+; 1H NMR (300 MHz, dimethylsulfoxide-$d_6$) δ 10.27 (s, 1H); 9.73 (s, 1H); 9.59 (d, 1H); 8.33 (d, 1H); 7.91 (m, 2H); 7.74 (d, 2H); 7.65 (m, 2H); 7.50 (t, 1H); 7.38 (t, 1H); 7.34-7.26 (m, 6H); 7.22 (t, 1H); 7.08 (t, 1H); 6.89 (d, 1H); 6.61 (d, 1H); 3.64 (s, 2H); 3.36 (s, 2H); 2.57 (d, 3H).

Example 228

N-(3-{3-[2-({3-[2-(methylamino)-2-oxoethyl]phenyl}amino)pyrimidin-4-yl]imidazo[1,2-a]pyridin-2-yl}phenyl)-2-thien-2-ylacetamide The title compound was prepared as described in EXAMPLE 1I, substituting EXAMPLE 226D for EXAMPLE 1H and 2-thienylacetyl chloride for 2,6-difluorobenzoyl chloride. MS (ESI(+)) m/e 574 (M+H)$^+$; $^1$H-NMR (300 MHz, dimethylsulfoxide-d$_6$) δ 10.32 (s, 1H); 9.73 (s, 1H); 9.59 (d, 1H); 8.33 (d, 1H); 7.91 (m, 2H); 7.75 (m, 2H); 7.63 (m, 2H); 7.50 (t, 1H); 7.40 (m, 2H); 7.32 (m, 1H); 7.22 (t, 1H); 7.08 (t, 1H); 6.98 (m, 2H); 6.89 (d, 1H); 6.61 (d, 1H); 3.87 (s, 2H); 3.36 (s, 2H), 2.57 (d, 3H).

Example 229

N-(3-{3-[2-({3-[2-(dimethylamino)-2-oxoethyl]phenyl}amino)pyrimidin-4-yl]imidazo[1,2-a]pyridin-2-yl}phenyl)-2,6-difluorobenzamide Example 229A The title compound was prepared as described in EXAMPLE 226A, substituting dimethylamine for methylamine.

Example 229B

The title compound was prepared as described in EXAMPLE 4E, substituting EXAMPLE 229A for EXAMPLE 4D.

Example 229C

The title compound was prepared as described in EXAMPLE 4F, substituting EXAMPLE 229B for EXAMPLE 4E.

Example 229D

The title compound was prepared as described in EXAMPLE 40, substituting EXAMPLE 229C for EXAMPLE 4F.

Example 229E

The title compound was prepared as described in EXAMPLE 1I, substituting EXAMPLE 229D for EXAMPLE 1H. MS (ESI(+)) m/e 604 (M+H)$^+$; $^1$H-NMR (300 MHz, dimethylsulfoxide-d$_6$) δ 10.89 (s, 1H); 9.74 (s, 1H); 9.55 (d, 1H); 8.36 (d, 1H); 8.03 (s, 1H); 7.82-7.75 (m, 2H); 7.65-7.39 (m, 6H); 7.29-7.20 (m, 3H); 7.09 (t, 1H); 6.84 (d, 1H); 6.67 (d, 1H); 3.64 (s, 2H); 2.97 (s, 3H); 2.82 (s, 3H).

Example 230

N-(3-{3-[2-({3-[2-(dimethylamino)-2-oxoethyl]phenyl}amino)pyrimidin-4-yl]imidazo[1,2-a]pyridin-2-yl}phenyl)-2-phenylacetamide The title compound was prepared as described in EXAMPLE 1I, substituting EXAMPLE 229D for EXAMPLE 1H and phenylacetyl chloride for 2,6-difluorobenzoyl chloride. MS (ESI(+)) m/e 582 (M+H)$^+$; $^1$H-NMR (300 MHz, dimethylsulfoxide-d$_6$) δ 10.28 (s, 1H); 9.75 (s, 1H); 9.55 (d, 1H); 8.34 (d, 1H); 7.91 (s, 1H); 7.75 (d, 2H); 7.62 (m, 2H); 7.50 (t, 1H); 7.38 (t, 1H); 7.34-7.25 (m, 6H); 7.22 (t, 1H); 7.08 (t, 1H); 6.84 (d, 1H); 6.61 (d, 1H); 3.64 (s, 4H); 2.97 (s, 3H); 2.82 (s, 3H).

Example 231

N-(3-{3-[2-({3-[2-(dimethylamino)-2-oxoethyl]phenyl}amino)pyrimidin-4-yl]imidazo[1,2-a]pyridin-2-yl}phenyl)-2-thien-2-ylacetamide The title compound was prepared as described in EXAMPLE 1I, substituting EXAMPLE 229D for EXAMPLE 1H and 2-thienylacetyl chloride for 2,6-difluorobenzoyl chloride. MS (ESI(+)) m/e 588 (M+H)$^+$; $^1$H-NMR (300 MHz, dimethylsulfoxide-d$_6$) δ 10.30 (s, 1H); 9.74 (s, 1H); 9.55 (d, 1H); 8.34 (d, 1H); 7.91 (s, 1H); 7.74 (m, 2H); 7.63 (m, 2H); 7.50 (t, 1H); 7.39 (m, 2H); 7.32 (m, 1H); 7.23 (t, 1H); 7.08 (t, 1H); 6.98 (m, 2H); 6.84 (d, 1H); 6.62 (d, 1H); 3.87 (s, 2H); 3.64 (s, 2H), 2.97 (s, 3H); 2.82 (s, 3H).

Example 232

N-{3-[3-(2-{[2-(dimethylamino)-2,3-dihydro-1H-inden-5-yl]amino}pyrimidin-4-yl)imidazo[1,2-a]pyridin-2-yl]phenyl}thiophene-2-carboxamide The title compound was prepared as described in EXAMPLE 98D substituting EXAMPLE 106D for EXAMPLE 98C and thiophene-2-carbonyl chloride for 2-(thiophen-2-yl)acetyl chloride. MS (ESI(+)) m/e 572 (M+H)$^+$, (ESI(−)) m/e 570 (M−H)$^−$; $^1$H-NMR (300 MHz, dimethylsulfoxide-d$_6$) δ 10.35 (s, 1H), 9.78 (s, 1H), 9.54 (d, 1H), 8.38 (d, 1H), 8.12 (m, 1H), 8.04 (dd, 1H), 7.89-7.73 (m, 4H), 7.59-7.48 (m, 2H), 7.43 (d, 1H), 7.35 (m, 1H), 7.24-7.12 (m, 3H), 6.96 (d, 1H), 4.09 (m, 1H), 3.29 (d, 1H), 3.23 (d, 1H), 3.10-3.03 (m, 2H), 2.82 (m, 6H).

Example 233

N-{3-[3-(2-{[2-(dimethylamino)-2,3-dihydro-1H-inden-5-yl]amino}pyrimidin-4-yl)imidazo[1,2-a]pyridin-2-yl]phenyl}-4-methylthiophene-2-carboxamide The title compound was prepared as described in EXAMPLE 98D substituting EXAMPLE 106D for EXAMPLE 98C and 4-methylthiophene-2-carbonyl chloride for 2-(thiophen-2-yl)acetyl chloride. MS (ESI(+)) m/e 586 (M+H)$^+$, (ESI(−)) m/e 584 (M−H)$^−$; $^1$H-NMR (300 MHz, dimethylsulfoxide-d$_6$) δ 10.28 (s, 1H), 9.78 (s, 1H), 9.55 (d, 1H), 8.38 (d, 1H), 8.12 (m, 1H), 7.89-7.74 (m, 4H), 7.60-7.42 (m, 4H), 7.33 (m, 1H), 7.18 (d, 1H), 7.12 (m, 1H), 6.69 (d, 1H), 4.09 (m, 1H), 3.29 (d, 1H), 3.23 (d, 1H), 3.16-3.03 (m, 2H), 2.83 (m, 6H), 2.49 (s, 3H).

Example 234

N-{3-[3-(2-{[2-(dimethylamino)-2,3-dihydro-1H-inden-5-yl]amino}pyrimidin-4-yl)imidazo[1,2-a]pyridin-2-yl]phenyl}-5-methylthiophene-2-carboxamide The title compound was prepared as described in EXAMPLE 98D substituting EXAMPLE 106D for EXAMPLE 98C and 5-methylthiophene-2-carbonyl chloride for 2-(thiophen-2-yl)acetyl chloride. MS (ESI(+)) m/e 586 (M+H)$^+$, (ESI(−)) m/e 584 (M−H)$^-$; $^1$H-NMR (300 MHz, dimethylsulfoxide-d$_6$) δ 10.28 (s, 1H), 9.78 (s, 1H), 9.55 (d, 1H), 8.38 (d, 1H), 8.12 (m, 1H), 7.89-7.74 (m, 4H), 7.60-7.42 (m, 4H), 7.33 (m, 1H), 7.18 (d, 1H), 7.12 (m, 1H), 6.69 (d, 1H), 4.09 (m, 1H), 3.29 (d, 1H), 3.23 (d, 1H), 3.16-3.03 (m, 2H), 2.83 (m, 6H), 2.49 (s, 3H).

Example 235

2-chloro-N-(3-{3-[2-({4-[2-(dimethylamino)ethyl] phenyl}amino)pyrimidin-4-yl]imidazo[1,2-a]pyridin-2-yl}phenyl)-5-fluorobenzamide The title compound was prepared as described in EXAMPLE 4H, substituting EXAMPLE 195D for EXAMPLE 4G, and 2-chloro-5-fluorobenzoyl chloride for 2,6-difluorobenzoyl chloride. MS (ESI(+)) m/e 606 (M+H)$^+$; $^1$H NMR (300 MHz, dimethylsulfoxide-d$_6$) δ ppm 10.67 (s, 1H), 9.78 (s, 1H), 9.52 (d, 1H), 8.37 (d, 1H), 8.08 (m, 1H), 7.77 (m, 2H), 7.72 (d, 2H), 7.66 (m, 1H), 7.62 (m, 1H), 7.52 (m, 2H), 7.44 (m, 1H), 7.39 (m, 2H), 7.27 (m, 1H), 7.20 (d, 2H), 7.08 (m, 1H), 6.67 (d, 1H), 2.94 (m, 2H), 2.83 (s, 6H).

Example 236

2,6-difluoro-N-(3-{3-[2-({4-[2-(methylamino)ethyl] phenyl}amino)pyrimidin-4-yl]imidazo[1,2-a]pyridin-2-yl}phenyl)benzamide Example 236A Into a 20 mL vial was charged methylamine (6.52 ml, 13.04 mmol), 4-nitrophenethyl bromide (1.000 g, 4.35 mmol), and acetonitrile (4.35 ml). The reaction was stirred at room temperature for 48 hours. The reaction was poured onto saturated aqueous sodium bicarbonate and extracted with ethyl acetate. The organic layer was washed with brine, dried over MgSO$_4$, filtered and concentrated. The reaction was purified by flash chromatography using an Argonaut Flashmaster Solo, 10 g column (100% CH$_2$Cl$_2$ for 5 minutes, then to 10% methanol: CH$_2$Cl$_2$ over 20 minutes, then held 5 minutes.) to provide the title compound. MS (DCI(+)) m/e 181 (M+H)$^+$.

Example 236B

Into a 25 mL round bottom flask was charged EXAMPLE 236A (0.2762 g, 1.533 mmol) and tetrahydrofuran (6.0 ml). Trifluoroacetic anhydride (0.321 ml, 2.299 mmol) was added, and the reaction stirred at room temperature for 96 hours. The reaction was quenched with water and extracted with ethyl acetate. The organic layer was washed with saturated aqueous sodium bicarbonate and brine, dried over MgSO$_4$, filtered and concentrated to provide the title compound. MS (DCI(+)) m/e 294 (M+NH$_4$)$^+$.

Example 236C

The title compound was prepared as described in EXAMPLE 4G, substituting EXAMPLE 236B for EXAMPLE 4F. MS (DCI(+)) m/e 247 (M+H)$^+$.

Example 236D

The title compound was prepared as described in EXAMPLE 4F, substituting EXAMPLE 236C for EXAMPLE 4E. MS (ESI(+)) m/e 562 (M+H)$^+$.

Example 236E

The title compound was prepared as described in EXAMPLE 4G, substituting EXAMPLE 236D for EXAMPLE 4F. MS (ESI(+)) m/e 532 (M+H)$^+$.

Example 236F

Into a 4 mL vial was charged EXAMPLE 236E (40 mg, 0.075 mmol) and tetrahydrofuran (1.0 ml). 2,6-Difluorobenzoyl chloride (14.0 mg, 0.079 mmol) was added. The reaction was stirred at room temperature overnight. Water (1 ml) and lithium hydroxide (9.01 mg, 0.376 mmol) were added. The reaction was stirred at room temperature for 7 hours, then partitioned between ethyl acetate and water. The organic layer was washed with brine, dried over MgSO$_4$, filtered and concentrated to provide the title compound. MS (ESI(+)) m/e 576 (M+H)$^+$; $^1$H NMR (300 MHz, dimethylsulfoxide-d$_6$) δ ppm 10.89 (s, 1H), 9.67 (s, 1H), 9.52 (d, 1H), 8.35 (d, 1H), 8.04 (m, 1H), 7.78 (m, 2H), 7.64 (d, 2H), 7.57 (m, 1H), 7.49 (m, 1H), 7.44 (m, 1H), 7.39 (m, 1H), 7.25 (m, 2H), 7.13 (m, 2H), 7.07 (m, 1H), 6.65 (d, 1H), 2.70 (m, 4H), 2.33 (s, 3H).

Example 237

2-chloro-N-(3-{3-[2-({4-[2-(methylamino)ethyl] phenyl}amino)pyrimidin-4-yl]imidazo[1,2-a]pyridin-2-yl}phenyl)benzamide The title compound was prepared as described in EXAMPLE 236F, substituting 2-chlorobenzoyl chloride for 2,6-difluorobenzoyl chloride. MS (ESI(+)) m/e 574 (M+H)$^+$; $^1$H NMR (300 MHz, dimethylsulfoxide-d$_6$) δ ppm 10.59 (s, 1H), 9.65 (s, 1H), 9.52 (d, 1H), 8.34 (d, 1H), 8.07 (m, 1H), 7.82 (m, 1H), 7.76 (m, 1H), 7.63 (d, 2H), 7.57 (m, 2H), 7.50 (m, 2H), 7.47 (m, 1H), 7.44 (m, 1H), 7.37 (m, 1H), 7.13 (d, 2H), 7.07 (m, 1H), 6.64 (d, 1H), 2.68 (m, 4H), 2.32 (s, 3H).

Example 238

N-(3-{3-[2-({-4-[2-(methylamino)ethyl] phenyl}amino)pyrimidin-4-yl]imidazo[1,2-a]pyridin-2-yl}phenyl)-2-phenylacetamide The title compound was prepared as described in EXAMPLE 236F, substituting phenylacetyl chloride for 2,6-difluorobenzoyl chloride. MS (ESI(+)) m/e 554 (M+H)$^+$; $^1$H NMR (300 MHz, dimethylsulfoxide-d$_6$) δ ppm 10.26 (s, 1H), 9.66 (s, 1H), 9.52 (d, 1H), 8.31 (d, 1H), 7.92 (m, 1H), 7.82 (m, 1H), 7.73 (m, 2H), 7.63 (d, 2H), 7.48 (m, 1H), 7.37 (m, 1H), 7.32 (m, 4H), 7.27 (m, 2H), 7.13 (d, 2H), 7.07 (m, 1H), 6.60 (d, 1H), 3.64 (s, 2H), 2.68 (m, 4H), 2.32 (s, 3H).

Example 239

N-(3-{3-[2-({4-[2-(methylamino)ethyl] phenyl}amino)pyrimidin-4-yl]imidazo[1,2-a]pyridin-2-yl}phenyl)-2-thien-2-ylacetamide The title compound was prepared as described in EXAMPLE 236F, substituting 2-thiopheneacetyl chloride for 2,6-difluorobenzoyl chloride. MS (ESI(+)) m/e 560 (M+H)$^+$; $^1$H NMR (300 MHz, dimethylsulfoxide-d$_6$) δ ppm 10.30 (s, 1H), 9.66 (s, 1H), 9.52 (d, 1H), 8.32 (d, 1H), 7.91 (m, 1H), 7.82 (m, 1H), 7.73 (m, 2H), 7.63 (d, 2H), 7.49 (m, 1H), 7.39 (m, 2H), 7.30 (m, 1H), 7.13 (d, 2H), 7.07 (m, 1H), 6.98 (m, 2H), 6.60 (d, 1H), 3.97 (s, 2H), 2.68 (m, 4H), 2.31 (s, 3H).

Example 240

N-(3-{3-[2-({4-[2-(methylamino)ethyl]phenyl}amino)pyrimidin-4-yl]imidazo[1,2-a]pyridin-2-yl}phenyl)-N'-phenylurea Into a 4 mL vial was added EXAMPLE 236F (0.040 g, 0.075 mmol) in tetrahydrofuran (1.0 ml). Phenyl isocyanate (8.60 μl, 0.079 mmol) was added. The reaction was stirred at room temperature overnight. Water (1.0 ml) and lithium hydroxide (9.01 mg, 0.376 mmol) were added. The reaction was stirred at room temperature for 7 hours, then partitioned between ethyl acetate and water. The organic layer was washed with brine, dried over MgSO$_4$, filtered and concentrated to provide the title compound. MS (ESI(+)) m/e 555 (M+H)$^+$; $^1$H NMR (300 MHz, dimethylsulfoxide-d$_6$) δ ppm 9.66 (s, 1H), 9.55 (d, 1H), 8.80 (s, 1H), 8.64 (s, 1H), 8.34 (d, 1H), 7.75 (m, 2H), 7.63 (d, 2H), 7.54 (m, 1H), 7.49 (m, 1H), 7.44 (m, 3H), 7.37 (m, 1H), 7.25 (m, 3H), 7.13 (d, 2H), 7.07 (m, 1H), 6.96 (m, 1H), 6.63 (d, 1H), 2.67 (m, 4H), 2.30 (s, 3H).

Example 241

N-(3-{3-[2-({4-[4-(dimethylamino)piperidin-1-yl]phenyl}amino)pyrimidin-4-yl]imidazo[1,2-a]pyridin-2-yl}phenyl)-2-methylbenzamide The title compound was prepared as described in EXAMPLE 98D substituting EXAMPLE 188D for EXAMPLE 98C and 2-methylbenzoyl chloride for 2-(thiophen-2-yl)acetyl chloride. MS (ESI(+)) m/e 623 (M+H)$^+$, (ESI(−)) m/e 621 (M−H)$^-$; $^1$H-NMR (300 MHz, dimethylsulfoxide-d$_6$) δ 10.43 (s, 1H), 9.59 (s, 1H), 9.53 (m, 1H), 8.34 (d, 1H), 8.15 (s, 1H), 7.82 (m, 2H), 7.62-7.55 (m, 3H), 7.48-7.26 (m, 6H), 7.15 (t, 1H), 6.96 (d, 2H), 6.63 (d, 1H), 3.76 (m, 2H), 3.28 (m, 1H), 2.79 (d, 6H), 2.68 (m, 2H), 2.38 (s, 3H), 2.07 (m, 2H), 1.72 (m, 2H).

Example 242

N-(3-{3-[2-({4-[4-(dimethylamino)piperidin-1-yl]phenyl}amino)pyrimidin-4-yl]imidazo[1,2-a]pyridin-2-yl}phenyl)-2-thien-3-ylacetamide The title compound was prepared as described in EXAMPLE 98D substituting EXAMPLE 188D for EXAMPLE 98C and 2-(thiophen-3-yl)acetyl chloride for 2-(thiophen-2-yl)acetyl chloride. MS (ESI(+)) m/e 629 (M+H)$^+$, (ESI(−)) m/e 627 (M−H)$^-$; $^1$H-NMR (300 MHz, dimethylsulfoxide-d$_6$) δ 10.28 (s, 1H), 9.60 (s, 1H), 9.55 (m, 1H), 8.32 (d, 1H), 7.96 (m, 1H), 7.81 (d, 1H), 7.71 (m, 1H), 7.62-7.55 (m, 3H), 7.48 (m, 1H), 7.41 (t, 1H), 7.31 (m, 2H), 7.15 (t, 1H), 7.08 (dd, 1H), 6.97 (d, 2H), 6.58 (d, 1H), 3.76 (m, 2H), 3.66 (s, 2H), 3.28 (m, 1H), 2.79 (d, 6H), 2.70 (m, 2H), 2.07 (m, 2H), 1.72 (m, 2H).

Example 243

N-(3-{3-[2-({4-[2-(dimethylamino)ethyl]phenyl}amino)-5-fluoropyrimidin-4-yl]imidazo[1,2-a]pyridin-2-yl}phenyl)-2,6-difluorobenzamide Example 243A In a 25 ml pressure tube was mixed 1-(2-(3-bromophenyl)imidazo[1,2-a]pyridin-3-yl)ethanone (718 mg, 2.28 mmol) from EXAMPLE 313B in glacial acetic acid (6 ml). To this solution at ambient temperature was added a solution of bromine (0.153 ml, 2.96 mmol) in glacial acetic acid (1 ml). The mixture was stirred for 1 hour at ambient temperature, and then for 12 hours at 50° C. The mixture was poured into a flask with saturated NaHCO$_3$. This was stirred 10 minutes at ambient temperature. Chloroform was then added, and the two phase solution stirred another 10 minutes. The mixture was poured into a separatory funnel, and layers were separated. The organic layer was washed with brine, and then the aqueous layer was extracted again with chloroform. The combined organic extracts were dried with Na$_2$SO$_4$, filtered, and concentrated. The residue was purified by flash chromatography on a 60 g silica gel column using an AnaLogix IntelliFlash 280 system eluting with 30% ethyl acetate in hexanes to provide the title compound. MS (ESI(+)) m/e 395 (M+H)$^+$.

Example 243B

In a 10 ml sealed tube were mixed 2-bromo-1-(2-(3-bromophenyl)imidazo[1,2-a]pyridin-3-yl)ethanone (450 mg, 1.14 mmol) and potassium fluoride (223 mg, 5.71 mmol) in anhydrous N,N-dimethylacetamide (9 ml). The solution which formed was stirred 30 minutes at ambient temperature and then was heated to 80° C. for 4 hours. The mixture was cooled and water and saturated NaHCO$_3$ were added. The mixture was stirred about 20 minutes at ambient temperature. Solids which formed were filtered, washed with water, and dried. The filtrate was extracted with chloroform and 10% methanol in dichloromethane. The extracts were dried with Na$_2$SO$_4$, filtered, and concentrated. This material was combined with the solids collected earlier. The combined residues were purified by flash chromatography on a 40 g silica gel column using an AnaLogix IntelliFlash 280 system eluting with 30% ethyl acetate in hexanes to provide the title compound. MS (ESI(+)) m/e 334 (M+H)$^+$.

Example 243C

The title compound was prepared as described in EXAMPLE 1D, substituting EXAMPLE 243B for EXAMPLE 1C. MS (ESI(+)) m/e 389 (M+H)$^+$.

Example 243D

The title compound was prepared as described in EXAMPLE 1G, substituting EXAMPLE 195B for EXAMPLE 1F, and EXAMPLE 243C for EXAMPLE 1D. MS (ESI(+)) m/e 532 (M+H)$^+$.

Example 243E

To an oven-dried 5 ml microwave vial under N$_2$ were added EXAMPLE 243D (20 mg, 0.038 mmol), 2,6-difluorobenzamide (14.8 mg, 0.094 mmol), XANTPHOS (4,5-bis(diphenylphosphino)-9,9-dimethylxanthene) (5.44 mg, 9.41 μmol), tris(dibenzylideneacetone)dipalladium(0) (4.31 mg, 4.70

μmol), and cesium carbonate (39.9 mg, 0.122 mmol). These solids were mixed in degassed, anhydrous dioxane (2 ml). The mixture was heated in a Biotage Initiator microwave for 20 minutes at 160° C. The reaction was diluted with water, and product was extracted twice with chloroform. The extracts were washed with brine, dried with Na$_2$SO$_4$, filtered, and concentrated. The residue was purified by reverse-phase HPLC on a Shimadzu LC10HPLC system with a Phenominex Luna 10 micron C18(2) 100 150×30 mm column, eluting with a gradient of 35-75% CH$_3$CN/water/0.1% NH$_4$OH to provide the title compound. MS (ESI(+)) m/e 608 (M+H)$^+$, $^1$H NMR (400 MHz, dimethylsulfoxide-d$_6$) δ ppm 10.82 (s, 0.5 H) 9.74 (m, 1 H) 8.83 (d, 1 H) 8.59 (t, 1 H) 8.09 (s, 0.5 H) 7.77 (m, 1 H) 7.70 (m, 1 H) 7.66 (m, 1 H) 7.45-7.62 (m, 4 H) 7.40 (m, 3 H) 7.24 (m, 1 H) 7.07 (m, 3 H) 2.62 (m, 2 H) 2.40 (m, 2 H) 2.16 (s, 6 H).

Example 244

N-[3-(3-{2-[(4-piperidin-4-ylphenyl)amino]pyrimidin-4-yl}imidazo[1,2-a]pyridin-2-yl)phenyl]-2-thien-3-ylacetamide

Example 244A

A solution of EXAMPLE 68A (0.43 g, 0.87 mmol) and di-tert-butyl dicarbonate (0.23 g, 1.05 mmol) in CH$_2$Cl$_2$ (10 mL) was stirred at room temperature for 4 hours. The mixture was concentrated and the residue purified on a silica gel column, eluting with 60% ethyl acetate in hexane to provide the title compound. MS ESI(+): m/e 592.2 (M+H)$^+$.

Example 244B

Example 244A was reduced as described in EXAMPLE 1H to give the title compound. MS ESI(+): m/e 562.3 (M+H)$^+$.

Example 244C

N-[3-(3-{2-[(4-piperidin-4-ylphenyl)amino]pyrimidin-4-yl}imidazo[1,2-a]pyridin-2-yl)phenyl]-2-thien-3-ylacetamide, trifluoroacetic acid salt A solution of EXAMPLE 244B (95 mg, 0.17 mmol), 2-(thiophen-3-yl)acetyl chloride (33 mg, 0.20 mmol) and pyridine (27 mg, 0.34 mmol) in anhydrous CH$_2$Cl$_2$ (4 mL) and 1-methyl-2-pyrrolidinone (1 mL) was stirred at room temperature for 6 hours. The mixture was concentrated, and the residue was treated with 6 ml of CH$_2$Cl$_2$/trifluoroacetic acid (50/50) for 4 hours. The mixture was concentrated, and the residue was purified by reverse phase HPLC using a trifluoroacetic acid-buffered water-acetonitrile gradient to provide the title compound as the trifluoroacetic acid salt. MS ESI(+): m/e 586.3 (M+H)$^+$. $^1$H NMR (400 MHz, dimethylsulfoxide-d$_6$) δ ppm 10.62 (s, 1 H), 9.75 (s, 1 H), 9.55 (bd, 1 H), 8.59 (bd, 1 H), 8.35 (d, 1 H), 8.33 (bs, 1 H), 7.96 (s, 1 H), 7.80 (d, 1 H), 7.72 (d, 1 H), 7.68 (d, 2 H), 7.60 (t, 1 H), 7.46 (dd, 1 H), 7.40 (t, 1 H), 7.29-7.31 (m, 2 H), 7.14-7.16 (m, 3 H), 7.07 (d, 1 H), 6.62 (d, 1 H), 3.65(s, 2 H), 3.35-3.39 (m, 2 H), 2.92-3.04 (m, 2 H), 2.74-2.82(m, 1 H), 1.90-1.96 (m, 2 H), 1.72-1.82 (m, 2H).

Example 245

2-chloro-N-[3-(3-{2-[(4-piperidin-4-ylphenyl)amino]pyrimidin-4-yl}imidazo[1,2-a]pyridin-2-yl)phenyl]benzamide The title compound was prepared as described in EXAMPLE 244, substituting 2-chlorobenzoyl chloride for 2-(thiophen-3-yl)acetyl chloride. MS ESI(+): m/e 600.3 (M+H)$^+$. $^1$H NMR (400 MHz, dimethylsulfoxide-d$_6$) δ ppm 10.63 (s, 1 H), 9.77 (s, 1 H), 9.55 (bd, 1 H), 8.62 (bd, 1 H), 8.38 (d, 1 H), 8.35 (bs, 1 H), 8.11 (s, 1 H), 7.81-7.85 (m, 2 H), 7.68 (d, 2 H), 7.44-7.64 (m, 6 H), 7.38 (d, 1 H), 7.15-7.19 (m, 3 H), 6.68 (d, 1 H), 3.35-3.42 (m, 2 H), 2.92-3.04 (m, 2 H), 2.76-2.82(m, 1 H), 1.90-1.96 (m, 2 H), 1.72-1.82 (m, 2H).

Example 246

N-[3-(3-{2-[(3-piperidin-4-ylphenyl)amino]pyrimidin-4-yl}imidazo[1,2-a]pyridin-2-yl)phenyl]-2-thien-3-ylacetamide

Example 246A

The title compound was prepared as described in EXAMPLE 244A, substituting EXAMPLE 204A for EXAMPLE 68A. MS ESI(+): m/e 592.4 (M+H)$^+$.

Example 246B

Example 246A was reduced as described in EXAMPLE 1H to give the title compound. MS ESI(+): m/e 562.3 (M+H)$^+$.

Example 246C

N-[3-(3-{2-[(3-piperidin-4-ylphenyl)amino]pyrimidin-4-yl}imidazo[1,2-a]pyridin-2-yl)phenyl]-2-thien-3-ylacetamide, trifluoroacetic acid salt The title compound was prepared as described in EXAMPLE 244 from EXAMPLE 246B and 2-(thiophen-3-yl)acetyl chloride. MS ESI(+): m/e 586.3 (M+H)$^+$. $^1$H NMR (400 MHz, dimethylsulfoxide-d$_6$) δ ppm 10.26 (s, 1 H), 9.80 (s, 1 H), 9.55 (bd, 1 H), 8.57 (bd, 1 H), 8.37 (d, 1 H), 8.32 (bd, 1 H), 7.98 (s, 1 H), 7.80 (d, 1 H), 7.71 (d, 1 H), 7.67 (s, 1 H), 7.57-7.63 (m, 2 H), 7.46 (dd, 1 H), 7.41 (t, 1 H), 7.25-7.32 (m, 3 H), 7.15 (t, 1 H), 7.08 (d, 1 H), 6.85 (d, 1 H), 6.65 (d, 1 H), 3.66 (s, 1 H), 3.35-3.39 (m, 2 H), 2.92-3.04 (m, 2 H), 2.76-2.85(m, 1 H), 1.90-1.96 (m, 2 H), 1.72-1.82 (m, 2H).

Example 247

N-[3-(3-{2-[(3-piperidin-4-ylphenyl)amino]pyrimidin-4-yl}imidazo[1,2-a]pyridin-2-yl)phenyl]-2-thien-2-ylacetamide The title compound was prepared as described in EXAMPLE 244 from EXAMPLE 246B and 2-(thiophen-2-yl)acetyl chloride. MS ESI(+): m/e 586.3 (M+H)$^+$. NMR (400 MHz, dimethylsulfoxide-d$_6$) δ ppm 10.34 (s, 1 H), 9.80 (s, 1 H), 9.55 (bd, 1 H), 8.59 (bd, 1 H), 8.37 (d, 1 H), 8.32 (bd, 1 H), 7.98 (s, 1 H), 7.80 (d, 1 H), 7.71 (d, 1 H), 7.68 (s, 1 H), 7.62 (d, 1 H), 7.58 (d, 1 H), 7.43 (d, 1 H), 7.39 (dd, 1 H), 7.33 (d, 1 H), 7.27 (t, 1 H), 7.15 (t, 1 H), 6.96-6.98 (m, 2 H), 6.86 (d, 1 H), 6.65 (d, 1 H), 3.97 (s, 1 H), 3.33-3.39 (m, 2 H), 2.92-3.04 (m, 2 H), 2.76-2.85(m, 1 H), 1.90-1.96 (m, 2 H), 1.73-1.82 (m, 2H).

Example 248

2-chloro-N-[3-(3-{2-[(3-piperidin-4-ylphenyl)amino]pyrimidin-4-yl}imidazo[1,2-a]pyridin-2-yl)phenyl]benzamide The title compound was prepared as described in EXAMPLE 244 from EXAMPLE 246B and 2-chlorobenzoyl chloride. MS ESI(+): m/e 600.3 (M+H)+. 1H NMR (400 MHz, dimethylsulfoxide-d6) δ ppm 10.63 (s, 1 H), 9.81 (s, 1 H), 9.55 (bd, 1 H), 8.61 (bd, 1 H), 8.40 (d, 1 H), 8.34 (bd, 1 H), 8.13 (s, 1 H), 7.80-7.85 (m, 2 H), 7.67 (s, 1 H), 7.39-7.63 9m, 8 H), 7.27 (t, 1 H), 7.18 (t, 1 H), 6.86 (d, 1 H), 6.70 (d, 1 H), 3.33-3.39 (m, 2 H), 2.96-3.04 (m, 2 H), 2.76-2.85(m, 1 H), 1.90-1.96 (m, 2 H), 1.73-1.82 (m, 2H).

Example 249

N-[3-(3-{2-[(3-piperidin-4-ylphenyl)amino]pyrimidin-4-yl}imidazo[1,2-a]pyridin-2-yl)phenyl]thiophene-2-carboxamide The title compound was prepared as described in EXAMPLE 244 from EXAMPLE 246B and thiophen-2-yl-carbonyl chloride. MS ESI(+): m/e 572.3 (M+H)+. 1H NMR (400 MHz, dimethylsulfoxide-d6) δ ppm 10.36 (s, 1 H), 9.82 (s, 1 H), 9.59 (bd, 1 H), 8.62 (bd, 1 H), 8.39 (d, 1 H), 8.35 (bd, 1 H), 8.14 (s, 1 H), 8.05 (d, 1 H), 7.82-7.90 (m, 3 H), 7.68 (s, 1 H), 7.60-7.64 (m, 2 H), 7.47 (t, 1 H), 7.38 (d, 1 H), 7.16-7.29 (m, 3 H), 6.87 (d, 1 H), 6.69 (d, 1 H), 3.33-3.39 (m, 2 H), 2.92-3.04 (m, 2 H), 2.76-2.85 (m, 1 H), 1.90-1.96 (m, 2 H), 1.73-1.82 (m, 2H).

Example 250

2-methyl-N-[3-(3-{2-[(3-piperidin-4-ylphenyl)amino]pyrimidin-4-yl}imidazo[1,2-a]pyridin-2-yl)phenyl]benzamide The title compound was prepared as described in EXAMPLE 244 from EXAMPLE 246B and 2-methylbenzoyl chloride. MS ESI(+): in/e 580.3 (M+H)+. 1H NMR (400 MHz, dimethylsulfoxide-d6) δ ppm 10.40 (s, 1 H), 9.78 (s, 1 H), 9.54 (bd, 1 H), 8.58 (bd, 1 H), 8.39 (d, 1 H), 8.32 (bd, 1 H), 8.15 (s, 1 H), 7.82 (d, 2 H), 7.66 (s, 1 H), 7.58-7.61 (m, 2 H), 7.43-7.47 (m, 2 H), 7.36-7.38 (m, 2 H), 7.23-7.30 (m, 3 H), 7.16 (t, 1 H), 6.85 (d, 1 H), 6.69 (d, 1 H), 3.32-3.39 (m, 2 H), 2.95-3.02 (m, 2 H), 2.76-2.80 (m, 1 H), 2.36 (s, 3 H), 1.90-1.96 (m, 2 H), 1.71-1.80 (m, 2H).

Example 251

N-[3-(3-{2-[(3-piperidin-4-ylphenyl)amino]pyrimidin-4-yl}imidazo[1,2-a]pyridin-2-yl)phenyl]indoline-1-carboxamide Example 251A A mixture of 20% (weight) toluene solution of phosgene (6.62 ml, 12.59 mmol) and anhydrous CH2Cl2 (10 mL) was cooled with an ice-bath. A solution of indoline (1.0 g, 8.39 mmol) and N-ethyl-N-isopropylpropan-2-amine (3.01 ml, 16.78 mmol) in CH2Cl2 (10 mL) was added via a syringe dropwise. The resulting solution was stirred for 3 hours (from 0° C. to room temperature). The mixture was diluted with CH2Cl2, washed with 0.1 N aqueous HCl and brine. The solution was then dried (MgSO4), filtered and concentrated. The residue was purified on a silica gel column, eluting with 20-25% ethyl acetate in hexane, providing the title compound. MS DCI/NH3: m/e 199.0 (M+NH4+).

Example 251B

N-[3-(3-{2-[(3-piperidin-4-ylphenyl)amino]pyrimidin-4-yl}imidazo[1,2-a]pyridin-2-yl)phenyl]indoline-1-carboxamide, trifluoroacetic acid salt The title compound was prepared as described in EXAMPLE 244 from EXAMPLE 246B and EXAMPLE 251A. MS ESI(+): m/e 607.3 (M+H)+. 1H NMR (400 MHz, dimethylsulfoxide-d6) δ ppm 9.73 (s, 1 H), 9.51 (bd, 1 H), 8.58 (s, 1 H), 8.51 (bd, 1 H), 8.32 (d, 1 H), 8.24 (bd, 1 H), 7.91 (s, 1 H), 7.73-7.78 (m, 2 H), 7.52-7.61 (m, 4 H), 7.32 (t, 1 H), 7.18-7.21 (m, 2 H), 7.08-7.12 (m, 2 H), 7.02 (t, 1 H), 6.82 (d, 1 H), 6.78 (d, 1 H), 6.61 (d, 1 H), 3.26-3.33 (m, 4 H), 3.07-3.11 (m, 2 H), 2.88-2.96 (m, 2 H), 2.68-2.78 (m, 1 H), 1.82-1.86 (m, 2 H), 1.65-1.71 (m, 2H).

Example 252

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2,6-difluorobenzamide Example 252A In a 20 mL scintillation vial was charged EXAMPLE 164A (0.53 g, 1.526 mmol) and CH2Cl2 (3.55 mL). The resulting solution was treated with 4M HCl in dioxane (1.9 mL, 7.63 mmol) and the reaction was stirred at ambient temperature for 24 hours. The reaction was diluted with ether (15 mL), stirred at ambient temperature 10 minutes and filtered. The collected solid was washed with ether and dried. The solids were suspended in 10% methanol/CH2Cl2 (200 mL) and 5% aqueous Na2CO3 (50 mL). The bilayer was stirred for 4 hours. The organic layer was separated, washed with brine, dried over MgSO4, and concentrated to give the title compound. MS (DCI(+)) m/e 248.1 (M+H)+.

Example 252B

To a 20 mL scintillation vial was charged EXAMPLE 252A (0.29 g, 1.173 mmol), potassium carbonate (0.243 g, 1.759 mmol) and N,N-dimethylformamide (5.5 mL). The resulting mixture was cooled to 0° C., treated with iodoethane (0.196 g, 1.255 mmol) and stirred at ambient temperature for 20 hours. The reaction was filtered and the filtrate was concentrated on a rotary evaporator. The residue was purified by flash chromatography on a 10 g silica gel column with a step gradient (0%, 3%, and 5%) methanol in CH2Cl2 to provide the title compound. MS (DCI(+)) m/e 276.0 (M+H)+.

Example 252C

The title compound was prepared as described in EXAMPLE 45B, substituting EXAMPLE 252B for EXAMPLE 45A. MS (DCI(+)) m/e 245.9 (M+H)+.

Example 252D

A 5 mL Biotage microwave reaction vessel equipped with a stir bar was charged with EXAMPLE 4C (0.095 g, 27 mmol), EXAMPLE 252C (0.076 g, 311 mmol), 2-propanol (2 ml) and 4 M HCl in dioxane (0.081 mL, 0.324 mmol). The vessel was sealed and the mixture was heated in an oil bath at 125° C. for 3.5 hours. The reaction was cooled to ambient temperature and the suspension was filtered and washed with 2-propanol (1 mL). The solid collected was dissolved in 50 mL 10% methanol/CH$_2$Cl$_2$ and washed with 5% aqueous NaHCO$_3$ and brine. The organic layer was dried (Na$_2$SO$_4$), filtered, and concentrated to give the title compound. MS (ESI(+)) m/e 561.2 (M+H)$^+$.

Example 252E

The title compound was prepared as described in EXAMPLE 4G, substituting EXAMPLE 252D for EXAMPLE 4F. MS (ESI(+)) m/e 531.2 (M+H)$^+$.

Example 252F

The title compound was prepared as described in EXAMPLE 164F, substituting EXAMPLE 252E for EXAMPLE 164E. MS (ESI(+)) m/e 671.3 (M+H)$^+$; $^1$H NMR (300 MHz, METHANOL-d$_4$) δ ppm 9.61 (d, 1 H) 8.12 (d, 1 H) 7.93 (m, 1 H) 7.87 (m, 1 H) 7.65 (d, 1 H) 7.34-7.57 (m, 6 H) 7.10 (m, 2 H) 6.93 (t, 1 H) 6.58 (m, 2 H) 6.52 (d, 1 H) 3.22-3.39 (m, 4 H) 2.53-2.83 (m, 6 H) 1.99-2.13 (m, 2 H) 1.93 (m, 2 H) 1.15 (t, 3 H).

Example 253

N-{3-[3-(2-{[4-(7-ethyl-2,7-diazaspiro[4.4]non-2-yl) phenyl]amino}pyrimidin-4-yl)imidazo[1,2-a]pyridin-2-yl]phenyl}-2-thien-2-ylacetamide The title compound was prepared as described in EXAMPLE 194, substituting EXAMPLE 252E for EXAMPLE 4G and 2-(thiophen-2-yl)acetyl chloride for 1-methyl-1H-pyrazole-3-carbonyl chloride. MS (ESI(+)) m/e 655.3 (M+H)$^+$; $^1$H NMR (300 MHz, METHANOL-d$_4$) δ ppm 9.72 (d, 1 H) 8.11 (d, 1 H) 7.99 (s, 1 H) 7.66-7.80 (m, 3 H) 7.50 (t, 1 H) 7.39 (m, 3 H) 7.28 (m, 1 H) 7.17 (m, 1 H) 6.96 (m, 2 H) 6.64 (m, 2 H) 6.57 (d, 1 H) 3.90 (s, 2 H) 3.69-3.85 (m, 2 H) 3.16-3.46 (m, 8 H) 2.05-2.34 (m, 4 H) 1.38 (t, 3 H).

Example 254

N-{3-[3-(2-{[4-(7-ethyl-2,7-diazaspiro[4.4]non-2-yl) phenyl]amino}pyrimidin-4-yl)imidazo[1,2-a]pyridin-2-yl]phenyl}thiophene-2-carboxamide The title compound was prepared as described in EXAMPLE 164F, substituting EXAMPLE 252E for EXAMPLE 164E and thiophene-2-carbonyl chloride for 2,6-difluorobenzoyl chloride. MS (ESI(+)) m/e 641.3 (M+H)$^+$; $^1$H NMR (300 MHz, METHANOL-d$_4$) δ ppm 9.63 (d, 1 H) 8.11 (d, 1 H) 7.86-7.95 (m, 3 H) 7.72 (m, 1 H) 7.66 (m, 1 H) 7.49 (m, 2 H) 7.37 (m, 3 H) 7.18 (m, 1 H) 6.94 (m, 6.94 Hz, 1 H) 6.58 (m, 2 H) 6.54 (d, 1 H) 3.24-3.41 (m, 4 H) 2.64-2.89 (m, 6 H) 1.88-2.11 (m, 4 H) 1.18 (t, 3 H).

Example 255

N-[3-(3-{2-[(4-pyrrolidin-3-ylphenyl)amino]pyrimidin-4-yl}imidazo[1,2-a]pyridin-2-yl)phenyl]-2-thien-3-ylacetamide Example 255A In a 20-ml scintillation vial was mixed EXAMPLE 4C (0.682 g, 1.938 mmol), tert-butyl 3-(4-aminophenyl)pyrrolidine-1-carboxylate (0.61 g, 2.325 mmol) and iso-propanol (15 ml). To the mixture was then added 4 M HCl in dioxane (0.53 ml, 2.13 mmol). The mixture was stirred at 80° C. for 2 days, then concentrated. The solid was suspended in CH$_2$Cl$_2$ (25 mL) and 1-methyl-2-pyrrolidinone (5 ml). N-ethyl-N-isopropylpropan-2-amine (0.69 ml, 3.88 mmol) and di-tert-butyl dicarbonate (0.592 g, 2.71 mmol) were added and the mixture was stirred overnight. The mixture was quenched with water (50 ml) and extracted with CH$_2$Cl$_2$. The organic solution was dried, (MgSO$_4$), filtered and concentrated. The residue was purified on a silica gel column with 60% ethyl acetate in hexane, giving the title compound. MS ESI(+): m/e 578.2 (M+H)$^+$.

Example 255B

Example 255A was reduced as described in EXAMPLE 1H to give the title compound. MS ESI(+): m/e 548.3 (M+H)$^+$.

Example 255C

N-[3-(3-{2-[(4-pyrrolidin-3-ylphenyl)amino]pyrimidin-4-yl}imidazo[1,2-a]pyridin-2-yl)phenyl]-2-thien-3-ylacetamide, trifluoroacetic acid salt The title compound was prepared as described in EXAMPLE 244 from EXAMPLE 255B and 2-(thiophen-3-yl)acetyl chloride. MS ESI(+): m/e 572.2 (M+H)$^+$. $^1$H NMR (400 MHz, dimethylsulfoxide-d$_6$) δ ppm 10.29 (s, 1 H), 9.82 (s, 1 H), 9.56 (bs, 1 H), 8.92 (bs, 1 H), 8.87 (bs, 1 H), 8.37 (d, 1 H), 7.97 (s, 1 H), 7.81 (d, 1 H), 7.70-7.73 (m, 3 H), 7.60 (t, 1 H), 7.47 (dd, 1 H), 7.41 (t, 1 H), 7.30-7.31 (m, 2 H), 7.26 (d, 2 H), 7.17 (t, 1 H), 7.08 (d, 1 H), 6.65 (d, 1 H), 3.66 (s, 2 H), 3.58-3.65 (m, 1 H), 3.35-3.43 (m, 2 H), 3.21-3.26 (m, 1 H), 3.01-3.08 (m, 1 H), 2.31-2.37 (m, 1 H), 1.89-1.98 (m, 1H).

Example 256

N-[3-(3-{2-[(4-pyrrolidin-3-ylphenyl)amino]pyrimidin-4-yl}imidazo[1,2-a]pyridin-2-yl)phenyl]-2-thien-2-ylacetamide The title compound was prepared as described in EXAMPLE 244 from EXAMPLE 255B and 2-(thiophen-2-yl)acetyl chloride. MS ESI(+): m/e 572.2 (M+H)$^+$. $^1$H NMR (400 MHz, dimethylsulfoxide-d$_6$) δ ppm 10.38 (s, 1 H), 8.94 (s, 1 H), 9.57 (bs, 1 H), 8.96 (bs, 1 H), 8.91 (bs, 1 H), 8.38 (d, 1 H), 7.97 (s, 1 H), 7.82 (d, 1 H), 7.70-7.73 (m, 3 H), 7.62 (t, 1 H), 7.43 (t, 1 H), 7.39 (dd, 1 H), 7.33 (d, 1 H), 7.27 (d, 2 H), 7.19 (t, 1 H), 6.96-98 (m, 1 H), 6.65 (d, 1 H), 3.88 (s, 2 H), 3.58-3.65 (m, 1 H), 3.35-3.45 (m, 2 H), 3.21-3.26 (m, 1 H), 3.01-3.08 (m, 1 H), 2.31-2.37 (m, 1 H), 1.89-1.98 (m, 1H).

Example 257

2-chloro-N-[3-(3-{2-[(4-pyrrolidin-3-ylphenyl) amino]pyrimidin-4-yl}imidazo[1,2-a]pyridin-2-yl) phenyl]benzamide The title compound was prepared as described in EXAMPLE 244 from EXAMPLE 255B and 2-chlorobenzoyl chloride. MS ESI(+): m/e 586.3 (M+H)$^+$. $^1$H NMR (400 MHz, dimethylsulfoxide-d$_6$) δ ppm 10.64 (s, 1 H), 9.83 (s, 1 H), 9.57 (bs, 1 H), 8.95 (bs, 1 H), 8.89 (bs, 1 H), 8.39 (d, 1 H), 8.11 (s, 1 H), 7.81-7.84 (m, 2 H), 7.72 (d, 2 H), 7.56-7.62 (m, 3 H), 7.44-7.54 (m, 3 H), 7.38 (d, 1 H), 7.26 (d, 2 H), 7.18 (t, 1 H), 6.68 (d, 1 H), 3.58-3.65 (m, 1 H), 3.35-3.43 (m, 2 H), 3.21-3.26 (m, 1 H), 3.01-3.08 (m, 1 H), 2.31-2.37 (m, 1 H), 1.90-1.98 (m, 1H).

Example 258

2,3-difluoro-N-[3-(3-{2-[(4-pyrrolidin-3-yl-phenyl)amino]pyrimidin-4-yl}imidazo[1,2-a]pyridin-2-yl)phenyl]benzamide The title compound was prepared as described in EXAMPLE 244 from EXAMPLE 255B and 2,3-difluorobenzoyl chloride. MS ESI(+): m/e 588.3 (M+H)$^+$. $^1$H NMR (400 MHz, dimethylsulfoxide-d$_6$) δ ppm 10.69 (s, 1 H), 9.82 (s, 1 H), 9.56 (bs, 1 H), 8.90 (bs, 1 H), 8.87 (bs, 1 H), 8.39 (d, 1 H), 8.10 (s, 1 H), 7.81-7.82 (m, 2 H), 7.72 (d, 2 H), 7.57-7.65 (m, 2 H), 7.46-7.49 (m, 2 H), 7.39 (d, 1 H), 7.33-7.38 (m, 1 H), 7.26 (d, 2 H), 7.16 (t, 1 H), 6.68 (d, 1 H), 3.58-3.65 (m, 1 H), 3.35-3.45 (m, 2 H), 3.21-3.26 (m, 1 H), 3.01-3.08 (m, 1 H), 2.31-2.37 (m, 1 H), 1.91-1.98 (m, 1H).

Example 259

2,5-difluoro-N-[3-(3-{2-[(4-pyrrolidin-3-ylphenyl)amino]pyrimidin-4-yl) imidazo[1,2-a]pyridin-2-yl)phenyl]benzamide The title compound was prepared as described in EXAMPLE 244 from EXAMPLE 255B and 2,5-difluorobenzoyl chloride. MS ESI(+): m/e 588.3 (M+H)$^+$. $^1$H NMR (400 MHz, dimethylsulfoxide-d$_6$) δ ppm 10.64 (s, 1 H), 9.82 (s, 1 H), 9.57 (bs, 1 H), 8.92 (bs, 1 H), 8.87 (bs, 1 H), 8.39 (d, 1 H), 8.10 (s, 1 H), 7.82 (d, 2 H), 7.72 (d, 2 H), 7.60 (t, 1 H), 7.50-7.56 (m, 1 H), 7.39-7.49 (m, 4 H), 7.27 (d, 2 H), 7.17 (t, 1 H), 6.67 (d, 1 H), 3.58-3.65 (m, 1 H), 3.35-3.46 (m, 2 H), 3.21-3.26 (m, 1 H), 3.01-3.08 (m, 1 H), 2.31-2.37 (m, 1 H), 1.89-1.98 (m, 1H).

Example 260

2-methyl-N-[3-(3-{2-[(4-pyrrolidin-3-yl-phenyl)amino]pyrimidin-4-yl}imidazo[1,2-a]pyridin-2-yl)phenyl]benzamide The title compound was prepared as described in EXAMPLE 244 from EXAMPLE 255B and 2-methylbenzoyl chloride. MS ESI(+): m/e 566.3 (M+H)$^+$. $^1$H NMR (400 MHz, dimethylsulfoxide-d$_6$) δ ppm 10.43 (s, 1 H), 9.82 (s, 1 H), 9.57 (bs, 1 H), 8.93 (bs, 1 H), 8.87 (bs, 1 H), 8.39 (d, 1 H), 8.15 (s, 1 H), 7.82-7.85 (m, 2 H), 7.72 (d, 2 H), 7.61 (t, 1 H), 7.44-7.47 (m, 2 H), 7.36-7.41 (m, 2 H), 7.30-7.31 (m, 2 H), 7.26 (d, 2 H), 7.18 (t, 1 H), 6.69 (d, 1 H), 3.58-3.65 (m, 1 H), 3.35-3.43 (m, 2 H), 3.21-3.26 (m, 1 H), 3.01-3.08 (m, 1 H), 2.38 (s, 3 H), 2.31-2.37 (m, 1 H), 1.89-1.98 (m, 1H).

Example 261

2,6-dimethyl-N-[3-(3-{2-[(4-pyrrolidin-3-ylphenyl)amino]pyrimidin-4-yl}imidazo[1,2-a]pyridin-2-yl)phenyl]benzamide The title compound was prepared as described in EXAMPLE 244 from EXAMPLE 255B and 2,6-dimethylbenzoyl chloride. MS ESI(+): m/e 580.3 (M+H)$^+$. $^1$H NMR (400 MHz, dimethylsulfoxide-d$_6$) δ ppm 10.49 (s, 1 H), 9.81 (s, 1 H), 9.52 (bs, 1 H), 8.88 (bs, 1 H), 8.85 (bs, 1 H), 8.38 (d, 1 H), 8.14 (s, 1 H), 7.82 (d, 1 H), 7.80 (d, 1 H), 7.71 (d, 2 H), 7.59 (t, 1 H), 7.45 (t, 1 H), 7.39 (d, 1 H), 7.26 (d, 2 H), 7.21 (d, 1 H), 7.16 (t, 1 H), 7.11 (d, 2 H), 6.71 (d, 1 H), 3.58-3.65 (m, 1 H), 3.35-3.43 (m, 2 H), 3.21-3.26 (m, 1 H), 3.01-3.08 (m, 1 H), 2.31-2.37 (m, 1 H), 2.27 (s, 6 H), 1.90-1.98 (m, 1H).

Example 262

N-[3-(3-{2-[(4-pyrrolidin-3-ylphenyl)amino]pyrimidin-4-yl}imidazo[1,2-a]pyridin-2-yl)phenyl]thiophene-2-carboxamide The title compound was prepared as described in EXAMPLE 244 from EXAMPLE 255B and thiophene-2-carbonyl chloride. MS ESI(+): m/e 558.3 (M+H)$^+$. $^1$H NMR (400 MHz, dimethylsulfoxide-d$_6$) δ ppm 10.38 (s, 1 H), 9.84 (s, 1 H), 9.60 (bs, 1 H), 8.94 (bs, 1 H), 8.89 (bs, 1 H), 8.39 (d, 1 H), 8.13 (s, 1 H), 8.04 (d, 1 H), 7.87-7.90 (m, 3 H), 7.82 (d, 1 H), 7.72 (d, 2 H), 7.63 (t, 1 H), 7.36 (d, 1 H), 7.26 (d, 2 H), 7.17-7.24 (m, 3 H), 6.69 (d, 1 H), 3.58-3.65 (m, 1 H), 3.35-3.43 (m, 2 H), 3.21-3.26 (m, 1 H), 3.01-3.08 (m, 1 H), 2.31-2.37 (m, 1 H), 1.89-1.98 (m, 1H).

Example 263

N-(3-{3-[2-({4-[4-(dimethylamino)piperidin-1-yl]phenyl}amino)pyrimidin-4-yl]imidazo[1,2-a]pyridin-2-yl}phenyl)-2,3-difluorobenzamide The title compound was prepared as described in EXAMPLE 98D substituting EXAMPLE 188D for EXAMPLE 98C and 2,3-difluorobenzoyl chloride for 2-(thiophen-2-yl)acetyl chloride. MS (ESI(+)) m/e 645 (M+H)$^+$, (ESI(−)) m/e 643 (M−H)$^−$; $^1$H-NMR (300 MHz, dimethylsulfoxide-d$_6$) δ 10.69 (s, 1H), 9.60 (s, 1H), 9.52 (m, 1H), 8.35 (d, 1H), 8.10 (s, 1H), 7.81 (d, 2H), 7.68-7.55 (m, 4H), 7.51-7.45 (m, 2H), 7.40-7.32 (m, 2H), 7.15 (t, 1H), 6.96 (d, 2H), 6.62 (d, 1H), 3.76 (m, 2H), 3.28 (m, 1H), 2.79 (d, 6H), 2.69 (m, 2H), 2.07 (m, 2H), 1.71 (m, 2H).

Example 264

N-(3-{3-[2-({4-[4-(dimethylamino)piperidin-1-yl]phenyl}amino)pyrimidin-4-yl]imidazo[1,2-a]pyridin-2-yl}phenyl)-2,5-difluorobenzamide The title compound was prepared as described in EXAMPLE 98D substituting EXAMPLE 188D for EXAMPLE 98C and 2,5-difluorobenzoyl chloride for 2-(thiophen-2-yl)acetyl chloride. MS (ESI(+)) m/e 645 (M+H)$^+$, (ESI(−)) m/e 643 (M−H)$^−$; $^1$H-NMR (300 MHz, dimethylsulfoxide-d$_6$) δ 10.63 (s, 1H), 9.59 (s, 1H), 9.53 (m, 1H), 8.33 (d, 1H), 8.10 (s, 1H), 7.81 (d, 2H), 7.61-7.52 (m, 41-1), 7.50-7.37 (m, 4H), 7.15 (t, 1H), 6.96 (d, 2H), 6.61 (d, 1H), 3.76 (m, 2H), 3.29 (m, 1H), 2.79 (d, 6H), 2.68 (m, 2H), 2.07 (m, 2H), 1.71 (m, 2H).

Example 265

2-chloro-N-(3-{3-[2-({4-[4-(dimethylamino)piperidin-1-yl]phenyl}amino)pyrimidin-4-yl]imidazo[1,2-a]pyridin-2-yl}phenyl)-5-fluorobenzamide The title compound was prepared as described in EXAMPLE 98D substituting EXAMPLE 188D for EXAMPLE 98C and 2-chloro-5-fluorobenzoyl chloride for 2-(thiophen-2-yl)acetyl chloride. MS (ESI(+)) m/e 661 (M+H)$^+$, (ESI(−)) m/e 659 (M−H)$^−$; $^1$H-NMR (300 MHz, dimethylsulfoxide-d$_6$) δ 10.59 (s, 1H), 9.59 (m, 1H), 9.47 (s, 1H), 8.27 (d, 1H), 8.10 (m, 1H), 7.82 (m, 1H), 7.74 (d, 1H), 7.60 (d, 2H), 7.56-7.38 (m, 5H), 7.29 (dt, 1H), 7.06 (t, 1H), 6.93 (d, 2H), 6.62 (d, 1H), 3.76 (m, 2H), 3.32 (m, 1H), 2.83 (d, 6H), 2.73 (m, 2H), 2.11 (m, 2H), 1.79 (m, 2H).

Example 266

N-(3-{3-[2-({4-[4-(dimethylamino)piperidin-1-yl]phenyl}amino)pyrimidin-4-yl]imidazo[1,2-a]pyridin-2-yl}phenyl)indoline-1-carboxamide The title compound was prepared as described in EXAMPLE 98D substituting EXAMPLE 188D for EXAMPLE 98C and indoline-1-carbonyl chloride for 2-(thiophen-2-yl)acetyl chloride. MS (ESI(+)) m/e 650 (M+H)$^+$, (ESI(−)) m/e 648 (M−H)$^−$; $^1$H-NMR (300 MHz, dimethylsulfoxide-d$_6$) δ 9.63 (m, 1H), 9.48 (s, 1H), 8.61 (s, 1H), 8.28 (d, 1H), 7.98 (m, 1H), 7.89 (d, 1H), 7.74 (m, 2H), 7.60-7.52 (m, 3H), 7.96 (t, 1H), 7.24 (m, 1H), 7.18 (d, 1H), 7.10 (m, 2H), 6.92 (d, 2H), 6.86 (m, 1H), 6.64 (d, 1H), 4.19 (t, 2H), 3.76 (m, 2H), 3.30 (m, 1H), 3.20 (t, 2H), 2.82 (d, 6H), 2.72 (m, 2H), 2.12 (m, 2H), 1.81 (m, 2H).

Example 267

N-{3-[3-(2-{[2-(dimethylamino)-2,3-dihydro-1H-inden-5-yl]amino}pyrimidin-4-yl)imidazo[1,2-a]pyridin-2-yl]phenyl}-2,3-difluorobenzamide The title compound was prepared as described in EXAMPLE 98D substituting EXAMPLE 106D for EXAMPLE 98C and 2,3-difluorobenzoyl chloride for 2-(thiophen-2-yl)acetyl chloride. MS (ESI(+)) m/e 602 (M+H)$^+$, (ESI(−)) m/e 600 (M−H); $^1$H-NMR (300 MHz, dimethylsulfoxide-d$_6$) δ 10.54 (s, 1H), 9.68 (s, 1H), 9.60 (d, 1H), 8.32 (d, 1H), 8.11 (s, 1H), 7.86-7.79 (m, 2H), 7.74 (m, 1H), 7.55-7.38 (m, 6H), 7.30 (m, 1H), 7.16 (d, 1H), 7.07 (dt, 1H), 6.69 (d, 1H), 4.12 (m, 1H), 3.32 (d, 1H), 3.26 (d, 1H), 3.21-3.03 (m, 2H), 2.87 (m, 6H).

Example 268

N-{3-[3-(2-{[2-(dimethylamino)-2,3-dihydro-1H-inden-5-yl]amino}pyrimidin-4-yl)imidazo[1,2-a]pyridin-2-yl]phenyl}-2,5-difluorobenzamide The title compound was prepared as described in EXAMPLE 98D substituting EXAMPLE 106D for EXAMPLE 98C and 2,5-difluorobenzoyl chloride for 2-(thiophen-2-yl)acetyl chloride. MS (ESI(+)) m/e 602 (M+H)$^+$, (ESI(−)) m/e 600 (M−H); $^1$H-NMR (300 MHz, dimethylsulfoxide-d$_6$) δ 10.65 (s, 1H), 9.82 (s, 1H), 9.54 (m, 1H), 8.39 (d, 1H), 8.10 (s, 1H), 7.81 (d, 2H), 7.75 (s, 1H), 7.59-7.38 (m, 7H), 7.20-7.12 (m, 2H) 6.67 (d, 1H), 4.09 (m, 1H), 3.29 (d, 1H), 3.23 (d, 1H), 3.16-3.03 (m, 2H), 2.83 (m, 6H).

Example 269

2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}-5-fluorobenzamide The title compound was prepared as described in EXAMPLE 98D substituting EXAMPLE 106D for EXAMPLE 98C and 2-chloro-5-fluorobenzoyl chloride for 2-(thiophen-2-yl)acetyl chloride. MS (ESI(+)) m/e 618 (M+H)$^+$, (ESI(−)) m/e 616(M−H)$^−$; $^1$H-NMR (300 MHz, dimethylsulfoxide-d$_6$) δ 10.71 (s, 1H), 9.82 (s, 1H), 9.53 (m, 1H), 8.38 (d, 1H), 8.09 (m, 1H), 7.82-7.76 (m, 3H), 7.65-7.37 (m, 7H), 7.20-7.12 (m, 2H), 6.68 (d, 1H), 4.09 (m, 1H), 3.29 (d, 1H), 3.23 (d, 1H), 3.16-3.02 (m, 2H), 2.83 (m, 6H).

Example 270

N-{3-[3-(2-{[2-(dimethylamino)-2,3-dihydro-1H-inden-5-yl]amino}pyrimidin-4-yl)imidazo[1,2-a]pyridin-2-yl]phenyl)indoline-1-carboxamide The title compound was prepared as described in EXAMPLE 98D substituting EXAMPLE 106D for EXAMPLE 98C and indoline-1-carbonyl chloride for 2-(thiophen-2-yl)acetyl chloride. MS (ESI(+)) m/e 607 (M+H)$^+$, (ESI(−)) m/e 605 (M−H); $^1$H-NMR (300 MHz, dimethylsulfoxide-d$_6$) δ 9.83 (s, 1H), 9.58 (m, 1H), 8.69 (s, 1H), 8.39 (d, 1H), 7.98 (m, 1), 7.85 (d, 1H), 7.81 (d, 1H), 7.75 (m, 1H), 7.70 (m, 1H), 7.59 (t, 1H), 7.52 (m, 1H), 7.39 (t, 1H), 7.26-7.08 (m, 5H), 6.91 (m, 1H), 6.69 (d, 1H), 4.16-4.05 (m, 3H), 3.30-3.02 (m, 6H), 2.82 (m, 6H).

Example 271

N-(3-{3-[2-({3-[(dimethylamino)methyl]-4-methoxyphenyl}amino)pyrimidin-4-yl]imidazo[1,2-a]pyridin-2-yl}phenyl)-2,6-difluorobenzamide Example 271A To a 20 mL vial was charged 2-(bromomethyl)-1-methoxy-4-nitrobenzene (1 g, 4.06 mmol), triethylamine (1.7 mL, 12.19 mmol), and dimethylamine (2M in methanol, 6.1 mL, 12.19 mmol) in acetonitrile. The mixture was stirred at ambient temperature for 20 hours. The reaction was concentrated under reduced pressure. The residue was partitioned between saturated aqueous NaHCO$_3$ and ethyl acetate. The organic layer was washed with brine, dried over Na$_2$SO$_4$, filtered, and concentrated to give the title compound. MS (DCI(+)) m/e 211.0 (M+H)$^+$.

Example 271B

The title compound was prepared as described in EXAMPLE 45B, substituting EXAMPLE 271A for EXAMPLE 45A. MS (DCI(+)) m/e 181.0 (M+H)$^+$.

Example 271C

The title compound was prepared as described in EXAMPLE 252D, substituting EXAMPLE 271B for EXAMPLE 252C. MS (ESI(+)) m/e 496.1 (M+H)$^+$.

Example 271D

The title compound was prepared as described in EXAMPLE 4G, substituting EXAMPLE 271C for EXAMPLE 4F. MS (ESI(+)) m/e 466.1 (M+H)$^+$.

Example 271E

The title compound was prepared as described in EXAMPLE 4H, substituting EXAMPLE 271D for EXAMPLE 4G. MS (ESI(+)) m/e 606.3 (M+H)$^+$; $^1$H NMR (300 MHz, dimethylsulfoxide-d$_6$) δ ppm 10.95 (s, 1 H) 9.77 (s, 1 H) 9.50 (m, 1 H) 9.14 (m, 1 H) 8.36 (d, 1 H) 8.11 (m, 1

H) 7.38-7.82 (m, 8 H) 7.26 (m, 2 H) 7.12 (m, 2 H) 6.66 (d, 1 H) 4.22 (d, 2 H) 3.84 (s, 3 H) 2.72 (d, 6 H).

Example 272

N-(3-{3-[2-({3-[(dimethylamino)methyl]-4-methoxyphenyl}amino)pyrimidin-4-yl]imidazo[1,2-a]pyridin-2-yl}phenyl)-2,3-difluorobenzamide The title compound was prepared as described in EXAMPLE 4H, substituting EXAMPLE 271D for EXAMPLE 4G and 2,3-difluorobenzoyl chloride for 2,6-difluorobenzoyl chloride. MS (ESI(+)) m/e 606.3 (M+H)$^+$; $^1$H NMR (300 MHz, dimethylsulfoxide-d$_6$) δ ppm 10.71 (s, 1 H) 9.77 (s, 1 H) 9.51 (m, 1 H) 9.15 (m, 1 H) 8.36 (d, 1 H) 8.12 (m, 1 H) 7.80 (m, 3 H) 7.32-7.73 (m, 7 H) 7.11 (m, 2 H) 6.66 (d, 1 H) 4.22 (d, 2 H) 3.84 (s, 3 H) 2.72 (d, 6 H).

Example 273

N-(3-{3-[2-({3-[(dimethylamino)methyl]-4-methoxyphenyl}amino)pyrimidin-4-yl]imidazo[1,2-a]pyridin-2-yl}phenyl)-2-thien-2-ylacetamide The title compound was prepared as described in EXAMPLE 4H, substituting EXAMPLE 271D for EXAMPLE 4G and 2-(thiophen-2-yl)acetyl chloride for 2,6-difluorobenzoyl chloride. MS (ESI(+)) m/e 590.3 (M+H)$^+$; $^1$H NMR (300 MHz, dimethylsulfoxide-d$_6$) δ ppm 10.37 (s, 1 H) 9.76 (s, 1 H) 9.51 (m, 1 H) 9.13 (m, 1 H) 8.34 (d, 1 H) 7.99 (m, 1 H) 7.78 (m, 2 H) 7.69 (m, 2 H) 7.56 (m, 1 H) 7.39 (m, 2 H) 7.30 (m, 1 H) 7.12 (m, 2 H) 6.98 (m, 2 H) 6.62 (d, 1 H) 4.21 (d, 2 H) 3.88 (s, 2 H) 3.84 (s, 3 H) 2.72 (d, 6 H).

Example 274

N-(3-{3-[2-({3-[(dimethylamino)methyl]-4-methoxyphenyl}amino)pyrimidin-4-yl]imidazo[1,2-a]pyridin-2-yl}phenyl)-N-thien-2-ylurea The title compound was prepared as described in EXAMPLE 7, substituting EXAMPLE 271D for EXAMPLE 4G and 2-isocyanatothiophene for isocyanatobenzene. MS (ESI(+)) m/e 591.3 (M+H)$^+$; $^1$H NMR (300 MHz, dimethylsulfoxide-d$_6$) δ ppm 9.80 (s, 1 H) 9.76 (s, 1 H) 9.54 (m, 1 H) 9.13 (m, 1 H) 9.04 (s, 1 H) 8.35 (d, 1 H) 7.88 (m, 1 H) 7.79 (m, 2 H) 7.70 (m, 1 H) 7.49-7.60 (m, 2 H) 7.38 (t, 1 H) 7.22 (m, 1 H) 7.11 (m, 2 H) 6.79-6.88 (m, 2 H) 6.65 (d, 1 H) 6.56 (dd, 1 H) 4.22 (d, 2 H) 3.84 (s, 3 H) 2.72 (d, 6 H).

Example 275

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]thiophene-2-carboxamide Example 275A To a 4 mL vial was charged EXAMPLE 402G (0.6 g, 1.867 mmol), (S)-3-fluoropyrrolidine hydrochloride (0.586 g, 4.67 mmol) and 2.5 mL acetonitrile. The resulting suspension was cooled to 0° C. and treated with triethylamine (1.3 mL, 9.34 mmol). The mixture was allowed to stir at ambient temperature for 20 hours. The reaction was concentrated under reduced pressure. The residue was partitioned between 1N HCl (30 mL) and ether (25 mL). The organic layer was separated and discarded. The aqueous layer was basified to pH 9 with 3N NaOH and was then extracted with 2×35 mL ether. The combined organic layers were dried over Na$_2$SO$_4$, filtered, and concentrated to give the title compound. MS (ESI(+)) m/e 239.0 (M+H)$^+$.

Example 275B

The title compound was prepared as described in EXAMPLE 4E, substituting EXAMPLE 275A for EXAMPLE 4D. MS (DCI(+)) m/e 209.1 (M+H)$^+$.

Example 275C

The title compound was prepared as described in EXAMPLE 252D, substituting EXAMPLE 275B for EXAMPLE 252C. MS (ESI(+)) m/e 524.2 (M+H)$^+$.

Example 275D

The title compound was prepared as described in EXAMPLE 4G, substituting EXAMPLE 275C for EXAMPLE 4F. MS (ESI(+)) m/e 494.1 (M+H)$^+$.

Example 275E

The title compound was prepared as described in EXAMPLE 4H, substituting EXAMPLE 275D for EXAMPLE 4G and thiophene-2-carbonyl chloride for 2,6-difluorobenzoyl chloride. MS (ESI(+)) m/e 604.3 (M+H)$^+$; $^1$H NMR (300 MHz, methanol-d$_4$) δ ppm 9.83 (d, 1 H) 8.38 (d, 1 H) 8.24 (m, 1 H) 7.94 (m, 3 H) 7.75 (m, 3 H) 7.59 (m, 2 H) 7.44 (m, 2 H) 7.34 (t, 1 H) 7.19 (dd, 1 H) 7.03 (d, 1 H) 6.76 (d, 1 H) 5.35-5.56 (m, 1 H) 3.50-4.01 (m, 5 H) 3.07 (m, 3 H) 2.25-2.51 (m, 2 H).

Example 276

2,6-difluoro-N-[3-(3-{2-[(3-{2-[(3S)-3-fluoropyrrolidin-1-yl)ethyl}phenyl)amino]pyrimidin-4-yl}imidazo[1,2-a]pyridin-2-yl)phenyl]benzamide The title compound was prepared as described in EXAMPLE 4H, substituting EXAMPLE 275D for EXAMPLE 4G. MS (ESI(+)) m/e 634.3 (M+H)$^+$; $^1$H NMR (300 MHz, methanol-d$_4$) δ ppm 9.78 (d, 1 H) 8.39 (d, 1 H) 8.27 (m, 1 H) 7.91 (m, 2 H) 7.72 (m, 2 H) 7.46-7.62 (m, 4 H) 7.30-7.42 (m, 2 H) 7.01-7.16 (m, 3 H) 6.77 (d, 1 H) 5.34-5.54 (m, 1 H) 3.48-4.02 (m, 5 H) 3.07 (m, 3 H) 2.29-2.50 (m, 2 H).

Example 277

2-chloro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide The title compound was prepared as described in EXAMPLE 4H, substituting EXAMPLE 275D for EXAMPLE 4G and 2-chlorobenzoyl chloride for 2,6-difluorobenzoyl chloride. MS (ESI(+)) m/e 632.2 (M+H)$^+$; $^1$H NMR (300 MHz, methanol-d$_4$) δ ppm 9.77 (d, 1 H) 8.38 (d, 1 H) 8.27 (m, 1 H) 7.92 (m, 2 H) 7.73 (m, 2 H) 7.30-7.61 (m, 9

H) 7.02 (m, 1 H) 6.77 (d, 1 H) 5.34-5.54 (m, 1 H) 3.48-3.99 (m, 5 H) 3.06 (m, 3 H) 2.26-2.54 (m, 2 H).

Example 278

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]-N'-thien-2-ylurea The title compound was prepared as described in EXAMPLE 7, substituting EXAMPLE 275D for EXAMPLE 4G and 2-isocyanatothiophene for isocyanatobenzene. MS (ESI(+)) m/e 619.3 (M+H)$^+$; $^1$H NMR (300 MHz, methanol-d$_4$) δ ppm 9.80 (d, 1 H) 8.38 (d, 1 H) 7.92-8.05 (m, 3 H) 7.72 (m, 1 H) 7.41-7.59 (m, 4 H) 7.33 (m, 2 H) 7.03 (m, 1 H) 6.83 (m, 2 H) 6.77 (d, 1 H) 6.61 (dd, 1 H) 5.35-5.53 (m, 1 H) 3.49-4.01 (m, 5 H) 3.06 (m, 3 H) 2.27-2.52 (m, 2 H).

Example 279

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]-N'-thien-3-ylurea The title compound was prepared as described in EXAMPLE 7, substituting EXAMPLE 275D for EXAMPLE 4G and 3-isocyanatothiophene for isocyanatobenzene. MS (ESI(+)) m/e 619.3 (M+H)$^+$; NMR (300 MHz, methanol-d$_4$) δ ppm 9.79 (d, 1 H) 8.38 (d, 1 H) 7.91-8.03 (m, 3 H) 7.73 (m, 1 H) 7.24-7.58 (m, 8 H) 7.02 (m, 2 H) 6.77 (d, 1 H) 5.35-5.53 (m, 1 H) 3.49-4.01 (m, 5 H) 3.06 (m, 3 H) 2.26-2.52 (m, 2 H).

Example 280

N-[3-(3-{2-[(4-pyrrolidin-3-ylphenyl)amino]pyrimidin-4-yl}imidazo[1,2-a]pyridin-2-yl)phenyl]indoline-1-carboxamide The title compound was prepared as described in EXAMPLE 244 from EXAMPLE 255B and EXAMPLE 251A. MS ESI(+): m/e 593.3 (M+H)$^+$. $^1$H NMR (400 MHz, dimethylsulfoxide-d$_6$) δ ppm 9.82 (s, 1 H), 9.60 (bd, 1 H), 8.92 (bs, 2 H), 8.68 (s, 1 H), 8.40 (d, 1 H), 7.99 (s, 1 H), 7.82-7.86 (m, 2 H), 7.70-7.74 (m, 3 H), 7.65 (t, 1 H), 7.41 (t, 1 H), 7.26-7.28 (m, 3 H), 7.19-7.22 (m, 2 H), 7.10 (t, 1 H), 6.90 (t, 1 H), 6.69 (d, 1 H), 4.14 (t, 2 H), 3.58-3.65 (m, 1 H), 3.37-3.44 (m, 2 H), 3.21-3.29 (m, 1 H), 3.17 (t, 2 H), 3.01-3.10 (m, 1 H), 2.30-2.38 (m, 1 H), 1.89-1.99 (m, 1H).

Example 281

N-ethyl-N-phenyl-N'-[3-(3-{2-[(4-pyrrolidin-3-ylphenyl)amino]pyrimidin-4-yl}imidazo[1,2-a]pyridin-2-yl)phenyl]urea

Example 281A

The title compound was prepared as described in EXAMPLE 251A, substituting N-ethyl aniline for indoline. MS DCI/NH$_3$: m/e 201.0 (M+HH$_4$).

Example 281B

N-ethyl-N-phenyl-N'-[3-(3-{2-[(4-pyrrolidin-3-ylphenyl)amino]pyrimidin-4-yl}imidazo[1,2-a]pyridin-2-yl)phenyl]urea, trifluoroacetic acid salt The title compound was prepared as described in EXAMPLE 244 from EXAMPLE 255B and EXAMPLE 281A. MS ESI(+): m/e 595.4 (M+H)$^+$. $^1$H NMR (400 MHz, dimethylsulfoxide-d$_6$) δ ppm 9.80 (s, 1 H), 9.60 (bd, 1 H), 8.93 (bs, 2 H), 8.38 (d, 1 H), 8.07 (s, 1 H), 7.79-7.81 (m, 2 H), 7.72 (d, 2 H), 7.62 (t, 1 H), 7.55 (d, 1 H), 7.42-7.45 (m, 2 H), 7.26-7.33 (m, 6 H), 7.16-7.20 (m, 2 H), 6.65 (d, 1 H), 3.70 (t, 2 H), 3.58-3.65 (m, 1 H), 3.37-3.44 (m, 2 H), 3.19-3.30 (m, 1 H), 3.01-3.10 (m, 1 H), 2.30-2.38 (m, 1 H), 1.89-1.99 (m, 1H), 1.05 (t, 3 H).

Example 282

N-[3-(3-{2-[(4-pyrrolidin-3-ylphenyl)amino]pyrimidin-4-yl)imidazo[1,2-a]pyridin-2-yl)phenyl]-1-benzothiophene-7-carboxamide To a solution of EXAMPLE 255B (65 mg, 0.12 mmol) and benzo[b]thiophene-7-carboxylic acid in anhydrous CH$_2$Cl$_2$ (4 mL) and 1-methyl-2-pyrrolidinone (1 mL) was added N$_1$-((ethylimino)methylene)-N$_3$,N$_3$-dimethylpropane-1,3-diamine hydrochloride (45 mg, 0.24 mmol). The solution was stirred at room temperature overnight. The mixture was evaporated to dryness, and the residue was treated with 6 ml of CH$_2$Cl$_2$/trifluoroacetic acid (50/50) for 4 hours. The mixture was concentrated and the residue was submitted for HPLC purification on a reverse phase column eluted with a trifluoroacetic acid buffered water-acetonitrile gradient to give the title compound. MS ESI(+): m/e 608.3 (M+H)$^+$. $^1$H NMR (400 MHz, dimethylsulfoxide-d$_6$) δ ppm 10.58 (s, 1 H), 9.80 (s, 1 H), 9.57 (bd, 1 H), 8.86 (bs, 2 H), 8.40 (d, 1 H), 8.26 (s, 1 H), 8.20 (d, 1 H), 8.14 (d, 1 H), 7.95 (d, 1 H), 7.86 (d, 1 H), 7.83 (d, 1 H), 7.73 (d, 2 H), 7.47-7.62 (m, 4 H), 7.39 (d, 1 H), 7.26 (d, 2 H), 7.16 (t, 1 H), 6.72 (d, 1 H), 3.58-3.65 (m, 1 H), 3.37-3.44 (m, 2 H), 3.19-3.30 (m, 1 H), 3.01-3.10 (m, 1 H), 2.30-2.38 (m, 1 H), 1.89-1.99 (m, 1H).

Example 283

N-(3-{3-[2-({4-[2-(dimethylamino)ethyl]phenyl}amino)-5-fluoropyrimidin-4-yl]imidazo[1,2-a]pyridin-2-yl}phenyl)-2-thien-2-ylacetamide The title compound was prepared as described in EXAMPLE 243E, substituting 2-(thiophen-2-yl)acetamide for 2,6-difluorobenzamide. MS (ESI(+)) m/e 592 (M+H)$^+$, $^1$H NMR (400 MHz, dimethylsulfoxide-d$_6$) δ ppm 10.25 (s, 0.5 H) 9.74 (s, 1 H) 8.82 (d, 1 H) 8.58 (m, 1 H) 7.97 (s, 0.5 H) 7.77 (d, 1 H) 7.65 (m, 1 H) 7.56 (m, 2 H) 7.48 (m, 1 H) 7.38 (m, 2 H) 7.26-7.33 (m, 2 H) 7.14-7.21 (m, 1 H) 7.08 (m, 3 H) 6.96 (m, 1 H) 3.85 (s, 2 H) 2.63 (m, 2 H) 2.41 (m, 2 H) 2.17 (s, 6 H).

Example 284

2,6-difluoro-N-{3-[3-(2-{[4-(4-hydroxypiperidin-1-yl)phenyl]amino)}pyrimidin-4-yl)imidazo[1,2-a]pyridin-2-yl]phenyl}benzamide

Example 284A

The title compound was prepared as described in EXAMPLE 221A, substituting 4-(methoxymethoxy)piperidine for N,N-dimethylpyrrolidin-3-amine. MS (DCI(+)) m/e 267 (M+H)$^+$.

Example 284B

The title compound was prepared as described in EXAMPLE 1H, substituting EXAMPLE 284A for EXAMPLE 1G. MS (DCI(+)) m/e 237 (M+H)$^+$.

Example 284C

The title compound was prepared as described in EXAMPLE 4F, substituting EXAMPLE 284B for EXAMPLE 4E. MS (ESI(+)) m/e 508 (M+H)$^+$.

Example 284D

The title compound was prepared as described in EXAMPLE 4G, substituting EXAMPLE 284C for EXAMPLE 4F. MS (ESI(+)) m/e 478 (M+H)$^+$.

Example 284E

The title compound was prepared as described in EXAMPLE 4H, substituting EXAMPLE 284D for EXAMPLE 4G. MS (ESI(+)) m/e 618 (M+H)$^+$, $^1$H NMR (400 MHz, dimethylsulfoxide-d$_6$) δ ppm 10.88 (s, 1 H) 9.48 (m, 2 H) 8.30 (m, 1 H) 8.03 (s, 1 H) 7.80 (d, 1 H) 7.75 (d, 1 H) 7.43-7.63 (m, 5 H) 7.39 (m, 1 H) 7.25 (m, 2 H) 7.05 (t, 1 H) 6.91 (m, 2 H) 6.59 (d, 1 H) 4.65 (bs, 1 H) 3.61 (m, 1 H) 3.45 (m, 2 H) 2.78 (m, 2 H) 1.83 (m, 2 H) 1.50 (m, 2 H).

Example 285

2-chloro-N-{3-[3-(2-{[4-(4-hydroxypiperidin-1-yl)phenyl]amino}pyrimidin-4-yl)imidazo[1,2-a]pyridin-2-yl]phenyl}benzamide The title compound was prepared as described in EXAMPLE 4H, substituting EXAMPLE 284D for EXAMPLE 4G, and 2-chlorobenzoyl chloride for 2,6-difluorobenzoyl chloride. MS (ESI(+)) m/e 617 (M+H)$^+$, $^1$H NMR (400 MHz, dimethylsulfoxide-d$_6$) δ ppm 10.58 (s, 1 H) 9.46 (m, 2 H) 8.30 (m, 1 H) 8.06 (s, 1 H) 7.82 (d, 1 H) 7.75 (d, 1 H) 7.40-7.59 (m, 8 H) 7.37 (m, 1 H) 7.05 (t, 1 H) 6.90 (m, 2 H) 6.58 (d, 1 H) 4.64 (s, 1 H) 3.61 (m, 1 H) 3.45 (m, 2 H) 2.78 (m, 2 H) 1.83 (m, 2 H) 1.50 (m, 2 H).

Example 286

N-{3-[3-(2-{[4-(4-hydroxypiperidin-1-yl)phenyl]amino}pyrimidin-4-yl)imidazo[1,2-a]pyridin-2-yl]phenyl}thiophene-2-carboxamide The title compound was prepared as described in EXAMPLE 4H, substituting EXAMPLE 284D for EXAMPLE 4G, and thiophene-2-carbonyl chloride for 2,6-difluorobenzoyl chloride. MS (ESI(+)) m/e 588 (M+H)$^+$, $^1$H NMR (400 MHz, dimethylsulfoxide-d$_6$) δ ppm 10.32 (s, 1 H) 9.48 (m, 2 H) 8.31 (m, 1 H) 8.08 (s, 1 H) 8.04 (s, 1 H) 7.88 (m, 2 H) 7.73 (d, 1 H) 7.49 (m, 3 H) 7.43 (t, 1 H) 7.33 (d, 1 H) 7.22 (dd, 1 H) 7.06 (m, 1 H) 6.90 (m, 2 H) 6.59 (m, 1 H) 4.63 (bs, 1 H) 3.60 (m, 1 H) 3.45 (m, 2 H) 2.75 (m, 2 H) 1.81 (m, 2 H) 1.50 (m, 2 H).

Example 287

N-{3-[3-(2-{[4-(4-hydroxypiperidin-1-yl)phenyl]amino}pyrimidin-4-yl)imidazo[1,2-a]pyridin-2-yl]phenyl}-2-thien-2-ylacetamide The title compound was prepared as described in EXAMPLE 4H, substituting EXAMPLE 284D for EXAMPLE 4G, and 2-thiopheneacetyl chloride for 2,6-difluorobenzoyl chloride. MS (ESI(+)) m/e 602 (M+H)$^+$, $^1$H NMR (500 MHz, dimethylsulfoxide-d$_6$) δ ppm 10.32 (s, 1 H) 9.48 (m, 2 H) 8.28 (d, 1 H) 7.91 (s, 1 H) 7.74 (d, 2 H) 7.50 (m, 3 H) 7.39 (m, 2 H) 7.30 (d, 1 H) 7.05 (t, 1 H) 6.98 (m, 2 H) 6.90 (m, 2 H) 6.54 (d, 1 H) 4.67 (s, 1 H) 3.87 (s, 2 H) 3.61 (m, 1 H) 3.45 (m, 2 H) 2.77 (m, 2 H) 1.83 (m, =2 H) 1.50 (m, 2 H).

Example 288

N-{3-(3-{2-[(4-{2-[(N,N-dimethylglycyl)amino]ethyl}phenyl)amino]pyrimidin-4-yl}imidazo[1,2-a]pyridin-2-yl)phenyl]-2,6-difluorobenzamide

Example 288A

A 100 ml round bottom flask was charged with sodium azide (0.848 g, 13.0 mmol) and anhydrous dimethylsulfoxide (26 ml) To this solution at ambient temperature was added 1-(2-bromoethyl)-4-nitrobenzene (3.00 g, 13.0 mmol) as a solid. Solution which formed was stirred 12 hours at ambient temperature. The reaction mixture was diluted with ethyl acetate, and washed with water and brine. Organic layer dried with Na$_2$SO$_4$, filtered, and concentrated to provide the title compound. MS (DCI(+)) m/e 193 (M+H)$^+$.

Example 288B

A 100 ml round bottom flask was charged with EXAMPLE 288A (1.40 g, 7.29 mmol) and tetrahydrofuran (30 ml). To this solution at ambient temperature were added triphenylphosphine (2.10 g, 8.01 mmol) and water (0.150 ml, 8.33 mmol). The reaction mixture was stirred for 60 hours at ambient temperature. The reaction mixture was diluted with 1N H$_3$PO$_4$, and mixture was extracted with ethyl acetate. The aqueous layer was made slightly basic (pH ~9) with 2M Na$_2$CO$_3$, and product was extracted out with dichloromethane and 10% methanol in dichloromethane. The extracts were dried with Na$_2$SO$_4$, filtered, and concentrated to provide the title compound. MS (DCI(+)) m/e 167 (M+H)$^+$.

Example 288C

A 25 ml round bottom flask was charged with EXAMPLE 288B (169 mg, 1.017 mmol), N,N-dimethylglycine (115 mg, 1.119 mmol), N-(3-dimethylaminopropyl)-N'-ethylcarbodiimide hydrochloride (234 mg, 1.220 mmol), and 1-hydroxybenzotriazole (187 mg, 1.220 mmol). Tetrahydrofuran (2 ml) was added, and the solution stirred 12 hours at ambient temperature. The reaction mixture was diluted with water and ethyl acetate, and the layers were separated. The organic layer was washed with saturated NaHCO$_3$ and brine. The organic layer was dried with Na$_2$SO$_4$, filtered, and concentrated to provide the title compound. MS (DCI(+)) m/e 252 (M+H)$^+$.

Example 288D

The title compound was prepared as described in EXAMPLE 1H, substituting EXAMPLE 288C for EXAMPLE 1G. MS (DCI(+)) m/e 222 (M+H)$^+$.

Example 288E

The title compound was prepared as described in EXAMPLE 4F, substituting EXAMPLE 288D for EXAMPLE 4E. MS (ESI(+)) m/e 537 (M+H)$^+$.

Example 288F

The title compound was prepared as described in EXAMPLE 4G, substituting EXAMPLE 288E for EXAMPLE 4F. MS (ESI(+)) m/e 507 (M+H)+.

Example 288G

The title compound was prepared as described in EXAMPLE 4H, substituting EXAMPLE 288F for EXAMPLE 4G. MS (ESI(+)) m/e 647 (M+H)+, $^1$H NMR (400 MHz, dimethylsulfoxide-$d_6$) δ ppm 10.88 (s, 1 H) 9.67 (s, 1 H) 9.52 (m, 1 H) 8.35 (d, 1 H) 8.04 (s, 1 H) 7.71-7.81 (m, 3 H) 7.65 (m, 2 H) 7.59 (m, 1 H) 7.38-7.51 (m, 3 H) 7.25 (m, 2 H) 7.13 (d, 2 H) 7.08 (t, 1 H) 6.65 (d, 1 H) 3.33 (m, 2 H) 2.84 (s, 2 H) 2.70 (m, 2 H) 2.16 (s, 6 H).

Example 289

2-chloro-N-[3-(3-{2-[(4-{2-[(N,N-dimethylglycyl)amino]ethyl}phenyl)amino]pyrimidin-4-yl}imidazo[1,2-a]pyridin-2-yl)phenyl]benzamide The title compound was prepared as described in EXAMPLE 4H, substituting EXAMPLE 288F for EXAMPLE 4G, and 2-chlorobenzoyl chloride for 2,6-difluorobenzoyl chloride. MS (ESI(+)) m/e 646 (M+H)+, $^1$H NMR (400 MHz, dimethylsulfoxide-$d_6$) δ ppm 10.58 (s, 1 H) 9.66 (s, 1 H) 9.53 (m, 1 H) 8.35 (d, 1 H) 8.06 (s, 1 H) 7.82 (d, 1 H) 7.76 (m, 2 H) 7.65 (d, 2 H) 7.58 (m, 2 H) 7.41-7.53 (m, 4 H) 7.38 (m, 1 H) 7.14 (d, 2 H) 7.08 (t, 1 H) 6.65 (d, 1 H) 3.32 (m, 2 H) 2.88 (s, 2 H) 2.70 (m, 2 H) 2.19 (s, 6 H).

Example 290

N-[3-(3-{2-[(4-{2-[(N,N-dimethylglycyl)amino]ethyl}phenyl)amino]pyrimidin-4-yl}imidazo[1,2-a]pyridin-2-yl)phenyl]thiophene-2-carboxamide The title compound was prepared as described in EXAMPLE 4H, substituting EXAMPLE 288F for EXAMPLE 4G, and thiophene-2-carbonyl chloride for 2,6-difluorobenzoyl chloride. MS (ESI(+)) m/e 617 (M+H)+, $^1$H NMR (400 MHz, dimethylsulfoxide-$d_6$) δ ppm 10.32 (s, 1 H) 9.68 (s, 1 H) 9.55 (m, 1 H) 8.35 (d, 1 H) 8.09 (s, 1 H) 8.04 (d, 1 H) 7.86 (m, 3 H) 7.76 (d, 1 H) 7.65 (d, 2 H) 7.50 (m, 1 H) 7.43 (t, 1 H) 7.33 (m, 1 H) 7.22 (dd, 1 H) 7.14 (d, 2 H) 7.08 (m, 1 H) 6.65 (d, 1 H) 3.33 (m, 2 H) 2.97 (s, 2 H) 2.70 (m, 2 H) 2.24 (s, 6 H).

Example 291

N$^2$,N$^2$-dimethyl-N$^1$-[2-(4-{[4-(2-{3-[(thien-2-ylacetyl)amino]phenyl}imidazo[1,2-a]pyridin-3-yl)pyrimidin-2-yl]amino}phenyl)ethyl]glycinamide The title compound was prepared as described in EXAMPLE 4H, substituting EXAMPLE 288F for EXAMPLE 4G, and 2-thiopheneacetyl chloride for 2,6-difluorobenzoyl chloride. MS (ESI(+)) m/e 631 (M+H)+, $^1$H NMR (400 MHz, dimethylsulfoxide-$d_6$) δ ppm 10.30 (s, 1 H) 9.67 (s, 1 H) 9.53 (m, 1 H) 8.33 (d, 1 H) 7.91 (s, 1 H) 7.73 (m, 3 H) 7.66 (d, 2 H) 7.49 (m, 1 H) 7.38 (m, 2 H) 7.31 (d, 1 H) 7.14 (d, 2 H) 7.07 (t, 1 H) 6.97 (m, 2 H) 6.61 (d, 1 H) 3.87 (s, 2 H) 3.33 (m, 2 H) 2.85 (s, 2 H) 2.70 (m, 2 H) 2.17 (s, 6 H).

Example 292

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,3-difluorobenzamide The title compound was prepared as described in EXAMPLE 4H, substituting EXAMPLE 288F for EXAMPLE 4G, and 2,3-difluorobenzoyl chloride for 2,6-difluorobenzoyl chloride. MS (ESI(+)) m/e 647 (M+H)+, $^1$H NMR (400 MHz, dimethylsulfoxide-$d_6$) δ ppm 10.63 (s, 1 H) 9.67 (s, 1 H) 9.53 (m, 1 H) 8.35 (d, 1 H) 8.06 (s, 1 H) 7.83 (d, 1 H) 7.75 (m, 2 H) 7.63 (m, 2 H) 7.31-7.51 (m, 6 H) 7.12 (d, 2 H) 7.08 (m, 1 H) 6.65 (d, 1 H) 3.33 (m, 2 H) 2.85 (s, 2 H) 2.70 (m, 2 H) 2.17 (s, 6 H).

Example 293

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,5-difluorobenzamide The title compound was prepared as described in EXAMPLE 4H, substituting EXAMPLE 288F for EXAMPLE 4G, and 2,5-difluorobenzoyl chloride for 2,6-difluorobenzoyl chloride. MS (ESI(+)) m/e 647 (M+H)+, $^1$H NMR (400 MHz, dimethylsulfoxide-$d_6$) δ ppm 10.58 (s, 1 H) 9.67 (s, 1 H) 9.53 (m, 1 H) 8.34 (s, 1 H) 8.06 (s, 1 H) 7.83 (d, 1 H) 7.75 (m, 2 H) 7.65 (d, 2 H) 7.36-7.55 (m, 6 H) 7.14 (d, 2 H) 7.08 (m, 1 H) 6.64 (d, 1 H) 3.33 (m, 2 H) 2.86 (s, 2 H) 2.70 (m, 2 H) 2.18 (s, 6 H).

Example 294

N$^2$,N$^2$-dimethyl-N$^1$-[2-(4-{[4-(2-{3-[(phenylacetyl)amino]phenyl}imidazo[1,2-a]pyridin-3-yl)pyrimidin-2-yl]amino}phenyl)ethyl]glycinamide The title compound was prepared as described in EXAMPLE 4H, substituting EXAMPLE 288F for EXAMPLE 4G, and phenylacetyl chloride for 2,6-difluorobenzoyl chloride. MS (ESI(+)) m/e 625 (M+H)+, $^1$H NMR (400 MHz, dimethylsulfoxide-$d_6$) δ ppm 10.26 (s, 1 H) 9.67 (s, 1 H) 9.52 (m, 1 H) 8.32 (m, 1 H) 7.92 (m, 1 H) 7.74 (m, 3 H) 7.66 (d, 2 H) 7.48 (dd, 1 H) 7.27-7.39 (m, 6 H) 7.26 (m, 1 H) 7.14 (d, 2 H) 7.07 (m, 1 H) 6.60 (d, 1 H) 3.64 (s, 2 H) 3.33 (m, 2 H) 2.85 (s, 2 H) 2.70 (m, 2 H) 2.17 (s, 6 H).

Example 295

2,6-difluoro-N-[3-(3-{2-[(4-{2-[(methoxyacetyl)amino]ethyl}phenyl)amino]pyrimidin-4-yl}imidazo[1,2-a]pyridin-2-yl)phenyl]benzamide

Example 295A

A 10 ml sealed tube was charged with EXAMPLE 288B (169 mg, 1.02 mmol) and anhydrous tetrahydrofuran (2 ml). To this solution at ambient temperature was added 2-methoxyacetyl chloride (121 mg, 1.12 mmol). The reaction mixture was stirred for 12 hours at ambient temperature, diluted with water, and extracted with chloroform. The combined organic extracts were dried with Na$_2$SO$_4$, filtered, and concentrated to provide the title compound. MS (DCI(+)) m/e 239 (M+H)+.

Example 295B

The title compound was prepared as described in EXAMPLE 1H, substituting EXAMPLE 295A for EXAMPLE 1G. MS (DCI(+)) m/e 209 (M+H)$^+$.

Example 295C

The title compound was prepared as described in EXAMPLE 4F, substituting EXAMPLE 295B for EXAMPLE 4E. MS (ESI(+)) m/e 524 (M+H)$^+$.

Example 295D

The title compound was prepared as described in EXAMPLE 4G, substituting EXAMPLE 295C for EXAMPLE 4F. MS (ESI(+)) m/e 494 (M+H)$^+$.

Example 295E

The title compound was prepared as described in EXAMPLE 4H, substituting EXAMPLE 295D for EXAMPLE 4G. MS (ESI(+)) m/e 634 (M+H)$^+$, $^1$H NMR (400 MHz, dimethylsulfoxide-d$_6$) δ ppm 10.88 (s, 1 H) 9.67 (s, 1 H) 9.52 (d, 1 H) 8.35 (d, 1 H) 8.03 (s, 1 H) 7.74-7.81 (m, 3 H) 7.65 (d, 2 H) 7.59 (m, 1 H) 7.38-7.52 (m, 3 H) 7.25 (m, 2 H) 7.13 (d, 2 H) 7.08 (m, 1 H) 6.65 (d, 1 H) 3.77 (s, 2 H) 3.33 (m, 2 H) 3.28 (s, 3 H) 2.71 (m, 2 H).

Example 296

2-methoxy-N-[2-(4-{[4-(2-(3-[(thien-2-ylacetyl)amino]phenyl}imidazo[1,2-a]pyridin-3-yl)pyrimidin-2-yl]amino}phenyl)ethyl]acetamide The title compound was prepared as described in EXAMPLE 4H, substituting EXAMPLE 295D for EXAMPLE 4G, and 2-thiopheneacetyl chloride for 2,6-difluorobenzoyl chloride. MS (ESI(+)) m/e 618 (M+H)$^+$, $^1$H NMR (400 MHz, dimethylsulfoxide-d$_6$) δ ppm 10.30 (s, 1 H) 9.68 (s, 1 H) 9.53 (d, 1 H) 8.33 (m, 1 H) 7.92 (s, 1 H) 7.70-7.81 (m, 3 H) 7.66 (d, 2 H) 7.50 (d, 1 H) 7.36-7.42 (m, 2 H) 7.31 (m, 1 H) 7.06-7.14 (m, 3 H) 6.98 (m, 2 H) 6.61 (d, 1 H) 3.87 (s, 2 H) 3.74-3.79 (s, 2 H) 3.32 (m, 2 H) 3.28 (s, 3 H) 2.71 (t, 2 H).

Example 297

N-(3-{3-[2-({4-[2-(4-aminopiperidin-1-yl)ethyl]phenyl}amino)pyrimidin-4-yl]imidazo[1,2-a]pyridin-2-yl}phenyl)thiophene-2-carboxamide

Example 297A

Into a 250 mL round bottom flask was charged 4-nitrophenethyl bromide (5.00 g, 21.73 mmol), tert-butyl piperidin-4-ylcarbamate (13.06 g, 65.2 mmol), and acetonitrile (21.73 ml) to give a suspension. Triethylamine (9.09 ml, 65.2 mmol) was added, and the reaction was stirred at room temperature overnight. The reaction was poured onto saturated aqueous sodium bicarbonate, and the mixture extracted with ethyl acetate. The organic layer was washed with brine, dried over MgSO$_4$, filtered and concentrated. The reaction was purified by flash chromatography using an Argonaut Flashmaster Solo, 70 g column (100% CH$_2$Cl$_2$ for 5 minutes, then 10% methanol:CH$_2$Cl$_2$ over 20 minutes, then held 5 minutes.) to provide the title compound. MS (ESI(+)) m/e 350 (M+H)$^+$.

Example 297B

The title compound was prepared as described in EXAMPLE 4G, substituting EXAMPLE 297A for EXAMPLE 4F. MS (ESI(+)) m/e 320 (M+H)$^+$.

Example 297C

The title compound was prepared as described in EXAMPLE 4F, substituting EXAMPLE 236C for EXAMPLE 4E. MS (ESI(+)) m/e 535 (M+H)$^+$.

Example 297D

Into a 250 mL round bottom flask was charged EXAMPLE 297C (0.686 g, 1.129 mmol) and dichloromethane (11.3 ml). Triethylamine (0.630 ml, 4.52 mmol) and trifluoroacetic anhydride (0.239 ml, 1.694 mmol) were added. The reaction was stirred at room temperature overnight. Tetrahydrofuran (12 mL) was added, and the reaction was stirred at room temperature for an additional 24 hours. Triethylamine (0.32 mL), and trifluoroacetic anhydride (0.16 mL) were added, and the reaction stirred at room temperature for an additional 72 hours. The reaction was diluted with water and extracted with ethyl acetate. The organic layer was washed with brine, dried over MgSO$_4$, filtered and concentrated to provide the title compound. MS (ESI(+)) m/e 631 (M+H)$^+$.

Example 297E

The title compound was prepared as described in EXAMPLE 4E, substituting EXAMPLE 297D for EXAMPLE 4D. MS (ESI(+)) m/e 320 (M+H)$^+$.

Example 297F

Into a 4 mL vial was charged EXAMPLE 297E (40.0 mg, 0.067 mmol) and 1-methyl-2-pyrrolidinone (1.0 ml). Thiophene-2-carbonyl chloride (10.0 mg, 0.070 mmol) was added. The reaction was stirred at room temperature overnight. Lithium hydroxide monohydrate (14.0 mg, 0.333 mmol) was added as a solution in 0.5 mL water. The reaction was stirred at room temperature overnight, and filtered through a syringe filter. The reaction was purified by HPLC using a Shimadzu SIL-10 HPLC system (2 mL injections, run on a 150×30 mm Phenominex Gemini 10 micron C18 column with 110 Angstrom pore size, flow rate of 20 mL/minute, mobile phase gradient from 40% to 80% acetonitrile/water with 0.1% NH$_4$OH over 25 minutes) to provide the title compound. MS (ESI(+)) m/e 615 (M+H)$^+$; $^1$H NMR (300 MHz, dimethylsulfoxide-d$_6$) δ ppm 10.36 (s, 1H), 9.65 (s, 1H), 9.55 (d, 1H), 8.34 (d, 1H), 8.06 (m, 1H), 8.02 (m, 1H), 7.87 (m, 2H), 7.75 (d, 1H), 7.62 (d, 2H), 7.50 (t, 1H), 7.41 (t, 1H), 7.31 (m, 1H), 7.21 (t, 1H), 7.13 (d, 2H), 7.07 (t, 1H), 6.65 (d, 1H), 2.80 (m, 2H), 2.65 (m, 2H), 2.44 (m, 2H), 1.94 (m, 2H), 1.67 (m, 2H), 1.35 (m, 1H), 1.21 (m, 2H).

Example 298

N-(3-{3-[2-({4-[2-(4-aminopiperidin-1-yl)ethyl]phenyl}amino)pyrimidin-4-yl]imidazo[1,2-a]pyridin-2-yl}phenyl)-2,6-difluorobenzamide The title compound was prepared as described in EXAMPLE 297F, substituting 2,6-difluorobenzoyl chloride for thiophene-2-carbonyl chloride. MS (ESI(+)) m/e 645 (M+H)$^+$; $^1$H NMR (300 MHz, dimethylsulfoxide-d$_6$) 3 ppm 10.89 (s, 1H), 9.65 (s, 1H), 9.51 (d, 1H), 8.34 (d, 1H), 8.03 (m, 1H), 8.02 (m, 1H), 7.80 (d, 1H), 7.76 (d, 1H), 7.60 (m, 3H), 7.51 (d, 1H), 7.45 (t, 1H), 7.39 (d, 1H), 7.25 (t, 2H), 7.12 (d, 2H), 7.07 (t, 1H), 6.65 (d, 1H), 2.82 (m, 2H), 2.66 (m, 2H), 2.45 (m, 2H), 1.95 (m, 2H), 1.66 (m, 2H), 1.35 (m, 1H), 1.21 (m, 2H).

Example 299

N-(3-{3-[2-({4-[2-(4-aminopiperidin-1-yl)ethyl]phenyl}amino)pyrimidin-4-yl]imidazo[1,2-a]pyridin-2-yl}phenyl)-2-chlorobenzamide The title compound was prepared as described in EXAMPLE 297F, substituting 2-chlorobenzoyl chloride for thiophene-2-carbonyl chloride. MS (ESI(+)) m/e 643 (M+H)$^+$; $^1$H NMR (300 MHz, dimethylsulfoxide-d$_6$) δ ppm 10.60 (s, 1H), 9.65 (s, 1H), 9.52 (d, 1H), 8.34 (d, 1H), 8.06 (m, 1H), 7.82 (d, 1H), 7.75 (d, 1H), 7.59 (m, 4H), 7.45 (m, 5H), 7.13 (m, 2H), 7.07 (t, 1H), 6.64 (d, 1H), 2.85 (m, 2H), 2.66 (m, 2H), 2.45 (m, 2H), 2.00 (m, 2H), 1.68 (m, 1H), 1.50 (m, 2H), 1.23 (m, 2H).

Example 300

N-(3-{3-[2-({4-[2-(4-aminopiperidin-1-yl)ethyl]phenyl}amino)pyrimidin-4-yl]imidazo[1,2-a]pyridin-2-yl}phenyl)-2-fluorobenzamide The title compound was prepared as described in EXAMPLE 297F, substituting 2-fluorobenzoyl chloride for thiophene-2-carbonyl chloride. MS (ESI(+)) m/e 627 (M+H)$^+$; $^1$H NMR (300 MHz, dimethylsulfoxide-d$_6$) δ ppm 10.52 (s, 1H), 9.64 (s, 1H), 9.54 (d, 1H), 8.34 (d, 1H), 8.06 (m, 1H), 7.84 (d, 1H), 7.76 (d, 1H), 7.68 (m, 1H), 7.61 (d, 2H), 7.56 (m, 1H), 7.45 (m, 1H), 7.42 (d, 1H), 7.35 (m, 3H), 7.12 (d, 2H), 7.07 (t, 1H), 6.64 (d, 1H), 2.83 (m, 2H), 2.66 (m, 2H), 2.45 (m, 2H), 1.95 (m, 2H), 1.65 (m, 2H), 1.37 (m, 1H), 1.23 (m, 2H).

Example 301

N-(3-{3-[2-({4-[2-(4-aminopiperidin-1-yl)ethyl]phenyl}amino)pyrimidin-4-yl]imidazo[1,2-a]pyridin-2-yl}phenyl)-2,3-difluorobenzamide The title compound was prepared as described in EXAMPLE 297F, substituting 2,3-difluorobenzoyl chloride for thiophene-2-carbonyl chloride. MS (ESI(+)) m/e 645 (M+H)$^+$; $^1$H NMR (300 MHz, dimethylsulfoxide-d$_6$) δ ppm 10.65 (s, 1H), 9.64 (s, 1H), 9.53 (d, 1H), 8.35 (d, 1H), 8.05 (m, 1H), 7.83 (d, 1H), 7.75 (d, 1H), 7.60 (m, 3H), 7.48 (m, 3H), 7.35 (m, 2H), 7.12 (d, 2H), 7.07 (t, 1H), 6.64 (d, 1H), 2.83 (m, 2H), 2.66 (m, 2H), 2.45 (m, 2H), 1.95 (m, 2H), 1.66 (m, 2H), 1.35 (m, 1H), 1.21 (m, 2H).

Example 302

N-(3-{3-[2-({4-[2-(4-aminopiperidin-1-yl)ethyl]phenyl}amino)pyrimidin-4-yl]imidazo[1,2-a]pyridin-2-yl}phenyl)-2,5-difluorobenzamide The title compound was prepared as described in EXAMPLE 297F, substituting 2,5-difluorobenzoyl chloride for thiophene-2-carbonyl chloride. MS (ESI(+)) m/e 645 (M+H)$^+$; $^1$H NMR (300 MHz, dimethylsulfoxide-d$_6$) δ ppm 10.59 (s, 1H), 9.64 (s, 1H), 9.52 (d, 1H), 8.34 (d, 1H), 8.05 (m, 1H), 7.83 (d, 1H), 7.75 (d, 1H), 7.61 (d, 2H), 7.52 (m, 2H), 7.42 (m, 4H), 7.12 (d, 2H), 7.07 (t, 1H), 6.64 (d, 1H), 2.83 (m, 2H), 2.66 (m, 2H), 2.45 (m, 2H), 1.95 (m, 2H), 1.65 (m, 2H), 1.36 (m, 1H), 1.21 (m, 2H).

Example 303

N-(3-{3-[2-({4-[2-(4-aminopiperidin-1-yl)ethyl]phenyl}amino)pyrimidin-4-yl]imidazo[1,2-a]pyridin-2-yl}phenyl)-2-chloro-5-fluorobenzamide The title compound was prepared as described in EXAMPLE 297F, substituting 2-chloro-5-fluorobenzoyl chloride for thiophene-2-carbonyl chloride. MS (ESI(+)) m/e 661 (M+H)$^+$; $^1$H NMR (300 MHz, dimethylsulfoxide-d$_6$) δ ppm 10.66 (s, 1H), 9.65 (s, 1H), 9.52 (d, 1H), 8.34 (d, 1H), 8.05 (m, 1H), 7.79 (d, 1H), 7.75 (d, 1H), 7.62 (m, 3H), 7.51 (m, 2H), 7.40 (m, 3H), 7.13 (m, 2H), 7.07 (t, 1H), 6.64 (d, 1H), 2.86 (m, 2H), 2.66 (m, 2H), 2.45 (m, 2H), 1.95 (m, 2H), 1.67 (m, 2H), 1.35 (m, 1H), 1.21 (m, 2H).

Example 304

N-(3-{3-[2-({4-[2-(4-aminopiperidin-1-yl)ethyl]phenyl}amino)pyrimidin-4-yl]imidazo[1,2-a]pyridin-2-yl}phenyl)-2-phenylacetamide The title compound was prepared as described in EXAMPLE 297F, substituting phenylacetyl chloride for thiophene-2-carbonyl chloride. MS (ESI(+)) m/e 623 (M+H)$^+$; $^1$H NMR (300 MHz, dimethylsulfoxide-d$_6$) δ ppm 10.28 (s, 1H), 9.65 (s, 1H), 9.52 (d, 1H), 8.32 (d, 1H), 7.91 (m, 1H), 7.73 (d, 2H), 7.62 (dd, 2H), 7.48 (ddd, 1H), 7.37 (t, 1H), 7.32 (m, 3H), 7.30 (m, 2H), 7.24 (m, 1H), 7.14 (m, 2H), 7.06 (t, 1H), 6.59 (d, 1H), 3.64 (s, 2H), 2.87 (m, 2H), 2.66 (m, 2H), 2.45 (m, 2H), 1.95 (m, 2H), 1.66 (m, 2H), 1.34 (m, 1H), 1.21 (m, 2H).

Example 305

N-(3-{3-[2-({4-[2-(4-aminopiperidin-1-yl)ethyl]phenyl}amino)pyrimidin-4-yl]imidazo[1,2-a]pyridin-2-yl}phenyl)-2-thien-2-ylacetamide The title compound was prepared as described in EXAMPLE 297F, substituting 2-thiopheneacetyl chloride for thiophene-2-carbonyl chloride. MS (ESI(+)) m/e 629 (M+H)$^+$; $^1$H NMR (300 MHz, dimethylsulfoxide-d$_6$) δ ppm 10.33 (s, 1H), 9.65 (s, 1H), 9.52 (d, 1H), 8.32 (d, 1H), 7.91 (m, 1H), 7.79 (d, 1H), 7.74 (m, 2H), 7.62 (d, 2H), 7.49 (ddd, 1H), 7.38 (m, 2H), 7.30 (m, 1H), 7.13 (m, 2H), 7.06 (t, 1H), 6.98 (m, 2H), 6.60 (d, 1H), 3.87 (s, 2H), 2.81 (m, 2H), 2.67 (m, 2H), 2.45 (m, 2H), 1.95 (m, 2H), 1.68 (m, 2H), 1.37 (m, 1H), 1.21 (m, 2H).

Example 306

N-(3-{3-[2-({4-[2-(4-aminopiperidin-1-yl)ethyl]phenyl}amino)pyrimidin-4-yl]imidazo[1,2-a]pyridin-2-yl}phenyl)-N'-phenylurea Into a 4 mL vial was charged EXAMPLE 297E (0.040 g, 0.067 mmol) and 1-methyl-2-pyrrolidinone (1.0 ml). Phenyl isocyanate (7.61 μl, 0.070 mmol) was added. The reaction was stirred at room temperature overnight. Lithium hydroxide monohydrate (0.014 g, 0.333 mmol) was added as a solution in 0.5 mL water. The reaction was stirred at room temperature overnight, then filtered through a syringe filter. The reaction was purified by HPLC using a Shimadzu SIL-10 HPLC system (2 mL injections, run on a 150×30 mm Phenominex Gemini 10 micron C18 column with 110 Angstrom pore size, flow rate of 20 mL/minutes, mobile phase gradient from 40% to 80% acetonitrile/water with 0.1% NH$_4$OH over 25 minutes) to provide the title compound. MS (ESI(+)) m/e 624 (M+H)$^+$; $^1$H NMR (300 MHz, dimethylsulfoxide-d$_6$) δ ppm 9.78 (s, 1H), 9.61 (m, 2H), 8.29 (m, 1H), 7.75 (m, 1H), 7.62 (m, 4H), 7.49 (m, 3H), 7.34 (m, 1H), 7.24 (m, 1H), 7.15 (m, 3H), 7.05 (d, 1H), 6.84 (m, 1H), 6.62 (d, 1H), 3.87 (s, 2H), 2.85 (m, 2H), 2.66 (m, 2H), 2.45 (m, 2H), 1.95 (m, 2H), 1.59 (m, 2H), 1.37 (m, 1H), 1.19 (m, 2H).

Example 307

N-(3-{3-[2-({4-[2-(4-aminopiperidin-1-yl)ethyl]phenyl}amino)pyrimidin-4-yl]imidazo[1,2-a]pyridin-2-yl}phenyl)indoline-1-carboxamide The title compound was prepared as described in EXAMPLE 306, substituting indoline-1-carbonyl chloride for phenyl isocyanate. MS (ESI(+)) m/e 650 (M+H)$^+$; $^1$H NMR (300 MHz, dimethylsulfoxide-d$_6$) δ ppm 9.64 (s, 1H), 9.56 (d, 1H), 8.64 (s, 1H), 8.34 (d, 1H), 7.94 (m, 1H), 7.86 (d, 1H), 7.76 (m, 1H), 7.70 (m, 1H), 7.61 (d, 2H), 7.50 (ddd, 1H), 7.36 (t, 1H), 7.24 (m, 1H), 7.19 (m, 1H), 7.13 (d, 2H), 7.11 (m, 1H), 7.07 (m, 1H), 6.89 (m, 1H), 6.65 (d, 1H), 4.14 (t, 2H), 3.17 (t, 2H), 2.83 (m, 2H), 2.67 (m, 2H), 2.45 (m, 2H), 1.95 (m, 2H), 1.65 (m, 2H), 1.37 (m, 1H), 1.22 (m, 2H).

Example 308

N-(3-{3-[2-({4-[2-(4-aminopiperidin-1-yl)ethyl]phenyl}amino)pyrimidin-4-yl]imidazo[1,2-a]pyridin-2-yl}phenyl)-2-chloro-3-fluorobenzamide Into a 4 mL vial was charged EXAMPLE 297E (0.040 g, 0.067 mmol) and 1-methyl-2-pyrrolidinone (1.0 ml) to give a tan solution. 2-Chloro-3-fluorobenzoic acid (0.014 g, 0.080 mmol), 1-hydroxybenzotriazole hydrate (10.20 mg, 0.067 mmol) and PS-carbodiimide (0.141 g, 0.200 mmol) were added. The reaction was stirred at room temperature overnight. The suspension was filtered through a syringe filter, and rinsed with 0.5 mL 1-methyl-2-pyrrolidinone. Lithium hydroxide monohydrate (14.0 mg, 0.333 mmol) was added as a solution in 0.5 mL water. The reaction was stirred at room temperature overnight, then filtered through a syringe filter. The reaction was purified by HPLC using a Shimadzu SIL-10 HPLC system (2 mL injections, run on a 150×30 mm Phenominex Gemini 10 micron C18 column with 110 Angstrom pore size, flow rate of 20 mL/minute, mobile phase gradient from 40% to 80% acetonitrile/water with 0.1% NH$_4$OH over 25 minutes) to provide the title compound. MS (ESI(+)) m/e 661 (M+H)$^+$; $^1$H NMR (300 MHz, dimethylsulfoxide-d$_6$) δ ppm 9.64 (s, 1H), 9.51 (d, 1H), 8.35 (d, 1H), 8.04 (m, 1H), 7.81 (m, 1H), 7.75 (d, 1H), 7.60 (d, 2H), 7.50 (m, 5H), 7.39 (m, 2H), 7.13 (d, 2H), 7.07 (t, 1H), 6.65 (d, 1H), 2.81 (m, 2H), 2.66 (m, 2H), 2.45 (m, 2H), 1.96 (m, 2H), 1.67 (m, 2H), 1.35 (m, 1H), 1.21 (m, 2H).

Example 309

N-[2-(4-{[4-(2-{3-[(2-thien-2-ylacetyl)amino]phenyl}imidazo[1,2-a]pyridin-3-yl)pyrimidin-2-yl]amino}phenyl)ethyl]cyclopropanecarboxamide Example 309A The title compound was prepared as described in EXAMPLE 295A, substituting cyclopropanecarbonyl chloride for 2-methoxyacetyl chloride. MS (DCI(+)) m/e 235 (M+H)$^+$.

Example 309B

The title compound was prepared as described in EXAMPLE 1H, substituting EXAMPLE 309A for EXAMPLE 1G. MS (DCI(+)) m/e 205 (M+H)$^+$.

Example 309C

The title compound was prepared as described in EXAMPLE 4F, substituting EXAMPLE 309B for EXAMPLE 4E. MS (ESI(+)) m/e 520 (M+H)$^+$.

Example 309D

The title compound was prepared as described in EXAMPLE 4G, substituting EXAMPLE 309C for EXAMPLE 4F. MS (ESI(+)) m/e 490 (M+H)$^+$.

Example 309E

The title compound was prepared as described in EXAMPLE 4H, substituting EXAMPLE 309D for EXAMPLE 4G, and 2-thiopheneacetyl chloride for 2,6-difluorobenzoyl chloride. MS (ESI(+)) m/e 614 (M+H)$^+$, $^1$H NMR (400 MHz, dimethylsulfoxide-d$_6$) δ ppm 10.30 (s, 1 H) 9.67 (s, 1 H) 9.53 (m, 1 H) 8.33 (d, 1 H) 8.09 (t, 1 H) 7.91 (s, 1 H) 7.73 (t, 2 H) 7.66 (d, 2 H) 7.49 (m, 1 H) 7.39 (m, 2 H) 7.31 (m, 1 H) 7.14 (d, 2 H) 7.07 (m, 1 H) 6.98 (m, 2 H) 6.61 (d, 1 H) 3.87 (s, 2 H) 3.27 (m, 2 H) 2.68 (m, 2 H) 1.53 (m, 1 H) 0.63 (m, 4 H).

Example 310

N-[3-(3-{2-[(4-{2-[(cyclopropylcarbonyl)amino]ethyl}phenyl)amino]pyrimidin-4-yl}imidazo[1,2-a]pyridin-2-yl)phenyl]-2,6-difluorobenzamide The title compound was prepared as described in EXAMPLE 4H, substituting EXAMPLE 309D for EXAMPLE 4G. MS (ESI(+)) m/e 630 (M+H)$^+$, $^1$H NMR (400 MHz, dimethylsulfoxide-d$_6$) δ ppm 10.88 (s, 1 H) 9.67 (s, 1 H) 9.52 (d, 1 H) 8.35 (d, 1 H) 8.09 (m, 1 H) 8.03 (m, 1 H) 7.79 (m, 2 H) 7.55-7.66 (m, 3 H) 7.39-7.51 (m, 3 H) 7.25 (m, 2 H) 7.15 (s, 2 H) 7.08 (t, 1 H) 6.65 (d, 1 H) 3.27 (m, 2 H) 2.68 (m, 2 H) 1.53 (m, 1 H) 0.62 (m, 4 H).

Example 311

2-chloro-N-[3-(3-{2-[(4-{2-[(cyclopropylcarbonyl)amino]ethyl}phenyl)amino]pyrimidin-4-yl}imidazo[1,2-a]pyridin-2-yl)phenyl]benzamide The title compound was prepared as described in EXAMPLE 4H, substituting EXAMPLE 309D for EXAMPLE 4G, and 2-chlorobenzoyl chloride for 2,6-difluorobenzoyl chloride. MS (ESI(+)) m/e 629 (M+H)$^+$, $^1$H NMR (400 MHz, dimethylsulfoxide-d$_6$) δ ppm 10.58 (s, 1 H) 9.66 (s, 1 H) 9.53 (m, 1 H) 8.35 (d, 1 H) 8.08 (m, 2 H) 7.82 (d, 1 H) 7.76 (d, 1 H) 7.66 (d, 2 H) 7.57 (m, 2 H) 7.41-7.53 (m, 4 H) 7.38 (m, 1 H) 7.12 (s, 2 H) 7.07 (m, 1 H) 6.65 (d, 1 H) 3.27 (m, 2 H) 2.68 (m, 2 H) 1.53 (m, 1 H) 0.63 (m, 4 H).

Example 312

N-[3-(3-{2-[(4-{2-[(cyclopropylcarbonyl)amino]ethyl}phenyl)amino]pyrimidin-4-yl}imidazo[1,2-a]pyridin-2-yl)phenyl]thiophene-2-carboxamide The title compound was prepared as described in EXAMPLE 4H, substituting EXAMPLE 309D for EXAMPLE 4G, and thiophene-2-carbonyl chloride for 2,6-difluorobenzoyl chloride. MS (ESI(+)) m/e 600 (M+H)$^+$, $^1$H NMR (400 MHz, dimethylsulfoxide-d$_6$) δ ppm 10.32 (s, 1 H) 9.68 (s, 1 H) 9.56 (m, 1 H) 8.35 (d, 1 H) 8.08 (m, 2 H) 8.04 (d, 1 H) 7.88 (m, 2 H) 7.76 (d, 1 H) 7.67 (d, 2 H) 7.47 (m, 2 H) 7.34 (m, 1 H) 7.22 (m, 1 H) 7.13 (d, 2 H) 7.08 (m, 1 H) 6.65 (d, 1 H) 3.26 (m, 2 H) 2.66 (m, 2 H) 1.53 (m, 1 H) 0.66 (m, 4 H).

Example 313

2,6-difluoro-N-[3-(3-{2-[(4-{2-[(methylsulfonyl)amino]ethyl}phenyl)amino]pyrimidin-4-yl}imidazo[1,2-a]pyridin-2-yl)phenyl]benzamide

Example 313A

A 25 ml round bottom flask was charged with EXAMPLE 288B (169 mg, 1.02 mmol) and anhydrous tetrahydrofuran (2 ml). To this solution at ambient temperature was added methanesulfonyl chloride (0.087 ml, 1.12 mmol). The mixture stirred for 12 hours at ambient temperature, was diluted with water, and extracted with chloroform. The combined extracts were dried with Na$_2$SO$_4$, filtered, and concentrated to provide the title compound. MS (DCI(+)) m/e 245 (M+H)$^+$.

Example 313B

The title compound was prepared as described in EXAMPLE 1H, substituting EXAMPLE 313A for EXAMPLE 1G. MS (DCI(+)) m/e 215 (M+H)$^+$.

Example 313C

The title compound was prepared as described in EXAMPLE 4F, substituting EXAMPLE 313B for EXAMPLE 4E. MS (ESI(+)) m/e 530 (M+H)$^+$.

Example 313D

The title compound was prepared as described in EXAMPLE 4G, substituting EXAMPLE 313C for EXAMPLE 4F. MS (ESI(+)) m/e 500 (M+H)$^+$.

Example 313E

The title compound was prepared as described in EXAMPLE 4H, substituting EXAMPLE 313D for EXAMPLE 4G. MS (ESI(+)) m/e 640 (M+H)$^+$, $^1$H NMR (400 MHz, dimethylsulfoxide-d$_6$) δ ppm 10.87 (m, 1 H) 9.68 (s, 1 H) 9.53 (m, 1 H) 8.35 (d, 1 H) 8.03 (s, 1 H) 7.78 (m, 2 H) 7.67 (d, 2 H) 7.59 (m, 1 H) 7.37-7.52 (m, 3 H) 7.25 (m, 2 H) 7.17 (d, 2 H) 7.07 (m, 2 H) 6.65 (d, 1 H) 3.16 (m, 2 H) 2.84 (s, 3 H) 2.73 (m, 2 H).

Example 314

2-chloro-N-[3-(3-{2-[(4-{2-[(methylsulfonyl)amino]ethyl}phenyl)amino]pyrimidin-4-yl}imidazo[1,2-a]pyridin-2-yl)phenyl]benzamide The title compound was prepared as described in EXAMPLE 4H, substituting EXAMPLE 313D for EXAMPLE 4G, and 2-chlorobenzoyl chloride for 2,6-difluorobenzoyl chloride. MS (ESI(+)) m/e 639 (M+H)$^+$, $^1$H NMR (400 MHz, dimethylsulfoxide-d$_6$) δ ppm 10.58 (s, 1 H) 9.68 (s, 1 H) 9.53 (m, 1 H) 8.35 (d, 1 H) 8.05 (d, 1 H) 7.82 (d, 1 H) 7.76 (d, 1 H) 7.67 (d, 2 H) 7.57 (m, 2 H) 7.41-7.52 (m, 4 H) 7.38 (m, 1 H) 7.16 (d, 2 H) 7.07 (m, 2 H) 6.65 (d, 1 H) 3.17 (m, 2 H) 2.84 (m, 3 H) 2.73 (m, 2 H).

Example 315

N-[3-(3-(2-[(4-{2-[(methylsulfonyl)amino]ethyl}phenyl)amino]pyrimidin-4-yl}imidazo[1,2-a]pyridin-2-yl)phenyl]thiophene-2-carboxamide The title compound was prepared as described in EXAMPLE 4H, substituting EXAMPLE 313D for EXAMPLE 4G, and thiophene-2-carbonyl chloride for 2,6-difluorobenzoyl chloride. MS (ESI(+)) m/e 610 (M+H)$^+$, $^1$H NMR (400 MHz, dimethylsulfoxide-d$_6$) δ ppm 10.32 (s, 1 H) 9.69 (s, 1 H) 9.57 (m, 1 H) 8.35 (d, 1 H) 8.09 (m, 1 H) 8.04 (t, 1 H) 7.84-7.90 (m, 2 H) 7.75 (m, 1 H) 7.68 (d, 1 H) 7.41-7.53 (m, 2 H) 7.31-7.38 (m, 2 H) 7.23 (m, 1 H) 7.18 (d, 2 H) 7.03-7.13 (m, 2 H) 6.64 (s, 1 H) 3.16 (m, 2 H) 2.84 (s, 3 H) 2.73 (m, 2 H).

Example 316

N-[3-(3-{2-[(4-{2-[(methylsulfonyl)amino]ethyl}phenyl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 313D for EXAMPLE 4G, and 2-thiopheneacetyl chloride for 2,6-difluorobenzoyl chloride. MS (ESI(+)) m/e 624 (M+H)$^+$, $^1$H NMR (500 MHz, dimethylsulfoxide-d$_6$) δ ppm 10.32 (s, 1 H) 9.71 (s, 1 H) 9.54 (m, 1 H) 8.33 (d, 1 H) 7.91 (s, 1 H) 7.74 (t, 2 H) 7.68 (d, 2 H) 7.48 (m, 1 H) 7.39 (m, 2 H) 7.30 (d, 1 H) 7.17 (d, 2 H) 7.08 (m, 2 H) 6.98 (m, 2 H) 6.61 (d, 1 H) 3.87 (s, 2 H) 3.16 (m, 2 H) 2.84 (s, 3 H) 2.72 (m, 2 H).

Example 317

2-chloro-N-[3-(3-{2-[(4-{2-[(methoxyacetyl)amino]ethyl}phenyl)amino]pyrimidin-4-yl}imidazo[1,2-a]pyridin-2-yl)phenyl]benzamide The title compound was prepared as described in EXAMPLE 4H, substituting EXAMPLE 295D for EXAMPLE 4G, and 2-chlorobenzoyl chloride for 2,6-difluorobenzoyl chloride. MS (ESI(+)) m/e 633 (M+H)$^+$, $^1$H NMR (400 MHz, dimethylsulfoxide-d$_6$) δ ppm 10.58 (s, 1 H) 9.67 (s, 1 H) 9.53 (d, 1 H) 8.35 (d, 1 H) 8.06 (s, 1 H) 7.71-7.88 (m, 2 H) 7.65 (d, 2 H) 7.57 (m, 2 H) 7.40-7.52 (m, 4 H) 7.38 (m, 2 H) 7.31 (m, 1 H) 7.13 (d, 2 H) 7.08 (m, 1 H) 3.77 (s, 2 H) 3.33 (m, 2 H) 3.26 (s, 3 H) 2.71 (t, 2 H).

Example 318

N-[3-(3-{2-[(4-{2-[(2-methoxyacetyl)amino]ethyl}phenyl)amino]pyrimidin-4-yl}imidazo[1,2-a]pyridin-2-yl)phenyl]thiophene-2-carboxamide The title compound was prepared as described in EXAMPLE 4H, substituting EXAMPLE 295D for EXAMPLE 4G, and thiophene-2-carbonyl chloride for 2,6-difluorobenzoyl chloride. MS (ESI(+)) m/e 604 (M+H)$^+$, $^1$H NMR (400 MHz, dimethylsulfoxide-d$_6$) δ ppm 10.32 (s, 1 H) 9.68 (s, 1 H) 9.57 (s, 1 H) 8.35 (d, 1 H) 8.08 (m, 1 H) 8.04 (m, 1 H) 7.83-7.91 (m, 2 H) 7.77 (m, 1 H) 7.66 (d, 2 H) 7.41-7.53 (m, 2 H) 7.34 (m, 1 H) 7.22 (m, 2 H) 7.14 (d, 2 H) 7.06 (m, 1 H) 6.64 (s, 1 H) 3.77 (s, 2 H) 3.33 (m, 2 H) 3.27 (s, 3 H) 2.71 (m, 2 H).

Example 319

N-(2,6-difluorophenyl)-3-[3-(2-{[4-(4-ethylpiperazin-1-yl)phenyl]amino}pyrimidin-4-yl)imidazo[1,2-a]pyridin-2-yl]benzamide The title compound was prepared as described in EXAMPLE 125, substituting 1-(4-(4-ethylpiperazin-1-yl)phenyl)guanidine hydrochloride for 1-(2-methyl-1,2,3,4-tetrahydroisoquinolin-7-yl)guanidine hydrochloride and substituting 2,6-difluoroaniline for 2-fluoroaniline. MS (ESI(+)) m/e 631.3 (M+H)$^+$, (ESI(−)) m/e 629.1 (M−H)$^−$; $^1$H-NMR (300 MHz, dimethylsulfoxide-d$_6$) δ 10.28 (s, 1H) 9.64 (s, 1H) 9.51 (s, 1H) 9.30 (s, 1H) 8.37 (t, 1H) 8.33 (d, 1H) 8.08 (dt, 1H) 7.86 (ddd, 1H) 7.77-7.83 (m, 1H) 7.36-7.68 (m, 6H) 7.21-7.29 (m, 2H) 7.11 (t, 1H) 6.98 (d, 2H) 6.61 (d, 1H) 3.56 (s, 3H) 3.21 (dd, 2H) 3.06-3.17 (m, 2H) 2.90 (t, 2H) 1.26 (t, 3H).

Example 320

2,6-difluoro-N-[3-(3-{2-[(4-{2-[(2-hydroxyethyl)(methyl)amino]ethyl}phenyl)amino]pyrimidin-4-yl}imidazo[1,2-a]pyridin-2-yl)phenyl]benzamide Example 320A The title compound was prepared as described in EXAMPLE 195D, substituting N-methylethanolamine for diethylamine. MS (ESI(+)) m/e 480 (M+H)$^+$, (ESI(−)) m/e 478 (M−H)$^−$.

Example 320B

The title compound was prepared as described in EXAMPLE 4H, substituting EXAMPLE 320A for EXAMPLE 4G and 2-fluorobenzoyl chloride for 2,6-difluorobenzoyl chloride. MS (ESI(+)) m/e 620.3 (M+H)$^+$, (ESI(−)) m/e 618.1 (M−H)$^−$; $^1$H-NMR (300 MHz, dimethylsulfoxide-d$_6$) δ 10.89 (s, 1H) 9.65 (s, 1H) 9.51 (d, 1H) 8.35 (d, 1H) 8.03 (t, 1H) 7.73-7.83 (m, 2H) 7.41-7.66 (m, 5H) 7.39 (dt, 1H) 7.20-7.30 (m, 2H) 7.14 (d, 2H) 7.07 (td, 1H) 6.65 (d, 1H) 4.27 (t, 1H) 3.46 (q, 2H) 2.62-2.70 (m, 2H) 2.54-2.60 (m, 2H) 2.46 (t, 2H) 2.24 (s, 3H).

Example 321

2-chloro-N-[3-(3-{2-[(4-{2-[(2-hydroxyethyl)(methyl)amino]ethyl}phenyl)amino]pyrimidin-4-yl}imidazo[1,2-a]pyridin-2-yl)phenyl]benzamide The title compound was prepared as described in EXAMPLE 4H, substituting EXAMPLE 320A for EXAMPLE 4G and 2-chlorobenzoyl chloride for 2,6-difluorobenzoyl chloride. MS (ESI(+)) m/e 618.3 (M+H)$^+$, (ESI(−)) m/e 616.1 (M−H)$^−$; $^1$H-NMR (300 MHz, dimethylsulfoxide-d$_6$) δ 10.59 (s, 1H) 9.64 (s, 1H) 9.53 (d, 1H) 8.34 (d, 1H) 8.06 (t, 1H) 7.82 (dt, 1H) 7.76 (d, 1H) 7.59-7.65 (m, 2H) 7.55-7.59 (m, 2H) 7.40-7.54 (m, 4H) 7.37 (dt, 1H) 7.14 (d, 2H) 7.07 (td, 1H) 6.64 (d, 1H) 4.27 (t, 1H) 3.41-3.52 (m, 2H) 2.61-2.70 (m, 2H) 2.53-2.60 (m, 2H) 2.46 (t, 2H) 2.24 (s, 3H).

Example 322

3-{3-[2-({4-[2-(dimethylamino)ethyl]phenyl}amino)pyrimidin-4-yl]imidazo[1,2-a]pyridin-2-yl}-N-phenylbenzamide Example 322A The title compound was prepared as described in EXAMPLE 125E, substituting guanidine hydrochloride for 1-(2-methyl-1,2,3,4-tetrahydroisoquinolin-7-yl)guanidine hydrochloride. MS (ESI(+)) m/e 366.7, 368.7 (M+H)$^+$.

Example 322B

In a 50 mL pear shaped flask was charged EXAMPLE 322A (1.3 g, 3.54 mmol) in glacial acetic acid (12.16 ml). In an addition funnel was dissolved sodium nitrite (0.733 g, 10.62 mmol) in water (2.004 ml) and it was slowly added over 20 minutes to the stirring solution. The reaction was allowed to stir at 60° C. for 30 minutes, it was cooled, and then transferred to 250 ml erlenmeyer flask. To the reaction mixture, cooled in ice bath, was added 1N NaOH (50 ml) and solid NaOH until the mixture reached pH 7.00. The solid was collected by filtration and washed with water to afford the title compound. MS (ESI(+)) m/e 367.8, 369.8 (M+H)$^+$, (ESI(−)) m/e 365.7, 367.7 (M−H)$^−$.

Example 322C

In a 4 ml vial was charged EXAMPLE 322B (0.856 g, 2.325 mmol) in phosphorous (V) oxychloride (2.93 ml, 31.4 mmol). The mixture was allowed to heat at 90° C. for 3 hours. The reaction was cooled, slowly added to cold water, and then the mixture was allowed to stand 60 hours to allow a precipitate to form. The mixture was filtered, and to the filtrate was added solid sodium hydroxide until the pH was ~10. The mixture was filtered saving the solid which was collected and placed under vacuum. The filtrate was extracted with 9:1 dichloromethane/methanol, the organics were dried over magnesium sulfate, and concentrated in vacuo. The crude solids were combined, placed on a 10 g silica gel column and purified by flash chromatography on an Argonaut Flash Master SOLO, eluting with a gradient 100% dichloromethane to 50:50 dichloromethane/methanol to afford the title compound. MS (DCI(+)) m/e 385.8, 387.8 (M+H)$^+$.

Example 322D

In a 250 mL round-bottomed flask was charged dimethylamine (19.56 ml, 39.1 mmol) and 4-nitrophenethyl bromide (3.000 g, 13.04 mmol) in acetonitrile (13.04 ml). Triethylamine (5.45 ml, 39.1 mmol) was added and the mixture was stirred at room temperature for 48 hours. The mixture was poured into saturated aqueous sodium bicarbonate and extracted with ethyl acetate. The organics were washed with brine, dried over magnesium sulfate, filtered, and concentrated in vacuo. The residue was dissolved in dichloromethane, added to a 25 g silica gel column, and purified by flash chromatography using an Argonaut Flashmaster Solo, (100% dichloromethane for 5 minutes, then to 10% methanol: dichloromethane over 20 minutes, then held 5 minutes) to afford the title compound. MS (DCI(+)) m/e 195.0 (M+H)$^+$.

Example 322E

Example 322D (2.06 g, 10.61 mmol) in ethanol (40 ml) was added to 5% Pd—C, wet (0.412 g, 3.87 mmol) under argon gas in a 100 mL stainless steel pressure bottle and shaken under 30 psi of hydrogen gas at room temperature for 2 hours. The mixture was filtered through a nylon membrane and concentrated in vacuo to afford the title compound. MS (DCI(+)) m/e 165.0 (M+H)$^+$.

Example 322F

The title compound was prepared as described in EXAMPLE 4F, substituting EXAMPLE 322E for EXAMPLE 4E and EXAMPLE 322C for EXAMPLE 4C. MS (ESI(+)) m/e 513.0, 515.0 (M+H)$^+$, (ESI(−)) m/e 511.0, 513.0 (M−H)$^-$.

Example 322G

The title compound was prepared as described in EXAMPLE 125F, substituting EXAMPLE 322F for EXAMPLE 125E. MS (ESI(+)) m/e 491.1 (M+H)$^+$, (ESI(−)) m/e 493.2 (M−H)$^-$.

Example 322H

The title compound was prepared as described in EXAMPLE 125G, substituting EXAMPLE 322G for EXAMPLE 125F. MS (ESI(+)) m/e 479.2 (M+H)$^+$, (ESI(−)) m/e 477.1 (M−H)$^-$.

Example 322I

The title compound was prepared as described in EXAMPLE 125H, substituting EXAMPLE 322H for EXAMPLE 125G and substituting aniline for 2-fluoroaniline. MS (ESI(+)) m/e 554.3 (M+H)$^+$, (ESI(−)) m/e 552.2 (M−H)$^-$; $^1$H-NMR (300 MHz, dimethylsulfoxide-d$_6$) δ 10.36 (s, 1H) 9.71 (s, 1H) 9.56 (d, 1H) 8.34 (d, 1H) 8.31 (t, 1H) 8.04 (ddd, 1H) 7.74-7.86 (m, 4H) 7.58-7.65 (m, 3H) 7.48-7.57 (m, 1H) 7.30-7.39 (m, 2H) 7.05-7.17 (m, 4H) 6.60 (d, 1H) 2.60-2.68 (m, 21-1) 2.39-2.46 (m, 2H) 2.17 (s, 6H).

Example 323

3-{3-[2-({-4-[2-(dimethylamino)ethyl]phenyl}amino)pyrimidin-4-yl]imidazo[1,2-a]pyridin-2-yl}-N-(2-fluorophenyl)benzamide The title compound was prepared as described in EXAMPLE 125H, substituting EXAMPLE 322H for EXAMPLE 125G. MS (ESI(+)) m/e 572 (M+H)$^+$, (ESI(−)) m/e 570 (M−H)$^-$; $^1$H-NMR (300 MHz, dimethylsulfoxide-d$_6$) δ 10.22 (s, 1H) 9.67 (s, 1H) 9.55 (d, 1H) 8.35 (d, 2H) 8.06 (d, 1H) 7.84 (d, 1H) 7.79 (d, 1H) 7.56-7.65 (m, 4H) 7.48-7.56 (m, 1H) 7.18-7.33 (m, 3H) 7.03-7.17 (m, 3H) 6.61 (d, 1H) 2.60-2.71 (m, 2H) 2.39-2.47 (m, 2H) 2.18 (s, 6H).

Example 324

3-{3-[2-({4-[2-(dimethylamino)ethyl]phenyl}amino)pyrimidin-4-yl]imidazo[1,2-a]pyridin-2-yl}-N-(3-fluorophenyl)benzamide The title compound was prepared as described in EXAMPLE 125H, substituting EXAMPLE 322H for EXAMPLE 125G and substituting 3-fluoroaniline for 2-fluoroaniline. MS (ESI(+)) m/e 572 (M+H)$^+$, (ESI(−)) m/e 570 (M−H)$^-$; $^1$H-NMR (300 MHz, dimethylsulfoxide-d$_6$) δ 10.52 (s, 1H) 9.68 (s, 1H) 9.54 (d, 1H) 8.34 (d, 1H) 8.31 (t, 1H) 8.01-8.06 (m, 1H) 7.81-0.87 (m, 1H) 7.71-7.81 (m, 2H) 7.56-7.66 (m, 4H) 7.52 (ddd, 1H) 7.39 (td, 1H) 7.06-7.16 (m, 3H) 6.94 (td, 1H) 6.60 (d, 1 H) 2.62-2.69 (m, 2H) 2.39-2.46 (m, 2H) 2.17 (s, 6H).

Example 325

3-{3-[2-({4-[2-(dimethylamino)ethyl]phenyl}amino)pyrimidin-4-yl]imidazo[1,2-a]pyridin-2-yl}-N-(4-fluorophenyl)benzamide The title compound was prepared as described in EXAMPLE 125H, substituting EXAMPLE 322H for EXAMPLE 125G and substituting 4-fluoroaniline for 2-fluoroaniline. MS (ESI(+)) m/e 572 (M+H)$^+$, (ESI(−)) m/e 570 (M−H)$^-$; $^1$H-NMR (300 MHz, dimethylsulfoxide-d$_6$) δ 10.42 (s, 1H) 9.71 (s, 1H) 9.55 (d, 1H) 8.34 (d, 1H) 8.31 (t, 1H) 7.97-8.08 (m, 1H) 7.80 (td, 4H) 7.58-7.67 (m, 3H) 7.53 (ddd, 1H) 7.05-7.26 (m, 5H) 6.59 (d, 1H) 2.61-2.70 (m, 2H) 2.37-2.47 (m, 2H) 2.17 (s, 6H).

Example 326

N-cyclopentyl-3-{3-[2-({4-[2-(dimethylamino)ethyl]phenyl}amino)pyrimidin-4-yl]imidazo[1,2-a]pyridin-2-yl}benzamide The title compound was prepared as described in EXAMPLE 125H, substituting EXAMPLE 322H for EXAMPLE 125G and substituting cyclopentylamine for 2-fluoroaniline. MS (ESI(+)) m/e 546 (M+H)$^+$, (ESI(−)) m/e 544 (M−H)$^-$; $^1$H-NMR (300 MHz, dimethylsulfoxide-d$_6$) δ 9.66 (s, 1H) 9.56 (d, 1H) 8.38 (d, 1H) 8.31 (d, 1H) 8.19 (s, 1H) 7.92 (d, 1H) 7.77 (d, 1H) 7.73 (d, 1H) 7.61 (d, 2H) 7.46-7.56 (m, 2H) 7.04-7.17 (m, 3H) 6.55 (d, 1H) 4.24 (td, 1H) 2.61-2.71 (m, 2H) 2.38-2.47 (m, 2H) 2.18 (s, 6H) 1.80-0.97 (m, 2H) 1.62-1.76 (m, 2H) 1.45-1.61 (m, 4H).

Example 327

N-cyclohexyl-3-{3-[2-({4-[2-(dimethylamino)ethyl]phenyl}amino)pyrimidin-4-yl]imidazo[1,2-a]pyridin-2-yl}benzamide The title compound was prepared as described in EXAMPLE 125H, substituting EXAMPLE 322H for EXAMPLE 125G and substituting cyclohexylamine for 2-fluoroaniline. MS (ESI(+)) m/e 560 (M+H)$^+$, (ESI(−)) m/e 558 (M−H)$^-$; $^1$H-NMR (300 MHz, dimethylsulfoxide-d$_6$) δ 9.66 (s, 1H) 9.55 (d, 1H) 8.31 (t, 2H) 8.20 (s, 1H) 7.91 (d, 1H)

7.77 (d, 1H) 7.73 (d, 1H) 7.60 (d, 2H) 7.52 (t, 2H) 7.05-7.18 (m, 3H) 6.56 (d, 1H) 3.70-3.86 (m, 1H) 2.62-2.70 (m, 2H) 2.39-2.46 (m, 2H) 2.18 (s, 6H) 1.78-1.87 (m, 2H) 1.68-1.77 (m, 2H) 1.61 (d, 1H) 1.22-1.41 (m, 4H) 1.05-1.19 (m, 1H).

Example 328

N-{4-[2-(dimethylamino)ethyl]phenyl}-4-{2-[3-(piperidin-1-ylcarbonyl)phenyl]imidazo[1,2-a]pyridin-3-yl}pyrimidin-2-amine The title compound was prepared as described in EXAMPLE 125H, substituting EXAMPLE 322H for EXAMPLE 125G and substituting piperidine for 2-fluoroaniline. MS (ESI(+)) m/e 546 (M+H)$^+$, (ESI(−)) m/e 544 (M−H)$^-$; $^1$H-NMR (300 MHz, dimethylsulfoxide-d$_6$) δ 9.71 (s, 1H) 9.46 (d, 1H) 8.35 (d, 1H) 7.69-7.81 (m, 2H) 7.46-7.65 (m, 5H) 7.40-7.47 (m, 1H) 7.06-7.17 (m, 3H) 6.62 (d, 1H) 3.45-3.63 (br m, 2H) 3.19-3.32 (br m, 2H) 2.61-2.70 (m, 2H) 2.38-2.46 (m, 2H) 2.17 (s, 6H) 1.21-1.66 (br m, 6H).

Example 329

3-{3-[2-({4-[2-(dimethylamino)ethyl]phenyl}amino)pyrimidin-4-yl]imidazo[1,2-a]pyridin-2-yl}-N-(2-methylphenyl)benzamide The title compound was prepared as described in EXAMPLE 125H, substituting EXAMPLE 322H for EXAMPLE 125G and substituting o-toluidine for 2-fluoroaniline. MS (ESI(+)) m/e 621 (M+H)$^+$, (ESI(−)) m/e 619 (M−H)$^-$; $^1$H-NMR (300 MHz, dimethylsulfoxide-d$_6$) δ 9.96 (s, 1H) 9.67 (s, 1H) 9.53 (d, 1H) 8.31-8.37 (m, 2H) 8.05 (d, 1H) 7.85 (d, 1H) 7.78 (d, 1H) 7.57-7.65 (m, 3H) 7.51 (ddd, 1H) 7.30-7.37 (m, 1H) 7.26 (td, 1H) 7.19 (td, 2H) 7.07-7.15 (m, 3H) 6.63 (d, 1H) 2.59-2.70 (m, 2H) 2.39-2.46 (m, 2H) 2.21 (s, 3H) 2.17 (s, 6H).

Example 330

N-(2-chlorophenyl)-3-{3-[2-({-4-[2-(dimethylamino)ethyl]phenyl}amino)pyrimidin-4-yl]imidazo[1,2-a]pyridin-2-yl}benzamide The title compound was prepared as described in EXAMPLE 125H, substituting EXAMPLE 322H for EXAMPLE 125G and substituting 2-chloroaniline for 2-fluoroaniline. MS (ESI(+)) m/e 588 (M+H)$^+$, (ESI(−)) m/e 586 (M−H)$^-$; $^1$H-NMR (300 MHz, dimethylsulfoxide-d$_6$) δ 10.18 (s, 1H) 9.71 (s, 11-1) 9.53 (d, 1H) 8.33-8.38 (m, 2H) 8.06 (ddd, 1H) 7.87 (dt, 1H) 7.76-7.82 (m, 11-1) 7.63 (t, 3H) 7.56 (dd, 2H) 7.48-7.53 (m, 1H) 7.39 (td, 1H) 7.30 (td, 1H) 7.07-7.17 (m, 3H) 6.62 (d, 1H) 2.60-2.69 (m, 2H) 2.38-2.46 (m, 2H) 2.17 (s, 6H).

Example 331

3-{3-[2-({4-[2-(dimethylamino)ethyl]phenyl}amino)pyrimidin-4-yl]imidazo[1,2-a]pyridin-2-yl}-N-(2-methoxyphenyl)benzamide The title compound was prepared as described in EXAMPLE 125H, substituting EXAMPLE 322H for EXAMPLE 125G and substituting 2-methoxyaniline for 2-fluoroaniline. MS (ESI(+)) m/e 584 (M+H)$^+$, (ESI(−)) m/e 582 (M−H)$^-$; $^1$H-NMR (300 MHz, dimethylsulfoxide-d$_6$) δ 9.67 (s, 1H) 9.55 (d, 1H) 9.48 (s, 1H) 8.35 (d, 1H) 8.29 (t, 1H) 8.03 (ddd, 1H) 7.85 (ddd, 1H) 7.73-7.82 (m, 2H) 7.57-7.66 (m, 3H) 7.52 (ddd, 1H) 7.05-7.23 (m, 5H) 6.97 (td, 1H) 6.62 (d, 1H) 3.82 (s, 3H) 2.61-2.70 (m, 2H) 2.39-2.46 (m, 2H) 2.18 (s, 6H).

Example 332

N-{4-[2-(dimethylamino)ethyl]phenyl}-4-{2-[3-(morpholin-4-ylcarbonyl)phenyl]imidazo[1,2-a]pyridin-3-yl}pyrimidin-2-amine The title compound was prepared as described in EXAMPLE 125H, substituting EXAMPLE 322H for EXAMPLE 125G and substituting morpholine for 2-fluoroaniline. MS (ESI(+)) m/e 548 (M+H)$^+$, (ESI(−)) m/e 546 (M−H)$^-$; $^1$H-NMR (300 MHz, dimethylsulfoxide-d$_6$) δ 9.71 (s, 1H) 9.46 (d, 1H) 8.36 (d, 1H) 7.73-7.81 (m, 2H) 7.43-7.66 (m, 6H) 7.03-7.16 (m, 3H) 6.63 (d, 1H) 3.38-3.73 (m, 8H) 2.60-2.70 (m, 2H) 2.37-2.46 (m, 2H) 2.17 (s, 6H).

Example 333

N-[3-(3-{2-[(3-pyrrolidin-3-ylphenyl)amino]pyrimidin-4-yl}imidazo[1,2-a]pyridin-2-yl)phenyl]indoline-1-carboxamide Example 333A The title compound was prepared as described in EXAMPLE 255A, substituting tert-butyl 3-(3-aminophenyl)pyrrolidine-1-carboxylate for tert-butyl 3-(4-aminophenyl)pyrrolidine-1-carboxylate. MS ESI(+): m/e 578.3 (M+H)$^+$.

Example 333B

Example 333A was reduced as described in EXAMPLE 1H to give the title compound. MS ESI(+): m/e 548.3 (M+H)$^+$.

Example 333C

N-[3-(3-{2-[(3-pyrrolidin-3-ylphenyl)amino]pyrimidin-4-yl}imidazo[1,2-a]pyridin-2-yl)phenyl]indoline-1-carboxamide, trifluoroacetic acid salt The title compound was prepared as described in EXAMPLE 244 from EXAMPLE 333B and EXAMPLE 251A. MS ESI(+): m/e 593.4 (M+H)$^+$. $^1$H NMR (400 MHz, dimethylsulfoxide-d$_6$) δ ppm 9.79 (s, 1 H), 9.57 (bd, 1 H), 8.92 (bs, 2 H), 8.65 (s, 1 H), 8.40 (d, 1 H), 7.98 (s, 1 H), 7.85 (d, 1 H), 7.80 (d, 1 H), 7.66-7.73 (m, 3 H), 7.57 (t, 1 H), 7.39 (t, 1 H), 7.25-7.32 (m, 2 H), 7.20 (d, 1 H), 7.08-7.16 (m, 2 H), 6.97 (d, 1 H), 6.90 (t, 1 H), 6.70 (d, 1 H), 4.14 (t, 2 H), 3.58-3.65 (m, 1 H), 3.37-3.44 (m, 2 H), 3.20-3.25 (m, 1 H), 3.17 (t, 2 H), 3.01-3.10 (m, 1 H), 2.30-2.38 (m, 1 H), 1.89-1.99 (m, 1H).

Example 334

N-[3-(3-{2-[(3-pyrrolidin-3-ylphenyl)amino]pyrimidin-4-yl}imidazo[1,2-a]pyridin-2-yl)phenyl]-3,4-dihydroquinoline-1(2 H)-carboxamide Example 334A A round-bottom flask was charged with EXAMPLE 333B (0.67 g, 1.223 mmol), 4-nitrophenyl chloroformate (0.283 g, 1.346 mmol) and anhydrous CH$_2$Cl$_2$ (15 mL). N-ethyl-N-isopropylpropan-2-amine (0.224 ml, 1.285 mmol) was added and the mixture was stirred at room temperature overnight. The mixture was concentrated and the crude material was used directly in the next step.

Example 334B

N-[3-(3-{2-[(3-pyrrolidin-3-ylphenyl)amino]pyrimidin-4-yl}imidazo[1,2-a]pyridin-2-yl)phenyl]-3,4-dihydroquinoline-1(2 H)-carboxamide, trifluoroacetic acid salt To solution of EXAMPLE 334A (100 mg, 0.14 mmol) in CH$_2$Cl$_2$ (2.5 ml) and 1-methyl-2-pyrrolidinone (1.0 ml) was added 1,2,3,4-tetrahydroquinoline (56 mg, 0.42 mmol). The mixture was stirred overnight at ambient temperature. The mixture was concentrated and the resulting residue was treated with CH$_2$Cl$_2$/trifluoroacetic acid (3 ml each for 3 hours). The mixture was concentrated and the residue was purified by HPLC on a reverse phase column eluting with trifluoroacetic acid buffer water-acetonitrile to give the title compound. MS ESI(+): m/e 607.3 (M+H)$^+$. $^1$H NMR (400 MHz, dimethylsulfoxide-d$_6$) δ ppm 9.78 (s, 1 H), 9.56 (bd, 1 H), 9.00 (s, 1 H), 8.84 (bs, 2 H), 8.40 (d, 1 H), 7.86 (s, 1 H), 7.77 (d, 1 H), 7.72 (s, 1 H), 7.54-7.65 (m, 3 H), 7.28-7.38 (m, 3 H), 7.23 (d, 1 H), 7.08-7.15 (m, 3 H), 94-6.98 (m, 2 H), 6.70 (d, 1 H), 3.70 (t, 2 H), 3.58-3.65 (m, 1 H), 3.35-3.44 (m, 2 H), 3.20-3.27 (m, 1 H), 3.01-3.10 (m, 1 H), 2.74 (t, 2 H), 2.29-2.38 (m, 1 H), 1.89-1.99 (m, 3H).

Example 335

N-[3-(3-{2-[(3-pyrrolidin-3-ylphenyl)amino]pyrimidin-4-yl}imidazo[1,2-a]pyridin-2-yl)phenyl]-3,4-dihydroisoquinoline-2(1H)-carboxamide The title compound was prepared as described in EXAMPLE 334, substituting 1,2,3,4-tetrahydroisoquinoline for 1,2,3,4-tetrahydroquinoline. MS ESI(+): m/e 607.4 (M+H)$^+$. $^1$H NMR (400 MHz, dimethylsulfoxide-d$_6$) δ ppm 9.67 (s, 1 H), 9.56 (bd, 1 H), 8.70 (s, 1 H), 8.84 (bs, 2 H), 8.33 (d, 1 H), 7.86 (s, 1 H), 7.73 (d, 1 H), 7.61-7.65 (m, 2 H), 7.49 (t, 1 H), 7.31 (t, 1 H), 7.22 (t, 1 H), 7.16-7.19 (m, 4 H), 7.06 (t, 1 H), 6.90 (d, 1 H), 6.64 (d, 1 H), 3.58-3.65 (m, 1 H), 3.35-3.44 (m, 2 H), 3.17 (s, 2 H), 3.08-3.15 (m, 1 H), 2.93-3.02 (m, 1 H), 2.84-2.86 (t, 2 H), 2.66-2.71 (t, 2 H), 2.11-2.18 (m, 1 H), 1.70-1.77 (m, 1H).

Example 336

4-{2-[3-(2,3-dihydro-1H-indol-1-ylcarbonyl)phenyl]imidazo[1,2-a]pyridin-3-yl}-N-{4-[2-(dimethylamino)ethyl]phenyl}pyrimidin-2-amine The title compound was prepared as described in EXAMPLE 125H, substituting EXAMPLE 322H for EXAMPLE 125G and substituting indoline for 2-fluoroaniline. MS (ESI(+)) m/e 580 (M+H)$^+$, (ESI(−)) m/e 578 (M−H)$^-$; $^1$H-NMR (300 MHz, dimethylsulfoxide-d$_6$) δ 9.66 (s, 1H) 9.48 (d, 1H) 8.34 (d, 1H) 7.79-7.85 (m, 2H) 7.73-7.79 (m, 1H) 7.56-7.64 (m, 4H) 7.50 (ddd, 1H) 7.27 (d, 1H) 6.97-7.18 (m, 5H) 6.64 (d, 1H) 3.98 (t, 2H) 3.06 (t, 2H) 2.60-2.69 (m, 2H) 2.38-2.46 (m, 2H) 2.18 (s, 6H).

Example 337

4-{2-[3-(1,3-dihydro-2H-isoindol-2-ylcarbonyl)phenyl]imidazo[1,2-a]pyridin-3-yl}-N-{4-[2-(dimethylamino)ethyl]phenyl}pyrimidin-2-amine The title compound was prepared as described in EXAMPLE 125H, substituting EXAMPLE 322H for EXAMPLE 125G and substituting isoindoline for 2-fluoroaniline. MS (ESI(+)) m/e 580 (M+H)$^+$, (ESI(−)) m/e 578 (M−H)$^-$; $^1$H-NMR (300 MHz, dimethylsulfoxide-d$_6$) δ 9.72 (s, 1H) 9.48 (d, 1H) 8.42 (d, 1H) 7.80-7.88 (m, 2H) 7.75-7.80 (m, 1H) 7.54-7.70 (m, 4H) 7.51 (ddd, 1H) 7.35-7.42 (m, 1H) 7.25-7.34 (m, 3H) 7.07-7.17 (m, 3H) 6.67 (d, 1H) 4.84 (s, 2H) 4.69 (s, 2H) 2.58-2.69 (m, 2H) 2.37-2.46 (m, 2H) 2.17 (s, 6H).

Example 338

N-{4-[2-(dimethylamino)ethyl)phenyl}-4-{2-[3-(pyrrolidin-1-ylcarbonyl)phenyl]imidazo[1,2-a]pyridin-3-yl}pyrimidin-2-amine The title compound was prepared as described in EXAMPLE 125H, substituting EXAMPLE 322H for EXAMPLE 125G and substituting pyrrolidine for 2-fluoroaniline. MS (ESI(+)) m/e 532 (M+H)$^+$, (ESI(−)) m/e 530 (M−H)$^-$; $^1$H-NMR (300 MHz, dimethylsulfoxide-d$_6$) δ 9.71 (s, 1H) 9.47 (d, 1H) 8.35 (d, 1H) 7.70-7.81 (m, 3H) 7.60 (d, 2H) 7.53-7.58 (m, 2H) 7.50 (ddd, 1H) 7.13 (d, 2H) 7.05-7.11 (m, 1H) 6.62 (d, 1H) 3.44 (t, 2H) 3.29-3.32 (m, 2H) 2.61-2.69 (m, 2H) 2.37-2.45 (m, 2H) 2.17 (s, 6H) 1.72-1.90 (m, 4H).

Example 339

N-{3-[3-(2-{[4-(1-acetylazetidin-3-yl)phenyl]amino}pyrimidin-4-yl)imidazo[1,2-a]pyridin-2-yl]phenyl}-2-chlorobenzamide Example 339A A 100 ml flask charged with 2-phenylpropane-1,3-diol (1.522 g, 10 mmol) and anhydrous acetonitrile (20 ml). The resulting solution was cooled to below −20° C. and trifluoromethanesulfonic anhydride (3.53 ml, 21 mmol) was added slowly over 10-20 minutes, maintaining the temperature below −10° C. This was followed immediately by the dropwise addition of N-ethyl-N-isopropylpropan-2-amine (4.35 ml, 25.00 mmol) over 20 minutes, maintaining the temperature below −10° C. The reaction was stirred 30 minutes from −20° to −10° C. and N-ethyl-N-isopropylpropan-2-amine was added (4.35 ml, 25.00 mmol) over 5 minutes followed by the addition of diphenylmethanamine (1.636 ml, 9.5 mmol) over 5 minutes. The reaction was heated at 70° C. for 2 hours. The reaction was concentrated and the residue was partitioned between brine (100 ml) and ethyl acetate (100 ml). The organic layer was washed with brine, dried over sodium sulfate, filtered and concentrated. The crude material was slurried in a mixture of methylene chloride and hexane (300 ml) and the insoluble solid was removed by filtration. The filtrate was concentrated and was purified on an ISCO chromatography system on a silica gel cartridge (150 g) eluted with a 50, 75, 100% methylene chloride in hexane step gradient to provide the title compound. MS (DCI) m/e 300 (M+H)$^+$.

Example 339B

EXAMPLE 339A (1.9 g) was hydrogenated with 20% palladium hydroxide (0.38 g) in methanol (100 ml) in a stainless steel pressure bottle at 30 psi for 24 hours at ambient temperature. HPLC indicated that all of the starting material had been consumed. The reaction mixture was filtered and concentrated.

Example 339C

A 250 ml flask was charged with EXAMPLE 339B (1.88 g), dichloromethane (80 ml) and N-ethyl-N-isopropylpropan-2-amine (1.730 ml, 9.93 mmol), and acetic anhydride (0.563 ml, 5.96 mmol) was added dropwise. The reaction mixture was stirred for 2 hours at ambient temperature and was concentrated to an oil which was purified on an ISCO chromatography system on a silica gel cartridge (115 g) eluted with a 2, 5, and 10% 7 N methanolic ammonia in methylene chloride step gradient to provide the title compound. MS (DCI) m/e 176 (M+H)$^+$, 193 (M+NH$_4$)$^+$;

Example 339D

A 5 ml tube was charged with fuming nitric acid, (2.0 ml, 48.2 mmol). This was cooled to ca. −30° C. and the 1-(3-phenylazetidin-1-yl)ethanone (300 mg, 1.712 mmol) was added very slowly dropwise. The reaction was kept at 0° C. for 20 minutes and was allowed to warm to ambient temperature. The reaction mixture then added to ice (40 ml) and neutralized with solid sodium bicarbonate. The mixture was extracted with ethyl acetate (3×50 ml) and the combined organics were dried over sodium sulfate, filtered and concentrated to provide the title compound. MS (DCI) m/e 221 (M+H)$^+$, 238 (M+NH$_4$)$^+$.

Example 339E

The title compound was prepared as described in EXAMPLE 4G substituting EXAMPLE 339D for EXAMPLE 4F. MS (DCI) m/e 191 (M+H)$^+$, 208 (M+NH$_4$)$^+$.

Example 339F

The title compound was prepared as described in EXAMPLE 103C substituting EXAMPLE 339E for EXAMPLE 103B. MS (ESI(+)) m/e 506 (M+H)$^+$, (ESI(−)) m/e 504 (M−H)$^-$.

Example 339G

The title compound was prepared as described in EXAMPLE 4G substituting EXAMPLE 339F for EXAMPLE 4F. MS (ESI(+)) m/e 476 (M+H)$^+$, (ESI(−)) m/e 474 (M−H)$^-$.

Example 339H

N-{3-[3-(2-{[4-(1-acetylazetidin-3-yl)phenyl]amino}pyrimidin-4-yl)imidazo[1,2-a]pyridin-2-yl]phenyl)-2-chlorobenzamide The title compound was prepared as described in EXAMPLE 98D substituting EXAMPLE 339G for EXAMPLE 98C and 2-chlorobenzoyl chloride for 2-(thiophen-2-yl)acetyl chloride. MS (ESI(+)) m/e 614 (M+H)$^+$, (ESI(−)) m/e 612 (M−H)$^-$; $^1$H-NMR (300 MHz, dimethylsulfoxide-d$_6$) δ 0.66 (s, 1H), 9.84 (s, 1H), 9.58 (m, 1H), 8.42 (d, 1H), 8.11 (m, 1H), 7.85 (t, 2H), 7.71 (m, 3H), 7.62-7.39 (m, 7H), 7.26 (m, 2H), 6.69 (m, 1H), 4.48 (m, 1H), 4.22 (m, 1H), 4.11 (m, 1H), 3.79 (m, 2H), 1.80 (s, 3H).

Example 340

N-{3-[3-(2-{[4-(1-acetylazetidin-3-yl)phenyl]amino}pyrimidin-4-yl)imidazo[1,2-a]pyridin-2-yl]phenyl}-2-thien-3-ylacetamide The title compound was prepared as described in EXAMPLE 98D substituting EXAMPLE 339G for EXAMPLE 98C and 2-(thiophen-3-yl)acetyl chloride for 2-(thiophen-2-yl)acetyl chloride. MS (ESI(+)) m/e 600 (M+H)$^+$, (ESI(−)) m/e 598 (M−H)$^-$; $^1$H-NMR (300 MHz, dimethylsulfoxide-d$_6$) δ 10.29 (s, 1H), 9.83 (s, 1H), 9.57 (m, 1H), 8.39 (m, 1H), 7.96 (m, 1H), 7.83 (d, 1H), 7.75-7.62 (m, 4H), 7.49-7.40 (m, 2H), 7.31 (m, 4H), 7.22 (t, 1H), 7.08 (dd, 1H), 6.65 (m, 1H), 4.48 (m, 1H), 4.22 (m, 1H), 4.09 (m, 1H), 3.79 (m, 2H), 3.66 (s, 2H), 1.80 (s, 3H).

Example 341

N-cyclohexyl-N'-(3-{3-[2-({3-[2-(dimethylamino)ethyl]phenyl}amino)pyrimidin-4-yl]imidazo[1,2-a]pyridin-2-yl}phenyl)urea Example 341A The title compound was prepared as described in EXAMPLE 252D, substituting EXAMPLE 402I for EXAMPLE 252C. MS (ESI(+)) m/e 480.1 (M+H)$^+$.

Example 341B

The title compound was prepared as described in EXAMPLE 4G, substituting EXAMPLE 341A for EXAMPLE 4F. MS (ESI(+)) m/e 450.1 (M+H)$^+$.

Example 341C

To a 4 mL vial was charged EXAMPLE 341B (40 mg, 0.089 mmol), tetrahydrofuran (1.3 mL) and N-methyl-2-pyrrolidinone (0.8 mL). The resulting solution was treated with isocyanatocyclohexane (33.4 mg, 0.267 mmol) and the reaction was heated at 60° C. for 24 hours. The reaction was concentrated under reduced pressure. The concentrate was purified by reverse-phase HPLC on a Shimadzu LC10 HPLC system with a Phenomenex C18 column (3×15 cm) eluting with a gradient of from 55% to 95% acetonitrile in 0.1% aqueous ammonium hydroxide. MS (ESI(+)) m/e 575.4 (M+H)$^+$; $^1$H NMR (300 MHz, dimethylsulfoxide-d$_6$) δ ppm 9.71 (s, 1 H) 9.58 (d, 1 H) 8.44 (s, 1 H) 8.34 (d, 1 H) 7.74 (m, 1 H) 7.46-7.65 (m, 5 H) 7.30 (t, 1 H) 7.05-7.23 (m, 3 H) 6.85 (d, 1 H) 6.60 (d, 1 H) 6.05 (d, 1 H) 3.47 (m, 1 H) 2.66 (m, 2 H) 2.42 (m, 2 H) 2.14 (s, 6 H) 1.46-1.82 (m, 5 H) 1.08-1.36 (m, 5 H).

Example 342

N-(sec-butyl)-N'-(3-{3-[2-({3-[2-(dimethylamino)ethyl]phenyl}amino)pyrimidin-4-yl]imidazo[1,2-a]pyridin-2-yl}phenyl)urea The title compound was prepared as described in EXAMPLE 341C, substituting 2-isocyanatobutane for isocyanatocyclohexane. MS (ESI(+)) m/e 549.3 (M+H)$^+$; $^1$H NMR (300 MHz, dimethylsulfoxide-d$_6$) δ ppm 9.71 (s, 1 H) 9.58 (d, 1 H) 8.46 (s, 1 H) 8.34 (d, 1 H) 7.75 (m, 1 H) 7.46-7.68 (m, 5 H) 7.30 (t, 1 H) 7.05-7.24 (m, 3 H) 6.85 (d, 1 H) 6.61 (d, 1 H) 5.97 (d, 1 H) 3.58 (m, 1 H) 2.66 (m, 2 H) 2.42 (m, 2 H) 2.14 (s, 6 H) 1.41 (m, 2 H) 1.06 (d, 3 H) 0.86 (t, 3 H).

Example 343

N-(tert-butyl)-N'-(3-{3-[2-({3-[2-(dimethylamino)ethyl]phenyl}amino)pyrimidin-4-yl]imidazo[1,2-a]pyridin-2-yl}phenyl)urea The title compound was prepared as described in EXAMPLE 341C, substituting 2-isocyanato-2-methylpropane for isocyanatocyclohexane. MS (ESI(+)) m/e 549.3 (M+H)$^+$; $^1$H NMR (300 MHz, dimethylsulfoxide-d$_6$) δ ppm 9.67 (s, 1 H) 9.57 (d, 1 H) 8.31-8.36 (m, 2 H) 7.74 (m, 1 H) 7.43-7.66 (m, 5 H) 7.28 (t, 1 H) 7.20 (t, 1 H) 7.04-7.13 (m, 2 H) 6.85 (m, 1 H) 6.61 (d, 1 H) 5.94 (s, 1 H) 2.66 (m, 2 H) 2.43 (m, 2 H) 2.14 (s, 6 H) 1.28 (s, 9 H).

Example 344

N-(3-{3-[2-({3-[2-(dimethylamino)ethyl]phenyl}amino)pyrimidin-4-yl]imidazo[1,2-a]pyridin-2-yl}phenyl)-N'-isopropylurea The title compound was prepared as described in EXAMPLE 341C, substituting 2-isocyanatopropane for isocyanatocyclohexane. MS (ESI(+)) m/e 535.3 (M+H)$^+$; $^1$H NMR (300 MHz, dimethylsulfoxide-d$_6$) δ ppm 9.67 (s, 1 H) 9.58 (d, 1 H) 8.41 (s, 1 H) 8.34 (d, 1 H) 7.74 (m, 1 H) 7.47-7.67 (m, 5 H) 7.30 (t, 1 H) 7.20 (t, 1 H) 7.04-7.15 (m, 2 H) 6.85 (m, 1 H) 6.61 (d, 1 H) 5.96 (d, 1 H) 3.74 (m, 1 H) 2.66 (m, 2 H) 2.42 (m, 2 H) 2.14 (s, 6 H) 1.09 (d, 6 H).

Example 345

N-cyclopentyl-N'-(3-{3-[2-({3-[2-(dimethylamino)ethyl]phenyl}amino)pyrimidin-4-yl]imidazo[1,2-a]pyridin-2-yl}phenyl)urea The title compound was prepared as described in EXAMPLE 341C, substituting isocyanatocyclopentane for isocyanatocyclohexane. MS (ESI(+)) m/e 561.3 (M+H)$^+$; $^1$H NMR (300 MHz, dimethylsulfoxide-d$_6$) δ ppm 9.71 (s, 1 H) 9.58 (d, 1 H) 8.40 (s, 1 H) 8.34 (d, 1 H) 7.74 (m, 1 H) 7.46-7.66 (m, 5 H) 7.30 (t, 1 H) 7.05-7.23 (m, 3 H) 6.85 (m, 1 H) 6.60 (d, 1 H) 6.14 (d, 1 H) 3.91 (m, 1 H) 2.66 (m, 2 H) 2.42 (m, 2 H) 2.14 (s, 6 H) 1.77-1.88 (m, 2 H) 1.49-1.66 (m, 4 H) 1.29-1.40 (m, 2 H).

Example 346

N-(3-{3-[2-({3-[2-(dimethylamino)ethyl]phenyl}amino)pyrimidin-4-yl]imidazo[1,2-a]pyridin-2-yl}phenyl)-N'-[(1S)-1,2-dimethylpropyl]urea The title compound was prepared as described in EXAMPLE 341C, substituting (S)-2-isocyanato-3-methylbutane for isocyanatocyclohexane. MS (ESI(+)) m/e 563.4 (M+H)$^+$; $^1$H NMR (300 MHz, dimethylsulfoxide-d$_6$) δ ppm 9.67 (s, 1 H) 9.58 (d, 1 H) 8.42 (s, 1 H) 8.34 (d, 1 H) 7.74 (m, 1 H) 7.57-7.68 (m, 3 H) 7.49 (m, 2 H) 7.30 (t, 1 H) 7.20 (t, 1 H) 7.04-7.15 (m, 2 H) 6.85 (m, 1 H) 6.61 (d, 1 H) 5.95 (d, 1 H) 3.54 (m, 1 H) 2.66 (m, 2 H) 2.43 (m, 2 H) 2.14 (s, 6 H) 1.65 (m, 1 H) 1.01 (d, 3 H) 0.86 (dd, 6 H).

Example 347

N-(3-{3-[2-({3-[2-(dimethylamino)ethyl]phenyl}amino)pyrimidin-4-yl]imidazo[1,2-a]pyridin-2-yl}phenyl)-N'-[(1S)-1-phenylethyl]urea To a 4 mL vial was charged EXAMPLE 341B (40 mg, 0.089 mmol), tetrahydrofuran (1.3 mL) and N-methyl-2-pyrrolidinone (0.8 mL). The resulting solution was treated with (S)-(1-isocyanatoethyl)benzene (22 mg, 0.15 mmol) and the reaction was stirred at ambient temperature for 40 hours. The reaction was concentrated under reduced pressure. The concentrate was purified by reverse-phase HPLC on a Shimadzu LC10 HPLC system with a Phenomenex C18 column (3×15 cm) eluting with a gradient of from 55% to 95% acetonitrile in 0.1% aqueous ammonium hydroxide to provide the title compound. MS (ESI(+)) m/e 597.4 (M+H)$^+$; $^1$H NMR (300 MHz, dimethylsulfoxide-d$_6$) δ ppm 9.67 (s, 1 H) 9.57 (d, 1 H) 8.51 (s, 1 H) 8.33 (d, 1 H) 7.44-7.76 (m, 6 H) 7.12-7.34 (m, 8 H) 7.06 (m, 1 H) 6.84 (m, 1 H) 6.59 (m, 2 H) 4.81 (m, 1 H) 2.66 (m, 2 H) 2.42 (m, 2 H) 2.14 (s, 6 H) 1.38 (d, 3 H).

Example 348

N-(3-{3-[2-({3-[2-(dimethylamino)ethyl]phenyl}amino)pyrimidin-4-yl]imidazo[1,2-a]pyridin-2-yl}phenyl)-N'-(3,5-dimethylisoxazol-4-yl)urea The title compound was prepared as described in EXAMPLE 347, substituting 4-isocyanato-3,5-dimethylisoxazole for (S)-(1-isocyanatoethyl)benzene. MS (ESI(+)) m/e 588.3 (M+H)$^+$; $^1$H NMR (300 MHz, dimethylsulfoxide-d$_6$) δ ppm 9.71 (s, 1 H) 9.55 (d, 1 H) 9.00 (s, 1 H) 8.36 (d, 1 H) 7.77 (m, 3 H) 7.64 (m, 1 H) 7.46-7.59 (m, 3 H) 7.35 (t, 1 H) 7.20 (m, 2 H) 7.08 (m, 1 H) 6.84 (m, 1 H) 6.62 (d, 1 H) 2.66 (m, 2 H) 2.42 (m, 2 H) 2.28 (s, 3 H) 2.14 (s, 6 H) 2.11 (s, 3 H).

Example 349

N-(3-{3-[2-({3-[2-(dimethylamino)ethyl]phenyl}amino)pyrimidin-4-yl]imidazo[1,2-a]pyridin-2-yl}phenyl)-N'-thien-2-ylurea The title compound was prepared as described in EXAMPLE 347, substituting 2-isocyanatothiophene for (S)-(1-isocyanatoethyl)benzene. MS (ESI(+)) m/e 575.3 (M+H)$^+$; $^1$H NMR (300 MHz, dimethylsulfoxide-d$_6$) δ ppm 9.68 (s, 1 H) 9.56 (d, 1 H) 8.94 (brs, 1 H) 8.36 (d, 1 H) 7.78 (m, 2 H) 7.46-7.64 (m, 5 H) 7.36 (t, 1 H) 7.21 (m, 2 H) 7.07 (m, 1 H) 6.82 (m, 3 H) 6.64 (d, 1 H) 6.55 (dd, 1 H) 2.66 (m, 2 H) 2.42 (m, 2 H) 2.14 (s, 6 H).

Example 350

N-(3-{3-[2-({3-[2-(dimethylamino)ethyl]phenyl}amino)pyrimidin-4-yl]imidazo[1,2-a]pyridin-2-yl}phenyl)-N'-(2-methylphenyl)urea The title compound was prepared as described in EXAMPLE 347, substituting 1-isocyanato-2-methylbenzene for (S)-(1-isocyanatoethyl)benzene. MS (ESI(+)) m/e 583.3 (M+H)$^+$; $^1$H NMR (300 MHz, dimethylsulfoxide-d$_6$) δ ppm 9.68 (s, 1 H) 9.56 (d, 1 H) 9.15 (s, 1 H) 8.37 (d, 1 H) 7.90 (s, 1 H) 7.79 (m, 3 H) 7.46-7.65 (m, 4 H) 7.37 (t, 1 H) 7.05-7.25 (m, 5 H) 6.94 (m, 1 H) 6.85 (m, 1 H) 6.65 (d, 1 H) 2.66 (m, 2 H) 2.42 (m, 2 H) 2.24 (s, 3 H) 2.14 (s, 6 H).

Example 351

N-(3-{3-[2-({3-[2-(dimethylamino)ethyl]
phenyl}amino)pyrimidin-4-yl]imidazo[1,2-a]pyri-
din-2-yl}phenyl)indoline-1-carboxamide To a 4 mL vial was charged EXAMPLE 341B (50 mg, 0.112 mmol), pyridine (0.027 mL, 0.336 mmol), tetrahydrofuran (1.3 mL), and N-methyl-2-pyrrolidinone (1 mL). The resulting solution was treated with EXAMPLE 251A (40.7 mg, 0.224 mmol) and stirred at 60° C. for 24 hours. The reaction was concentrated and purified by reverse-phase HPLC on a Waters Nova-Pakâ FIR C18 6 um 60 Å Prep-Pakâ cartridge column (25 mm×100 mm) eluting with a gradient of acetonitrile and 0.1% trifluoroacetic acid in water to provide the title compound. MS (ESI(+)) m/e 595.4 (M+H)$^+$; $^1$H NMR (300 MHz, dimethylsulfoxide-d$_6$) δ ppm 9.86 (s, 1 H) 9.62 (d, 1 H) 9.39 (brs, 1 H) 8.69 (s, 1 H) 8.40 (d, 1 H) 7.99 (m, 1 H) 7.83 (m, 2 H) 7.71 (m, 2 H) 7.60 (m, 2 H) 7.40 (t, 1 H) 7.08-7.33 (m, 5 H) 6.90 (m, 2 H) 6.70 (d, 1 H) 4.14 (t, 2 H) 3.28 (m, 2 H) 3.18 (t, 2 H) 2.92 (m, 2 H) 2.82 (d,6 H).

Example 352

N-(3-{3-[2-({3-[2-(dimethylamino)ethyl]
phenyl}amino)pyrimidin-4-yl]imidazo[1,2-a]pyri-
din-2-yl}phenyl) piperidine-1-carboxamide The title compound was prepared as described in EXAMPLE 351, substituting piperidine-1-carbonyl chloride for EXAMPLE 251A. The crude reaction product was purified by reverse-phase HPLC on a Shimadzu LC10 HPLC system with a Phenomenex C18 column (3×15 cm) eluting with a gradient of from 35% to 75% acetonitrile in 0.1% aqueous ammonium hydroxide to provide the title compound. MS (ESI(+)) m/e 561.2 (M+H)$^+$; $^1$H NMR (300 MHz, dimethylsulfoxide-d$_6$) δ ppm 9.68 (s, 1 H) 9.59 (d, 1 H) 8.55 (s, 1 H) 8.34 (d, 1 H) 7.81 (m, 1 H) 7.73 (m, 1 H) 7.60 (m, 3 H) 7.49 (m, 1 H) 7.29 (t, 1 H) 7.17 (m, 2 H) 7.06 (m, 1 H) 6.85 (d, 1 H) 6.62 (d, 1 H) 3.41 (m, 4 H) 2.66 (m, 2 H) 2.42 (m, 2 H) 2.14 (s, 6 H) 1.44-1.62 (m, 6 H).

Example 353

N-(3-{3-[2-({3-[2-(dimethylamino)ethyl]
phenyl}amino)pyrimidin-4-yl]imidazo[1,2-a]pyri-
din-2-yl}phenyl)-N'-thien-3-ylurea The title compound was prepared as described in EXAMPLE 347, substituting 3-isocyanatothiophene for (S)-(1-isocyanatoethyl)benzene. MS (ESI(+)) m/e 575.3 (M+H)$^+$; $^1$H NMR (300 MHz, dimethylsulfoxide-d$_6$) δ ppm 9.68 (s, 1 H) 9.55 (d, 1 H) 8.95 (s, 1 H) 8.80 (s, 1 H) 8.36 (d, 1 H) 7.75 (m, 2 H) 7.41-7.64 (m, 5 H) 7.36 (t, 1 H) 7.16-7.28 (m, 3 H) 7.05 (m, 2 H) 6.85 (d, 1 H) 6.64 (d, 1 H) 2.67 (m, 2 H) 2.42 (m, 2 H) 2.15 (s, 6 H).

Example 354

N-(3-{3-[2-({3-[2-(dimethylamino)ethyl]
phenyl}amino)pyrimidin-4-yl]imidazo[1,2-a]pyri-
din-2-yl}phenyl)morpholine-4-carboxamide The title compound was prepared as described in EXAMPLE 351, substituting morpholine-4-carbonyl chloride for EXAMPLE 251A. MS (ESI(+)) m/e 563.3 (M+H)$^+$; $^1$H NMR (300 MHz, dimethylsulfoxide-d$_6$) $^1$H NMR (300 MHz, methanol-d$_4$) δ ppm 9.83 (d, 1 H) 8.35 (d, 1 H) 7.92 (m, 2 H) 7.84 (m, 1 H) 7.72 (m, 1 H) 7.30-7.60 (m, 6 H) 7.03 (m, 1 H) 6.74 (d, 1 H) 3.70 (m, 4 H) 3.52 (m, 4 H) 3.41 (m, 2 H) 3.05 (m, 2 H) 2.93 (s, 6 H).

Example 355

2,3-dimethyl-N-[3-(3-{2-[(4-pyrrolidin-3-ylphenyl)
amino]pyrimidin-4-yl)imidazo[1,2-a]pyridin-2-yl)
phenyl]benzamide The title compound was prepared as described in EXAMPLE 244 from EXAMPLE 255B and 2,3-dimethylbenzoyl chloride. MS ESI(+): m/e 580.3 (M+H)$^+$. $^1$H NMR (400 MHz, dimethylsulfoxide-d$_6$) δ ppm 10.42 (s, 1 H), 9.81 (s, 1 H), 9.56 (bd, 1 H), 8.91 (bs, 2 H), 8.40 (d, 1 H), 8.15 (s, 1 H), 7.82-7.85 (m, 2 H), 7.72 (d, 2 H), 7.64 (t, 1 H), 7.46 (t, 1 H), 7.37 (d, 1 H), 7.16-7.29 (m, 6 H), 6.70 (d, 1 H), 3.58-3.65 (m, 1 H), 3.35-3.48 (m, 2 H), 3.21-3.26 (m, 1 H), 3.01-3.08 (m, 1 H), 2.31-2.37 (m, 1 H), 2.29 (s, 3 H), 2.24 (s, 3 H), 1.89-1.98 (m, 1H).

Example 356

N-[3-(3-{2-[(4-pyrrolidin-2-ylphenyl)amino]pyrimi-
din-4-yl}imidazo[1,2-a]pyridin-2-yl)phenyl]-2-thien-
2-ylacetamide

Example 356A

The title compound was prepared as described in EXAMPLE 255A, substituting tert-butyl 2-(4-aminophenyl)pyrrolidine-1-carboxylate for tert-butyl 3-(3-aminophenyl)pyrrolidine-1-carboxylate. MS ESI(-): m/e 576.1 (M-H)$^-$.

Example 356B

EXAMPLE 356B was reduced as described in EXAMPLE 1H to give the title compound. MS ESI(-): m/e 548.3 (M+H)$^+$.

Example 356C

N-[3-(3-{2-[(4-pyrrolidin-2-ylphenyl)amino]pyrimi-
din-4-yl)imidazo[1,2-a]pyridin-2-yl)phenyl]-2-thien-
2-ylacetamide, trifluoroacetic acid salt The title compound was prepared as described in EXAMPLE 244 from EXAMPLE 356B and 2-(thiophen-2-yl)acetyl chloride. MS ESI(+): m/e 572.2 (M+H)$^+$. $^1$H NMR (400 MHz, dimethylsulfoxide-d$_6$) δ ppm 10.34 (s, 1 H), 9.94 (s, 1 H), 9.56 (bd, 1 H), 9.37 (bs, 1 H), 8.59 (bs, 1 H), 8.40 (d, 1 H), 7.98 (s, 1 H), 7.82 (d, 2 H), 7.80 (m, 1 H), 7.70 (d, 1 H), 7.60 (t, 1 H), 7.38-7.44 (m, 4 H), 7.32 (d, 1 H), 7.17 (t, 1 H), 6.96-6.99 (m, 2 H), 6.70 (d, 1 H), 4.48-4.52 (m, 1 H), 3.88 (s, 2 H), 3.27-3.37 (m, 2 H), 2.30-2.36 (m, 1 H), 2.02-2.20 (m, 3H).

Example 357

2-chloro-N-[3-(3-{2-[(4-pyrrolidin-2-ylphenyl)
amino]pyrimidin-4-yl) imidazo[1,2-a]pyridin-2-yl)
phenyl]benzamide The title compound was prepared as described in EXAMPLE 244 from EXAMPLE 356B and 2-chlorobenzoyl chloride. MS ESI(+): m/e 586.2 (M+H)$^+$. $^1$H NMR (400

MHz, dimethylsulfoxide-d$_6$) δ ppm 10.63 (s, 1 H), 9.96 (s, 1 H), 9.56 (bd, 1 H), 9.38 (bs, 1 H), 8.59 (bs, 1 H), 8.43 (d, 1 H), 8.13 (s, 1 H), 7.79-7.86 (m, 4 H), 7.64 (t, 1 H), 7.39-7.59 (m, 8 H), 7.20 (t, 1 H), 6.73 (d, 1 H), 4.48-4.54 (m, 1 H), 3.27-3.37 (m, 2 H), 2.30-2.36 (m, 1 H), 2.02-2.20 (m, 3H).

Example 358

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,6-difluorobenzamide Example 358A The title compound was prepared as described in EXAMPLE 195A, substituting EXAMPLE 402G for 4-nitrophenethyl bromide, and N,N-dimethylpyrrolidin-3-amine for dimethylamine. MS (DCI(+)) m/e 264 (M+H)$^+$.

Example 358B

The title compound was prepared as described in EXAMPLE 1H, substituting EXAMPLE 358A for EXAMPLE 1G. MS (DCI(+)) m/e 234 (M+H)$^+$.

Example 358C

The title compound was prepared as described in EXAMPLE 4F, substituting EXAMPLE 358B for EXAMPLE 4E. MS (ESI(+)) m/e 549 (M+H)$^+$.

Example 358D

The title compound was prepared as described in EXAMPLE 4G, substituting EXAMPLE 358C for EXAMPLE 4F. MS (ESI(+)) m/e 519 (M+H)$^+$.

Example 358E

The title compound was prepared as described in EXAMPLE 4H, substituting EXAMPLE 358D for EXAMPLE 4G. MS (ESI(+)) m/e 659 (M+H)$^+$, $^1$H NMR (400 MHz, dimethylsulfoxide-d$_6$) δ ppm 10.88 (s, 1 H) 9.67 (s, 1 H) 9.51 (d, 1 H) 8.36 (s, 1 H) 8.05 (s, 1H) 7.77 (m, 2 H) 7.67 (s, 1 H) 7.53-7.62 (m, 2 H) 7.39-7.51 (m, 3 H) 7.25 (t, 2 H) 7.19 (m, 1 H) 7.07 (m, 1 H) 6.83 (s, 1 H) 6.67 (d, 1 H) 2.64-2.71 (d, 4 H) 2.58 (m, 2 H) 2.40 (m, 1 H) 2.27 (m, 1 H) 2.17 (m, 0.5 H) 2.08 (s, 6 H) 1.90 (m, 0.5 H) 1.78 (m, 1 H) 1.56 (m, 1 H).

Example 359

2-chloro-N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]benzamide The title compound was prepared as described in EXAMPLE 4H, substituting EXAMPLE 358D for EXAMPLE 4G, and 2-chlorobenzoyl chloride for 2,6-difluorobenzoyl chloride. MS (ESI(+)) m/e 658 (M+H)$^+$, $^1$H NMR (400 MHz, dimethylsulfoxide-d$_6$) δ ppm 10.58 (s, 1 H) 9.67 (s, 1 H) 9.51 (s, 1 H) 8.36 (d, 1 H) 8.07 (s, 1 H) 7.82 (d, 1 H) 7.76 (d, 1 H) 7.66 (s, 1 H) 7.52-7.59 (m, 3 H) 7.37-7.51 (m, 5 H) 7.19 (t, 1 H) 7.07 (t, 1 H) 6.84 (d, 1 H) 6.66 (d, 1 H) 2.64-2.71 (m, 4 H) 2.58 (m, 2 H) 2.40 (m, 1 H) 2.28 (m, 1 H) 2.18 (m, 0.5 H) 2.09 (s, 6 H) 1.90 (m, 0.5 H) 1.79 (m, 1 H) 1.55 (m, 1 H).

Example 360

N-[3-(3-{2-[(3-{2-[3-(dimethylamino)pyrrolidin-1-yl]ethyl}phenyl)amino)]pyrimidin-4-yl}imidazo[1,2-a]pyridin-2-yl)phenyl]thiophene-2-carboxamide The title compound was prepared as described in EXAMPLE 4H, substituting EXAMPLE 358D for EXAMPLE 4G, and thiophene-2-carbonyl chloride for 2,6-difluorobenzoyl chloride. MS (ESI(+)) m/e 629 (M+H)$^+$, $^1$H NMR (400 MHz, dimethylsulfoxide-d$_6$) δ ppm 10.32 (s, 1 H) 9.68 (s, 1 H) 9.55 (d, 1 H) 8.37 (d, 1 H) 8.10 (s, 1 H) 8.04 (d, 1 H) 7.89 (s, 1 H) 7.86 (d, 1 H) 7.76 (d, 1 H) 7.68 (s, 1 H) 7.57 (s, 1 H) 7.49 (d, 1 H) 7.42 (d, 1 H) 7.34 (s, 1 H) 7.20 (m, 2 H) 7.07 (m, 1 H) 6.84 (s, 1 H) 6.66 (d, 1 H) 2.64-2.69 (m, 4 H) 2.59 (m, 2 H) 2.42 (d, 1 H) 2.28 (m, 1 H) 2.18 (m, 0.5 H) 2.10 (s, 6 H) 1.89 (m, 0.5 H) 1.79 (m, 1 H) 1.56 (m, 1 H).

Example 361

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2-thien-2-ylacetamide The title compound was prepared as described in EXAMPLE 4H, substituting EXAMPLE 358D for EXAMPLE 4G, and 2-thiopheneacetyl chloride for 2,6-difluorobenzoyl chloride. MS (ESI(+)) m/e 643 (M+H)$^+$, $^1$H NMR (400 MHz, dimethylsulfoxide-d$_6$) δ ppm 10.30 (s, 1 H) 9.67 (s, 1 H) 9.51 (s, 1 H) 8.35 (d, 1 H) 7.92 (s, 1 H) 7.73 (m, 2 H) 7.67 (s, 1 H) 7.56 (d, 1 H) 7.48 (m, 1 H) 7.38 (m, 2 H) 7.32 (m, 1 H) 7.19 (m, 1 H) 7.06 (m, 1 H) 6.97 (m, 2 H) 6.84 (s, 1 H) 6.62 (d, 1 H) 3.87 (s, 2 H) 2.64-2.71 (m, 4 H) 2.58 (m, 2 H) 2.40 (m, 1 H) 2.27 (m, 1 H) 2.18 (m, 0.5 H) 2.08 (s, 6 H) 1.90 (m, 0.5 H) 1.79 (m, 1 H) 1.56 (m, 1 H).

Example 362

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,3-difluorobenzamide The title compound was prepared as described in EXAMPLE 4H, substituting EXAMPLE 358D for EXAMPLE 4G, and 2,3-difluorobenzoyl chloride for 2,6-difluorobenzoyl chloride. MS (ESI(+)) m/e 659 (M+H)$^+$, $^1$H NMR (400 MHz, dimethylsulfoxide-d$_6$) δ ppm 10.64 (s, 1 H) 9.68 (s, 1 H) 9.52 (d, 1 H) 8.37 (m, 1 H) 8.07 (s, 1 H) 7.82 (s, 1 H) 7.76 (d, 1 H) 7.55-7.67 (m, 3 H) 7.40-7.50 (m, 4 H) 7.34 (m, 1 H) 7.19 (t, 1 H) 7.07 (t, 1 H) 6.84 (s, 1 H) 6.66 (d, 1 H) 2.64-2.71(m, 4 H) 2.58 (m, 2 H) 2.40 (m, 1 H) 2.28 (m, 1 H) 2.17 (m, 0.5 H) 2.06 (s, 6 H) 1.90 (d, 0.5 H) 1.78 (m, 1 H) 1.56 (m, 1 H).

Example 363

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,5-difluorobenzamide The title compound was prepared as described in EXAMPLE 4H, substituting EXAMPLE 358D for EXAMPLE 4G, and 2,5-difluorobenzoyl chloride for 2,6-difluorobenzoyl chloride. MS (ESI(+)) m/e 659 (M+H)$^+$, $^1$H NMR (400 MHz, dimethylsulfoxide-d$_6$) δ ppm 10.58 (s, 1 H) 9.68 (s, 1 H) 9.52 (s, 1 H) 8.37 (d, 1 H) 8.07 (s, 1 H) 7.83 (d, 1 H) 7.76 (d, 1 H) 7.67 (s, 1 H) 7.45-7.57 (m, 3 H) 7.38-7.45

(m, 4 H) 7.19 (t, 1 H) 7.07 (t, 1 H) 6.85 (d, 1 H) 6.65 (d, 1 H) 2.64-2.71 (m, 4 H) 2.53-2.62 (m, 2 H) 2.41 (m, 1 H) 2.28 (m, 1 H) 2.18 (m, 0.5 H) 2.06 (s, 6 H) 1.90 (m, 0.5 H) 1.79 (m, 1 H) 1.55 (m, 1 H).

Example 364

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2-phenylacetamide The title compound was prepared as described in EXAMPLE 4H, substituting EXAMPLE 358D for EXAMPLE 4G, and phenylacetyl chloride for 2,6-difluorobenzoyl chloride. MS (ESI(+)) m/e 637 (M+H)$^+$, $^1$H NMR (400 MHz, dimethylsulfoxide-$d_6$) δ ppm 10.26 (s, 1 H) 9.67 (s, 1 H) 9.52 (d, 1 H) 8.34 (d, 1 H) 7.93 (s, 1 H) 7.74 (d, 2 H) 7.67 (s, 1 H) 7.56 (d, 1 H) 7.47 (d, 1 H) 7.37 (t, 1 H) 7.28-7.34 (m, 5 H) 7.24 (m, 1 H) 7.19 (t, 1 H) 7.06 (t, 1 H) 6.84 (s, 1 H) 6.62 (d, 1 H) 3.64 (s, 2 H) 2.64-2.70 (m, 4 H) 2.57 (m, 2 H) 2.40 (m, 1 H) 2.27 (m, 1 H) 2.18 (m, 0.5 H) 2.08 (s, 6 H) 1.91 (m, 0.5 H) 1.78 (m, 1 H) 1.55 (m, 1 H).

Example 365

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-N'-phenylurea The title compound was prepared as described in EXAMPLE 3, substituting EXAMPLE 358D for EXAMPLE 1H. MS (ESI(+)) m/e 638 (M+H)$^+$, $^1$H NMR (400 MHz, dimethylsulfoxide-$d_6$) δ ppm 9.67 (s, 1 H) 9.55 (d, 1 H) 8.80 (s, 1 H) 8.64 (s, 1 H) 8.36 (d, 1 H) 7.76 (m, 2 H) 7.67 (s, 1 H) 7.56 (m, 2 H) 7.42-7.51 (m, 3 H) 7.37 (m, 1 H) 7.17-7.29 (m, 4 H) 7.07 (m, 1 H) 6.96 (m, 1 H) 6.85 (d, 1 H) 6.65 (d, 1 H) 2.63-2.67 (m, 4 H) 2.58 (m, 2 H) 2.39 (m, 1 H) 2.26 (m, 1 H) 2.17 (m, 0.5 H) 2.07 (s, 6 H) 190 (m, 0.5 H) 1.79 (dd, 1 H) 1.55 (m, 1 H).

Example 366

N-{3-[3-(2-{[4-(1-acetylazetidin-3-yl)phenyl]amino}pyrimidin-4-yl)imidazo[1,2-a]pyridin-2-yl]phenyl}indoline-1-carboxamide The title compound was prepared as described in EXAMPLE 98D substituting EXAMPLE 339G for EXAMPLE 98C and indoline-1-carbonyl chloride for 2-(thiophen-2-yl)acetyl chloride. MS (ESI(+)) m/e 621 (M+H)$^+$, (ESI(−)) m/e 619 (M−H)$^-$; $^1$H-NMR (300 MHz, dimethylsulfoxide-$d_6$) δ 9.84 (s, 1H), 9.62 (m, 1H), 8.69 (s, 1H), 8.42 (m, 1H), 7.99 (m, 1H), 7.85 (d, 2H), 7.71 (m, 4H), 7.43 (t, 1H), 7.30-7.17 (m, 5H), 7.11 (t, 1H), 6.90 (t, 1H), 6.69 (m, 1H), 4.48 (m, 1H), 4.26-4.05 (m, 4H), 3.79 (m, 2H), 3.17 (t, 2H), 1.79 (s, 31-1).

Example 367

N-{3-[3-(2-{[2-(dimethylamino)-2,3-dihydro-1H-inden-5-yl]amino}pyrimidin-4-yl)imidazo[1,2-a]pyridin-2-yl]phenyl}-2,3-dimethylbenzamide The title compound was prepared as described in EXAMPLE 98D substituting EXAMPLE 106D for EXAMPLE 98C and 2,3-dimethylbenzoyl chloride for 2-(thiophen-2-yl)acetyl chloride. MS (ESI(+)) m/e 594 (M+H)$^+$, (ESI(−)) m/e 592 (M−H)$^-$; $^1$H-NMR (300 MHz, dimethylsulfoxide-$d_6$) δ 10.40 (s, 1H), 9.77 (s, 1H), 9.53 (d, 1H), 8.38 (d, 1H), 8.14 (m, 1H), 7.82-7.75 (m, 3H), 7.59-7.34 (m, 4H), 7.29-7.11 (m, 5H), 6.69 (d, 1H), 4.08 (m, 1H), 3.29 (d, 1H), 3.23 (d, 1H), 3.16-3.03 (m, 2H), 2.83 (m, 6H), 2.29 (s, 3H), 2.24 (s, 3H).

Example 368

N-(3-{3-[2-({4-[4-(dimethylamino)piperidin-1-yl]phenyl}amino)pyrimidin-4-yl]imidazo[1,2-a]pyridin-2-yl}phenyl)-2,3-dimethylbenzamide The title compound was prepared as described in EXAMPLE 98D substituting EXAMPLE 188D for EXAMPLE 98C and 2,3-dimethylbenzoyl chloride for 2-(thiophen-2-yl)acetyl chloride. MS (ESI(+)) m/e 637 (M+H)$^+$; $^1$H-NMR (300 MHz, dimethylsulfoxide-$d_6$) δ 10.42 (s, 1H), 9.58 (s, 1H), 9.53 (m, 1H), 8.33 (d, 1H), 8.14 (m, 1H), 7.82 (m, 2H), 7.58 (m, 3H), 7.45 (t, 1H), 7.35 (m, 1H), 7.29-7.13 (m, 4H), 6.96 (d, 2H), 6.62 (d, 1H), 3.76 (m, 2H), 3.30 (m, 1H), 2.79 (d, 6H), 2.68 (m, 2H), 2.79 (m, 2H), 2.29 (s, 3H), 2.25 (s,3H), 1.71 (m, 2H).

Example 369

2-amino-N-[3-(3-{2-[(4-pyrrolidin-3-ylphenyl)amino]pyrimidin-4-yl}imidazo[1,2-a]pyridin-2-yl)phenyl]-2-thien-2-ylacetamide The title compound was prepared as described in EXAMPLE 282 from EXAMPLE 255B and 2-(tert-butoxycarbonylamino)-2-(thiophen-2-yl)acetic acid. MS ESI(+): m/e 587.3 (M+H)$^+$. $^1$H NMR (400 MHz, dimethylsulfoxide-$d_6$) δ ppm 10.80 (s, 1 H), 9.79 (s, 1 H), 9.51 (bd, 1 H), 8.91 (bs, 2 H), 8.80 (bs, 3 H), 8.34 (d, 1 H), 7.96 (s, 1 H), 7.78 (d, 1 H), 7.73 (d, 2 H), 7.65-7.68 (m, 2 H), 7.56 (t, 1 H), 7.46 (t, 1 H), 7.40 (d, 1 H), 7.31 (d, 1 H), 7.27 (d, 2 H), 7.11-7.14 (m, 2 H), 6.62 (d, 1 H), 5.39 (s, 1 H), 3.58-3.65 (m, 1 H), 3.35-3.45 (m, 2 H), 3.21-3.26 (m, 1 H), 3.01-3.08 (m, 1 H), 2.31-2.38 (m, 1 H), 1.89-1.98 (m, 1H).

Example 370

2-amino-N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-2-ylacetamide The title compound was prepared as described in EXAMPLE 282 from EXAMPLE 106D and 2-(tert-butoxycarbonylamino)-2-(thiophen-2-yl)acetic acid. MS ESI(+): m/e 601.3 (M+H)$^+$. $^1$H NMR (400 MHz, dimethylsulfoxide-$d_6$) δ ppm 10.84 (s, 1 H), 10.08 (bs, 1 H), 9.80 (s, 1 H), 9.52 (bs, 1 H), 8.82 (bs, 3 H), 8.34 (d, 1 H), 7.96 (s, 1 H), 7.79 (d, 1 H), 7.73 (s, 1 H), 7.65-7.68 (m, 2 H), 7.53-7.56 (m, 2 H), 7.47 (t, 1 H), 7.40 (d, 1 H), 7.32 (d, 1 H), 7.20 (d, 1 H), 7.12-7.15 (m, 2 H), 6.62 (d, 1 H), 5.41 (s, 1 H), 4.07-4.12 (m, 1 H), 3.24-3.32 (m, 2 H), 3.06-3.18 (m, 2 H), 2.83 (s, 6 H).

Example 371

2-amino-N-(3-{3-[2-({4-[4-(dimethylamino)piperidin-1-yl]phenyl}amino)pyrimidin-4-yl]imidazo[1,2-a]pyridin-2-yl}phenyl)-2-thien-2-ylacetamide The title compound was prepared as described in EXAMPLE 282 from EXAMPLE 188D and 2-(tert-butoxycarbonylamino)-2-(thiophen-2-yl)acetic acid. MS ESI(+): m/e 644.3 (M+H)+. 1H NMR (400 MHz, dimethylsulfoxide-d6) δ ppm 10.84 (s, 1 H), 9.78 (bs, 1 H), 9.11 (s, 1 H), 9.51 (bs, 1 H), 8.81 (bs, 3 H), 8.29 (d, 1 H) 7.95 (s, 1 H), 7.79 (d, 1 H), 7.66 (d, 2 H), 7.56-7.60 (m, 3 H), 7.47 (t, 1 H), 7.40 (d, 1 H), 7.32 (d, 1 H), 7.11-7.15 (m, 2 H), 7.00 (d, 2 H), 6.55 (d, 1 H), 5.21 (s, 1 H), 3.75-3.78 (m, 2 H), 3.29-3.33 (m, 2 H), 2.79 (s, 3 H), 2.80 (s, 3 H), 2.70-2.71 (m, 1 H), 2.08-2.10 (m, 2 H), 1.73-1.77 (m, 2H).

Example 372

N-(3-{3-[2-({3-[2-(dimethylamino)ethyl] phenyl}amino)pyrimidin-4-yl]imidazo[1,2-a]pyridin-2-yl}phenyl)-N'-[(1R)-1-phenylethyl]urea The title compound was prepared as described in EXAMPLE 347, substituting (R)-(1-isocyanatoethyl)benzene for (S)-(1-isocyanatoethyl)benzene. The crude reaction product was purified by reverse-phase HPLC on a Shimadzu LC10 HPLC system with a Phenomenex C18 column (3×15 cm) eluting with a gradient of from 15% to 55% acetonitrile in 0.15% aqueous trifluoroacetic acid to provide the title compound. MS (ESI(+)) m/e 597.3 (M+H)+; 1H NMR (300 MHz, dimethylsulfoxide-d6) δ ppm 9.84 (s, 1 H) 9.62 (d, 1 H) 9.38 (brs, 1 H) 8.59 (s, 1 H) 8.36 (d, 1 H) 7.76 (m, 3 H) 7.59 (m, 2 H) 7.42 (m, 1 H) 7.21-7.37 (m, 7 H) 7.13 (m, 2 H) 6.91 (m, 1 H) 6.68 (d, 1 H) 6.63 (d, 1 H) 4.80 (m, 1 H) 3.28 (m, 2 H) 2.92 (m, 2 H) 2.81 (d, 6 H) 1.38 (d, 3 H).

Example 373

N-(3-{3-[2-({3-[2-(dimethylamino)ethyl] phenyl}amino)pyrimidin-4-yl]imidazo[1,2-a]pyridin-2-yl}phenyl)-N'-(2-phenylcyclopropyl)urea The title compound was prepared as described in EXAMPLE 347, substituting ((1S,2R)-2-isocyanatocyclopropyl)benzene for (S)-(1-isocyanatoethyl)benzene. The crude reaction product was purified by reverse-phase HPLC on a Shimadzu LC10 HPLC system with a Phenomenex C18 column (3×15 cm) eluting with a gradient of from 15% to 55% acetonitrile in 0.15% aqueous trifluoroacetic acid to provide the title compound. MS (ESI(+)) m/e 609.3 (M+H)+; 1H NMR (300 MHz, dimethylsulfoxide-d6) δ ppm 9.84 (s, 1 H) 9.62 (d, 1 H) 9.38 (brs, 1 H) 8.60 (s, 1 H) 8.37 (d, 1 H) 7.78 (m, 3 H) 7.59 (m, 2 H) 7.48 (m, 1 H) 7.23-7.36 (m, 4 H) 7.14 (m, 5 H) 6.92 (m, 1 H) 6.65 (m, 2 H) 3.28 (m, 2 H) 2.92 (m, 2 H) 2.81 (d, 6 H) 2.71 (m, 1 H) 1.96 (m, 1 H) 1.15 (m, 2 H).

Example 374

N'-(3-{3-[2-({3-[2-(dimethylamino)ethyl] phenyl}amino)pyrimidin-4-yl]imidazo[1,2-a]pyridin-2-yl}phenyl)-N,N-dimethylurea The title compound was prepared as described in EXAMPLE 351, substituting dimethylcarbamic chloride for EXAMPLE 251A. MS (ESI(+)) m/e 609.3 (M+H)+; 1H NMR MHz, dimethylsulfoxide-d6) δ ppm 9.80 (s, 1 H) 9.62 (d, 1 H) 9.37 (brs, 1 H) 8.42 (s, 1 H) 8.37 (d, 1 H) 7.87 (m, 1 H) 7.77 (m, 2 H) 7.59 (m, 3 H) 7.29 (m, 2 H) 7.14 (m, 2 H) 6.92 (d, 1 H) 6.66 (d, 1 H) 3.28 (m, 2 H) 2.93 (m, 8 H) 2.82 (d, 6 H).

Example 375

N'-(3-{3-[2-({3-[2-(dimethylamino)ethyl] phenyl}amino)pyrimidin-4-yl]imidazo[1,2-a]pyridin-2-yl}phenyl)-N-methyl-N-phenylurea The title compound was prepared as described in EXAMPLE 351, substituting methyl(phenyl)carbamic chloride for EXAMPLE 251A. MS (ESI(+)) m/e 583.3 (M+H)+; 1H NMR (300 MHz, dimethylsulfoxide-d6) δ ppm 9.80 (s, 1 H) 9.60 (d, 1 H) 9.34 (brs, 1 H) 8.37 (d, 1 H) 8.34 (s, 1 H) 7.82 (m, 1 H) 7.75 (m, 2 H) 7.56 (m, 3 H) 7.41 (m, 2 H) 7.06-7.34 (m, 7 H) 6.92 (m, 1 H) 6.67 (d, 1 H) 3.27 (m, 5 H) 2.92 (m, 2 H) 2.82 (d, 6 H).

Example 376

N-(3-{3-[2-({3-[2-(dimethylamino)ethyl] phenyl}amino)pyrimidin-4-yl]imidazo[1,2-a]pyridin-2-yl}phenyl)pyrrolidine-1-carboxamide The title compound was prepared as described in EXAMPLE 351, substituting pyrrolidine-1-carbonyl chloride for EXAMPLE 251A. MS (ESI(+)) m/e 583.3 (M+H)+; 1H NMR (300 MHz, dimethylsulfoxide-d6) δ ppm 9.81 (s, 1 H) 9.63 (d, 1 H) 9.38 (brs, 1 H) 8.37 (d, 1 H) 8.26 (s, 1 H) 7.92 (m, 1 H) 7.77 (m, 2 H) 7.54-7.66 (m, 3 H) 7.30 (m, 2 H) 7.14 (m, 2 H) 6.92 (d, 1 H) 6.66 (d, 1 H) 3.25-3.39 (m, 6 H) 2.93 (m, 2 H) 2.82 (d, 6 H) 1.85 (m, 4 H).

Example 377

N-{3-[3-[2-({3-[2-(dimethylamino)ethyl] phenyl}amino)pyrimidin-4-yl]-7-(trifluoromethyl) imidazo[1,2-a]pyridin-2-yl]phenyl}-2,6-difluorobenzamide Example 377A The title compound was prepared as described in EXAMPLE 1A, substituting 4-(trifluoromethyl)pyridin-2-amine for pyridin-2-amine. MS (ESI(+)) m/e 308 (M+H)+.

Example 377B

The title compound was prepared as described in EXAMPLE 402B, substituting EXAMPLE 377A for EXAMPLE 402A. MS (ESI(+)) m/e 350 (M+H)+.

Example 377C

The title compound was prepared as described in EXAMPLE 1D, substituting EXAMPLE 377B for EXAMPLE 1C. MS (ESI(+)) m/e 405 (M+H)+.

Example 377D

The title compound was prepared as described in EXAMPLE 1G, substituting EXAMPLE 377C for EXAMPLE 1D, and EXAMPLE 402I for EXAMPLE 1F. MS (ESI(+)) m/e 548 (M+H)+.

Example 377E

The title compound was prepared as described in EXAMPLE 4G, substituting EXAMPLE 377D for EXAMPLE 4F. MS (ESI(+)) m/e 518 (M+H)+.

Example 377F

The title compound was prepared as described in EXAMPLE 4H, substituting EXAMPLE 377E for EXAMPLE 4G. MS (ESI(+)) m/e 658 (M+H)+, 1H NMR (400 MHz, dimethylsulfoxide-d6) δ ppm 10.91 (m, 1 H) 9.75 (s, 1 H) 9.53 (d, 1 H) 8.45 (d, 1 H) 8.28 (s, 1 H) 8.08 (m, 1 H) 7.78 (s, 1 H) 7.66 (s, 1 H) 7.40-7.63 (m, 4 H) 7.30 (dd, 1 H) 7.17-7.27 (m, 3 H) 6.85 (d, 1 H) 6.74 (d, 1 H) 2.65 (m, 2 H) 2.44 (m, 2 H) 2.15 (s, 6 H).

Example 378

N-{3-[3-[2-((3-[2-(dimethylamino)ethyl]phenyl}amino)pyrimidin-4-yl]-7-(trifluoromethyl)imidazo[1,2-a]pyridin-2-yl]phenyl}-2-thien-2-ylacetamide The title compound was prepared as described in EXAMPLE 4H, substituting EXAMPLE 377E for EXAMPLE 4G, and 2-thiopheneacetyl chloride for 2,6-difluorobenzoyl chloride. MS (ESI(+)) m/e 642 (M+H)+, 1H NMR (400 MHz, dimethylsulfoxide-d6) δ ppm 10.33 (s, 1 H) 9.76 (s, 1 H) 9.54 (d, 1 H) 8.43 (d, 1 H) 8.26 (s, 1 H) 7.98 (s, 1 H) 7.73 (d, 1 H) 7.66 (s, 1 H) 7.53 (d, 1 H) 7.27-7.43 (m, 4 H) 7.20 (t, 1 H) 6.95-7.00 (m, 2 H) 6.85 (d, 1 H) 6.70 (d, 1 H) 3.87 (s, 2 H) 2.66 (m, 2 H) 2.44 (m, 2 H) 2.14 (s, 6 H).

Example 379

N-{3-[3-[2-({3-[2-(dimethylamino)ethyl]phenyl}amino)pyrimidin-4-yl]-7-(trifluoromethyl)imidazo[1,2-a]pyridin-2-yl]phenyl)-N'-phenylurea The title compound was prepared as described in EXAMPLE 3, substituting EXAMPLE 377E for EXAMPLE 1H. MS (ESI(+)) m/e 637 (M+H)+, 1H NMR (400 MHz, dimethylsulfoxide-d6) δ ppm 9.76 (s, 1 H) 9.57 (d, 1 H) 8.85 (s, 1 H) 8.67 (s, 1 H) 8.45 (d, 1 H) 8.27 (s, 1 H) 7.83 (s, 1 H) 7.66 (s, 1 H) 7.51-7.60 (m, 2 H) 7.45 (d, 2 H) 7.38 (t, 1 H) 7.24-7.31 (m, 4 H) 7.21 (t, 1 H) 6.96 (t, 1 H) 6.85 (s, 1 H) 6.72 (d, 1 H) 2.65 (d, 2 H) 2.43 (d, 2 H) 2.13 (s 6 H).

Example 380

N-{3-[3-[2-({3-[2-(dimethylamino)ethyl]phenyl}amino)pyrimidin-4-yl]-7-(trifluoromethyl)imidazo[1,2-a]pyridin-2-yl]phenyl)-N'-[(1S)-1-phenylethyl]urea The title compound was prepared as described in EXAMPLE 3, substituting EXAMPLE 377E for EXAMPLE 1H, and (S)-(1-isocyanatoethyl)benzene for phenyl isocyanate. MS (ESI(+)) m/e 665 (M+H)+, 1H NMR (400 MHz, dimethylsulfoxide-d6) δ ppm 9.75 (s, 1 H) 9.58 (d, 1 H) 8.56 (s, 1 H) 8.42 (d, 1 H) 8.25 (s, 1 H) 7.73 (s, 1 H) 7.66 (s, 1 H) 7.54 (d, 1 H) 7.48 (m, 1 H) 7.26-7.36 (m, 6 H) 7.14-7.25 (m, 3 H) 6.86 (d, 1 H) 6.67 (s, 1 H) 6.61 (d, 1 H) 4.81 (m, 1 H) 2.66 (m, 2 H) 2.44 (m, 2 H) 2.15 (s, 6 H) 1.39 (d, 3 H).

Example 381

N-{3-[3-(2-([4-(1-ethylpyrrolidin-2-yl)phenyl]amino}pyrimidin-4-yl)imidazo[1,2-a]pyridin-2-yl]phenyl}-2-thien-2-ylacetamide To a mixture of EXAMPLE 356 (free base, 70 mg, 0.12 mmol) and N-ethyl-N-isopropylpropan-2-amine (32.0 μl, 0.184 mmol) in acetonitrile (5 mL) was added iodoethane (12.8 μl, 0.16 mmol). The mixture was stirred at 45° C. overnight and then concentrated. The residue was dissolved in dimethylsulfoxide/methanol and purified by reverse-phase HPLC with trifluoroacetic acid buffer water-acetonitrile as the mobile phase, giving the title compound. MS ESI(+): m/e 600.3 (M+H)+. 1H NMR (400 MHz, dimethylsulfoxide-D6) δ ppm 10.32 (s, 1 H), 9.97 (s, 1 H), 9.51 (bd, 1 H), 9.30 (bs, 1 H), 8.40 (d, 1 H), 7.97 (s, 1 H), 7.83 (d, 2 H), 7.79 (d, 1 H), 7.67 (d, 1 H), 7.58 (t, 1 H), 7.45 (d, 2 H), 7.37-7.42 (m, 2 H), 7.30 (d, 1 H), 7.14 (t, 1 H), 6.94-6.99 (m, 2 H), 6.70 (d, 1 H), 4.30-4.36 (m, 1 H), 3.86 (s, 2 H), 3.27-3.37 (m, 2 H), 2.98-3.01 (m, 2 H), 2.30-2.39 (m, 1 H), 2.02-2.20 (m, 3 H), 1.14 (t, 3 H).

Example 382

2-chloro-N-[3-[3-(2-{[4-(1-ethylpyrrolidin-2-yl)phenyl]amino}pyrimidin-4-yl)imidazo[1,2-a]pyridin-2-yl]phenyl}benzamide The title compound was prepared according to the EXAMPLE 381, substituting EXAMPLE 357 for EXAMPLE 356. MS ESI(+): m/e 614.2 (M+H)+. 1H NMR (400 MHz, dimethylsulfoxide-d6) δ ppm 10.59 (s, 1 H), 9.97 (s, 1 H), 9.51 (bd, 1 H), 9.27 (bs, 1 H), 8.41 (d, 1 H), 8.11 (s, 1 H), 7.84 (d, 2 H), 7.76-7.80 (m, 2 H), 7.37-7.59 (m, 9 H), 7.14 (t, 1 H), 6.70 (d, 1 H), 4.30-4.36 (m, 1 H), 3.27-3.37 (m, 2 H), 2.96-3.01 (m, 2 H), 2.30-2.39 (m, 1 H), 2.08-2.20 (m, 3 H), 1.13 (t, 3 H).

Example 383

N-{3-[3-(2-{[4-(1-isopropylpyrrolidin-3-yl)phenyl]amino)}pyrimidin-4-yl)imidazo[1,2-a]pyridin-2-yl]phenyl}-2-thien-3-ylacetamide

Example 383A

To a solution of tert-butyl 3-(4-aminophenyl)pyrrolidine-1-carboxylate (1.72 g, 6.56 mmol) and N-ethyl-N-isopropylpropan-2-amine (1.71 ml, 9.83 mmol) in CH2Cl2 (20 mL) was added dropwise benzyl chloroformate (2.55 ml, 7.54 mmol) as a 50% wt solution in toluene. After stirring overnight at the ambient temperature, the mixture was diluted with CH2Cl2 (50 mL) and washed with aqueous NH4Cl, then dried (MgSO4). The crude product was purified on a silica gel column eluting with 30% ethyl acetate in hexane, giving the title compound. MS DCI/NH3: m/e 414.3 (M+NH4)+.

Example 383B

EXAMPLE 383A was treated with 50% trifluoroacetic acid in CH2Cl2 at room temperature for 3 hours to give the title compound. MS ESI(+): m/e 297.3 (M+H)+.

Example 383C

To a mixture of EXAMPLE 383B (free base, 1.25 g, 4.22 mmol) and N-ethyl-N-isopropylpropan-2-amine (0.955 ml, 5.48 mmol) in acetonitrile (50 mL) was added 2-iodopropane (0.547 ml, 5.48 mmol). The mixture was stirred at 45° C. overnight. The mixture was concentrated. The residue was taken up in 5% aqueous Na2CO3 solution (40 mL) and extracted with ethyl acetate. The organic solution was dried (MgSO4), filtered, and concentrated. The crude product was used as is for the next step.

Example 383D

A solution of EXAMPLE 383C (1.3 g, 3.84 mmol) in methanol (100 mL) was hydrogenated with Pd/C (10% wt, 100 mg) under 60 psi of hydrogen overnight at room temperature to give the title compound. MS ESI(+): m/e 205.3 (M+H)$^+$.

Example 383E

The title compound was prepared as described in EXAMPLE 4F, substituting EXAMPLE 383D for EXAMPLE 4E. MS ESI(+): m/e 520.1 (M+H)$^+$.

Example 383F

EXAMPLE 383E was reduced as described in EXAMPLE 1H to give the title compound. MS ESI(+): m/e 490.2 (M+H)$^+$.

Example 383G

N-{3-[3-(2-{[4-(1-isopropylpyrrolidin-3-yl)phenyl]amino}pyrimidin-4-yl)imidazo[1,2-a]pyridin-2-yl]phenyl}-2-thien-3-ylacetamide, trifluoroacetic acid salt The title compound was prepared as described in EXAMPLE 244 from EXAMPLE 383F and 2-(thiophen-3-yl)acetyl chloride. MS ESI(+): m/e 614.3 (M+H)$^+$. $^1$H NMR (400 MHz, dimethylsulfoxide-d$_6$) δ ppm 10.25 (s, 1 H), 9.79 (s, 1 H), 9.77 (bd, 1 H), 9.53 (bd, 1 H), 8.36 (d, 1 H), 7.96 (s, 1 H), 7.79 (d, 1 H), 7.70-7.73 (m, 3 H), 7.58 (t, 1 H), 7.46-7.47 (m, 1 H), 7.39 (t, 1 H), 7.24-7.30 (m, 4 H), 7.15 (t, 1 H), 7.07 (d, 1 H), 6.64 (d, 1 H), 3.80-3.85 (m, 1 H), 3.67-3.71 (m, 1 H), 3.65 (s, 2 H), 3.58-3.65 (m, 1 H), 3.46-3.53 (m, 1 H), 3.32-3.42 (m, 1 H), 3.03-3.11 (m, 1 H), 2.32-2.40 (m, 1 H), 1.88-2.10 (m, 1 H), 1.29 (d, 6 H).

Example 384

N-{3-[3-(2-{[4-(1-isopropylpyrrolidin-3-yl)phenyl]amino}pyrimidin-4-yl)imidazo[1,2-a]pyridin-2-yl]phenyl}-2-thien-2-ylacetamide The title compound was prepared as described in EXAMPLE 244 from EXAMPLE 383F and 2-(thiophen-2-yl)acetyl chloride. MS ESI(+): m/e 614.3 (M+H)$^+$. $^1$H NMR (400 MHz, dimethylsulfoxide-d$_6$) δ ppm 10.34 (s, 1 H), 9.85 (bd, 1 H), 9.80 (s, 1 H), 9.54 (bd, 1 H), 8.36 (d, 1 H), 7.96 (s, 1 H), 7.79 (d, 1 H), 7.69-7.73 (m, 3 H), 7.59 (dd, 1 H), 7.42 (d, 1 H), 7.36-7.38 (m, 1 H), 7.24-7.32 (m, 3 H), 7.16 (t, 1 H), 6.93-6.97 (m, 2 H), 6.64 (d, 1 H), 3.85 (s, 2 H), 3.35-3.69 (m, 5 H), 3.03-3.11 (m, 1 H), 2.32-2.40 (m, 1 H), 1.91-2.08 (m, 1H), 1.29 (d, 6 H).

Example 385

2-chloro-N-{3-[3-(2-{[4-(1-isopropylpyrrolidin-3-yl)phenyl]amino}pyrimidin-4-yl)imidazo[1,2-a]pyridin-2-yl]phenyl}benzamide The title compound was prepared as described in EXAMPLE 244 from EXAMPLE 383F and 2-chlorobenzoyl chloride. MS ESI(+): m/e 628.3 (M+H)$^+$. $^1$H NMR (400 MHz, dimethylsulfoxide-d$_6$) δ ppm 10.61 (s, 1 H), 9.90 (bd, 1 H), 9.79 (s, 1 H), 9.54 (bd, 1 H), 8.38 (d, 1 H), 8.10 (s, 1 H), 7.78-7.82 (m, 2 H), 7.72 (d, 2 H), 7.44-7.60 (m, 6 H), 7.38 (d, 1 H), 7.24-7.30 (m, 2 H), 7.15 (t, 1 H), 6.68 (d, 1 H), 3.80-3.85 (m, 1 H), 3.67-3.71 (m, 1 H), 3.58-3.65 (m, 1 H), 3.46-3.53 (m, 1 H), 3.32-3.42 (m, 1 H), 3.03-3.11 (m, 1 H), 2.32-2.40 (m, 1 H), 1.88-2.10 (m, 1 H), 1.29 (d, 6 H).

Example 386

2,3-difluoro-N-{3-[3-(2-{[4-(1-isopropylpyrrolidin-3-yl)phenyl]amino}pyrimidin-4-yl)imidazo[1,2-a]pyridin-2-yl]phenyl}benzamide The title compound was prepared as described in EXAMPLE 244 from EXAMPLE 383F and 2,3-difluorobenzoyl chloride. MS ESI(+): m/e 630.3 (M+H)$^+$. $^1$H NMR (400 MHz, dimethylsulfoxide-d$_6$) δ ppm 10.66 (s, 1 H), 9.93 (bs, 1 H), 9.80 (s, 1 H), 9.54 (bd, 1 H), 8.38 (d, 1 H), 8.09 (s, 1 H), 7.80 (d, 2 H), 7.72 (d, 2 H), 7.56-7.63 (m, 2 H), 7.45-7.49 (m, 2 H), 7.24-7.40 (m, 4 H), 7.15 (t, 1 H), 6.67 (d, 1 H), 3.80-3.85 (m, 1 H), 3.32-3.72 (m, 4 H), 3.03-3.11 (m, 1 H), 2.32-2.43 (m, 1 H), 1.90-2.10 (m, 1 H), 1.29 (d, 6 H).

Example 387

N-{3-[3-(2-{[4-1-isopropylpyrrolidin-3-yl)phenyl]amino}pyrimidin-4-yl)imidazo[1,2-a]pyridin-2-yl]phenyl}-N'-[(1S)-1-phenylethyl]urea A scintillation vial was charged with EXAMPLE 383F (60 mg, 0.12 mmol), (S)-(1-isocyanatoethyl)benzene (52 μl, 0.36 mmol) and anhydrous CH$_2$Cl$_2$ (4 mL) and 1-methyl-2-pyrrolidinone (1 ml). After stirring overnight at room temperature, the mixture was evaporated to dryness and the residue was purified by reverse-phase HPLC with trifluoroacetic acid buffer water-acetonitrile as the mobile phase. MS ESI(+): m/e 637.4 (M+H)$^+$. $^1$H NMR (400 MHz, dimethylsulfoxide-d$_6$) δ ppm 9.82 (bd, 1H0, 9.78 (s, 1 H), 9.59 (bd, 1 H), 8.59 (s, 1 H), 8.34 (d, 1 H), 7.78 (d, 1 H), 7.71-7.73 (m, 3 H), 7.58 (t, 1 H), 7.45 (d, 1 H), 7.52-7.33 (m, 8 H), 7.11-7.15 (m, 2 H), 6.66 (d, 1 H), 6.62 (d, 1 H), 4.80 (q, 1 H), 3.80-3.85 (m, 1 H), 3.32-3.72 (m, 4 H), 3.03-3.11 (m, 1 H), 2.32-2.43 (m, 1 H), 1.90-2.10 (m, 1 H), 1.38 (d, 3 H), 1.29 (d, 6 H).

Example 388

N-(2-fluorophenyl)-3-{3-[2-({3-[2-(4-hydroxypiperidin-1-yl)ethyl]phenyl}amino)pyrimidin-4-yl]imidazo[1,2-a]pyridin-2-yl}benzamide

Example 388A

In a 100 mL round-bottomed flask was charged 2-(3-nitrophenyl)ethanol (2.5 g, 14.96 mmol) and triphenylphosphine (4.16 g, 15.85 mmol) in dichloromethane (37.4 ml). To the stirring solution, carbon tetrabromide (5.26 g, 15.85 mmol) was added slowly over 20 minutes. The reaction mixture was stirred overnight at room temperature. The solution was concentrated in vacuo and washed 3 times with diethyl ether saving the filtrate. The filtrate was concentrated in vacuo and transferred to a 20 g silica gel column. The residue was purified by flash chromatography on an Argonaut Flash Master SOLO, eluting with a gradient 100% dichloromethane to 50:50 dichloromethane/methanol to afford the title compound. MS (DCI(+)) m/e 246.9, 248.9 (M+H)$^+$.

Example 388B

In a 20 mL vial was 1-(2-bromoethyl)-3-nitrobenzene (1 g, 4.35 mmol), piperidin-4-ol (0.484 g, 4.78 mmol), and potassium carbonate (1.502 g, 10.87 mmol) in acetonitrile (12.42 ml). The mixture was allowed to stir at room temperature overnight. The mixture was filtered and the filtrate was concentrated in vacuo and transferred to a 10 g silica gel column. The residue was purified by flash chromatography on an Argonaut Flash Master SOLO, eluting with a gradient 100% dichloromethane to 50:50 dichloromethane/methanol to afford the title compound. MS (DCI(+)) m/e 251.1 (M+H)$^+$.

Example 388C

The title compound was prepared as described in EXAMPLE 322E, substituting EXAMPLE 338B for EXAMPLE 322D. MS (DCI(+)) m/e 221.1 (M+H)$^+$, (ESI (−)).

Example 388D

The title compound was prepared as described in EXAMPLE 4F, substituting EXAMPLE 388C for EXAMPLE 4E and EXAMPLE 322C for EXAMPLE 4C. MS (ESI(+)) m/e 569, 571 (M+H)$^+$, (ESI(−)) m/e 567, 569 (M−H)$^-$.

Example 388E

The title compound was prepared as described in EXAMPLE 125F, substituting EXAMPLE 388D for EXAMPLE 125E. MS (ESI(+)) m/e 549.3 (M+H)$^+$, (ESI(−)) m/e 547.2 (M−H)$^-$.

Example 388F

The title compound was prepared as described in EXAMPLE 125G, substituting EXAMPLE 322F for EXAMPLE 125F. MS (ESI(+)) m/e 535.2 (M+H)$^+$, (ESI(−)) m/e 533.2 (M−H)$^-$.

Example 388G

The title compound was prepared as described in EXAMPLE 125H, substituting EXAMPLE 388F for EXAMPLE 125G. MS (ESI(+)) m/e 628 (M+H)$^+$, (ESI(−)) m/e 626 (M−H)$^-$; $^1$H-NMR (400 MHz, dimethylsulfoxide-d$_6$) δ ppm 10.21 (s, 1H) 9.82 (s, 1H) 9.56 (dd, 1H) 9.17 (s, 1H) 8.38 (d, 1H) 8.32 (s, 1H) 8.08 (dd, 1H) 7.86 (dt, 1H) 7.82 (d, 1 H) 7.68-7.74 (m, 1H) 7.63 (t, 1H) 7.54-7.61 (m, 3H) 7.18-7.32 (m, 4H) 7.11-7.19 (m, 1H) 6.91 (t, 1 H) 6.65 (d, 1H) 3.57-3.68 (m, 1H) 3.45-3.56 (m, 1H) 3.19-3.39 (m, 4H) 3.16 (dd, 1H) 2.87-3.02 (m, 3H) 1.97 (dd, 1H) 1.71-1.89 (m, 2H) 1.46-1.61 (m, 1H).

Example 389

3-{3-[2-({3-(2-(4-hydroxypiperidin-1-yl)ethyl] phenyl}amino)pyrimidin-4-yl]imidazo[1,2-a]pyridin-2-yl}-N-phenylbenzamide The title compound was prepared as described in EXAMPLE 125H, substituting EXAMPLE 388F for EXAMPLE 125G and substituting aniline for 2-fluoroaniline. MS (ESI(+)) m/e 610 (M+H)$^+$, (ESI(−)) m/e 608 (M−H)$^-$; $^1$H-NMR (400 MHz, dimethylsulfoxide-d$_6$) δ ppm 10.32 (s, 1H) 9.81 (s, 1H) 9.56 (d, 1H) 9.14 (s, 1H) 8.37 (d, 1H) 8.29 (t, 1H) 8.02-8.08 (m, 1H) 7.84 (dt, 1H) 7.81 (dd, 1H) 7.76 (dd, 2H) 7.69-7.74 (m, 1H) 7.58-7.66 (m, 2H) 7.52-7.58 (m, 1H) 7.31-7.37 (m, 2H) 7.27 (t, 1H) 7.06-7.16 (m, 2H) 6.91 (t, 1 H) 6.64 (dd, 1H) 3.49 (d, 2H) 3.20-3.37 (m, 4H) 3.13-3.19 (m, 1H) 2.88-3.01 (m, 31-1) 1.92-2.02 (m, 1H) 1.70-1.88 (m, 2H) 1.47-1.61 (m, 1H).

Example 390

N'-{3-[3-(2-{[4-(1-isopropylpyrrolidin-3-yl)phenyl] amino}pyrimidin-4-yl)imidazo[1,2-a]pyridin-2-yl] phenyl}-N,N-dimethylurea The title compound was prepared as described in EXAMPLE 244 from EXAMPLE 383F and N,N-dimethylcarbamoyl chloride. MS ESI(+): m/e 561.3 (M+H)$^+$. $^1$H NMR (400 MHz, dimethylsulfoxide-d$_6$) δ ppm 10.01 (bd, 1 H), 9.81 (s, 1 H), 9.63 (bd, 1 H), 8.44 (s, 1 H), 8.37 (d, 1 H), 7.87 (s, 1 H), 7.82 (d, 1 H), 7.72 (d, 2 H), 7.60-7.69 (m, 2 H), 7.20-7.36 (m, 4 H), 7.16 (d, 1 H), 6.65 (d, 1 H), 3.80-3.85 (m, 1 H), 3.32-3.72 (m, 4 H), 3.03-3.11 (m, 1 H), 2.92 (s, 6 H), 2.32-2.43 (m, 1 H), 1.90-2.10 (m, 1H), 1.29 (d, 6 H).

Example 391

N'-{3-[3-(2-{[4-(1-isopropylpyrrolidin-3-yl)phenyl] amino}pyrimidin-4-yl)imidazo[1,2-a]pyridin-2-yl] phenyl}-N-methyl-N-phenylurea The title compound was prepared as described in EXAMPLE 244 from EXAMPLE 383F and N-methyl-N-phenylcarbamoyl chloride. MS ESI(+): m/e 623.4 (M+H)$^+$. $^1$H NMR (400 MHz, dimethylsulfoxide-d$_6$) δ ppm 9.90 (bd, 1 H), 9.78 (s, 1 H), 9.59 (bd, 1 H), 8.37 (d, 1 H), 8.31 (s, 1 H), 7.78-7.81 (m, 2 H), 7.72 (d, 2 H), 7.57-7.62 (m, 2 H), 7.38-7.42 (m, 3 H), 7.23-7.34 (m, 6 H), 7.18 (d, 2 H), 6.65 (d, 1 H), 3.80-3.85 (m, 1 H), 3.32-3.72 (m, 4 H), 3.26 (s, 3 H), 3.03-3.11 (m, 1 H), 2.32-2.43 (m, 1 H), 1.90-2.10 (m, 1 H), 1.29 (d, 6 H).

Example 392

3-{3-[2-({3-[2-(4-hydroxypiperidin-1-yl)ethyl] phenyl}amino)pyrimidin-4-yl]imidazo[1,2-a]pyridin-2-yl}-N-thien-2-ylbenzamide The title compound was prepared as described in EXAMPLE 125H, substituting EXAMPLE 388F for EXAMPLE 125G and substituting thiophen-2-amine for 2-fluoroaniline. MS (ESI(+)) m/e 616 (M+H)$^+$, $^1$H NMR (300 MHz, dimethylsulfoxide-d$_6$) δ 11.62 (s, 1H) 9.71 (s, 1H) 9.56 (d, 1H) 8.33-8.40 (m, 2H) 8.08 (d, 1H) 7.85 (d, 1H) 7.79 (d, 1H) 7.49-7.68 (m, 4H) 7.19 (t, 1H) 7.11 (t, 1H) 7.01 (d, 1H) 6.87-6.96 (m, 2H) 6.84 (d, 1H) 6.60 (d, 1H) 4.50 (d, 1H) 3.41 (m, 1H) 2.60-2.76 (m, 4H) 2.39-2.47 (m, 2H) 2.00 (t, 2H) 1.68 (dd, 2H) 1.27-1.43 (m, 2 H).

Example 393

N-(3-{3-[2-({3-[2-(dimethylamino)ethyl] phenyl}amino)pyrimidin-4-yl]-8-fluoroimidazo[1,2-a]pyridin-2-yl}phenyl)-2,6-difluorobenzamide Example 393A The title compound was prepared as described in EXAMPLE 1A, substituting 3-fluoropyridin-2-amine for pyridin-2-amine. MS (DCI(+)) m/e 258 (M+H)$^+$.

Example 393B

The title compound was prepared as described in EXAMPLE 402B, substituting EXAMPLE 393A for EXAMPLE 402A. MS (ESI(+)) m/e 300 (M+H)$^+$.

Example 393C

The title compound was prepared as described in EXAMPLE 1D, substituting EXAMPLE 393B for EXAMPLE 1C. MS (ESI(+)) m/e 355 (M+H)$^+$.

Example 393D

The title compound was prepared as described in EXAMPLE 1G, substituting EXAMPLE 393C for EXAMPLE 1D, and EXAMPLE 402I for EXAMPLE 1F. MS (ESI(+)) m/e 498 (M+H)$^+$.

Example 393E

The title compound was prepared as described in EXAMPLE 4G, substituting EXAMPLE 393D for EXAMPLE 4F. MS (ESI(+)) m/e 468 (M+H)$^+$.

Example 393F

The title compound was prepared as described in EXAMPLE 4H, substituting EXAMPLE 393E for EXAMPLE 4G. MS (ESI(+)) m/e 608 (M+H)$^+$, $^1$H NMR (400 MHz, dimethylsulfoxide-d$_6$) δ ppm 10.90 (s, 1 H) 9.72 (s, 1 H) 9.28 (d, 1 H) 8.42 (d, 1 H) 8.07 (s, 1 H) 7.82 (d, 1 H) 7.54-7.64 (m, 3 H) 7.36-7.48 (m, 3 H) 7.17-7.28 (m, 3 H) 7.04 (m, 1 H) 6.86 (d, 1 H) 6.71 (d, 1 H) 2.69 (m, 2 H) 2.55 (d, 2 H) 2.23 (s, 6 H).

Example 394

N-(3-{3-[2-({3-[2-(dimethylamino)ethyl] phenyl}amino)pyrimidin-4-yl]-8-fluoroimidazo[1,2-a]pyridin-2-yl}phenyl)-2-phenylacetamide The title compound was prepared as described in EXAMPLE 4H, substituting EXAMPLE 393E for EXAMPLE 4G, and phenylacetyl chloride for 2,6-difluorobenzoyl chloride. MS (ESI(+)) m/e 586 (M+H)$^+$, $^1$H NMR (400 MHz, dimethylsulfoxide-d$_6$) δ ppm 10.27 (s, 1 H) 9.70 (s, 1 H) 9.28 (d, 1 H) 8.39 (d, 1 H) 7.95 (s, 1 H) 7.76 (d, 1 H) 7.63 (s, 1 H) 7.56 (d, 1 H) 7.28-7.42 (m, 7 H) 7.24 (m, 1 H) 7.19 (t, 1 H) 7.02 (m, 1 H) 6.85 (d, 1 H) 6.66 (d, 1 H) 3.64 (s, 2 H) 2.66 (m, 2 H) 2.44 (m, 2 H) 2.16 (s, 6 H).

Example 395

N-(3-{3-[2-({3-[2-(dimethylamino)ethyl] phenyl}amino)pyrimidin-4-yl]-8-fluoroimidazo[1,2-a]pyridin-2-yl}phenyl)-2-thien-2-ylacetamide The title compound was prepared as described in EXAMPLE 4H, substituting EXAMPLE 393E for EXAMPLE 4G, and 2-thiopheneacetyl chloride for 2,6-difluorobenzoyl chloride. MS (ESI(+)) m/e 592 (M+H)$^+$, $^1$H NMR (400 MHz, dimethylsulfoxide-d$_6$) δ ppm 10.31 (s, 1 H) 9.70 (s, 1 H) 9.28 (d, 1 H) 8.40 (d, 1 H) 7.94 (s, 1 H) 7.75 (d, 1 H) 7.63 (s, 1 H) 7.56 (d, 1 H) 7.29-7.44 (m, 4 H) 7.19 (t, 1 H) 7.00 (m, 3 H) 6.85 (d, 1 H) 6.67 (d, 1 H) 3.87 (s, 2 H) 2.66 (m, 2 H) 2.44 (m, 2 H) 2.16 (s, 6 H).

Example 396

N-(3-{3-[2-({3-[2-(dimethylamino)ethyl] phenyl}amino)pyrimidin-4-yl]-8-fluoroimidazo[1,2-a]pyridin-2-yl}phenyl)-N'-phenylurea The title compound was prepared as described in EXAMPLE 3, substituting EXAMPLE 393E for EXAMPLE 1H. MS (ESI(+)) m/e 587 (M+H)$^+$, $^1$H NMR (400 MHz, dimethylsulfoxide-d$_6$) δ ppm 9.70 (s, 1 H) 9.31 (d, 1 H), 8.84 (s, 1 H) 8.65 (s, 1 H) 8.41 (d, 1 H) 7.80 (m, 1 H) 7.63 (s, 1 H) 7.56 (m, 2 H) 7.33-7.48 (m, 4 H) 7.16-7.31 (m, 4 H) 7.04 (m, 1 H) 6.96 (t, 1 H) 6.85 (d, 1 H) 6.69 (d, 1 H) 2.66 (m, 2 H) 2.44 (m, 2 H) 2.15 (s, 6 H).

Example 397

N-{3-[3-(2-{[4-(1-isopropylpyrrolidin-3-yl)phenyl] amino}pyrimidin-4-yl)imidazo[1,2-a]pyridin-2-yl] phenyl}-3,4-dihydroquinoline-1(2H)-carboxamide

Example 397A

The title compound was prepared as described in EXAMPLE 251A, substituting 1, 2, 3, 4-tetrahydroquinoline for indoline.

Example 397B

N-{3-[3-(2-{[4-(1-isopropylpyrrolidin-3-yl)phenyl] amino}pyrimidin-4-yl)imidazo[1,2-a]pyridin-2-yl] phenyl}-3,4-dihydroquinoline-1(2H)-carboxamide, trifluoroacetic acid salt The title compound was prepared as described in EXAMPLE 244 from EXAMPLE 383F and EXAMPLE 397A. MS ESI(+): m/e 649.4 (M+H)$^+$. $^1$H NMR (400 MHz, dimethylsulfoxide-d$_6$) δ ppm 9.90 (bd, 1 H), 9.78 (s, 1 H), 9.58 (bd, 1 H), 8.99 (s, 1 H), 8.38 (d, 1 H), 7.85 (s, 1 H), 7.78 (d, 1 H), 7.73 (d, 2 H), 7.56-7.64 (m, 2 H), 7.22-7.39 (m, 5 H), 7.06-7.17 (m, 3 H), 6.96 (t, 1 H), 6.69 (d, 1 H), 3.80-3.85 (m, 1 H), 3.32-3.72 (m, 4 H), 3.03-3.11 (m, 1 H), 2.74 (t, 2 H), 2.32-2.43 (m, 1 H), 1.90-2.10 (m, 5H), 1.30 (d, 6 H).

Example 398

N-benzyl-N'-{3-[3-(2-{[4-(1-isopropylpyrrolidin-3-yl)phenyl]amino}pyrimidin-4-yl)imidazo[1,2-a]pyridin-2-yl]phenyl}-N-methylurea

Example 398A

The title compound was prepared as described in EXAMPLE 251 A, substituting N-methyl-N-benzylamine for indoline.

Example 398B

N-benzyl-N'-{3-[3-(2-{[4-(1-isopropylpyrrolidin-3-yl)phenyl]amino}pyrimidin-4-yl)imidazo[1,2-a]pyridin-2-yl]phenyl}-N-methylurea, trifluoroacetic acid salt The title compound was prepared as described in EXAMPLE 244 from EXAMPLE 383F and EXAMPLE 398A. MS ESI(+): m/e 637.4 (M+H)⁺. ¹H NMR (400 MHz, dimethylsulfoxide-d₆) δ ppm 9.87 (bd, 1 H), 9.77 (s, 1 H), 9.59 (bd, 1 H), 8.56 (s, 1 H), 8.35 (d, 1 H), 7.90 (s, 1 H), 7.78 (d, 1 H), 7.72 (d, 2 H), 7.56-7.63 (m, 2 H), 7.24-7.36 (m, 8 H), 7.13-7.20 (m, 2 H), 6.66 (d, 1 H), 4.54 (s, 2 H), 3.80-3.85 (m, 1 H), 3.32-3.72 (m, 4 H), 3.03-3.11 (m, 1 H), 2.90 (s, 3 H), 2.32-2.43 (m, 1 H), 1.90-2.10 (m, 1H), 1.30 (d, 6 H).

Example 399

N-benzyl-N-(2-cyanoethyl)-N'-{3-[3-(2-{[4-(1-isopropylpyrrolidin-3-yl)phenyl]amino}pyrimidin-4-yl)imidazo[1,2-a]pyridin-2-yl]phenyl}urea

Example 399A

The title compound was prepared as described in EXAMPLE 251A, substituting 3-(benzylamino)propanenitrile for indoline.

Example 399B

N-benzyl-N-(2-cyanoethyl)-N'-{3-[3-(2-{[4-(1-isopropylpyrrolidin-3-yl)phenyl]amino}pyrimidin-4-yl)imidazo[1,2-a]pyridin-2-yl]phenyl}urea, trifluoroacetic acid salt The title compound was prepared as described in EXAMPLE 244 from EXAMPLE 383F and EXAMPLE 399A. MS ESI(+): m/e 676.3 (M+H)⁺. ¹H NMR (400 MHz, dimethylsulfoxide-d₆) δ ppm 9.87 (bd, 1 H), 9.78 (s, 1 H), 9.59 (bd, 1 H), 8.74 (s, 1 H), 8.35 (d, 1 H), 7.89 (s, 1 H), 7.78 (d, 1 H), 7.74 (d, 2 H), 7.63 (d, 1 H), 7.57 (t, 1 H), 7.19-7.38 (m, 9 H), 7.14 (t, 1 H), 6.66 (d, 1 H), 4.69 (s, 2 H), 3.80-3.85 (m, 3 H), 3.32-3.72 (m, 4 H), 3.03-3.11 (m, 1 H), 2.75 (t, 2 H), 2.32-2.43 (m, 1 H), 1.90-2.10 (m, 1H), 1.30 (d, 6 H).

Example 400

N'-{3-[3-(2-{[4-(1-isopropylpyrrolidin-3-yl)phenyl]amino}pyrimidin-4-yl)imidazo[1,2-a]pyridin-2-yl]phenyl}-N-methyl-N-[(1S)-1-phenylethyl]urea

Example 400A

The title compound was prepared as described in EXAMPLE 251 A, substituting (5)-N-methyl-1-phenylethanamine for indoline.

Example 400B

N'-{3-[3-(2-{[4-(1-isopropylpyrrolidin-3-yl)phenyl]amino}pyrimidin-4-yl)imidazo[1,2-a]pyridin-2-yl]phenyl}-N-methyl-N-[(1S)-1-phenylethyl]urea, trifluoroacetic acid salt The title compound was prepared as described in EXAMPLE 244 from EXAMPLE 383F and EXAMPLE 400A. MS ESI(+): m/e 651.4 (M+H)⁺. ¹H NMR (400 MHz, dimethylsulfoxide-d₆) δ ppm 9.85 (bd, 1 H), 9.78 (s, 1 H), 9.61 (bd, 1 H), 8.49 (s, 1 H), 8.37 (d, 1 H), 7.93 (s, 1 H), 7.79 (d, 1 H), 7.74 (d, 2 H), 7.65 (d, 1 H), 7.58 (t, 1 H), 7.23-7.38 (m, 8 H), 7.13-7.19 (m, 2 H), 6.67 (d, 1 H), 5.62 (q, 1 H), 3.80-3.85 (m, 1 H), 3.32-3.72 (m, 4 H), 3.03-3.11 (m, 1 H), 2.68 (s, 3 H), 2.32-2.43 (m, 1 H), 1.90-2.10 (m, 1H), 1.49 (d, 3 H), 1.30 (d, 6 H).

Example 401

N-{3-[3-(2-{[4-(1-isopropylpyrrolidin-3-yl)phenyl]amino}pyrimidin-4-yl)imidazo[1,2-a]pyridin-2-yl]phenyl}-5-methylindoline-1-carboxamide

Example 401A

The title compound was prepared as described in EXAMPLE 251A, substituting 5-methylindoline for indoline.

Example 401B

N-{3-[3-(2-{[4-(1-isopropylpyrrolidin-3-yl)phenyl]amino}pyrimidin-4-yl)imidazo[1,2-a]pyridin-2-yl]phenyl}-5-methylindoline-1-carboxamide, trifluoroacetic acid salt The title compound was prepared as described in EXAMPLE 244 from EXAMPLE 383F and EXAMPLE 401A. MS ESI(+): m/e 649.4 (M+H)⁺. ¹H NMR (400 MHz, dimethylsulfoxide-d₆) δ ppm 9.95 (bd, 1 H), 9.79 (s, 1 H), 9.59 (bd, 1 H), 8.60 (s, 1 H), 8.39 (d, 1 H), 7.97 (s, 1 H), 7.81 (d, 1 H), 7.69-7.75 (m, 4 H), 7.61 (t, 1 H), 7.39 (t, 1 H), 7.24-7.31 (m, 3 H), 7.17 (t, 1 H), 7.01 (s, 1 H), 6.91 (d, 1 H), 6.69 (d, 1 H), 4.11 (t, 2 H), 3.80-3.85 (m, 1 H), 3.32-3.72 (m, 4 H), 3.03-3.11 (m+s, 3 H), 2.32-2.43 (m, 1 H), 2.24 (s, 3 H), 1.90-2.10 (m, 1H), 1.30 (d, 6 H).

Example 402

N-(3-{3-[2-({3-[2-(dimethylamino)ethyl]phenyl}amino)pyrimidin-4-yl]-6-fluoroimidazo[1,2-a]pyridin-2-yl}phenyl)-N'-phenylurea

Example 402A

The title compound was prepared as described in EXAMPLE 1A, substituting 2-amino-5-fluoropyridine for pyridine-2-amine. MS (ESI(+)) m/e 258 (M+H)⁺.

Example 402B

Into a 250 mL round bottom flask was charged EXAMPLE 402A (3.5698 g, 13.88 mmol), acetic anhydride (57.6 ml, 611 mmol), and sulfuric acid (0.740 ml, 13.88 mmol). The reaction was heated to 130° C. for 60 hours. The suspension became a solution upon heating. The reaction was cooled to room temperature, then poured onto ice water. The mixture was extracted with ethyl acetate. The organic layer was washed with 1N NaOH (2×) and brine, dried over MgSO₄, filtered and concentrated onto silica gel. The reaction was purified by flash chromatography using an Argonaut Flashmaster Solo, 50 g column (20% ethyl acetate:hexanes for 20 minutes, then to 30% ethyl acetate:hexanes over 10 minutes, then held 20 minutes, then to 70% ethyl acetate:hexanes over 10 minutes, then held 5 minutes, then to 100% ethyl acetate for 30 minutes) to provide the title compound. MS (ESI(+)) m/e 300 (M+H)⁺.

Example 402C

The title compound was prepared as described in EXAMPLE 1D, substituting EXAMPLE 402B for EXAMPLE 1C. MS (ESI(+)) m/e 355 (M+H)⁺.

Example 402D

The title compound was prepared as described in EXAMPLE 4A, substituting EXAMPLE 402C for EXAMPLE 1D. MS (ESI(+)) m/e 351 (M+H)$^+$.

Example 402E

The title compound was prepared as described in EXAMPLE 4B, substituting EXAMPLE 402D for EXAMPLE 4A. MS (ESI(+)) m/e 352 (M+H)$^+$.

Example 402F

The title compound was prepared as described in EXAMPLE 4C, substituting EXAMPLE 402E for EXAMPLE 4B. MS (ESI(+)) m/e 370 (M+H)$^+$.

Example 402G

Into a 500 mL round bottom flask was charged 2-(3-nitrophenyl)ethanol (1.0235 g, 6.12 mmol), 4-(dimethylamino)pyridine (0.075 g, 0.612 mmol), p-toluenesulfonyl chloride (1.401 g, 7.35 mmol), and dichloromethane (61.2 ml). Triethylamine (1.707 ml, 12.25 mmol) was added, and the reaction was stirred for 3 hours. The reaction was then washed with water and brine, dried over MgSO$_4$, filtered and concentrated onto silica gel. The reaction was purified by flash chromatography using an Argonaut Flashmaster Solo, 25 g column (100% hexanes to 30% ethyl acetate:hexanes over 25 minutes, then to 100% ethyl acetate over 10 minutes) to provide the title compound. MS (ESI(+)) m/e 339 (M+NH$_4$)$^+$.

Example 402H

The title compound was prepared as described in EXAMPLE 195A, substituting EXAMPLE 402G for 4-nitrophenethyl bromide. MS (ESI(+)) m/e 195 (M+H)$^+$.

Example 402I

The title compound was prepared as described in EXAMPLE 4E, substituting EXAMPLE 402H for EXAMPLE 4D. MS (DCI(+)) m/e 165 (M+H)$^+$.

Example 402J

The title compound was prepared as described in EXAMPLE 4F, substituting EXAMPLE 402F for EXAMPLE 4C, and EXAMPLE 402I for EXAMPLE 4E. MS (ESI(+)) m/e 498 (M+H)$^+$.

Example 402K

The title compound was prepared as described in EXAMPLE 4G, substituting EXAMPLE 402J for EXAMPLE 4F. MS (ESI(+)) m/e 468 (M+H)$^+$.

Example 402L

The title compound was prepared as described in EXAMPLE 3, substituting EXAMPLE 402K for EXAMPLE 1H. MS (ESI(+)) m/e 587 (M+H)$^+$; $^1$H NMR (300 MHz, dimethylsulfoxide-d$_6$) δ ppm 9.78 (s, 1H), 9.79 (m, 1H), 8.84 (s, 1H), 8.67 (s, 1H), 8.35 (d, 1H), 7.84 (dd, 1H), 7.78 (m, 1H), 7.61 (m, 3H), 7.54 (m, 1H), 7.44 (m, 2H), 7.38 (t, 1H), 7.25 (m, 4H), 6.96 (t, 1H), 6.88 (d, 1H), 6.63 (d, 1H), 2.72 (m, 2H), 2.60 (m, 2H), 2.28 (s, 3H).

Example 403

N-(3-{3-[2-({3-[2-(dimethylamino)ethyl]phenyl}amino)pyrimidin-4-yl]-6-fluoroimidazo[1,2-a]pyridin-2-yl}phenyl)-2-thien-2-ylacetamide The title compound was prepared as described in EXAMPLE 4H, substituting EXAMPLE 402K for EXAMPLE 4G, and 2-thiopheneacetyl chloride for 2,6-difluorobenzamide. MS (ESI(+)) m/e 592 (M+H)$^+$; $^1$H NMR (300 MHz, dimethylsulfoxide-d$_6$) δ ppm 10.32 (s, 1H), 9.78 (s, 1H), 9.72 (m, 1H), 8.42 (d, 1H), 7.94 (m, 2H), 7.72 (m, 2H), 7.56 (m, 2H), 7.40 (m, 3H), 7.16 (t, 1H), 6.97 (m, 2H), 6.84 (d, 1H), 6.67 (d, 1H), 3.87 (s, 2H), 2.67 (m, 2H), 2.37 (m, 2H), 2.09 (s, 3H).

Example 404

N-(3-{3-[2-({3-[2-(dimethylamino)ethyl]phenyl}amino)pyrimidin-4-yl]-6-fluoroimidazo[1,2-a]pyridin-2-yl}phenyl)-2,6-difluorobenzamide The title compound was prepared as described in EXAMPLE 4H, substituting EXAMPLE 402K for EXAMPLE 4G. MS (ESI(+)) m/e 608 (M+H)$^+$; $^1$H NMR (300 MHz, dimethylsulfoxide-d$_6$) δ ppm 10.01 (s, 1H), 9.75 (s, 1H), 9.70 (m, 1H), 8.36 (d, 1H), 8.04 (m, 1H), 7.85 (dd, 1H), 7.80 (d, 1H), 7.59 (m, 4H), 7.47 (t, 1H), 7.40 (d, 1H), 7.23 (m, 3H), 6.86 (d, 2H), 6.64 (d, 1H), 2.66 (m, 2H), 2.42 (m, 2H), 2.14 (s, 3H).

Example 405

N-{3-[3-[2-({3-[2-(dimethylamino)ethyl]phenyl}amino)pyrimidin-4-yl]-6-(trifluoromethyl)imidazo[1,2-a]pyridin-2-yl]phenyl)-N'-phenylurea

Example 405A

The title compound was prepared as described in EXAMPLE 402B, substituting EXAMPLE 405A for EXAMPLE 402A. MS (ESI(+)) m/e 350 (M+H)$^+$.

Example 405B

The title compound was prepared as described in EXAMPLE 1A, substituting 2-amino-5-trifluoromethylpyridine for pyridine-2-amine. MS (ESI(+)) m/e 308 (M+H)$^+$.

Example 405C

The title compound was prepared as described in EXAMPLE 1D, substituting EXAMPLE 405B for EXAMPLE 1C. MS (ESI(+)) m/e 405 (M+H)$^+$.

Example 405D

The title compound was prepared as described in EXAMPLE 4A, substituting EXAMPLE 405C for EXAMPLE 1D. MS (ESI(+)) m/e 401 (M+H)$^+$.

Example 405E

The title compound was prepared as described in EXAMPLE 4B, substituting EXAMPLE 405D for EXAMPLE 4A. MS (ESI(+)) m/e 402 (M+H)+.

Example 405F

The title compound was prepared as described in EXAMPLE 4C, substituting EXAMPLE 405E for EXAMPLE 4B. MS (ESI(+)) m/e 420 (M+H)+.

Example 405G

The title compound was prepared as described in EXAMPLE 4F, substituting EXAMPLE 405F for EXAMPLE 4C, and EXAMPLE 402I for EXAMPLE 4E. MS (ESI(+)) m/e 548 (M+H)+.

Example 405H

The title compound was prepared as described in EXAMPLE 4G, substituting EXAMPLE 405G for EXAMPLE 4F. MS (ESI(+)) m/e 518 (M+H)+.

Example 405I

The title compound was prepared as described in EXAMPLE 3, substituting EXAMPLE 405H for EXAMPLE 1H. MS (ESI(+)) m/e 637 (M+H)+; $^1$H NMR (300 MHz, dimethylsulfoxide-$d_6$) δ ppm 9.79 (s, 1H), 9.74 (s, 1H), 8.82 (s, 1H), 8.63 (s, 1H), 8.44 (d, 1H), 7.96 (d, 1H), 7.82 (m, 1H), 7.71 (dd, 1H), 7.57 (m, 3H), 7.44 (d, 2H), 7.38 (t, 1H), 7.27 (m, 3H), 7.17 (t, 1H), 6.97 (t, 1H), 6.85 (d, 1H), 6.70 (d, 1H), 2.62 (m, 2H), 2.38 (m, 2H), 2.14 (s, 3H).

Example 406

N-{3-[3-[2-({3-[2-(dimethylamino)ethyl]phenyl}amino)pyrimidin-4-yl]-6-(trifluoromethyl)imidazo[1,2-a]pyridin-2-yl]phenyl}-2-thien-2-ylacetamide The title compound was prepared as described in EXAMPLE 4H, substituting EXAMPLE 405H for EXAMPLE 4G, and 2-thiopheneacetyl chloride for 2,6-difluorobenzamide. MS (ESI(+)) m/e 642 (M+H)+; $^1$H NMR (300 MHz, dimethylsulfoxide-$d_6$) δ ppm 10.32 (s, 1H), 9.78 (s, 1H), 9.72 (s, 1H), 8.42 (d, 1H), 7.94 (m, 2H), 7.72 (m, 2H), 7.56 (m, 2H), 7.40 (m, 3H), 7.16 (t, 1H), 6.98 (m, 2H), 6.84 (d, 1H), 6.67 (d, 1H), 3.87 (s, 2H), 2.62 (m, 2H), 2.37 (m, 2H), 2.09 (s, 3H).

Example 407

N-{3-[3-[2-({3-[2-(dimethylamino)ethyl]phenyl}amino)pyrimidin-4-yl]-6-(trifluoromethyl)imidazo[1,2-a]pyridin-2-yl]phenyl}-2,6-difluorobenzamide The title compound was prepared as described in EXAMPLE 4H, substituting EXAMPLE 405H for EXAMPLE 4G. MS (ESI(+)) m/e 658 (M+H)+; $^1$H NMR (300 MHz, dimethylsulfoxide-$d_6$) δ ppm 10.90 (s, 1H), 9.78 (s, 1H), 9.72 (s, 1H), 8.44 (d, 1H), 8.09 (m, 1H), 7.96 (dd, 1H), 7.81 (dt, 1H), 7.71 (dd, 1H), 7.58 (m, 3H), 7.46 (m, 2H), 7.25 (t, 2H), 7.16 (t, 1H), 6.84 (d, 1H), 6.72 (d, 1H), 2.62 (m, 2H), 2.36 (m, 2H), 2.09 (s, 3H).

The foregoing is meant to illustrate the invention but not to limit it. Variations and changes obvious to one skilled in the art are intended to be within the scope of the invention as defined in the claims.

We claim:
1. A compound having Formula I

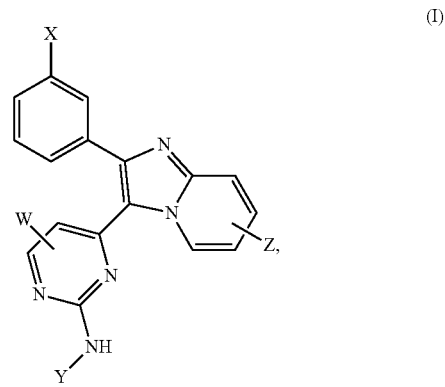

(I)

or a pharmaceutically acceptable salt thereof, wherein
W is alkyl, H, F, Cl, Br or I;
X is C(O)R$^1$, C(O)NHR$^{1A}$, C(O)N(R$^1$)$_2$, NHC(O)R$^{1A}$, NR$^1$C(O)R$^1$, NHC(O)NHR$^1$, NHC(O)N(R$^1$)$_2$, or NR$^1$C(O)N(R$^1$)$_2$;
wherein R$^1$ is R$^2$, R$^3$, R$^4$ or R$^5$;
R$^2$ is aryl;
R$^3$ is heteroaryl;
R$^4$ is cycloalkyl, cycloalkenyl, or heterocyclyl;
R$^5$ is C1-C6 alkyl; each of which is unsubstituted or substituted with one or two independently selected R$^6$, NH$_2$ or CN;
R$^6$ is R$^7$, R$^8$, or R$^9$;
R$^7$ is aryl;
R$^8$ is heteroaryl;
R$^9$ is cycloalkyl, cycloalkenyl, or heterocyclyl;
wherein R$^{1A}$ is R$^{2A}$, R$^{3A}$, R$^{4A}$ or R$^{5A}$;
R$^{2A}$ is aryl;
R$^{3A}$ is heteroaryl;
R$^{4A}$ is cycloalkyl, cycloalkenyl, or heterocyclyl;
R$^{5A}$ is C1-C6 alkyl; each of which is unsubstituted or substituted with one or two independently selected R$^{6A}$, NH$_2$ or CN;
R$^{6A}$ is R$^{7A}$; R$^{8A}$; or R$^{9A}$;
R$^{7A}$ is aryl;
R$^{8A}$ is heteroaryl;
R$^{9A}$ is cycloalkyl, cycloalkenyl, or heterocyclyl;
wherein the moieties represented by R$^2$, R$^3$, R$^4$, R$^7$, R$^8$, R$^9$, R$^{3A}$, R$^{4A}$, R$^{7A}$, R$^{8A}$, and R$^{9A}$ are independently unsubstituted or substituted with one or two or three or four of independently selected, R$^{10}$, OR$^{10}$, SR$^{10}$, S(O)R$^{10}$, SO$_2$R$^{10}$, NH$_2$, NHR$^{10}$, N(R$^{10}$)$_2$, C(O)R$^{10}$, C(O)OR$^{10}$, C(O)NH$_2$, C(O)NHR$^{10}$, C(O)N(R$^{10}$)$_2$, C(NOH)NH$_2$, NHC(O)R$^{10}$, NR$^{10}$C(O)R$^{10}$, NHSO$_2$R$^{10}$, NR$^{10}$SO$_2$R$^{10}$, NHC(O)OR$^{10}$, NR$^{10}$C(O)OR$^{10}$, NHSO$_2$NH$_2$, NHSO$_2$NHR$^{10}$, NHSO$_2$N(R$^{10}$)$_2$, SO$_2$NH$_2$, SO$_2$NHR$^{10}$, SO$_2$N(R$^{10}$)$_2$, NHC(O)NH$_2$, NHC(O)NHR$^{10}$, NHC(O)N(R$^{10}$)$_2$, NR$^{10}$C(O)N(R$^{10}$)$_2$, NO$_2$, OH, (O), C(O)H, C(O)OH, CN, CF$_3$, OCF$_3$, CF$_2$CF$_3$, F, Cl, Br or I;

wherein the moiety represented by $R^{24}$ is independently unsubstituted or substituted with one or two or three or four of independently selected, $R^{10}$, $OR^{10}$, $SR^{10}$, $S(O)R^{10}$, $SO_2R^{10}$, $NH_2$, $NHR^{10}$, $N(R^{10})_2$, $C(O)R^{10}$, $C(O)OR^{10}$, $C(O)NH_2$, $C(O)NHR^{10}$, $C(O)N(R^{10})_2$, $C(NOH)NH_2$, $NHC(O)R^{10}$, $NR^{10}C(O)R^{10}$, $NHSO_2R^{10}$, $NR^{10}SO_2R^{10}$, $NHC(O)OR^{10}$, $NR^{10}C(O)OR^{10}$, $NHSO_2NH_2$, $NHSO_2NHR^{10}$, $NHSO_2N(R^{10})_2$, $SO_2NH_2$, $SO_2NHR^{10}$, $SO_2N(R^{10})_2$, $NHC(O)NH_2$, $NHC(O)NHR^{10}$, $NHC(O)N(R^{10})_2$, $NR^{10}C(O)N(R^{10})_2$, $NO_2$, $OH$, $(O)$, $C(O)H$, $C(O)OH$, $CN$, $CF_3$, $OCF_3$, or $CF_2CF_3$;

$R^{10}$ is alkyl, alkenyl, alkynyl, aryl, heteroaryl, cycloalkyl, cycloalkenyl, or heterocyclyl;

Y is $R^{12}$ or $R^{13}$;

$R^{12}$ is aryl;

$R^{13}$ is heteroaryl;

Z is alkyl, H, $CF_3$, F, Cl, Br or I;

wherein the moieties represented by $R^{12}$ and $R^{13}$ are independently unsubstituted or substituted with one or two or three or four of independently selected, $R^{14}$, $OR^{14}$, $SR^{14}$, $S(O)R^{14}$, $SO_2R^{14}$, $NH_2$, $NHR^{14}$, $N(R^{14})_2$, $C(O)R^{14}$, $C(O)OR^{14}$, $C(O)NH_2$, $C(O)NHR^{14}$, $C(O)N(R^{14})_2$, $C(NOH)NH_2$, $NHC(O)R^{14}$, $NR^{14}C(O)R^{14}$, $NHSO_2R^{14}$, $NR^{14}SO_2R^{14}$, $NHC(O)OR^{14}$, $NR^{14}C(O)OR^{14}$, $NHSO_2NH_2$, $NHSO_2NHR^{14}$, $NHSO_2N(R^{14})_2$, $SO_2NH_2$, $SO_2NHR^{14}$, $SO_2N(R^{14})_2$, $NHC(O)NH_2$, $NHC(O)NHR^{14}$, $NHC(O)N(R^{14})_2$, $NR^{14}C(O)N(R^{14})_2$, $NO_2$, $OH$, $(O)$, $C(O)H$, $C(O)OH$, $CN$, $CF_3$, $OCF_3$, $CF_2CF_3$, F, Cl, Br or I;

wherein each $R^{14}$ is $R^{15}$, $R^{16}$, $R^{17}$ or $R^{18}$;

$R^{15}$ is aryl;

$R^{16}$ is heteroaryl;

$R^{17}$ is cycloalkyl, cycloalkenyl, or heterocyclyl;

$R^{18}$ is alkyl, alkenyl or alkynyl; each of which is unsubstituted or substituted with one or two of independently selected $R^{19}$, $OR^{19}$, $SR^{19}$, $S(O)_2R^{19}$, $NHS(O)_2R^{19}$, $C(O)OH$, $NH_2$, $NHR^{19}$, $N(R^{19})_2$, $C(O)R^{19}$, $C(O)OR^{19}$, $C(O)NH_2$, $C(O)NHR^{19}$, $C(O)N(R^{19})_2$, $NHC(O)R^{19}$, $NR^{19}C(O)R^{19}$, $NHC(O)OR^{19}$, $NR^{19}C(O)OR^{19}$, $OH$, F, Cl, Br or I;

wherein each $R^{19}$ is $R^{20}$ or $R^{21}$;

$R^{20}$ is aryl, heteroaryl, cycloalkyl, cycloalkenyl, or heterocyclyl;

$R^{21}$ is alkyl, alkenyl or alkynyl; each of which is unsubstituted or substituted with one or two of independently selected $R^{22}$, $OR^{22}$, $C(O)OH$, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, $OH$, F, Cl, Br or I;

wherein each $R^{22}$ is alkyl, alkenyl, alkynyl, aryl, heteroaryl, cycloalkyl, cycloalkenyl, or heterocyclyl;

wherein the moieties represented by $R^{15}$, $R^{16}$, $R^{17}$, and $R^{20}$ are independently unsubstituted or substituted with one or two or three or four of independently selected $R^{23}$, $OR^{23}$, $SR^{23}$, $S(O)R^{23}SO_2R^{23}$, $C(O)R^{23}$, $CO(O)R^{23}$, $OC(O)R^{23}$, $OC(O)OR^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)^2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, $C(O)NHOH$, $C(O)NHOR^{23}$, $C(O)NHSO_2R^{23}$, $C(O)NR^{23}SO_2R^{23}$, $SO_2NH_2$, $SO_2NHR^{23}$, $SO_2N(R^{23})_2$, $C(O)H$, $C(O)OH$, $C(N)NH_2$, $C(N)NHR^{23}$, $C(N)N(R^{23})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

wherein each $R^{23}$ is $R^{24}$, $R^{25}$, $R^{26}$, $R^{27}$ or $R^{28}$;

$R^{24}$ is spirocycloalkyl or spiroheterocycloalkyl;

$R^{25}$ is aryl;

$R^{26}$ is heteroaryl;

$R^{27}$ is cycloalkyl, cycloalkenyl, or heterocyclyl;

$R^{28}$ is alkyl, alkenyl or alkynyl; each of which is unsubstituted or substituted with one or two of independently selected $R^{29}$, $OR^{29}$, $SR^{29}$, $S(O)_2R^{29}$, $C(O)OH$, $NH_2$, $NHR^{29}N(R^{29})_2$, $C(O)R^{29}$, $C(O)NH_2$, $C(O)NHR^{29}$, $C(O)N(R^{29})_2$, $NHC(O)R^{29}$, $NR^{29}C(O)R^{29}$, $NHC(O)OR^{29}$, $NR^{29}C(O)OR^{29}$, $NHS(O)_2R^{29}$, $NR^{29}S(O)_2R^{29}$, $OH$, $(O)$, F, Cl, Br or I;

wherein each $R^{29}$ is alkyl, alkenyl or alkynyl each of which is unsubstituted or substituted with one or two of independently selected F, Cl, Br or I;

wherein the moieties represented by $R^{24}$, $R^{25}$, $R^{26}$, and $R^{27}$ are independently unsubstituted or substituted with one or two of independently selected $R^{30}$, $OR^+$, $C(O)R^{30}$, $C(O)OR^{30}$, $OH$, $(O)$, $C(O)OH$, $CN$, $CF_3$, $OCF_3$, $CF_2CF_3$, F, Cl, Br or I; and $R^{30}$ is alkyl alkenyl, or alkynyl.

2. The compound of claim 1 wherein
X is $C(O)R^1$, $NHC(O)NHR^1$, $NHC(O)N(R^1)_2$, or $NR^1C(O)N(R^1)_2$.

3. A compound according to claim 1 selected from
2,6-difluoro-N-[3-(3-{2-[(3-morpholin-4-ylphenyl)amino]pyrimidin-4-yl}imidazo[1,2-a]pyridin-2-yl)phenyl]benzamide;

N-[3-(3-{2-[(3-morpholin-4-ylphenyl)amino]pyrimidin-4-yl}imidazo[1,2-a]pyridin-2-yl)phenyl]-2-phenylacetamide;

N-[3-(3-{2-[(3-morpholin-4-ylphenyl)amino]pyrimidin-4-yl}imidazo[1,2-a]pyridin-2-yl)phenyl]-N'-phenylurea;

2,6-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-2-phenylacetamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-2-thien-2-ylacetamide;

N-[3-(3-{2-[(2-methyl-1,2,3,4-tetrahydroisoquinolin-7-yl)amino]pyrimidin-4-yl}imidazo[1,2-a]pyridin-2-yl)phenyl]-N'-phenylurea;

N-benzyl-N'-[3-(3-{2-[(3-morpholin-4-ylphenyl)amino]pyrimidin-4-yl}imidazo[1,2-a]pyridin-2-yl)phenyl]urea;

N-(2,6-difluorophenyl)-N'-[3-(3-{2-[(3-morpholin-4-ylphenyl)amino]pyrimidin-4-yl}imidazo[1,2-a]pyridin-2-yl)phenyl]urea;

N-(2-methylphenyl)-N'-[3-(3-{2-[(3-morpholin-4-ylphenyl)amino]pyrimidin-4-yl}imidazo[1,2-a]pyridin-2-yl)phenyl]urea;

N-(2-chlorophenyl)-N'-[3-(3-{2-[(3-morpholin-4-ylphenyl)amino]pyrimidin-4-yl}imidazo[1,2-a]pyridin-2-yl)phenyl]urea;

N-(4-fluorophenyl)-N'-[3-(3-{2-[(3-morpholin-4-ylphenyl)amino]pyrimidin-4-yl}imidazo[1,2-a]pyridin-2-yl)phenyl]urea;

N-(3-methoxyphenyl)-N'-[3-(3-{2-[(3-morpholin-4-ylphenyl)amino]pyrimidin-4-yl}imidazo[1,2-a]pyridin-2-yl)phenyl]urea;

N-[3-(3-{2-[(3-morpholin-4-ylphenyl)amino]pyrimidin-4-yl}imidazo[1,2-a]pyridin-2-yl)phenyl]cyclopropanecarboxamide;

N-isopropyl-N'-[3-(3-{2-[(3-morpholin-4-ylphenyl)amino]pyrimidin-4-yl}imidazo[1,2-a]pyridin-2-yl)phenyl]urea;

2,6-difluoro-N-{3-[3-(2-{[3-(2-oxopyrrolidin-1-yl)phenyl]amino}pyrimidin-4-yl)imidazo[1,2-a]pyridin-2-yl]phenyl}benzamide;

2-fluoro-N-{3-[3-(2-{[3-(2-oxopyrrolidin-1-yl)phenyl]amino}pyrimidin-4-yl)imidazo[1,2-a]pyridin-2-yl]phenyl}benzamide;

N-{3-[3-(2-{[3-(2-oxopyrrolidin-1-yl)phenyl]amino}pyrimidin-4-yl)imidazo[1,2-a]pyridin-2-yl]phenyl}-2-phenylacetamide;

N-{3-[3-(2-{[3-(2-oxopyrrolidin-1-yl)phenyl]amino}pyrimidin-4-yl)imidazo[1,2-a]pyridin-2-yl]phenyl}-2-thien-2-ylacetamide;

N-{3-[3-(2-{[3-(2-oxopyrrolidin-1-yl)phenyl]amino}pyrimidin-4-yl)imidazo[1,2-a]pyridin-2-yl]phenyl}-N'-phenylurea;

N-(2-fluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea;

N-(2,6-difluorophenyl)-N'-{3-[3-(2-{[3-(2-oxopyrrolidin-1-yl)phenyl]amino}pyrimidin-4-yl)imidazo[1,2-a]pyridin-2-yl]phenyl}urea;

2-(2-fluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide;

2-(2,6-difluorophenyl)-N-{3-[3-(2-{[3-(2-oxopyrrolidin-1-yl)phenyl]amino}pyrimidin-4-yl)imidazo[1,2-a]pyridin-2-yl]phenyl}acetamide;

N-benzyl-N'-{3-[3-(2-{[3-(2-oxopyrrolidin-1-yl)phenyl]amino}pyrimidin-4-yl)imidazo[1,2-a]pyridin-2-yl]phenyl}urea;

N-(3-{3-[2-({3-[(dimethylamino)methyl]phenyl}amino)pyrimidin-4-yl]imidazo[1,2-a]pyridin-2-yl}phenyl)benzamide;

N-(3-{3-[2-({3-[(dimethylamino)methyl]phenyl}amino)pyrimidin-4-yl]imidazo[1,2-a]pyridin-2-yl}phenyl)-2-fluorobenzamide;

N-(3-{3-[2-({3-[(dimethylamino)methyl]phenyl}amino)pyrimidin-4-yl]imidazo[1,2-a]pyridin-2-yl}phenyl)-2,6-difluorobenzamide;

N-(3-{3-[2-({3-[(dimethylamino)methyl]phenyl}amino)pyrimidin-4-yl]imidazo[1,2-a]pyridin-2-yl}phenyl)-2-phenylacetamide;

N-(3-{3-[2-({3-[(dimethylamino)methyl]phenyl}amino)pyrimidin-4-yl]imidazo[1,2-a]pyridin-2-yl}phenyl)-2-thien-2-ylacetamide;

N-(3-{3-[2-({3-[(dimethylamino)methyl]phenyl}amino)pyrimidin-4-yl]imidazo[1,2-a]pyridin-2-yl}phenyl)-N'-phenylurea;

N-(2,6-difluorophenyl)-N'-(3-{3-[2-({3-[(dimethylamino)methyl]phenyl}amino)pyrimidin-4-yl]imidazo[1,2-a]pyridin-2-yl}phenyl)urea;

N-[3-(8-chloro-3-{2-[(3-morpholin-4-ylphenyl)amino]pyrimidin-4-yl}imidazo[1,2-a]pyridin-2-yl)phenyl]-2,6-difluorobenzamide;

N-[3-(8-chloro-3-{2-[(3-morpholin-4-ylphenyl)amino]pyrimidin-4-yl}imidazo[1,2-a]pyridin-2-yl)phenyl]-2-phenylacetamide;

N-[3-(8-chloro-3-{2-[(3-morpholin-4-ylphenyl)amino]pyrimidin-4-yl}imidazo[1,2-a]pyridin-2-yl)phenyl]-2-thien-2-ylacetamide;

N-[3-(8-chloro-3-{2-[(3-morpholin-4-ylphenyl)amino]pyrimidin-4-yl}imidazo[1,2-a]pyridin-2-yl)phenyl]-N'-phenylurea;

N-(3-{3-[2-({3-[2-(dimethylamino)ethyl]phenyl}amino)pyrimidin-4-yl]imidazo[1,2-a]pyridin-2-yl}phenyl)-2,6-difluorobenzamide;

N-(3-{3-[2-({3-[2-(dimethylamino)ethyl]phenyl}amino)pyrimidin-4-yl]imidazo[1,2-a]pyridin-2-yl}phenyl)-2-phenylacetamide;

N-(3-{3-[2-({3-[2-(dimethylamino)ethyl]phenyl}amino)pyrimidin-4-yl]imidazo[1,2-a]pyridin-2-yl}phenyl)-2-thien-2-ylacetamide;

N-(3-{3-[2-({3-[2-(dimethylamino)ethyl]phenyl}amino)pyrimidin-4-yl]imidazo[1,2-a]pyridin-2-yl}phenyl)-N'-phenylurea;

N-{3-[3-(2-{[4-(4-ethylpiperazin-1-yl)phenyl]amino}pyrimidin-4-yl)imidazo[1,2-a]pyridin-2-yl]phenyl}-2-phenylacetamide;

N-{3-[3-(2-{[4-(4-ethylpiperazin-1-yl)phenyl]amino}pyrimidin-4-yl)imidazo[1,2-a]pyridin-2-yl]phenyl}-2-thien-2-ylacetamide;

N-{3-[3-(2-{[4-(4-ethylpiperazin-1-yl)phenyl]amino}pyrimidin-4-yl)imidazo[1,2-a]pyridin-2-yl]phenyl}benzamide;

N-{3-[3-(2-{[4-(4-ethylpiperazin-1-yl)phenyl]amino}pyrimidin-4-yl)imidazo[1,2-a]pyridin-2-yl]phenyl}-2,6-difluorobenzamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2,6-difluorobenzamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2-phenylacetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-2-thien-2-ylacetamide;

N-(3-{3-[2-({3-[2-(dimethylamino)ethoxy]phenyl}amino)pyrimidin-4-yl]imidazo[1,2-a]pyridin-2-yl}phenyl)-2,6-difluorobenzamide;

N-(3-{3-[2-({3-[2-(dimethylamino)ethoxy]phenyl}amino)pyrimidin-4-yl]imidazo[1,2-a]pyridin-2-yl}phenyl)-2-phenylacetamide;

N-(3-{3-[2-({3-[2-(dimethylamino)ethoxy]phenyl}amino)pyrimidin-4-yl]imidazo[1,2-a]pyridin-2-yl}phenyl)-2-thien-2-ylacetamide;

N-[3-(3-{2-[(3-{[4-(dimethylamino)piperidin-1-yl]methyl}phenyl)amino]pyrimidin-4-yl}imidazo[1,2-a]pyridin-2-yl)phenyl]-5-methylthiophene-2-carboxamide;

N-(3-{3-[2-({3-[2-(dimethylamino)ethoxy]phenyl}amino)pyrimidin-4-yl]imidazo[1,2-a]pyridin-2-yl}phenyl)-5-methylthiophene-2-carboxamide;

N-(3-{3-[2-({4-[2-(dimethylamino)ethyl]phenyl}amino)pyrimidin-4-yl]imidazo[1,2-a]pyridin-2-yl}phenyl)-2,6-difluorobenzamide;

N-(3-{3-[2-({4-[2-(dimethylamino)ethyl]phenyl}amino)pyrimidin-4-yl]imidazo[1,2-a]pyridin-2-yl}phenyl)-2-phenylacetamide;

N-(3-{3-[2-({4-[2-(dimethylamino)ethyl]phenyl}amino)pyrimidin-4-yl]imidazo[1,2-a]pyridin-2-yl}phenyl)-2-thien-2-ylacetamide;

2,6-difluoro-N-{3-[3-(2-{[3-(2-pyrrolidin-1-ylethyl)phenyl]amino}pyrimidin-4-yl)imidazo[1,2-a]pyridin-2-yl]phenyl}benzamide;

2-phenyl-N-{3-[3-(2-{[3-(2-pyrrolidin-1-ylethyl)phenyl]amino}pyrimidin-4-yl)imidazo[1,2-a]pyridin-2-yl]phenyl}acetamide;

N-{3-[3-(2-{[3-(2-pyrrolidin-1-ylethyl)phenyl]amino}pyrimidin-4-yl)imidazo[1,2-a]pyridin-2-yl]phenyl}-2-thien-2-ylacetamide;

2,6-difluoro-N-(3-{3-[2-({3-[(3-hydroxyazetidin-1-yl)methyl]phenyl}amino)pyrimidin-4-yl]imidazo[1,2-a]pyridin-2-yl}phenyl)benzamide;

N-(3-{3-[2-({3-[(3-hydroxyazetidin-1-yl)methyl]
  phenyl}amino)pyrimidin-4-yl]imidazo[1,2-a]pyridin-
  2-yl}phenyl)-2-phenylacetamide;
N-(3-{3-[2-({3-[(3-hydroxyazetidin-1-yl)methyl]
  phenyl}amino)pyrimidin-4-yl]imidazo[1,2-a]pyridin-
  2-yl}phenyl)-2-thien-2-ylacetamide;
2,6-difluoro-N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]benzamide;
N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]-2-phenylacetamide;
N-[3-(3-{2-[(3-{2-[(2-hydroxyethyl)(methyl)amino]ethyl}phenyl)amino]pyrimidin-4-yl}imidazo[1,2-a]pyridin-2-yl)phenyl]-2-thien-2-ylacetamide;
N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2,6-difluorobenzamide;
N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-phenylacetamide;
N-[3-(3-{2-[(3-{[3-(dimethylamino)pyrrolidin-1-yl]methyl}phenyl)amino]pyrimidin-4-yl}imidazo[1,2-a]pyridin-2-yl)phenyl]-2-thien-2-ylacetamide;
N-{3-[3-(2-{[4-(1-acetylpiperidin-4-yl)phenyl]amino}pyrimidin-4-yl)imidazo[1,2-a]pyridin-2-yl]phenyl}-2-thien-2-ylacetamide;
N-{3-[3-(2-{[4-(1-acetylpiperidin-4-yl)phenyl]amino}pyrimidin-4-yl)imidazo[1,2-a]pyridin-2-yl]phenyl}-2,6-difluorobenzamide;
N-[3-(3-{2-[(3-cyanophenyl)amino]pyrimidin-4-yl}imidazo[1,2-a]pyridin-2-yl)phenyl]-2,6-difluorobenzamide;
N-[3-(3-{2-[(3-cyanophenyl)amino]pyrimidin-4-yl}imidazo[1,2-a]pyridin-2-yl)phenyl]-2-phenylacetamide;
N-[3-(3-{2-[(3-cyanophenyl)amino]pyrimidin-4-yl}imidazo[1,2-a]pyridin-2-yl)phenyl]-2-thien-2-ylacetamide;
2,6-difluoro-N-(3-{3-[2-({3-[2-(methylsulfonyl)ethoxy]phenyl}amino)pyrimidin-4-yl]imidazo[1,2-a]pyridin-2-yl}phenyl)benzamide;
N-(3-{3-[2-({3-[2-(methylsulfonyl)ethoxy]phenyl}amino)pyrimidin-4-yl]imidazo[1,2-a]pyridin-2-yl}phenyl)-2-phenylacetamide;
N-(3-{3-[2-({3-[2-(methylsulfonyl)ethoxy]phenyl}amino)pyrimidin-4-yl]imidazo[1,2-a]pyridin-2-yl}phenyl)-2-thien-2-ylacetamide;
2,6-difluoro-N-{3-[3-(2-{[4-(1-isopropylpiperidin-4-yl)phenyl]amino}pyrimidin-4-yl)imidazo[1,2-a]pyridin-2-yl]phenyl}benzamide;
N-{3-[3-(2-{[4-(1-isopropylpiperidin-4-yl)phenyl]amino}pyrimidin-4-yl)imidazo[1,2-a]pyridin-2-yl]phenyl}-2-thien-2-ylacetamide;
N-(3-{3-[2-({3-[(Z)-amino(hydroxyimino)methyl]phenyl}amino)pyrimidin-4-yl]imidazo[1,2-a]pyridin-2-yl}phenyl)-2,6-difluorobenzamide;
N-(3-{3-[2-({3-[(Z)-amino(hydroxyimino)methyl]phenyl}amino)pyrimidin-4-yl]imidazo[1,2-a]pyridin-2-yl}phenyl)-2-thien-2-ylacetamide;
N-{3-[3-(2-{[3-(2-amino-2-oxoethyl)phenyl]amino}pyrimidin-4-yl)imidazo[1,2-a]pyridin-2-yl]phenyl}-2,6-difluorobenzamide;
N-{3-[3-(2-{[3-(2-amino-2-oxoethyl)phenyl]amino}pyrimidin-4-yl)imidazo[1,2-a]pyridin-2-yl]phenyl}-2-thien-2-ylacetamide;
N-{3-[3-(2-{[3-(2-amino-2-oxoethyl)phenyl]amino}pyrimidin-4-yl)imidazo[1,2-a]pyridin-2-yl]phenyl}-2-phenylacetamide;
isopropyl (3-{[4-(2-{3-[(phenylacetyl)amino]phenyl}imidazo[1,2-a]pyridin-3-yl)pyrimidin-2-yl]amino}phenyl)acetate;
N-{3-[3-(2-{[4-(1-ethylpiperidin-4-yl)phenyl]amino}pyrimidin-4-yl)imidazo[1,2-a]pyridin-2-yl]phenyl}-2-thien-2-ylacetamide;
N-{3-[3-(2-{[4-(1-ethylpiperidin-4-yl)phenyl]amino}pyrimidin-4-yl)imidazo[1,2-a]pyridin-2-yl]phenyl}-2,6-difluorobenzamide;
N-{3-[3-(2-{[4-(1-ethylpiperazin-1-yl)phenyl]amino}pyrimidin-4-yl)imidazo[1,2-a]pyridin-2-yl]phenyl}-2-(1-methyl-1H-imidazol-4-yl)acetamide;
2,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
3,5-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2,3-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
N-{3-[3-(2-{[4-(4-ethylpiperazin-1-yl)phenyl]amino}pyrimidin-4-yl)imidazo[1,2-a]pyridin-2-yl]phenyl}-2-thien-3-ylacetamide;
N-{3-[3-(2-{[4-(4-ethylpiperazin-1-yl)phenyl]amino}pyrimidin-4-yl)imidazo[1,2-a]pyridin-2-yl]phenyl}-2-(3-methylisoxazol-5-yl)acetamide;
N-[3-(3-{2-[(1-acetyl-2,3-dihydro-1H-indol-5-yl)amino]pyrimidin-4-yl}imidazo[1,2-a]pyridin-2-yl)phenyl]-2,6-difluorobenzamide;
N-[3-(3-{2-[(1-acetyl-2,3-dihydro-1H-indol-5-yl)amino]pyrimidin-4-yl}imidazo[1,2-a]pyridin-2-yl)phenyl]-2-phenylacetamide;
N-[3-(3-{2-[(1-acetyl-2,3-dihydro-1H-indol-5-yl)amino]pyrimidin-4-yl}imidazo[1,2-a]pyridin-2-yl)phenyl]-2-thien-2-ylacetamide;
2,4-difluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2-chloro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
2-fluoro-N-[3-(3-{2-[(2-methyl-1,2,3,4-tetrahydroisoquinolin-7-yl)amino]pyrimidin-4-yl}imidazo[1,2-a]pyridin-2-yl)phenyl]benzamide;
N-{3-[3-(2-{[4-(1-ethylpyrrolidin-3-yl)phenyl]amino}pyrimidin-4-yl)imidazo[1,2-a]pyridin-2-yl]phenyl}-2-thien-2-ylacetamide;
N-{3-[3-(2-{[3-(1-ethylpyrrolidin-3-yl)phenyl]amino}pyrimidin-4-yl)imidazo[1,2-a]pyridin-2-yl]phenyl}-2-thien-2-ylacetamide;
N-{3-[3-(2-{[4-(1-acetylpyrrolidin-3-yl)phenyl]amino}pyrimidin-4-yl)imidazo[1,2-a]pyridin-2-yl]phenyl}-2-thien-2-ylacetamide;
N-{3-[3-(2-{[3-(1-acetylpyrrolidin-3-yl)phenyl]amino}pyrimidin-4-yl)imidazo[1,2-a]pyridin-2-yl]phenyl}-2-thien-2-ylacetamide;
N-{3-[3-(2-{[3-(1-acetylpyrrolidin-3-yl)phenyl]amino}pyrimidin-4-yl)imidazo[1,2-a]pyridin-2-yl]phenyl}-2,6-difluorobenzamide;
N-[3-(3-{2-[(2-ethyl-2,3-dihydro-1H-isoindol-5-yl)amino]pyrimidin-4-yl}imidazo[1,2-a]pyridin-2-yl)phenyl]-2-thien-2-ylacetamide;

N-[3-(3-{2-[(2-ethyl-2,3-dihydro-1H-isoindol-5-yl)
amino]pyrimidin-4-yl}imidazo[1,2-a]pyridin-2-yl)
phenyl]-2,6-difluorobenzamide;
N-[3-(3-{2-[(2-ethyl-2,3-dihydro-1H-isoindol-5-yl)
amino]pyrimidin-4-yl}imidazo[1,2-a]pyridin-2-yl)
phenyl]-2-phenylacetamide;
N-{3-[3-(2-{[2-(dimethylamino)-2,3-dihydro-1H-inden-
5-yl]amino}pyrimidin-4-yl)imidazo[1,2-a]pyridin-2-
yl]phenyl}-2-thien-2-ylacetamide;
N-{3-[3-(2-{[2-(dimethylamino)-2,3-dihydro-1H-inden-
5-yl]amino}pyrimidin-4-yl)imidazo[1,2-a]pyridin-2-
yl]phenyl}-2,6-difluorobenzamide;
N-{3-[3-(2-{[2-(dimethylamino)-2,3-dihydro-1H-inden-
5-yl]amino}pyrimidin-4-yl)imidazo[1,2-a]pyridin-2-
yl]phenyl}-2-phenylacetamide;
2,6-difluoro-N-methyl-N-[3-(3-{2-[(2-methyl-1,2,3,4-
tetrahydroisoquinolin-7-yl)amino]pyrimidin-4-
yl}imidazo[1,2-a]pyridin-2-yl)phenyl]benzamide;
2,6-difluoro-N-{3-[3-(2-{[4-(2-pyrrolidin-1-ylethyl)phe-
nyl]amino}pyrimidin-4-yl)imidazo[1,2-a]pyridin-2-yl]
phenyl}benzamide;
4-methyl-N-{3-[3-(2-{[4-(2-pyrrolidin-1-ylethyl)phenyl]
amino}pyrimidin-4-yl)imidazo[1,2-a]pyridin-2-yl]
phenyl}thiophene-2-carboxamide;
2-phenyl-N-{3-[3-(2-{[4-(2-pyrrolidin-1-ylethyl)phenyl]
amino}pyrimidin-4-yl)imidazo[1,2-a]pyridin-2-yl]
phenyl}acetamide;
N-{3-[3-(2-{[4-(2-pyrrolidin-1-ylethyl)phenyl]
amino}pyrimidin-4-yl)imidazo[1,2-a]pyridin-2-yl]
phenyl}-2-thien-2-ylacetamide;
5-methyl-N-[3-(3-{2-[(2-methyl-1,2,3,4-tetrahydroiso-
quinolin-7-yl)amino]pyrimidin-4-yl}imidazo[1,2-a]
pyridin-2-yl)phenyl]thiophene-2-carboxamide;
N-[3-(3-{2-[(2-methyl-1,2,3,4-tetrahydroisoquinolin-7-
yl)amino]pyrimidin-4-yl}imidazo[1,2-a]pyridin-2-yl)
phenyl]thiophene-2-carboxamide;
4-methyl-N-[3-(3-{2-[(2-methyl-1,2,3,4-tetrahydroiso-
quinolin-7-yl)amino]pyrimidin-4-yl}imidazo[1,2-a]
pyridin-2-yl)phenyl]thiophene-2-carboxamide;
2,5-dichloro-N-[3-(3-{2-[(2-methyl-1,2,3,4-tetrahy-
droisoquinolin-7-yl)amino]pyrimidin-4-yl}imidazo[1,
2-a]pyridin-2-yl)phenyl]thiophene-3-carboxamide;
5-chloro-N-[3-(3-{2-[(2-methyl-1,2,3,4-tetrahydroiso-
quinolin-7-yl)amino]pyrimidin-4-yl}imidazo[1,2-a]
pyridin-2-yl)phenyl]thiophene-2-carboxamide;
3-methyl-N-[3-(3-{2-[(2-methyl-1,2,3,4-tetrahydroiso-
quinolin-7-yl)amino]pyrimidin-4-yl}imidazo[1,2-a]
pyridin-2-yl)phenyl]thiophene-2-carboxamide;
N-[3-(3-{2-[(2-methyl-1,2,3,4-tetrahydroisoquinolin-7-
yl)amino]pyrimidin-4-yl}imidazo[1,2-a]pyridin-2-yl)
phenyl]-1-benzothiophene-2-carboxamide;
N-{3-[3-(2-{[2-(methoxyacetyl)-1,2,3,4-tetrahydroiso-
quinolin-7-yl]amino}pyrimidin-4-yl)imidazo[1,2-a]
pyridin-2-yl]phenyl}-2-thien-2-ylacetamide;
N-{3-[3-(2-{[4-(1-acetylpyrrolidin-3-yl)phenyl]
amino}pyrimidin-4-yl)imidazo[1,2-a]pyridin-2-yl]
phenyl}-2,6-difluorobenzamide;
N-{3-[3-(2-{[2-(3-methoxypropanoyl)-1,2,3,4-tetrahy-
droisoquinolin-7-yl]amino}pyrimidin-4-yl)imidazo[1,
2-a]pyridin-2-yl]phenyl}-2-thien-2-ylacetamide;
N-[3-(3-{2-[(2-methyl-1,2,3,4-tetrahydroisoquinolin-7-
yl)amino]pyrimidin-4-yl}imidazo[1,2-a]pyridin-2-yl)
phenyl]thiophene-3-carboxamide;
N-(2-fluorophenyl)-3-(3-{2-[(2-methyl-1,2,3,4-tetrahy-
droisoquinolin-7-yl)amino]pyrimidin-4-yl}imidazo[1,
2-a]pyridin-2-yl)benzamide;
3-(3-{2-[(2-methyl-1,2,3,4-tetrahydroisoquinolin-7-yl)
amino]pyrimidin-4-yl}imidazo[1,2-a]pyridin-2-yl)-N-
(thien-2-ylmethyl)benzamide;
2-chloro-N-{3-[3-(2-{[4-(4-ethylpiperazin-1-yl)phenyl]
amino}pyrimidin-4-yl)imidazo[1,2-a]pyridin-2-yl]
phenyl}benzamide;
2-chloro-N-{3-[3-(2-{[4-(4-ethylpiperazin-1-yl)phenyl]
amino}pyrimidin-4-yl)imidazo[1,2-a]pyridin-2-yl]
phenyl}-6-fluorobenzamide;
N-{3-[3-(2-{[4-(4-ethylpiperazin-1-yl)phenyl]
amino}pyrimidin-4-yl)imidazo[1,2-a]pyridin-2-yl]
phenyl}-2-(5-methylthien-2-yl)acetamide;
N-{3-[3-(2-{[4-(4-ethylpiperazin-1-yl)phenyl]
amino}pyrimidin-4-yl)imidazo[1,2-a]pyridin-2-yl]
phenyl}-2-(2-methyl-1,3-thiazol-5-yl)acetamide;
N-{3-[3-(2-{[4-(4-isopropylpiperazin-1-yl)phenyl]
amino}pyrimidin-4-yl)imidazo[1,2-a]pyridin-2-yl]
phenyl}-2-thien-2-ylacetamide;
N-{3-[3-(2-{[4-(4-isopropylpiperazin-1-yl)phenyl]
amino}pyrimidin-4-yl)imidazo[1,2-a]pyridin-2-yl]
phenyl}-2-phenylacetamide;
2,6-difluoro-N-{3-[3-(2-{[4-(4-isopropylpiperazin-1-yl)
phenyl]amino}pyrimidin-4-yl)imidazo[1,2-a]pyridin-
2-yl]phenyl}benzamide;
2-chloro-N-{3-[3-(2-{[4-(4-isopropylpiperazin-1-yl)phe-
nyl]amino}pyrimidin-4-yl)imidazo[1,2-a]pyridin-2-yl]
phenyl}benzamide;
N-[3-(3-{2-[(1-methyl-2,3-dihydro-1H-indol-5-yl)
amino]pyrimidin-4-yl}imidazo[1,2-a]pyridin-2-yl)
phenyl]-2-phenylacetamide;
2-phenyl-N-{3-[3-(2-{[3-(pyrrolidin-1-ylmethyl)phenyl]
amino}pyrimidin-4-yl)imidazo[1,2-a]pyridin-2-yl]
phenyl}acetamide;
N-{3-[3-(2-{[3-(pyrrolidin-1-ylmethyl)phenyl]
amino}pyrimidin-4-yl)imidazo[1,2-a]pyridin-2-yl]
phenyl}-2-thien-2-ylacetamide;
2,6-difluoro-N-{3-[3-(2-{[3-(1H-imidazol-1-ylmethyl)
phenyl]amino}pyrimidin-4-yl)imidazo[1,2-a]pyridin-
2-yl]phenyl}benzamide;
N-{3-[3-(2-{[3-(1H-imidazol-1-ylmethyl)phenyl]
amino}pyrimidin-4-yl)imidazo[1,2-a]pyridin-2-yl]
phenyl}-2-phenylacetamide;
N-{3-[3-(2-{[3-(1H-imidazol-1-ylmethyl)phenyl]
amino}pyrimidin-4-yl)imidazo[1,2-a]pyridin-2-yl]
phenyl}-2-thien-2-ylacetamide;
2,6-difluoro-N-{3-[3-(2-{[3-(1H-1,2,4-triazol-1-ylm-
ethyl)phenyl]amino}pyrimidin-4-yl)imidazo[1,2-a]py-
ridin-2-yl]phenyl}benzamide;
5-methyl-N-{3-[3-(2-{[3-(1H-1,2,4-triazol-1-ylmethyl)
phenyl]amino}pyrimidin-4-yl)imidazo[1,2-a]pyridin-
2-yl]phenyl}thiophene-2-carboxamide;
2-phenyl-N-{3-[3-(2-{[3-(1H-1,2,4-triazol-1-ylmethyl)
phenyl]amino}pyrimidin-4-yl)imidazo[1,2-a]pyridin-
2-yl]phenyl}acetamide;
2-thien-2-yl-N-{3-[3-(2-{[3-(1H-1,2,4-triazol-1-ylm-
ethyl)phenyl]amino}pyrimidin-4-yl)imidazo[1,2-a]py-
ridin-2-yl]phenyl}acetamide;
2,6-difluoro-N-[3-(3-{2-[(1-methyl-2,3-dihydro-1H-in-
dol-5-yl)amino]pyrimidin-4-yl}imidazo[1,2-a]pyridin-
2-yl)phenyl]benzamide;
5-methyl-N-[3-(3-{2-[(1-methyl-2,3-dihydro-1H-indol-
5-yl)amino]pyrimidin-4-yl}imidazo[1,2-a]pyridin-2-
yl)phenyl]thiophene-2-carboxamide;
N-[3-(3-{2-[(1-methyl-2,3-dihydro-1H-indol-5-yl)
amino]pyrimidin-4-yl}imidazo[1,2-a]pyridin-2-yl)
phenyl]-2-thien-2-ylacetamide;

2,6-difluoro-N-(3-{3-[2-({3-[(3-hydroxypyrrolidin-1-yl) methyl]phenyl}amino)pyrimidin-4-yl]imidazo[1,2-a] pyridin-2-yl}phenyl)benzamide;
N-(3-{3-[2-({3-[(3-hydroxypyrrolidin-1-yl)methyl] phenyl}amino)pyrimidin-4-yl]imidazo[1,2-a]pyridin-2-yl}phenyl)-2-phenylacetamide;
N-(3-{3-[2-({3-[(3-hydroxypyrrolidin-1-yl)methyl] phenyl}amino)pyrimidin-4-yl]imidazo[1,2-a]pyridin-2-yl}phenyl)-2-thien-2-ylacetamide;
N-[3-(3-{2-[(2-ethyl-2,3-dihydro-1H-isoindol-5-yl) amino]pyrimidin-4-yl}imidazo[1,2-a]pyridin-2-yl) phenyl]-2-thien-3-ylacetamide;
2-chloro-N-[3-(3-{2-[(2-ethyl-2,3-dihydro-1H-isoindol-5-yl)amino]pyrimidin-4-yl}imidazo[1,2-a]pyridin-2-yl)phenyl]benzamide;
N-{3-[3-(2-{[2-(dimethylamino)-2,3-dihydro-1H-inden-5-yl]amino}pyrimidin-4-yl)imidazo[1,2-a]pyridin-2-yl]phenyl}-2-thien-3-ylacetamide;
2-chloro-N-{3-[3-(2-{[2-(dimethylamino)-2,3-dihydro-1H-inden-5-yl]amino}pyrimidin-4-yl)imidazo[1,2-a] pyridin-2-yl]phenyl}benzamide;
2,6-difluoro-N-{3-[3-(2-{[2-(methoxyacetyl)-1,2,3,4-tetrahydroisoquinolin-6-yl]amino}pyrimidin-4-yl)imidazo[1,2-a]pyridin-2-yl]phenyl}benzamide;
N-{3-[3-(2-{[2-(methoxyacetyl)-1,2,3,4-tetrahydroisoquinolin-6-yl]amino}pyrimidin-4-yl)imidazo[1,2-a] pyridin-2-yl]phenyl}-2-thien-2-ylacetamide;
N-{3-[3-(2-{[2-(methoxyacetyl)-1,2,3,4-tetrahydroisoquinolin-6-yl]amino}pyrimidin-4-yl)imidazo[1,2-a] pyridin-2-yl]phenyl}-2-phenylacetamide;
N-{3-[3-(2-{[2-(methoxyacetyl)-1,2,3,4-tetrahydroisoquinolin-6-yl]amino}pyrimidin-4-yl)imidazo[1,2-a] pyridin-2-yl]phenyl}-N'-phenylurea;
N-{3-[3-(2-{[4-(4-ethylpiperazin-1-yl)phenyl] amino}pyrimidin-4-yl)imidazo[1,2-a]pyridin-2-yl] phenyl}-2-(1,3-thiazol-5-yl)acetamide;
N-[3-(3-{2-[(3-{[4-(dimethylamino)piperidin-1-yl] methyl}phenyl)amino]pyrimidin-4-yl}imidazo[1,2-a] pyridin-2-yl)phenyl]-N'-phenylurea;
N-{3-[3-(2-{[4-(2,7-diazaspiro[4.4]non-2-yl)phenyl] amino}pyrimidin-4-yl)imidazo[1,2-a]pyridin-2-yl] phenyl}-2-thien-2-ylacetamide;
N-{3-[3-(2-{[4-(7-acetyl-2,7-diazaspiro[4.4]non-2-yl) phenyl]amino}pyrimidin-4-yl)imidazo[1,2-a]pyridin-2-yl]phenyl}-2,6-difluorobenzamide;
tert-butyl 7-(4-{[4-(2-{3-[(2,6-difluorobenzoyl)amino] phenyl}imidazo[1,2-a]pyridin-3-yl)pyrimidin-2-yl] amino}phenyl)-2,7-diazaspiro[4.4]nonane-2-carboxylate;
tert-butyl 7-(4-{[4-(2-{3-[(thien-2-ylacetyl)amino] phenyl}imidazo[1,2-a]pyridin-3-yl)pyrimidin-2-yl] amino}phenyl)-2,7-diazaspiro[4.4]nonane-2-carboxylate;
N-(3-{3-[2-({3-[2-(dimethylamino)ethyl]phenyl}amino) pyrimidin-4-yl]imidazo[1,2-a]pyridin-2-yl}phenyl)-5-methylthiophene-2-carboxamide;
N-(2,6-difluorophenyl)-N'-(3-{3-[2-({3-[2-(dimethylamino)ethyl]phenyl}amino)pyrimidin-4-yl]imidazo[1,2-a]pyridin-2-yl}phenyl)urea;
N-{3-[3-(2-{[4-(2,7-diazaspiro[4.4]non-2-yl)phenyl] amino}pyrimidin-4-yl)imidazo[1,2-a]pyridin-2-yl] phenyl}-2,6-difluorobenzamide;
3-[3-(2-{[4-(4-ethylpiperazin-1-yl)phenyl] amino}pyrimidin-4-yl)imidazo[1,2-a]pyridin-2-yl]-N-(2-fluorophenyl)benzamide;
3-[3-(2-{[4-(4-ethylpiperazin-1-yl)phenyl] amino}pyrimidin-4-yl)imidazo[1,2-a]pyridin-2-yl]N-phenylbenzamide;
N-benzyl-3-[3-(2-{[4-(4-ethylpiperazin-1-yl)phenyl] amino)}pyrimidin-4-yl)imidazo[1,2-a]pyridin-2-yl] benzamide;
2,6-difluoro-N-{3-[3-(2-{[3-(2-pyrrolidin-1-ylethoxy) phenyl]amino}pyrimidin-4-yl)imidazo[1,2-a]pyridin-2-yl]phenyl}benzamide;
2,6-difluoro-N-{3-[3-(2-{[3-(tetrahydrofuran-2-yl-methoxy)phenyl]amino}pyrimidin-4-yl)imidazo[1,2-a] pyridin-2-yl]phenyl}benzamide;
2-chloro-N-{3-[3-(2-{[3-(tetrahydrofuran-2-ylmethoxy) phenyl]amino}pyrimidin-4-yl)imidazo[1,2-a]pyridin-2-yl]phenyl}benzamide;
N-{3-[3-(2-{[3-(tetrahydrofuran-2-ylmethoxy)phenyl] amino}pyrimidin-4-yl)imidazo[1,2-a]pyridin-2-yl] phenyl}thiophene-2-carboxamide;
N-{3-[3-(2-{[3-(tetrahydrofuran-2-ylmethoxy)phenyl] amino}pyrimidin-4-yl)imidazo[1,2-a]pyridin-2-yl] phenyl}-2-thien-2-ylacetamide;
N-{3-[3-(2-{[3-(tetrahydrofuran-2-ylmethoxy)phenyl] amino}pyrimidin-4-yl)imidazo[1,2-a]pyridin-2-yl] phenyl}-N'-thien-2-ylurea;
2,6-difluoro-N-{3-[3-(2-{[3-(tetrahydrofuran-3-yloxy) phenyl]amino}pyrimidin-4-yl)imidazo[1,2-a]pyridin-2-yl]phenyl}benzamide;
2-chloro-N-{3-[3-(2-{[3-(tetrahydrofuran-3-yloxy)phenyl]amino}pyrimidin-4-yl)imidazo[1,2-a]pyridin-2-yl] phenyl}benzamide;
N-{3-[3-(2-{[3-(tetrahydrofuran-3-yloxy)phenyl] amino}pyrimidin-4-yl)imidazo[1,2-a]pyridin-2-yl] phenyl}-2-thien-2-ylacetamide;
N-[3-(3-{2-[(2-methyl-1,2,3,4-tetrahydro isoquinolin-7-yl)amino]pyrimidin-4-yl}imidazo[1,2-a]pyridin-2-yl) phenyl]-1,3-thiazole-2-carboxamide;
N-[3-(3-{2-[(2-methyl-1,2,3,4-tetrahydroisoquinolin-7-yl)amino]pyrimidin-4-yl}imidazo[1,2-a]pyridin-2-yl) phenyl]-1,3-thiazole-5-carboxamide;
4-bromo-N-[3-(3-{2-[(2-methyl-1,2,3,4-tetrahydroisoquinolin-7-yl)amino]pyrimidin-4-yl}imidazo[1,2-a] pyridin-2-yl)phenyl]thiophene-2-carboxamide;
4-bromo-N-[3-(3-{2-[(2-methyl-1,2,3,4-tetrahydroisoquinolin-7-yl)amino]pyrimidin-4-yl}imidazo[1,2-a] pyridin-2-yl)phenyl]thiophene-3-carboxamide;
N-{3-[3-(2-{[3-(tetrahydrofuran-3-yloxy)phenyl] amino}pyrimidin-4-yl)imidazo[1,2-a]pyridin-2-yl] phenyl}-N'-thien-2-ylurea;
N-(3-{3-[2-({3-[(dimethylamino)sulfonyl]-4-methoxyphenyl}amino)pyrimidin-4-yl]imidazo[1,2-a] pyridin-2-yl}phenyl)-2,6-difluorobenzamide;
N-(3-{3-[2-({3-[(dimethylamino)sulfonyl]-4-methoxyphenyl}amino)pyrimidin-4-yl]imidazo[1,2-a] pyridin-2-yl}phenyl)-2-thien-2-ylacetamide;
N-(3-{3-[2-({4-[4-(dimethylamino)piperidin-1-yl] phenyl}amino)pyrimidin-4-yl]imidazo[1,2-a]pyridin-2-yl}phenyl)-2-thien-2-ylacetamide;
N-(3-{3-[2-({4-[4-(dimethylamino)piperidin-1-yl] phenyl}amino)pyrimidin-4-yl]imidazo[1,2-a]pyridin-2-yl}phenyl)-2,6-difluorobenzamide;
N-(3-{3-[2-({4-[4-(dimethylamino)piperidin-1-yl] phenyl}amino)pyrimidin-4-yl]imidazo[1,2-a]pyridin-2-yl}phenyl)-2-phenylacetamide;
2-chloro-N-(3-{3-[2-({4-[4-(dimethylamino)piperidin-1-yl]phenyl}amino)pyrimidin-4-yl]imidazo[1,2-a]pyridin-2-yl}phenyl)benzamide;

N-(3-{3-[2-({4-[4-(dimethylamino)piperidin-1-yl]
  phenyl}amino)pyrimidin-4-yl]imidazo[1,2-a]pyridin-
  2-yl}phenyl)thiophene-2-carboxamide;
N-(3-{3-[2-({4-[4-(dimethylamino)piperidin-1-yl]
  phenyl}amino)pyrimidin-4-yl]imidazo[1,2-a]pyridin-
  2-yl}phenyl)-4-methylthiophene-2-carboxamide;
1-methyl-N-[3-(3-{2-[(2-methyl-1,2,3,4-tetrahydroiso-
  quinolin-7-yl)amino]pyrimidin-4-yl}imidazo[1,2-a]py-
  ridin-2-yl)phenyl]-1H-pyrazole-3-carboxamide;
2-chloro-N-(3-{3-[2-({4-[2-(dimethylamino)ethyl]
  phenyl}amino)pyrimidin-4-yl]imidazo[1,2-a]pyridin-
  2-yl}phenyl)-3-fluorobenzamide;
N-(3-{3-[2-({4-[2-(dimethylamino)ethyl]phenyl}amino)
  pyrimidin-4-yl]imidazo[1,2-a]pyridin-2-yl}phenyl)-2-
  fluorobenzamide;
2-chloro-N-(3-{3-[2-({4-[2-(dimethylamino)ethyl]
  phenyl}amino)pyrimidin-4-yl]imidazo[1,2-a]pyridin-
  2-yl}phenyl)benzamide;
N-(3-{3-[2-({4-[2-(dimethylamino)ethyl]phenyl}amino)
  pyrimidin-4-yl]imidazo[1,2-a]pyridin-2-yl}phenyl)-2,
  3-difluorobenzamide;
N-(3-{3-[2-({4-[2-(dimethylamino)ethyl]phenyl}amino)
  pyrimidin-4-yl]imidazo[1,2-a]pyridin-2-yl}phenyl)-2,
  5-difluorobenzamide;
N-(3-{3-[2-({4-[2-(dimethylamino)ethyl]phenyl}amino)
  pyrimidin-4-yl]imidazo[1,2-a]pyridin-2-yl}phenyl)-3,
  5-difluorobenzamide;
N-(3-{3-[2-({4-[2-(dimethylamino)ethyl]phenyl}amino)
  pyrimidin-4-yl]imidazo[1,2-a]pyridin-2-yl}phenyl)-
  N'-phenylurea;
N-(3-{3-[2-({4-[1-(methoxyacetyl)piperidin-4-yl]
  phenyl}amino)pyrimidin-4-yl]imidazo[1,2-a]pyridin-
  2-yl}phenyl)-2-thien-2-ylacetamide;
2,6-difluoro-N-(3-{3-[2-({4-[1-(methoxyacetyl)piperi-
  din-4-yl]phenyl}amino)pyrimidin-4-yl]imidazo[1,2-a]
  pyridin-2-yl}phenyl)benzamide;
N-(3-{3-[2-({4-[1-(methoxyacetyl)piperidin-4-yl]
  phenyl}amino)pyrimidin-4-yl]imidazo[1,2-a]pyridin-
  2-yl}phenyl)-2-thien-2-ylacetamide;
2,6-difluoro-N-(3-{3-[2-({3-[1-(methoxyacetyl)piperi-
  din-4-yl]phenyl}amino)pyrimidin-4-yl]imidazo[1,2-a]
  pyridin-2-yl}phenyl)benzamide;
N-{3-[3-(2-{[4-(4-ethylpiperazin-1-yl)-3-fluorophenyl]
  amino}pyrimidin-4-yl)imidazo[1,2-a]pyridin-2-yl]
  phenyl}-2-thien-2-ylacetamide;
2-chloro-N-{3-[3-(2-{[4-(4-ethylpiperazin-1-yl)-3-fluo-
  rophenyl]amino}pyrimidin-4-yl)imidazo[1,2-a]pyri-
  din-2-yl]phenyl}benzamide;
N-(3-{3-[2-({4-[1-(2-hydroxy-2-methylpropyl)piperidin-
  4-yl]phenyl}amino)pyrimidin-4-yl]imidazo[1,2-a]py-
  ridin-2-yl}phenyl)-2-thien-2-ylacetamide;
N-(3-{3-[2-({4-[1-(2-hydroxy-2-methylpropyl)piperidin-
  4-yl]phenyl}amino)pyrimidin-4-yl]imidazo[1,2-a]py-
  ridin-2-yl}phenyl)-2-thien-3-ylacetamide;
2,6-difluoro-N-(3-{3-[2-({4-[1-(2-hydroxy-2-methylpro-
  pyl)piperidin-4-yl]phenyl}amino)pyrimidin-4-yl]imi-
  dazo[1,2-a]pyridin-2-yl}phenyl)benzamide;
2-chloro-N-(3-{3-[2-({4-[1-(2-hydroxy-2-methylpropyl)
  piperidin-4-yl]phenyl}amino)pyrimidin-4-yl]imidazo
  [1,2-a]pyridin-2-yl}phenyl)benzamide;
N-(3-{3-[2-({3-[(N,N-dimethylglycyl)amino]
  phenyl}amino)pyrimidin-4-yl]imidazo[1,2-a]pyridin-
  2-yl}phenyl)-2,6-difluorobenzamide;
2-chloro-N-(3-{3-[2-({3-[(N,N-dimethylglycyl)amino]
  phenyl}amino)pyrimidin-4-yl]imidazo[1,2-a]pyridin-
  2-yl}phenyl)benzamide;
N-(3-{3-[2-({3-[(N,N-dimethylglycyl)amino]
  phenyl}amino)pyrimidin-4-yl]imidazo[1,2-a]pyridin-
  2-yl}phenyl)thiophene-2-carboxamide;
$N^2,N^2$-dimethyl-N'-(3-{[4-(2-{3-[(thien-2-ylacetyl)
  amino]phenyl}imidazo[1,2-a]pyridin-3-yl)pyrimidin-
  2-yl]amino}phenyl)glycinamide;
2,6-difluoro-N-(3-{3-[2-({3-[(methoxyacetyl)amino]
  phenyl}amino)pyrimidin-4-yl]imidazo[1,2-a]pyridin-
  2-yl}phenyl)benzamide;
2-chloro-N-(3-{3-[2-({3-[(methoxyacetyl)amino]
  phenyl}amino)pyrimidin-4-yl]imidazo[1,2-a]pyridin-
  2-yl}phenyl)benzamide;
N-(3-{3-[2-({3-[(2-methoxyacetyl)amino]phenyl}amino)
  pyrimidin-4-yl]imidazo[1,2-a]pyridin-2-yl}phenyl)
  thiophene-2-carboxamide;
2-methoxy-N-(3-{[4-(2-{3-[(thien-2-ylacetyl)amino]
  phenyl}imidazo[1,2-a]pyridin-3-yl)pyrimidin-2-yl]
  amino}phenyl)acetamide;
2-methoxy-N-[3-({4-[2-(3-{[(thien-2-ylamino)carbonyl]
  amino}phenyl)imidazo[1,2-a]pyridin-3-yl]pyrimidin-
  2-yl}amino)phenyl]acetamide;
N-(3-{3-[2-({4-[3-(dimethylamino)pyrrolidin-1-yl]
  phenyl}amino)pyrimidin-4-yl]imidazo[1,2-a]pyridin-
  2-yl}phenyl)-2,6-difluorobenzamide;
2-chloro-N-(3-{3-[2-({4-[3-(dimethylamino)pyrrolidin-
  1-yl]phenyl}amino)pyrimidin-4-yl]imidazo[1,2-a]py-
  ridin-2-yl}phenyl)benzamide;
N-(3-{3-[2-({4-[3-(dimethylamino)pyrrolidin-1-yl]
  phenyl}amino)pyrimidin-4-yl]imidazo[1,2-a]pyridin-
  2-yl}phenyl)thiophene-2-carboxamide;
N-(3-{3-[2-({4-[3-(dimethylamino)pyrrolidin-1-yl]
  phenyl}amino)pyrimidin-4-yl]imidazo[1,2-a]pyridin-
  2-yl}phenyl)-2-thien-2-ylacetamide;
N-(3-{3-[2-({4-[3-(dimethylamino)pyrrolidin-1-yl]
  phenyl}amino)pyrimidin-4-yl]imidazo[1,2-a]pyridin-
  2-yl}phenyl)-N'-thien-2-ylurea;
2,6-difluoro-N-(3-{3-[2-({3-[2-(methylamino)-2-oxoet-
  hyl]phenyl}amino)pyrimidin-4-yl]imidazo[1,2-a]pyri-
  din-2-yl}phenyl)benzamide;
N-(3-{3-[2-({3-[2-(methylamino)-2-oxoethyl]
  phenyl}amino)pyrimidin-4-yl]imidazo[1,2-a]pyridin-
  2-yl}phenyl)-2-phenylacetamide;
N-(3-{3-[2-({3-[2-(methylamino)-2-oxoethyl]
  phenyl}amino)pyrimidin-4-yl]imidazo[1,2-a]pyridin-
  2-yl}phenyl)-2-thien-2-ylacetamide;
N-(3-{3-[2-({3-[2-(dimethylamino)-2-oxoethyl]
  phenyl}amino)pyrimidin-4-yl]imidazo[1,2-a]pyridin-
  2-yl}phenyl)-2,6-difluorobenzamide;
N-(3-{3-[2-({3-[2-(dimethylamino)-2-oxoethyl]
  phenyl}amino)pyrimidin-4-yl]imidazo[1,2-a]pyridin-
  2-yl}phenyl)-2-phenylacetamide;
N-(3-{3-[2-({3-[2-(dimethylamino)-2-oxoethyl]
  phenyl}amino)pyrimidin-4-yl]imidazo[1,2-a]pyridin-
  2-yl}phenyl)-2-thien-2-ylacetamide;
N-{3-[3-(2-{[2-(dimethylamino)-2,3-dihydro-1H-inden-
  5-yl]amino}pyrimidin-4-yl)imidazo[1,2-a]pyridin-2-
  yl]phenyl}thiophene-2-carboxamide;
N-{3-[3-(2-{[2-(dimethylamino)-2,3-dihydro-1H-inden-
  5-yl]amino}pyrimidin-4-yl)imidazo[1,2-a]pyridin-2-
  yl]phenyl}-4-methylthiophene-2-carboxamide;
N-{3-[3-(2-{[2-(dimethylamino)-2,3-dihydro-1H-inden-
  5-yl]amino}pyrimidin-4-yl)imidazo[1,2-a]pyridin-2-
  yl]phenyl}-5-methylthiophene-2-carboxamide;
2-chloro-N-(3-{3-[2-({4-[2-(dimethylamino)ethyl]
  phenyl}amino)pyrimidin-4-yl]imidazo[1,2-a]pyridin-
  2-yl}phenyl)-5-fluorobenzamide;

2,6-difluoro-N-(3-{3-[2-({4-[2-(methylamino)ethyl]phenyl}amino)pyrimidin-4-yl]imidazo[1,2-a]pyridin-2-yl}phenyl)benzamide;

2-chloro-N-(3-{3-[2-({4-[2-(methylamino)ethyl]phenyl}amino)pyrimidin-4-yl]imidazo[1,2-a]pyridin-2-yl}phenyl)benzamide;

N-(3-{3-[2-({4-[2-(methylamino)ethyl]phenyl}amino)pyrimidin-4-yl]imidazo[1,2-a]pyridin-2-yl}phenyl)-2-phenylacetamide;

N-(3-{3-[2-({4-[2-(methylamino)ethyl]phenyl}amino)pyrimidin-4-yl]imidazo[1,2-a]pyridin-2-yl}phenyl)-2-thien-2-ylacetamide;

N-(3-{3-[2-({-4-[2-(methylamino)ethyl]phenyl}amino)pyrimidin-4-yl]imidazo[1,2-a]pyridin-2-yl}phenyl)-N'-phenylurea;

N-(3-{3-[2-({4-[4-(dimethylamino)piperidin-1-yl]phenyl}amino)pyrimidin-4-yl]imidazo[1,2-a]pyridin-2-yl}phenyl)-2-methylbenzamide;

N-(3-{3-[2-({4-[4-(dimethylamino)piperidin-1-yl]phenyl}amino)pyrimidin-4-yl]imidazo[1,2-a]pyridin-2-yl}phenyl)-2-thien-3-ylacetamide;

N-(3-{3-[2-({4-[2-(dimethylamino)ethyl]phenyl}amino)-5-fluoropyrimidin-4-yl]imidazo[1,2-a]pyridin-2-yl}phenyl)-2,6-difluorobenzamide;

N-[3-(3-{2-[(4-piperidin-4-ylphenyl)amino]pyrimidin-4-yl}imidazo[1,2-a]pyridin-2-yl)phenyl]-2-thien-3-ylacetamide;

2-chloro-N-[3-(3-{2-[(4-piperidin-4-ylphenyl)amino]pyrimidin-4-yl}imidazo[1,2-a]pyridin-2-yl)phenyl]benzamide;

N-[3-(3-{2-[(3-piperidin-4-ylphenyl)amino]pyrimidin-4-yl}imidazo[1,2-a]pyridin-2-yl)phenyl]-2-thien-3-ylacetamide;

N-[3-(3-{2-[(3-piperidin-4-ylphenyl)amino]pyrimidin-4-yl}imidazo[1,2-a]pyridin-2-yl)phenyl]-2-thien-2-ylacetamide;

2-chloro-N-[3-(3-{2-[(3-piperidin-4-ylphenyl)amino]pyrimidin-4-yl}imidazo[1,2-a]pyridin-2-yl)phenyl]benzamide;

N-[3-(3-{2-[(3-piperidin-4-ylphenyl)amino]pyrimidin-4-yl}imidazo[1,2-a]pyridin-2-yl)phenyl]thiophene-2-carboxamide;

2-methyl-N-[3-(3-{2-[(3-piperidin-4-ylphenyl)amino]pyrimidin-4-yl}imidazo[1,2-a]pyridin-2-yl)phenyl]benzamide;

N-[3-(3-{2-[(3-piperidin-4-ylphenyl)amino]pyrimidin-4-yl}imidazo[1,2-a]pyridin-2-yl)phenyl]indoline-1-carboxamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2,6-difluorobenzamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}-2-thien-2-ylacetamide;

N-{3-[3-(2-{[4-(7-ethyl-2,7-diazaspiro[4.4]non-2-yl)phenyl]amino}pyrimidin-4-yl)imidazo[1,2-a]pyridin-2-yl]phenyl}thiophene-2-carboxamide;

N-[3-(3-{2-[(4-pyrrolidin-3-ylphenyl)amino]pyrimidin-4-yl}imidazo[1,2-a]pyridin-2-yl)phenyl]-2-thien-3-ylacetamide;

N-[3-(3-{2-[(4-pyrrolidin-3-ylphenyl)amino]pyrimidin-4-yl}imidazo[1,2-a]pyridin-2-yl)phenyl]-2-thien-2-ylacetamide;

2-chloro-N-[3-(3-{2-[(4-pyrrolidin-3-ylphenyl)amino]pyrimidin-4-yl}imidazo[1,2-a]pyridin-2-yl)phenyl]benzamide;

2,3-difluoro-N-[3-(3-{2-[(4-pyrrolidin-3-ylphenyl)amino]pyrimidin-4-yl}imidazo[1,2-a]pyridin-2-yl)phenyl]benzamide;

2,5-difluoro-N-[3-(3-{2-[(4-pyrrolidin-3-ylphenyl)amino]pyrimidin-4-yl}imidazo[1,2-a]pyridin-2-yl)phenyl]benzamide;

2-methyl-N-[3-(3-{2-[(4-pyrrolidin-3-ylphenyl)amino]pyrimidin-4-yl}imidazo[1,2-a]pyridin-2-yl)phenyl]benzamide;

2,6-dimethyl-N-[3-(3-{2-[(4-pyrrolidin-3-ylphenyl)amino]pyrimidin-4-yl}imidazo[1,2-a]pyridin-2-yl)phenyl]benzamide;

N-[3-(3-{2-[(4-pyrrolidin-3-ylphenyl)amino]pyrimidin-4-yl}imidazo[1,2-a]pyridin-2-yl)phenyl]thiophene-2-carboxamide;

N-(3-{3-[2-({4-[4-(dimethylamino)piperidin-1-yl]phenyl}amino)pyrimidin-4-yl]imidazo[1,2-a]pyridin-2-yl}phenyl)-2,3-difluorobenzamide;

N-(3-{3-[2-({4-[4-(dimethylamino)piperidin-1-yl]phenyl}amino)pyrimidin-4-yl]imidazo[1,2-a]pyridin-2-yl}phenyl)-2,5-difluorobenzamide;

2-chloro-N-(3-{3-[2-({4-[4-(dimethylamino)piperidin-1-yl]phenyl}amino)pyrimidin-4-yl]imidazo[1,2-a]pyridin-2-yl}phenyl)-5-fluorobenzamide;

N-(3-{3-[2-({4-[4-(dimethylamino)piperidin-1-yl]phenyl}amino)pyrimidin-4-yl]imidazo[1,2-a]pyridin-2-yl}phenyl)indoline-1-carboxamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-2,3-difluorobenzamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-2,5-difluorobenzamide;

2-chloro-N-{3-[3-(2-{[2-(dimethylamino)-2,3-dihydro-1H-inden-5-yl]amino}pyrimidin-4-yl)imidazo[1,2-a]pyridin-2-yl]phenyl}-5-fluorobenzamide;

N-{3-[3-(2-{[2-(dimethylamino)-2,3-dihydro-1H-inden-5-yl]amino}pyrimidin-4-yl)imidazo[1,2-a]pyridin-2-yl]phenyl}indoline-1-carboxamide;

N-(3-{3-[2-({3-[(dimethylamino)methyl]-4-methoxyphenyl}amino)pyrimidin-4-yl]imidazo[1,2-a]pyridin-2-yl}phenyl)-2,6-difluorobenzamide;

N-(3-{3-[2-({3-[(dimethylamino)methyl]-4-methoxyphenyl}amino)pyrimidin-4-yl]imidazo[1,2-a]pyridin-2-yl}phenyl)-2,3-difluorobenzamide;

N-(3-{3-[2-({3-[(dimethylamino)methyl]-4-methoxyphenyl}amino)pyrimidin-4-yl]imidazo[1,2-a]pyridin-2-yl}phenyl)-2-thien-2-ylacetamide;

N-(3-{3-[2-({3-[(dimethylamino)methyl]-4-methoxyphenyl}amino)pyrimidin-4-yl]imidazo[1,2-a]pyridin-2-yl}phenyl)-N'-thien-2-ylurea;

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]thiophene-2-carboxamide;

2,6-difluoro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide;

2-chloro-N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]benzamide;

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]-N'-thien-2-ylurea;

N-[3-(3-{2-[(3-{2-[(3S)-3-fluoropyrrolidin-1-yl]ethyl}phenyl)amino]pyrimidin-4-yl}imidazo[1,2-a]pyridin-2-yl)phenyl]-N'-thien-3-ylurea;

N-[3-(3-{2-[(4-pyrrolidin-3-ylphenyl)amino]pyrimidin-4-yl}imidazo[1,2-a]pyridin-2-yl)phenyl]indoline-1-carboxamide;

N-ethyl-N-phenyl-N'-[3-(3-{2-[(4-pyrrolidin-3-ylphenyl)amino]pyrimidin-4-yl}imidazo[1,2-a]pyridin-2-yl)phenyl]urea;

N-[3-(3-{2-[(4-pyrrolidin-3-ylphenyl)amino]pyrimidin-4-yl}imidazo[1,2-a]pyridin-2-yl)phenyl]-1-benzothiophene-7-carboxamide;

N-(3-{3-[2-({4-[2-(dimethylamino)ethyl]phenyl}amino)-5-fluoropyrimidin-4-yl]imidazo[1,2-a]pyridin-2-yl}phenyl)-2-thien-2-ylacetamide;

2,6-difluoro-N-{3-[3-(2-{[4-(4-hydroxypiperidin-1-yl)phenyl]amino}pyrimidin-4-yl)imidazo[1,2-a]pyridin-2-yl]phenyl}benzamide;

2-chloro-N-{3-[3-(2-{[4-(4-hydroxypiperidin-1-yl)phenyl]amino}pyrimidin-4-yl)imidazo[1,2-a]pyridin-2-yl]phenyl}benzamide;

N-{3-[3-(2-{[4-(4-hydroxypiperidin-1-yl)phenyl]amino}pyrimidin-4-yl)imidazo[1,2-a]pyridin-2-yl]phenyl}thiophene-2-carboxamide;

N-{3-[3-(2-{[4-(4-hydroxypiperidin-1-yl)phenyl]amino}pyrimidin-4-yl)imidazo[1,2-a]pyridin-2-yl]phenyl}-2-thien-2-ylacetamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,6-difluorobenzamide;

2-chloro-N-[3-(3-{2-[(4-{2-[(N,N-dimethylglycyl)amino]ethyl}phenyl)amino]pyrimidin-4-yl}imidazo[1,2-a]pyridin-2-yl)phenyl]benzamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]thiophene-2-carboxamide;

$N^2,N^2$-dimethyl-$N^1$-[2-(4-{[4-(2-{3-[(thien-2-ylacetyl)amino]phenyl}imidazo[1,2-a]pyridin-3-yl)pyrimidin-2-yl]amino}phenyl)ethyl]glycinamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,3-difluorobenzamide;

N-[3-(3-{2-[(4-{2-[(N,N-dimethylglycyl)amino]ethyl}phenyl)amino]pyrimidin-4-yl}imidazo[1,2-a]pyridin-2-yl)phenyl]-2,5-difluorobenzamide;

$N^2,N^2$-dimethyl-$N^1$-[2-(4-{[4-(2-{3-[(phenylacetyl)amino]phenyl}imidazo[1,2-a]pyridin-3-yl)pyrimidin-2-yl]amino}phenyl)ethyl]glycinamide;

2,6-difluoro-N-[3-(3-{2-[(4-{2-[(methoxyacetyl)amino]ethyl}phenyl)amino]pyrimidin-4-yl}imidazo[1,2-a]pyridin-2-yl)phenyl]benzamide;

2-methoxy-N-[2-(4-{[4-(2-{3-[(thien-2-ylacetyl)amino]phenyl}imidazo[1,2-a]pyridin-3-yl)pyrimidin-2-yl]amino}phenyl)ethyl]acetamide;

N-(3-{3-[2-({4-[2-(4-aminopiperidin-1-yl)ethyl]phenyl}amino)pyrimidin-4-yl]imidazo[1,2-a]pyridin-2-yl}phenyl)thiophene-2-carboxamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2,6-difluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-chlorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-fluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2,3-difluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2,5-difluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-chloro-5-fluorobenzamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-phenylacetamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-thien-2-ylacetamide;

N-(3-{3-[2-({4-[2-(4-aminopiperidin-1-yl)ethyl]phenyl}amino)pyrimidin-4-yl]imidazo[1,2-a]pyridin-2-yl}phenyl)-N'-phenylurea;

N-(3-{3-[2-({4-[2-(4-aminopiperidin-1-yl)ethyl]phenyl}amino)pyrimidin-4-yl]imidazo[1,2-a]pyridin-2-yl}phenyl)indoline-1-carboxamide;

N-(3-{3-[2-({4-[2-(4-aminopiperidin-1-yl)ethyl]phenyl}amino)pyrimidin-4-yl]imidazo[1,2-a]pyridin-2-yl}phenyl)-2-chloro-3-fluorobenzamide;

N-[2-(4-{[4-(2-{3-[(2-thien-2-ylacetyl)amino]phenyl}imidazo[1,2-a]pyridin-3-yl)pyrimidin-2-yl]amino}phenyl)ethyl]cyclopropanecarboxamide;

N-[3-(3-{2-[(4-{2-[(cyclopropylcarbonyl)amino]ethyl}phenyl)amino]pyrimidin-4-yl}imidazo[1,2-a]pyridin-2-yl)phenyl]-2,6-difluorobenzamide;

2-chloro-N-[3-(3-{2-[(4-{2-[(cyclopropylcarbonyl)amino]ethyl}phenyl)amino]pyrimidin-4-yl}imidazo[1,2-a]pyridin-2-yl)phenyl]benzamide;

N-[3-(3-{2-[(4-{2-[(cyclopropylcarbonyl)amino]ethyl}phenyl)amino]pyrimidin-4-yl}imidazo[1,2-a]pyridin-2-yl)phenyl]thiophene-2-carboxamide;

2,6-difluoro-N-[3-(3-{2-[(4-{2-[(methylsulfonyl)amino]ethyl}phenyl)amino]pyrimidin-4-yl}imidazo[1,2-a]pyridin-2-yl)phenyl]benzamide;

2-chloro-N-[3-(3-{2-[(4-{2-[(methylsulfonyl)amino]ethyl}phenyl)amino]pyrimidin-4-yl}imidazo[1,2-a]pyridin-2-yl)phenyl]benzamide;

N-[3-(3-{2-[(4{2-[(methylsulfonyl)amino]ethyl}phenyl)amino]pyrimidin-4-yl}imidazo[1,2-a]pyridin-2-yl)phenyl]thiophene-2-carboxamide;

N-[3-(3-{2-[(4-{2-[(methylsulfonyl)amino]ethyl}phenyl)amino]pyrimidin-4-yl}imidazo[1,2-a]pyridin-2-yl)phenyl]-2-thien-2-ylacetamide;

2-chloro-N-[3-(3-{2-[(4-{2-[(methoxyacetyl)amino]ethyl}phenyl)amino]pyrimidin-4-yl}imidazo[1,2-a]pyridin-2-yl)phenyl]benzamide;

N-[3-(3-{2-[(4-{2-[(2-methoxyacetyl)amino]ethyl}phenyl)amino]pyrimidin-4-yl}imidazo[1,2-a]pyridin-2-yl)phenyl]thiophene-2-carboxamide;

N-(2,6-difluorophenyl)-3-[3-(2-{[4-(4-ethylpiperazin-1-yl)phenyl]amino}pyrimidin-4-yl)imidazo[1,2-a]pyridin-2-yl]benzamide;

2,6-difluoro-N-[3-(3-{2-[(4-{2-[(2-hydroxyethyl)(methyl)amino]ethyl}phenyl)amino]pyrimidin-4-yl}imidazo[1,2-a]pyridin-2-yl)phenyl]benzamide;

2-chloro-N-[3-(3-{2-[(4-{2-[(2-hydroxyethyl)(methyl)amino]ethyl}phenyl)amino]pyrimidin-4-yl}imidazo[1,2-a]pyridin-2-yl)phenyl]benzamide;

3-{3-[2-({4-[2-(dimethylamino)ethyl]phenyl}amino)pyrimidin-4-yl]imidazo[1,2-a]pyridin-2-yl}-N-phenyl-benzamide;

3-{3-[2-({4-[2-(dimethylamino)ethyl]phenyl}amino)pyrimidin-4-yl]imidazo[1,2-a]pyridin-2-yl}-N-(2-fluorophenyl)benzamide;

3-{3-[2-({4-[2-(dimethylamino)ethyl]phenyl}amino)pyrimidin-4-yl]imidazo[1,2-a]pyridin-2-yl}-N-(3-fluorophenyl)benzamide;

3-{3-[2-({4-[2-(dimethylamino)ethyl]phenyl}amino)pyrimidin-4-yl]imidazo[1,2-a]pyridin-2-yl}-N-(4-fluorophenyl)benzamide;

N-cyclopentyl-3-{3-[2-({4-[2-(dimethylamino)ethyl]phenyl}amino)pyrimidin-4-yl]imidazo[1,2-a]pyridin-2-yl}benzamide;

N-cyclohexyl-3-{3-[2-({4-[2-(dimethylamino)ethyl]phenyl}amino)pyrimidin-4-yl]imidazo[1,2-a]pyridin-2-yl}benzamide;

N-{4-[2-(dimethylamino)ethyl]phenyl}-4-{2-[3-(piperidin-1-ylcarbonyl)phenyl]imidazo[1,2-a]pyridin-3-yl}pyrimidin-2-amine;

3-{3-[2-({4-[2-(dimethylamino)ethyl]phenyl}amino)pyrimidin-4-yl]imidazo[1,2-a]pyridin-2-yl}-N-(2-methylphenyl)benzamide;

N-(2-chlorophenyl)-3-{3-[2-({4-[2-(dimethylamino)ethyl]phenyl}amino)pyrimidin-4-yl]imidazo[1,2-a]pyridin-2-yl}benzamide;

3-{3-[2-({4-[2-(dimethylamino)ethyl]phenyl}amino)pyrimidin-4-yl]imidazo[1,2-a]pyridin-2-yl}-N-(2-methoxyphenyl)benzamide;

N-{4-[2-(dimethylamino)ethyl]phenyl}-4-{2-[3-(morpholin-4-ylcarbonyl)phenyl]imidazo[1,2-a]pyridin-3-yl}pyrimidin-2-amine;

N-[3-(3-{2-[(3-pyrrolidin-3-ylphenyl)amino]pyrimidin-4-yl}imidazo[1,2-a]pyridin-2-yl)phenyl]indoline-1-carboxamide;

N-[3-(3-{2-[(3-pyrrolidin-3-ylphenyl)amino]pyrimidin-4-yl}imidazo[1,2-a]pyridin-2-yl)phenyl]-3,4-dihydroquinoline-1(2H)-carboxamide;

N-[3-(3-{2-[(3-pyrrolidin-3-ylphenyl)amino]pyrimidin-4-yl}imidazo[1,2-a]pyridin-2-yl)phenyl]-3,4-dihydroisoquinoline-2(1H)-carboxamide;

4-{2-[3-(2,3-dihydro-1H-indol-1-ylcarbonyl)phenyl]imidazo[1,2-a]pyridin-3-yl}-N-(4-[2-(dimethylamino)ethyl]phenyl}pyrimidin-2-amine;

4-{2-[3-(1,3-dihydro-2H-isoindol-2-ylcarbonyl)phenyl]imidazo[1,2-a]pyridin-3-yl}-N-{4-[2-(dimethylamino)ethyl]phenyl}pyrimidin-2-amine;

N-{4-[2-(dimethylamino)ethyl]phenyl}-4-{2-[3-(pyrrolidin-1-ylcarbonyl)phenyl]imidazo[1,2-a]pyridin-3-yl}pyrimidin-2-amine;

N-{3-[3-(2-{[4-(1-acetylazetidin-3-yl)phenyl]amino}pyrimidin-4-yl)imidazo[1,2-a]pyridin-2-yl]phenyl}-2-chlorobenzamide;

N-{3-[3-(2-{[4-(1-acetylazetidin-3-yl)phenyl]amino}pyrimidin-4-yl)imidazo[1,2-a]pyridin-2-yl]phenyl}-2-thien-3-ylacetamide;

N-cyclohexyl-N'-(3-{3-[2-({3-[2-(dimethylamino)ethyl]phenyl}amino)pyrimidin-4-yl]imidazo[1,2-a]pyridin-2-yl}phenyl)urea;

N-(sec-butyl)-N'-(3-{3-[2-({3-[2-(dimethylamino)ethyl]phenyl}amino)pyrimidin-4-yl]imidazo[1,2-a]pyridin-2-yl}phenyl)urea;

N-(tert-butyl)-N'-(3-{3-[2-({3-[2-(dimethylamino)ethyl]phenyl}amino)pyrimidin-4-yl]imidazo[1,2-a]pyridin-2-yl}phenyl)urea;

N-(3-{3-[2-({3-[2-(dimethylamino)ethyl]phenyl}amino)pyrimidin-4-yl]imidazo[1,2-a]pyridin-2-yl}phenyl)-N'-isopropylurea;

N-cyclopentyl-N'-(3-{3-[2-({3-[2-(dimethylamino)ethyl]phenyl}amino)pyrimidin-4-yl]imidazo[1,2-a]pyridin-2-yl}phenyl)urea;

N-(3-{3-[2-({3-[2-(dimethylamino)ethyl]phenyl}amino)pyrimidin-4-yl]imidazo[1,2-a]pyridin-2-yl}phenyl)-N'-[(1S)-1,2-dimethylpropyl]urea;

N-(3-{3-[2-({3-[2-(dimethylamino)ethyl]phenyl}amino)pyrimidin-4-yl]imidazo[1,2-a]pyridin-2-yl}phenyl)-N'-[(1S)-1-phenylethyl]urea;

N-(3-{3-[2-({3-[2-(dimethylamino)ethyl]phenyl}amino)pyrimidin-4-yl]imidazo[1,2-a]pyridin-2-yl}phenyl)-N'-(3,5-dimethylisoxazol-4-yl)urea;

N-(3-{3-[2-({3-[2-(dimethylamino)ethyl]phenyl}amino)pyrimidin-4-yl]imidazo[1,2-a]pyridin-2-yl}phenyl)-N'-thien-2-ylurea;

N-(3-{3-[2-({3-[2-(dimethylamino)ethyl]phenyl}amino)pyrimidin-4-yl]imidazo[1,2-a]pyridin-2-yl}phenyl)-N'-(2-methyl-phenyl)urea;

N-(3-{3-[2-({3-[2-(dimethylamino)ethyl]phenyl}amino)pyrimidin-4-yl]imidazo[1,2-a]pyridin-2-yl}phenyl)indoline-1-carboxamide;

N-(3-{3-[2-({3-[2-(dimethylamino)ethyl]phenyl}amino)pyrimidin-4-yl]imidazo[1,2-a]pyridin-2-yl}phenyl)piperidine-1-carboxamide;

N-(3-{3-[2-({3-[2-(dimethylamino)ethyl]phenyl}amino)pyrimidin-4-yl]imidazo[1,2-a]pyridin-2-yl}phenyl)-N'-thien-3-ylurea;

N-(3-{3-[2-({3-[2-(dimethylamino)ethyl]phenyl}amino)pyrimidin-4-yl]imidazo[1,2-a]pyridin-2-yl}phenyl)morpholine-4-carboxamide;

2,3-dimethyl-N-[3-(3-{2-[(4-pyrrolidin-3-ylphenyl)amino]pyrimidin-4-yl}imidazo[1,2-a]pyridin-2-yl)phenyl]benzamide;

N-[3-(3-{2-[(4-pyrrolidin-2-ylphenyl)amino]pyrimidin-4-yl}imidazo[1,2-a]pyridin-2-yl)phenyl]-2-thien-2-ylacetamide;

2-chloro-N-[3-(3-{2-[(4-pyrrolidin-2-ylphenyl)amino]pyrimidin-4-yl}imidazo[1,2-a]pyridin-2-yl)phenyl]benzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,6-difluorobenzamide;

2-chloro-N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]benzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]thiophene-2-carboxamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2-thien-2-ylacetamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,3-difluorobenzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2,5-difluorobenzamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-2-phenylacetamide;

N-[3-(3-{2-[(3-{2-[3-(dimethylamino)pyrrolidin-1-yl]ethyl}phenyl)amino]pyrimidin-4-yl}imidazo[1,2-a]pyridin-2-yl)phenyl]-N'-phenylurea;

N-{3-[3-(2-{[4-(1-acetylazetidin-3-yl)phenyl]amino}pyrimidin-4-yl)imidazo[1,2-a]pyridin-2-yl]phenyl}indoline-1-carboxamide;

N-{3-[3-(2-{[2-(dimethylamino)-2,3-dihydro-1H-inden-5-yl]amino}pyrimidin-4-yl)imidazo[1,2-a]pyridin-2-yl]phenyl}-2,3-dimethylbenzamide;

N-(3-{3-[2-({4-[4-(dimethylamino)piperidin-1-yl]
  phenyl}amino)pyrimidin-4-yl]imidazo[1,2-a]pyridin-
  2-yl}phenyl)-2,3-dimethylbenzamide;
2-amino-N-[3-{3-(2-[(4-pyrrolidin-3-ylphenyl)amino]py-
  rimidin-4-yl}imidazo[1,2-a]pyridin-2-yl)phenyl]-2-
  thien-2-ylacetamide;
2-amino-N-{3-[3-(2-{[2-(dimethylamino)-2,3-dihydro-
  1H-inden-5-yl]amino}pyrimidin-4-yl)imidazo[1,2-a]
  pyridin-2-yl]phenyl}-2-thien-2-ylacetamide;
2-amino-N-(3-{3-[2-({4-[4-(dimethylamino)piperidin-1-
  yl]phenyl}amino)pyrimidin-4-yl]imidazo[1,2-a]pyri-
  din-2-yl}phenyl}-2-thien-2-ylacetamide;
N-(3-{3-[2-({3-[2-(dimethylamino)ethyl]phenyl}amino)
  pyrimidin-4-yl]imidazo[1,2-a]pyridin-2-yl}phenyl)-
  N'-[(1R)-1-phenylethyl]urea;
N-(3-{3-[2-({3-[2-(dimethylamino)ethyl]phenyl}amino)
  pyrimidin-4-yl]imidazo[1,2-a]pyridin-2-yl}phenyl)-
  N'-(2-phenylcyclopropyl)urea;
N'-(3-{3-[2-({3-[2-(dimethylamino)ethyl]phenyl}amino)
  pyrimidin-4-yl]imidazo[1,2-a]pyridin-2-yl}phenyl)-N,
  N-dimethylurea;
N'-(3-{3-[2-({3-[2-(dimethylamino)ethyl]phenyl}amino)
  pyrimidin-4-yl]imidazo[1,2-a]pyridin-2-yl}phenyl)-N-
  methyl-N-phenylurea;
N-(3-{3-[2-({3-[2-(dimethylamino)ethyl]phenyl}amino)
  pyrimidin-4-yl]imidazo[1,2-a]pyridin-2-yl}phenyl)
  pyrrolidine-1-carboxamide;
N-{3-[3-[2-({3-[2-(dimethylamino)ethyl]phenyl}amino)
  pyrimidin-4-yl]-7-(trifluoromethyl)imidazo[1,2-a]pyri-
  din-2-yl]phenyl}-2,6-difluorobenzamide;
N-{3-[3-[2-({3-[2-(dimethylamino)ethyl]phenyl}amino)
  pyrimidin-4-yl]-7-(trifluoromethyl)imidazo[1,2-a]pyri-
  din-2-yl]phenyl}-2-thien-2-ylacetamide;
N-{3-[3-[2-({3-[2-(dimethylamino)ethyl]phenyl}amino)
  pyrimidin-4-yl]-7-(trifluoromethyl)imidazo[1,2-a]pyri-
  din-2-yl]phenyl}-N'-phenylurea;
N-{3-[3-[2-({3-[2-(dimethylamino)ethyl]phenyl}amino)
  pyrimidin-4-yl]-7-(trifluoromethyl)imidazo[1,2-a]pyri-
  din-2-yl]phenyl}-N'-[(1S)-1-phenylethyl]urea;
N-{3-[3-(2-{[4-(1-ethylpyrrolidin-2-yl)phenyl]
  amino}pyrimidin-4-yl)imidazo[1,2-a]pyridin-2-yl]
  phenyl}-2-thien-2-ylacetamide;
2-chloro-N-{3-[3-(2-{[4-(1-ethylpyrrolidin-2-yl)phenyl]
  amino}pyrimidin-4-yl)imidazo[1,2-a]pyridin-2-yl]
  phenyl}benzamide;
N-{3-[3-(2-{[4-(1-isopropylpyrrolidin-3-yl)phenyl]
  amino}pyrimidin-4-yl)imidazo[1,2-a]pyridin-2-yl]
  phenyl}-2-thien-3-ylacetamide;
N-{3-[3-(2-{[4-(1-isopropylpyrrolidin-3-yl)phenyl]
  amino}pyrimidin-4-yl)imidazo[1,2-a]pyridin-2-yl]
  phenyl}-2-thien-2-ylacetamide;
2-chloro-N-{3-[3-(2-{[4-(1-isopropylpyrrolidin-3-yl)
  phenyl]amino}pyrimidin-4-yl)imidazo[1,2-a]pyridin-
  2-yl]phenyl}benzamide;
2,3-difluoro-N-{3-[3-(2-{[4-(1-isopropylpyrrolidin-3-yl)
  phenyl]amino}pyrimidin-4-yl)imidazo[1,2-a]pyridin-
  2-yl]phenyl}benzamide;
N-{3-[3-(2-{[4-(1-isopropylpyrrolidin-3-yl)phenyl]
  amino}pyrimidin-4-yl)imidazo[1,2-a]pyridin-2-yl]
  phenyl}-N'-[(1S)-1-phenylethyl]urea;
N-(2-fluorophenyl)-3-{3-[2-({3-[2-(4-hydroxypiperidin-
  1-yl)ethyl]phenyl}amino)pyrimidin-4-yl]imidazo[1,2-
  a]pyridin-2-yl}benzamide;
3-{3-[2-({3-[2-(4-hydroxypiperidin-1-yl)ethyl]
  phenyl}amino)pyrimidin-4-yl]imidazo[1,2-a]pyridin-
  2-yl}-N-phenylbenzamide;
N'-{3-[3-(2-{[4-(1-isopropylpyrrolidin-3-yl)phenyl]
  amino}pyrimidin-4-yl)imidazo[1,2-a]pyridin-2-yl]
  phenyl}-N,N-dimethylurea;
N'-{3-[3-(2-{[4-(1-isopropylpyrrolidin-3-yl)phenyl]
  amino}pyrimidin-4-yl)imidazo[1,2-a]pyridin-2-yl]
  phenyl}-N-methyl-N-phenylurea;
3-{3-[2-({3-[2-(4-hydroxypiperidin-1-yl)ethyl]
  phenyl}amino)pyrimidin-4-yl]imidazo[1,2-a]pyridin-
  2-yl}-N-thien-2-ylbenzamide;
N-(3-{3-[2-({3-[2-(dimethylamino)ethyl]phenyl}amino)
  pyrimidin-4-yl]-8-fluoroimidazo[1,2-a]pyridin-2-
  yl}phenyl)-2,6-difluorobenzamide;
N-(3-{3-[2-({3-[2-(dimethylamino)ethyl]phenyl}amino)
  pyrimidin-4-yl]-8-fluoroimidazo[1,2-a]pyridin-2-
  yl}phenyl)-2-phenylacetamide;
N-(3-{3-[2-({3-[2-(dimethylamino)ethyl]phenyl}amino)
  pyrimidin-4-yl]-8-fluoroimidazo[1,2-a]pyridin-2-
  yl}phenyl)-2-thien-2-ylacetamide;
N-(3-{3-[2-({3-[2-(dimethylamino)ethyl]phenyl}amino)
  pyrimidin-4-yl]-8-fluoroimidazo[1,2-a]pyridin-2-
  yl}phenyl)-N'-phenylurea;
N-{3-[3-(2-{[4-(1-isopropylpyrrolidin-3-yl)phenyl]
  amino}pyrimidin-4-yl)imidazo[1,2-a]pyridin-2-yl]
  phenyl}-3,4-dihydroquinoline-1(2H)-carboxamide;
N-benzyl-N'-{3-[3-(2-{[4-(1-isopropylpyrrolidin-3-yl)
  phenyl]amino}pyrimidin-4-yl)imidazo[1,2-a]pyridin-
  2-yl]phenyl}-N-methylurea;
N-benzyl-N-(2-cyanoethyl)-N'-{3-[3-(2-{[4-(1-isopropy-
  lpyrrolidin-3-yl)phenyl]amino}pyrimidin-4-yl)imidazo
  [1,2-a]pyridin-2-yl]phenyl}urea;
N'-{3-[3-(2-{[4-(1-isopropylpyrrolidin-3-yl)phenyl]
  amino}pyrimidin-4-yl)imidazo[1,2-a]pyridin-2-yl]
  phenyl}-N-methyl-N-[(1S)-1-phenylethyl]urea;
N-{3-[3-(2-{([4-(1-isopropylpyrrolidin-3-yl)phenyl]
  amino}pyrimidin-4-yl)imidazo[1,2-a]pyridin-2-yl]
  phenyl}-5-methylindoline-1-carboxamide;
N-(3-{3-[2-({3-[2-(dimethylamino)ethyl]phenyl}amino)
  pyrimidin-4-yl]-6-fluoroimidazo[1,2-a]pyridin-2-
  yl}phenyl)-N'-phenylurea;
N-(3-{3-[2-({3-[2-(dimethylamino)ethyl]phenyl}amino)
  pyrimidin-4-yl]-6-fluoroimidazo[1,2-a]pyridin-2-
  yl}phenyl)-2-thien-2-ylacetamide;
N-(3-{3-[2-({3-[2-(dimethylamino)ethyl]phenyl}amino)
  pyrimidin-4-yl]-6-fluoroimidazo[1,2-a]pyridin-2-
  yl}phenyl)-2,6-difluorobenzamide;
N-{3-[3-[2-({3-[2-(dimethylamino)ethyl]phenyl}amino)
  pyrimidin-4-yl]-6-(trifluoromethyl)imidazo[1,2-a]pyri-
  din-2-yl]phenyl}-N'-phenylurea;
N-{3-[3-[2-({3-[2-(dimethylamino)ethyl]phenyl}amino)
  pyrimidin-4-yl]-6-(trifluoromethyl)imidazo[1,2-a]pyri-
  din-2-yl]phenyl}-2-thien-2-ylacetamide; and
N-{3-[3-[2-({3-[2-(dimethylamino)ethyl]phenyl}amino)
  pyrimidin-4-yl]-6-(trifluoromethyl)imidazo[1,2-a]pyri-
  din-2-yl]phenyl}-2,6-difluorobenzamide; and salts,
  esters, amides, prodrugs and salts of esters, amides and
  prodrugs thereof.

4. A composition comprising an excipient and a therapeutically effective amount of a compound of claim 1.

\* \* \* \* \*